United States Patent
Jiricek et al.

(10) Patent No.: US 11,384,078 B2
(45) Date of Patent: Jul. 12, 2022

(54) 5,6-FUSED-BICYCLIC COMPOUNDS AND COMPOSITIONS FOR THE TREATMENT OF PARASITIC DISEASES

(71) Applicant: NOVARTIS AG, Basel (CH)

(72) Inventors: Jan Jiricek, Emeryville, CA (US); Isabelle K. Lerario, San Diego, CA (US); Fang Liang, Encinitas, CA (US); Xiaodong Liu, San Diego, CA (US); Valentina Molteni, San Diego, CA (US); Advait Suresh Nagle, San Diego, CA (US); Shuyi Pearly Ng, Singapore (SG); Maxim Ratnikov, San Diego, CA (US); Jeffrey M. Smith, San Diego, CA (US); Yongping Xie, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/615,749

(22) PCT Filed: May 29, 2018

(86) PCT No.: PCT/IB2018/053818
§ 371 (c)(1),
(2) Date: Nov. 21, 2019

(87) PCT Pub. No.: WO2018/220531
PCT Pub. Date: Dec. 6, 2018

(65) Prior Publication Data
US 2020/0109142 A1 Apr. 9, 2020

Related U.S. Application Data

(60) Provisional application No. 62/513,211, filed on May 31, 2017, provisional application No. 62/581,919, filed on Nov. 6, 2017.

(51) Int. Cl.
*A61K 31/7048* (2006.01)
*A61K 31/541* (2006.01)
*A61K 31/197* (2006.01)
*A61K 31/155* (2006.01)
*A61K 31/555* (2006.01)
*A61K 31/417* (2006.01)
*C07D 519/00* (2006.01)
*C07D 471/04* (2006.01)
*C07D 487/04* (2006.01)
*A61P 33/02* (2006.01)

(52) U.S. Cl.
CPC ............ *C07D 471/04* (2013.01); *A61P 33/02* (2018.01); *C07D 519/00* (2013.01); *A61K 31/155* (2013.01); *A61K 31/197* (2013.01); *A61K 31/417* (2013.01); *A61K 31/541* (2013.01); *A61K 31/555* (2013.01); *A61K 31/7048* (2013.01)

(58) Field of Classification Search
CPC .............. A61K 31/7048; A61K 31/541; A61K 31/197; A61K 31/155; A61K 31/555; A61K 31/417; C07D 519/00; C07D 471/04; C07D 487/04; A61P 33/02
See application file for complete search history.

(56) References Cited

FOREIGN PATENT DOCUMENTS

| RU | 2268887 C2 | 1/2006 |
| WO | 2004076450 A1 | 9/2004 |
| WO | 2012116246 A2 | 8/2012 |
| WO | 2014078802 A1 | 5/2014 |
| WO | 2014151784 A1 | 9/2014 |
| WO | 2015095477 A1 | 6/2015 |
| WO | 2016087368 A1 | 6/2016 |
| WO | 2016144351 A1 | 9/2016 |
| WO | 2016193111 A1 | 12/2016 |
| WO | 2017025416 A1 | 2/2017 |

OTHER PUBLICATIONS

Fraley, et al., "synthesis and Initial SAR Studies of 3,6-Disubstituted Pyrazolo[1,5-a] pyrimidines: A New class of KDR Kinase Inhibitors", Bioorganic & Medicinal Chemistry Letters, 2001, vol. 12, pp. 2767-2770, Elsevier Science Ltd.
Khare, et al., "Proteasome inhibition for treatment of Ieishmaniasis, Chagas disease and sleeping sickness", Nature, Sep. 8, 2016, Vo. 537, pp. 229-233, Macmillan Publishers Limited.
Novinson, et al., "Novel Heterocyclic Nitrofurfural Hydrazones. In vivo Antitrypanosomal Activity" Journal of Medicinal Chemistry, Jan. 1, 1976, vol. 19, No. 4, pp. 512-516, American Chemical Society.

*Primary Examiner* — Sun Jae Yoo
(74) *Attorney, Agent, or Firm* — Emily T. Wu

(57) ABSTRACT

The present invention provides a compound of Formula (I) or a pharmaceutically acceptable salt thereof; (I) a method for manufacturing the compounds of the invention, and its therapeutic uses. The present invention further provides a combination of pharmacologically active agents and a pharmaceutical composition.

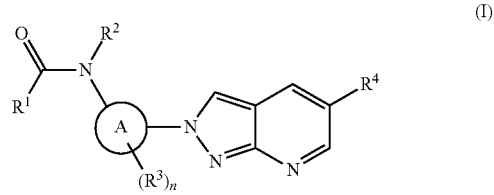

20 Claims, No Drawings

5,6-FUSED-BICYCLIC COMPOUNDS AND COMPOSITIONS FOR THE TREATMENT OF PARASITIC DISEASES

CROSS-REFERENCE TO RELATED APPLICATIONS

This application is a 371 U.S. national phase application of international application number PCT/IB2018/053818, filed 29 May 2018, which claims the benefit of U.S. provisional application Ser. No. 62/513,211 filed 31 May 2017, and U.S. provisional Ser. No. 62/581,919 filed 6 Nov. 2017; each of which is incorporated by reference herein in its entirety.

FIELD OF THE INVENTION

The present invention relates to compounds having antiparasitic activity against kinatoplastid protozoa.

BACKGROUND OF THE INVENTION

Leishmaniasis is a disease caused by protozoan parasites that belong to the genus *Leishmania* and is transmitted by the bite of certain species of sand fly. There are four main forms of Leishmaniasis. Cutaneous leishmaniasis is the most common form of leishmaniasis. Visceral leishmaniasis, the most serious form in which the parasites migrate to the vital organs, is caused by the parasite *Leishmania donovani*, and is potentially fatal if untreated. It affects as many as 12 million people worldwide, with 1.5-2 million new cases each year. The visceral form of leishmaniasis has an estimated incidence of 500,000 new cases and 60,000 deaths each year.

The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects. Amphotericin (AmBisome®) is now the treatment of choice. Miltefosine (Impavido®) and paromomycin are the other treatment alternatives.

Amphotericin (AmBisome) is expensive and has to be given intravenously. Paromomycin requires intramuscular injections for 3 weeks; compliance is a major issue. Miltefosine is an oral drug and has shown to be more effective and better tolerated than other drugs. However, there are problems associated with the use of miltefosine that arise from its teratogenicity and pharmacokinetics. Miltefosine was shown to be much slower eliminated from the body and was still detectable five months after the end of treatment. The presence of subtherapeutic miltefosine concentrations in the blood beyond five months after treatment might contribute to the selection of resistant parasites; moreover, the measures for preventing the teratogenic risks of miltefosine must be reconsidered. Currently, no vaccines are in routine use.

Chagas disease, also called American trypanosomiasis, is a tropical parasitic disease caused by the flagellate protozoan *Trypanosoma cruzi*. *T. cruzi* is commonly transmitted to humans and other mammals by the blood-sucking "kissing bugs" of the subfamily Triatominae (family Reduviidae). Each year, an estimated 10 to 15 million people across the world are infected with Chagas disease, most of whom do not know they are infected. Every year, 14,000 people die as a consequence of the disease. In Central and South America, Chagas kills more people than any other parasite-borne disease, including malaria. The CDC estimates that more than 300,000 persons with *Trypanosoma cruzi* infection live in the United States.

The symptoms of Chagas disease vary over the course of an infection. In the early, acute stage, symptoms are mild and usually produce no more than local swelling at the site of infection. The initial acute phase is responsive to antiparasitic treatments, with 60-90% cure rates. After 4-8 weeks, individuals with active infections enter the chronic phase of Chagas disease that is asymptomatic for 60-80% of chronically infected individuals through their lifetime. However, the remaining 20-40% of infected people will develop debilitating and sometimes life-threatening medical problems over the course of their lives.

Treatment for Chagas disease focuses on killing the parasite and managing signs and symptoms. During the acute phase of Chagas disease, the drugs currently available for treatment are benznidazole and nifurtimox. Once Chagas disease reaches the chronic phase, medications are not effective for curing the disease. Instead, treatment depends on the specific signs and symptoms. However, problems with these current therapies include their diverse side effects, the length of treatment, and the requirement for medical supervision during treatment. Resistance to the two frontline drugs has already occurred. The antifungal agent Amphotericin b has been proposed as a second-line drug, but is costly and relatively toxic. There is no vaccine against Chagas disease.

Human African trypanosomiasis (HAT), also known as African sleeping sickness, is a vector-borne parasitic disease caused by the protozoa *Trypanosoma brucei*. There are two subspecies that infect humans, *T.b. gambiense* and *T.b. rhodesiense*, with the former accounting for over 95% of reported cases and the latter accounting for the remaining reported cases. The parasites are transmitted to humans by tsetse fly (*Glossina* genus) bites, which have acquired their infection from human beings or from animals harboring the human pathogenic parasites. About 48,000 people died of sleeping sickness in 2008. Public health efforts in prevention and the eradication of the tsetse fly population have been successful in controlling the spread of the disease; under 10,000 new cases were reported in 2009 according to WHO figures, which represents a huge decrease from the estimated 300,000 new cases in 1998.

African trypanosomiasis symptoms occur in two stages. In the first stage, known as the haemolymphatic phase, the trypanosomes multiply in subcutaneous tissues, blood and lymph. The haemolymphatic phase is characterized by bouts of fever, headaches, joint pains and itching. In the second stage, the neurological phase, the parasites cross the blood-brain barrier to infect the central nervous system. It is in this stage when more obvious signs and symptoms of the disease appear (e.g., changes of behavior, confusion, sensory disturbances and poor coordination). Disturbance of the sleep cycle, which gives the disease its name, is an important feature of the second stage of the disease. Without treatment, the disease is invariably fatal, with progressive mental deterioration leading to coma, systemic organ failure, and death.

Four drugs are registered for the treatment of sleeping sickness. The protocol depends on the stage of the disease. The current standard treatment for first-stage disease is intravenous or intramuscular pentamidine (for *T.b. gambiense*), or intravenous suramin (for *T.b. rhodesiense*). The current standard treatment for second-stage disease is intravenous melarsoprol, or intravenous melarsoprol in combination with oral nifurtimox, intravenous eflornithine only or eflornithine in combination with nifurtimox. All of the drugs have undesirable or potentially serious side effects. For example, 3-10% of patients those injected with melarsoprol (Arsobal®), developed reactive encephalopathy (convulsions, progressive coma, or psychotic reactions), and 10-70% of such cases result in death.

Thus, there remains a need for new and better treatments and therapies for leishmaniasis, Chagas disease and HAT.

SUMMARY OF THE INVENTION

Within certain aspects, provided herein is a compound of Formula (I) or subformulae thereof:

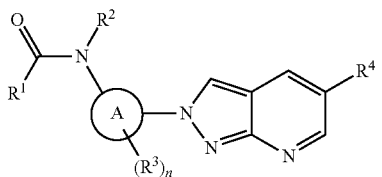

or a pharmaceutically acceptable salt, or stereoisomer thereof; wherein

Ring A is phenyl or pyridinyl;
$R^1$ is selected from:
(a) $C_{1-6}$alkyl that is unsubstituted or substituted by 1 to 3 substituents independently selected from halogen and $C_{3-6}$cycloalkyl; and said $C_{3-6}$cycloalkyl is unsubstituted or substituted by 1 to 2 substituents independently selected from halogen and $C_{1-4}$alkyl;
(b) $C_{1-4}$alkoxy that is unsubstituted or substituted by $C_{1-4}$haloalkyl;
(c) —$NR^{5a}R^{5b}$ wherein $R^{5a}$ and $R^{5b}$ are independently hydrogen, $C_{1-4}$alkyl or $C_{1-4}$ haloalkyl; or $R^{5a}$ and $R^{5b}$ together with the nitrogen atom to which both are attached form a 4- to 7-membered heterocycloalkyl comprising 1 to 3 heteroatoms independently selected from N, O and S as ring atoms;
wherein the 4 to 7-membered heterocycloalkyl is unsubstituted or substituted by 1 to 2 substituents independently selected from halogen, $C_{1-4}$alkyl, and $C_{1-4}$ alkoxy; or two substituents on the same or different ring atoms of the 4- to 7-membered heterocycloalkyl, together with the atoms to which they are attached, form a spiro, bridged or fused Ring B attached to the 4- to 7-membered heterocycloalkyl;
wherein Ring B is $C_{3-6}$cycloalkyl or a 3- to 7-membered heterocycloalkyl comprising 1 to 3 heteroatoms independently selected from N, O or S as ring atoms;
(d) monocyclic $C_{3-6}$cycloalkyl, $C_{3-6}$ cycloalkenyl or spiropentyl; each of which is unsubstituted or substituted by 1 to 3 substituents independently selected from halogen, cyano, $C_{1-4}$alkyl, and $C_{1-4}$haloalkyl, and $C_{1-4}$alkoxy;
(e) phenyl or a 5-6 membered heteroaryl comprising 1 to 2 heteroatoms independently selected from N, O and S as ring atoms; each of which is unsubstituted or substituted by 1 to 2 substituents independently selected from halogen, cyano, $C_{1-4}$alkyl, $C_{1-4}$haloalkyl, di-$C_{1-4}$ alkylamino-$C_{1-4}$alkyl, $C_{1-4}$alkoxy$C_{1-4}$alkyl, $C_{1-4}$ hydroxyalkyl, $C_{1-4}$alkoxy, and $C_{3-6}$cycloalkyl;
$R^2$ and $R^7$ are independently hydrogen or $C_{1-4}$alkyl;
$R^3$ is hydrogen or halogen, and n is 0 or 1; and $R^4$ is selected from
(a) hydrogen;
(b) halogen;
(c) $C_{1-6}$haloalkyl or $C_{1-6}$alkyl that is unsubstituted or substituted by $C_{3-6}$cycloalkyl; and said $C_{3-6}$cycloalkyl is unsubstituted or substituted by 1 to 2 substituents independently selected from halogen and $C_{1-4}$alkyl;
(d) —$NR^{6a}R^{6b}$ wherein $R^{6a}$ is hydrogen or $C_{1-4}$alkyl; $R^{6b}$ is hydrogen, $C_{1-4}$alkoxycarbonyl, $C_{1-4}$ haloalkyl, $C_{3-6}$ cycloalkyl, or $C_{1-4}$alkyl that is unsubstituted or substituted by $C_{1-4}$alkoxy; or $R^{6a}$ and $R^{6b}$ together with the nitrogen atom to which both are attached form a 4- to 7-membered heterocycloalkyl comprising 1 to 2 heteroatoms independently selected from N, O and S as ring atoms;
wherein the 4- to 7-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, oxo, 1,1-dioxo, —C(O)—$OR^7$ or a 4-6 membered heterocycloalkyl comprising 1-2 heteroatoms independently selected from N, O and S; or two substituents on the same or different ring atoms of the 4- to 7-membered heterocycloalkyl, together with the atoms to which they are attached, form a spiro, bridged or fused Ring C attached to the 4- to 7-membered heterocycloalkyl;
wherein Ring C is selected from $C_{3-6}$cycloalkyl, and 3- to 7-membered heterocycloalkyl comprising 1 to 3 heteroatoms independently selected from N, O or S as ring atoms; and is independently unsubstituted or substituted by 1 to 2 substituents independently selected from halogen, and oxo;
(e) $C_{3-6}$cycloalkyl;
(f) 4- to 6-membered heterocycloalkyl comprising 1 to 2 heteroatoms independently selected from N, O and S as ring atoms; and is unsubstituted or substituted by —C(O)$OR^8$, —C(O)$R^8$ wherein $R^8$ is $C_{1-4}$alkyl, and aryl$C_{1-4}$ alkyl that is unsubstituted or substituted by 1 to 2 halo substituents; and
(g) 5- to 6-membered heteroaryl comprising 1 to 2 heteroatoms independently selected from N, O and S as ring atoms; which is unsubstituted or substituted by 1 to 2 substituents independently selected from halogen, $C_{1-4}$alkyl, $C_{1-4}$ hydroxyalkyl, and $C_{3-6}$cycloalkyl.

In another aspect, the invention provides a pharmaceutical composition comprising a therapeutically effective amount of a compound of Formula (I) or subformulae thereof, or a pharmaceutically acceptable salt or stereoisomer thereof; and one or more pharmaceutically acceptable carriers.

In yet another aspect, the invention provides a combination, in particular a pharmaceutical combination, comprising a therapeutically effective amount of a compound of Formula (I) or subformulae thereof, or a pharmaceutically acceptable salt or stereoisomer thereof; and one or more therapeutically active agent(s).

Compounds of Formula (I) or subformulae thereof, in free form or in pharmaceutically acceptable salt form, may be useful as a therapy for a disease or condition that can be benefit from inhibition of growth and proliferation of kinetoplastid parasites. In one aspect, the present invention provides a compound of Formula (I) or subformulae thereof, a pharmaceutically acceptable salt thereof, or a stereoisomer thereof, for use in treating, preventing, inhibiting, ameliorating, or eradicating the pathology and/or symptomology of a disease caused by a kinetoplastid parasite. In another aspect, the present invention provides the use of a compound selected from Formula (I), or subformulae thereof, or a pharmaceutically acceptable salt or stereoisomer thereof, in the manufacture of a medicament for treating a disease in a subject caused by a kinetoplastid parasite. The kinetoplastid parasites include, but is not limited to, a parasite of the *Leishmania* genus, for example, *Leishmania donovani, Leishmania infantum, Leishmania braziliensis, Leishmania panamensis, Leishmania guayanensis, Leishmania amazonensis, Leishmania mexicana, Leishmania tropica, Leishmania major*; or a parasite of the *Trypanosoma* genus, for example, *Trypanosoma cruzi* and *Trypanosoma brucei*. Accordingly, compounds of the invention may be useful in the treatment of an indication selected from: leishmaniasis, Chagas disease (also call American Trypanosomiasis), more particularly, Chagas disease caused by the protozoa *Trypanosoma cruzi*; and human African trypanosomiasis, more particularly, Human African Trypanosomiasis caused by the protozoa *Trypanosoma brucei*.

Unless specified otherwise, the term "compounds of the present invention" refers to compounds of Formula I and subformulae thereof, salts of the compound, hydrates or solvates of the compounds, salts, as well as all stereoisomers (including diastereoisomers and enantiomers), tautomers and isotopically labeled compounds (including deuterium substitutions). Compounds of the present invention further comprise polymorphs of compounds of Formula (I) (or subformulae thereof) and salts thereof.

DETAILED DESCRIPTION OF THE INVENTION

Definitions

As used herein, the term "a," "an," "the" and similar terms used in the context of the present invention (especially in the context of the claims) are to be construed to cover both the singular and plural unless otherwise indicated herein or clearly contradicted by the context.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-4}$alkyl" is to be construed accordingly. As used herein, the term "n-alkyl" to refers to straight chain (un-branched) alkyl radical as defined herein. Examples of $C_{1-6}$alkyl include, but are not limited to, methyl, ethyl, n-propyl, iso-propyl, n-butyl, isobutyl (—CH—$_2$CH(CH$_3$)$_2$), sec-butyl (—CH(CH$_3$)CH$_2$CH$_3$), t-butyl (—C(CH$_3$)$_3$), n-pentyl, isopentyl (—(CH—$_2$)$_2$CH(CH$_3$)$_2$), neopentyl (—CH$_2$C(CH$_3$)$_3$), tert-pentyl (—C(CH$_3$)$_2$CH$_2$CH$_3$), 2-pentan-yl (—CH(CH$_3$)(CH$_2$)$_2$CH$_3$), n-hexyl, and the like.

As used herein, the term "$C_{1-4}$alkylamino" refers to a radical of the formula —NH—$R^a$, where $R^a$ is a $C_{1-4}$alkyl radical as defined above.

As used herein, the term "di-($C_{1-4}$alkyl)amino" refers to a radical of the formula —N($R^a$)—$R^a$, where each $R^a$ is a $C_{1-4}$alkyl radical, which may be the same or different, as defined above.

As used herein, the term "$C_{1-6}$alkoxy" refers to a radical of the formula —OR$_a$, where $R_a$ is a $C_{1-6}$alkyl radical as generally defined above. Examples of $C_{1-6}$alkoxy include, but are not limited to, methoxy, ethoxy, propoxy, iso-propoxy, butoxy, isobutoxy, pentoxy, and hexoxy As used herein, the term "$C_{1-4}$alkoxy$C_{1-4}$alkyl" refers to a radical of the formula —$R^a$—O—$R^a$ where each $R^a$ is independently a $C_{1-6}$alkyl radical as defined above. The oxygen atom may be bonded to any carbon atom in either alkyl radical. Examples of $C_{1-4}$alkoxy$C_{1-4}$alkyl include, but are not limited to, methoxy-methyl, methoxy-ethyl, ethoxy-ethyl, 1-ethoxy-propyl and 2-methoxy-butyl.

As used herein, the term "$C_{1-6}$alkoxycarbonyl" refers to a radical of the formula —C(=O)—O—$R^a$ where $R^a$ is a $C_{1-6}$alkyl radical as defined above.

"Aryl" as used herein refers to a 6-14 membered monocyclic or polycyclic aromatic ring assembly where all the ring atoms are carbon atoms. Typically, the aryl is a 6 membered monocyclic, a 10-12 membered bicyclic or a 14-membered fused tricyclic aromatic ring system. $C_X$aryl and $C_{X-Y}$aryl as used herein describe an aryl group where X and Y indicate the number of carbon atoms in the ring system. $C_{6-14}$aryls include, but are not limited to, phenyl, biphenyl, naphthyl, azulenyl, and anthracenyl.

"Bridging ring" or "bridged rings" as used herein refers to a polycyclic ring system where two ring atoms that are common to two rings are not directly bound to each other. One or more rings of the ring system may include $C_{3-6}$cycloalkyl or 4- to 6-membered heterocyclic rings comprising heteroatoms selecting from N, O and S as ring atoms. Non-exclusive examples of bridging rings include adamantanyl, azabicyclo[3.2.1]oct-3-en-3-yl,

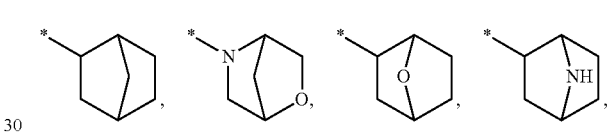

and the like.

As used herein, the term "cyano" means the radical *—C≡N

The term "cycloalkyl" refers to nonaromatic carbocyclic ring that is a fully hydrogenated ring, including mono-, bi- or poly-cyclic, fused, bridged or spiro, ring systems. Examples of cycloalkyl groups include, but are not limited to, cyclopropyl, cyclobutyl, cyclopentyl, bicyclo[1,1,1]pentanyl, cyclohexyl, norbornyl, and cubanyl.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halogen" or "halo" refers to bromo, chloro, fluoro or iodo; preferably fluoro, chloro or bromo.

As used herein, "$C_{1-6}$haloalkyl" refers to a $C_{1-6}$alkyl radical as defined above, substituted by one or more halo radicals as defined above. Examples of $C_{1-6}$haloalkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

The term "heteroaryl" refers to aromatic moieties containing at least one heteroatom (e.g., oxygen, sulfur, nitrogen or combinations thereof) within a 5- to 10-membered aromatic ring system. Examples of heteroaryl include, but are not limited to pyrrolyl, pyrazolyl, indolyl, indazolyl, thienyl, furanyl, benzofuranyl, oxazolyl, isoxazolyl, imidazolyl, triazolyl, tetrazolyl, triazinyl, pyridyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl and 1H-benzo[d][1,2,3]triazolyl. The heteroaromatic moiety may consist of a single or fused ring system. A typical single heteroaryl ring is a 5- to 6-membered ring containing one to four heteroatoms independently selected from N, O and S and a typical fused heteroaryl ring system is a 9- to 10-membered ring system containing one to four heteroatoms independently selected from N, O and S. The fused heteroaryl ring system may consist of two heteroaryl rings fused together or a heteroaryl fused to an aryl (e.g., phenyl).

As used herein, the term "heteroatoms" refers to nitrogen (N), oxygen (O) or sulfur (S) atoms. Unless otherwise indicated, any heteroatom with unsatisfied valences is assumed to have hydrogen atoms sufficient to satisfy the valences, and when the heteroatom is sulfur, it can be unoxidized (S) or oxidized to S(O) or S(O)$_2$.

The term "hydroxyl" or "hydroxy", as used herein, refers to the radical —OH.

"Heterocycloalkyl" means cycloalkyl, as defined in this application, provided that one or more of the ring carbons indicated, are replaced by a moiety selected from —O—, —N=, —NH—, —S—, —S(O)— and —S(O)$_2$—. Examples of 3 to 8 membered heterocycloalkyl include, but are not limited to oxiranyl, aziridinyl, azetidinyl, imidazolidinyl, pyrazolidinyl, tetrahydrofuranyl, tetrahydrothienyl, tetrahydrothienyl 1,1-dioxide, oxazolidinyl, thiazolidinyl, pyrrolidinyl, pyrrolidinyl-2-one, morpholinyl, piperazinyl, piperidinyl, pyrazolidinyl, hexahydropyrimidinyl, 1,4-dioxa-8-aza-spiro[4.5]dec-8-yl, thiomorpholinyl, sulfanomorpholinyl, sulfonomorpholinyl and octahydropyrrolo[3,2-b]pyrrolyl.

The term "oxo", as used herein, refers to the divalent radical =O.

The term "spiro" as used herein includes C$_{3-6}$cycloalkyl or 4- to 6-membered heterocyclic rings having one or two heteroatoms selected from N, O and S as ring members, wherein the spiro ring is fused onto a single carbon atom of a non-aromatic ring, making the carbon atom shared by both rings a spirocyclic center. The spiro ring can optionally be substituted as defined, e.g., halo, hydroxyl or C$_{1-4}$alkyl. Illustrative examples of spiro groups are:

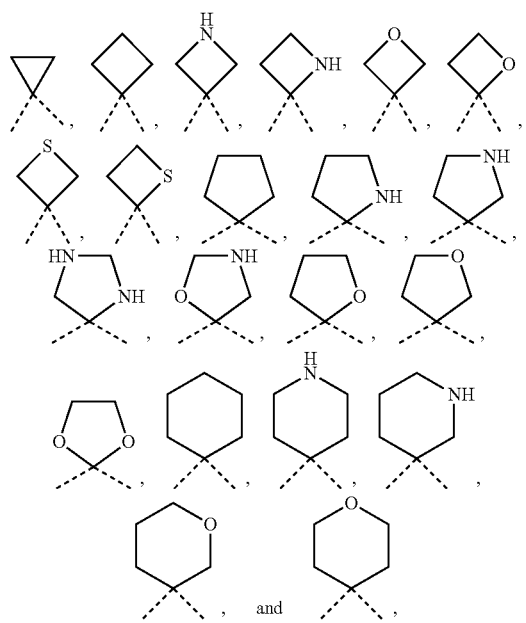

where the dashed bonds in each structure represent bonds of a non-aromatic ring with which the spirocyclic group shares one atom.

As referred to herein, the term "substituted" means that at least one hydrogen atom is replaced with a non-hydrogen group, provided that normal valencies are maintained and that the substitution results in a stable compound. When a substituent is oxo (i.e., =O), then 2 hydrogens on the atom are replaced. In cases wherein there are nitrogen atoms (e.g., amines) present in compounds of the present invention, these may be converted to N-oxides by treatment with an oxidizing agent (e.g., mCPBA and/or hydrogen peroxides) to give other compounds of the invention.

As a person of ordinary skill in the art would be able to understand, for example, a ketone (—CH—C(=O)—) group in a molecule may tautomerize to its enol form (—C=C(OH)—). Thus, this invention is intended to cover all possible tautomers even when a structure depicts only one of them.

When any variable occurs more than one time in any constituent or formula for a compound, its definition at each occurrence is independent of its definition at every other occurrence. Thus, for example, if a group is shown to be substituted with 0-3 R groups, then said group may be unsubstituted or substituted with up to three R groups, and at each occurrence R is selected independently from the definition of R.

As used herein, $$\text{"X}\diagup^*\text{"}$$

denotes the point of attachment of X, to other part of the molecule.

The term "IC$_{50}$", as used herein, refers to the molar concentration of an inhibitor that produces 50% of the inhibition effect.

The term "EC$_{50}$", as used herein, refers to the molar concentration of an inhibitor or modulator that produces 50% efficacy.

As used herein, the term "pharmaceutical composition" refers to a compound of the invention, or a pharmaceutically acceptable salt thereof, together with at least one pharmaceutically acceptable carrier, in a form suitable for topical or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "prevent", "preventing" or "prevention" of any disease or disorder refers to the prophylactic treatment of the disease or disorder; or delaying the onset or progression of the disease or disorder.

As used herein, the term "subject" refers to primates (e.g., humans, male or female, dogs, rabbits, guinea pigs, pigs, rats and mice). In certain embodiments, the subject is a primate. In yet other embodiments, the subject is a human.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease caused by the proliferation of a kinetoplastid parasite; or (2) reduce or inhibit the proliferation of a kinetoplastid parasite.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

EMBODIMENTS OF THE INVENTION

The present invention relates to compounds having antiparasitic activity against kinatoplastid protozoa. It relates particularly to compounds that inhibit growth of kinatoplastid parasite cells through inhibition of the parasitic proteasome, and thereof useful as a therapy for leishmaniasis, Chagas disease and African sleeping sickness.

Various (enumerated) embodiments of the invention are described herein. Features specified in each embodiment may be combined with other specified features to provide further embodiments of the present invention.

Embodiment 1

A compound of Formula (I) or a pharmaceutically acceptable salt thereof, as described in the Summary of the Invention.

Embodiment 2

The compound according to Embodiment 1 or a pharmaceutically acceptable salt thereof, wherein Ring A is phenyl.

Embodiment 3

The compound according to Embodiment 1 or a pharmaceutically acceptable salt thereof, wherein Ring A is pyridinyl.

Embodiment 4

The compound according to any one of Embodiments 1-3 or a pharmaceutically acceptable salt thereof, wherein $R^1$ is selected from —$(CH_2)_{1-3}CF_3$, —$(CH_2)$—$CH(CH_3)$—$CF_3$, —$(CH_2)$—$C(CH_3)_3$, —$O(CH_2)_2CF_3$, —$(CH_2)_{0-2}$-cyclopropyl, —$(CH_2)_{0-2}$-cyclobutyl, —$NHCH_3$, —$N(CH_3)_2$, —$N(CD_3)_2$, —$N(CH_3)(CH_2CH_3)$, —$N(CH_3)(CH_2CF_3)$,

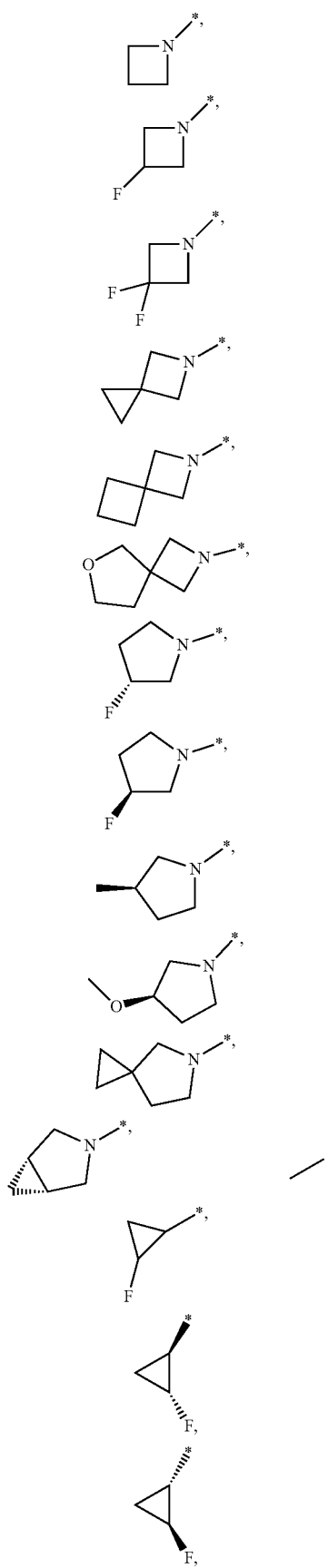

-continued
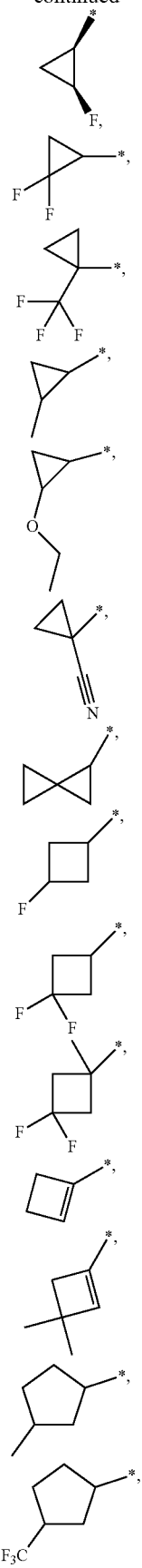
-continued
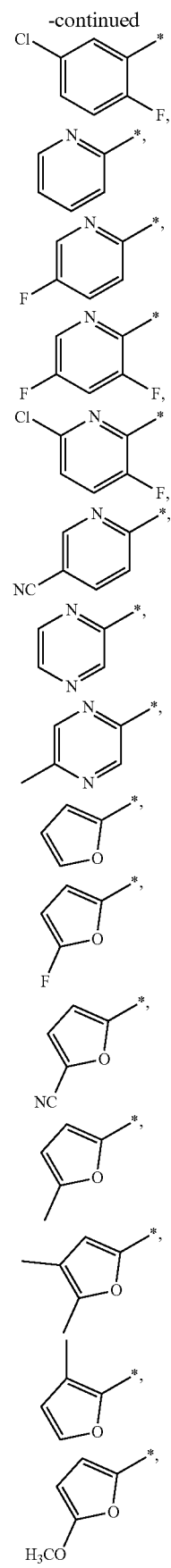

13
-continued

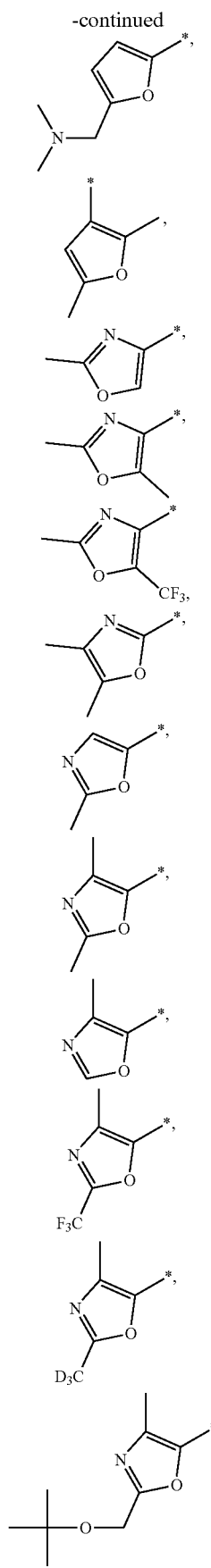

14
-continued

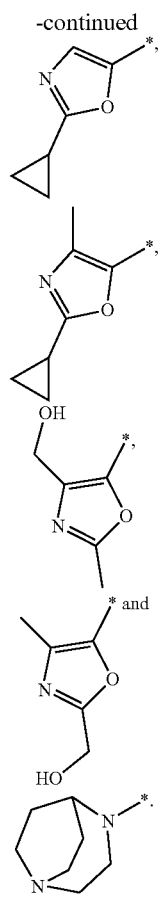

Embodiment 5

The compound according to any one of Embodiments 1-3 or a pharmaceutically acceptable salt thereof, wherein $R^1$ is azetidinyl, which is unsubstituted or substituted by 1 to 2 substituents independently selected from halogen and $C_{1-4}$alkyl; or two substituents on the same ring atom of the azetidinyl, together with the ring atom to which both are attached, form a spiro cyclopropyl or spiro tetrahydrofuranyl attached to the azetidinyl ring.

Embodiment 6

The compound according to any one of Embodiments 1-3 or a pharmaceutically acceptable salt thereof, wherein $R^1$ is selected from

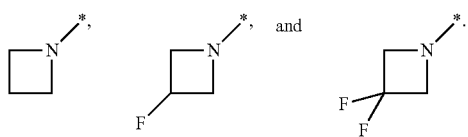

Embodiment 7

The compound according to any one of Embodiments 1-6 or a pharmaceutically acceptable salt thereof, wherein $R^3$ is halo and n is 1.

Embodiment 8

The compound according to Embodiment 7 or a pharmaceutically acceptable salt thereof, wherein $R^3$ is fluoro.

Embodiment 9

The compound according to any one of Embodiments 1-8 or a pharmaceutically acceptable salt thereof, wherein $R^4$ is selected from hydrogen, chloro, bromo, methyl, iso-propyl, —$(CH_2)_{1-2}CH(CH_3)_2$, —$(CH_2)_{0-1}C(CH_3)_3$, —$C(CH_3)_2$ $CH_2CH_3$, —$CH(CH_3)(CH_2)_{1-2}CH_3$, —$CH_2$-cyclobutyl, —$(CH_2)_{0-1}CF_3$, —NH—$(CH_2)_{0-1}CH_3$, —N—$(CD_3)_2$, —$N(CH_3)_2$, —NH—CH—$(CH_3)_2$, —NH—$(CH_2)$—CH—$(CH_3)_2$, —NHC(O)OCH$(CH_3)_2$, —NH$(CH_2)_2OCH_3$,

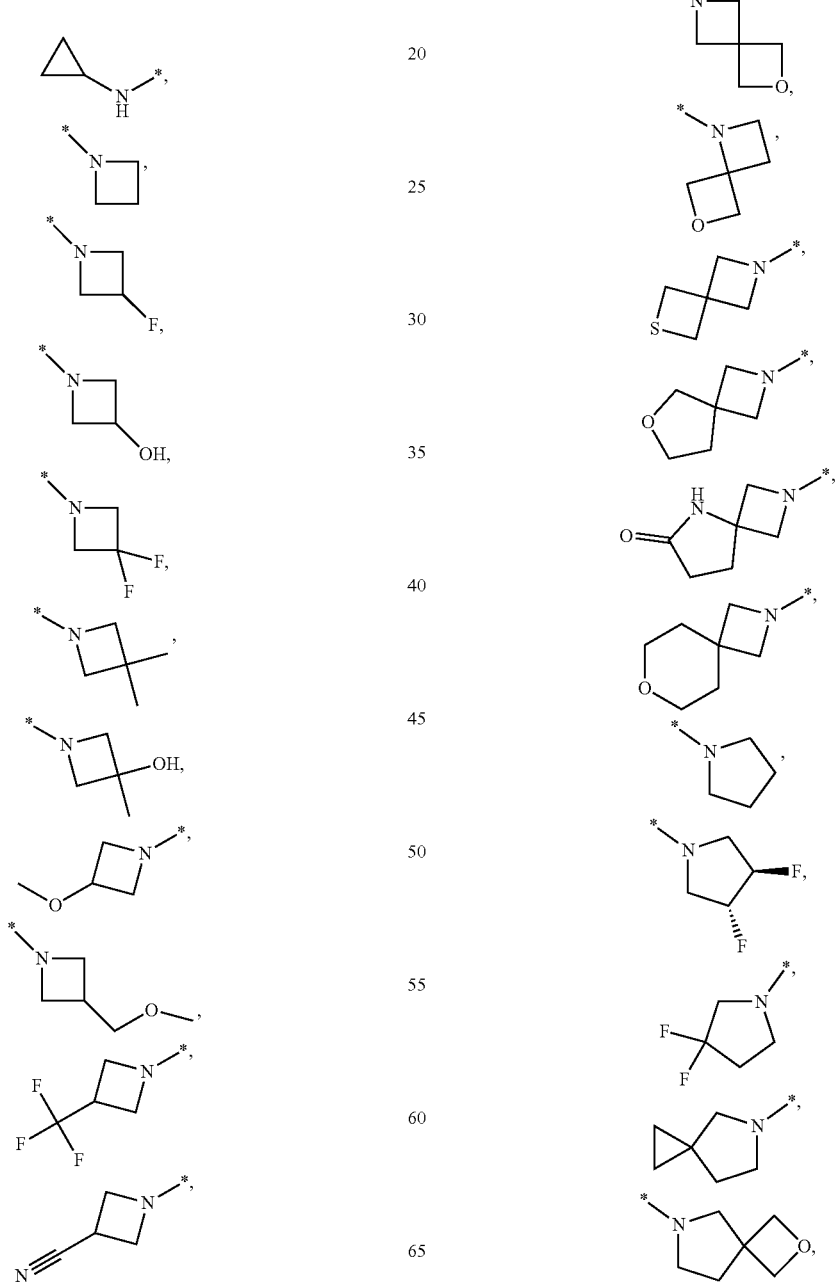

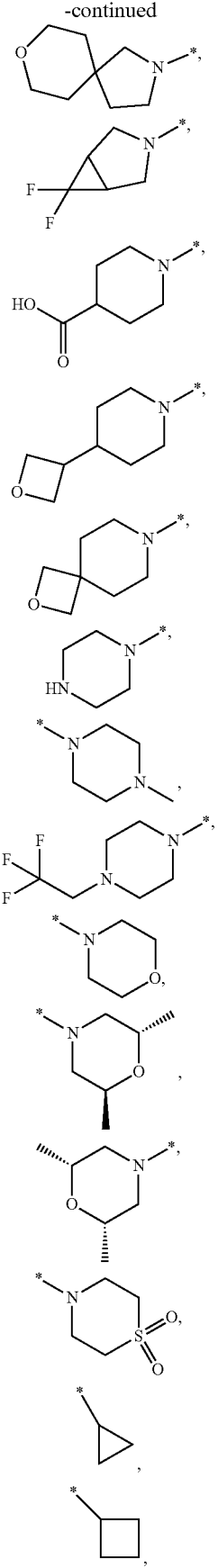
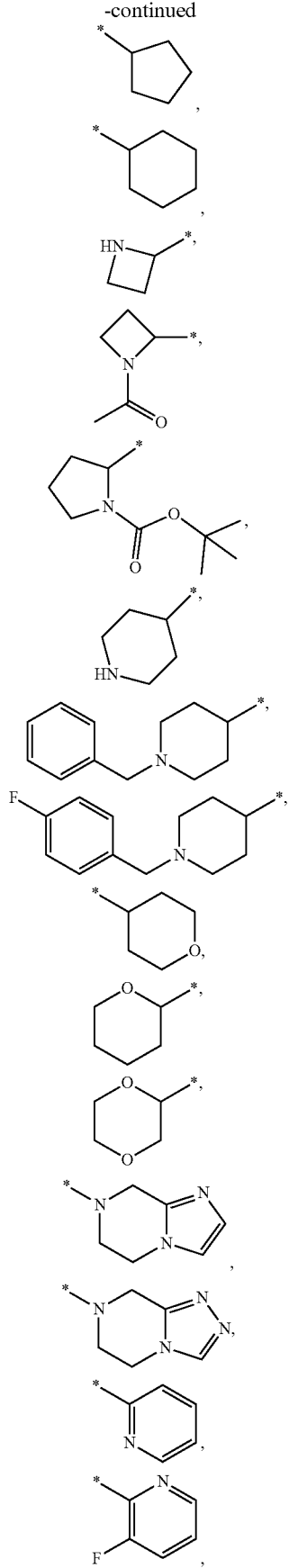

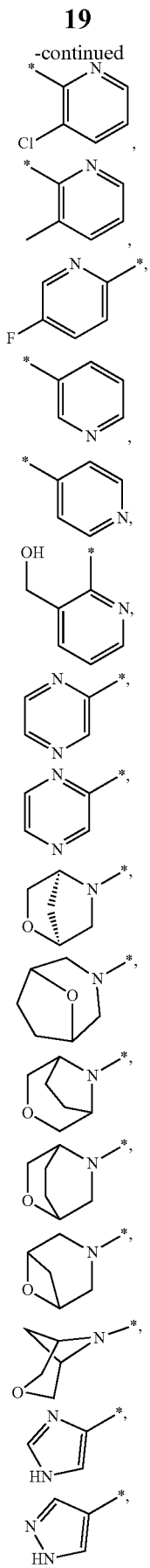

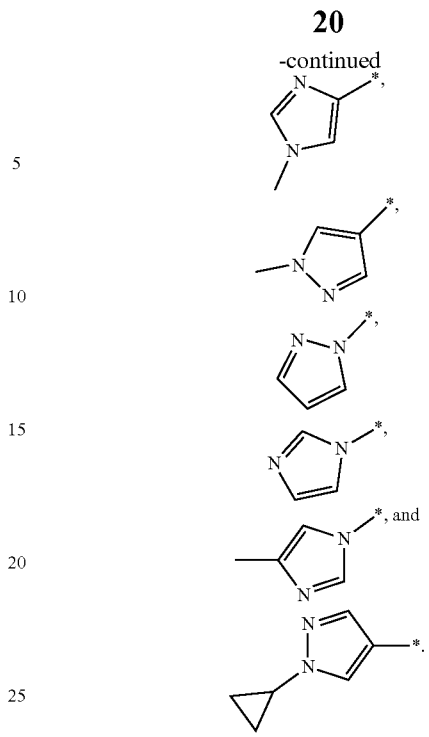

Embodiment 10

The compound according to any one of Embodiments 1-8 or a pharmaceutically acceptable salt thereof, wherein $R^4$ is $-NR^{6a}R^{6b}$;

$R^{6a}$ is hydrogen or $C_{1-4}$alkyl;

$R^{6b}$ is hydrogen, $C_{1-4}$alkoxycarbonyl or $C_{1-4}$alkyl that is unsubstituted or substituted by $C_{1-4}$alkoxy; or $R^{6a}$ and $R^{6b}$ together with the nitrogen atom to which both are attached form a 4- to 6-membered heterocycloalkyl optionally comprising 1 to 2 additional heteroatoms independently selected from N, O and S as ring atoms;

wherein the 4- to 6-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, and oxo; or two substituents on the same or different ring atoms of the 4- to 6-membered heterocycloalkyl, together with the atoms to which they are attached, form a spiro, bridged or fused, Ring C attached to the 4- to 6-membered heterocycloalkyl;

wherein Ring C is selected from $C_{3-6}$cycloalkyl; and 3- to 5-membered heterocycloalkyl comprising 1 to 3 heteroatoms independently selected from N, O or S as ring atoms; and Ring C is independently unsubstituted or substituted by 1 to 2 substituents independently selected from halogen, and oxo.

Embodiment 11

The compound according to any one of Embodiments 1-8 or a pharmaceutically acceptable salt thereof, wherein $R^4$ is selected from

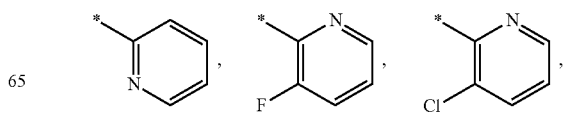

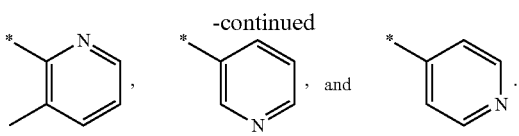

Embodiment 12

The compound according to any one of Embodiments 1-3 or a pharmaceutically acceptable salt thereof;
wherein $R^1$ is azetidinyl, which is unsubstituted or substituted by 1 to 2 substituents independently selected from halogen and $C_{1-4}$alkyl; or two substituents on the same ring atom of the azetidinyl, together with the ring atom to which both are attached, form a spiro cyclopropyl or spiro tetrahydrofuranyl attached to the azetidinyl ring;
$R^2$ is hydrogen or $C_{1-4}$alkyl;
$R^3$ is selected from halo, and n is 1; and
$R^4$ is —$NR^{6a}R^{6b}$ wherein $R^{6a}$ is hydrogen or $C_{1-4}$alkyl; $R^{6b}$ is hydrogen, $C_{1-4}$alkoxycarbonyl, or $C_{1-4}$alkyl that is unsubstituted or substituted by $C_{1-4}$alkoxy; or $R^{6a}$ and $R^{6b}$ together with the nitrogen atom to which both are attached form a 4- to 6-membered heterocycloalkyl optionally comprising 1 to 2 additional heteroatoms independently selected from N, O and S as ring atoms;
wherein the 4- to 6-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, and oxo; or two substituents on the same or different ring atoms of the 4- to 6-membered heterocycloalkyl, together with the atoms to which they are attached, form to a spiro, bridged or fused, Ring C attached to the 4- to 6-membered heterocycloalkyl;
wherein Ring C is selected from $C_{3-6}$cycloalkyl; 3- to 5-membered heterocycloalkyl comprising 1 to 3 heteroatoms independently selected from N, O or S as ring atoms; and Ring C is independently unsubstituted or substituted by 1 to 2 substituents independently selected from halogen and oxo.

Embodiment 13

The compound according to any one of Embodiments 1-12 or a pharmaceutically acceptable salt thereof, wherein $R^4$ is selected from

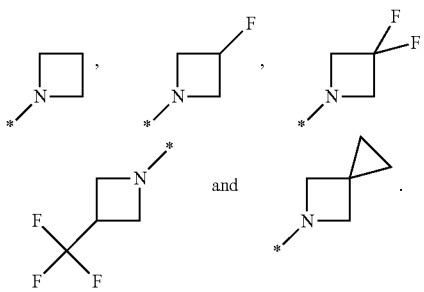

Embodiment 14

The compound according to any one of Embodiments 1-12 or a pharmaceutically acceptable salt thereof, wherein $R^4$ is selected from

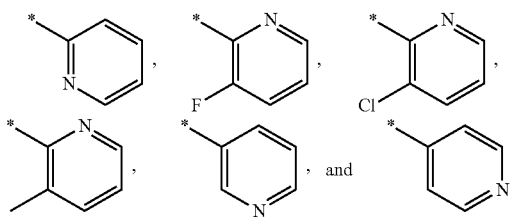

Embodiment 15

A compound of Formula (I) or a pharmaceutically acceptable salt thereof:

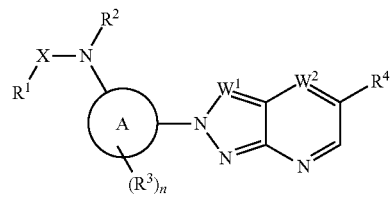

or a pharmaceutically acceptable salt, or stereoisomer thereof; wherein
$W^1$ and $W^2$ are each independently CH or N;
Ring A is phenyl or pyridyl;
X is —C(O)— or —S(O)$_2$—;
$R^1$ is selected from
(a) $C_{1-4}$alkyl that is unsubstituted or substituted by 1 to 3 substituents independently selected from halogen and $C_{3-6}$cycloalkyl, wherein the $C_{3-6}$cycloalkyl substituent is unsubstituted or substituted by 1 to 2 substituents independently selected from halogen and $C_{1-4}$alkyl;
(b) $C_{1-4}$alkoxy that is unsubstituted or substituted by $C_{1-4}$haloalkyl;
(c) —$NR^{5a}R^{5b}$, wherein
 (1) $R^{5a}$ and $R^{5b}$ are each independently hydrogen or $C_{1-4}$alkyl; or
 (2) $R^{5a}$ and $R^{5b}$ together with the nitrogen atom to which both are attached form a 4- to 6-membered heterocycloalkyl optionally comprising 1 to 3 additional heteroatoms independently selected from N, O and S as ring atoms, wherein
  the 4 to 6-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$ alkoxy, and oxo; or
 two substituents on the same or different ring atoms of the 4- to 6-membered heterocycloalkyl, together with the atoms to which they are attached, form a spiro, bridged or fused Ring B attached to the 4- to 6-membered heterocycloalkyl; wherein Ring B is selected from
  (i) $C_{3-6}$cycloalkyl,
  (ii) 3- to 5-membered heterocycloalkyl comprising 1 to 3 heteroatoms independently selected from N, O or S as ring atoms; and
  (iii) 5- to 6-membered heteroaryl comprising 1 to 3 heteroatoms independently selected from N or O as ring atoms;
 wherein Ring B of (i) to (iii) are each unsubstituted or substituted by 1 to 2 substituents independently selected from halogen, cyano, $C_{1-4}$alkyl, $C_{1-4}$haloalkyl, and oxo;

(d) monocyclic $C_{3-6}$cycloalkyl and polycyclic $C_{5-9}$cycloalkyl, each of which is unsubstituted or substituted by 1 to 3 substituents independently selected from halogen, cyano, $C_{1-4}$alkyl, $C_{1-4}$haloalkyl, and $C_{1-4}$alkoxycarbonyl;

(e) 4- to 6-membered heterocycloalkyl comprising 1 to 2 heteroatoms independently selected from N, O and S as ring atoms, which is unsubstituted or substituted by 1 to 2 substituents independently selected from halogen, cyano, hydroxyl, $C_{1-4}$alkyl, $C_{1-4}$haloalkyl, $C_{1-4}$ alkoxy, oxo, and $C_{1-4}$alkylcarbonyl;

(f) phenyl that is unsubstituted or substituted by 1 to 2 substituents independently select from halogen, cyano, $C_{1-4}$alkyl, $C_{1-4}$haloalkyl, $C_{1-4}$alkoxy$C_{1-4}$alkyl, $C_{1-4}$alkylamino-$C_{1-4}$alkyl, di-$C_{1-4}$alkylamino-$C_{1-4}$alkyl, $C_{1-4}$alkoxy, and $C_{3-6}$cycloalkyl;

(g) monocyclic 5- to 6-membered heteroaryl and polycyclic 7- to 10-membered heteroaryl, each of which comprises 1 to 2 heteroatoms independently selected from N, O and S as ring atoms, and each of which is unsubstituted or substituted by 1 to 2 substituents independently selected from halogen, cyano, $C_{1-4}$alkyl, $C_{1-4}$haloalkyl, $C_{1-4}$alkylamino-$C_{1-4}$alkyl, di-$C_{1-4}$alkylamino-$C_{1-4}$alkyl, $C_{1-4}$alkoxy$C_{1-4}$alkyl, $C_{1-4}$alkoxy, and $C_{3-6}$cycloalkyl;

$R^2$ is hydrogen or $C_{1-4}$alkyl;
$R^3$ is halogen or $C_{1-4}$alkyl, and n is 0, 1 or 2;
$R^4$ is selected from
(a) halogen;
(b) $C_{1-6}$alkyl that is unsubstituted or substituted by 1 to 3 substituents independently selected halogen and $C_{3-6}$cycloalkyl, wherein the $C_{3-6}$cycloalkyl substituent is unsubstituted or substituted by 1 to 2 substituents independently selected from halogen and $C_{1-4}$alkyl;
(c) —$NR^{6a}R^{6b}$, wherein
  (1) $R^{6a}$ is hydrogen or $C_{1-4}$alkyl;
  (2) $R^{6b}$ is hydrogen or $C_{1-4}$alkyl that is unsubstituted or substituted by $C_{1-4}$alkoxy or $C_{1-4}$alkoxycarbonyl;
  (3) or $R^{6a}$ and $R^{6b}$ together with the nitrogen atom to which both are attached form a 4- to 6-membered heterocycloalkyl optionally comprising 1 to 2 additional heteroatoms independently selected from N, O and S as ring atoms, wherein
    the 4- to 6-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, and oxo; or
    two substituents on the same or different ring atoms of the 4- to 6-membered heterocycloalkyl, together with the atoms to which they are attached, form a spiro, bridged or fused Ring C attached to the 4- to 6-membered heterocycloalkyl; wherein Ring C is selected from
      (i) $C_{3-6}$cycloalkyl,
      (ii) 3- to 5-membered heterocycloalkyl comprising 1 to 3 heteroatoms independently selected from N, O or S as ring atoms; and
      (iii) 5- to 6-membered heteroaryl comprising 1 to 3 heteroatoms independently selected from N or O as ring atoms;
      wherein Ring C of (i) to (iii) are each unsubstituted or substituted by 1 to 2 substituents independently selected from halogen, cyano, $C_{1-4}$alkyl, $C_{1-4}$haloalkyl, and oxo;
(d) $C_{3-6}$cycloalkyl that is unsubstituted or substituted by 1 to 2 substituents selected from halogen, cyano, $C_{1-4}$alkyl, and $C_{1-4}$haloalkyl;

(e) 4- to 6-membered heterocycloalkyl comprising 1 to 2 heteroatoms independently selected from N, O and S as ring atoms, which is unsubstituted or substituted by 1 to 2 substituents independently selected from halogen, cyano, hydroxyl, $C_{1-4}$alkyl, $C_{1-4}$haloalkyl, and oxo;

(f) phenyl that is unsubstituted or substituted by 1 to 2 substituents independently selected from halogen, cyano, $C_{1-4}$alkyl, $C_{1-4}$haloalkyl, $C_{1-4}$alkoxy$C_{1-4}$alkyl, $C_{1-4}$alkylamino-$C_{1-4}$alkyl, di-$C_{1-4}$alkylamino-$C_{1-4}$alkyl, $C_{1-4}$alkoxy, and $C_{3-6}$cycloalkyl;

(g) 5- to 6-membered heteroaryl comprising 1 to 2 heteroatoms independently selected from N, O and S as ring atoms, which is unsubstituted or substituted by 1 to 2 substituents independently selected from halogen, cyano, $C_{1-4}$alkyl, $C_{1-4}$haloalkyl, $C_{1-4}$alkylamino$C_{1-4}$alkyl, di-$C_{1-4}$ alkylamino$C_{1-4}$alkyl, $C_{1-4}$alkoxy$C_{1-4}$alkyl, $C_{1-4}$alkoxy, and $C_{3-6}$cycloalkyl.

Embodiment 16

A compound of Formula (I) or a pharmaceutically acceptable salt thereof, according to Embodiment 15, wherein the compound is of Formula (I-B):

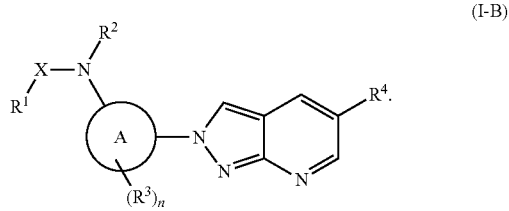

(I-B)

Embodiment 17

A compound or a pharmaceutically acceptable salt thereof, according to Embodiment 15 or 16, wherein Ring A is phenyl.

Embodiment 18

A compound or a pharmaceutically acceptable salt thereof, according to Embodiment 15 or 16, wherein Ring A is pyridinyl.

Embodiment 19

A compound or a pharmaceutically acceptable salt thereof, according to any one of Embodiments 15-18, wherein X is —C(O)—.

Embodiment 20

A compound of Formula (I) or a pharmaceutically acceptable salt thereof, according to any one of Embodiments 15-19, wherein $R^1$ is azetidinyl, which is unsubstituted or substituted by 1 to 2 substituents independently selected from halogen and $C_{1-4}$alkyl; or two substituents on the same ring atom of the azetidinyl, together with the ring atom to which both are attached, form a spiro cyclopropyl or spiro tetrahydrofuranyl attached to the azetidinyl ring.

Embodiment 21

A compound of Formula (I) or a pharmaceutically acceptable salt thereof, according to Embodiment 20, wherein $R^1$ is

25

Embodiment 22

A compound of Formula (I) or a pharmaceutically acceptable salt thereof, according to Embodiment 20, wherein $R^1$ is

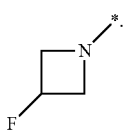

Embodiment 23

A compound of Formula (I) or a pharmaceutically acceptable salt thereof, according to Embodiment 20, wherein $R^1$ is

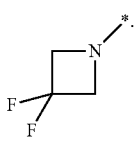

Embodiment 24

A compound of Formula (I) or a pharmaceutically acceptable salt thereof, according to any one of Embodiments 15-23, wherein $R^3$ is selected from halo or $C_{1-4}$ alkyl, and n is 1.

Embodiment 25

A compound of Formula (I) or a pharmaceutically acceptable salt thereof, according to Embodiment 24, wherein $R^3$ is halo.

Embodiment 26

A compound of Formula (I) or a pharmaceutically acceptable salt thereof, according to Embodiment 25, wherein $R^3$ is fluoro.

Embodiment 27

A compound of Formula (I) or a pharmaceutically acceptable salt thereof, according to any one of Embodiments 15-26, wherein $R^4$ is —$NR^{6a}R^{6b}$; wherein $R^{6a}$ is to hydrogen or $C_{1-4}$alkyl; and $R^{6b}$ is hydrogen or $C_{1-4}$alkyl that is unsubstituted or substituted by $C_{1-4}$alkoxy or $C_{1-4}$alkoxycarbonyl; or wherein $R^{6a}$ and $R^{6b}$ together with the nitrogen atom to which both are attached form a 4- to 6-membered heterocycloalkyl optionally comprising 1 to 2 additional heteroatoms independently selected from N, O and S as ring atoms;

26 wherein the 4- to 6-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, and oxo; or two substituents on the same or different ring atoms of the 4- to 6-membered heterocycloalkyl together with the atoms to which they are attached form a spiro, bridged or fused Ring C attached to the 4- to 6-membered heterocycloalkyl;

wherein Ring C is selected from $C_{3-6}$cycloalkyl; 3- to 5-membered heterocycloalkyl comprising 1 to 3 heteroatoms independently selected from N, O or S as ring atoms; and 5-membered heteroaryl comprising 1 to 3 heteroatoms independently selected from N or O as ring atoms; and Ring C is unsubstituted or substituted by 1 to 2 substituents independently selected from halogen, cyano, $C_{1-4}$alkyl, $C_{1-4}$haloalkyl, and oxo.

Embodiment 28

A compound of Formula (I) or a pharmaceutically acceptable salt thereof, according to any one of Embodiments 15-27, wherein $R^4$ is selected from

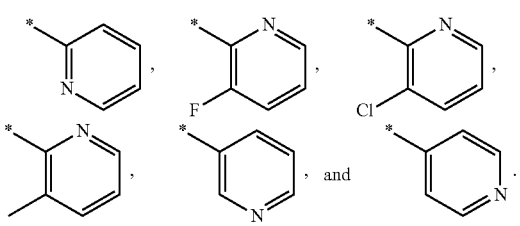

Embodiment 29

A compound of Formula (I) or a pharmaceutically acceptable salt thereof, according to Embodiment 15, wherein the compound is of Formula (I)D:

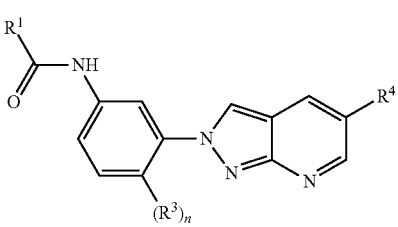

ID wherein $R_1$ is selected from
(a) —$NR^{5a}R^{5b}$, wherein $R^{5a}$ and $R^{5b}$ together with the nitrogen atom to which both are attached form a 4- to 5-membered heterocycloalkyl, which is unsubstituted or substituted by 1 to 2 substituents independently selected from halogen and $C_{1-4}$alkyl; and
(b) monocyclic 5-membered heteroaryl comprising 1 to 2 heteroatoms independently selected from N and O as ring atoms, and each of which is unsubstituted or substituted by 1 to 2 substituents independently selected from halogen and $C_{1-4}$alkyl;

$R^3$ is halogen or $C_{1-4}$alkyl, and n is 0 or 1;

$R^4$ is selected from
(a) —$NR^{6a}R^{6b}$, wherein $R^{6a}$ and $R^{6b}$ together with the nitrogen atom to which both are attached to form a 4- or 5-membered heterocycloalkyl, which is unsubstituted or substituted by 1 to 2 substituents independently selected from halogen, hydroxyl and $C_{1-4}$alkyl; or
2 substituents on the same or different ring atoms of the 4- or 5-membered heterocycloalkyl together with the atoms to which they are attached form a spiro Ring C attached to the 4- to 5-membered heterocycloalkyl, wherein Ring C is $C_{3-6}$cycloalkyl; and
(b) 6-membered heteroaryl comprising 1 to 2 nitrogen atoms as ring atoms, which is unsubstituted or substituted by 1 to 2 substituents independently selected from halogen and $C_{1-4}$alkyl.

Embodiment 30

The compound according to Embodiment 29, wherein $R^1$ is selected from

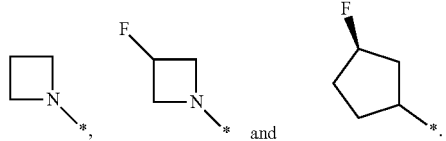

Embodiment 31

A compound of Formula (I)D or a pharmaceutically acceptable salt thereof, according to Embodiments 29 or 30, wherein $R^3$ is fluoro or chloro, and n is 1.

Embodiment 32

A compound of Formula (I)D or a pharmaceutically acceptable salt thereof, according to any one of Embodiments 29-31, wherein $R^4$ is selected from

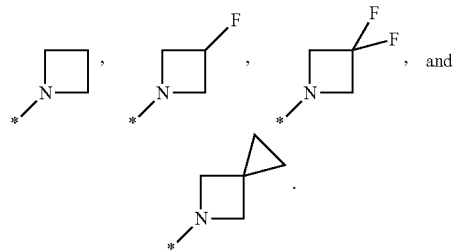

Embodiment 33

A compound of Formula (I)D or a pharmaceutically acceptable salt thereof, according to any one of Embodiments 29-31 wherein $R^4$ is selected from

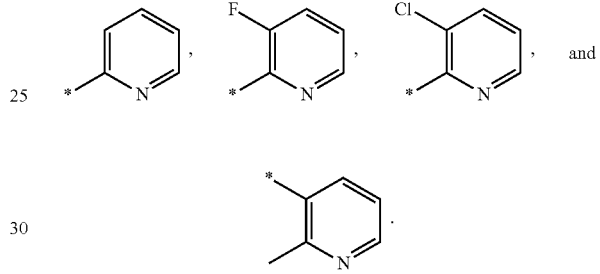

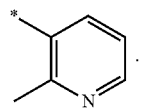

Embodiment 34

A compound of Formula (I) or a pharmaceutically acceptable salt thereof, selected from Table 1.

TABLE 1

| | |
|---|---|
| 1 | N-{4-fluoro-3-[5-(3-methylpyridin-2-yl)-2H-pyrazolo[3,4-b]pyridin-2-yl]phenyl}-2,4-dimethyl-1,3-oxazole-5-carboxamide |
| 2 | N-{4-fluoro-3-[5-(3-methylpyridin-2-yl)-2H-pyrazolo[3,4-b]pyridin-2-yl]phenyl}furan-2-carboxamide |
| 3 | N-{4-fluoro-3-[5-(3-methylpyridin-2-yl)-2H-pyrazolo[3,4-b]pyridin-2-yl]phenyl}azetidine-1-carboxamide |
| 4 | (3R)-3-fluoro-N-{4-fluoro-3-[5-(3-methylpyridin-2-yl)-2H-pyrazolo[3,4-b]pyridin-2-yl]phenyl}pyrrolidine-1-carboxamide |
| 5 | 3,3-difluoro-N-{4-fluoro-3-[5-(3-methylpyridin-2-yl)-2H-pyrazolo[3,4-b]pyridin-2-yl]phenyl}azetidine-1-carboxamide |
| 6 | 3-fluoro-N-{4-fluoro-3-[5-(3-methylpyridin-2-yl)-2H-pyrazolo[3,4-b]pyridin-2-yl]phenyl}azetidine-1-carboxamide |
| 7 | N-{4-fluoro-3-[5-(2-methylpropyl)-2H-pyrazolo[3,4-b]pyridin-2-yl]phenyl}azetidine-1-carboxamide |
| 8 | 3,3-difluoro-N-{4-fluoro-3-[5-(2-methylpropyl)-2H-pyrazolo[3,4-b]pyridin-2-yl]phenyl}azetidine-1-carboxamide |
| 9 | N-{3-[5-(dimethylamino)-2H-pyrazolo[3,4-b]pyridin-2-yl]-4-fluorophenyl}-3,3-difluoroazetidine-1-carboxamide |
| 10 | N-{3-[5-(azetidin-1-yl)-2H-pyrazolo[3,4-b]pyridin-2-yl]-4-fluorophenyl}azetidine-1-carboxamide |
| 11 | 5-fluoro-N-{4-fluoro-3-[5-(pyridin-2-yl)-2H-pyrazolo[3,4-b]pyridin-2-yl]phenyl}furan-2-carboxamide |
| 12 | N-{4-fluoro-3-[5-(pyridin-2-yl)-2H-pyrazolo[3,4-b]pyridin-2-yl]phenyl}cyclopropanecarboxamide |
| 13 | 2-cyclopropyl-N-{4-fluoro-3-[5-(pyridin-2-yl)-2H-pyrazolo[3,4-b]pyridin-2-yl]phenyl}acetamide |
| 14 | 3-fluoro-N-{4-fluoro-3-[5-(2-methylpropyl)-2H-pyrazolo[3,4-b]pyridin-2-yl]phenyl}azetidine-1-carboxamide |
| 15 | N-(3-{5-cyclopropyl-2H-pyrazolo[3,4-b]pyridin-2-yl}-4-fluorophenyl)-3-fluoroazetidine-1-carboxamide |

TABLE 1-continued

| | |
|---|---|
| 16 | N-{4-fluoro-3-[5-(2-methylpropyl)-2H-pyrazolo[3,4-b]pyridin-2-yl]phenyl}-2,4-dimethyl-1,3-oxazole-5-carboxamide |
| 17 | N-(3-{5-cyclopropyl-2H-pyrazolo[3,4-b]pyridin-2-yl}-4-fluorophenyl)-2,4-dimethyl-1,3-oxazole-5-carboxamide |
| 18 | N-(3-{5-cyclopentyl-2H-pyrazolo[3,4-b]pyridin-2-yl}-4-fluorophenyl)-3-fluoroazetidine-1-carboxamide |
| 19 | N-(3-{5-cyclohexyl-2H-pyrazolo[3,4-b]pyridin-2-yl}-4-fluorophenyl)-3-fluoroazetidine-1-carboxamide |
| 20 | N-(3-{5-cyclobutyl-2H-pyrazolo[3,4-b]pyridin-2-yl}-4-fluorophenyl)-3-fluoroazetidine-1-carboxamide |
| 21 | N-{3-[5-(2,2-dimethylpropyl)-2H-pyrazolo[3,4-b]pyridin-2-yl]-4-fluorophenyl}-3-fluoroazetidine-1-carboxamide |
| 22 | N-(3-{5-tert-butyl-2H-pyrazolo[3,4-b]pyridin-2-yl}-4-fluorophenyl)-3-fluoroazetidine-1-carboxamide |
| 23 | 3-fluoro-N-{4-fluoro-3-[5-(pentan-2-yl)-2H-pyrazolo[3,4-b]pyridin-2-yl]phenyl}azetidine-1-carboxamide |
| 24 | 3-fluoro-N-{4-fluoro-3-[5-(2-methylbutan-2-yl)-2H-pyrazolo[3,4-b]pyridin-2-yl]phenyl}azetidine-1-carboxamide |
| 25 | N-{3-[5-(butan-2-yl)-2H-pyrazolo[3,4-b]pyridin-2-yl]-4-fluorophenyl}-3-fluoroazetidine-1-carboxamide |
| 26 | N-{3-[5-(cyclobutylmethyl)-2H-pyrazolo[3,4-b]pyridin-2-yl]-4-fluorophenyl}-3-fluoroazetidine-1-carboxamide |
| 27 | 3-fluoro-N-{4-fluoro-3-[5-(3-methylbutyl)-2H-pyrazolo[3,4-b]pyridin-2-yl]phenyl}azetidine-1-carboxamide |
| 28 | 3-fluoro-N-{4-fluoro-3-[5-(pyridin-2-yl)-2H-pyrazolo[3,4-b]pyridin-2-yl]phenyl}azetidine-1-carboxamide |
| 29 | N-(3-{5-cyclopropyl-2H-pyrazolo[3,4-b]pyridin-2-yl}-4-fluorophenyl)-3,3-difluoroazetidine-1-carboxamide |
| 30 | N-(3-{5-cyclopentyl-2H-pyrazolo[3,4-b]pyridin-2-yl}-4-fluorophenyl)-3,3-difluoroazetidine-1-carboxamide |
| 31 | N-(3-{5-cyclobutyl-2H-pyrazolo[3,4-b]pyridin-2-yl}-4-fluorophenyl)-3,3-difluoroazetidine-1-carboxamide |
| 32 | N-{3-[5-(2,2-dimethylpropyl)-2H-pyrazolo[3,4-b]pyridin-2-yl]-4-fluorophenyl}-3,3-difluoroazetidine-1-carboxamide |
| 33 | N-(3-{5-tert-butyl-2H-pyrazolo[3,4-b]pyridin-2-yl}-4-fluorophenyl)-3,3-difluoroazetidine-1-carboxamide |
| 34 | 3,3-difluoro-N-{4-fluoro-3-[5-(pentan-2-yl)-2H-pyrazolo[3,4-b]pyridin-2-yl]phenyl}azetidine-1-carboxamide |
| 35 | 3,3-difluoro-N-{4-fluoro-3-[5-(2-methylbutan-2-yl)-2H-pyrazolo[3,4-b]pyridin-2-yl]phenyl}azetidine-1-carboxamide |
| 36 | N-{3-[5-(butan-2-yl)-2H-pyrazolo[3,4-b]pyridin-2-yl]-4-fluorophenyl}-3,3-difluoroazetidine-1-carboxamide |
| 37 | N-{3-[5-(cyclobutylmethyl)-2H-pyrazolo[3,4-b]pyridin-2-yl]-4-fluorophenyl}-3,3-difluoroazetidine-1-carboxamide |
| 38 | 3,3-difluoro-N-{4-fluoro-3-[5-(3-methylbutyl)-2H-pyrazolo[3,4-b]pyridin-2-yl]phenyl}azetidine-1-carboxamide |
| 39 | 3,3-difluoro-N-{4-fluoro-3-[5-(pyridin-2-yl)-2H-pyrazolo[3,4-b]pyridin-2-yl]phenyl}azetidine-1-carboxamide |
| 40 | N-{4-fluoro-3-[5-(3-fluoroazetidin-1-yl)-2H-pyrazolo[3,4-b]pyridin-2-yl]phenyl}azetidine-1-carboxamide |
| 41 | (3R)-3-fluoro-N-{4-fluoro-3-[5-(2-methylpropyl)-2H-pyrazolo[3,4-b]pyridin-2-yl]phenyl}pyrrolidine-1-carboxamide |
| 42 | (3R)-N-(3-{5-cyclopropyl-2H-pyrazolo[3,4-b]pyridin-2-yl}-4-fluorophenyl)-3-fluoropyrrolidine-1-carboxamide |
| 43 | (3R)-N-(3-{5-cyclopentyl-2H-pyrazolo[3,4-b]pyridin-2-yl}-4-fluorophenyl)-3-fluoropyrrolidine-1-carboxamide |
| 44 | (3R)-N-(3-{5-cyclohexyl-2H-pyrazolo[3,4-b]pyridin-2-yl}-4-fluorophenyl)-3-fluoropyrrolidine-1-carboxamide |
| 45 | (3R)-N-(3-{5-cyclobutyl-2H-pyrazolo[3,4-b]pyridin-2-yl}-4-fluorophenyl)-3-fluoropyrrolidine-1-carboxamide |
| 46 | (3R)-N-{3-[5-(2,2-dimethylpropyl)-2H-pyrazolo[3,4-b]pyridin-2-yl]-4-fluorophenyl}-3-fluoropyrrolidine-1-carboxamide |
| 47 | (3R)-N-(3-{5-tert-butyl-2H-pyrazolo[3,4-b]pyridin-2-yl}-4-fluorophenyl)-3-fluoropyrrolidine-1-carboxamide |
| 48 | (3R)-3-fluoro-N-{4-fluoro-3-[5-(pentan-2-yl)-2H-pyrazolo[3,4-b]pyridin-2-yl]phenyl}pyrrolidine-1-carboxamide |
| 49 | (3R)-3-fluoro-N-{4-fluoro-3-[5-(2-methylbutan-2-yl)-2H-pyrazolo[3,4-b]pyridin-2-yl]phenyl}pyrrolidine-1-carboxamide |
| 50 | (3R)-N-{3-[5-(butan-2-yl)-2H-pyrazolo[3,4-b]pyridin-2-yl]-4-fluorophenyl}-3-fluoropyrrolidine-1-carboxamide |
| 51 | (3R)-N-{3-[5-(cyclobutylmethyl)-2H-pyrazolo[3,4-b]pyridin-2-yl]-4-fluorophenyl}-3-fluoropyrrolidine-1-carboxamide |
| 52 | (3R)-3-fluoro-N-{4-fluoro-3-[5-(3-methylbutyl)-2H-pyrazolo[3,4-b]pyridin-2-yl]phenyl}pyrrolidine-1-carboxamide |
| 53 | (3R)-3-fluoro-N-{4-fluoro-3-[5-(pyridin-2-yl)-2H-pyrazolo[3,4-b]pyridin-2-yl]phenyl}pyrrolidine-1-carboxamide |
| 54 | N-{4-fluoro-3-[5-(2-methylpropyl)-2H-pyrazolo[3,4-b]pyridin-2-yl]phenyl}furan-2-carboxamide |
| 55 | N-(3-{5-cyclopropyl-2H-pyrazolo[3,4-b]pyridin-2-yl}-4-fluorophenyl)furan-2-carboxamide |
| 56 | N-(3-{5-cyclopentyl-2H-pyrazolo[3,4-b]pyridin-2-yl}-4-fluorophenyl)furan-2-carboxamide |

TABLE 1-continued

| | |
|---|---|
| 57 | N-(3-{5-cyclohexyl-2H-pyrazolo[3,4-b]pyridin-2-yl}-4-fluorophenyl)furan-2-carboxamide |
| 58 | 3-fluoro-N-{4-fluoro-3-[5-(3-fluoroazetidin-1-yl)-2H-pyrazolo[3,4-b]pyridin-2-yl]phenyl}azetidine-1-carboxamide |
| 59 | N-{3-[5-(2,2-dimethylpropyl)-2H-pyrazolo[3,4-b]pyridin-2-yl]-4-fluorophenyl}furan-2-carboxamide |
| 60 | N-{4-fluoro-3-[5-(2-methylbutan-2-yl)-2H-pyrazolo[3,4-b]pyridin-2-yl]phenyl}furan-2-carboxamide |
| 61 | N-{3-[5-(butan-2-yl)-2H-pyrazolo[3,4-b]pyridin-2-yl]-4-fluorophenyl}furan-2-carboxamide |
| 62 | N-{3-[5-(cyclobutylmethyl)-2H-pyrazolo[3,4-b]pyridin-2-yl]-4-fluorophenyl}furan-2-carboxamide |
| 63 | N-{4-fluoro-3-[5-(3-methylbutyl)-2H-pyrazolo[3,4-b]pyridin-2-yl]phenyl}furan-2-carboxamide |
| 64 | N-{4-fluoro-3-[5-(pyridin-2-yl)-2H-pyrazolo[3,4-b]pyridin-2-yl]phenyl}furan-2-carboxamide |
| 65 | N-{4-fluoro-3-[5-(propan-2-yl)-2H-pyrazolo[3,4-b]pyridin-2-yl]phenyl}-5-methylpyrazine-2-carboxamide |
| 66 | N-{4-fluoro-3-[5-(propan-2-yl)-2H-pyrazolo[3,4-b]pyridin-2-yl]phenyl}-3-methylcyclopentane-1-carboxamide |
| 67 | 5-fluoro-N-{4-fluoro-3-[5-(propan-2-yl)-2H-pyrazolo[3,4-b]pyridin-2-yl]phenyl}pyridine-2-carboxamide |
| 68 | N-{4-fluoro-3-[5-(propan-2-yl)-2H-pyrazolo[3,4-b]pyridin-2-yl]phenyl}-2-methyl-5-(trifluoromethyl)-1,3-oxazole-4-carboxamide |
| 69 | 2-cyclopropyl-N-{4-fluoro-3-[5-(propan-2-yl)-2H-pyrazolo[3,4-b]pyridin-2-yl]phenyl}acetamide |
| 70 | 3,5-difluoro-N-{4-fluoro-3-[5-(propan-2-yl)-2H-pyrazolo[3,4-b]pyridin-2-yl]phenyl}pyridine-2-carboxamide |
| 71 | N-{4-fluoro-3-[5-(propan-2-yl)-2H-pyrazolo[3,4-b]pyridin-2-yl]phenyl}-3-(trifluoromethyl)cyclopentane-1-carboxamide |
| 72 | N-{4-fluoro-3-[5-(propan-2-yl)-2H-pyrazolo[3,4-b]pyridin-2-yl]phenyl}-2,5-dimethylfuran-3-carboxamide |
| 73 | N-{4-fluoro-3-[5-(propan-2-yl)-2H-pyrazolo[3,4-b]pyridin-2-yl]phenyl}-4-methyl-1,3-oxazole-5-carboxamide |
| 74 | N-{4-fluoro-3-[5-(propan-2-yl)-2H-pyrazolo[3,4-b]pyridin-2-yl]phenyl}-2,5-dimethyl-1,3-oxazole-4-carboxamide |
| 75 | 2-cyclopropyl-N-{4-fluoro-3-[5-(propan-2-yl)-2H-pyrazolo[3,4-b]pyridin-2-yl]phenyl}-1,3-oxazole-5-carboxamide |
| 76 | 2-cyclopropyl-N-{4-fluoro-3-[5-(propan-2-yl)-2H-pyrazolo[3,4-b]pyridin-2-yl]phenyl}-4-methyl-1,3-oxazole-5-carboxamide |
| 77 | N-{4-fluoro-3-[5-(propan-2-yl)-2H-pyrazolo[3,4-b]pyridin-2-yl]phenyl}-2-methyloxolane-2-carboxamide |
| 78 | N{4-fluoro-3-[5-(propan-2-yl)-2H-pyrazolo[3,4-b]pyridin-2-yl]phenyl}-4-methyl-2-(trifluoromethyl)-1,3-oxazole-5-carboxamide |
| 79 | 2-[(tert-butoxy)methyl]-N-{4-fluoro-3-[5-(propan-2-yl)-2H-pyrazolo[3,4-b]pyridin-2-yl]phenyl}-4-methyl-1,3-oxazole-5-carboxamide |
| 80 | N-{4-fluoro-3-[5-(propan-2-yl)-2H-pyrazolo[3,4-b]pyridin-2-yl]phenyl}oxane-2-carboxamide |
| 81 | N-{4-fluoro-3-[5-(propan-2-yl)-2H-pyrazolo[3,4-b]pyridin-2-yl]phenyl}-4,5-dimethyl-1,3-oxazole-2-carboxamide |
| 82 | N-{4-fluoro-3-[5-(propan-2-yl)-2H-pyrazolo[3,4-b]pyridin-2-yl]phenyl}pyridine-2-carboxamide |
| 83 | N-{4-fluoro-3-[5-(propan-2-yl)-2H-pyrazolo[3,4-b]pyridin-2-yl]phenyl}-2-methyl-1,3-oxazole-5-carboxamide |
| 84 | 5-cyano-N-{4-fluoro-3-[5-(propan-2-yl)-2H-pyrazolo[3,4-b]pyridin-2-yl]phenyl}pyridine-2-carboxamide |
| 85 | N-{4-fluoro-3-[5-(propan-2-yl)-2H-pyrazolo[3,4-b]pyridin-2-yl]phenyl}-2-methyl-1,3-oxazole-4-carboxamide |
| 86 | 6-chloro-3-fluoro-N-{4-fluoro-3-[5-(propan-2-yl)-2H-pyrazolo[3,4-b]pyridin-2-yl]phenyl}pyridine-2-carboxamide |
| 87 | N-{4-fluoro-3-[5-(propan-2-yl)-2H-pyrazolo[3,4-b]pyridin-2-yl]phenyl}pyrazine-2-carboxamide |
| 88 | N-{4-fluoro-3-[5-(propan-2-yl)-2H-pyrazolo[3,4-b]pyridin-2-yl]phenyl}oxolane-2-carboxamide |
| 89 | 5-chloro-2-fluoro-N-{4-fluoro-3-[5-(propan-2-yl)-2H-pyrazolo[3,4-b]pyridin-2-yl]phenyl}benzamide |
| 90 | N-{4-fluoro-3-[5-(propan-2-yl)-2H-pyrazolo[3,4-b]pyridin-2-yl]phenyl}cyclopropanecarboxamide |
| 91 | N-(3-{5-cyclopropyl-2H-pyrazolo[3,4-b]pyridin-2-yl}-4-fluorophenyl)azetidine-1-carboxamide |
| 92 | N-{3-[5-(3,3-difluoroazetidin-1-yl)-2H-pyrazolo[3,4-b]pyridin-2-yl]-4-fluorophenyl}azetidine-1-carboxamide |
| 93 | N-(3-{5-cyclobutyl-2H-pyrazolo[3,4-b]pyridin-2-yl}-4-fluorophenyl)azetidine-1-carboxamide |
| 94 | N-{3-[5-(2,2-dimethylpropyl)-2H-pyrazolo[3,4-b]pyridin-2-yl]-4-fluorophenyl}azetidine-1-carboxamide |
| 95 | N-{4-fluoro-3-[5-(pentan-2-yl)-2H-pyrazolo[3,4-b]pyridin-2-yl]phenyl}azetidine-1-carboxamide |
| 96 | N-{3-[5-(butan-2-yl)-2H-pyrazolo[3,4-b]pyridin-2-yl]-4-fluorophenyl}azetidine-1-carboxamide |
| 97 | N-{3-[5-(cyclobutylmethyl)-2H-pyrazolo[3,4-b]pyridin-2-yl]-4-fluorophenyl}azetidine-1-carboxamide |
| 98 | N-{4-fluoro-3-[5-(3-methylbutyl)-2H-pyrazolo[3,4-b]pyridin-2-yl]phenyl}azetidine-1-carboxamide |
| 99 | N-{4-fluoro-3-[5-(pyridin-2-yl)-2H-pyrazolo[3,4-b]pyridin-2-yl]phenyl}azetidine-1-carboxamide |
| 100 | N-{4-fluoro-3-[5-(propan-2-yl)-2H-pyrazolo[3,4-b]pyridin-2-yl]phenyl}azetidine-1-carboxamide |
| 101 | N-(3-{5-cyclobutyl-2H-pyrazolo[3,4-b]pyridin-2-yl}-4-fluorophenyl)-2,4-dimethyl-1,3-oxazole-5-carboxamide |

TABLE 1-continued

| | |
|---|---|
| 102 | N-{3-[5-(2,2-dimethylpropyl)-2H-pyrazolo[3,4-b]pyridin-2-yl]-4-fluorophenyl}-2,4-dimethyl-1,3-oxazole-5-carboxamide |
| 103 | N-(3-{5-tert-butyl-2H-pyrazolo[3,4-b]pyridin-2-yl}-4-fluorophenyl)-2,4-dimethyl-1,3-oxazole-5-carboxamide |
| 104 | N-{4-fluoro-3-[5-(2-methylbutan-2-yl)-2H-pyrazolo[3,4-b]pyridin-2-yl]phenyl}-2,4-dimethyl-1,3-oxazole-5-carboxamide |
| 105 | N-{3-[5-(butan-2-yl)-2H-pyrazolo[3,4-b]pyridin-2-yl]-4-fluorophenyl}-2,4-dimethyl-1,3-oxazole-5-carboxamide |
| 106 | N-{3-[5-(cyclobutylmethyl)-2H-pyrazolo[3,4-b]pyridin-2-yl]-4-fluorophenyl}-2,4-dimethyl-1,3-oxazole-5-carboxamide |
| 107 | N-{4-fluoro-3-[5-(3-methylbutyl)-2H-pyrazolo[3,4-b]pyridin-2-yl]phenyl}-2,4-dimethyl-1,3-oxazole-5-carboxamide |
| 108 | N-{4-fluoro-3-[5-(pyridin-2-yl)-2H-pyrazolo[3,4-b]pyridin-2-yl]phenyl}-2,4-dimethyl-1,3-oxazole-5-carboxamide |
| 109 | N-{4-fluoro-3-[5-(propan-2-yl)-2H-pyrazolo[3,4-b]pyridin-2-yl]phenyl}-5-methylfuran-2-carboxamide |
| 110 | N-{4-fluoro-3-[5-(propan-2-yl)-2H-pyrazolo[3,4-b]pyridin-2-yl]phenyl}-5-methoxyfuran-2-carboxamide |
| 111 | 5-[(dimethylamino)methyl]-N-{4-fluoro-3-[5-(propan-2-yl)-2H-pyrazolo[3,4-b]pyridin-2-yl]phenyl}furan-2-carboxamide |
| 112 | 5-cyano-N-{4-fluoro-3-[5-(propan-2-yl)-2H-pyrazolo[3,4-b]pyridin-2-yl]phenyl}furan-2-carboxamide |
| 113 | 5-fluoro-N-{4-fluoro-3-[5-(propan-2-yl)-2H-pyrazolo[3,4-b]pyridin-2-yl]phenyl}furan-2-carboxamide |
| 114 | N-{4-fluoro-3-[5-(propan-2-yl)-2H-pyrazolo[3,4-b]pyridin-2-yl]phenyl}-4,5-dimethylfuran-2-carboxamide |
| 115 | N-{4-fluoro-3-[5-(propan-2-yl)-2H-pyrazolo[3,4-b]pyridin-2-yl]phenyl}-3-methylfuran-2-carboxamide |
| 116 | N-{4-fluoro-3-[5-(propan-2-yl)-2H-pyrazolo[3,4-b]pyridin-2-yl]phenyl}-1-benzofuran-2-carboxamide |
| 117 | 3,3-difluoro-N-{4-fluoro-3-[5-(propan-2-yl)-2H-pyrazolo[3,4-b]pyridin-2-yl]phenyl}-1-methylcyclobutane-1-carboxamide |
| 118 | 3,3-difluoro-N-{4-fluoro-3-[5-(propan-2-yl)-2H-pyrazolo[3,4-b]pyridin-2-yl]phenyl}cyclobutane-1-carboxamide |
| 119 | methyl 8-({4-fluoro-3-[5-(propan-2-yl)-2H-pyrazolo[3,4-b]pyridin-2-yl]phenyl}carbamoyl)cubane-1-carboxylate |
| 120 | methyl 3-({4-fluoro-3-[5-(propan-2-yl)-2H-pyrazolo[3,4-b]pyridin-2-yl]phenyl}carbamoyl)bicyclo[1.1.1]pentane-1-carboxylate |
| 121 | 3-fluoro-N-{4-fluoro-3-[5-(propan-2-yl)-2H-pyrazolo[3,4-b]pyridin-2-yl]phenyl}cyclobutane-1-carboxamide |
| 122 | N-{4-fluoro-3-[5-(morpholin-4-yl)-2H-pyrazolo[3,4-b]pyridin-2-yl]phenyl}furan-2-carboxamide |
| 123 | propan-2-yl N-{2-[2-fluoro-5-(furan-2-amido)phenyl]-2H-pyrazolo[3,4-b]pyridin-5-yl}carbamate |
| 124 | 3,3-difluoro-N-{4-fluoro-3-[5-(propan-2-yl)-2H-pyrazolo[3,4-b]pyridin-2-yl]phenyl}azetidine-1-carboxamide |
| 125 | N-(3-{5-bromo-2H-pyrazolo[3,4-b]pyridin-2-yl}-4-fluorophenyl)-3,3-difluoroazetidine-1-carboxamide |
| 126 | N-(3-{5-bromo-2H-pyrazolo[3,4-b]pyridin-2-yl}-4-fluorophenyl)-3-fluoroazetidine-1-carboxamide |
| 127 | (3R)-N-(3-{5-bromo-2H-pyrazolo[3,4-b]pyridin-2-yl}-4-fluorophenyl)-3-fluoropyrrolidine-1-carboxamide |
| 128 | N-(3-{5-bromo-2H-pyrazolo[3,4-b]pyridin-2-yl}-4-fluorophenyl)-2,4-dimethyl-1,3-oxazole-5-carboxamide |
| 129 | N-(3-{5-bromo-2H-pyrazolo[3,4-b]pyridin-2-yl}-4-fluorophenyl)azetidine-1-carboxamide |
| 130 | N-(3-{5-bromo-2H-pyrazolo[3,4-b]pyridin-2-yl}-4-fluorophenyl)furan-2-carboxamide |
| 131 | 3-fluoro-N-{4-fluoro-3-[5-(pyrrolidin-1-yl)-2H-pyrazolo[3,4-b]pyridin-2-yl]phenyl}azetidine-1-carboxamide |
| 132 | 3-fluoro-N-{4-fluoro-3-[5-(morpholin-4-yl)-2H-pyrazolo[3,4-b]pyridin-2-yl]phenyl}azetidine-1-carboxamide |
| 133 | (3R)-N-{3-[5-(dimethylamino)-2H-pyrazolo[3,4-b]pyridin-2-yl]-4-fluorophenyl}-3-fluoropyrrolidine-1-carboxamide |
| 134 | (3R)-3-fluoro-N-{4-fluoro-3-[5-(pyrrolidin-1-yl)-2H-pyrazolo[3,4-b]pyridin-2-yl]phenyl}pyrrolidine-1-carboxamide |
| 135 | (3R)-3-fluoro-N-{4-fluoro-3-[5-(morpholin-4-yl)-2H-pyrazolo[3,4-b]pyridin-2-yl]phenyl}pyrrolidine-1-carboxamide |
| 136 | propan-2-yl N-[2-(2-fluoro-5-{[(3R)-3-fluoropyrrolidine-1-carbonyl]amino}phenyl)-2H-pyrazolo[3,4-b]pyridin-5-yl]carbamate |
| 137 | N-{4-fluoro-3-[5-(morpholin-4-yl)-2H-pyrazolo[3,4-b]pyridin-2-yl]phenyl}azetidine-1-carboxamide |
| 138 | propan-2-yl N-(2-{5-[(azetidine-1-carbonyl)amino]-2-fluorophenyl}-2H-pyrazolo[3,4-b]pyridin-5-yl)carbamate |
| 139 | N-{4-fluoro-3-[5-(methylamino)-2H-pyrazolo[3,4-b]pyridin-2-yl]phenyl}furan-2-carboxamide |
| 140 | N-{3-[5-(dimethylamino)-2H-pyrazolo[3,4-b]pyridin-2-yl]-4-fluorophenyl}furan-2-carboxamide |
| 141 | N-{4-fluoro-3-[5-(pyrrolidin-1-yl)-2H-pyrazolo[3,4-b]pyridin-2-yl]phenyl}furan-2-carboxamide |
| 142 | 1-{4-fluoro-3-[5-(methylamino)-2H-pyrazolo[3,4-b]pyridin-2-yl]phenyl}-3-methylurea |
| 143 | 1-{3-[5-(dimethylamino)-2H-pyrazolo[3,4-b]pyridin-2-yl]-4-fluorophenyl}-3,3-dimethylurea |
| 144 | N-{3-[5-(azetidin-1-yl)-2H-pyrazolo[3,4-b]pyridin-2-yl]-4-fluorophenyl}-3,3-difluoroazetidine-1-carboxamide |

TABLE 1-continued

| | |
|---|---|
| 145 | 3,3-difluoro-N-{4-fluoro-3-[5-(morpholin-4-yl)-2H-pyrazolo[3,4-b]pyridin-2-yl]phenyl}azetidine-1-carboxamide |
| 146 | propan-2-yl N-(2-{5-[(3,3-difluoroazetidine-1-carbonyl)amino]-2-fluorophenyl}-2H-pyrazolo[3,4-b]pyridin-5-yl)carbamate |
| 147 | N-{3-[5-(azetidin-1-yl)-2H-pyrazolo[3,4-b]pyridin-2-yl]-4-fluorophenyl}-3-fluoroazetidine-1-carboxamide |
| 148 | 3-fluoro-N-{4-fluoro-3-[5-(oxan-4-yl)-2H-pyrazolo[3,4-b]pyridin-2-yl]phenyl}azetidine-1-carboxamide |
| 149 | (3R)-N-{345-(azetidin-1-yl)-2H-pyrazolo[3,4-b]pyridin-2-yl]-4-fluorophenyl}-3-fluoropyrrolidine-1-carboxamide |
| 150 | (3R)-3-fluoro-N-{4-fluoro-3-[5-(oxan-4-yl)-2H-pyrazolo[3,4-b]pyridin-2-yl]phenyl}pyrrolidine-1-carboxamide |
| 151 | N-{3-[5-(azetidin-1-yl)-2H-pyrazolo[3,4-b]pyridin-2-yl]-4-fluorophenyl}furan-2-carboxamide |
| 152 | 3-fluoro-N-{4-fluoro-3-[5-(2,2,2-trifluoroethyl)-2H-pyrazolo[3,4-b]pyridin-2-yl]phenyl}azetidine-1-carboxamide |
| 153 | N-{4-fluoro-3-[5-(methylamino)-2H-pyrazolo[3,4-b]pyridin-2-yl]phenyl}-2,4-dimethyl-1,3-oxazole-5-carboxamide |
| 154 | N-{3-[5-(dimethylamino)-2H-pyrazolo[3,4-b]pyridin-2-yl]-4-fluorophenyl}-2,4-dimethyl-1,3-oxazole-5-carboxamide |
| 155 | N-{3-[5-(azetidin-1-yl)-2H-pyrazolo[3,4-b]pyridin-2-yl]-4-fluorophenyl}-2,4-dimethyl-1,3-oxazole-5-carboxamide |
| 156 | 3-fluoro-N-{4-fluoro-3-[5-(propan-2-yl)-2H-pyrazolo[3,4-b]pyridin-2-yl]phenyl}azetidine-1-carboxamide |
| 157 | N-{4-fluoro-3-[5-(pyrrolidin-1-yl)-2H-pyrazolo[3,4-b]pyridin-2-yl]phenyl}-2,4-dimethyl-1,3-oxazole-5-carboxamide |
| 158 | N-{4-fluoro-3-[5-(morpholin-4-yl)-2H-pyrazolo[3,4-b]pyridin-2-yl]phenyl}-2,4-dimethyl-1,3-oxazole-5-carboxamide |
| 159 | propan-2-yl N-{2-[5-(dimethyl-1,3-oxazole-5-amido)-2-fluorophenyl]-2H-pyrazolo[3,4-b]pyridin-5-yl}carbamate |
| 160 | N-{4-fluoro-3-[5-(oxan-4-yl)-2H-pyrazolo[3,4-b]pyridin-2-yl]phenyl}azetidine-1-carboxamide |
| 161 | 3,3-difluoro-N-{4-fluoro-3-[5-(pyrrolidin-1-yl)-2H-pyrazolo[3,4-b]pyridin-2-yl]phenyl}azetidine-1-carboxamide |
| 162 | (3R)-3-fluoro-N-{4-fluoro-3-[5-(2,2,2-trifluoroethyl)-2H-pyrazolo[3,4-b]pyridin-2-yl]phenyl}pyrrolidine-1-carboxamide |
| 163 | N-{4-fluoro-3-[5-(pyrrolidin-1-yl)-2H-pyrazolo[3,4-b]pyridin-2-yl]phenyl}azetidine-1-carboxamide |
| 164 | N-{4-fluoro-3-[5-(2,2,2-trifluoroethyl)-2H-pyrazolo[3,4-b]pyridin-2-yl]phenyl}azetidine-1-carboxamide |
| 165 | 3,3-difluoro-N-{4-fluoro-3-[5-(oxan-4-yl)-2H-pyrazolo[3,4-b]pyridin-2-yl]phenyl}azetidine-1-carboxamide |
| 166 | 3,3-difluoro-N-{4-fluoro-3-[5-(2,2,2-trifluoroethyl)-2H-pyrazolo[3,4-b]pyridin-2-yl]phenyl}azetidine-1-carboxamide |
| 167 | N-{3-[5-(dimethylamino)-2H-pyrazolo[3,4-b]pyridin-2-yl]-4-fluorophenyl}-3-fluoroazetidine-1-carboxamide |
| 168 | propan-2-yl N-(2-{2-fluoro-5-[(3-fluoroazetidine-1-carbonyl)amino]phenyl}-2H-pyrazolo[3,4-b]pyridin-5-yl)carbamate |
| 169 | N-{4-fluoro-3-[5-(oxan-4-yl)-2H-pyrazolo[3,4-b]pyridin-2-yl]phenyl}-2,4-dimethyl-1,3-oxazole-5-carboxamide |
| 170 | N-{3-[5-(dimethylamino)-2H-pyrazolo[3,4-b]pyridin-2-yl]-4-fluorophenyl}azetidine-1-carboxamide |
| 171 | 3-fluoro-N-[4-fluoro-3-(5-{2-oxa-6-azaspiro[3.3]heptan-6-yl}-2H-pyrazolo[3,4-b]pyridin-2-yl)phenyl]azetidine-1-carboxamide |
| 172 | 3-fluoro-N-(4-fluoro-3-{5-[(1S,4S)-2-oxa-5-azabicyclo[2.2.1]heptan-5-yl]-2H-pyrazolo[3,4-b]pyridin-2-yl}phenyl)azetidine-1-carboxamide |
| 173 | 4,4,4-trifluoro-N-{4-fluoro-3-[5-(propan-2-yl)-2H-pyrazolo[3,4-b]pyridin-2-yl]phenyl}butanamide |
| 174 | 3,3,3-trifluoropropyl N-{4-fluoro-3-[5-(propan-2-yl)-2H-pyrazolo[3,4-b]pyridin-2-yl]phenyl}carbamate |
| 175 | N-{4-fluoro-3-[5-(2,2,2-trifluoroethyl)-2H-pyrazolo[3,4-b]pyridin-2-yl]phenyl}-2,4-dimethyl-1,3-oxazole-5-carboxamide |
| 176 | N-{4-fluoro-3-[5-(2,2,2-trifluoroethyl)-2H-pyrazolo[3,4-b]pyridin-2-yl]phenyl}furan-2-carboxamide |
| 177 | N-(3-{5-[(2S,6S)-2,6-dimethylmorpholin-4-yl]-2H-pyrazolo[3,4-b]pyridin-2-yl]-4-fluorophenyl)-3-fluoroazetidine-1-carboxamide |
| 178 | N-{3-[5-(1,1-dioxo-1$l^{6},4-thiomorpholin-4-yl)-2H-pyrazolo[3,4-b]pyridin-2-yl]-4-fluorophenyl}-3-fluoroazetidine-1-carboxamide |
| 179 | 3-fluoro-N-{4-fluoro-3-[5-(4-methylpiperazin-1-yl)-2H-pyrazolo[3,4-b]pyridin-2-yl]phenyl}azetidine-1-carboxamide |
| 180 | 3-fluoro-N-[4-fluoro-3-(5-{5H,6H,7H,8H-imidazo[1,2-a]pyrazin-7-yl}-2H-pyrazolo[3,4-b]pyridin-2-yl)phenyl]azetidine-1-carboxamide |
| 181 | 3-fluoro-N-{4-fluoro-3-[5-(3-hydroxyazetidin-1-yl)-2H-pyrazolo[3,4-b]pyridin-2-yl]phenyl}azetidine-1-carboxamide |
| 182 | 3-fluoro-N-{4-fluoro-3-[5-(pyridin-4-yl)-2H-pyrazolo[3,4-b]pyridin-2-yl]phenyl}azetidine-1-carboxamide |
| 183 | 3-fluoro-N-[4-fluoro-3-(5-{2-oxa-6-azaspiro[3.4]octan-6-yl}-2H-pyrazolo[3,4-b]pyridin-2-yl)phenyl]azetidine-1-carboxamide |
| 184 | 3-fluoro-N-[4-fluoro-3-(5-{8-oxa-3-azabicyclo[3.2.1]octan-3-yl}-2H-pyrazolo[3,4-b]pyridin-2-yl)phenyl]azetidine-1-carboxamide |
| 185 | 3-fluoro-N-(4-fluoro-3-{5-[(2-methoxyethyl)amino]-2H-pyrazolo[3,4-b]pyridin-2-yl}phenyl)azetidine-1-carboxamide |

TABLE 1-continued

| | |
|---|---|
| 186 | 3-fluoro-N-[4-fluoro-3-(5-{5H,6H,7H,8H-[1,2,4]triazolo[4,3-a]pyrazin-7-yl}-2H-pyrazolo[3,4-b]pyridin-2-yl)phenyl]azetidine-1-carboxamide |
| 187 | 3-fluoro-N-{4-fluoro-3-[5-(3-fluoropyridin-2-yl)-2H-pyrazolo[3,4-b]pyridin-2-yl]phenyl}azetidine-1-carboxamide |
| 188 | N-{3-[5-(3-chloropyridin-2-yl)-2H-pyrazolo[3,4-b]pyridin-2-yl]-4-fluorophenyl}-3-fluoroazetidine-1-carboxamide |
| 189 | 3-fluoro-N-{4-fluoro-3-[5-(pyridin-3-yl)-2H-pyrazolo[3,4-b]pyridin-2-yl]phenyl}azetidine-1-carboxamide |
| 190 | N-(3-{5-[(2R,6S)-2,6-dimethylmorpholin-4-yl]-2H-pyrazolo[3,4-b]pyridin-2-yl]-4-fluorophenyl)-3-fluoroazetidine-1-carboxamide |
| 191 | 3-fluoro-N-[4-fluoro-3-(5-{6-oxa-1-azaspiro[3.3]heptan-1-yl}-2H-pyrazolo[3,4-b]pyridin-2-yl)phenyl]azetidine-1-carboxamide |
| 192 | 3-fluoro-N-(4-fluoro-3-{5-[3-(methoxymethypazetidin-1-yl]-2H-pyrazolo[3,4-b]pyridin-2-yl}phenyl)azetidine-1-carboxamide |
| 193 | N-[3-(5-{5-azaspiro[2.3]hexan-5-yl}-2H-pyrazolo[3,4-b]pyridin-2-yl)-4-fluorophenyl]-3-fluoroazetidine-1-carboxamide |
| 194 | N-(3-{5-[(3R,4R)-3,4-difluoropyrrolidin-1-yl]-2H-pyrazolo[3,4-b]pyridin-2-yl]-4-fluorophenyl)-3-fluoroazetidine-1-carboxamide |
| 195 | (3R)-3-fluoro-N-{4-fluoro-3-[5-(propan-2-yl)-2H-pyrazolo[3,4-b]pyridin-2-yl]phenyl}pyrrolidine-1-carboxamide |
| 196 | N-{4-fluoro-3-[5-(propan-2-yl)-2H-pyrazolo[3,4-b]pyridin-2-yl]phenyl}furan-2-carboxamide |
| 197 | 3-fluoro-N-[4-fluoro-3-(5-{2-oxa-5-azabicyclo[2.2.2]octan-5-yl}-2H-pyrazolo[3,4-b]pyridin-2-yl)phenyl]azetidine-1-carboxamide |
| 198 | 3-fluoro-N-(4-fluoro-3-{5-[(2-methylpropyl)amino]-2H-pyrazolo[3,4-b]pyridin-2-yl}phenyl)azetidine-1-carboxamide |
| 199 | N-{3-[5-(ethylamino)-2H-pyrazolo[3,4-b]pyridin-2-yl]-4-fluorophenyl}-3-fluoroazetidine-1-carboxamide |
| 200 | 3-fluoro-N-(4-fluoro-3-{5-[(propan-2-yl)amino]-2H-pyrazolo[3,4-b]pyridin-2-yl}phenyl)azetidine-1-carboxamide |
| 201 | 3-fluoro-N-[4-fluoro-3-(5-{1-oxa-6-azaspiro[3.3]heptan-6-yl}-2H-pyrazolo[3,4-b]pyridin-2-yl)phenyl]azetidine-1-carboxamide |
| 202 | 3-fluoro-N-[4-fluoro-3-(5-{6-oxa-2-azaspiro[3.4]octan-2-yl}-2H-pyrazolo[3,4-b]pyridin-2-yl)phenyl]azetidine-1-carboxamide |
| 203 | 3-fluoro-N-[4-fluoro-3-(5-{7-oxa-2-azaspiro[3.5]nonan-2-yl}-2H-pyrazolo[3,4-b]pyridin-2-yl)phenyl]azetidine-1-carboxamide |
| 204 | N-[3-(5-{6,6-difluoro-3-azabicyclo[3.1.0]hexan-3-yl}-2H-pyrazolo[3,4-b]pyridin-2-yl)-4-fluorophenyl]-3-fluoroazetidine-1-carboxamide |
| 205 | 3-fluoro-N-{4-fluoro-3-[5-(3-methoxyazetidin-1-yl)-2H-pyrazolo[3,4-b]pyridin-2-yl]phenyl}azetidine-1-carboxamide |
| 206 | 5-cyano-N-{4-fluoro-3-[5-(pyridin-2-yl)-2H-pyrazolo[3,4-b]pyridin-2-yl]phenyl}furan-2-carboxamide |
| 207 | 2-ethoxy-N-{4-fluoro-3-[5-(propan-2-yl)-2H-pyrazolo[3,4-b]pyridin-2-yl]phenyl}cyclopropane-1-carboxamide |
| 208 | 2,2-difluoro-N-{4-fluoro-3-[5-(propan-2-yl)-2H-pyrazolo[3,4-b]pyridin-2-yl]phenyl}cyclopropane-1-carboxamide |
| 209 | N-{4-fluoro-3-[5-(propan-2-yl)-2H-pyrazolo[3,4-b]pyridin-2-yl]phenyl}-1-(trifluoromethyl)cyclopropane-1-carboxamide |
| 210 | N-{4-fluoro-3-[5-(propan-2-yl)-2H-pyrazolo[3,4-b]pyridin-2-yl]phenyl}cyclobutanecarboxamide |
| 211 | N-{4-fluoro-3-[5-(propan-2-yl)-2H-pyrazolo[3,4-b]pyridin-2-yl]phenyl}-2-methylcyclopropane-1-carboxamide |
| 212 | 3,3,3-trifluoro-N-{4-fluoro-3-[5-(propan-2-yl)-2H-pyrazolo[3,4-b]pyridin-2-yl]phenyl}propanamide |
| 213 | 4,4,4-trifluoro-N-{4-fluoro-3-[5-(propan-2-yl)-2H-pyrazolo[3,4-b]pyridin-2-yl]phenyl}-3-methylbutanamide |
| 214 | 5,5,5-trifluoro-N-{4-fluoro-3-[5-(propan-2-yl)-2H-pyrazolo[3,4-b]pyridin-2-yl]phenyl}pentanamide |
| 215 | 3-cyclopropyl-N-{4-fluoro-3-[5-(propan-2-yl)-2H-pyrazolo[3,4-b]pyridin-2-yl]phenyl}propanamide |
| 216 | 2-cyclobutyl-N-{4-fluoro-3-[5-(propan-2-yl)-2H-pyrazolo[3,4-b]pyridin-2-yl]phenyl}acetamide |
| 217 | N-{4-fluoro-3-[5-(propan-2-yl)-2H-pyrazolo[3,4-b]pyridin-2-yl]phenyl}-3,3-dimethylbutanamide |
| 218 | N-{4-fluoro-3-[5-(pyridin-2-yl)-2H-pyrazolo[3,4-b]pyridin-2-yl]phenyl}cyclobut-1-ene-1-carboxamide |
| 219 | 1-{4-fluoro-3-[5-(propan-2-yl)-2H-pyrazolo[3,4-b]pyridin-2-yl]phenyl}-3,3-bis($^2$H$_3$)methylurea |
| 220 | N-{4-fluoro-3-[5-(propan-2-yl)-2H-pyrazolo[3,4-b]pyridin-2-yl]phenyl}-5-azaspiro[2.4]heptane-5-carboxamide |
| 221 | (3R)-N-{4-fluoro-3-[5-(propan-2-yl)-2H-pyrazolo[3,4-b]pyridin-2-yl]phenyl}-3-methylpyrrolidine-1-carboxamide |
| 222 | N-{4-fluoro-3-[5-(propan-2-yl)-2H-pyrazolo[3,4-b]pyridin-2-yl]phenyl}-5-azaspiro[2.3]hexane-5-carboxamide |
| 223 | (1R,5S)-N-{4-fluoro-3-[5-(propan-2-yl)-2H-pyrazolo[3,4-b]pyridin-2-yl]phenyl}-3-azabicyclo[3.1.0]hexane-3-carboxamide |
| 224 | 3-ethyl-1-{4-fluoro-3-[5-(propan-2-yl)-2H-pyrazolo[3,4-b]pyridin-2-yl]phenyl}-3-methylurea |
| 225 | (3R)-N-{4-fluoro-3-[5-(propan-2-yl)-2H-pyrazolo[3,4-b]pyridin-2-yl]phenyl}-3-methoxypyrrolidine-1-carboxamide |
| 226 | N-{4-fluoro-3-[5-(propan-2-yl)-2H-pyrazolo[3,4-b]pyridin-2-yl]phenyl}-2-azaspiro[3.3]heptane-2-carboxamide |
| 227 | 1-{4-fluoro-3-[5-(propan-2-yl)-2H-pyrazolo[3,4-b]pyridin-2-yl]phenyl}-3-methyl-3-(2,2,2-trifluoroethyl)urea |

TABLE 1-continued

| | |
|---|---|
| 228 | 1-{4-fluoro-3-[5-(propan-2-yl)-2H-pyrazolo[3,4-b]pyridin-2-yl]phenyl}-3,3-dimethylurea |
| 229 | N-{4-fluoro-3-[5-(propan-2-yl)-2H-pyrazolo[3,4-b]pyridin-2-yl]phenyl}-1,4-diazabicyclo[3.2.2]nonane-4-carboxamide |
| 230 | N-(3-{5-[(2R,6S)-2,6-dimethylmorpholin-4-yl]-2H-pyrazolo[3,4-b]pyridin-2-yl}-4-fluorophenyl)-3-fluoroazetidine-1-carboxamide |
| 231 | 3-fluoro-N-{4-fluoro-3-(5-{6-oxa-1-azaspiro[3.3]heptan-1-yl}-2H-pyrazolo[3,4-b]pyridin-2-yl)phenyl}azetidine-1-carboxamide |
| 232 | 3-fluoro-N-(4-fluoro-3-{5-[3-(methoxymethyl)azetidin-1-yl]-2H-pyrazolo[3,4-b]pyridin-2-yl}phenyl)azetidine-1-carboxamide |
| 233 | N-[3-(5-{5-azaspiro[2.3]hexan-5-yl}-2H-pyrazolo[3,4-b]pyridin-2-yl)-4-fluorophenyl]-3-fluoroazetidine-1-carboxamide |
| 234 | N-(3-{5-[(3R,4R)-3,4-difluoropyrrolidin-1-yl]-2H-pyrazolo[3,4-b]pyridin-2-yl}-4-fluorophenyl)-3-fluoroazetidine-1-carboxamide |
| 235 | 3-fluoro-N-[4-fluoro-3-(5-{3-oxa-8-azabicyclo[3.2.1]octan-8-yl}-2H-pyrazolo[3,4-b]pyridin-2-yl)phenyl]azetidine-1-carboxamide |
| 236 | 1-(2-{2-fluoro-5-[(3-fluoroazetidine-1-carbonyl)amino]phenyl}-2H-pyrazolo[3,4-b]pyridin-5-yl)piperidine-4-carboxylic acid |
| 237 | 3-fluoro-N-(4-fluoro-3-{5-[4-(2,2,2-trifluoroethyl)piperazin-1-yl]-2H-pyrazolo[3,4-b]pyridin-2-yl}phenyl)azetidine-1-carboxamide |
| 238 | 3-fluoro-N-(4-fluoro-3-{5-[4-(oxetan-3-yl)piperidin-1-yl]-2H-pyrazolo[3,4-b]pyridin-2-yl}phenyl)azetidine-1-carboxamide |
| 239 | 3-fluoro-N-[4-fluoro-3-(5-{2-thia-6-azaspiro[3.3]heptan-6-yl}-2H-pyrazolo[3,4-b]pyridin-2-yl)phenyl]azetidine-1-carboxamide |
| 240 | 3-fluoro-N-[4-fluoro-3-(5-{6-oxa-3-azabicyclo[3.1.1]heptan-3-yl}-2H-pyrazolo[3,4-b]pyridin-2-yl)phenyl]azetidine-1-carboxamide |
| 241 | N-[3-(5-{5-azaspiro[2.4]heptan-5-yl}-2H-pyrazolo[3,4-b]pyridin-2-yl)-4-fluorophenyl]-3-fluoroazetidine-1-carboxamide |
| 242 | N-[3-(5-{5-azaspiro[2.4]heptan-5-yl}-2H-pyrazolo[3,4-b]pyridin-2-yl)-4-fluorophenyl]-5-azaspiro[2.4]heptane-5-carboxamide |
| 243 | N-[3-(5-{2-azaspiro[3.3]heptan-2-yl}-2H-pyrazolo[3,4-b]pyridin-2-yl)-4-fluorophenyl]-3-fluoroazetidine-1-carboxamide |
| 244 | 3-fluoro-N-[4-fluoro-3-(5-{8-oxa-2-azaspiro[4.5]decan-2-yl}-2H-pyrazolo[3,4-b]pyridin-2-yl)phenyl]azetidine-1-carboxamide |
| 245 | 3-fluoro-N-[4-fluoro-3-(5-{6-oxo-2,5-diazaspiro[3.4]octan-2-yl}-2H-pyrazolo[3,4-b]pyridin-2-yl)phenyl]azetidine-1-carboxamide |
| 246 | N-[4-fluoro-3-(5-{6-oxa-2-azaspiro[3.4]octan-2-yl}-2H-pyrazolo[3,4-b]pyridin-2-yl)phenyl]-6-oxa-2-azaspiro[3.4]octane-2-carboxamide |
| 247 | tert-butyl 2-(2-{5-[(azetidine-1-carbonyl)amino]-2-fluorophenyl}-2H-pyrazolo[3,4-b]pyridin-5-yl)pyrrolidine-1-carboxylate |
| 248 | 3-fluoro-N-[4-fluoro-3-(5-{2-oxa-7-azaspiro[3.5]nonan-7-yl}-2H-pyrazolo[3,4-b]pyridin-2-yl)phenyl]azetidine-1-carboxamide |
| 249 | N-{3-[5-(cyclopropylamino)-2H-pyrazolo[3,4-b]pyridin-2-yl]-4-fluorophenyl}-3-fluoroazetidine-1-carboxamide |
| 250 | N-(4-fluoro-3-{5-[4-(2,2,2-trifluoroethyl)piperazin-1-yl]-2H-pyrazolo[3,4-b]pyridin-2-yl}phenyl)azetidine-1-carboxamide |
| 251 | 3-fluoro-N-{4-fluoro-3-[5-(3-hydroxy-3-methylazetidin-1-yl)-2H-pyrazolo[3,4-b]pyridin-2-yl]phenyl}azetidine-1-carboxamide |
| 252 | 3,3-difluoro-N-(4-fluoro-3-{5-[4-(2,2,2-trifluoroethyl)piperazin-1-yl]-2H-pyrazolo[3,4-b]pyridin-2-yl}phenyl)azetidine-1-carboxamide |
| 253 | (3R)-3-fluoro-N-(4-fluoro-3-{5-[4-(2,2,2-trifluoroethyl)piperazin-1-yl]-2H-pyrazolo[3,4-b]pyridin-2-yl}phenyl)pyrrolidine-1-carboxamide |
| 254 | N-(3-{5-bromo-2H-pyrazolo[3,4-b]pyridin-2-yl}-4-fluorophenyl)-5-azaspiro[2.3]hexane-5-carboxamide |
| 255 | N-{3-[5-(3,3-dimethylazetidin-1-yl)-2H-pyrazolo[3,4-b]pyridin-2-yl]-4-fluorophenyl}-3-fluoroazetidine-1-carboxamide |
| 256 | (1S,2R)-2-fluoro-N-{4-fluoro-3-[5-(pyridin-2-yl)-2H-pyrazolo[3,4-b]pyridin-2-yl]phenyl}cyclopropane-1-carboxamide |
| 257 | N-[3-(5-{5-azaspiro[2.3]hexan-5-yl}-2H-pyrazolo[3,4-b]pyridin-2-yl)-4-fluorophenyl}azetidine-1-carboxamide |
| 258 | N-[3-(5-{5-azaspiro[2.3]hexan-5-yl}-2H-pyrazolo[3,4-b]pyridin-2-yl)-4-fluorophenyl]-3,3-difluoroazetidine-1-carboxamide |
| 259 | (3R)-N-[3-(5-{5-azaspiro[2.3]hexan-5-yl}-2H-pyrazolo[3,4-b]pyridin-2-yl)-4-fluorophenyl]-3-fluoropyrrolidine-1-carboxamide |
| 260 | N-{3-[5-(dimethylamino)-2H-pyrazolo[3,4-b]pyridin-2-yl]-4-fluorophenyl}-5-azaspiro[2.3]hexane-5-carboxamide |
| 261 | N-[3-(5-{1,1-difluoro-5-azaspiro[2.3]hexan-5-yl}-2H-pyrazolo[3,4-b]pyridin-2-yl)-4-fluorophenyl]-3-fluoroazetidine-1-carboxamide |
| 262 | N-{3-[5-(3,3-difluoropyrrolidin-1-yl)-2H-pyrazolo[3,4-b]pyridin-2-yl]-4-fluorophenyl}-3-fluoroazetidine-1-carboxamide |
| 263 | 3-fluoro-N-[4-fluoro-3-(5-{3-oxa-6-azabicyclo[3.1.1]heptan-6-yl}-2H-pyrazolo[3,4-b]pyridin-2-yl)phenyl]azetidine-1-carboxamide |
| 264 | N-{3-[5-(azetidin-2-yl)-2H-pyrazolo[3,4-b]pyridin-2-yl]-4-fluorophenyl}-3-fluoroazetidine-1-carboxamide |
| 265 | 3-fluoro-N-(4-fluoro-3-{5-[3-(trifluoromethyl)azetidin-1-yl]-2H-pyrazolo[3,4-b]pyridin-2-yl}phenyl)azetidine-1-carboxamide |
| 266 | N-{3-[5-(3-cyanoazetidin-1-yl)-2H-pyrazolo[3,4-b]pyridin-2-yl]-4-fluorophenyl}-3-fluoroazetidine-1-carboxamide |
| 267 | N-{3-[5-(1-acetylazetidin-2-yl)-2H-pyrazolo[3,4-b]pyridin-2-yl]-4-fluorophenyl}-3-fluoroazetidine-1-carboxamide |

TABLE 1-continued

| | |
|---|---|
| 268 | (1S,2R)-N-{3-[5-(3,3-difluoroazetidin-1-yl)-2H-pyrazolo[3,4-b]pyridin-2-yl]-4-fluorophenyl}-2-fluorocyclopropane-1-carboxamide |
| 269 | (1R,2S)-2-fluoro-N-{4-fluoro-3-[5-(pyridin-2-yl)-2H-pyrazolo[3,4-b]pyridin-2-yl]phenyl}cyclopropane-1-carboxamide |
| 270 | 3-fluoro-N-{4-fluoro-3-[5-(piperazin-1-yl)-2H-pyrazolo[3,4-b]pyridin-2-yl]phenyl}azetidine-1-carboxamide |
| 271 | (1R,2S)-N-{3-[5-(3,3-difluoroazetidin-1-yl)-2H-pyrazolo[3,4-b]pyridin-2-yl]-4-fluorophenyl}-2-fluorocyclopropane-1-carboxamide |
| 272 | (1R,2S)-N-{3-(5-{5-azaspiro[2.3]hexan-5-yl}-2H-pyrazolo[3,4-b]pyridin-2-yl]-4-fluorophenyl}-2-fluorocyclopropane-1-carboxamide |
| 273 | (1S,2R)-2-fluoro-N-{4-fluoro-3-[5-(pyridin-2-yl)-2H-pyrazolo[3,4-b]pyridin-2-yl]phenyl}cyclopropane-1-carboxamide |
| 274 | N-(4-fluoro-3-{5-[3-(trifluoromethypazetidin-1-yl]-2H-pyrazolo[3,4-b]pyridin-2-yl}phenyl)azetidine-1-carboxamide |
| 275 | (3R)-3-fluoro-N-(4-fluoro-3-{5-[3-(trifluoromethypazetidin-1-yl]-2H-pyrazolo[3,4-b]pyridin-2-yl}phenyl)pyrrolidine-1-carboxamide |
| 276 | N-(3-{5-chloro-2H-pyrazolo[3,4-b]pyridin-2-yl}-4-fluorophenyl)-3-fluoroazetidine-1-carboxamide |
| 277 | N-{4-fluoro-3-[5-(3-methylpyridin-2-yl)-2H-pyrazolo[3,4-b]pyridin-2-yl]phenyl}-4-(hydroxymethyl)-2-methyl-1,3-oxazole-5-carboxamide |
| 278 | N-{4-fluoro-3-[5-(3-methylpyridin-2-yl)-2H-pyrazolo[3,4-b]pyridin-2-yl]phenyl}-2-($^2$H$_3$)methyl-4-methyl-1,3-oxazole-5-carboxamide |
| 279 | N-(4-fluoro-3-{5-[3-(trifluoromethypazetidin-1-yl]-2H-pyrazolo[3,4-b]pyridin-2-yl}phenyl)-2,4-dimethyl-1,3-oxazole-5-carboxamide |
| 280 | N-{2-[5-(3,3-difluoroazetidin-1-yl)-2H-pyrazolo[3,4-b]pyridin-2-yl]pyridin-4-yl}azetidine-1-carboxamide |
| 281 | 3,3-difluoro-N-{2-[5-(pyridin-2-yl)-2H-pyrazolo[3,4-b]pyridin-2-yl]pyridin-4-yl}azetidine-1-carboxamide |
| 282 | N-[2-(5-{5-azaspiro[2.3]hexan-5-yl}-2H-pyrazolo[3,4-b]pyridin-2-yl)pyridin-4-yl]azetidine-1-carboxamide |
| 283 | N-{4-chloro-3-[5-(pyridin-2-yl)-2H-pyrazolo[3,4-b]pyridin-2-yl]phenyl}-3-fluoroazetidine-1-carboxamide |
| 284 | N-{4-chloro-3-[5-(3,3-difluoroazetidin-1-yl)-2H-pyrazolo[3,4-b]pyridin-2-yl]phenyl}azetidine-1-carboxamide |
| 285 | N-{4-chloro-3-[5-(pyridin-2-yl)-2H-pyrazolo[3,4-b]pyridin-2-yl]phenyl}azetidine-1-carboxamide |
| 286 | N-[3-(5-{5-azaspiro[2.3]hexan-5-yl}-2H-pyrazolo[3,4-b]pyridin-2-yl)-4-chlorophenyl]azetidine-1-carboxamide |
| 287 | N-[3-(5-{5-azaspiro[2.3]hexan-5-yl}-2H-pyrazolo[3,4-b]pyridin-2-yl)phenyl]azetidine-1-carboxamide |
| 288 | N-{4-fluoro-3-[5-(oxan-2-yl)-2H-pyrazolo[3,4-b]pyridin-2-yl]phenyl}azetidine-1-carboxamide |
| 289 | N-{3-[5-(1,4-dioxan-2-yl)-2H-pyrazolo[3,4-b]pyridin-2-yl]-4-fluorophenyl}azetidine-1-carboxamide |
| 290 | N-{3-[5-(3,3-difluoroazetidin-1-yl)-2H-pyrazolo[3,4-b]pyridin-2-yl]-4-fluorophenyl)azetidine-1-carboxamide |
| 291 | 3-fluoro-N-{4-fluoro-3-[5-(3-fluoroazetidin-1-yl)-2H-pyrazolo[3,4-b]pyridin-2-yl]phenyl}azetidine-1-carboxamide |
| 292 | N-{4-fluoro-3-[5-(3-fluoroazetidin-1-yl)-2H-pyrazolo[3,4-b]pyridin-2-yl]phenyl}azetidine-1-carboxamide |
| 293 | 3-fluoro-N-{4-fluoro-3-[5-(piperidin-4-yl)-2H-pyrazolo[3,4-b]pyridin-2-yl]phenyl}azetidine-1-carboxamide |
| 294 | 3-fluoro-N-{4-fluoro-3-[5-(pyrazin-2-yl)-2H-pyrazolo[3,4-b]pyridin-2-yl]phenyl}azetidine-1-carboxamide |
| 295 | 3-fluoro-N-{4-fluoro-3-[5-(1H-imidazol-4-yl)-2H-pyrazolo[3,4-b]pyridin-2-yl]phenyl}azetidine-1-carboxamide |
| 296 | N-{3-[5-(1-benzylpiperidin-4-yl)-2H-pyrazolo[3,4-b]pyridin-2-yl]-4-fluorophenyl}-3-fluoroazetidine-1-carboxamide |
| 297 | 3-fluoro-N-{4-fluoro-3-[5-(1H-pyrazol-4-yl)-2H-pyrazolo[3,4-b]pyridin-2-yl]phenyl}azetidine-1-carboxamide |
| 298 | N-{3-[5-(3,3-difluoroazetidin-1-yl)-2H-pyrazolo[3,4-b]pyridin-2-yl]-4-fluorophenyl}-3-fluoroazetidine-1-carboxamide |
| 299 | N-{3-[5-(3,3-difluoroazetidin-1-yl)-2H-pyrazolo[3,4-b]pyridin-2-yl]-4-fluorophenyl}-3,3-difluoroazetidine-1-carboxamide |
| 300 | (3R)-N-{3-[5-(3,3-difluoroazetidin-1-yl)-2H-pyrazolo[3,4-b]pyridin-2-yl]-4-fluorophenyl}-3-fluoropyrrolidine-1-carboxamide |
| 301 | 3-fluoro-N-{4-fluoro-3-[5-(1-methyl-1H-imidazol-4-yl)-2H-pyrazolo[3,4-b]pyridin-2-yl]phenyl}azetidine-1-carboxamide |
| 302 | (3R)-3-fluoro-N-{4-fluoro-3-[5-(3-fluoroazetidin-1-yl)-2H-pyrazolo[3,4-b]pyridin-2-yl]phenyl}pyrrolidine-1-carboxamide |
| 303 | 3,3-difluoro-N-{4-fluoro-3-[5-(3-fluoroazetidin-1-yl)-2H-pyrazolo[3,4-b]pyridin-2-yl]phenyl}azetidine-1-carboxamide |
| 304 | 3-fluoro-N-{4-fluoro-3-[5-(1-methyl-1H-pyrazol-4-yl)-2H-pyrazolo[3,4-b]pyridin-2-yl]phenyl}azetidine-1-carboxamide |
| 305 | 3-fluoro-N-[4-fluoro-3-(5-{1-[(4-fluorophenyl)methyl]piperidin-4-yl}-2H-pyrazolo[3,4-b]pyridin-2-yl)phenyl]azetidine-1-carboxamide |
| 306 | N-(3-{5-[bis($^2$H$_3$)methylamino]-2H-pyrazolo[3,4-b]pyridin-2-yl}-4-fluorophenyl)azetidine-1-carboxamide |
| 307 | N-(3-{5-[bis($^2$H$_3$)methylamino]-2H-pyrazolo[3,4-b]pyridin-2-yl}-4-fluorophenyl)-3,3-difluoroazetidine-1-carboxamide |

TABLE 1-continued

| | |
|---|---|
| 308 | (3R)-N-(3-{5-[bis(²H₃)methylamino]-2H-pyrazolo[3,4-b]pyridin-2-yl}-4-fluorophenyl)-3-fluoropyrrolidine-1-carboxamide |
| 309 | 3,3-difluoro-N-{4-fluoro-3-[5-(3-fluoropyridin-2-yl)-2H-pyrazolo[3,4-b]pyridin-2-yl]phenyl}azetidine-1-carboxamide |
| 310 | N-{3-[5-(3-chloropyridin-2-yl)-2H-pyrazolo[3,4-b]pyridin-2-yl]-4-fluorophenyl}-3,3-difluoroazetidine-1-carboxamide |
| 311 | 3-fluoro-N-(4-fluoro-3-{2H-pyrazolo[3,4-b]pyridin-2-yl}phenyl)azetidine-1-carboxamide |
| 312 | 3-fluoro-N-{4-fluoro-3-[5-(3-methylpyrazin-2-yl)-2H-pyrazolo[3,4-b]pyridin-2-yl]phenyl}azetidine-1-carboxamide |
| 313 | N-{4-fluoro-3-[5-(3-fluoropyridin-2-yl)-2H-pyrazolo[3,4-b]pyridin-2-yl]phenyl}azetidine-1-carboxamide |
| 314 | N-(3-[5-[bis(²H₃)methylamino]-2H-pyrazolo[3,4-b]pyridin-2-yl}-4-fluorophenyl)-3-fluoroazetidine-1-carboxamide |
| 315 | N-{3-[5-(3-chloropyridin-2-yl)-2H-pyrazolo[3,4-b]pyridin-2-yl]-4-fluorophenyl}azetidine-1-carboxamide |
| 316 | (3R)-N-{3-[5-(3-chloropyridin-2-yl)-2H-pyrazolo[3,4-b]pyridin-2-yl]-4-fluorophenyl}-3-fluoropyrrolidine-1-carboxamide |
| 317 | (3R)-3-fluoro-N-{4-fluoro-3-[5-(3-fluoropyridin-2-yl)-2H-pyrazolo[3,4-b]pyridin-2-yl]phenyl}pyrrolidine-1-carboxamide |
| 318 | 3-fluoro-N-(4-fluoro-3-{5-methyl-2H-pyrazolo[3,4-b]pyridin-2-yl}phenyl)azetidine-1-carboxamide |
| 319 | 3-fluoro-N-{4-fluoro-3-[5-(1H-pyrazol-1-yl)-2H-pyrazolo[3,4-b]pyridin-2-yl]phenyl}azetidine-1-carboxamide |
| 320 | N-{4-fluoro-3-[5-(trifluoromethyl)-2H-pyrazolo[3,4-b]pyridin-2-yl]phenyl}azetidine-1-carboxamide |
| 321 | 3-fluoro-N-{4-fluoro-3-[5-(trifluoromethyl)-2H-pyrazolo[3,4-b]pyridin-2-yl]phenyl}azetidine-1-carboxamide |
| 322 | (3R)-3-fluoro-N-{4-fluoro-3-[5-(trifluoromethyl)-2H-pyrazolo[3,4-b]pyridin-2-yl]phenyl}pyrrolidine-1-carboxamide |
| 323 | 3-fluoro-N-{4-fluoro-3-[5-(1H-imidazol-1-yl)-2H-pyrazolo[3,4-b]pyridin-2-yl]phenyl}azetidine-1-carboxamide |
| 324 | 3,3-difluoro-N-{4-fluoro-3-[5-(trifluoromethyl)-2H-pyrazolo[3,4-b]pyridin-2-yl]phenyl}azetidine-1-carboxamide |
| 325 | N-{3-[5-(1-cyclopropyl-1H-pyrazol-4-yl)-2H-pyrazolo[3,4-b]pyridin-2-yl]-4-fluorophenyl}-3-fluoroazetidine-1-carboxamide |
| 326 | N-{3-[5-(3,3-difluoroazetidin-1-yl)-2H-pyrazolo[3,4-b]pyridin-2-yl]-4-fluorophenyl}cyclopropanecarboxamide |
| 327 | N-{4-fluoro-3-[5-(3-fluoroazetidin-1-yl)-2H-pyrazolo[3,4-b]pyridin-2-yl]phenyl}cyclopropanecarboxamide |
| 328 | 3-fluoro-N-{4-fluoro-3-[5-(4-methyl-1H-imidazol-1-yl)-2H-pyrazolo[3,4-b]pyridin-2-yl]phenyl}azetidine-1-carboxamide |
| 329 | 3-fluoro-N-{4-fluoro-3-[5-(5-fluoropyridin-2-yl)-2H-pyrazolo[3,4-b]pyridin-2-yl]phenyl}azetidine-1-carboxamide |
| 330 | N-{4-fluoro-3-[5-(5-fluoropyridin-2-yl)-2H-pyrazolo[3,4-b]pyridin-2-yl]phenyl}azetidine-1-carboxamide |
| 331 | N-{3-[5-(dimethylamino)-2H-pyrazolo[3,4-b]pyridin-2-yl]-4-fluorophenyl}cyclopropanecarboxamide |
| 332 | N-{4-fluoro-3-[5-(3-fluoropyridin-2-yl)-2H-pyrazolo[3,4-b]pyridin-2-yl]phenyl}cyclopropanecarboxamide |
| 333 | N-{3-[5-(3-chloropyridin-2-yl)-2H-pyrazolo[3,4-b]pyridin-2-yl]-4-fluorophenyl}cyclopropanecarboxamide |
| 334 | N-{4-fluoro-3-[5-(3-methylpyridin-2-yl)-2H-pyrazolo[3,4-b]pyridin-2-yl]phenyl}-2-(hydroxymethyl)-4-methyl-1,3-oxazole-5-carboxamide |
| 335 | N-(4-fluoro-3-{5-[3-(hydroxymethyhpyridin-2-yl]-2H-pyrazolo[3,4-b]pyridin-2-yl}phenyl)-2,4-dimethyl-1,3-oxazole-5-carboxamide |
| 336 | N-{4-fluoro-3-[5-(pyridin-2-yl)-2H-pyrazolo[3,4-b]pyridin-2-yl]phenyl}pyrrolidine-1-carboxamide |
| 337 | N-[3-(5-{5-azaspiro[2.3]hexan-5-yl}-2H-pyrazolo[3,4-b]pyridin-2-yl)-4-fluorophenyl]pyrrolidine-1-carboxamide |
| 338 | N-{3-[5-(3,3-difluoroazetidin-1-yl)-2H-pyrazolo[3,4-b]pyridin-2-yl]-4-fluorophenyl}pyrrolidine-1-carboxamide |
| 339 | (1R,2S)-N-{3-[5-(3,3-difluoroazetidin-1-yl)-2H-pyrazolo[3,4-b]pyridin-2-yl]-4-fluorophenyl}-2-fluorocyclopropane-1-carboxamide |
| 340 | (3R)-N-(2-{5-bromo-2H-pyrazolo[3,4-b]pyridin-2-yl}pyridin-4-yl)-3-fluoropyrrolidine-1-carboxamide |
| 341 | N-{2-[5-(pyridin-2-yl)-2H-pyrazolo[3,4-b]pyridin-2-yl]pyridin-4-yl}azetidine-1-carboxamide |
| 342 | 3-fluoro-N-{2-[5-(pyridin-2-yl)-2H-pyrazolo[3,4-b]pyridin-2-yl]pyridin-4-yl}azetidine-1-carboxamide |
| 343 | N-{3-[5-(3,3-difluoroazetidin-1-yl)-2H-pyrazolo[3,4-b]pyridin-2-yl]phenyl}azetidine-1-carboxamide |
| 344 | N-{3-[5-(pyridin-2-yl)-2H-pyrazolo[3,4-b]pyridin-2-yl]phenyl}azetidine-1-carboxamide |
| 345 | N-{4-fluoro-3-[5-(pyridin-2-yl)-2H-pyrazolo[3,4-b]pyridin-2-yl]phenyl}pyrazine-2-carboxamide |
| 346 | N-{4-fluoro-3-[5-(pyridin-2-yl)-2H-pyrazolo[3,4-b]pyridin-2-yl]phenyl}spiro[2.2]pentane-1-carboxamide |
| 347 | N-{4-fluoro-3-[5-(pyridin-2-yl)-2H-pyrazolo[3,4-b]pyridin-2-yl]phenyl}-3,3-dimethylcyclobut-1-ene-1-carboxamide |
| 348 | 1-cyano-N-{4-fluoro-3-[5-(pyridin-2-yl)-2H-pyrazolo[3,4-b]pyridin-2-yl]phenyl}cyclopropane-1-carboxamide |
| 349 | (1S,2S)-2-fluoro-N-{4-fluoro-3-[5-(pyridin-2-yl)-2H-pyrazolo[3,4-b]pyridin-2-yl]phenyl}cyclopropane-1-carboxamide |

TABLE 1-continued

| | |
|---|---|
| 350 | N-{4-fluoro-3-[5-(3-methylpyridin-2-yl)-2H-pyrazolo[3,4-b]pyridin-2-yl]phenyl}-3,3-dimethylcyclobut-1-ene-1-carboxamide |
| 351 | N-(4-fluoro-3-(5-isopropyl-2H-pyrazolo[3,4-b]pyridin-2-yl)phenyl)-2,4-dimethyloxazole-5-carboxamide |
| 352 | N-(4-fluoro-3-(5-phenyl-2H-pyrazolo[3,4-b]pyridin-2-yl)phenyl)-2,4-dimethyloxazole-5-carboxamide |
| 353 | 3,3-difluoro-N-(4-fluoro-3-(5-phenyl-2H-pyrazolo[3,4-b]pyridin-2-yl)phenyl)azetidine-1-carboxamide |

Embodiment 38

A compound according to any one of Embodiments 1-35, or a pharmaceutical composition according to Embodiment 36, for use in therapy.

Embodiment 39

A compound according to any one of Embodiments 1-35, or a pharmaceutical composition according to Embodiment 36, for use in the treatment of a disease selected from leishmaniasis, Chagas diseases and human African trypanosomiasis.

Embodiment 40

Use of a compound according to any one of Embodiments 1-35, or a pharmaceutical composition according to Embodiment 36, in the manufacture of a medicament for the treatment of a disease selected from leishmaniasis, Chagas diseases and human African trypanosomiasis.

Embodiment 41

A method of inhibiting growth and proliferation of a kinetoplastid parasite in a subject, comprising administering to a subject in need thereof, a therapeutically effective amount of a compound of Formula (I) or a pharmaceutically acceptable salt thereof, according to any one of Embodiments 1-35.

Embodiment 42

A method of treating a disorder or disease caused by a kinetoplastid parasite, comprising administering to a subject in need thereof a therapeutically effective amount of a compound of Formula (I) or a pharmaceutically acceptable salt thereof according to any one of Embodiments 1-35, and optionally in combination with a second agent; wherein the disease is selected from leishmaniasis, Chagas diseases and human African trypanosomiasis.

Embodiment 43

The method according to Embodiment 42, wherein said disease is leishmaniasis selected from visceral leishmaniasis and cutaneous leishmaniasis.

Embodiment 44

The method according to Embodiment 43, wherein said second agent selected from stibogluconate, meglumine antimoniate, amphotericin, miltefosine, and paromomycin.

Embodiment 45

The method according to Embodiment 42, wherein said disease is Chagas disease; and said second agent is selected from benznidazole, nifurtimox and amphotericin.

Embodiment 46

The method according to Embodiment 42, wherein said disease is human African trypanosomiasis; and said second agent is pentamidine, suramin, melarsoprol, eflornithine, and nifurtimox.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of Formula (I) or subformulae thereof, in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, glucepatate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds of Formula (I) or subformulae thereof, in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of Formula (I). The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$O, $^{14}$O, $^{15}$N, $^{18}$F $^{31}$P, $^{32}$P, $^{35}$S, $^{36}$Cl, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for to example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Pharmacology and Utility

In one aspect, the invention relates to small molecules compounds of Formula (I) that target the proteasome of kinetoplastid parasites and are useful as a therapy; particularly, for preventing and treating diseases and conditions that are caused by the infection of kinetoplastid parasites. The activity of a compound according to the present invention can be assessed by the in vitro and in vivo methods described in the Biological Assay section infra. It is understood that the assays illustrate the invention without in any way limiting the scope of the invention.

Thus, as a further aspect, the present invention provides for the use of a compound of Formula (I) or subformulae thereof, or a pharmaceutically acceptable salt thereof, or a stereoisomer thereof, as a therapy for a disease or condition that can benefit from inhibition of growth and proliferation of kinetoplastid parasites; and for the manufacture of a medicament, such as for the treatment of a disease caused by the growth and proliferation of a kinetoplastid parasite. In one embodiment, the disease being treated is selected from leishmaniasis, Chagas disease and Human African trypanosomiasis. In another embodiment, the disease being treated is Leishmaniasis caused by the parasite including, but is not limited to, *Leishmania donovani, Leishmania infantum, Leishmania braziliensis, Leishmania panamensis, Leishmania guayanensis, Leishmania amazonensis, Leishmania mexicana, Leishmania tropica, Leishmania major*. In one embodiment, the disease being treated is visceral leishmaniasis. In another embodiment, the disease being treated is cutaneous leishmaniasis. In another embodiment, the disease being treated is Chagas disease caused by *Trypanosoma cruzi*. In yet another embodiment, the disease being treated is human African trypanosomiasis caused by *Trypanosoma brucei, Trypanosoma brucei* gambiense or *Trypanosoma brucei* rhodesiense.

In accordance with the foregoing, the present invention further provides a method for preventing or treating leishmaniasis, Chagas disease or Human African trypanosomiasis in a subject in need of such treatment, comprising administering to said subject a therapeutically effective amount of a compound selected from Formula (I) or subformulae thereof, a pharmaceutically acceptable salt or stereoisomer thereof. The required dosage will vary depending on the mode of administration, the particular condition to be treated and the effect desired.

Pharmaceutical Compositions, Dosage and Administration

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Compounds of the invention can be administered in therapeutically effective amounts in combination with one or more therapeutic agents (pharmaceutical combinations). The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

Products provided as a combined preparation include a composition comprising the compound of Formula (I) or subformulae thereof, a pharmaceutically acceptable salt thereof, or a stereoisomer thereof, and the other therapeutic agent(s) together in the same pharmaceutical composition, or the compound of Formula (I) and the other therapeutic agent(s) in separate form, e.g. in the form of a kit. In one embodiment, the invention provides a pharmaceutical composition comprising a compound of Formula (I) or subformulae thereof, a pharmaceutically acceptable salt thereof, or a stereoisomer thereof, and another therapeutic agent(s). Optionally, the pharmaceutical composition may comprise a pharmaceutically acceptable carrier, as described above. In another embodiment, the invention provides a product comprising a compound of Formula (I) and at least one other therapeutic agent as a combined preparation for simultaneous, separate or sequential use in therapy.

In one embodiment, the invention provides a kit comprising two or more separate pharmaceutical compositions, at least one of which contains a compound of Formula (I) or subformulae thereof, a pharmaceutically acceptable salt thereof, or a stereoisomer thereof. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of Formula (I) for treating a disease or condition caused by the growth and proliferation of a kinetoplastid parasite, wherein the medicament is prepared for administration with another therapeutic agent. The invention also provides the use of another therapeutic agent for treating a disease or condition caused by the growth and proliferation of a kinetoplastid parasite, wherein the medicament is administered with a compound of Formula (I).

The invention also provides the use of a compound of Formula (I) for treating a disease or condition caused by the growth and proliferation of a kinetoplastid parasite, wherein the patient has previously (e.g. within 24 hours) been treated with another therapeutic agent. The invention also provides the use of another therapeutic agent for treating a disease or condition caused by the growth and proliferation of a kinetoplastid parasite, wherein the patient has previously (e.g. within 24 hours) been treated with a compound of Formula (I).

In one embodiment, for the treatment of Leishmaniasis, the other therapeutic agent is selected from tstibogluconate, meglumine antimoniate, Amphotericin, Miltefosine and paromomycin. In one embodiment, for the treatment of Chagas disease, the other therapeutic agent is selected from benznidazole, nifurtimox and/or Amphotericin. In another embodiment, for treatment of human African trypanosomiasis, the other therapeutic agent is selected from pentamidine, suramin, melarsoprol, eflornithine, and/or nifurtimox. Where the compounds of the invention are administered in conjunction with other therapies, dosages of the co-administered compounds will of course vary depending on the type of co-drug employed, on the specific drug employed, on the condition being treated and so forth.

Preparation of Compounds

The compounds of the present invention can be prepared in a number of ways known to one skilled in the art of organic synthesis in view of the methods, reaction schemes and examples provided herein. For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be substituted to provide a variety of derivatives and/or reaction conditions. In addition, many of the compounds prepared by the methods described below can be further modified in light of this disclosure using conventional chemistry well known to those skilled in the art. All methods described herein can be performed in any suitable order, unless otherwise indicated or otherwise clearly contradicted by context.

Compounds of Formula (I) can be prepared as generally illustrated in Schemes 1-3 below, wherein $R^1$, $R^2$, $R^3$, $R^4$ and n are as defined in the Summary of the Invention.

Compounds of Formula (I) can be prepared as generally illustrated in Schemes 1-3 below, wherein X is chloro, bromo or trifluoromethyl; and $R^1$, $R^2$, $R^3$, $R^4$ and n are as defined in the Summary of the Invention.

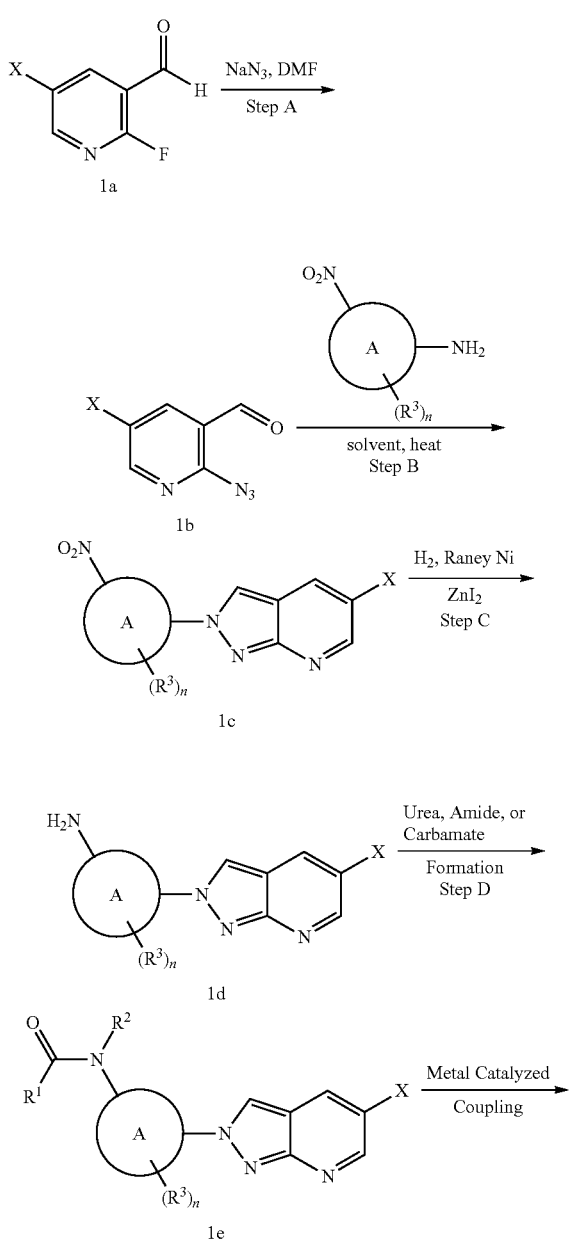

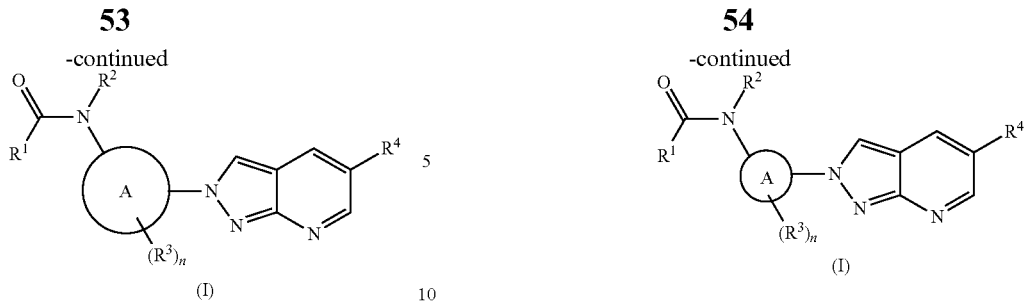

Alternatively, Formula (I) can be prepared from intermediate (1d) following the procedures in Scheme 2.

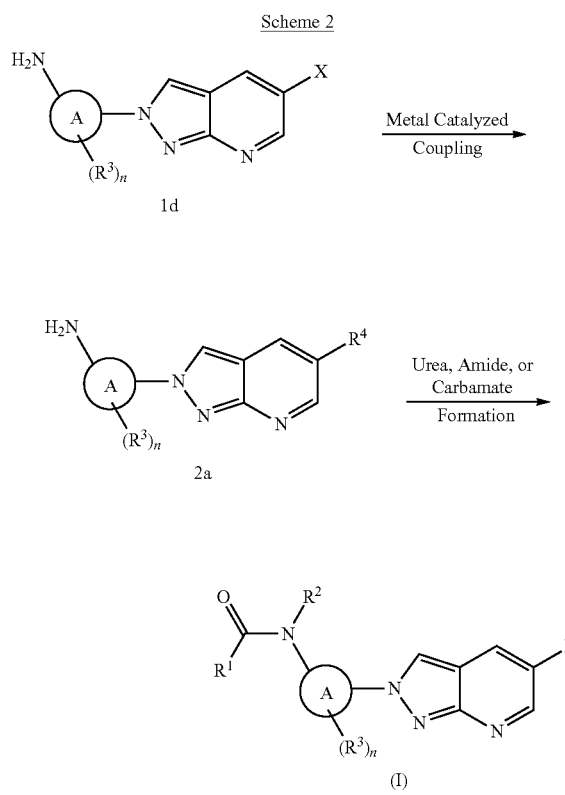

Alternatively, Formula (I) can be prepared from intermediate (1e) following the procedures in Scheme 3.

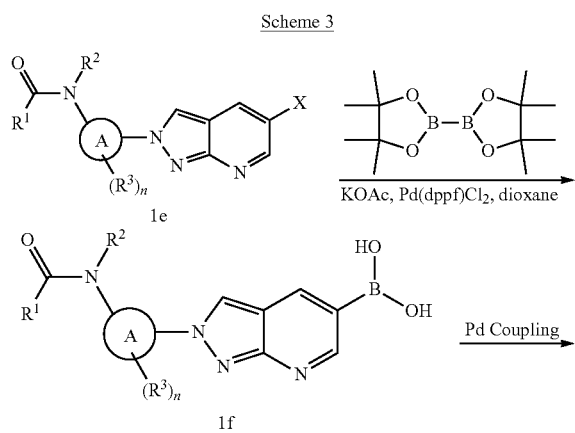

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

EXAMPLES

The Examples herein merely illuminate the invention and does not limit the scope of the invention otherwise claimed.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples. Where desired, conventional protecting groups are used to protect reactive functional groups in accordance with standard practice, for example, see T. W. Greene and P. G. M. Wuts in "Protecting Groups in Organic Synthesis", John Wiley and Sons, 1991.

Unless specified otherwise, the starting materials are generally available from non-excluding commercial sources such as Aldrich Chemicals (Milwaukee, Wis.), TCI Fine Chemicals (Japan), Shanghai Chemhere Co., Ltd. (Shanghai, China), Aurora Fine Chemicals LLC (San Diego, Calif.), FCH Group (Ukraine), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA), Rieke Metals (USA), Silicycle Inc (Canada) and Ukrorgsyntez Ltd (Latvia); or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, $2^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database).

Abbreviations

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" or "ml" for milliliter or milliliters, "µL" or "µl" for microliter or microliters, "N" for normal, "M" for molar, "µM" for micromolar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "aq" for aqueous, "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "1H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "r", "S", "s", "E", and "Z" are stereochemical designations familiar to one skilled in the art.

The following abbreviations used herein below have the corresponding meanings:
 AIBN azobisisobutyronitrile
 Bn benzyl
 Boc tert-butoxy carbonyl
 $Boc_2O$ di-tert-butyl dicarbonate
 Bu butyl
 $Cs_2CO_3$ cesium carbonate anhydrous
 $CHCl_3$ chloroform
 DAST diethylaminosulfurtrifluoride
 DBA dibenzylideneacetone
 DBU 2,3,4,6,7,8,9,10-octahydropyrimido[1,2-a]azepine
 DCM dichloromethane
 DIEA N,N-Diisopropylethylamine
 DMAP 4-dimethylaminopyridine
 DMF dimethylformamide
 DMSO dimethylsulfoxide
 DPP diphenylphosphine
 DPPA diphenylphosphoryl azide
 Dppf 1,1'-Bis(diphenylphosphino)ferrocene
 EA ethyl acetate
 Equiv. equivalence
 Et ethyl
 $Et_2O$ diethyl ether
 EtOH ethanol
 EtOAc ethyl acetate
 FA formic acid
 HATU 2-(7-Aza-1H-benzotriazole-1-yl)-1,1,3,3-tetramethyluronium hexafluorophosphate
 HCl hydrochloric acid
 i-Bu isobutyl
 i-Pr isopropyl
 KOAc potassium acetate
 $LiAlH_4$ lithium aluminium hydride
 Me methyl
 mCPBA 3-chloroperoxybenzoic acid
 MeCN acetonitrile
 $MnO_2$ manganese dioxide
 $N_2$ nitrogen
 $NaBH_4$ sodium borohydride
 $NaHCO_3$ sodium bicarbonate
 $Na_2SO_4$ sodium sulfate
 NBS N-Bromosuccinimide
 Ph phenyl
 $PPh_3$ triphenylphosphine
 $Ph_3P=O$ triphenylphosphine oxide
 $R_f$ retention factor
 RT room temperature (° C.)
 SFC supercritical fluid chromatography
 t-Bu or $Bu^t$ tert-butyl
 T3P® Propane phosphonic acid anhydride
 TEA triethylamine
 TFA trifluoroacetic acid
 THF tetrahydrofuran
 Troc 2,2,2-Trichloroethyl LCMS
Method 1:
Waters Acquity UPLC system:
 Acquity Binary Gradient Manager with Degasser
 Acquity Column Compartment set at 50° C.
 Acquity Diode Array Detector
Leap Technologies HTS Pal Autosampler
Antek Chemiluminescent Nitrogen Detector (CLND)
Waters 3100 Mass Spectrometer
HPLC Column: Thermo Syncronis C18 30×2.1 mm
Mobile Phase: (A) 95% H2O/5% MeOH/IPA (75/25, v/v)+0.05% formic acid, (B) MeOH/IPA (75/25, v/v)+0.035% formic acid
Gradient: 0.4 mL/minute, initial 2% B for 1.0 minutes, ramp to 95% B over 2.5 minutes, until 4.0 minutes, return to 2% B to at 4.25 minutes until end of run at 5.0.
MS Scan: 150 to 1000 amu in 1 second
Diode Array Detector: 190 nm-400 nm
Method 2:
Waters Acquity UPLC system:
 Acquity Binary Gradient Manager with Degasser
 Acquity Column Compartment set at 50° C.
 Acquity Diode Array Detector
 Acquity ELSD
Leap Technologies HTS Pal Autosampler
Waters Qda Mass Detector
HPLC Column: Waters Acquity C18 1.7 µm 2.1×30 mm
Mobile Phase: (A) H2O+0.05% TFA and (B) Acetonitrile+0.05% TFA
Gradient: 1 mL/minute, initial 5% B for 0.1 minutes, ramp to 95% B over 1.5 minutes, hold until 1.6 minutes then to 100% B at 1.7 and return to 5% B to at 1.9 minutes until end of run at 2.25.
MS Scan: 160 to 1000 amu in 0.4 seconds
Diode Array Detector: 214 nm-400 nm
NMR.
Proton spectra are recorded on a Bruker AVANCE II 400 MHz with 5 mm QNP Cryoprobe or a Bruker AVANCE III 500 MHz with 5 mm QNP probe unless otherwise noted. Chemical shifts are reported in ppm relative to dimethyl sulfoxide (b 2.50), chloroform (b 7.26), methanol (b 3.34), or dichloromethane (b 5.32). A small amount of the dry sample (2-5 mg) is dissolved in an appropriate deuterated solvent (1 mL).

Intermediate 1: 3-(5-bromo-2H-pyrazolo[3,4-b]pyridin-2-yl)-4-fluoroaniline (I-1)

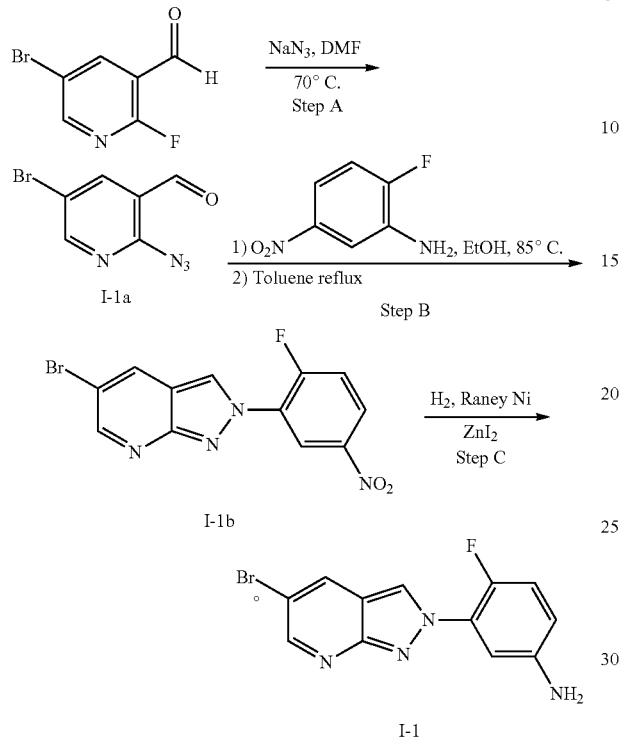

Step A:

The reaction mixture of NaN₃ (8 g, 122.5 mmol, 1 eq), 5-bromo-2-fluoro-pyridine-3-carbaldehyde (25 g, 122.5 mmol, 1 eq) in DMF (250 mL) was stirred at 70° C. for 1 hour. The reaction mixture was diluted with ethyl acetate (500 mL) and poured into ice-water (500 mL). The water layer was separated and extracted with ethyl acetate (500 mL*6). The combined organic layers were washed with brine (300 mL*3), dried over sodium sulfate and concentrated. The residue was triturated with Et₂O (100 mL) to give compound I-1a as a yellow solid. $^1$H NMR: (400 MHz, DMSO-d$_6$) δ ppm 10.26-10.46 (m, 1H), 10.12 (d, J=1.51 Hz, 1H), 8.64 (d, J=1.51 Hz, 1H). For safe handling of low molecular weight azides, several batches of this reaction were carried out and combined for use in Step B.

Step B:

The reaction mixture of 1-1a (30 g, 132.1 mmol, 1 eq) and 2-fluoro-5-nitro-aniline (20.6 g, 132.1 mmol, 1 eq) in EtOH (500 mL) was stirred at 85° C. for 4 hours under a N₂ atmosphere. The reaction mixture was concentrated in vacuo. Toluene (700 mL) was added to to the crude material and the reaction mixture was refluxed for 16 hr. The reaction mixture was concentrated and the material was purified by silica gel chromatography eluting with 0-50% EtOAc in DCM. The resulting material was triturated with EtOAc (100 mL) to give 1-1b as a yellow solid. $^1$H NMR: (400 MHz, DMSO-d6) δ ppm 9.04 (d, J=2.26 Hz, 1H), 8.85 (dd, J=6.53, 3.01 Hz, 1H), 8.79 (d, J=2.26 Hz, 1H), 8.60-8.71 (m, 1H), 8.47 (dt, J=9.03, 3.39 Hz, 1H), 7.92 (dd, J=10.54, 9.29 Hz, 1H).

Step C:

The reaction mixture of compound 1-1b (25 g, 74.2 mmol, 1 eq), diiodozinc (9.5 g, 29.7 mmol, 0.4 eq) and Raney-Ni (50 g, 583.6 mmol, 7.9 eq) in THF (500 mL) was stirred at 20° C. for 12 hour under 15 psi of H₂. The reaction mixture was diluted with MeOH (450 mL), filtered and the filter cake was washed with MeOH (200 mL*3). The filtrate was concentrated and triturated with water (500 mL) and dried in vacuo to give I-1 as a yellow solid. $^1$H NMR (400 MHz, DMSO-d6) δ ppm 8.81 (br d, J=1.51 Hz, 1H), 8.71 (br d, J=1.76 Hz, 1H), 8.58 (br d, J=1.76 Hz, 1H), 7.10-7.41 (m, 2H), 6.56-6.85 (m, 1H), 5.45 (br s, 2H).

Intermediate 2: 2,2,2-trichloroethyl (3-(5-bromo-2H-pyrazolo[3,4-b]pyridin-2-yl)-4-fluorophenyl) carbamate (I-2)

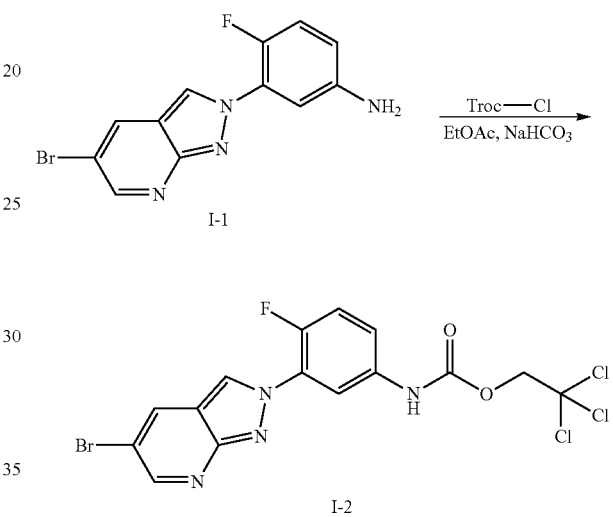

To a solution I-1 (5 g, 16.3 mmol, 1 eq) in EtOAc (150 mL) was added saturated aqueous NaHCO₃ (150 mL). The reaction mixture was cooled to 0° C. followed by dropwise addition of 2,2,2-trichloroethyl carbonochloridate (6.9 g, 32.6 mmol, 2 eq). The mixture was stirred at 00° C. for 2 hr and then stirred at 25° C. for 20 hr. The solid was collected by filtration and washed with water (150 mL) and ethyl acetate (20 mL) to give compound I-2 as a yellow solid. $^1$H NMR (400 MHz, DMSO-d$_6$), δ ppm, 10.57 (br s, 1H), 8.92 (d, J=2.51 Hz, 1H), 8.76 (d, J=2.26 Hz, 1H), 8.63 (d, J=2.51 Hz, 1H), 8.27 (br d, J=4.52 Hz, 1H), 7.62-7.67 (m, 1H), 7.55-7.61 (m, 1H), 4.99 (s, 2H).

Intermediate 3: N-(3-(5-bromo-2H-pyrazolo[3,4-b]pyridin-2-yl)-4-fluorophenyl)-3,3-difluoroazetidine-1-carboxamide (I-3) (also Compound 125)

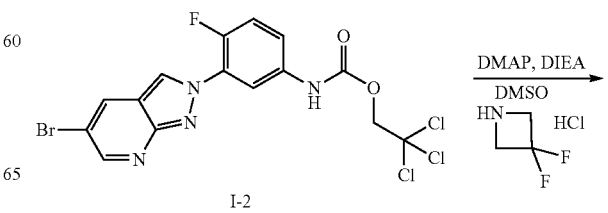

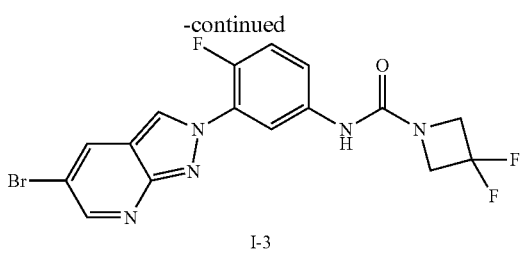

I-3

To a solution of I-2 (2 g, 4.14 mmol, 1 eq) and 3,3-difluoroazetidine HCl (1.1 g, 8.3 mmol, 2 eq) in DMSO (15 mL) was added DMAP (25.3 mg, 207 μmol, 0.05 eq) and DIEA (1.1 g, 8.3 mmol, 1.45 mL, 2 eq). The mixture was stirred at 60° C. for 15 hrs. The product was precipitated out by addition of 60 mL water and 10 mL ethyl acetate and collected by filtration. The filter cake was washed with 40 mL of water and 10 mL of ethyl acetate and the resulting solid was dried under reduced pressure to give a I-3 as a white solid. $^1$H NMR (400 MHz, DMSO-d$_6$), δ ppm, 9.25 (s, 1H), 8.91 (br s, 1H), 8.76 (br s, 1H), 8.63 (br s, 1H), 8.25 (br s, 1H), 7.69 (br s, 1H), 7.51 (br t, J=10.16 Hz, 1H), 4.41 (br t, J=12.67 Hz, 4H).

Intermediate 4: N-(3-(5-bromo-2H-pyrazolo[3,4-b]pyridin-2-yl)-4-fluorophenyl)-3-fluoroazetidine-1-carboxamide (I-4) (also Compound 126)

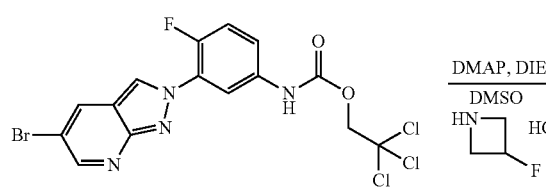

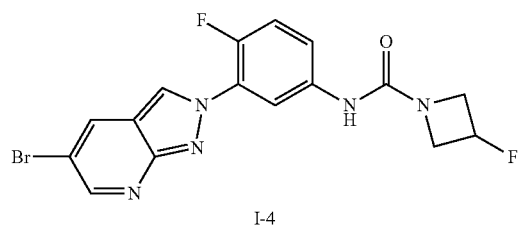

I-4

To a solution of I-2 (2 g, 4.14 mmol, 1 eq) and 3-fluoroazetidine HCl (924 mg, 8.28 mmol, 2 eq) in DMSO (15 mL) was added DMAP (25.3 mg, 207 μmol, 0.05 eq) and DIEA (1.07 g, 8.28 mmol, 1.45 mL, 2 eq). The mixture was stirred at 60° C. for 15 hrs. The product was precipitated out by addition of 60 mL water and 10 mL ethyl acetate and collected by filtration. The filter cake was washed with 40 mL of water and 10 mL of ethyl acetate and the resulting solid was dried under reduced pressure to give a I-4 as a solid. $^1$H NMR (400 MHz, DMSO-d$_6$), δ ppm, 8.98 (s, 1H), 8.90 (d, J=2.51 Hz, 1H), 8.76 (d, J=2.51 Hz, 1H), 8.63 (d, J=2.51 Hz, 1H), 8.24 (dd, J=7.03, 2.76 Hz, 1H), 7.67-7.74 (m, 1H), 7.49 (dd, J=11.17, 9.16 Hz, 1H), 5.29-5.51 (m, 1H), 4.25-4.39 (m, 2H), 3.96-4.10 (m, 2H).

Intermediate 5: (R)—N-(3-(5-bromo-2H-pyrazolo[3,4-b]pyridin-2-yl)-4-fluorophenyl)-3-fluoropyrrolidine-1-carboxamide (I-5) (also Compound 127)

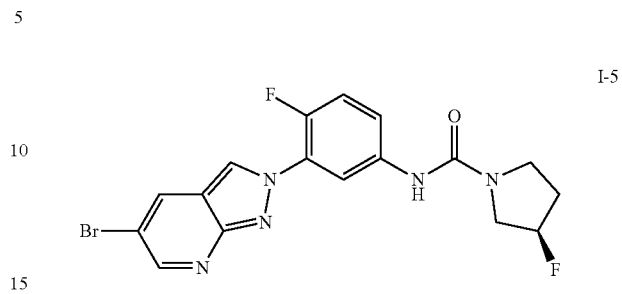

The intermediate I-5 was prepared in a similar manner as intermediate I-3 using (R)-3-fluoropyrrolidine HCl as a starting material. $^1$H NMR (400 MHz, DMSO-d$_6$), δ ppm, 8.90 (d, J=2.26 Hz, 1H), 8.76 (d, J=2.51 Hz, 1H), 8.66 (s, 1H), 8.63 (d, J=2.26 Hz, 1H), 8.27 (dd, J=7.03, 2.76 Hz, 1H), 7.71-7.77 (m, 1H), 7.48 (dd, J=11.17, 9.16 Hz, 1H), 5.28-5.48 (m, 1H), 3.40-3.78 (m, 4H), 2.01-2.27 (m, 2H).

Intermediate 6: N-(3-(5-bromo-2H-pyrazolo[3,4-b]pyridin-2-yl)-4-fluorophenyl)azetidine-1-carboxamide I-6 (also compound 129)

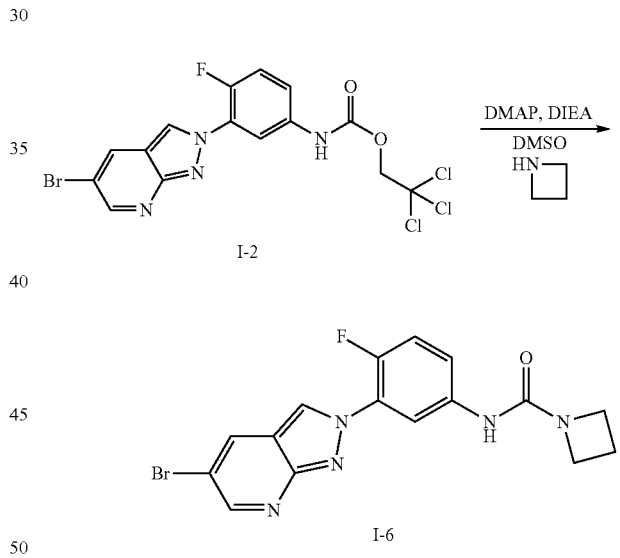

To a solution of I-2 (1.6 g, 3.32 mmol, 1 eq) and azetidine (379 mg, 6.63 mmol, 2 eq) in DMSO (15 mL) was added DMAP (20.3 mg, 166 μmol, 0.05 eq) and DIEA (857 mg, 6.63 mmol, 2 eq). The mixture was stirred at 60° C. for 15 hrs. The product was precipitated out by addition of 60 mL water and 10 mL ethyl acetate and collected by filtration. The filter cake was washed with 40 mL of water and 10 mL of ethyl acetate and the resulting solid was dried under reduced pressure. The resulting solid was triturated with 10 mL of ethyl acetate to give a I-6 as a yellow solid. $^1$H NMR (400 MHz, DMSO-d6), δ ppm, 8.89 (d, J=2.01 Hz, 1H), 8.70-8.80 (m, 2H), 8.62 (d, J=2.26 Hz, 1H), 8.25 (dd, J=6.90, 2.38 Hz, 1H), 7.72 (br d, J=9.03 Hz, 1H), 7.46 (br t, J=10.16 Hz, 1H), 3.98 (br t, J=7.53 Hz, 4H), 2.20 (quin, J=7.59 Hz, 2H).

Intermediate 7: N-(3-(5-bromo-2H-pyrazolo[3,4-b]pyridin-2-yl)-4-fluorophenyl)-2,4-dimethyloxazole-5-carboxamide (I-7) (also Compound 128)

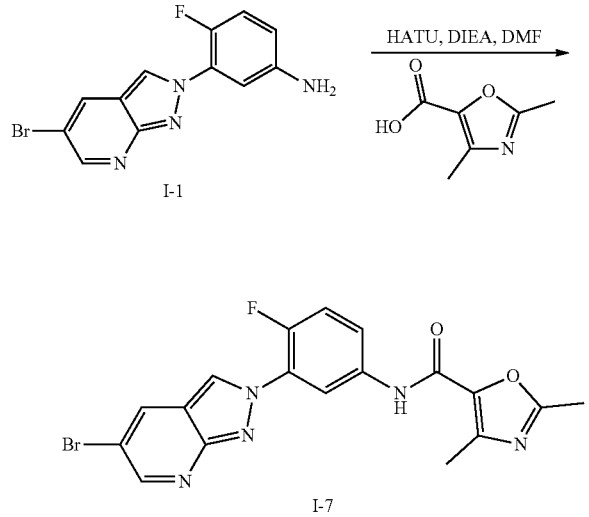

To a solution of I-1 (1 g, 3.3 mmol, 1 eq) and 2,4-dimethyloxazole-5-carboxylic acid (552.1 mg, 3.9 mmol, 1.2 eq) in DMF (15 mL) was added HATU (1.5 g, 3.9 mmol, 1.2 eq) and DIEA (632 mg, 4.9 mmol, 854 uL, 1.50 eq). The mixture was stirred at 25° C. for 13 hours. Saturated aqueous NaHCO₃ (40 mL) was added to the reaction mixture and the solid was collected by filtration. The filter cake was washed with water (30 mL) and ethyl acetate (10 mL). The resulting solid was triturated in water (20 mL) to give I-7 as a brown solid. ¹H NMR (400 MHz, DMSO-d₆), δ ppm, 10.53 (s, 1H), 8.94 (d, J=2.51 Hz, 1H), 8.77 (d, J=2.26 Hz, 1H), 8.64 (d, J=2.26 Hz, 1H), 8.58 (dd, J=7.15, 2.64 Hz, 1H), 7.89-7.97 (m, 1H), 7.59 (dd, J=11.17, 9.16 Hz, 1H), 2.52-2.53 (s, 3H), 2.40 (s, 3H).

Intermediate 8: N-(3-(5-bromo-2H-pyrazolo[3,4-b]pyridin-2-yl)-4-fluorophenyl)furan-2-carboxamide (I-8) (also Compound 130)

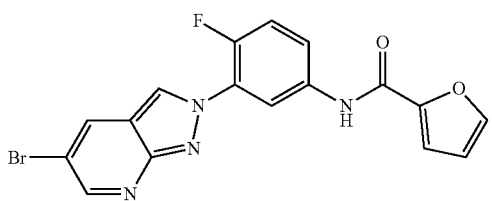

The intermediate I-8 was prepared in a similar manner as intermediate I-7 using furan-2-carboxylic acid as a starting material. ¹H NMR (400 MHz, DMSO-d₆), δ ppm, 10.58 (br s, 1H), 8.94 (d, J=2.26 Hz, 1H), 8.77 (d, J=2.26 Hz, 1H), 8.64 (d, J=2.26 Hz, 1H), 8.53 (dd, J=7.03, 2.51 Hz, 1H), 7.92-8.02 (m, 2H), 7.60 (dd, J=11.04, 9.29 Hz, 1H), 7.40 (d, J=3.26 Hz, 1H), 6.74 (dd, J=3.26, 1.51 Hz, 1H).

Intermediate 9: 4-fluoro-3-(5-isopropyl-2H-pyrazolo[3,4-b]pyridin-2-yl)aniline (I-9)

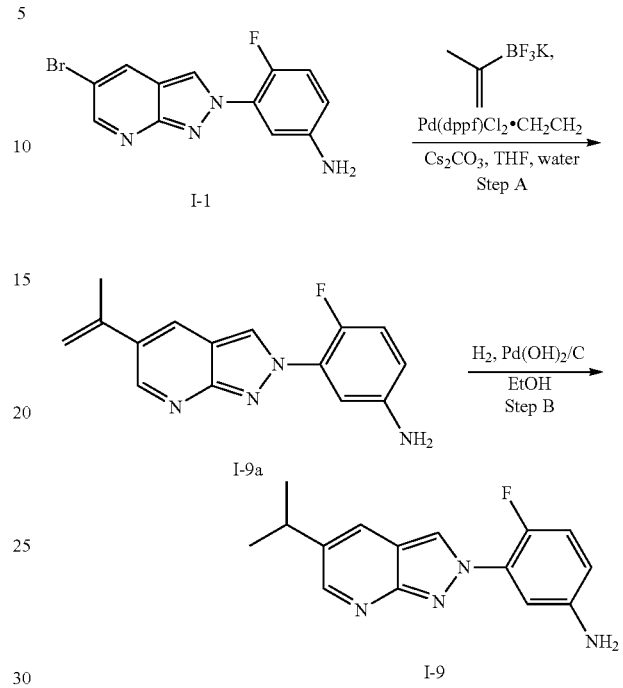

Step A:

To a solution of intermediate I-1 (4 g, 13.0 mmol, 1 eq) in THF (60 mL) and H₂O (9 mL) was added Cs₂CO₃ (12.7 g, 39.1 mmol, 3 eq), Pd(dppf)Cl₂.CH₂Cl₂ (531.8 mg, 651.2 μmol, 0.05 eq) and potassium trifluoro(prop-1-en-2-yl)borate (2.2 g, 14.7 mmol, 1.1 eq). The mixture was stirred at 80° C. for 16 hr. The reaction mixture was extracted with EtOAc (100 mL*2). The combined organic layers were washed with brine (100 mL), dried over Na₂SO₄, filtered and concentrated under reduced pressure to give a residue. The residue was purified by silica chromatography eluting with petroleum ether:EtOAc=1:2) to give compound I-9a as a white solid. ¹H NMR (400 MHz, DMSO-d₆) δ ppm 9.00 (d, J=2.26 Hz, 1H), 8.78 (d, J=2.38 Hz, 1H), 8.23 (d, J=2.26 Hz, 1H), 7.09-7.29 (m, 2H), 6.68 (dt, J=8.88, 3.34 Hz, 1H), 5.64 (s, 1H), 5.44 (s, 2H), 5.22 (s, 1H), 2.18 (s, 3H), M+H=269.1.

Step B:

To a solution of intermediate I-9a (3.4 g, 12.7 mmol, 1 eq) in EtOH (216 mL) was added 20% Pd(OH)₂/C (5.3 g, 7.60 mmol, 0.6 eq) and the mixture was stirred at 25° C. for 4 hr under a 15 psi H₂ atmosphere. The reaction mixture was filtered through celite and the filter cake was washed with ethanol (30 mL). The filtrate was concentrated, the resulting residue was dissolved in EtOAc (10 mL) and 4M HCl in EtOAc (2 mL) was added. The solid was collected by filtration and dried under vacuo to give the HCl salt of I-9 as a yellow solid. ¹H NMR (400 MHz, DMSO-d₆) δ ppm 9.10 (d, J=2.26 Hz, 1H), 8.90 (d, J=2.01 Hz, 1H), 8.47 (br d, J=1.63 Hz, 1H), 8.07 (br dd, J=6.46, 2.45 Hz, 1H), 7.72 (br dd, J=10.85, 9.10 Hz, 1H), 7.58 (dt, J=8.50, 3.28 Hz, 1H), 3.07-3.25 (m, 1H), 1.32 (d, J=6.78 Hz, 6H), M+H=271.1.

Intermediate 10: (2-(2-fluoro-5-(3-fluoroazetidine-1-carboxamido)phenyl)-2H-pyrazolo[3,4-b]pyridin-5-yl)boronic acid (I-10)

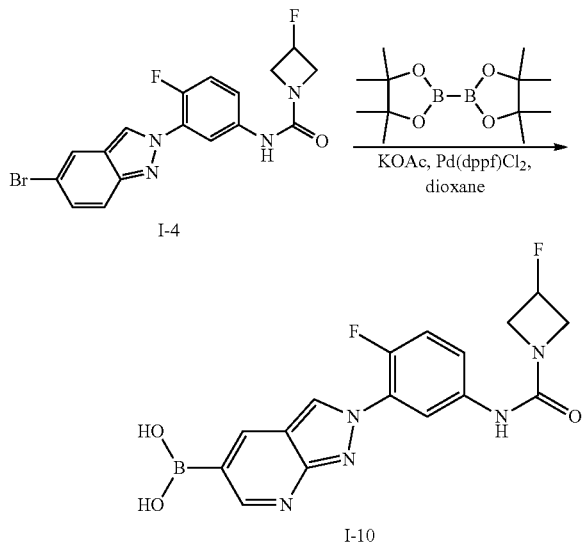

To a solution of intermediate I-4 (300 mg, 734.9 μmol, 1 eq) in dioxane (18 mL) was added 4,4,4',4',5,5,5',5'-octamethyl-2,2'-bi(1,3,2-dioxaborolane) (223.9 mg, 881.9 μmol, 1.2 eq), Pd(dppf)Cl$_2$ (53.8 mg, 73.5 μmol, 0.1 eq) and KOAc (144.3 mg, 1.5 mmol, 2 eq). The mixture was stirred at 100° C. for 16 hr. The reaction mixture was concentrated and the residue was washed with EtOAc (5 mL), water (5 mL), and dried under reduced pressure to give compound I-10 as a black solid. $^1$H NMR (400 MHz, DMSO-d$_6$) δ ppm 9.00 (br s, 2H), 8.70 (br s, 1H), 8.45 (br s, 1H), 8.24 (br s, 1H), 7.69 (br s, 1H), 7.56 (br s, 1H), 7.50 (br s, 1H), 6.59 (br s, 1H), 5.25-5.56 (m, 1H), 4.33 (br s, 2H), 3.90-4.13 (m, 2H), M+H=374.2.

Intermediate 11: 4-fluoro-3-(5-(pyridin-2-yl)-2H-pyrazolo[3,4-b]pyridin-2-yl)aniline I-11

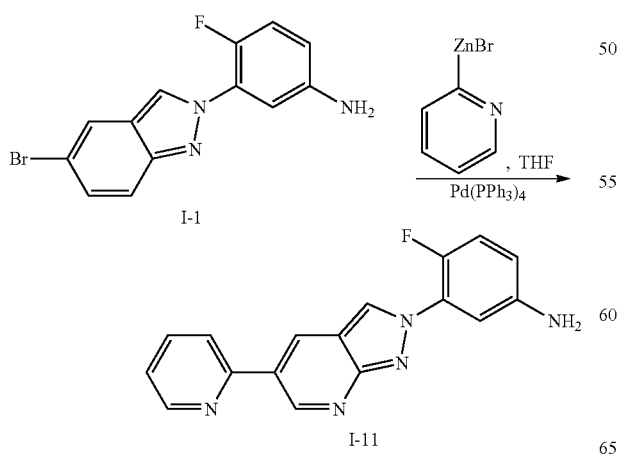

I-1 (947 mg, 3.1 mmol) and Pd(Ph3P)$_4$ (178 mg, 0.15 mmol) were combined in a flask and placed under a nitrogen atmosphere. Pyridin-2-ylzinc(II) bromide 0.5 M in THF (24.7 mL, 12.3 mmol) was added and the reaction was heated to 65° C. for 4 hrs. The reaction was quenched with water and concentrated. The crude material was purified by C18 flash chromatography eluting with 10-80% acetonitrile in water to give I-11 as a pale yellow solid. $^1$H NMR (400 MHz, DMSO-d6) δ 9.45 (d, J=2.3 Hz, 1H), 8.93 (dd, J=3.4, 2.4 Hz, 2H), 8.73 (ddd, J=4.8, 1.8, 0.9 Hz, 1H), 8.12 (dt, J=8.0, 1.0 Hz, 1H), 7.95 (td, J=7.7, 1.8 Hz, 1H), 7.46-7.40 (m, 1H), 7.26-7.16 (m, 2H), 6.69 (ddd, J=8.9, 3.9, 2.9 Hz, 1H), 5.46 (s, 2H).

Intermediate 12: 2-(5-amino-2-fluorophenyl)-N,N-dimethyl-2H-pyrazolo[3,4-b]pyridin-5-amine (I-12)

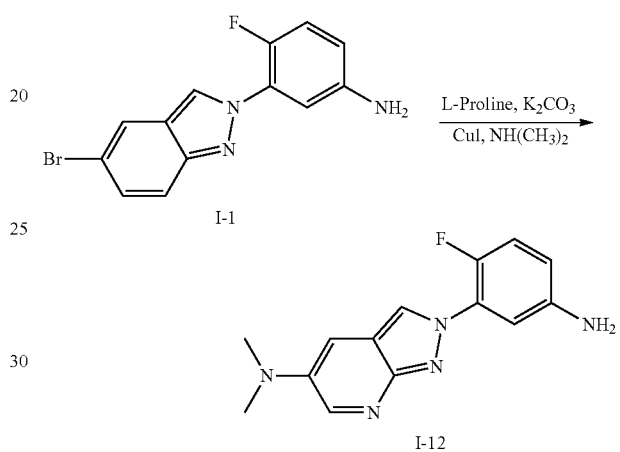

The reaction mixture of N-methylmethanamine (4.4 g, 98.7 mmol, 5 mL, 50.5 eq), I-1 (0.6 g, 1.9 mmol, 1 eq), L-proline (22.5 mg, 195.4 μmol, 0.1 eq), CuI (37.2 mg, 195.4 μmol, 0.1 eq) and K$_2$CO$_3$ (540 mg, 3.9 mmol, 2 eq) in DMSO (5 mL) was stirred at 90° C. for 12 hrs. The reaction was quenched with 10% aqueous NH$_4$OH (20 mL) and extracted with ethyl acetate (25 mL*4). The combined ethyl acetate layers were washed with brine (15 mL*3), dried over sodium sulfate and concentrated. The residue was purified by silica chromatography eluting with 20% ethyl acetate and 20% DCM in petroleum ether to give 1-12 as a yellow solid. $^1$H NMR: (400 MHz, DMSO-d$_6$) δ ppm 8.68 (br s, 1H), 8.48 (br s, 1H), 7.16 (br s, 3H), 6.63 (br s, 1H), 5.38 (br s, 2H), 2.95 (br s, 6H). M+H=391.1.

Intermediate 13: 2,2,2-trichloroethyl (3-(5-(dimethylamino)-2H-pyrazolo[3,4-b]pyridin-2-yl)-4-fluorophenyl)carbamate (I-13)

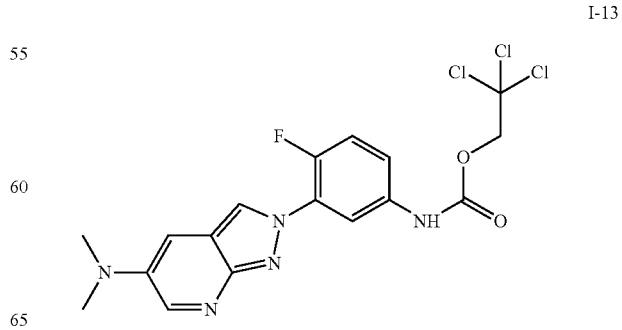

The synthesis of I-13 is described in Example 9.

Intermediate 14: (R)—N-(3-(5-(3,6-dihydro-2H-pyran-4-yl)-2H-pyrazolo[3,4-b]pyridin-2-yl)-4-fluorophenyl)-3-fluoropyrrolidine-1-carboxamide (I-14)

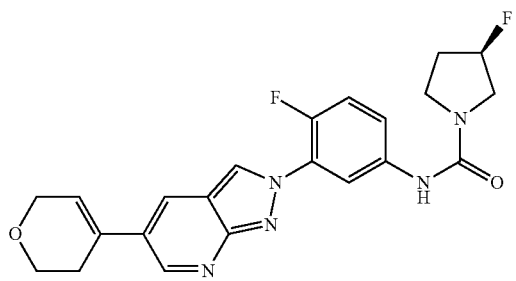

The synthesis of I-14 is described in Example 18.

Intermediate 15: N-(3-(5-bromo-2H-pyrazolo[3,4-b]pyridin-2-yl)-4-fluorophenyl)-5-azaspiro[2.3]hexane-5-carboxamide I-15 (also Compound 254)

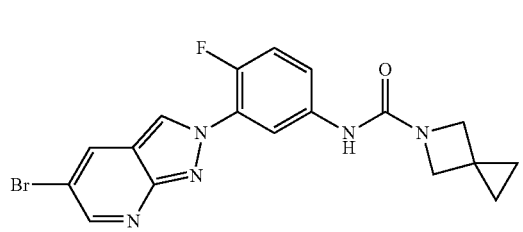

Intermediate I-15 (compound 254) was prepared in a similar manner as intermediate I-3 using 5-azaspiro[2.3]hexane hemioxalate as a starting material. $^1$H NMR (400 MHz, DMSO-d$_6$), δ ppm, 8.90 (d, J=2.45 Hz, 1H), 8.85 (s, 1H), 8.74-8.78 (m, 1H), 8.61-8.65 (m, 1H), 8.26 (dd, J=7.09, 2.69 Hz, 1H), 7.69-7.76 (m, 1H), 7.47 (dd, J=11.25, 9.29 Hz, 1H), 4.05 (s, 4H), 0.66 (s, 4H). Method 1: RT=2.95 min.; M+H=416.0, 418.0.

Intermediate 16: 3-(5-chloro-2H-pyrazolo[3,4-b]pyridin-2-yl)-4-fluoroaniline (I-16)

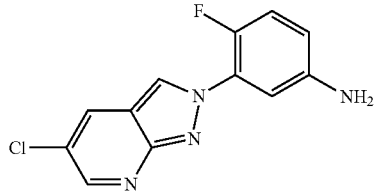

Intermediate I-16 was prepared in a similar manner as intermediate I-1 using 5-chloro-2-fluoronicotinaldehyde as the starting material. $^1$H NMR (400 MHz, DMSO-d$_6$) δ ppm 8.82 (d, J=2.26 Hz, 1H), 8.67 (d, J=2.51 Hz, 1H), 8.44 (d, J=2.51 Hz, 1H), 7.12-7.28 (m, 2H), 6.61-6.75 (m, 1H), 5.44 (br s, 2H).

Intermediate 17: 2-(5-bromo-2H-pyrazolo[3,4-b]pyridin-2-yl)pyridin-4-amine (I-17)

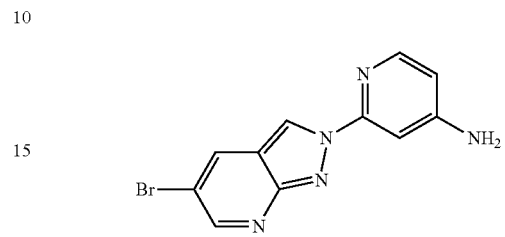

Intermediate I-17 was prepared in a similar manner as intermediate I-1 using 4-nitropyridin-2-amine as a starting material in Step B. $^1$H NMR (400 MHz, DMSO) δ ppm 9.19 (br s, 1H), 8.73 (br s, 1H), 8.59 (br s, 1H), 8.01 (br d, J=5.27 Hz, 1H), 7.42 (br s, 1H), 6.54-6.74 (m, 3H).

Intermediate 18: 3-(5-bromo-2H-pyrazolo[3,4-b]pyridin-2-yl)-4-chloroaniline (I-18)

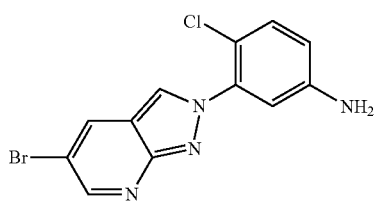

Intermediate I-18 was prepared in a similar manner as intermediate I-1 using 2-chloro-5-nitro-aniline as a starting material in Step B. M+H=325.0.

Intermediate 19: 3-(5-bromo-2H-pyrazolo[3,4-b]pyridin-2-yl)aniline (I-19)

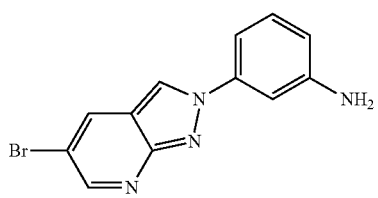

Intermediate I-19 was prepared in a similar manner as intermediate I-1 using 3-nitroaniline as a starting material in Step B. $^1$H NMR (400 MHz, DMSO-d$_6$) δ ppm 8.99 (s, 1H), 8.69 (d, J=2.44 Hz, 1H), 8.56 (d, J=2.45 Hz, 1H), 7.31 (t, J=2.08 Hz, 1H), 7.12-7.26 (m, 2H), 6.61-6.72 (m, 1H), 5.56 (br s, 2H).

Intermediate 20: 2,2,2-trichloroethyl (2-(5-bromo-2H-pyrazolo[3,4-b]pyridin-2-yl)pyridin-4-yl)carbamate (I-20)

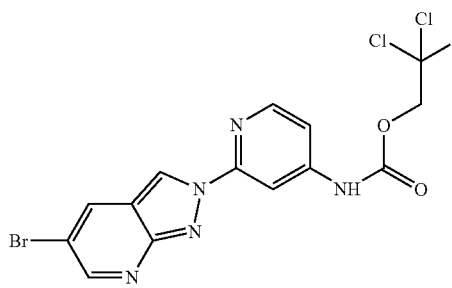

The synthesis of I-20 is described in Example 21.

Intermediate 21: 3-(2-(5-bromo-2H-pyrazolo[3,4-b]pyridin-2-yl)pyridin-4-yl)-1,1-dimethylurea (I-21)

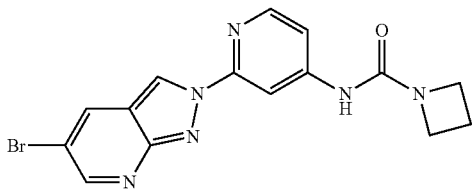

The synthesis of I-21 is described in Example 21.

Intermediate 22: N-(2-(5-bromo-2H-pyrazolo[3,4-b]pyridin-2-yl)pyridin-4-yl)-3,3-difluoroazetidine-1-carboxamide (I-22)

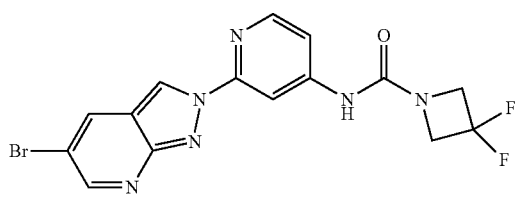

The synthesis of I-22 is described in Example 22.

Intermediate 23: 4-fluoro-3-(5-(trifluoromethyl)-2H-pyrazolo[3,4-b]pyridin-2-yl)aniline (I-23)

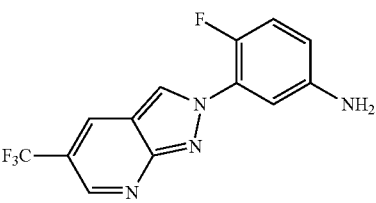

Intermediate I-23 was prepared in a similar manner as intermediate I-1 using 2-fluoro-5-(trifluoromethyl)nicotinaldehyde as a starting material. $^1$H NMR (400 MHz, DMSO), δ ppm, 9.06 (d, J=2.01 Hz, 1H), 8.98 (d, J=2.26 Hz, 1H), 8.85 (s, 1H), 7.16-7.30 (m, 2H), 6.72 (dt, J=8.91, 3.33 Hz, 1H), 5.48 (s, 2H).

Intermediate 24: N-(3-(5-bromo-2H-pyrazolo[3,4-b]pyridin-2-yl)-4-fluorophenyl)cyclopropanecarboxamide (I-24)

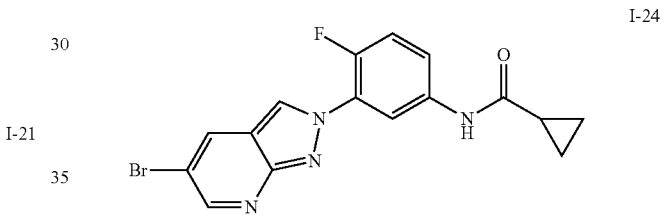

Intermediate I-24 was prepared in a similar manner as intermediate I-7 using cyclopropanecarboxylic acid as a starting material. $^1$H NMR (400 MHz, DMSO-d6) δ ppm 8.90 (d, J=2.38 Hz, 1H), 8.75 (d, J=2.38 Hz, 1H), 8.62 (d, J=2.38 Hz, 1H), 8.38 (dd, J=7.03, 2.51 Hz, 1H), 8.25-8.30 (m, 1H), 7.66-7.75 (m, 1H), 7.53 (dd, J=11.17, 9.16 Hz, 1H), 1.72-1.83 (m, 1H), 0.83 (d, J=6.15 Hz, 4H).

Intermediate 25: 3-(5-(1H-pyrazol-1-yl)-2H-pyrazolo[3,4-b]pyridin-2-yl)-4-fluoroaniline (I-25)

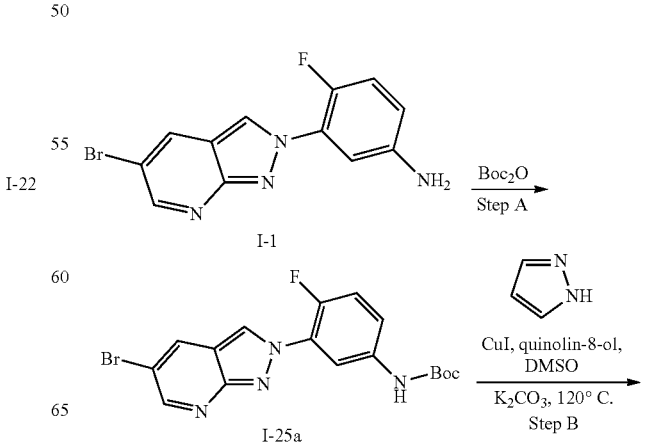

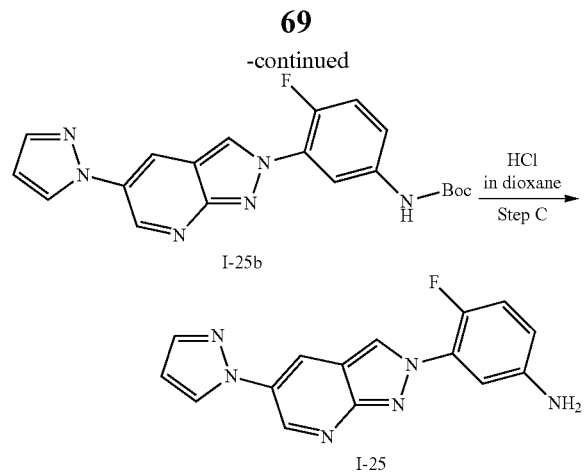

I-25b

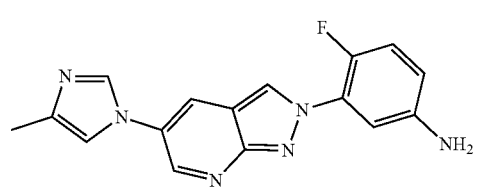

I-25

Step A:

The reaction mixture of I-1 (10 g, 32.6 mmol, 1 eq) and Boc₂O (21.3 g, 97.7 mmol, 22.4 mL, 3 eq) in THF (100 mL) was stirred at 76° C. for 12 hr. The reaction mixture was concentrated and the residue was triturated with petroleum ether (100 mL) to give I-25a as a brown solid. M+H=408.9.

Step B:

The reaction mixture of I-25a (0.5 g, 1.2 mmol, 1 eq), 1H-pyrazole (126 mg, 1.8 mmol, 1.5 eq), CuI (35 mg, 184.5 µmol, 0.15 eq), quinolin-8-ol (27 mg, 184.5 µmol, 31.9 uL, 0.15 eq) and K₂CO₃ (221 mg, 1.6 mmol, 1.3 eq) in DMSO (5 mL) was stirred at 120° C. for 12 hr. The reaction mixture was poured into water 20 mL, extracted with DCM (20 mL×3). The combined organic layers were washed with brine (10 mL), dried over Na₂SO₄ and concentrated to give I-25b as a black solid. M+H=395.3.

Step C:

The reaction mixture of I-25b (0.4 g, 1.0 mmol, 1 eq) in HCl/dioxane (10 mL) was stirred at 25° C. for 12 hr. The reaction mixture was concentrated and purified by prep-HPLC (Phenomenex Gemini 150*25 mm*10 um; mobile phase: [water (0.05% ammonia hydroxide v/v)-acetonitrile]; B %: 18%-48%, 12 min) to give 1-25 as a yellow solid. ¹H NMR (400 MHz, DMSO) δ ppm 9.28 (d, J=2.69 Hz, 1H), 8.90 (d, J=2.45 Hz, 1H), 8.61 (dd, J=10.64, 2.57 Hz, 2H), 7.84 (d, J=1.47 Hz, 1H), 7.14-7.31 (m, 2H), 6.66-6.75 (m, 1H), 6.57-6.65 (m, 1H), 5.45 (s, 2H).

Intermediate 26: 4-fluoro-3-(5-(4-methyl-1H-imidazol-1-yl)-2H-pyrazolo[3,4-b]pyridin-2-yl)aniline (I-26)

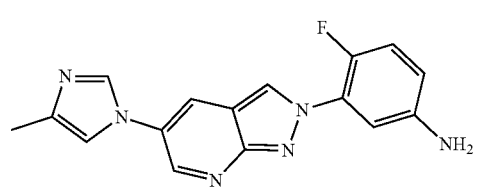

I-26

Intermediate I-26 was prepared in a similar manner as intermediate I-25 using 4-methyl-1H-imidazole as a starting material in Step B. ¹H NMR: (400 MHz, DMSO) δ ppm 9.00 (d, J=2.69 Hz, 1H), 8.89 (d, J=2.20 Hz, 1H), 8.37-8.49 (m, 1H), 8.20 (s, 1H), 7.53 (s, 1H), 7.13-7.30 (m, 3H), 6.61-6.80 (m, 1H), 5.45 (s, 2H), 2.21 (s, 3H).

Intermediate 27: N-(3-(5-bromo-2H-pyrazolo[3,4-b]pyridin-2-yl)-4-fluorophenyl)pyrrolidine-1-carboxamide (I-27)

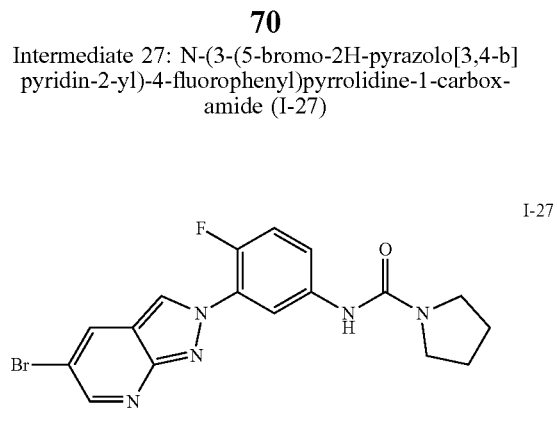

I-27

The intermediate I-27 was prepared in a similar manner as intermediate I-3 using pyrrolidine as a starting material. ¹H NMR (400 MHz, DMSO-d₆) δ ppm 8.89 (d, J=2.26 Hz, 1H), 8.75 (d, J=2.26 Hz, 1H), 8.62 (d, J=2.51 Hz, 1H), 8.51 (s, 1H), 8.28 (dd, J=7.03, 2.51 Hz, 1H), 7.74 (dt, J=9.10, 3.48 Hz, 1H), 7.46 (dd, J=11.29, 9.29 Hz, 1H), 3.39 (br s, 4H), 1.87 (br t, J=6.40 Hz, 4H).

Intermediate 28: 4-fluoro-3-(5-(3-methylpyridin-2-yl)-2H-pyrazolo[3,4-b]pyridin-2-yl)aniline I-28

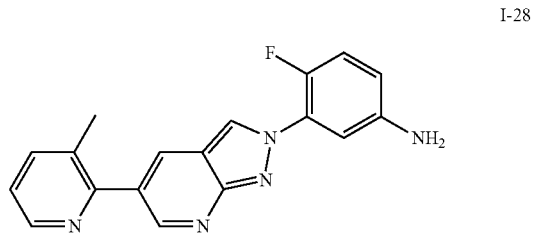 [SMILES: Cc1cccnc1-c1cnc2nn(-c3cc(N)ccc3F)cc2c1]

I-28

The intermediate I-28 was prepared in a similar manner as intermediate I-11 using (3-methylpyridin-2-yl)zinc(II) bromide as a starting material. ¹H NMR (400 MHz, DMSO-d6) 8.89 (dd, J=8.2, 2.4 Hz, 2H), 8.56 (dd, J=4.6, 1.7 Hz, 1H), 8.47 (d, J=2.2 Hz, 1H), 7.80 (ddd, J=7.7, 1.7, 0.8 Hz, 1H), 7.40-7.32 (m, 1H), 7.24-7.14 (m, 2H), 6.69 (ddd, J=9.0, 3.9, 2.8 Hz, 1H), 5.46 (s, 2H), 2.44 (s, 3H).

Intermediate 29: 4-fluoro-3-(5-(3-(trifluoromethyl)azetidin-1-yl)-2H-pyrazolo[3,4-b]pyridin-2-yl)aniline I-29

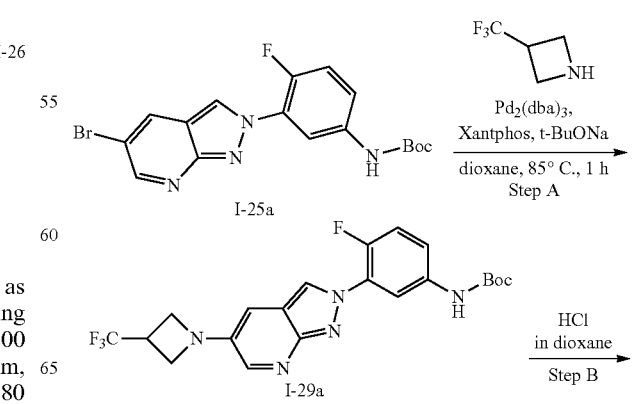

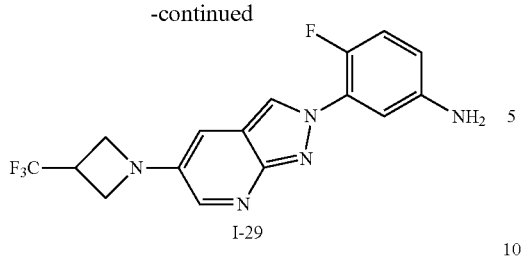

I-29

Step A:

A mixture of I-25a (100 mg, 245.6 μmol, 1 eq), 3-(trifluoromethyl)azetidine (48 mg, 294.7 μmol, 1.2 eq, HCl), NaOBu-t (2 M, 368.3 uL, 3 eq), XantPhos (28 mg, 49.11 μmol, 0.2 eq) and Pd₂(dba)₃ (22 mg, 24.6 μmol, 0.1 eq) in dioxane (2 mL) was de-gassed and then stirred at 80° C. for 1 hour under N₂. The mixture was quenched and adjusted to pH=7 with 1 M HOAc. The mixture was purified by silica chromatography (Petroleum ether/Ethyl acetate=1/1) to give I-29a as a yellow solid. M+H=452.3.

Step B:

This step was performed in a similar manner as I-25 step C to give I-29. ¹H NMR (400 MHz, DMSO) δ ppm 8.49 (d, J=2.45 Hz, 1H), 8.29 (d, J=2.81 Hz, 1H), 7.09-7.22 (m, 2H), 7.02 (d, J=2.69 Hz, 1H), 6.63 (dt, J=8.74, 3.33 Hz, 1H), 5.38 (s, 2H), 4.07-4.23 (m, 2H), 3.98 (dd, J=7.95, 5.38 Hz, 2H), 3.66-3.83 (m, 1H).

Intermediate 30: tert-butyl 2-(2-(2-fluoro-5-(3-fluoroazetidine-1-carboxamido)phenyl)-2H-pyrazolo[3,4-b]pyridin-5-yl)azetidine-1-carboxylate (I-30)

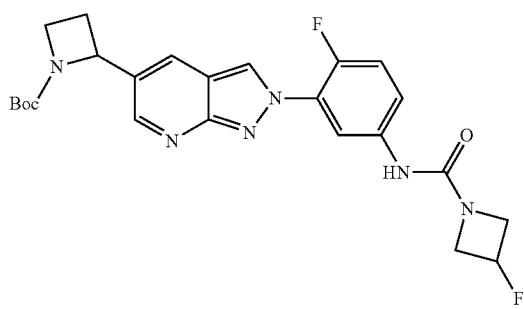

I-30

The synthesis of I-30 is described in Example 24.

Intermediate 31: trans-N-(3-(5-bromo-2H-pyrazolo[3,4-b]pyridin-2-yl)-4-fluorophenyl)-2-fluorocyclopropane-1-carboxamide (I-31)

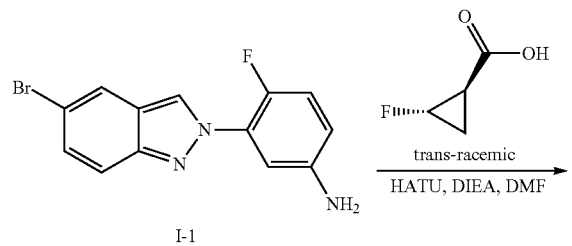

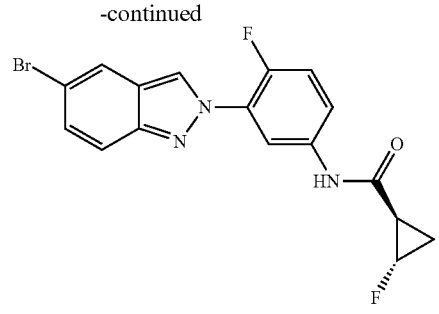

trans-racemic
I-31

To a solution of I-1 (2.5 g, 8.1 mmol, 1 eq) and trans-2-fluorocyclopropanecarboxylic acid (1.0 g, 9.8 mmol, 1.2 eq) in DMF (20 mL) was added HATU (3.7 g, 9.8 mmol, 1.2 eq) and DIEA (1.6 g, 12.2 mmol, 2.1 mL, 1.5 eq). The mixture was stirred at 25° C. for 16 hr. The reaction was diluted with ethyl acetate (150 mL) and was washed with saturated NaHCO₃ (50 mL) and brine 100 mL (50 mL*2), dried over Na₂SO₄, filtered and concentrated under reduced pressure to give a residue. The residue was triturated in tert-butyl methyl ether (20 mL) and collected by filtration to give I-31 as a yellow solid. ¹H NMR (400 MHz, DMSO-d₆) δ ppm 10.74 (s, 1H), 8.91 (d, J=2.51 Hz, 1H), 8.75 (d, J=2.26 Hz, 1H), 8.62 (d, J=2.26 Hz, 1H), 8.36 (dd, J=7.03, 2.51 Hz, 1H), 7.60-7.74 (m, 1H), 7.55 (dd, J=11.17, 9.16 Hz, 1H), 4.70-5.12 (m, 1H), 2.89 (s, 1H), 2.23-2.41 (m, 1H), 1.46-1.66 (m, 1H).

Intermediate 32:
4-(methoxymethyl)-2-methyloxazole-5-carboxylic acid (I-32)

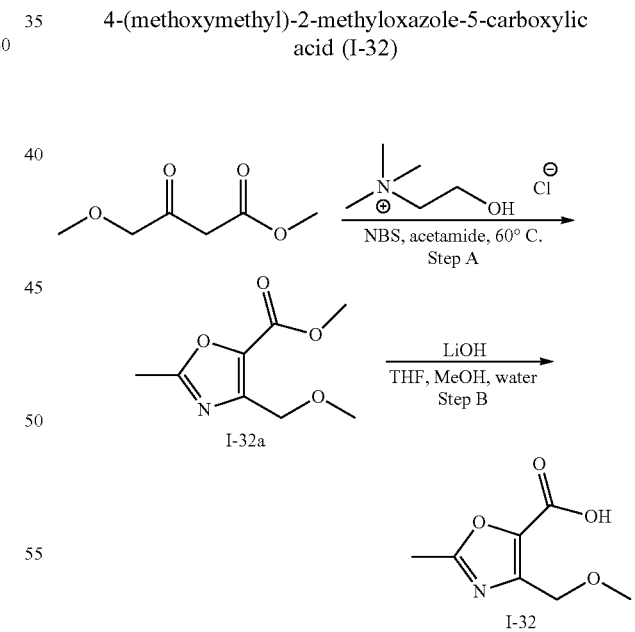

Step A:

Acetamide (1.7 g, 28.6 mmol, 4 eq) and 2-hydroxy-N,N,N-trimethylethan-1-aminium chloride (1 g, 7.2 mmol, 1 eq) were combined and heated to 60° C. for 30 min. NBS (2.5 g, 14.3 mmol, 2 eq) and methyl 4-methoxy-3-oxo-butanoate (2.1 g, 14.3 mmol, 2 eq) were added to the reaction and heated to 60° C. for 1 h. The reaction mixture was purified by prep-TLC eluting with 50% ethyl acetate in petroleum either to give I-32a as a light yellow oil. ¹HNMR: (400 MHz, CDCl₃) δ ppm 4.66 (s, 2H), 3.94 (s, 3H), 3.47 (s, 3H), 2.55 (s, 3H).

Step B:

A mixture of I-32a (60 mg, 324.01 μmol, 1 eq) and LiOH.H₂O (27.2 mg, 648.0 μmol, 2 eq) in THF (1 mL), MeOH (1 mL) and H₂O (0.5 mL) was stirred at 25° C. for 16 hr under a N₂ atmosphere. The reaction mixture was concentrated under vacuo to give 60 mg of a lithium salt of I-32 as a yellow solid.

Intermediate 33: N-(4-fluoro-3-(5-(3-methylpyridin-2-yl)-2H-pyrazolo[3,4-b]pyridin-2-yl)phenyl)-4-(methoxymethyl)-2-methyloxazole-5-carboxamide (I-33)

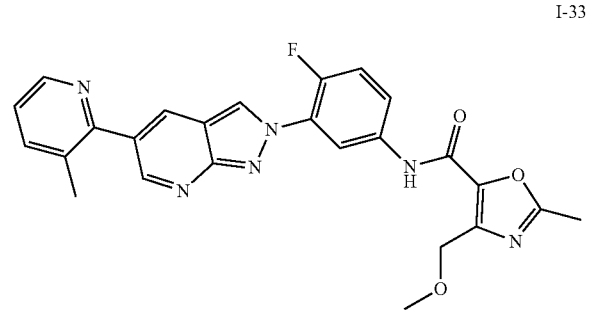 [SMILES: COCc1nc(C)oc1C(=O)Nc1ccc(F)c(-n2cc3cc(-c4ncccc4C)cnc3n2)c1]

The synthesis of I-33 is described in Example 28.

Intermediate 34: 4-methyl-2-(methyl-d3)oxazole-5-carboxylic acid (I-34)

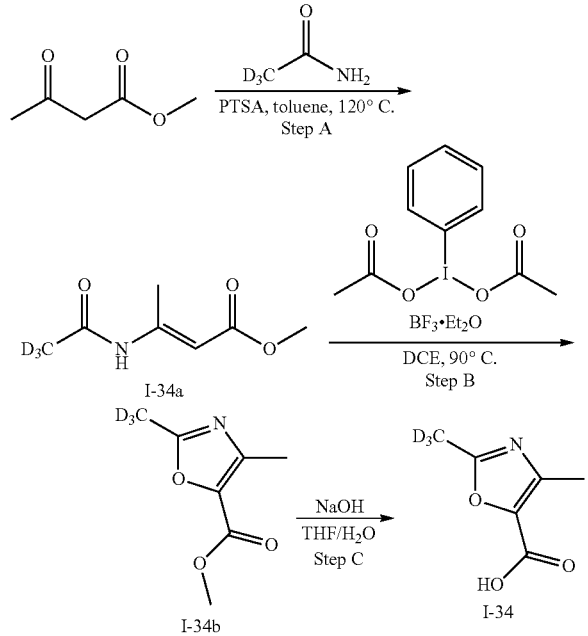

Step A:

To a solution of methyl 3-oxobutanoate (900 mg, 7.7 mmol, 833 uL, 1 eq) in toluene (15 mL) was added 2,2,2-trideuterioacetamide (962 mg, 15.5 mmol, 2 eq) and TsOH (13.3 mg, 77.5 μmol, 0.01 eq). The mixture was stirred at 120° C. for 12 h. The mixture was concentrated under vacuum to give a residue which was purified by silica chromatography eluting with petroleum ether:ethyl acetate in a 30:1-10:1 gradient to give I-34a as a white solid. ¹H NMR (400 MHz, DMSO-d6) δ ppm 10.88 (br s, 1H), 5.02 (s, 1H), 3.63 (s, 3H), 2.29 (s, 3H).

Step B:

To a solution of I-34a (250 mg, 1.6 mmol, 1 eq) in DCE (8 mL) was added (diacetoxyiodo)benzene (654 mg, 2.0 mmol, 1.3 eq) and BF₃.Et₂O (443 mg, 3.1 mmol, 385 uL, 2 eq). The mixture was stirred at 90° C. for 2 h. The mixture was concentrated under vacuum to give a residue which was purified by silica chromatography eluting with petroleum ether:ethyl acetate in a 30:1-10:1 gradient to give I-34b as a white solid. ¹H NMR: (400 MHz, DMSO-d6) δ ppm 3.81 (s, 3H), 2.33 (s, 3H).

Step C:

To a solution of I-34b (100 mg, 632 μmol, 1 eq) in THF (1 mL) and H₂O (1 mL) was added a 15% aqueous NaOH (1 mL) solution. The mixture was stirred at 70° C. for 2 h. The pH was adjusted to 5 by addition of aqueous HCl solution (1 M) and a white solid was formed. The suspension was filtered and the filter cake was washed with H₂O (5 mL). The filter cake was dried under reduced pressure to give I-34 as a white solid. ¹H NMR: (400 MHz, DMSO-d6) δ ppm 13.30 (br s, 1H), 2.32 (s, 3H).

Intermediate 35: 2-(tert-butoxymethyl)-N-(4-fluoro-3-(5-(3-methylpyridin-2-yl)-2H-pyrazolo[3,4-b]pyridin-2-yl)phenyl)-4-methyloxazole-5-carboxamide (I-35)

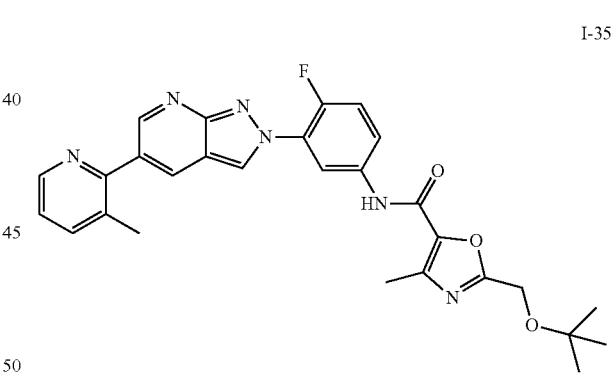

The synthesis of I-35 is described in Example 29.

Intermediate 36: 4-fluoro-3-(5-phenyl-2H-pyrazolo[3,4-b]pyridin-2-yl)aniline (I-36)

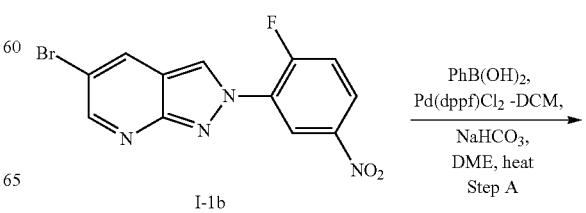

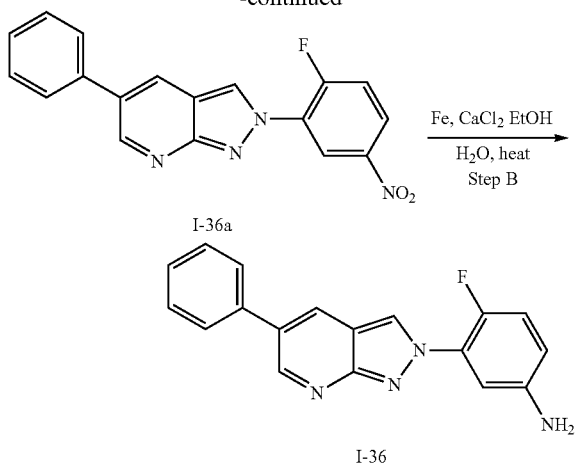

Step A:

A 100 ml sealed tube containing I-1b (500 mg, 1.483 mmol) and Phenyl boronic acid (181 mg, 1.483 mmol) in DME:H₂O (8:2) (15 mL) was purged with Argon gas for 15 min. NaHCO₃ (249 mg, 2.966 mmol) and Pd(dppf)Cl₂.DCM (61 mg, 0.074 mmol) were added and the reaction was stirred at 80° C. for 1 h. The reaction mixture was diluted with water, extracted with EtOAc (100 mL×2). The combined organic layers were washed with 1× with water (150 mL) an 1× with brine (100 mL) and then dried over sodium sulphate and concentrated in vacuo. The crude compound was purified by silica gel chromatography eluting with 25% EtOAc in n-Hexane to afford I-36a. ¹H NMR (300 MHz, CDCl₃): δ 9.32-9.29 (m, 1H), 9.10 (s, 1H), 8.69 (s, 1H), 8.34-8.29 (m, 1H), 8.23 (s, 1H), 7.65 (d, J=6.9 Hz, 2H), 7.55-7.41 (m, 4H); M+H=335.2

Step B:

To a flask containing I-36a (150 mg, 0.449 mmol) in EtOH:H₂O (8:2) (20 mL) was added Iron powder (370 mg, 6.730 mmol) and CaCl₂ (995 mg, 8.973 mmol) and the reaction was stirred at 65° C. for 2 h. The reaction mixture was diluted with water and extracted with EtOAc (100 mL×2). The combined organic layers were washed 1× with water (100 mL) and 1× with brine (100 mL) and then dried over sodium sulphate and concentrated invacuo. The crude compound was purified by n-Pentane washings to afford I-36. 1H NMR (300 MHz, CDCl₃): δ 9.04 (s, 1H), 8.61 (s, 1H), 8.22 (s, 1H), 7.70-7.40 (m, 6H), 7.20-7.00 (m, 1H), 6.75-6.60 (m, 1H); M+H=305.30.

Example 1: N-(4-fluoro-3-(5-(3-methylpyridin-2-yl)-2H-pyrazolo[3,4-b]pyridin-2-yl)phenyl)-2,4-dimethyloxazole-5-carboxamide (Compound 1)

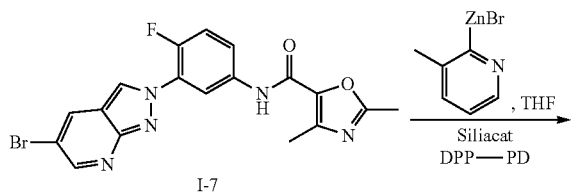

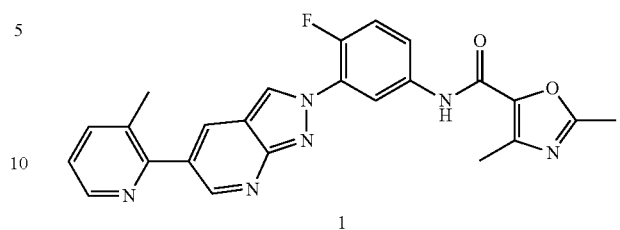

To a mixture of I-7 (30 mg, 0.070 mmol) and Siliacat DPP-Pd 0.25 mmol/g (0.014 g, 3.52 μmol, 0.05 eq) was added 0.5 mL anhydrous THF. The reaction mixture was placed under a nitrogen atmosphere and (3-methylpyridin-2-yl)zinc(II) bromide (0.5M in THF, 0.56 mL, 0.28 mmol, 4 eq) was added and the reaction was stirred at 65° C. overnight. The reaction was quenched with 0.2 mL water and purified by prep-HPLC (Waters Atlantis T3 C18 19*50 mm*10 um column) eluting with 20-80% acetonitrile (0.035% TFA) in water (0.05% TFA) to give compound 1. ¹H NMR (400 MHz, Methanol-d₄) δ 8.90 (dd, J=13.2, 2.3 Hz, 2H), 8.59-8.43 (m, 3H), 7.97-7.81 (m, 2H), 7.55-7.35 (m, 2H), 2.56 (s, 3H), 2.48-2.45 (m, 6H). Method 1: RT=2.69 min.; M+H=443.1.

Compounds 16, 17, 101, 102, 103, 104, 105, 106, 107 and 108 were synthesized according to the protocol described above using the corresponding zinc(II) bromides.

Example 2: N-(4-fluoro-3-(5-(3-methylpyridin-2-yl)-2H-pyrazolo[3,4-b]pyridin-2-yl)phenyl)furan-2-carboxamide (Compound 2)

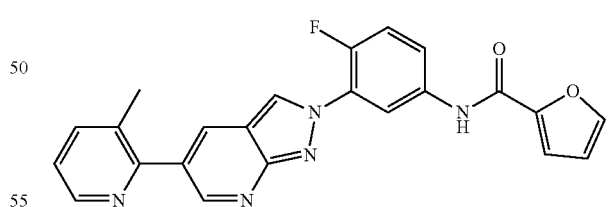

Compound 2 was prepared in a similar manner as compound 1 utilizing I-8 as a starting material. ¹H NMR (400 MHz, Methanol-d4) δ 8.92 (d, J=2.4 Hz, 1H), 8.88 (d, J=2.2 Hz, 1H), 8.55-8.45 (m, 3H), 7.96 (m, 1H), 7.87 (m, 1H), 7.78 (m, 1H), 7.52-7.39 (m, 2H), 7.32 (m, 1H), 6.68 (m, 1H), 2.46 (s, 3H). Method 2: RT=0.89 min.; M+H=414.3.

Compounds 54, 55, 56, 57, 59, 60, 61, 62, 63 and 64 were synthesized according to the protocol described above using the corresponding zinc(II) bromides.

Example 3: N-(4-fluoro-3-(5-(3-methylpyridin-2-yl)-2H-pyrazolo[3,4-b]pyridin-2-yl)phenyl)azetidine-1-carboxamide (Compound 3)

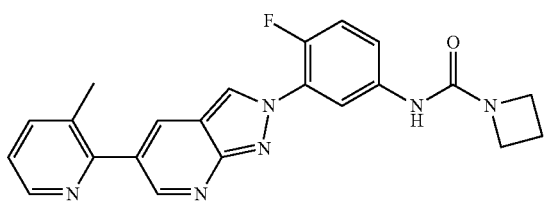

Compound 3 was prepared in a similar manner as compound 1 utilizing I-6 as a starting material. $^1$H NMR (400 MHz, Methanol-d4) δ 8.89-8.84 (m, 2H), 8.52 (m, 1H), 8.48 (m, 1H), 8.18 (m, 1H), 7.86 (m, 1H), 7.67 (m, 1H), 7.44-7.32 (m, 2H), 4.18-4.06 (m, 4H), 2.46 (s, 3H), 2.41-2.26 (m, 2H). Method 1: RT=2.41 min.; M+H=403.3.

Compound 99 was synthesized according to the protocol described above using the corresponding zinc(II) bromide.

Example 4: (R)-3-fluoro-N-(4-fluoro-3-(5-(3-methylpyridin-2-yl)-2H-pyrazolo[3,4-b]pyridin-2-yl)phenyl)pyrrolidine-1-carboxamide (Compound 4)

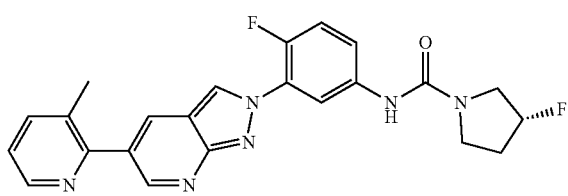

Compound 4 was prepared in a similar manner as compound 1 utilizing I-5 as a starting material. $^1$H NMR (400 MHz, Methanol-d4) δ 8.87 (dd, J=4.7, 2.3 Hz, 2H), 8.52 (m, 1H), 8.49 (m, 1H), 8.19 (m, 1H), 7.86 (m, 1H), 7.67 (m, 1H), 7.45-7.34 (m, 2H), 5.42-5.25 (m, 1H), 3.85-3.55 (m, 4H), 2.46 (s, 3H), 2.39-2.19 (m, 2H). Method 1: RT=2.41 min.; M+H=435.3.

Compounds 41, 42, 43, 44, 45, 46, 47, 48, 49, 50, 51, 52 and 53 were synthesized according to the protocol described above using the corresponding zinc(II) bromides.

Example 5: 3,3-difluoro-N-(4-fluoro-3-(5-(3-methylpyridin-2-yl)-2H-pyrazolo[3,4-b]pyridin-2-yl)phenyl)azetidine-1-carboxamide (Compound 5)

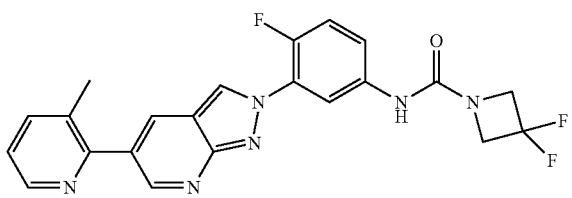

Compound 5 was prepared in a similar manner as compound 1 utilizing I-3 as a starting material. $^1$H NMR (400 MHz, Methanol-d4) δ 8.88 (dd, J=5.4, 2.3 Hz, 2H), 8.52 (m, 1H), 8.48 (m, 1H), 8.22 (m, 1H), 7.86 (m, 1H), 7.69 (m, 1H), 7.45-7.36 (m, 2H), 4.44 (m, 4H), 2.46 (s, 3H). Method 2: RT=0.76 min.; M+H=439.1.

Example 6: 3-fluoro-N-(4-fluoro-3-(5-(3-methylpyridin-2-yl)-2H-pyrazolo[3,4-b]pyridin-2-yl)phenyl)azetidine-1-carboxamide (Compound 6)

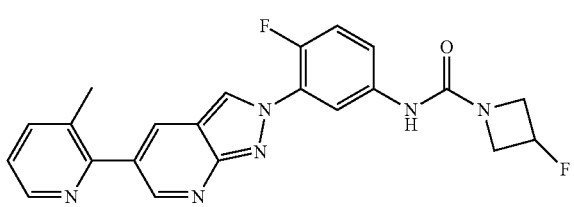

Compound 6 was prepared in a similar manner as compound 1 utilizing I-4 as a starting material. $^1$H NMR (500 MHz, DMSO-d6) δ 8.98 (s, 1H), 8.94 (dd, J=16.9, 2.3 Hz, 2H), 8.57 (ddd, J=4.8, 1.7, 0.7 Hz, 1H), 8.49 (d, J=2.3 Hz, 1H), 8.28 (dd, J=7.0, 2.7 Hz, 1H), 7.80 (ddd, J=7.7, 1.7, 0.8 Hz, 1H), 7.72 (ddd, J=9.1, 4.1, 2.7 Hz, 1H), 7.49 (dd, J=11.2, 9.1 Hz, 1H), 7.37 (dd, J=7.7, 4.7 Hz, 1H), 5.41 (dtt, J=57.5, 6.1, 3.1 Hz, 1H), 4.34 (dddd, J=21.7, 10.4, 6.0, 1.4 Hz, 2H), 4.04 (dddd, J=24.9, 10.4, 3.1, 1.4 Hz, 2H), 2.44 (s, 3H). Method 1: RT=2.39 min.; M+H=421.1.

Compounds 14, 15, 18, 19, 20, 21, 23, 24, 25, 26, 27 and 28 were synthesized according to the protocol described above using the corresponding zinc(II) bromides.

Compound 318 was synthesized according to the protocol described above using dimethylzinc.

Example 7: N-(4-fluoro-3-(5-isobutyl-2H-pyrazolo[3,4-b]pyridin-2-yl)phenyl)azetidine-1-carboxamide (Compound 7)

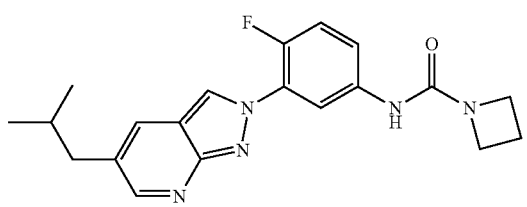

Compound 7 was prepared in a similar manner as compound 1 utilizing I-6 and isobutylzinc(II) bromide as starting materials. $^1$H NMR (400 MHz, Methanol-d4) δ 8.66 (d, J=2.4 Hz, 1H), 8.56 (d, J=2.2 Hz, 1H), 8.12 (m, 1H), 8.07 (m, 1H), 7.64 (m, 1H), 7.34 (m, 1H), 4.19-4.01 (m, 4H), 2.67 (m, 2H), 2.41-2.24 (m, 2H), 1.97 (m, 1H), 0.99 (m, 6H). Method 1: RT=3.11 min.; M+H=368.3.

Compounds 91, 93, 94, 95, 96, 97 and 98 were synthesized according to the protocol described above using the corresponding zinc(II) bromides.

Example 8: 3,3-difluoro-N-(4-fluoro-3-(5-isobutyl-2H-pyrazolo[3,4-b]pyridin-2-yl)phenyl)azetidine-1-carboxamide (Compound 8)

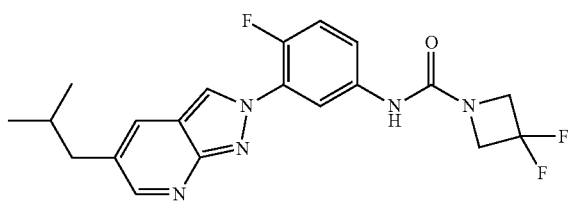

Compound 8 was prepared in a similar manner as compound 1 utilizing I-3 and isobutylzinc(II) bromide as starting materials. $^1$H NMR (400 MHz, Methanol-d4) δ 8.59 (d, J=2.5 Hz, 1H), 8.46 (d, J=2.2 Hz, 1H), 8.06 (m, 1H), 7.97 (m, 1H), 7.56 (m, 1H), 7.30-7.24 (m, 1H), 4.33 (m, 4H), 2.57 (m, 2H), 1.92-1.81 (m, 1H), 0.89 (m, 6H). Method 2: RT=1.09 min. M+H=404.1.

Compounds 29, 30, 31, 32, 33, 34, 35, 36, 37 and 38 were synthesized according to the protocol described above using the corresponding zinc(II) bromides.

Example 9: N-(3-(5-(dimethylamino)-2H-pyrazolo[3,4-b]pyridin-2-yl)-4-fluorophenyl)-3,3-difluoroazetidine-1-carboxamide (Compound 9)

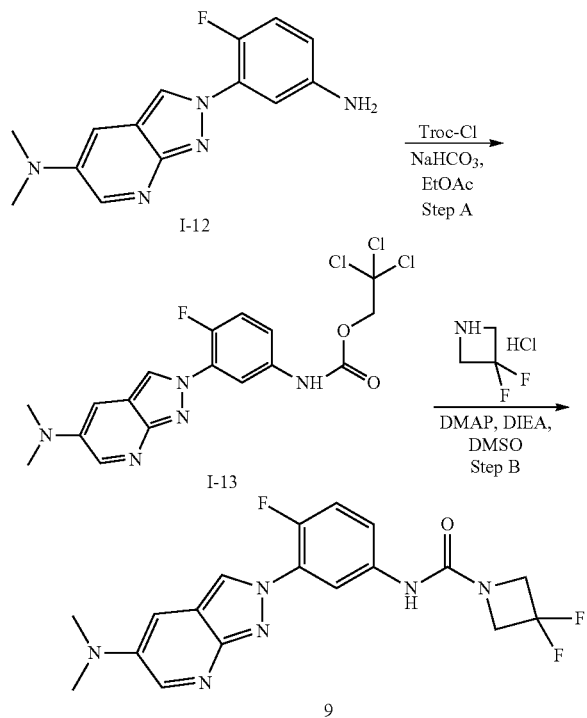

Step A:
To a solution of I-12 (0.5 g, 1.8 mmol, 1 eq) in ethyl acetate (5 mL) and saturated aqueous NaHCO$_3$ (5 mL) was added 2,2,2-trichloroethyl carbonochloridate (585.7 mg, 2.8 mmol, 370.7 uL, 1.5 eq) at 0° C. and the reaction was stirred at 0° C. for 1 hr. The reaction mixture was extracted with EtOAc (30 mL*3) and the combined organics were dried over sodium sulfate and concentrated. The resulting residue was purified by silica chromatography eluting with 20% EtOAc and 20% DCM in petroleum ether to give I-13 as a yellow solid. $^1$H NMR (400 MHz, DMSO-d$_6$) δ ppm 10.52 (br s, 1H), 8.71 (d, J=2.93 Hz, 1H), 8.57 (d, J=2.69 Hz, 1H), 8.25 (br d, J=5.14 Hz, 1H), 7.44-7.64 (m, 2H), 7.16 (d, J=2.69 Hz, 1H), 4.99 (s, 2H), 2.96 (s, 6H).

Step B:
The reaction mixture of I-13 (60 mg, 134.3 μmol, 1 eq), 3,3-difluoroazetidine HCl (25 mg, 268.6 μmol, 2 eq), DIEA (34.6 mg, 268.6 μmol, 46.7 μL, 2 eq), DMAP (1.6 mg, 13.4 μmol, 0.1 eq) in DMSO (1 mL) was stirred at 60° C. for 12 hours and at 70° C. for another 12 hours. The reaction mixture was purified by Prep-HPLC column: Phenomenex Gemini C18 250*50 mm*10 um; mobile phase: [water (0.05% ammonia hydroxide v/v)-acetonitrile]; B %: 25%-55%, 12 min to give 9 as a yellow solid. $^1$H NMR (400 MHz, DMSO-d6) δ ppm 9.18 (s, 1H), 8.70 (d, J=3.01 Hz, 1H), 8.55 (d, J=2.76 Hz, 1H), 8.20 (dd, J=6.90, 2.64 Hz, 1H), 7.56-7.78 (m, 1H), 7.45 (dd, J=11.42, 9.16 Hz, 1H), 7.15 (d, J=3.01 Hz, 1H), 4.41 (t, J=12.67 Hz, 4H), 2.95 (s, 6H). Method 1: RT=2.84 min.; M+H=391.1.

Compounds 100, 124, 133, 142, 143, 156, 167, 170 195, 219, 220, 221, 222, 223, 224, 225, 226, 227, 228, 229, 260, 276, 319, 320, 321, 322, 323, 324, and 328, were synthesized according to the protocol described above using intermediates 1-9, I-12, I-16, I-23, I-25 or I-26 and the corresponding amine.

Example 10: N-(3-(5-(azetidin-1-yl)-2H-pyrazolo[3,4-b]pyridin-2-yl)-4-fluorophenyl)azetidine-1-carboxamide (Compound 10)

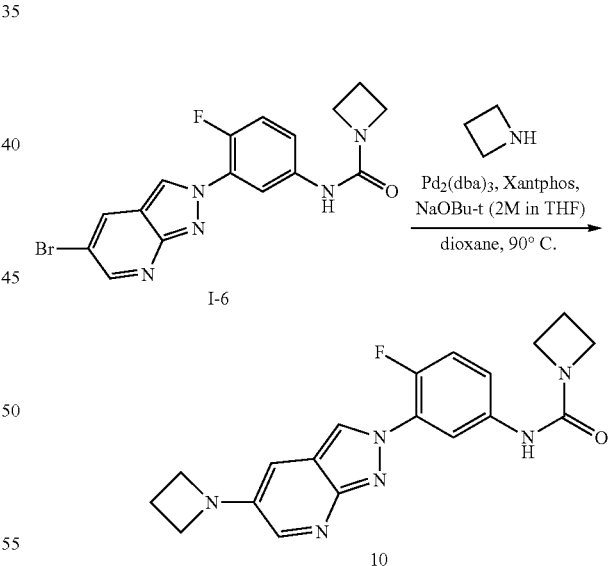

A mixture of I-6 (80 mg, 205 μmol, 1 eq), azetidine (17.6 mg, 307.5 mol, 20.7 μL, 1.5 eq), NaOt-Bu (2 M in THF, 307.5 μL, 3 eq), XantPhos (23.7 mg, 41 μmol, 0.20 to eq) and Pd$_2$(dba)$_3$ (18.8 mg, 20.5 μmol, 0.10 eq) in dioxane (3 mL) was de-gassed with Argon and heated to 90° C. for 4 h. The reaction was quenched with 1 M HOAc and purified by prep-HPLC (column: Phenomenex Gemini C18 250*50 mm*10 μm; mobile phase: [water (0.05% ammonia hydroxide v/v)-acetonitrile]; B %: 28%-58%, 12 min) to give 10 as a yellow solid. $^1$H NMR (400 MHz, Methanol-d4), δ ppm, 8.42 (d, J=2.51 Hz, 1H), 8.22 (d, J=2.76 Hz, 1H), 8.05 (dd, J=6.78, 2.76 Hz, 1H), 7.58-7.62 (m, 1H), 7.30 (dd, J=11.04, 9.16 Hz, 1H), 7.01 (d, J=2.64 Hz, 1H), 4.10 (t, J=7.65 Hz, 4H), 3.99 (t, J=7.22 Hz, 4H), 2.41-2.49 (m, 2H), 2.27-2.35 (m, 2H). Method 1: RT=2.80 min.; M+H=367.1.

Compounds 40, 58, 92, 122, 131, 132, 134, 135, 137, 141, 144, 145, 147, 149, 151, 155, 157, 158, 161, 163, 171, 172, 177, 178, 179, 180, 181, 183, 184, 185, 186, 190, 191, 192, 193, 194, 197, 198, 199, 200, 201, 202, 203, 204, 205, 230, 231, 232, 234, 235, 236 237, 238, 239, 240, 241, 243, 244, 245, 248, 249, 250, 251, 252, 253, 255, 263, 266, 272 290, 291, 292, 298, 299, 300, 302, 303, 306, 307, 308, 314, 326, 327, 338 and 339 were synthesized according to the protocol described above using the corresponding intermediate I-3, I-4, I-5, I-6, I-7, I-8, I-24, I-27 or I-31 and the corresponding amines.

Compounds 242 was isolated in addition to compound 241 using the above reaction conditions. Similarly compound 246 was isolated in addition to compound 202 using the above reaction conditions.

Compound 270 was synthesized using the protocol described above using Boc-piperidine after which the Boc group was removed using 0.36:1 ratio of TFA in DCM followed by neutralization to pH=7 with Et₃N and then prep-HPLC purification (column: Phenomenex Synergi C18 150*25*10 um; mobile phase: [water (0.225% FA)-acetonitrile]; B %: 3%-30%, 10 min) to give compound 270.

Example 11: 4,4,4-trifluoro-N-(4-fluoro-3-(5-isopropyl-2H-pyrazolo[3,4-b]pyridin-2-yl)phenyl)butanamide (Compound 173)

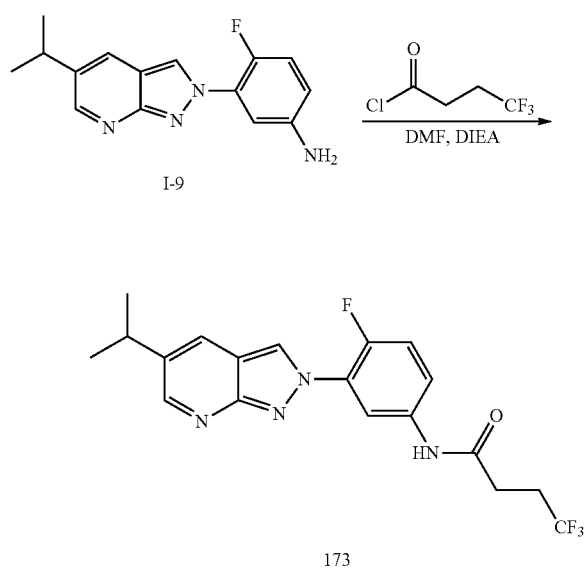

To a solution of I-9 (25 mg, 0.092 mmol) in DMF (1.5 ml) and DIEA (0.040 ml, 0.23 mmol) was added 4,4,4-trifluorobutanoyl chloride (14.9 mg, 0.092 mmol) and the reaction was stirred for 12 hrs at room temperature. The crude reaction mixture was purified directly on a 15 g C18 flash chromatography column eluting with 20-90% acetonitrile in water to give compound 173 as a white solid. ¹H NMR (400 MHz, DMSO-d6) δ 10.45 (s, 1H), 8.81 (d, J=2.7 Hz, 1H), 8.69 (d, J=2.3 Hz, 1H), 8.36 (dd, J=7.0, 2.7 Hz, 1H), 8.05 (dd, J=2.3, 0.8 Hz, 1H), 7.68 (ddd, J=9.1, 4.2, 2.7 Hz, 1H), 7.54 (dd, J=11.2, 9.0 Hz, 1H), 3.08 (pd, J=6.9, 0.8 Hz, 1H), 2.72-2.55 (m, 4H), 1.30 (d, J=6.9 Hz, 6H). Method 1: RT=3.19 min.; M+H=395.2.

Compound 174 was synthesized according to the protocol described above using the corresponding chloroformate in place of the acid chloride.

Example 12: N-(4-fluoro-3-(5-isopropyl-2H-pyrazolo[3,4-b]pyridin-2-yl)phenyl)pyrazine-2-carboxamide (Compound 87)

Pyrazine-2-carboxylic acid (16.5 mg, 0.13 mmol) was added to a flask followed by I-9 (30 mg, 0.11 mmol) dissolved in 0.25 mL DMF. A solution of DIEA (0.058 mL, 0.33 mmol) and HATU (50.6 mg, 0.13 mmol) in 0.25 mL DMF was added to the reaction and the resulting mixture was stirred overnight. The reaction was filtered through a 0.2 micron syringe filter and the material was purified by prep-HPLC (Waters Atlantis T3 C18 19*50 mm*10 um column) eluting with 20-80% acetonitrile (0.035% TFA) in water (0.05% TFA) to give compound 87. ¹H NMR (400 MHz, Methanol-d4) δ 9.36 (m, 1H), 8.84 (m, 1H), 8.76 (m, 1H), 8.72 (m, 1H), 8.66 (m, 1H), 8.57 (m, 1H), 8.13 (m, 1H), 7.99 (m, 1H), 7.46 (m, 1H), 3.13 (m, 1H), 1.38 (2s, 6H). Method 1: RT=3.05 min.; M+H=377.3.

Compounds 65, 67, 68, 69, 70, 71, 72, 73, 74, 75, 76, 77, 78, 79, 80, 81, 82, 83, 84, 85, 86, 87, 88, 89, 90, 109, 110, 111, 112, 113, 114, 115, 116, 117, 118, 119, 120, 196, 207, 208, 209, 210, 211, 212, 213, 214, 215, 216, 217, 261, 262 and 351 were synthesized according to the protocol described above using the corresponding carboxylic acids.

Compounds 139, 140, 153, 154, 279, 330 and 352 were synthesized according to the protocol described above using I-12, I-29 or I-36 and the corresponding carboxylic acids.

Compound 278 was synthesized according to the protocol described above using I-28 and I-34 as starting materials.

Example 13: 3-fluoro-N-(4-fluoro-3-(5-(2,2,2-trifluoroethyl)-2H-pyrazolo[3,4-b]pyridin-2-yl)phenyl)azetidine-1-carboxamide (Compound 152)

Example 14: Isopropyl (2-(2-fluoro-5-(3-fluoroazetidine-1-carboxamido)phenyl)-2H-pyrazolo[3,4-b]pyridin-5-yl)carbamate (Compound 168)

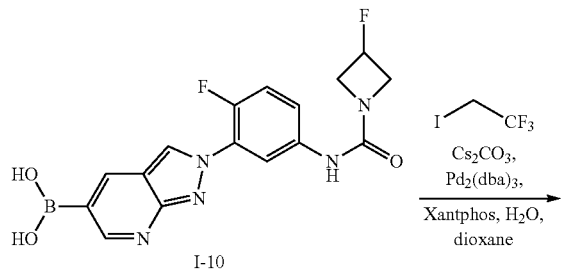

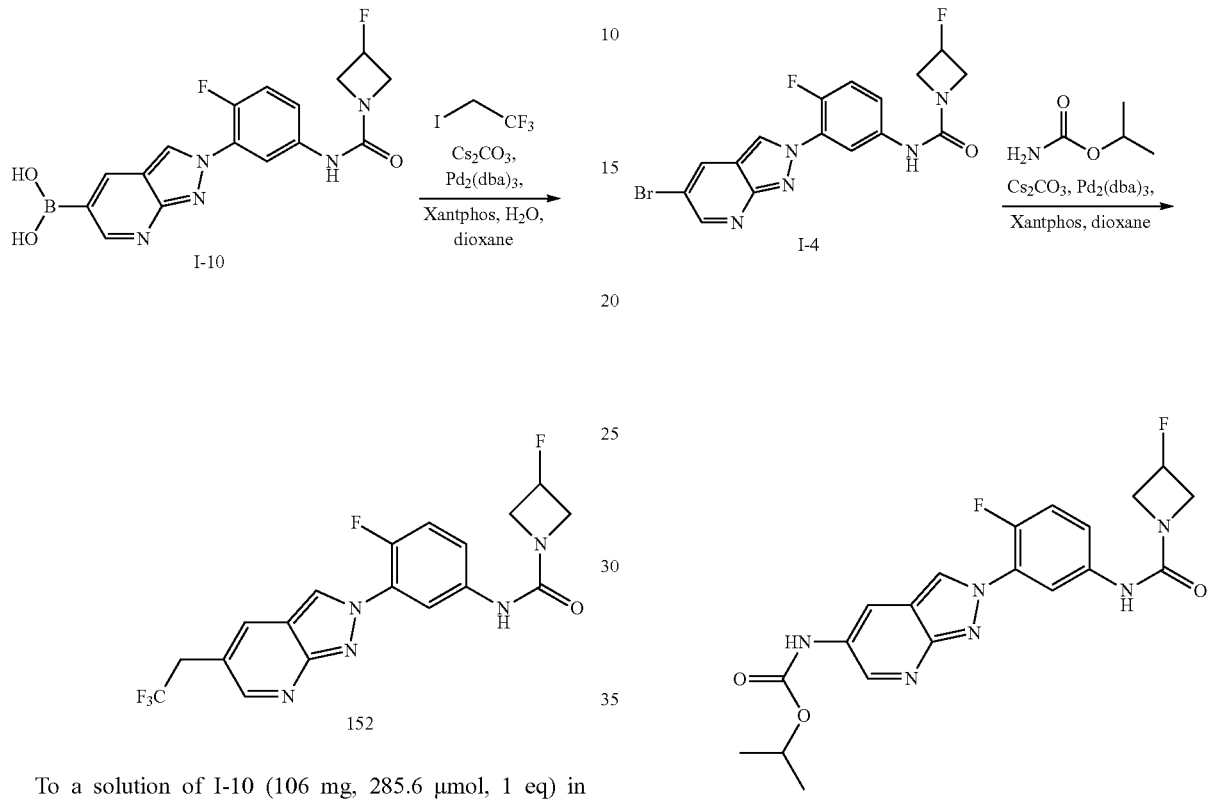

To a solution of I-10 (106 mg, 285.6 μmol, 1 eq) in dioxane (1 mL) was added 1,1,1-trifluoro-2-iodo-ethane (119.9 mg, 571.10 μmol, 56.03 uL, 2 eq), Pd$_2$(dba)$_3$ (13.1 mg, 14.3 μmol, 0.05 eq), XantPhos (28.1 mg, 48.5 μmol, 0.2 eq) and Cs$_2$CO$_3$ (372.15 mg, 1.1 mmol, 4 eq) under a N$_2$ atmosphere. After 1 min. water (92.6 mg, 5.1 mmol, 92.6 uL, 18 eq) was added and the mixture was stirred at 80° C. for 16 hr. The reaction mixture was concentrated under reduced pressure. The residue was diluted with DCM (30 mL) and the organic layer was washed with water (10 mL*2), dried over Na$_2$SO$_4$, filtered and concentrated to give a residue. The residue was purified by prep-TLC (SiO$_2$, DCM:Methanol=10:1) and further purified by prep-HPLC (column: Phenomenex Gemini C18 250*50 mm*10 um; mobile phase: [water (0.05% ammonia hydroxide v/v)-acetonitrile]; B %: 28%-58%, 12 min) to give compound 152 as a yellow solid. $^1$H NMR (400 MHz, DMSO-d6), δ ppm, 8.98 (s, 1H), 8.95 (d, J=2.51 Hz, 1H), 8.69 (d, J=2.01 Hz, 1H), 8.33 (d, J=1.76 Hz, 1H), 8.24 (dd, J=6.90, 2.63 Hz, 1H), 7.67-7.74 (m, 1H), 7.48 (dd, J=11.29, 9.29 Hz, 1H), 5.30-5.52 (m, 1H), 4.26-4.39 (m, 2H), 3.97-4.09 (m, 2H), 3.87 (q, J=11.71 Hz, 2H). Method 1: RT=2.76 min.; M+H=412.2.

Compounds 162, 164, 166, 175 and 176 were synthesized according to the protocol described above using the corresponding boronic acid prepared from intermediate I-3, I-5, I-6, I-7 or I-8 prepared in the same manner as I-10.

To a mixture of I-4 (120 mg, 294 μmol, 1 eq), isopropyl carbamate (45.5 mg, 441 mol, 1.5 eq) and Cs$_2$CO$_3$ (287.3 mg, 881.9 μmol, 3 eq) in dioxane (3 mL) was added XantPhos (34.0 mg, 58.8 μmol, 0.20 eq) and Pd$_2$(dba)$_3$ (26.9 mg, 29.4 μmol, 0.10 eq) under an Argon atmosphere. The mixture was heated to 90° C. and stirred for 4 hours. The mixture was quenched by addition of 1 M HOAc and purified by prep-HPLC (column: Boston pH-lex 150*25 10 um; mobile phase: [water (0.225% Formic Acid)-acetonitrile]; B %: 33%-63%, 10 min followed by further purification on column: Phenomenex Gemini C18 250*50 mm*10 um; mobile phase: [water (0.05% ammonia hydroxide v/v)-acetonitrile]; B %: 28%-58%, 12 min). Compound 168 was obtained as a yellow solid. $^1$H NMR (400 MHz, Methanol-d4), € ppm, 8.64 (br d, J=2.26 Hz, 1H), 8.61 (br d, J=2.64 Hz, 1H), 8.44 (br s, 1H), 8.10 (dd, J=6.71, 2.70 Hz, 1H), 7.60-7.67 (m, 1H), 7.33 (dd, J=10.92, 9.16 Hz, 1H), 5.25-5.47 (m, 1H), 5.01 (dt, J=12.52, 6.23 Hz, 1H), 4.32-4.43 (m, 2H), 4.07-4.19 (m, 2H), 1.33 (d, J=6.27 Hz, 6H). Method 1: RT=2.88 min.; M+H=431.1.

Compounds 123, 136, 138, 146 and 159 were synthesized according to the protocol described above using the corresponding intermediate I-3, I-5, I-6, I-7 or I-8.

Example 15: 3-fluoro-N-(4-fluoro-3-(5-(3-fluoro-pyridin-2-yl)-2H-pyrazolo[3,4-b]pyridin-2-yl)phenyl)azetidine-1-carboxamide (Compound 187)

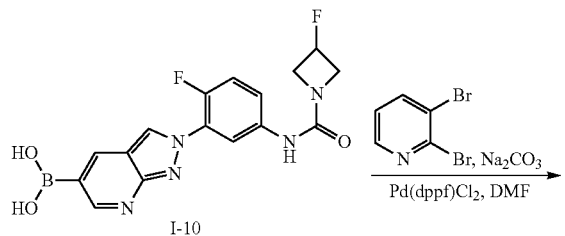

I-10

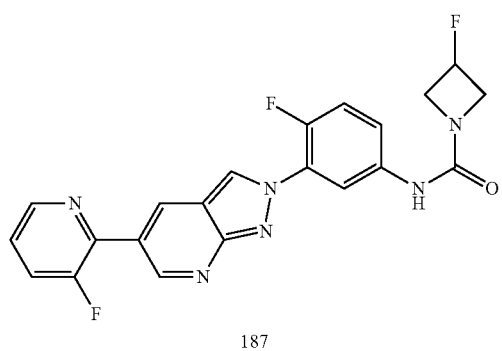

187

To a solution of intermediate I-10 (95 mg, 254.6 μmol, 1 eq) in DMF (3 mL) was added Pd(dppf)Cl₂ (18.6 mg, 25.5 μmol, 0.1 eq), Na₂CO₃ (81 mg, 763.8 μmol, 3 eq) and 2-bromo-3-fluoropyridine (89.5 mg, 509.2 μmol, 2 eq). The mixture was stirred at 90° C. for 16 hr. The reaction mixture was concentrated under reduced pressure and purified by prep-HPLC (column: Boston Green ODS 150*30 5u; mobile phase: [water (0.225% FA)-acetonitrile]; B %: 35%-65%, 10 min) to give compound 187 as a yellow solid. ¹H NMR (400 MHz, DMSO-d6) δ ppm 9.27 (s, 1H), 9.00-9.09 (m, 2H), 8.82 (s, 1H), 8.63 (br d, J=4.39 Hz, 1H), 8.29 (dd, J=6.90, 2.51 Hz, 1H), 7.93 (dd, J=10.73, 8.47 Hz, 1H), 7.72 (dt, J=8.60, 3.48 Hz, 1H), 7.52-7.58 (m, 1H), 7.46-7.51 (m, 1H), 5.28-5.55 (m, 1H), 4.25-4.44 (m, 2H), 3.93-4.14 (m, 2H). Method 1: RT=2.74 min.; M+H=425.1.

Compounds 188, 294, 295, 297, 301, 304, 312, 325, 329, 330, and 335 were synthesized according to the protocol described above using the corresponding bromides.

Example 16: 5-fluoro-N-(4-fluoro-3-(5-(pyridin-2-yl)-2H-pyrazolo[3,4-b]pyridin-2-yl)phenyl)furan-2-carboxamide (Compound 11)

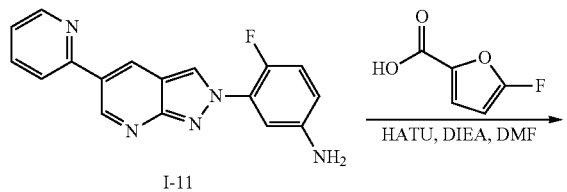

I-11

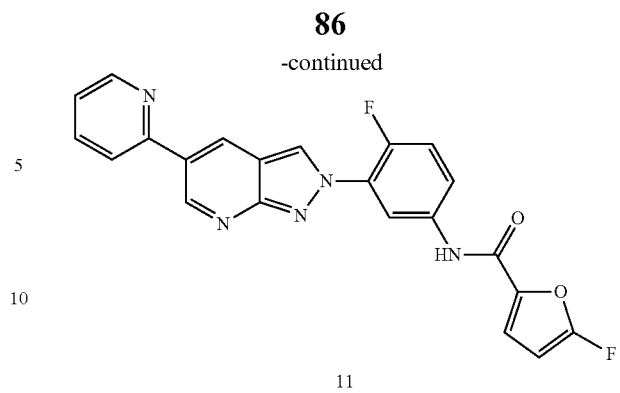

11

I-11 (40 mg, 0.131 mmol) was dissolved in 2 mL of DMF. 5-fluorofuran-2-carboxylic acid (25.6 mg, 0.20 mmol), DIEA (0.058 mL, 0.33 mmol) and HATU (50.6 mg, 0.13 mmol) were added to the reaction and the resulting mixture was stirred overnight. The reaction was diluted with EtOAc and washed 1× with sat. aq Na₂CO₃ solution and 1× with water. The organics were dried over Na2SO4 and concentrated. The crude material was purified on silica chromatography eluting with 0-100% 3:1 EtOAc:EtOH in heptanes to give compound 11. ¹H NMR (400 MHz, DMSO-d₆) δ 10.53 (s, 1H), 9.49 (d, J=2.3 Hz, 1H), 9.06 (d, J=2.6 Hz, 1H), 8.96 (d, J=2.3 Hz, 1H), 8.74 (ddd, J=4.8, 1.9, 0.9 Hz, 1H), 8.53 (dd, J=7.0, 2.7 Hz, 1H), 8.14 (dt, J=8.0, 1.1 Hz, 1H), 8.01-7.91 (m, 2H), 7.62 (dd, J=11.2, 9.1 Hz, 1H), 7.50-7.38 (m, 2H), 6.14 (dd, J=7.0, 3.7 Hz, 1H). Method 2: RT=0.91 min.; M+H=418.1.

Compounds 12, 13, 206, 218, 345, 346, 347, 348, and 349 were synthesized according to the protocol described above using the corresponding carboxylic acid.

Compound 350 was synthesized according to the protocol described above using the corresponding carboxylic acid and I-28.

Example 17: 3-fluoro-N-(4-fluoro-3-(5-(pyridin-4-yl)-2H-pyrazolo[3,4-b]pyridin-2-yl)phenyl)azetidine-1-carboxamide (Compound 182)

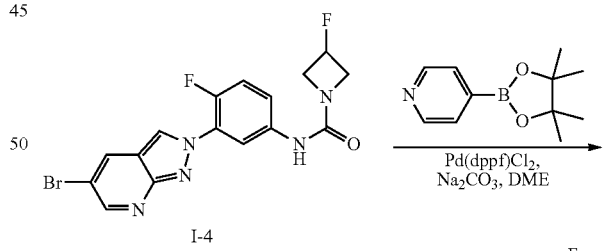

I-4

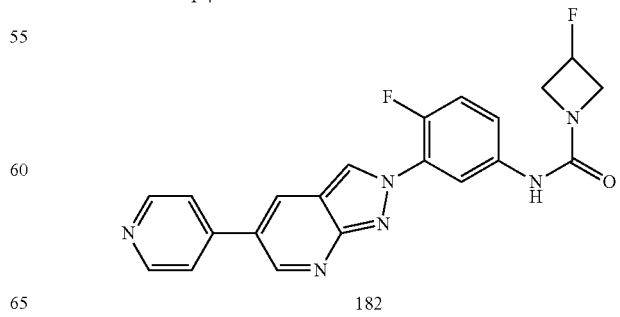

182

To a solution of I-4 (80 mg, 196 μmol, 1 eq) and 4-(4,4,5,5-tetramethyl-1,3,2-dioxaborolan-2-yl)pyridine (60.3 mg, 294 μmol, 1.5 eq) in DME (3 mL) was added Pd(dppf)Cl$_2$ (14.34 mg, 19.6 μmol, 0.1 eq) and Na$_2$CO$_3$ (2 M, 294 uL, 3 eq) under a N$_2$ atmosphere. The mixture was stirred at 90° C. for 20 hrs. The reaction mixture was concentrated and the residue was diluted with EtOAc (30 mL). The organic layer was washed with water (10 mL*2), dried over anhydrous Na$_2$SO$_4$, filtered and concentrated. The residue was purified by prep-HPLC (column: Phenomenex Gemini C18 250*50 mm*10 um; mobile phase: [water (0.05% ammonia hydroxide v/v)-acetonitrile]; B %: 18%-48%, 12 min) to give compound 182 as a white solid. $^1$H NMR (400 MHz, DMSO-d6), δ ppm, 9.17 (d, J=2.26 Hz, 1H), 9.03 (d, J=2.51 Hz, 1H), 9.00 (s, 1H), 8.75 (d, J=2.51 Hz, 1H), 8.67-8.73 (m, 2H), 8.28 (dd, J=6.90, 2.64 Hz, 1H), 7.84-7.90 (m, 2H), 7.68-7.75 (m, 1H), 7.50 (dd, J=11.29, 9.03 Hz, 1H), 5.30-5.52 (m, 1H), 4.27-4.40 (m, 2H), 3.97-4.10 (m, 2H). Method 2: RT=0.58 min.; M+H=407.1.

Compound 189 was synthesized according to the protocol described above using the corresponding boronic ester.

Example 18: (R)-3-fluoro-N-(4-fluoro-3-(5-(tetrahydro-2H-pyran-4-yl)-2H-pyrazolo[3,4-b]pyridin-2-yl)phenyl)pyrrolidine-1-carboxamide (Compound 150)

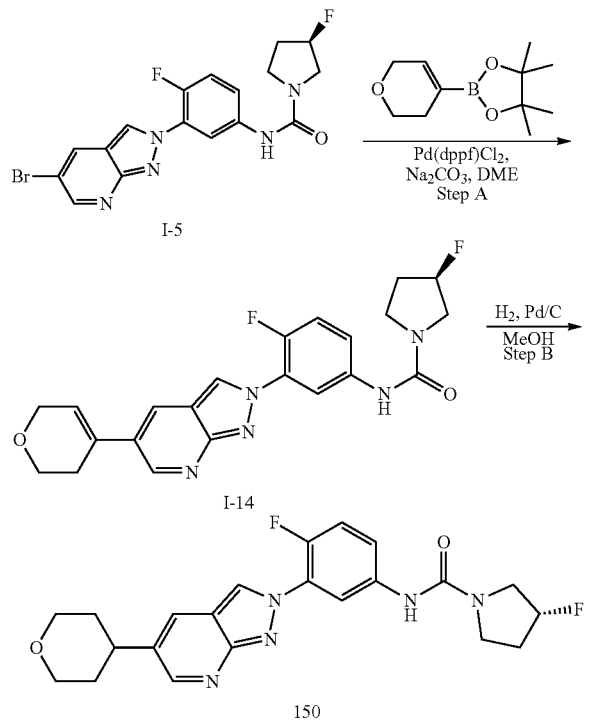

Step A:
To a mixture of 2-(3,6-dihydro-2H-pyran-4-yl)-4,4,5,5-tetramethyl-1,3,2-dioxaborolane (65.7 mg, 312.6 μmol, 1.1 eq), I-5 (120 mg, 284.2 μmol, 1 eq) and Na$_2$CO$_3$ (2 M, 426.3 uL, 3 eq) in DME (3 mL) and water (0.5 mL) under an Argon atmosphere was added Pd(dppf)Cl$_2$ (20.8 mg, 28.4 μmol, 0.1 eq). The mixture was heated to 90° C. for 4 hrs. The mixture was purified by prep-TLC eluting with 90% EtOAc in petroleum ether to give I-14 as white solid. M+H=426.2.

Step B:
To a mixture of I-14 (85 mg, 199.8 μmol, 1 eq) in methanol (10 mL) was added Pd/C (30 mg, 10% purity). The suspension was degassed under vacuum and purged with H$_2$ several times. The mixture was stirred under H$_2$ (15 psi) at 10° C. for 1 h. The mixture was filtered and the filtrate was concentrated to give a residue. The residue was purified by prep-HPLC (column: Boston Green ODS 150*30 5u; mobile phase: [water (0.225% FA)-acetonitrile]; B %: 27%-51%, 10 min) to give compound 150 as a yellow solid. $^1$H NMR (400 MHz, Methanol-d$_4$), δ ppm, 9.15 ((d, J=2.01 Hz, 1H)), 8.98 (s, 1H), 8.85 (d, J=1.88 Hz, 1H), 8.33 (dd, J=6.78, 9.16 Hz, 1H), 7.61-7.65 (m, 1H), 7.42 (dd, J=11.04, 9.16 Hz, 1H), 5.28-5.41 (m, 1H), 4.11-4.14 (m, 2H), 3.57-3.85 (m, 6H), 3.14-3.20 (m, 1H), 2.11-2.32 (m, 2H), 1.91-1.97 (m, 4H). Method 1: RT=2.60 min.; M+H=428.2.

Compounds 148, 160, 165, 169, 296, and 305 were synthesized according to the protocol described above using intermediates I-3, I-4, I-6 or I-7 and the corresponding boronic acid or boronic ester.

Compound 293 was synthesized using the protocol described above using I-4 and tert-butyl 4-(4,4,5,5-tetramethyl-1,3,2-dioxaborolan-2-yl)-3,6-dihydropyridine-1 (2H)-carboxylate after which the Boc group was removed using 1:5 ratio of TFA in DCM followed by concentration and then prep-HPLC purification (column: Phenomenex Synergi C18 150*25*10 um; mobile phase: [water (0.225% FA)-acetonitrile]; B %: 2%-22%, 10 min) to give compound 293.

Example 19: N-(3-(5-(5-azaspiro[2.3]hexan-5-yl)-2H-pyrazolo[3,4-b]pyridin-2-yl)-4-fluorophenyl)azetidine-1-carboxamide (Compound 257)

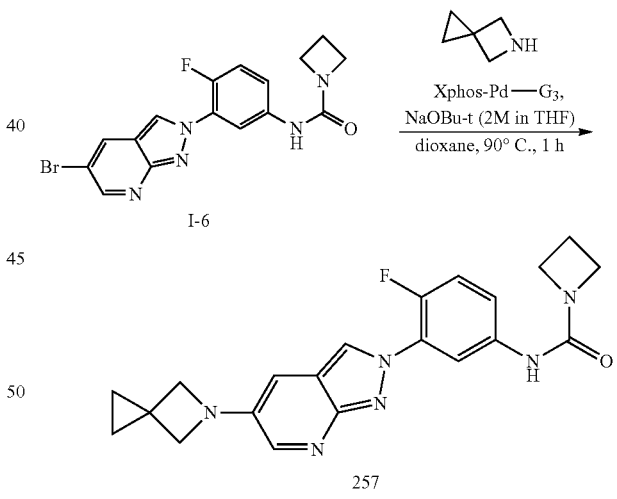

A mixture of I-6 (400 mg, 1.0 mmol, 1 eq), 5-azaspiro[2.3]hexane hemioxalate (128 mg, 1.0 mmol, 1 eq), NaOBu-t (2 M in THF, 1.5 mL, 3 eq) and Xphos Pd G3 (87 mg, 102.5 μmol, 0.1 eq) in dioxane (10 mL) was de-gassed, placed under an Argon atmosphere and heated to 90° C. for 1 hour. The reaction was quenched by addition of saturated NH$_4$Cl (40 mL). The resulting mixture was extracted by dichloromethane (30 mL×6) and the organic phase was dried over Na$_2$SO$_4$ and filtered. The filtrate was concentrated and the residue was purified by silica gel chromatography eluting with 50% MeOH in DCM followed by prep-HPLC purification (column: Phenomenex Synergi C18 150*25*10 um; mobile phase: [water (0.225% FA)-acetonitrile]; B %: 30%-60%, 10 min) to give compound 257 as a yellow solid. $^1$H NMR (400 MHz, DMSO) δ ppm 8.69 (s, 1H), 8.52 (d, J=2.63 Hz, 1H), 8.28 (d, J=2.76 Hz, 1H), 8.20 (dd, J=7.03, 2.63 Hz, 1H), 7.62-7.69 (m, 1H), 7.40 (dd, J=11.29, 9.16 Hz, 1H), 6.91 (d, J=2.76 Hz, 1H), 4.01 (s, 4H), 3.97 (t, J=7.53 Hz, 4H), 2.19 (quin, J=7.56 Hz, 2H), 0.68 (s, 4H). Method 1: RT=2.90 min.; M+H=393.2.

Compounds 233, 258, 259, and 337 were synthesized according to the protocol described above using the corresponding intermediates I-3, I-4, I-5 or I-27.

Example 20: 3-fluoro-N-(4-fluoro-3-(5-(3-(trifluoromethyl)azetidin-1-yl)-2H-pyrazolo[3,4-b]pyridin-2-yl)phenyl)azetidine-1-carboxamide (Compound 265)

Compounds 274 and 275 were synthesized according to the protocol described above using the corresponding intermediates I-5 or I-6.

Example 21: N-(2-(5-(3,3-difluoroazetidin-1-yl)-2H-pyrazolo[3,4-b]pyridin-2-yl)pyridin-4-yl)azetidine-1-carboxamide (Compound 280)

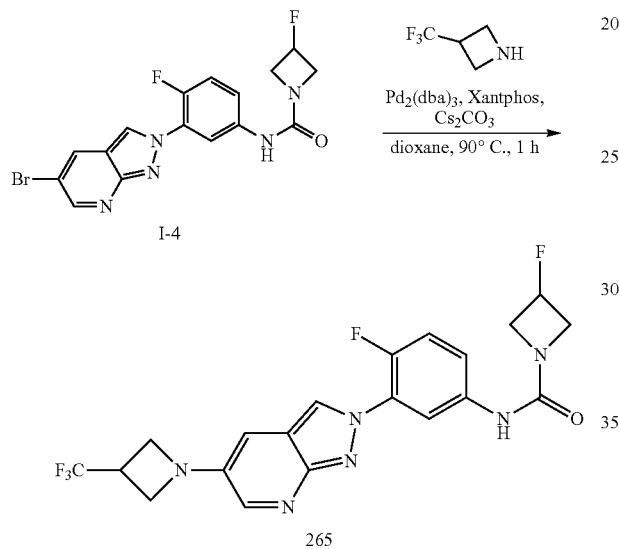

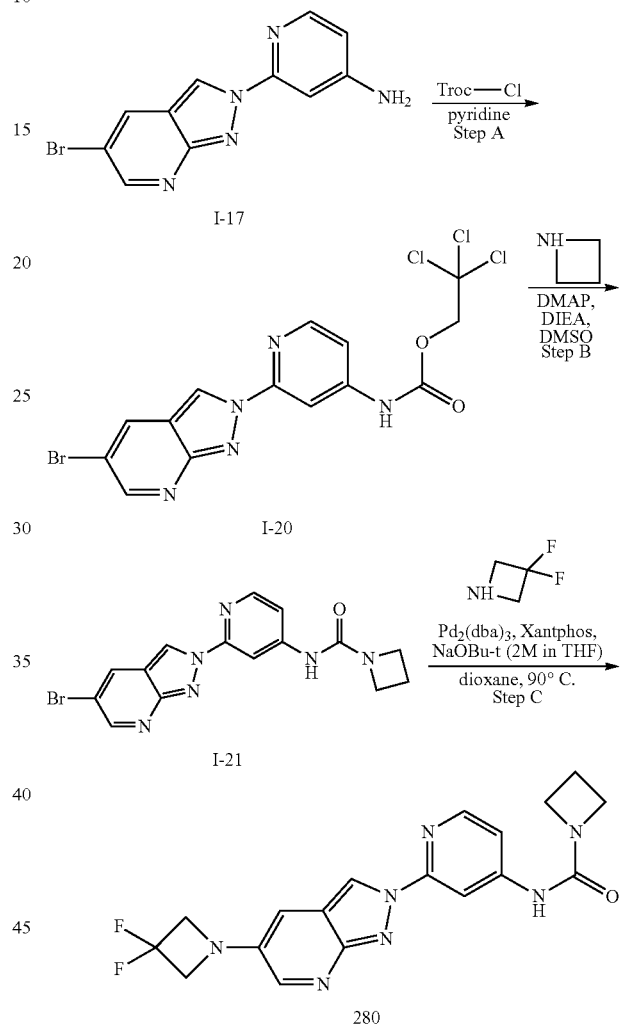

A mixture of I-4 (3.5 g, 8.6 mmol, 1 eq), 3-(trifluoromethyl)azetidine HCl salt (1.7 g, 10.3 mmol, 1.2 eq), Pd$_2$(dba)$_3$ (785 mg, 857.4 μmol, 0.1 eq), XantPhos (992 mg, 1.7 mmol, 0.2 eq) and Cs$_2$CO$_3$ (8.4 g, 25.7 mmol, 3 eq) in dioxane (60 mL) was de-gassed and then heated to 85° C. for 1.2 hr under a N$_2$ atmosphere. The reaction mixture was quenched with sat NH$_4$Cl solution (400 mL) and extracted with EtOAc (300 mL×2). The combined organic layers were washed with brine (200 mL), dried over Na$_2$SO$_4$ and concentrated. The residue was purified by to silica chromatography eluting with MeOH/Ethyl acetate/DCM=0:1:1 to 1:5:1 to give a yellow solid, which was further purified by prep HPLC; column: Phenomenex Synergi Max-RP 250*80 mm*10 um; mobile phase: [water (0.225% FA)-acetonitrile]; B %: 30%-60%, 35 min. The pH of the solution was adjusted to pH=7 by 20% NH$_3$ in H$_2$O and acetonitrile was removed under vacuo at 30° C. The resulting yellow solid was collected by filtration, washed with water 100 mL×4, and lyophilized to give compound 265 as yellow solid. $^1$H NMR (400 MHz, DMSO) δ ppm 8.93 (s, 1H), 8.58 (d, J=2.76 Hz, 1H), 8.32 (d, J=2.76 Hz, 1H), 8.20 (dd, J=7.03, 2.64 Hz, 1H), 7.65 (dd, J=7.34, 4.58 Hz, 1H), 7.44 (dd, J=11.17, 9.16 Hz, 1H), 7.03 (d, J=2.89 Hz, 1H), 5.29-5.51 (m, 1H), 4.24-4.38 (m, 2H), 4.18 (t, J=8.34 Hz, 2H), 3.95-4.10 (m, 4H), 3.65-3.85 (m, 1H). Method 1: RT=2.86 min.; M+H=453.1.

Step A:
To a solution I-17 (2.5 g, 8.6 mmol, 1 eq) in pyridine (30 mL) was added 2,2,2-trichloroethyl carbonochloridate (3.6 g, 17.2 mmol, 2.3 mL, 2 eq). The mixture was stirred at 30° C. for 22 hr. The reaction mixture was precipitated by addition water 100 mL, and then filtered. The filter cake was washed with water 50 mL and dried under reduced pressure. The precipitate was then triturated in tert-butyl methyl ether (20 mL) and collected by filtration to give I-20 as a brown solid. $^1$H NMR (400 MHz, DMSO) δ ppm 11.08 (s, 1H), 9.32 (s, 1H), 8.77 (d, J=1.71 Hz, 1H), 8.62 (d, J=1.96 Hz, 1H), 8.52 (d, J=1.71 Hz, 1H), 8.49 (d, J=3.91 Hz, 1H), 7.75 (dd, J=5.38, 1.71 Hz, 1H), 5.05 (s, 2H).

Step B:
To a solution of I-20 (1.2 g, 2.6 mmol, 1 eq) and azetidine hydrochloride (482 mg, 5.2 mmol, 2 eq) in DMSO (12 mL) was added DMAP (31 mg, 257.8 μmol, 0.10 eq) and DIEA (666 mg, 5.2 mmol, 898.0 uL, 2 eq). The mixture was stirred at 60° C. for 144 hr. The reaction mixture was precipitated by addition water 100 mL and then filtered. The filter cake was washed with water 50 mL, dried under reduced pressure to give I-21 as a brown solid. $^1$H NMR (400 MHz, DMSO) δ ppm 9.24 (s, 2H), 8.75 (d, J=20.45 Hz, 1H), 8.60 (d, J=2.20 Hz, 1H), 8.49 (d, J=1.71 Hz, 1H), 8.35 (d, J=5.62 Hz, 1H), 7.73 (dd, J=5.75, 1.83 Hz, 1H), 4.04 (br t, J=7.58 Hz, 4H), 2.23 (quin, J=7.64 Hz, 2H).

Step C:

A mixture of I-21 (180 mg, 482.3 μmol, 1 eq), 3,3-difluoroazetidine (125 mg, 964.6 μmol, 2 eq, HCl), Xant-Phos (56 mg, 96.5 μmol, 0.20 eq), Pd$_2$(dba)$_3$ (44 mg, 48.2 mol, 0.10 eq) and NaOBu-t (2 M, 964.6 uL, 4 eq) in dioxane (3 mL) was stirred at 90° C. for 16 hr under N$_2$ atmosphere. The reaction mixture was concentrated under reduced pressure to remove solvent. The residue was purified by silica chromatography eluting with 10-100% petroleum ether in Ethyl acetate to give 65 mg of a residue. The residue was triturated in MeOH (3 mL) and the solid collected by filtration to give compound 280 as a yellow solid. $^1$H NMR (400 MHz, DMSO-d6) δ ppm 9.18 (s, 1H), 8.99 (s, 1H), 8.44 (d, J=1.76 Hz, 1H), 8.36 (d, J=2.76 Hz, 1H), 8.31 (d, J=5.77 Hz, 1H), 7.67 (dd, J=5.52, 2.01 Hz, 1H), 7.14 (d, J=2.76 Hz, 1H), 4.42 (t, J=12.17 Hz, 4H), 4.04 (t, J=7.53 Hz, 4H), 2.16-2.29 (m, 2H). Method 1: RT=2.76 min.; M+H=386.0.

Compounds 282, 284, 286, 287, and 343 were synthesized according to the protocol described above using intermediates I-17, I-18, or I-19 and the corresponding amines.

Compound 340 was synthesized according to the protocol described in Step A and Step B using (R)-3-fluoropyrrolidine.

Example 22: 3,3-difluoro-N-(2-(5-(pyridin-2-yl)-2H-pyrazolo[3,4-b]pyridin-2-yl)pyridin-4-yl)azetidine-1-carboxamide (Compound 281)

Step A:

To a solution of I-20 (800 mg, 1.7 mmol, 1 eq) and 3,3-difluoroazetidine HCl salt (445 mg, 3.4 mmol, 2 eq) in DMSO (10 mL) was added DMAP (21 mg, 171.8 μmol, 0.1 eq) and DIEA (444 mg, 3.4 mmol, 598.7 uL, 2 eq). The mixture was stirred at 60° C. for 320 hr. The reaction mixture was precipitated by addition water (100 mL) and then filtered. The filter cake was washed with water 50 mL, dried under reduced pressure to give I-22 as a brown solid. $^1$H NMR (400 MHz, DMSO-d$_6$) δ ppm 9.69 (s, 1H), 9.23-9.27 (m, 1H), 8.75 (d, J=2.45 Hz, 1H), 8.61 (d, J=2.44 Hz, 1H), 8.47 (d, J=1.96 Hz, 1H), 8.41 (d, J=5.62 Hz, 1H), 7.71 (dd, J=5.62, 1.96 Hz, 1H), 4.48 (t, J=12.72 Hz, 4H).

Step B:

To a solution of I-22 (460 mg, 1.12 mmol, 1 eq) and tributyl(2-pyridyl)stannane (497 mg, 1.3 mmol, 1.2 eq) in DMF (10 mL) was added Pd(PPh$_3$)$_4$ (130 mg, 112.4 μmol, 0.1 eq) and CuI (21 mg, 112.4 μmol, 0.1 eq). The mixture was stirred at 85° C. for 16 hr under a N$_2$ atmosphere. The reaction mixture was concentrated under reduced pressure to remove solvent. The residue was purified by silica eluting with 10-100% petroleum ether in ethyl acetate to give a solid, which was triturated in DCM (3 mL). The resulting solid was collected by filtration to give compound 281 as an off-white solid. $^1$H NMR (400 MHz, DMSO-d6) δ ppm 9.70 (s, 1H), 9.47 (d, J=2.20 Hz, 1H), 9.38 (s, 1H), 8.95 (d, J=2.20 Hz, 1H), 8.71-8.77 (m, 1H), 8.49 (d, J=1.71 Hz, 1H), 8.42 (d, J=5.62 Hz, 1H), 8.12 (d, J=8.07 Hz, 1H), 7.96 (td, J=7.76, 1.83 Hz, 1H), 7.72 (dd, J=5.62, 1.96 Hz, 1H), 7.39-7.47 (m, 1H), 4.49 (t, J=12.72 Hz, 4H). Method 1: RT=2.81 min.; M+H=408.0.

Compounds 283, 285, 309, 310, 313, 315, 317, 341, 342, and 344 were synthesized according to the protocol described above using intermediate I-1, I-17, I-18 or I-19 and the corresponding amine and corresponding organotin.

Compounds 256, 332, 333, and 336 was synthesized according the protocol in Step B using I-24, I-27 or I-31 and the corresponding organotin.

Example 23: 3-fluoro-N-(4-fluoro-3-(2H-pyrazolo[3,4-b]pyridin-2-yl)phenyl)azetidine-1-carboxamide (Compound 311)

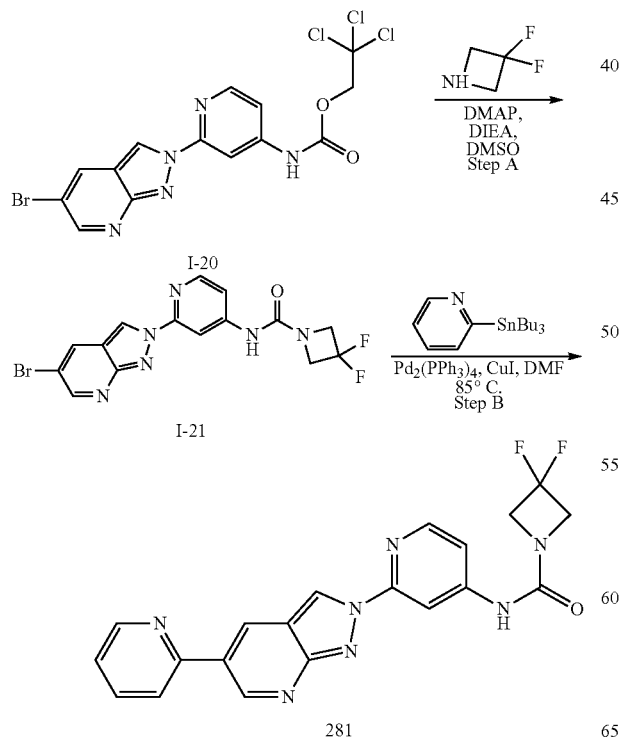

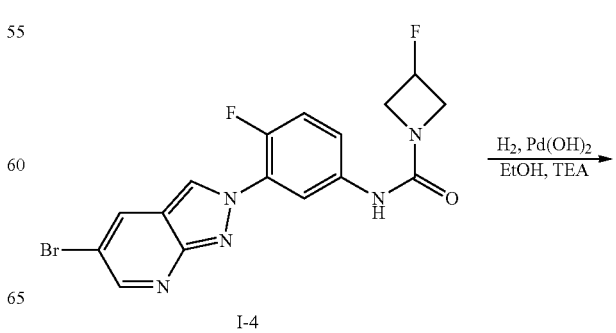

-continued

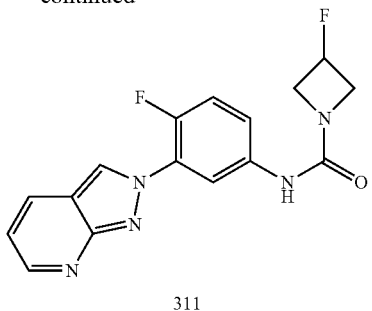

311

To a solution of I-4 (100 mg, 245 μmol, 1 eq) in EtOH (2 mL) was added TEA (25 mg, 245 μmol, 34.1 uL, 1 eq) and Pd(OH)$_2$/C (34 mg, 24.5 μmol, 10% purity, 0.1 eq) under N$_2$ atmosphere. The suspension was degassed and purged with H$_2$ 3 times. The mixture was stirred under H$_2$ (15 Psi) at 25° C. for 3 hrs. The reaction mixture was filtered and concentrated under reduced pressure to give a residue. The residue was purified by prep-HPLC (column: Luna C18 150*25*5 um; mobile phase: [water (0.225% FA)-acetonitrile]; B %: 17%-44%, 10 min) and lyophilized to give compound 311 as a white solid. $^1$H NMR (400 MHz, DMSO-d$_6$), ppm, 8.98 (s, 1H), 8.90 (d, J=2.26 Hz, 1H), 8.72 (d, J=3.01 Hz, 1H), 8.31 (d, J=8.28 Hz, 1H), 8.25 (dd, J=7.03, 2.51 Hz, 1H), 7.66-7.73 (m, 1H), 7.43-7.51 (m, 1H), 7.20 (dd, J=8.41, 4.14 Hz, 1H), 5.29-5.51 (m, 1H), 4.24-4.39 (m, 2H), 3.96-4.10 (m, 2H). Method 1: RT=2.41 min.; M+H=330.1.

Example 24: N-(3-(5-(1-acetylazetidin-2-yl)-2H-pyrazolo[3,4-b]pyridin-2-yl)-4-fluorophenyl)-3-fluoroazetidine-1-carboxamide (Compound 267)

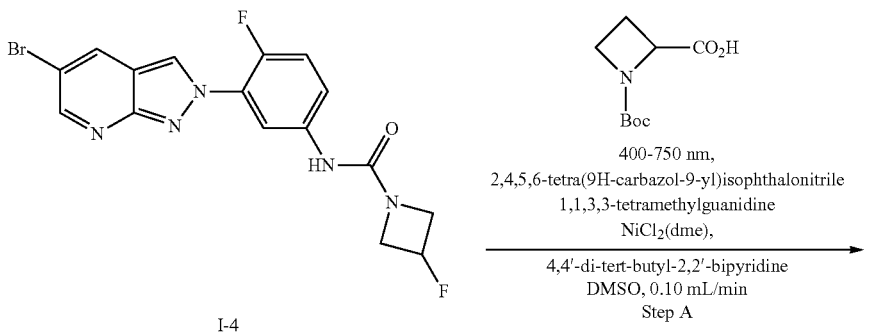

I-4

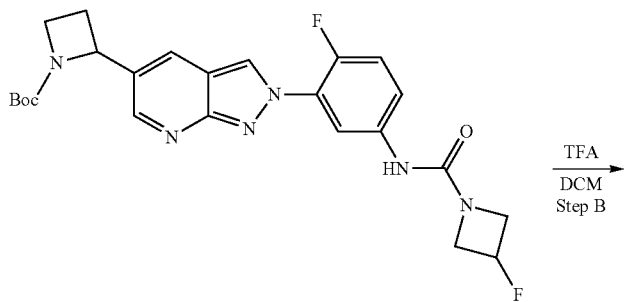

I-30

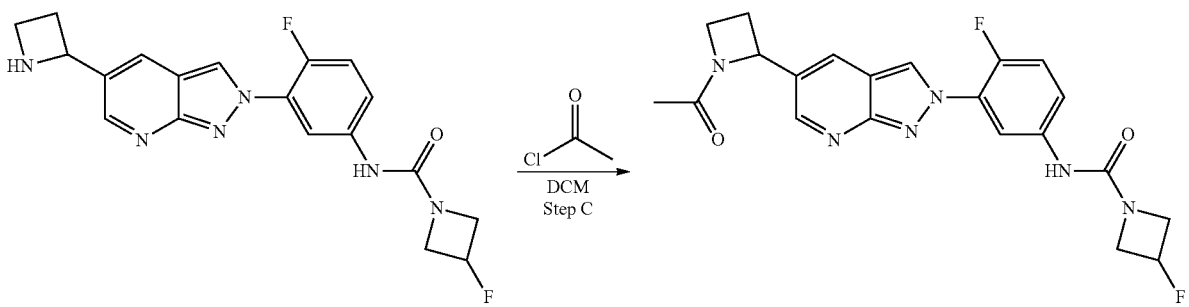

264    267

Step A:

1-(tert-butoxycarbonyl)azetidine-2-carboxylic acid (394 mg, 2 mmol), I-4 (400 mg, 1 mmol), 1,1,3,3-tetramethylguanidine (226 mg, 1.96 mmol), NiCl$_2$(dme) (22 mg, 0.1 mmol), 4,4'-di-tert-butyl-2,2'-bipyridine (26 mg, 0.1 mol) and 2,4,5,6-tetra(9H-carbazol-9-yl)isophthalonitrile (23 mg, 0.03 mmol) were dissolved in DMSO (9.8 mL) upon heating and sonication. The solution was pumped (0.10 mL/min) via photoreactor (reactor volume—0.9 mL; PFA tubing 0.04" ID, 0.0625" ID; irradiated area 20 cm$^2$; 1 cm distance to LED board; 400-750 nm LED; 8800 lm brightness) and collected in a vial. The reaction was purified by C18 flash chromatography eluting with 15-85% acetonitrile in water and concentrated. The material was further purified by silica chromatography eluting with 40-100% EtOAc in heptane to give I-30. $^1$H NMR (400 MHz, DMSO-d6) δ 8.98 (s, 1H), 8.94 (d, J=2.3 Hz, 1H), 8.71 (d, J=4.3 Hz, 1H), 8.22 (dd, J=7.0, 2.7 Hz, 1H), 7.70 (ddd, J=9.1, 4.1, 2.8 Hz, 1H), 7.48 (dd, J=11.1, 9.1 Hz, 1H), 7.13 (d, J=4.4 Hz, 1H), 5.55 (dd, J=9.0, 6.4 Hz, 1H), 5.48-5.30 (m, 1H), 4.32 (dddd, J=21.7, 10.4, 6.0, 1.4 Hz, 2H), 4.11-3.94 (m, 6H), 1.27 (s, 9H).

Step B:

I-30 (83 mg, 0.171 mmol) was dissolved in DCM (1 mL) and TFA (0.5 mL) was added. The reaction was stirred for 3 hrs and concentrated, dissolved in MeOH and purified by C18 flash chromatography eluting with 5-40% acetonitrile in water. Lyophilization gave compound 264 as a white solid. $^1$H NMR (400 MHz, DMSO-d6) δ 9.38 (s, 1H), 9.07-8.96 (m, 2H), 8.84 (d, J=4.3 Hz, 1H), 8.30 (dd, J=7.0, 2.7 Hz, 1H), 7.72-7.62 (m, 1H), 7.52 (dd, J=11.2, 9.1 Hz, 1H), 7.33 (dd, J=4.4, 1.2 Hz, 1H), 6.04 (s, 1H), 5.41 (dtt, J=57.4, 6.1, 3.1 Hz, 1H), 4.40-4.25 (m, 2H), 4.27-4.16 (m, 1H), 4.10-3.94 (m, 2H), 3.90-3.77 (m, 1H), 3.06-2.94 (m, 1H), 2.86 (dtd, J=11.7, 8.7, 4.4 Hz, 1H). Method 1: RT=1.69 min.; M+H=385.2.

Step C:

Compound 264 (20 mg, 0.052 mmol) was dissolved in DCM (Volume: 1 mL) and DIEA (0.027 mL, 0.16 mmol) and acetyl chloride (5.55 µl, 0.078 mmol) were added and stirred for 60 hrs. The reaction was purified by SFC on Princeton PPU 250×21.2 mm column eluting with 20-60% MeOH in liquid CO$_2$ to give compound 267. $^1$H NMR (400 MHz, Methanol-d4) δ 8.86 (dd, J=3.4, 2.2 Hz, 1H), 8.74 (d, J=4.4 Hz, 0.5H), 8.67 (d, J=4.5 Hz, 0.5H), 8.17 (dd, J=6.8, 2.7 Hz, 0.5H), 8.13 (dd, J=6.8, 2.7 Hz, 0.5H), 7.66 (dddd, J=8.8, 4.3, 2.7, 1.7 Hz, 1H), 7.37 (ddd, J=10.9, 9.1, 3.7 Hz, 1H), 7.28 (dd, J=4.4, 0.8 Hz, 0.5H), 7.18 (dd, J=4.5, 0.9 Hz, 0.5H), 5.93 (dd, J=9.2, 5.6 Hz, 0.5H), 5.73 (dd, J=9.3, 6.1 Hz, 0.5H), 5.37 (dtt, J=57.1, 6.1, 3.2 Hz, 1H), 4.48-4.32 (m, 3H), 4.24-4.15 (m, 2H), 4.11 (ddd, J=10.3, 3.2, 1.4 Hz, 1H), 3.05-2.91 (m, 1H), 2.34-2.21 (m, 1H), 2.03 (s, 1.5H), 1.71 (s, 1.5H). Method 2: RT=0.66 min.; M+H=427.2.

Compound 247 was synthesized according the above protocol in Step A using 1-(tert-butoxycarbonyl)pyrrolidine-2-carboxylic acid as a starting material.

Example 25: N-(4-fluoro-3-(5-(tetrahydro-2H-pyran-2-yl)-2H-pyrazolo[3,4-b]pyridin-2-yl)phenyl) azetidine-1-carboxamide (Compound 288)

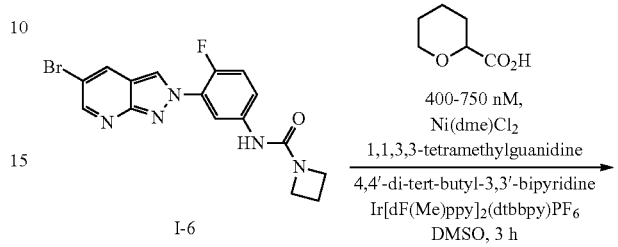

I-6 (30 mg, 0.077 mmol), Nickel(II) chloride ethylene glycol dimethyl ether complex (1.7 mg, 7.8 µmol), 1,1,3,3-tetramethyguanidine (53 mg, 0.46 mmol), 4,4'-di-tert-butyl-3,3'-bipyridine (2.1 mg, 7.7 µmol), tetrahydro-2H-pyran-2-carboxylic acid (60 mg, 0.46 mmol) and [4,4'-bis(tert-butyl)-2,2'-bipyridine]bis[3,5-difluoro-2-[5-methyl-2-pyridinyl]phenyl]iridium(III) hexafluorophosphate (3.90 mg, 3.84 µmol) were dissolved in DMSO (769 µL) upon heating and sonication. The solution was added into 0.3 mL well of 96 Teflon well-plate and irradiated for 3 hours (irradiated area 20 cm$^2$; 10 cm distance to LED board; 400-750 nm LED; 7600 lm brightness). The resulting solution was purified by prep-HPLC (Waters Atlantis T3 C18 19*50 mm*10 um column) eluting with acetonitrile (0.035% TFA) in water (0.05% TFA) to give compound 288. $^1$H NMR (400 MHz, Methanol-d4) δ 9.03 (d, J=2.2 Hz, 1H), 8.73 (d, J=4.9 Hz, 1H), 8.19 (dd, J=6.8, 2.7 Hz, 1H), 7.63 (ddd, J=9.1, 4.2, 2.7 Hz, 1H), 7.37 (dd, J=10.9, 9.1 Hz, 1H), 7.32 (dd, J=5.0, 0.9 Hz, 1H), 4.92 (ddt, J=2.7, 1.4, 0.7 Hz, 1H), 4.23 (d, J=10.3 Hz, 1H), 4.17-4.07 (m, 2H), 3.74 (td, J=11.6, 2.5 Hz, 1H), 3.37-3.32 (m, 2H), 2.33 (p, J=7.6 Hz, 2H), 2.15-1.98 (m, 2H), 1.92-1.57 (m, 4H). Method 2: RT=0.89 min.; M+H=396.0.

Compound 289 was synthesized according the above protocol in using 1,4-dioxane-2-carboxylic acid as a starting material.

Example 26A and B: (1S,2R)-2-fluoro-N-(4-fluoro-3-(5-(pyridin-2-yl)-2H-pyrazolo[3,4-b]pyridin-2-yl)phenyl)cyclopropane-1-carboxamide or (1R,2S)-2-fluoro-N-(4-fluoro-3-(5-(pyridin-2-yl)-2H-pyrazolo[3,4-b]pyridin-2-yl)phenyl)cyclopropane-1-carboxamide (Compounds 269 and 273)

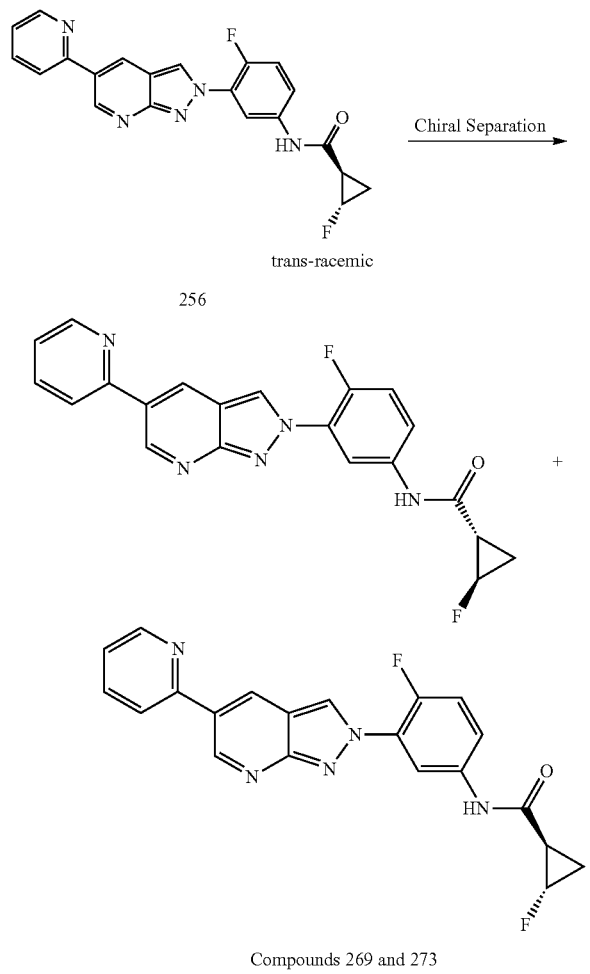

Compounds 269 and 273

Compound 256 (170 mg) was separated by SFC (column: CHIRALCEL® OJ-H (250 mm*25 mm, 10 um); mobile phase: [CO₂-MeOH (0.1% NH3H2O]; B %: 50%) to give compound 269 (peak 1, RT=5.42 min) as a yellow solid and compound 273 (peak 2, RT=6.75 min) as an off-white solid.

269 (peak 1): SFC RT: 5.42 min. ¹H NMR (400 MHz, DMSO-d6) δ ppm 10.75 (s, 1H), 9.48 (d, J=2.26 Hz, 1H), 9.03 (d, J=2.38 Hz, 1H), 8.95 (d, J=2.26 Hz, 1H), 8.74 (d, J=4.14 Hz, 1H), 8.39 (dd, J=6.96, 2.57 Hz, 1H), 8.13 (d, J=8.03 Hz, 1H), 7.96 (td, J=7.75, 1.69 Hz, 1H), 7.65-7.74 (m, 1H), 7.57 (dd, J=11.11, 9.10 Hz, 1H), 7.42 (dd, J=7.22, 5.21 Hz, 1H), 4.78-5.06 (m, 1H), 2.26-2.35 (m, 1H), 1.49-1.66 (m, 1H), 1.24-1.33 (m, 1H). Method 1: RT=2.80 min.; M+H=392.2.

273 (peak 2): SFC RT: 6.75 min. ¹H NMR (400 MHz, DMSO-d6) δ ppm 10.75 (s, 1H), 9.48 (d, J=2.08 Hz, 1H), 9.03 (d, J=2.32 Hz, 1H), 8.95 (d, J=2.20 Hz, 1H), 8.74 (d, J=4.52 Hz, 1H), 8.40 (dd, J=7.03, 2.51 Hz, 1H), 8.13 (d, J=8.07 Hz, 1H), 7.96 (td, J=7.79, 1.77 Hz, 1H), 7.69 (dt, J=8.47, 3.53 Hz, 1H), 7.57 (dd, J=11.00, 9.17 Hz, 1H), 7.42 (dd, J=7.09, 5.14 Hz, 1H), 4.80-5.05 (m, 1H), 2.25-2.34 (m, 1H), 1.48-1.67 (m, 1H), 1.28 (dq, J=13.13, 6.67 Hz, 1H). Method 1: RT=2.82 min.; M+H=392.2.

Example 27A and B: (1S,2R)—N-(3-(5-(3,3-difluoroazetidin-1-yl)-2H-pyrazolo[3,4-b]pyridin-2-yl)-4-fluorophenyl)-2-fluorocyclopropane-1-carboxamide or (1R,2S)—N-(3-(5-(3,3-difluoroazetidin-1-yl)-2H-pyrazolo[3,4-b]pyridin-2-yl)-4-fluorophenyl)-2-fluorocyclopropane-1-carboxamide (Compounds 268 and 271)

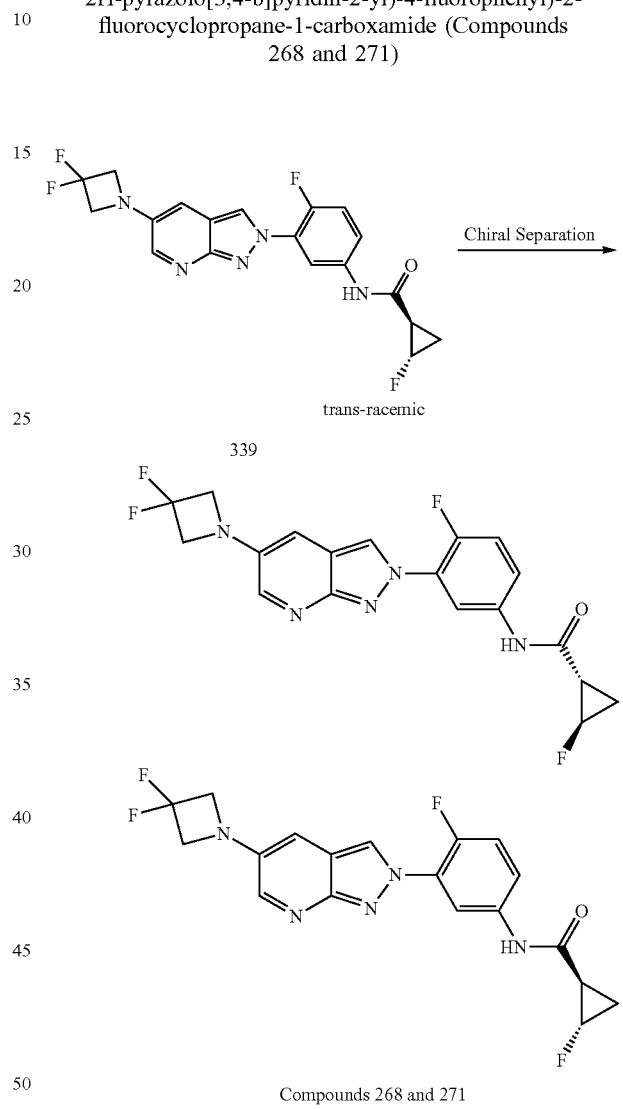

Compounds 268 and 271

Compound 339 (130 mg) was separated by SFC (column: CHIRALCEL® OD-H (250 mm*25 mm, 10 um); mobile phase: [CO₂-MeOH (0.1% NH3H2O]; B %: 50%) to give compound 271 (peak 1, RT=4.58 min) as a yellow solid and compound 268 (peak 2, RT=8.01 min) as a yellow solid.

268 (peak 2): SFC RT: 8.01 min. ¹H NMR (400 MHz, DMSO-d6) δ ppm 10.69 (s, 1H), 8.64 (d, J=2.69 Hz, 1H), 8.37 (d, J=2.81 Hz, 1H), 8.32 (dd, J=7.03, 2.51 Hz, 1H), 7.61-7.67 (m, 1H), 7.52 (dd, J=11.19, 9.11 Hz, 1H), 7.15 (d, J=2.81 Hz, 1H), 4.80-5.03 (m, 1H), 4.41 (t, J=12.29 Hz, 4H), 2.24-2.33 (m, 1H), 1.46-1.67 (m, 1H), 1.27 (dd, J=13.27, 6.54 Hz, 1H).

Method 1: RT=2.89 min.; M+H=406.0.

271 (peak 1): SFC RT: 4.58 min. ¹H NMR (400 MHz, DMSO-d6) δ ppm 10.75 (s, 1H), 8.70 (d, J=2.69 Hz, 1H), 8.43 (d, J=2.81 Hz, 1H), 8.38 (dd, J=6.97, 2.57 Hz, 1H), 7.66-7.77 (m, 1H), 7.52-7.63 (m, 1H), 7.20 (d, J=2.81 Hz, 1H), 4.85-5.08 (m, 1H), 4.47 (t, J=12.23 Hz, 4H), 2.27-2.39 (m, 1H), 1.52-1.72 (m, 1H), 1.33 (dq, J=13.11, 6.43 Hz, 1H). Method 1: RT=2.89 min.; M+H=406.0.

Example 28: N-(4-fluoro-3-(5-(3-methylpyridin-2-yl)-2H-pyrazolo[3,4-b]pyridin-2-yl)phenyl)-4-(hydroxymethyl)-2-methyloxazole-5-carboxamide (Compound 277)

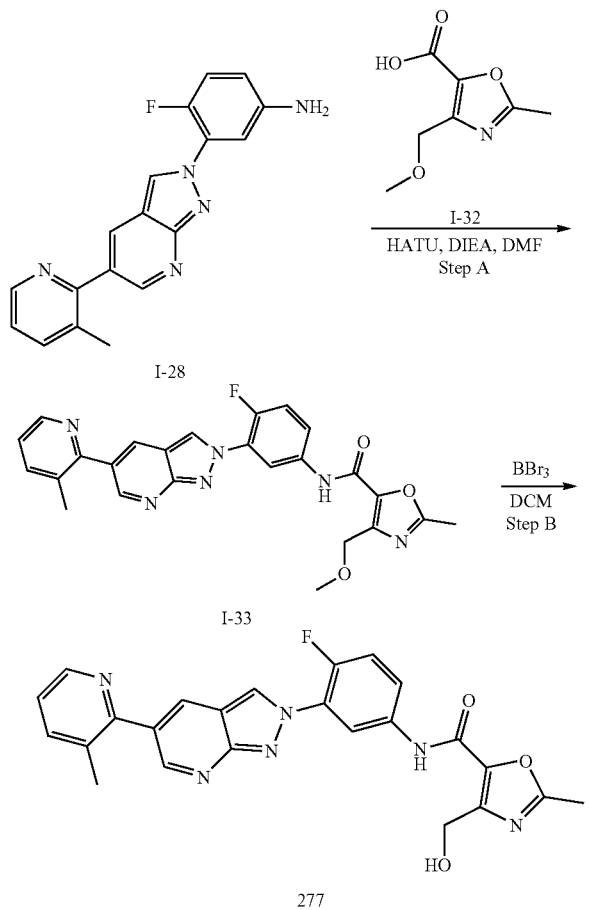

Step A:
Intermediate I-33 was prepared in a similar manner to Example 12 using I-28 and I-32 as starting materials. ¹H NMR (400 MHz, DMSO-d₆) δ ppm 10.70 (s, 1H), 9.04 (d, J=2.45 Hz, 1H), 8.95 (d, J=2.20 Hz, 1H), 8.60-8.66 (m, 2H), 8.55 (d, J=2.20 Hz, 1H), 7.89-7.96 (m, 2H), 7.62 (dd, J=11.00, 9.29 Hz, 1H), 7.44-7.52 (m, 1H), 4.64 (s, 2H), 3.31 (s, 3H), 2.57 (s, 3H), 2.46 (s, 3H). M+H=473.0.

Step B:
To a solution of I-33 (15 mg, 28.9 μmol, 1 eq, FA) in DCM (1 mL) was added dropwise BBr₃ (14.5 mg, 57.9 μmol, 5.6 uL, 2 eq) in DCM (0.5 mL) at −78° C. The mixture was stirred at 20° C. for 18 hr under a N₂ atmosphere. Saturated NaHCO₃ (3 mL) was added and the mixture was extracted with DCM (10 mL). The organic layer was dried over Na₂SO₄, filtered and concentrated under reduced pressure to give a residue. The residue was purified by prep-HPLC (column: Phenomenex Gemini 150*25 mm*10 um; mobile phase: [water (0.05% ammonia hydroxide v/v)-acetonitrile]; B %: 30%-60%, 12 min) and lyophilized to give compound 277 as a white solid. ¹H NMR (400 MHz, DMSO-d6) δ ppm 9.00 (d, J=2.20 Hz, 1H), 8.94 (d, J=1.96 Hz, 1H), 8.53-8.63 (m, 2H), 8.51 (d, J=2.20 Hz, 1H), 7.85-7.95 (m, 1H), 7.81 (br d, J=7.34 Hz, 1H), 7.55-7.67 (m, 1H), 7.37 (dd, J=7.46, 4.77 Hz, 1H), 4.69 (s, 2H), 2.55 (s, 3H), 2.45 (s, 3H). Method 1: RT=2.50 min.; M+H=459.0.

Example 29: N-(4-fluoro-3-(5-(3-methylpyridin-2-yl)-2H-pyrazolo[3,4-b]pyridin-2-yl)phenyl)-2-(hydroxymethyl)-4-methyloxazole-5-carboxamide (Compound 334)

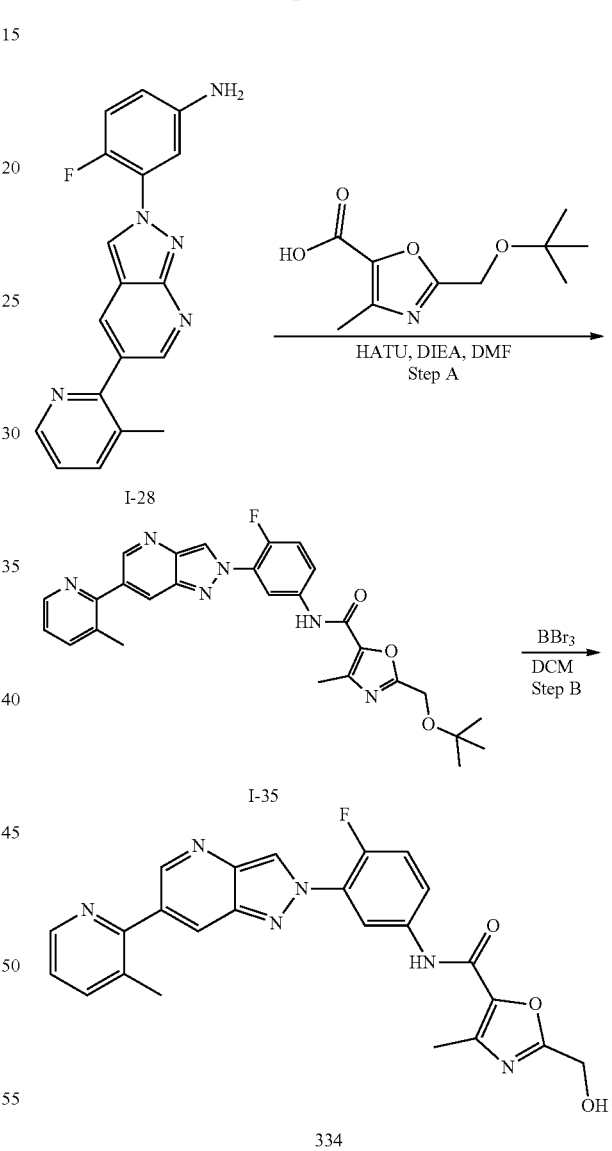

Step A:
Intermediate I-35 was prepared in a similar manner to Example 12 using I-28 and 2-(tert-butoxymethyl)-4-methyloxazole-5-carboxylic acid as starting materials. ¹H NMR (400 MHz, DMSO-d₆) δ ppm 10.55-10.67 (m, 1H) 9.00 (d, J=2.45 Hz, 1H) 8.91-8.97 (m, 1H) 8.54-8.65 (m, 2H) 8.47-8.53 (m, 1H) 7.96 (s, 1H) 7.80 (dd, J=7.70, 0.86 Hz, 1H) 7.55-7.65 (m, 1H) 7.37 (dd, J=7.70, 4.77 Hz, 1H) 4.54 (s, 2H) 2.69 (s, 3H) 2.44 (s, 3H) 1.24 (s, 9H).

Step B:

To a solution of I-35 (70 mg, 136.04 µmol, 1 eq) in DCM (2 mL) was added TFA (0.5 mL, 6.75 mmol, 49.6 eq). The mixture was stirred at 25° C. for 3 hr. The reaction mixture was concentrated under reduced pressure to remove solvent. The pH was adjusted to 7 with TEA. The residue was purified by prep-HPLC (column: Phenomenex Gemini 150*25 mm*10 um; mobile phase: [water (0.05% ammonia hydroxide v/v)-acetonitrile]; B %: 20%-50%, 12 min) and lyophilized to give compound 334 as a white solid. $^1$H NMR (400 MHz, DMSO-d6) δ ppm, 10.63 (s, 1H), 9.00 (d, J=2.20 Hz, 1H), 8.94 (d, J=2.20 Hz, 1H), 8.62 (dd, J=7.09, 2.45 Hz, 1H), 8.57 (d, J=3.67 Hz, 1H), 8.51 (d, J=2.20 Hz, 1H), 7.91-8.01 (m, 1H), 7.81 (d, J=7.34 Hz, 1H), 7.60 (dd, J=11.00, 9.05 Hz, 1H), 7.37 (dd, J=7.70, 4.77 Hz, 1H), 5.83 (t, J=5.99 Hz, 1H), 4.60 (d, J=6.11 Hz, 2H), 2.45 (s, 6H). Method 1: RT=2.57 min.; M+H=459.0.

Example 30: 3,3-difluoro-N-(4-fluoro-3-(5-(pyridin-2-yl)-2H-pyrazolo[3,4-b]pyridin-2-yl)phenyl)azetidine-1-carboxamide (Compound 39)

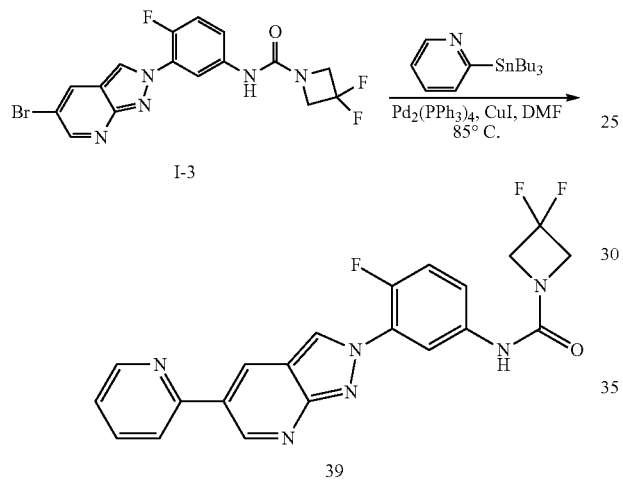

To a solution of I-3 (3.00 g, 7.04 mmol, 1 eq) and tributyl(2-pyridyl)stannane (3.4 g, 9.1 mmol, 1.3 eq) in DMF (40 mL) was added Pd(PPh$_3$)$_4$ (813 mg, 703.9 mol, 0.1 eq) and CuI (134 mg, 703.9 µmol, 0.1 eq) under a N$_2$ atmosphere. The mixture was stirred at 85° C. for 2 hr. The reaction mixture was concentrated under reduced pressure to remove solvent. The residue was purified by silica chromatography eluting with petroleum ether/Ethyl acetate=2:1 to 0:1 to give compound 39 as a white solid. $^1$H NMR (400 MHz, Methanol-d4) δ 9.36 (d, J=2.3 Hz, 1H), 9.00-8.93 (m, 2H), 8.79-8.75 (m, 1H), 8.26 (dd, J=6.8, 2.7 Hz, 1H), 8.19-8.14 (m, 2H), 7.70-7.64 (m, 1H), 7.64-7.56 (m, 1H), 7.46-7.35 (m, 1H), 4.44 (td, J=12.3, 3.0 Hz, 4H). Method 2: RT=0.99 min.; M+H=425.0.

Example 31: 3,3-difluoro-N-(4-fluoro-3-(5-phenyl-2H-pyrazolo[3,4-b]pyridin-2-yl)phenyl)azetidine-1-carboxamide (Compound 353)

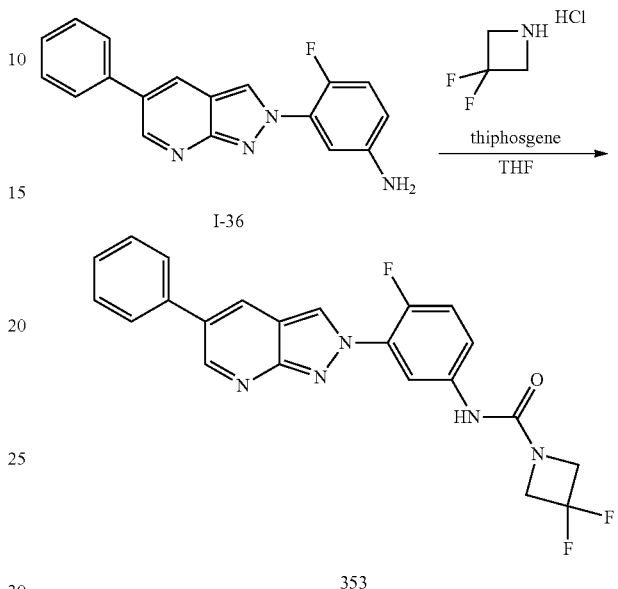

To a stirred solution of triphosgene (23 mg, 0.079 mmol) in dry THF (1 mL) was added I-36 (40 mg, 0.131 mmol) in dry THF (2 mL) at −5° C.-0° C. and stirred at RT for 10 min. 3,3-difluoroazetidine hydrochloride (34 mg, 0.263 mmol) and DIEA (51 mg, 0.394 mmol) in dry THF (2 mL) were added dropwise at 0° C. and the reaction was stirred at RT for 1 h. The reaction mixture was quenched with saturated NH4Cl solution and extracted with EtOAc (50 mL×2). The combined organic layers were washed with water (20 mL), brine (10 mL) and dried over sodium sulphate and concentrated in vacuo. The crude compound was purified by silica gel chromatography eluting with 50% EtOAc in n-Hexane to afford compound 353 as an off-white solid. 1H NMR (400 MHz, DMSO-d6) 9.25 (s, 1H), 9.06-9.05 (d, J=2.8, 1H), 8.96-8.95 (d, J=2.0, 1H), 8.52-8.51 (d, J=2.4, 1H), 8.27-8.25 (m, 1H), 7.80-7.78 (d, J=7.2, 2H), 7.72-7.67 (m, 1H), 7.56-7.48 (m, 3H), 7.44-7.41 (m, 1H), 4.44-4.38 (t, J=16.4, 4H).

Table 2 lists compounds prepared according to the Examples above.

TABLE 2

| Cpd No. | Structure | $^1$HNMR and HPLC retention time and/or MS |
|---|---|---|
| 1 | ![structure] | $^1$H NMR (400 MHz, Methanol-d$_4$) δ 8.90 (dd, J = 13.2, 2.3 Hz, 2H), 8.59-8.43 (m, 3H), 7.97-7.81 (m, 2H), 7.55-7.35 (m, 2H), 2.56 (s, 3H), 2.48-2.45 (m, 6H). Method 1: RT = 2.69 min; M + H = 443.1 |

TABLE 2-continued

| Cpd No. | Structure | ¹HNMR and HPLC retention time and/or MS |
|---|---|---|
| 2 | 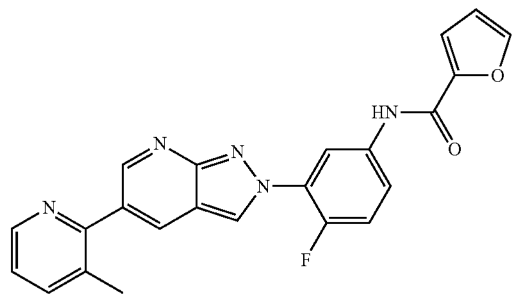 [SMILES: Cc1cccnc1-c1cnc2nn(-c3cc(NC(=O)c4ccco4)ccc3F)cc2c1] | ¹H NMR (400 MHz, Methanol-d4) δ 8.92 (d, J = 2.4 Hz, 1H), 8.88 (d, J = 2.2 Hz, 1H), 8.55-8.45 (m, 3H), 7.96 (m, 1H), 7.87 (m, 1H), 7.78 (m, 1H), 7.52-7.39 (m, 2H), 7.32 (m, 1H), 6.68 (m, 1H), 2.46 (s, 3H). Method 2: RT = 0.89 min.; M + H = 414.3 |
| 3 | 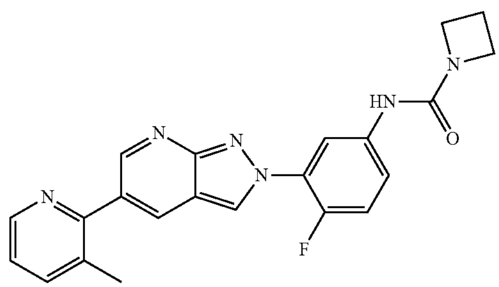 [SMILES: Cc1cccnc1-c1cnc2nn(-c3cc(NC(=O)N4CCC4)ccc3F)cc2c1] | ¹H NMR (400 MHz, Methanol-$d_4$) δ 8.89-8.84 (m, 2H), 8.52 (m, 1H), 8.48 (m, 1H), 8.18 (m, 1H), 7.86 (m, 1H), 7.67 (m, 1H), 7.44-7.32 (m, 2H), 4.18-4.06 (m, 4H), 2.46 (s, 3H), 2.41-2.26 (m, 2H). Method 1: RT = 2.41 min.; M + H = 403.3 |
| 4 | 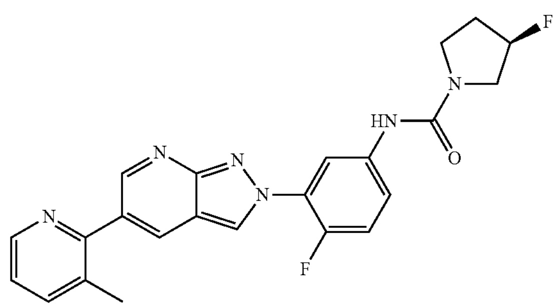 [SMILES: Cc1cccnc1-c1cnc2nn(-c3cc(NC(=O)N4CC[C@@H](F)C4)ccc3F)cc2c1] | ¹H NMR (400 MHz, Methanol-$d_4$) δ 8.87 (dd, J = 4.7, 2.3 Hz, 2H), 8.52 (m, 1H), 8.49 (m, 1H), 8.19 (m, 1H), 7.86 (m, 1H), 7.67(m, 1H), 7.45-7.34 (m, 2H), 5.42-5.25 (m, 1H), 3.85-3.55 (m, 4H), 2.46 (s, 3H), 2.39-2.19 (m, 2H). Method 1: RT = 2.41 min.; M + H = 435.3 |
| 5 | 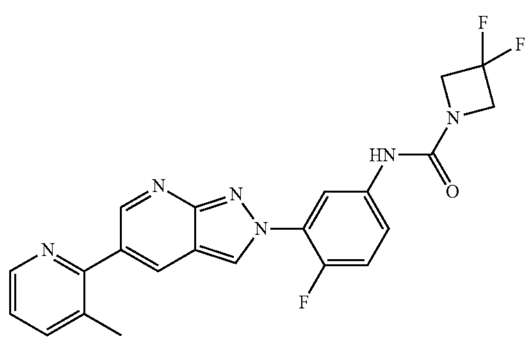 [SMILES: Cc1cccnc1-c1cnc2nn(-c3cc(NC(=O)N4CC(F)(F)C4)ccc3F)cc2c1] | ¹H NMR (400 MHz, Methanol-$d_4$) δ 8.88 (dd, J = 5.4, 2.3 Hz, 2H), 8.52 (m, 1H), 8.48 (m, 1H), 8.22 (m, 1H), 7.86 (m, 1H), 7.69 (m, 1H), 7.45-7.36 (m, 2H), 4.44 (m, 4H), 2.46 (s, 3H). Method 2: RT = 0.76 min.; M + H = 439.1 |
| 6 | 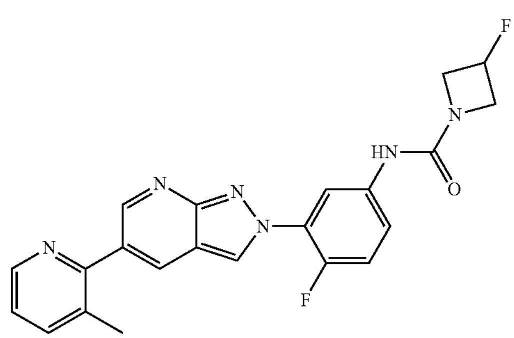 [SMILES: Cc1cccnc1-c1cnc2nn(-c3cc(NC(=O)N4CC(F)C4)ccc3F)cc2c1] | ¹H NMR (500 MHz, DMSO-d6) δ 8.98 (s, 1H), 8.94 (dd, J = 16.9, 2.3 Hz, 2H), 8.57 (ddd, J = 4.8, 1.7, 0.7 Hz, 1H), 8.49 (d, J = 2.3 Hz, 1H), 8.28 (dd, J = 7.0, 2.7 Hz, 1H), 7.80 (ddd, J = 7.7, 1.7, 0.8 Hz, 1H), 7.72 (ddd, J = 9.1, 4.1, 2.7 Hz, 1H), 7.49 (dd, J = 11.2, 9.1 Hz, 1H), 7.37 (dd, J = 7.7, 4.7 Hz, 1H), 5.41 (dtt, J = 57.5, 6.1, 3.1 Hz, 1H), 4.34 (dddd, J = 21.7, 10.4, 6.0, 1.4 Hz, 2H), 4.04 (dddd, J = 24.9, 10.4, 3.1, 1.4 Hz, 2H), 2.44 (s, 3H). Method 1: RT = 2.39 min.; M + H = 421.1 |

TABLE 2-continued

| Cpd No. | Structure | ¹HNMR and HPLC retention time and/or MS |
|---|---|---|
| 7 | 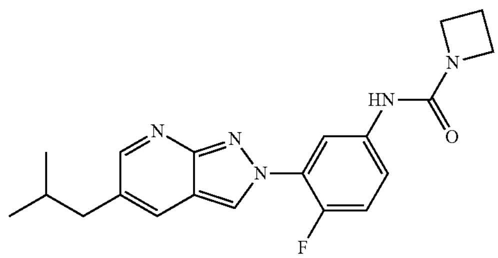 [SMILES: CC(C)Cc1cnc2nn(-c3cc(NC(=O)N4CCC4)ccc3F)cc2c1] | ¹H NMR (400 MHz, Methanol-d₄) δ 8.66 (d, J = 2.4 Hz, 1H), 8.56 (d, J = 2.2 Hz, 1H), 8.12 (m, 1H), 8.07 (m, 1H), 7.64 (m, 1H), 7.34 (m, 1H), 4.19-4.01 (m, 4H), 2.67 (m, 2H), 2.41-2.24 (m, 2H), 1.97 (m, 1H), 0.99 (m, 6H). Method 1: RT = 3.11 min.; M + H = 368.3 |
| 8 | 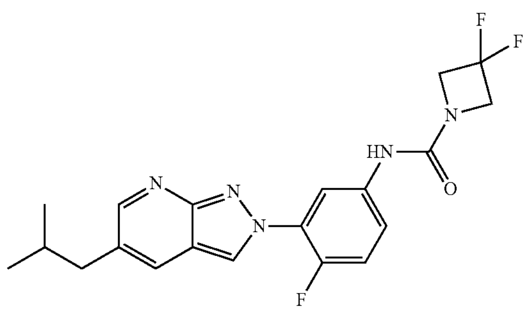 [SMILES: CC(C)Cc1cnc2nn(-c3cc(NC(=O)N4CC(F)(F)C4)ccc3F)cc2c1] | ¹H NMR (400 MHz, Methanol-d₄) δ 8.59 (d, J = 2.5 Hz, 1H), 8.46 (d, J = 2.2 Hz, 1H), 8.06 (m, 1H), 7.97 (m, 1H), 7.56 (m, 1H), 7.30-7.24 (m, 1H), 4.33 (m, 4H), 2.57 (m, 2H), 1.92-1.81 (m, 1H), 0.89 (m, 6H). Method 2: RT = 1.09 min. M + H = 404.1 |
| 9 | 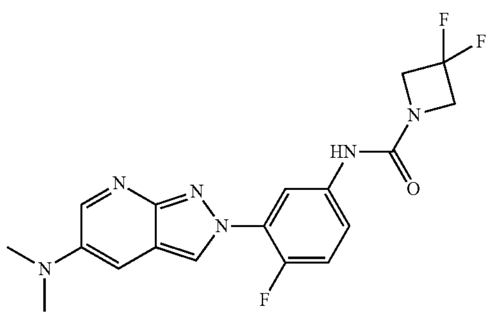 [SMILES: CN(C)c1cnc2nn(-c3cc(NC(=O)N4CC(F)(F)C4)ccc3F)cc2c1] | ¹H NMR (400 MHz, DMSO-d6) δ 9.18 (s, 1 H), 8.70 (d, J = 3.01 Hz, 1 H), 8.55 (d, J = 2.76 Hz, 1 H), 8.20 (dd, J = 6.90, 2.64 Hz, 1 H), 7.56-7.78 (m, 1 H), 7.45 (dd, J = 11.42, 9.16 Hz, 1 H), 7.15 (d, J = 3.01 Hz, 1 H), 4.41 (t, J = 12.67 Hz, 4 H), 2.95 (s, 6 H). Method 1: RT = 2.84 min.; M + H = 391.1 |
| 10 | 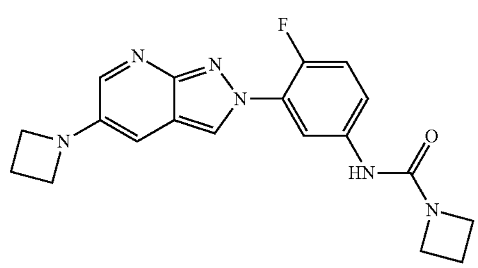 [SMILES: O=C(Nc1ccc(F)c(-n2cc3cc(N4CCC4)cnc3n2)c1)N1CCC1] | ¹H NMR (400 MHz, Methanol-d₄), δ 8.42 (d, J = 2.51 Hz, 1 H), 8.22 (d, J = 2.76 Hz, 1 H), 8.05 (dd, J = 6.78, 2.76 Hz, 1 H), 7.58-7.62 (m, 1 H), 7.30 (dd, J = 11.04, 9.16 Hz, 1 H), 7.01 (d, J = 2.64 Hz, 1 H), 4.10 (t, J = 7.65 Hz, 4 H), 3.99 (t, J = 7.22 Hz, 4 H), 2.41-2.49 (m, 2 H), 2.27-2.35 (m, 2 H). Method 1: RT = 2.80 min.; M + H = 367.1 |
| 11 | 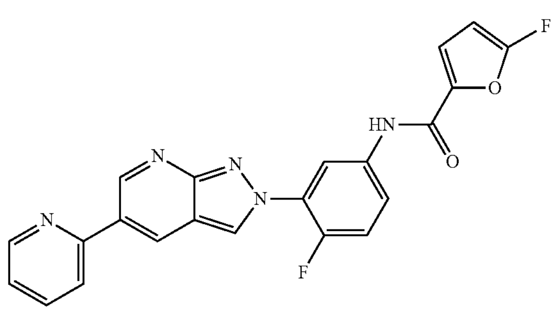 [SMILES: O=C(Nc1ccc(F)c(-n2cc3cc(-c4ccccn4)cnc3n2)c1)c1ccc(F)o1] | ¹H NMR (400 MHz, DMSO-d₆) δ 10.53 (s, 1H), 9.49 (d, J = 2.3 Hz, 1H), 9.06 (d, J = 2.6 Hz, 1H), 8.96 (d, J = 2.3 Hz, 1H), 8.74 (ddd, J = 4.8, 1.9, 0.9 Hz, 1H), 8.53 (dd, J = 7.0, 2.7 Hz, 1H), 8.14 (dt, J = 8.0, 1.1 Hz, 1H), 8.01-7.91 (m, 2H), 7.62 (dd, J = 11.2, 9.1 Hz, 1H), 7.50-7.38 (m, 2H), 6.14 (dd, J = 7.0, 3.7 Hz, 1H). Method 2: RT = 0.91 min.; M + H = 418.1 |

TABLE 2-continued

| Cpd No. | Structure | ¹HNMR and HPLC retention time and/or MS |
|---|---|---|
| 12 | 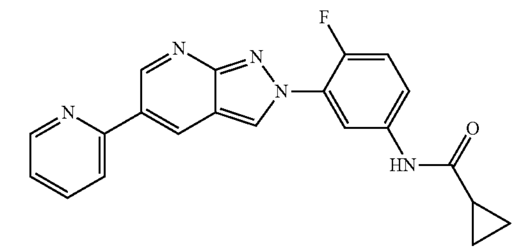 [SMILES: O=C(Nc1ccc(F)c(-n2cc3cc(-c4ccccn4)cnc3n2)c1)C1CC1] | ¹H NMR (400 MHz, DMSO-d₆) δ 10.59 (s, 1H), 9.48 (d, J = 2.3 Hz, 1H), 9.03 (d, J = 2.5 Hz, 1H), 8.95 (d, J = 2.3 Hz, 1H), 8.74 (ddd, J = 4.8, 1.9, 0.9 Hz, 1H), 8.42 (dd, J = 7.0, 2.7 Hz, 1H), 8.13 (dt, J = 8.1, 1.0 Hz, 1H), 7.96 (td, J = 7.7, 1.9 Hz, 1H), 7.73 (ddd, J = 9.0, 4.2, 2.7 Hz, 1H), 7.55 (dd, J = 11.2, 9.1 Hz, 1H), 7.42 (ddd, J = 7.5, 4.8, 1.0 Hz, 1H), 3.17 (d, J = 5.3 Hz, 1H), 0.85 (d, J = 5.9 Hz, 4H). Method 1: RT = 2.74 min.; M + H = 374.1 |
| 13 | 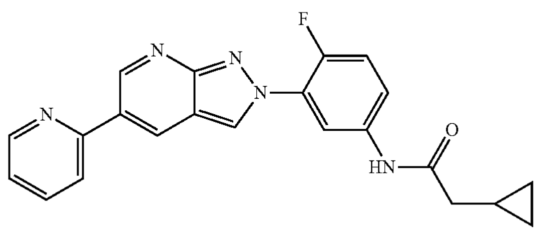 [SMILES: O=C(CC1CC1)Nc1ccc(F)c(-n2cc3cc(-c4ccccn4)cnc3n2)c1] | ¹H NMR (400 MHz, DMSO-d₆) δ 9.99 (s, 1H), 9.26 (d, J = 2.3 Hz, 1H), 8.82 (d, J = 2.5 Hz, 1H), 8.73 (d, J = 2.4 Hz, 1H), 8.52 (ddd, J = 4.8, 1.8, 1.0 Hz, 1H), 8.22 (dd, J = 7.1, 2.7 Hz, 1H), 7.91 (dt, J = 8.0, 1.1 Hz, 1H), 7.74 (td, J = 7.7, 1.8 Hz, 1H), 7.52 (ddd, J = 9.0, 4.2, 2.7 Hz, 1H), 7.34 (dd, J = 11.2, 9.1 Hz, 1H), 7.21 (ddd, J = 7.5, 4.8, 1.0 Hz, 1H), 2.04 (d, J = 7.0 Hz, 2H), 0.92-0.80 (m, 1H), 0.37-0.22 (m, 2H), 0.01 (dd, J = 4.8, 1.6 Hz, 2H). Method 1: RT = 2.80 min.; M + H = 388.1 |
| 14 | 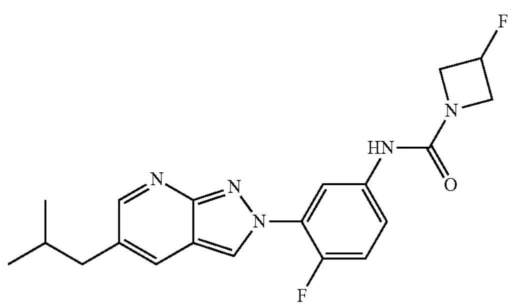 [SMILES: CC(C)Cc1cnc2nn(-c3cc(NC(=O)N4CC(F)C4)ccc3F)cc2c1] | ¹H NMR (400 MHz, Methanol-d4) δ 8.67 (m, 1H), 8.56 (m, 1H), 8.13 (m, 1H), 8.08-8.04 (m, 1H), 7.65 (m, 1H), 7.35 (m, 1H), 5.44-5.30 (m, 1H), 4.39 (m, 2H), 4.14 (m, 2H), 2.67 (m, 2H), 1.97 (m, 1H), 0.99 (m, 6H). Method 1: RT = 3.15 min.; M + H = 386.1 |
| 15 | 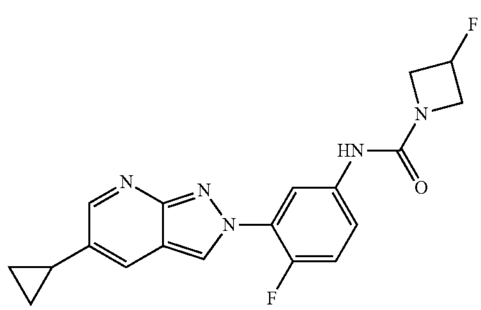 [SMILES: O=C(Nc1ccc(F)c(-n2cc3cc(C4CC4)cnc3n2)c1)N1CC(F)C1] | ¹H NMR (400 MHz, Methanol-d4) δ 8.61 (m, 2H), 8.12 (m, 1H), 7.92 (m, 1H), 7.64 (m, 1H), 7.35 (m, 1H), 5.44-5.29 (m, 1H), 4.39 (m, 2H), 4.14 (m, 2H), 2.15-2.08 (m, 1H), 1.15-1.03 (m, 2H), 0.88-0.77 (m, 2H). Method 1: RT = 2.79 min.; M + H = 370.1 |
| 16 | 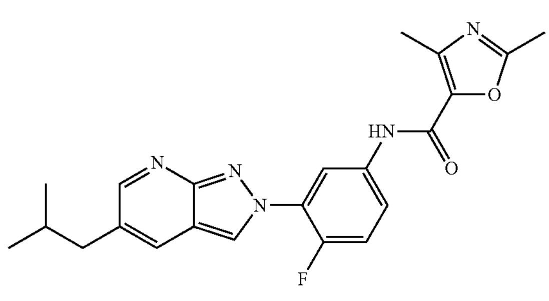 [SMILES: Cc1nc(C)c(C(=O)Nc2ccc(F)c(-n3cc4cc(CC(C)C)cnc4n3)c2)o1] | ¹H NMR (400 MHz, Methanol-d4) δ 8.72 (m, 1H), 8.57 (m, 1H), 8.43 (m, 1H), 8.13-8.06 (m, 1H), 7.89 (m, 1H), 7.45 (m, 1H), 2.67 (m, 2H), 2.55 (s, 3H), 2.47 (s, 3H), 1.98 (dt, J = 13.5, 6.8 Hz, 1H), 1.00 (s, 3H), 0.98 (s, 3H). Method 1: RT = 3.21 min.; M + H = 408.1 |

TABLE 2-continued

| Cpd No. | Structure | ¹HNMR and HPLC retention time and/or MS |
|---|---|---|
| 17 | 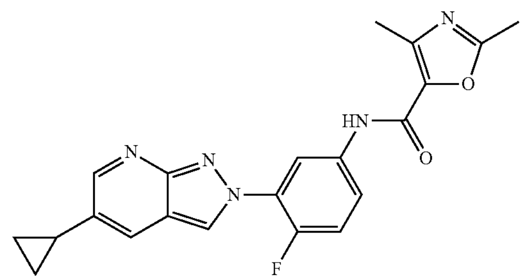 [SMILES: Cc1nc(C)c(C(=O)Nc2ccc(F)c(-n3cc4cc(C5CC5)cnc4n3)c2)o1] | ¹H NMR (400 MHz, Methanol-d₄) δ 8.67 (m, 1H), 8.61 (m, 1H), 8.42 (m, 1H), 7.93 (m, 1H), 7.88 (m, 1H), 7.44 (m, 1H), 2.55 (s, 3H), 2.47 (s, 3H), 2.18-2.07 (m, 1H), 1.13-1.06 (m, 2H), 0.87-0.79 (m, 2H). Method 1: RT = 3.03 min.; M + H = 392.1 |
| 18 | 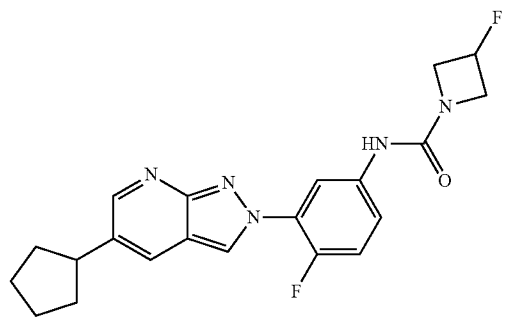 [SMILES: O=C(Nc1ccc(F)c(-n2cc3cc(C4CCCC4)cnc3n2)c1)N1CC(F)C1] | ¹H NMR (400 MHz, Methanol-d4) δ 8.77 (m, 1H), 8.49 (m, 1H), 8.02 (m, 1H), 7.56 (m, 1H), 7.29-7.24 (m, 1H), 7.01 (m, 1H), 5.35-5.20 (m, 1H), 4.30 (m, 2H), 4.04 (m, 2H), 2.16 (m, 1H), 1.85-1.67 (m, 4H), 1.56 (m, 2H), 0.81 (m, 2H). Method 1: RT = 3.03 min.; M + H = 398.1 |
| 19 | 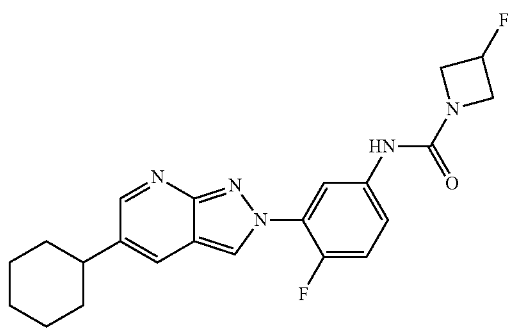 [SMILES: O=C(Nc1ccc(F)c(-n2cc3cc(C4CCCCC4)cnc3n2)c1)N1CC(F)C1] | ¹H NMR (400 MHz, Methanol-d4) δ 8.75-8.47 (m, 2H), 8.16-8.07 (m, 1H), 7.74-7.61 (m, 1H), 7.41-7.31 (m, 1H), 7.24-7.01 (m, 1H), 5.47-5.26 (m, 1H), 4.46-4.31 (m, 2H), 4.21-4.06 (m, 2H), 2.10-1.31 (m, 10H), 0.96-0.83 (m, 1H). Method 1: RT = 2.99 min.; M + H = 412.1 |
| 20 | 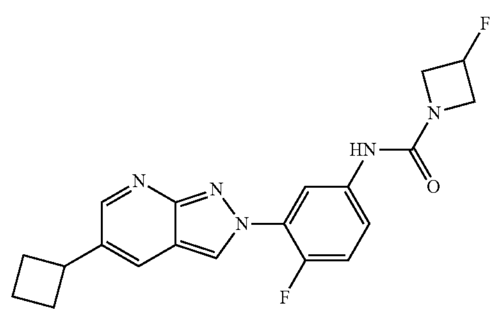 | ¹H NMR (400 MHz, Methanol-d₄) δ 8.70 (m, 1H), 8.60 (m, 1H), 8.16-8.08 (m, 1H), 7.63 (m, 1H), 7.38-7.30 (m, 1H), 7.06 (m, 1H), 5.44-5.29 (m, 1H), 4.46-4.31 (m, 2H), 4.20-4.06 (m, 2H), 2.61-2.51 (m, 1H), 2.46 (m, 1H), 2.41-2.31 (m, 1H), 2.32-2.20 (m, 1H), 2.20-2.05 (m, 1H), 2.05-1.91 (m, 1H), 1.84-1.57 (m, 1H). Method 1: RT = 2.92 min.; M + H = 384.1 |
| 21 | 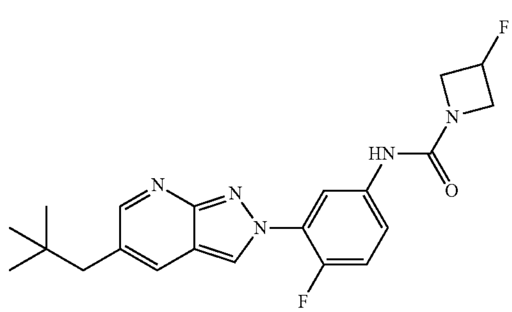 [SMILES: CC(C)(C)Cc1cnc2nn(-c3cc(NC(=O)N4CC(F)C4)ccc3F)cc2c1] | ¹H NMR (400 MHz, Methanol-d₄) δ 8.69 (m, 1H), 8.54 (m, 1H), 8.16-8.10 (m, 1H), 8.07 (m, 1H), 7.68-7.61 (m, 1H), 7.39-7.32 (m, 1H), 5.44-5.30 (m, 1H), 4.39 (m, 2H), 4.14 (m, 2H), 2.70 (s, 2H), 0.99 (s, 9H). Method 1: RT = 2.62 min.; M + H = 400.2 |

TABLE 2-continued

| Cpd No. | Structure | ¹HNMR and HPLC retention time and/or MS |
|---|---|---|
| 22 | 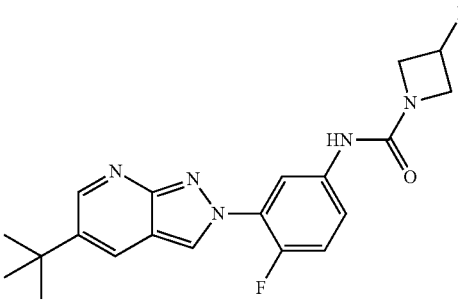 | ¹H NMR (400 MHz, Methanol-d₄) δ 8.69-8.54 (m, 2H), 7.83 (m, 1H), 7.66 (m, 1H), 7.40-7.25 (m, 1H), 7.20-7.10 (m, 1H), 5.43-5.28 (m, 1H), 4.43-4.31 (m, 2H), 4.20-4.05 (m, 2H), 1.49 (s, 9H). Method 1: RT = 2.72 min.; M + H = 386.1 |
| 23 | 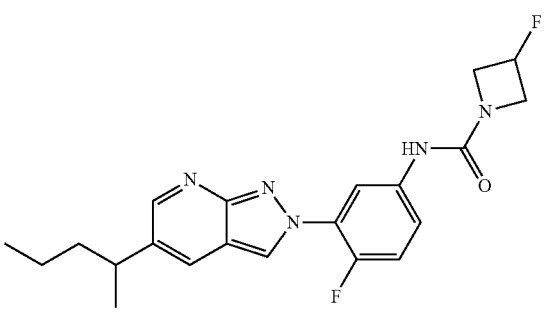 [SMILES: CCCC(C)c1cnc2nn(-c3cc(NC(=O)N4CC(F)C4)ccc3F)cc2c1] | ¹H NMR (400 MHz, Methanol-d₄) δ 8.76-8.57 (m, 2H), 8.16-8.06 (m, 1H), 7.65 (m, 1H), 7.44-7.31 (m, 2H), 5.44-5.30 (m, 1H), 4.44-4.34 (m, 2H), 4.21-4.08 (m, 2H), 2.85-2.72 (m, 1H), 1.87-1.57 (m, 3H), 1.46-1.33 (m, 3H), 0.98-0.67 (m, 4H). Method 1: RT = 3.13 min.; M + H = 400.1 |
| 24 | 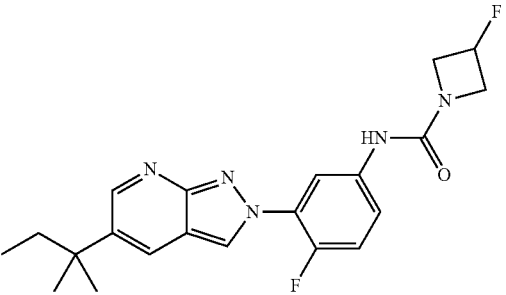 [SMILES: CCC(C)(C)c1cnc2nn(-c3cc(NC(=O)N4CC(F)C4)ccc3F)cc2c1] | ¹H NMR (400 MHz, Methanol-d4) δ 8.55 (m, 1H), 8.45 (m, 1H), 7.73 (m, 1H), 7.56 (m, 1H), 7.19 (m, 1H), 7.07 (m, 1H), 5.33-5.18 (m, 1H), 4.33-4.21 (m, 2H), 4.10-3.96 (m, 2H), 1.90-1.67 (m, 2H), 1.39 (s, 3H), 1.27 (s, 3H), 0.66 (t, J = 7.4 Hz, 3H). Method 1: RT = 2.89 min.; M + H = 400.1 |
| 25 | 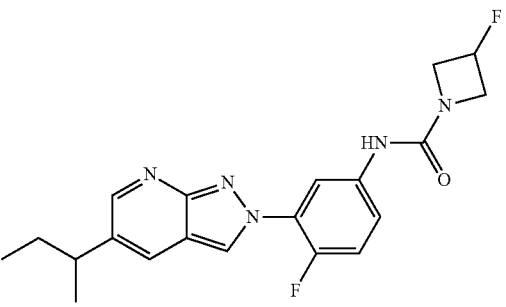 [SMILES: CCC(C)c1cnc2nn(-c3cc(NC(=O)N4CC(F)C4)ccc3F)cc2c1] | ¹H NMR (400 MHz, Methanol-d4) δ 8.74-8.63(m, 1H), 8.62-8.52 (m, 1H), 8.16-8.05 (m, 1H), 7.73-7.59 (m, 1H), 7.40-7.29 (m, 1H), 7.08 (m, 1H), 5.44-5.26 (m, 1H), 4.39 (m, 2H), 4.20-4.06 (m, 2H), 1.90-1.61 (m, 2H), 1.52-1.30 (m, 3H), 1.03-0.81 (m, 3H), 0.77 (m, 1H). Method 1: RT = 2.78 min.; M + H = 386.1 |
| 26 | 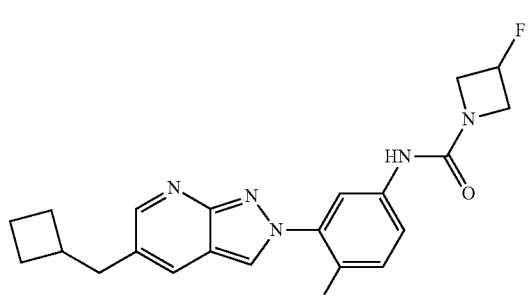 | ¹H NMR (400 MHz, Methanol-d₄) δ 8.67 (m, 1H), 8.58 (m, 1H), 8.16-8.08 (m, 1H), 8.05 (m, 1H), 7.64 (m, 1H), 7.38-7.31 (m, 1H), 5.44-5.30 (m, 1H), 4.39 (m, 2H), 4.14 (m, 2H), 2.87 (m, 1H), 2.68 (m, 1H), 2.19-2.04 (m, 2H), 1.98-1.66 (m, 4H), 0.91 (m, 1H). Method 1: RT = 3.10 min.; M + H = 398.1 |

TABLE 2-continued

| Cpd No. | Structure | ¹HNMR and HPLC retention time and/or MS |
|---|---|---|
| 27 | 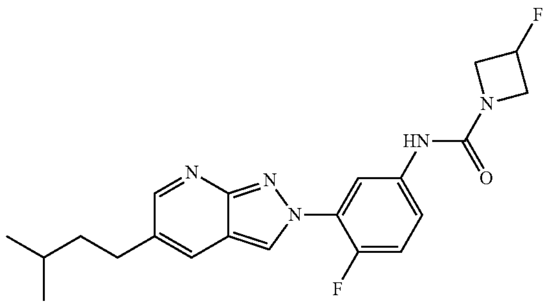 [SMILES: CC(C)CCc1cnc2nn(-c3cc(NC(=O)N4CC(F)C4)ccc3F)cc2c1] | ¹H NMR (400 MHz, Methanol-d4) δ 8.67 (m, 1H), 8.57 (m, 1H), 8.13 (m, 1H), 8.11-8.05 (m, 1H), 7.65 (m, 1H), 7.39-7.31 (m, 1H), 5.44-5.30 (m, 1H), 4.39 (m, 2H), 4.14 (m, 2H), 2.87-2.76 (m, 2H), 1.69-1.57 (m, 2H), 1.04-0.85 (m, 6H), 0.76 (m, 1H). Method 1: RT = 3.18 min.; M + H = 400.1 |
| 28 | 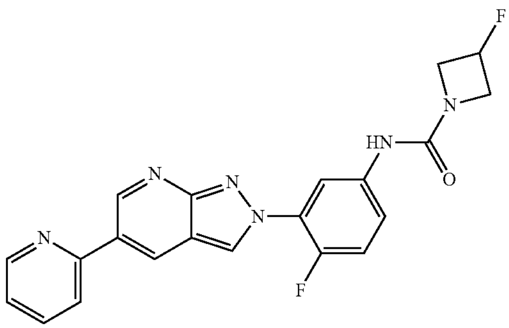 [SMILES: O=C(Nc1ccc(F)c(-n2cc3cc(-c4ccccn4)cnc3n2)c1)N1CC(F)C1] | ¹H NMR (400 MHz, Methanol-d4) δ 9.37 (m, 1H), 8.86 (m, 2H), 8.70 (m, 1H), 8.19 (m, 1H), 8.04-7.92 (m, 2H), 7.66 (m, 1H), 7.45-7.31 (m, 2H), 5.45-5.30 (m, 1H), 4.46-4.34 (m, 2H), 4.21-4.08 (m, 2H). Method 1: RT = 2.67 min.; M + H = 407.1 |
| 29 | 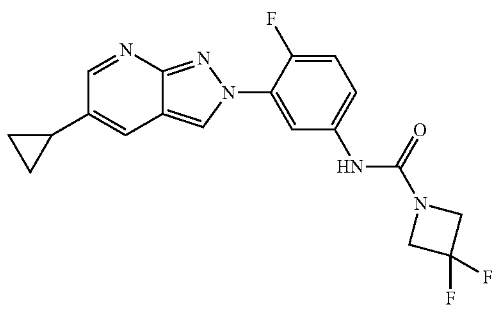 [SMILES: O=C(Nc1ccc(F)c(-n2cc3cc(C4CC4)cnc3n2)c1)N1CC(F)(F)C1] | ¹H NMR (400 MHz, Methanol-d₄) δ 8.53 (m, 1H), 8.49 (m, 1H), 8.04 (m, 1H), 7.85-7.79 (m, 1H), 7.54 (m, 1H), 7.29-7.22 (m, 1H), 4.32 (t, J = 12.3 Hz, 4H), 2.07-1.95 (m, 1H), 0.98 (m, 2H), 0.71 (m, 2H). Method 2: RT = 1.10 min.; M + H = 388.1 |
| 30 | 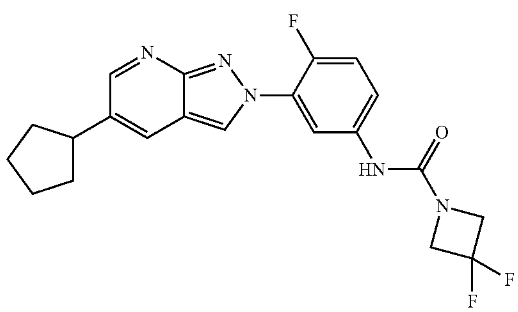 | ¹H NMR (400 MHz, Methanol-d₄) δ 8.71-8.62 (m, 1H), 8.25-8.12 (m, 1H), 7.94 (m, 1H), 7.73-7.60 (m, 1H), 7.45-7.29 (m, 2H), 4.44 (m, 4H), 2.19 (m, 1H), 1.97-1.49 (m, 6H), 0.90 (m, 2H). Method 2: RT = 1.09 min.; M + H = 416.1 |
| 31 | 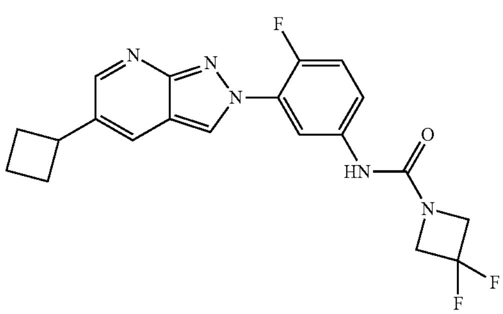 | ¹H NMR (400 MHz, Methanol-d₄) δ 8.59 (m, 1H), 8.50 (m, 1H), 8.05 (m, 1H), 8.02 (m, 1H), 7.55 (m, 1H), 7.29-7.23 (m, 1H), 4.32 (t, J = 12.3 Hz, 4H), 2.37 (m, 2H), 2.27-1.98 (m, 4H), 1.91-1.83 (m, 1H). Method 1: RT = 3.16 min.; M + H = 402.1 |

TABLE 2-continued

| Cpd No. | Structure | ¹HNMR and HPLC retention time and/or MS |
|---|---|---|
| 32 | 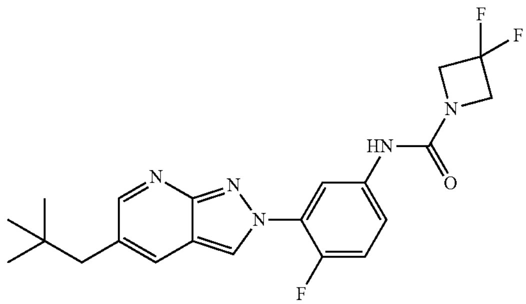 [SMILES: CC(C)(C)Cc1cnc2nn(-c3cc(NC(=O)N4CC(F)(F)C4)ccc3F)cc2c1] | ¹H NMR (400 MHz, Methanol-d₄) δ 8.70 (m, 1H), 8.54 (m, 1H), 8.16 (m, 1H), 8.07(m, 1H), 7.66 (m, 1H), 7.41-7.34 (m, 1H), 4.43 (t, J = 12.3 Hz, 4H), 2.69 (s, 2H), 0.99 (s, 9H). Method 2: RT = 1.27 min.; M + H = 418.1 |
| 33 | 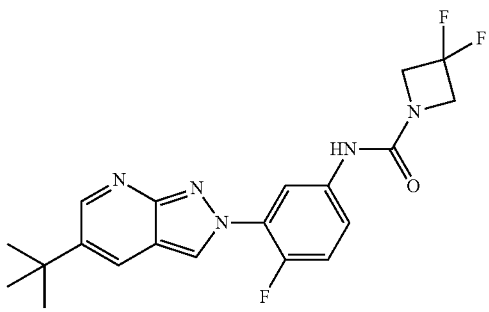 [SMILES: CC(C)(C)c1cnc2nn(-c3cc(NC(=O)N4CC(F)(F)C4)ccc3F)cc2c1] | ¹H NMR (400 MHz, Methanol-d₄) δ 8.64 (m, 1H), 8.61-8.55 (m, 1H), 7.84 (m, 1H), 7.71-7.64 (m, 1H), 7.37-7.28 (m, 1H), 7.17 (m, 1H), 4.42 (m, 4H), 1.52 (m, 9H). Method 2: RT = 1.04 min.; M + H = 404.1 |
| 34 | 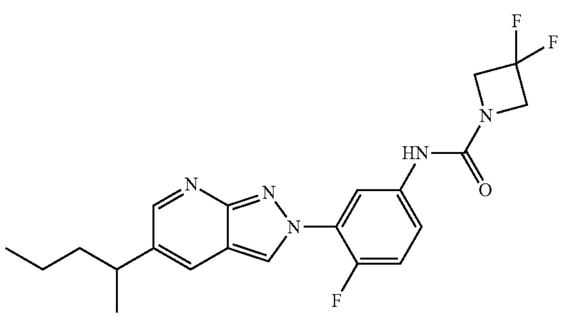 [SMILES: CCCC(C)c1cnc2nn(-c3cc(NC(=O)N4CC(F)(F)C4)ccc3F)cc2c1] | ¹H NMR (400 MHz, Methanol-d₄) δ 8.68 (m, 1H), 8.63-8.57 (m, 1H), 8.15 (m, 1H), 7.98-7.91 (m, 1H), 7.69-7.62 (m, 1H), 7.39-7.32 (m, 1H), 4.42 (m, 4H), 1.53-1.33 (m, 5H), 1.00-0.72 (m, 6H). Method 2: RT = 1.14 min.; M + H = 418.1 |
| 35 | 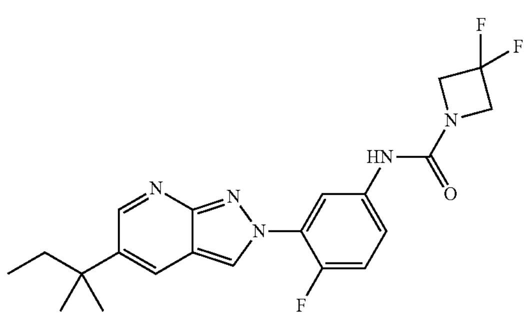 [SMILES: CCC(C)(C)c1cnc2nn(-c3cc(NC(=O)N4CC(F)(F)C4)ccc3F)cc2c1] | ¹H NMR (400 MHz, Methanol-d₄) δ 8.65 (m, 1H), 8.55 (m, 1H), 7.84 (m, 1H), 7.67 (m, 1H), 7.40-7.31 (m, 1H), 7.17 (m, 1H), 4.42 (m, 4H), 1.93-1.79 (m, 2H), 1.50 (m, 3H), 1.37 (m, 3H), 0.81-0.66 (m, 3H). Method 2: RT = 1.10 min.; M + H = 418.1 |
| 36 | 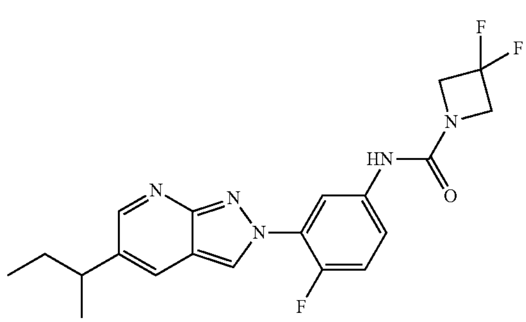 [SMILES: CCC(C)c1cnc2nn(-c3cc(NC(=O)N4CC(F)(F)C4)ccc3F)cc2c1] | ¹H NMR (400 MHz, Methanol-d₄) δ 8.68 (m, 1H), 8.46 (m, 1H), 8.14 (m, 1H), 7.70-7.63 (m, 1H), 7.39-7.33 (m, 1H), 7.18 (m, 1H), 4.43 (m, 4H), 1.91-1.79 (m, 2H), 1.54-1.36 (m, 4H), 0.92 (m, 3H). Method 2: RT = 1.14 min.; M + H = 404.1 |

TABLE 2-continued

| Cpd No. | Structure | ¹HNMR and HPLC retention time and/or MS |
|---|---|---|
| 37 | 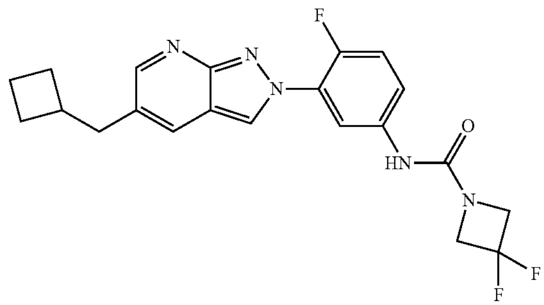 [SMILES: O=C(Nc1ccc(F)c(-n2cc3cc(CC4CCC4)cnc3n2)c1)N1CC(F)(F)C1] | ¹H NMR (400 MHz, Methanol-d₄) δ 8.59-8.54 (m, 1H), 8.45 (m, 1H), 8.07-8.00 (m, H), 7.96-7.92 (m, 1H), 7.55 (m, 1H), 7.29-7.23 (m, 1H), 4.32 (t, J = 12.3 Hz, 4H), 2.76 (m, 2H), 2.63-2.51 (m, 1H), 2.04-1.93 (m, 2H), 1.87-1.64 (m, 4H). Method 1: RT = 3.26 min.; M + H = 416.1 |
| 38 | 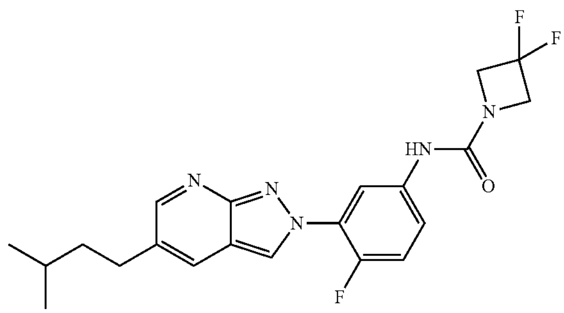 [SMILES: CC(C)CCc1cnc2nn(-c3cc(NC(=O)N4CC(F)(F)C4)ccc3F)cc2c1] | ¹H NMR (400 MHz, Methanol-d₄) δ 8.67 (m, 1H), 8.58 (m, 1H), 8.16 (m, 1H), 8.10-8.04 (m, 1H), 7.69-7.62 (m, 1H), 7.40-7.33 (m, 1H), 4.43 (t, J = 12.3 Hz, 4H), 2.89-2.78 (m, 2H), 1.72-1.53 (m, 3H), 1.04-0.86 (m, 6H). Method 2: RT = 1.30 min.; M + H = 418.1 |
| 39 | 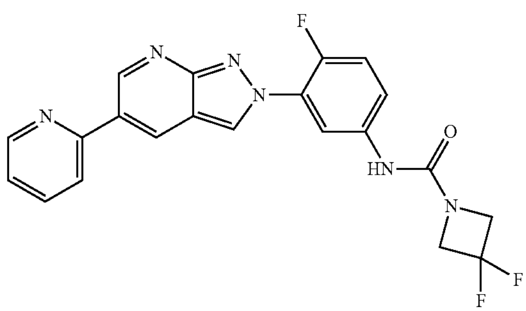 [SMILES: O=C(Nc1ccc(F)c(-n2cc3cc(-c4ccccn4)cnc3n2)c1)N1CC(F)(F)C1] | ¹H NMR (400 MHz, Methanol-d4) δ 9.36 (d, J = 2.3 Hz, 1H), 9.00-8.93 (m, 2H), 8.79-8.75 (m, 1H), 8.26 (dd, J = 6.8, 2.7 Hz, 1H), 8.19-8.14 (m, 2H), 7.70-7.64 (m, 1H), 7.64-7.56 (m, 1H), 7.46-7.35 (m, 1H), 4.44 (td, J = 12.3, 3.0 Hz, 4H). Method 2: RT = 9 min., M + H = 425.0 |
| 40 | 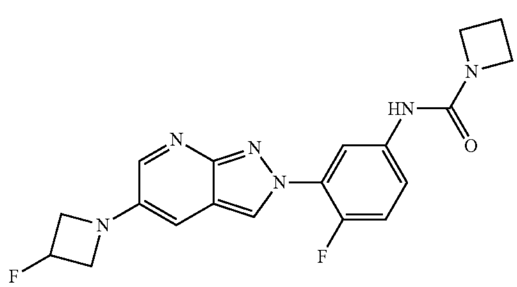 [SMILES: O=C(Nc1ccc(F)c(-n2cc3cc(N4CC(F)C4)cnc3n2)c1)N1CCC1] | ¹H NMR (400 MHz, DMSO) δ 8.70 (s, 1 H), 8.56 (d, J = 2.76 Hz, 1 H), 8.31 (d, J = 2.76 Hz, 1 H), 8.21 (dd, J = 7.03, 2.64 Hz, 1 H), 7.59-7.72 (m, 1 H), 7.41 (dd, J = 11.36, 9.10 Hz, 1 H), 7.01 (d, J = 2.76 Hz, 1 H), 5.39-5.66 (m, 1 H), 4.20-4.36 (m, 2 H), 3.89-4.09 (m, 6 H), 2.12-2.28 (m, 2 H). Method 1: RT = 2.66 min. M + H = 385.3 |
| 41 | 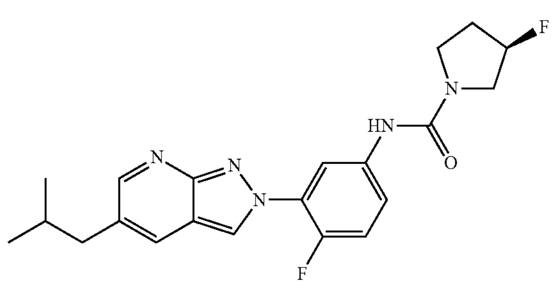 [SMILES: CC(C)Cc1cnc2nn(-c3cc(NC(=O)N4CC[C@@H](F)C4)ccc3F)cc2c1] | ¹H NMR (400 MHz, Methanol-d4) δ 8.68 (m, 1H), 8.56 (m, 1H), 8.12 (m, 1H), 8.07(m, 1H), 7.65 (m, 1H), 7.36 (m, 1H), 5.40-5.27 (m, 1H), 3.85-3.68 (m, 2H), 3.59 (m, 2H), 2.67 (m, 2H), 2.28 (m, 2H), 1.97 (m, 1H), 0.99 (d, J = 6.6 Hz, 6H). M + H = 400.3 |

TABLE 2-continued

| Cpd No. | Structure | ¹HNMR and HPLC retention time and/or MS |
|---|---|---|
| 42 | 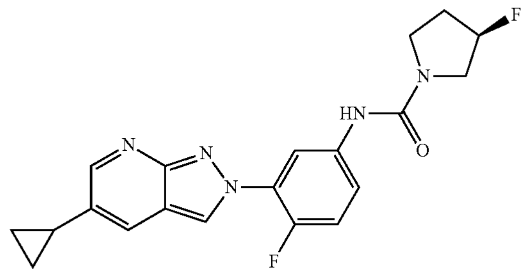 [SMILES: O=C(Nc1ccc(F)c(-n2cc3cc(C4CC4)cnc3n2)c1)N1CC[C@@H](F)C1] | ¹H NMR (400 MHz, Methanol-d4) δ 8.63 (m, 1H), 8.59 (m, 1H), 8.11 (m, 1H), 7.92 (m, 1H), 7.63 (m, 1H), 7.34 (m, 1H), 5.40-5.26 (m, 1H), 3.80-3.67 (m, 2H), 3.59 (m, 2H), 2.37-2.18 (m, 2H), 2.12 (m, 1H), 1.08 (m, 2H), 0.85-0.79 (m, 2H). Method 2: RT = 1.03 min.; M + H = 384.3 |
| 43 | 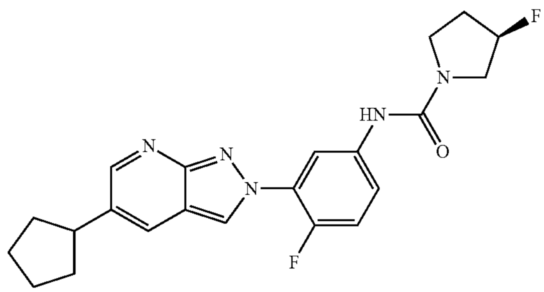 [SMILES: O=C(Nc1ccc(F)c(-n2cc3cc(C4CCCC4)cnc3n2)c1)N1CC[C@@H](F)C1] | ¹H NMR (400 MHz, Methanol-d$_4$) δ 8.77-8.54 (m, 2H), 8.27-8.07 (m, 2H), 7.64 (m, 1H), 7.36 (m, 1H), 5.40-5.23 (m, 1H), 3.87-3.51 (m, 4H), 3.20 (m, 1H), 2.46-1.96 (m, 5H), 1.98-1.56 (m, 5H). Method 2: RT = 1.04 min.; M + H = 412.3 |
| 44 | 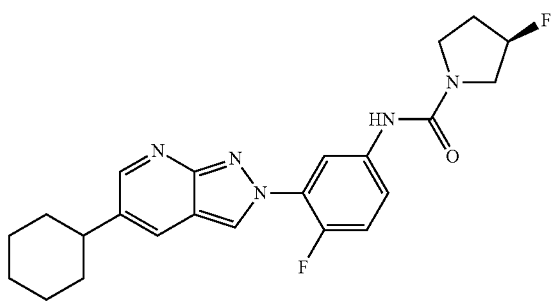 [SMILES: O=C(Nc1ccc(F)c(-n2cc3cc(C4CCCCC4)cnc3n2)c1)N1CC[C@@H](F)C1] | ¹H NMR (400 MHz, Methanol-d$_4$) δ 8.67 (m, 1H), 8.65-8.57 (m, 1H), 8.26-8.08 (m, 2H), 7.64 (m, 1H), 7.35 (m, 1H), 5.40-5.26 (m, 1H), 3.84-3.54 (m, 4H), 2.79-2.68 (m, 1H), 2.39-1.92 (m, 6H), 1.82 (m, 1H), 1.66-1.19 (m, 5H). Method 2: RT = 1.26 min.; M + H = 426.4 |
| 45 | 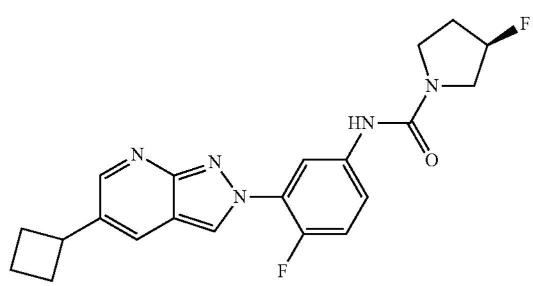 [SMILES: O=C(Nc1ccc(F)c(-n2cc3cc(C4CCC4)cnc3n2)c1)N1CC[C@@H](F)C1] | ¹H NMR (400 MHz, Methanol-d$_4$) δ 8.77 (m, 1H), 8.69 (m, 1H), 8.61 (m, 1H), 8.17-8.09 (m, 1H), 7.63 (m, 1H), 7.40-7.32 (m, 1H), 5.42-5.25 (m, 1H), 3.82-3.53 (m, 4H), 2.63-2.07 (m, 6H), 1.90-1.89 (m, 3H). Method 1: RT = 2.93 min.; M + H = 398.3 |
| 46 | 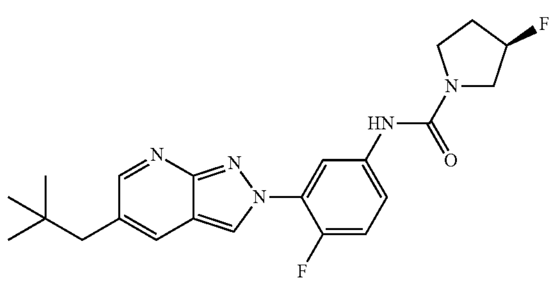 [SMILES: CC(C)(C)Cc1cnc2nn(-c3cc(NC(=O)N4CC[C@@H](F)C4)ccc3F)cc2c1] | ¹H NMR (400 MHz, Methanol-d$_4$) δ 8.69 (m, 1H), 8.54 (m, 1H), 8.12 (m, 1H), 8.07(m, 1H), 7.64 (m, 1H), 7.35 (m, 1H), 5.39-5.26 (m, 1H), 3.82-3.70 (m, 2H), 3.59 (m, 2H), 2.69 (s, 2H), 2.33-2.09 (m, 2H), 0.99 (s, 9H). Method 2: RT = 1.21 min.; M + H = 414.4 |

TABLE 2-continued

| Cpd No. | Structure | ¹HNMR and HPLC retention time and/or MS |
|---|---|---|
| 47 | 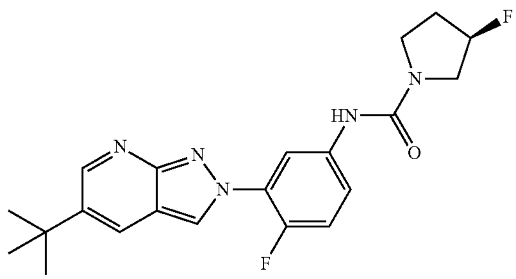 [SMILES: CC(C)(C)c1cnc2nn(-c3cc(NC(=O)N4CC[C@@H](F)C4)ccc3F)cc2c1] | ¹H NMR (400 MHz, Methanol-d₄) δ 8.69-8.62 (m, 1H), 8.58 (m, 1H), 7.81 (m, 1H), 7.69 (m, 1H), 7.30 (m, 1H), 7.17 (m, 1H), 5.38-5.23 (m, 1H), 3.78-3.66 (m, 2H), 3.57 (m, 2H), 2.35-2.11 (m, 2H), 1.71-1.22 (m, 9H). Method 2: RT = 0.98 min.; M + H = 400.3 |
| 48 | 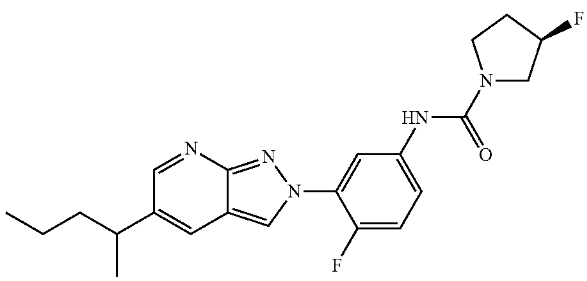 [SMILES: CCCC(C)c1cnc2nn(-c3cc(NC(=O)N4CC[C@@H](F)C4)ccc3F)cc2c1] | ¹H NMR (400 MHz, Methanol-d₄) δ 8.72-8.65 (m, 1H), 8.47(m, 1H), 8.18-8.08 (m, 1H), 7.74-7.60 (m, 1H), 7.43-7.33 (m, 1H), 7.26-7.14 (m, 1H), 5.39-5.26 (m, 1H), 3.83-3.53 (m, 4H), 3.16-3.01 (m, 1H), 2.85-2.72 (m, 1H), 2.40-2.05 (m, 4H), 1.54-1.15 (m, 4H), 1.03-0.88 (m, 2H), 0.84-0.74 (m, 1H). Method 2: RT = 1.08 min.; M + H = 414.4 |
| 49 | 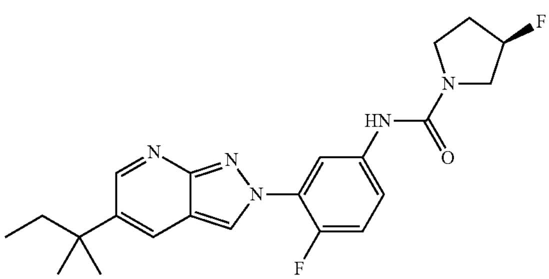 [SMILES: CCC(C)(C)c1cnc2nn(-c3cc(NC(=O)N4CC[C@@H](F)C4)ccc3F)cc2c1] | ¹H NMR (400 MHz, Methanol-d₄) δ 8.65 (m, 1H), 8.56 (m, 1H), 7.82 (m, 1H), 7.69 (m, 1H), 7.30 (m, 1H), 7.19 (m, 1H), 5.40-5.26 (m, 1H), 3.81-3.69 (m, 2H), 3.58 (m, 2H), 2.35-2.19 (m, 2H), 1.87-1.79 (m, 2H), 1.55-1.43 (s, 3H), 1.39 (s, 3H), 0.85-0.68 (m, 3H). Method 2: RT = 1.04 min.; M + H = 414.3 |
| 50 | 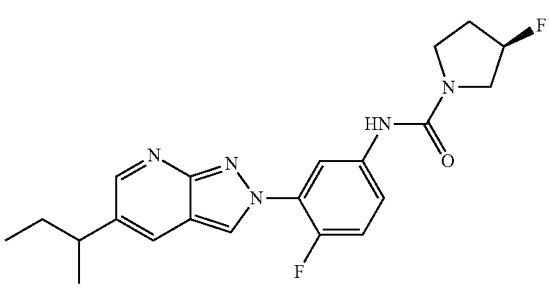 [SMILES: CCC(C)c1cnc2nn(-c3cc(NC(=O)N4CC[C@@H](F)C4)ccc3F)cc2c1] | ¹H NMR (400 MHz, Methanol-d₄) δ 8.67 (m, 1H), 8.64-8.56 (m, 1H), 8.12 (m, 1H), 7.69-7.59 (m, 1H), 7.41-7.30 (m, 1H), 7.22-7.14 (m, 1H), 5.40-5.26 (m, 1H), 3.82-3.55 (m, 4H), 2.97-2.77 (m, 2H), 2.37-2.21 (m, 2H), 1.75-1.65 (m, 1H), 1.52-1.21 (m, 3H), 1.11-0.82 (m, 3H). Method 2: RT = 1.18 min.; M + H = 400.3 |
| 51 | 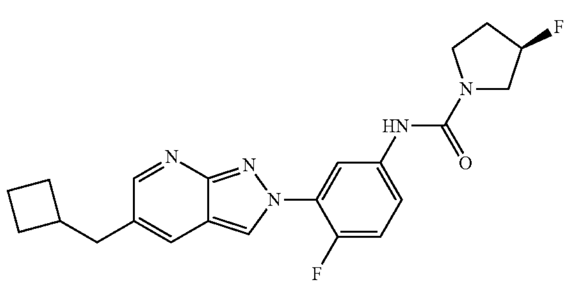 [SMILES: O=C(Nc1ccc(F)c(-n2cc3cc(CC4CCC4)cnc3n2)c1)N1CC[C@@H](F)C1] | ¹H NMR (400 MHz, Methanol-d₄) δ 8.66 (m, 1H), 8.55 (m, 1H), 8.13 (m, 1H), 8.07-8.03 (m, 1H), 7.62 (m, 1H), 7.35 (m, 1H), 5.40-5.25 (m, 1H), 3.83-3.69 (m, 2H), 3.66-3.50 (m, 2H), 2.90-2.78 (m, 2H), 2.73-2.62 (m, 1H), 2.59-2.45 (m, 1H), 2.39-2.18 (m, 2H), 2.15-2.04 (m, 2H), 1.89-1.78 (m, 3H). Method 1: RT = 3.16 min.; M + H = 412.3 |

TABLE 2-continued

| Cpd No. | Structure | ¹HNMR and HPLC retention time and/or MS |
|---|---|---|
| 52 | 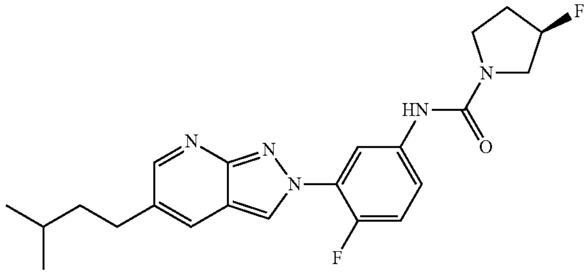 [SMILES: CC(C)CCc1cnc2nn(-c3cc(NC(=O)N4CC[C@@H](F)C4)ccc3F)cc2c1] | ¹H NMR (400 MHz, Methanol-d₄) δ 8.67 (m, 1H), 8.57 (m, 1H), 8.12 (m, 1H), 8.10-8.05 (m, 1H), 7.64 (m, 1H), 7.35 (m, 1H), 5.40-5.26 (m, 1H), 3.83-3.69 (m, 2H), 3.59 (m, 2H), 2.89-2.77 (m, 2H), 2.38-2.05 (m, 3H), 1.70-1.57 (m, 2H), 1.04-0.88 (m, 6H). Method 2: RT = 1.25 min.; M + H = 414.4 |
| 53 | 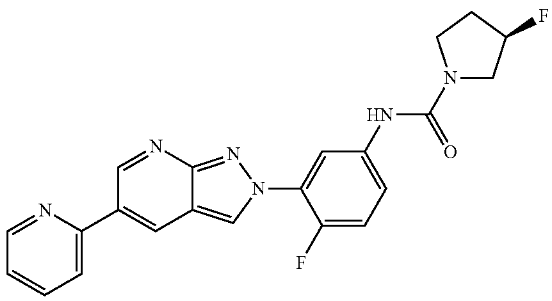 [SMILES: O=C(Nc1ccc(F)c(-n2cc3cc(-c4ccccn4)cnc3n2)c1)N1CC[C@@H](F)C1] | ¹H NMR (400 MHz, Methanol-d₄) δ 9.37 (m, 1H), 8.88 (m, 1H), 8.86 (m, 1H), 8.70 (m, 1H), 8.17(m, 1H), 8.05-7.92 (m, 2H), 7.66 (m, 1H), 7.43 (m, 1H), 7.37 (m, 1H), 5.40-5.27 (m, 1H), 3.85-3.70 (m, 2H), 3.60 (m, 2H), 2.38-2.09 (m, 2H). Method 2: RT = 0.93 min.; M + H = 421.3 |
| 54 | 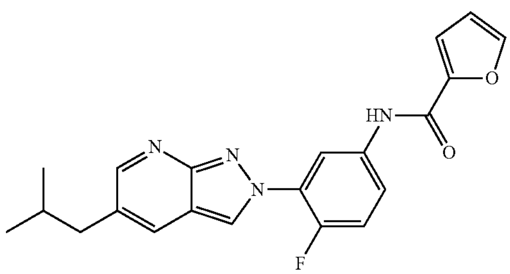 [SMILES: CC(C)Cc1cnc2nn(-c3cc(NC(=O)c4ccco4)ccc3F)cc2c1] | ¹H NMR (400 MHz, Methanol-d₄) δ 8.72 (m, 1H), 8.58 (m, 1H), 8.43 (m, 1H), 8.08 (m, 1H), 7.93 (m, 1H), 7.78 (m, 1H), 7.46 (m, 1H), 7.31 (m, 1H), 6.71-6.63 (m, 1H), 2.68 (d, J = 7.1 Hz, 2H), 1.98 (m, 1H), 0.99 (2s, 6H). Method 1: RT = 3.20 min.; M + H = 379.3 |
| 55 | 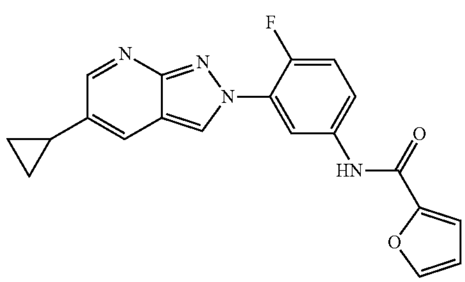 [SMILES: O=C(Nc1ccc(F)c(-n2cc3cc(C4CC4)cnc3n2)c1)c1ccco1] | ¹H NMR (400 MHz, Methanol-d₄) δ 8.67 (m, 1H), 8.61 (m, 1H), 8.42 (m, 1H), 7.95-7.87 (m, 2H), 7.78 (m, 1H), 7.44 (m, 1H), 7.31 (m, 1H), 6.67 (m, 1H), 2.17-2.08 (m, 1H), 1.09 (m, 2H), 0.86-0.79 (m, 2H). Method 2: RT = 1.11 min.; M + H = 363.3 |
| 56 | 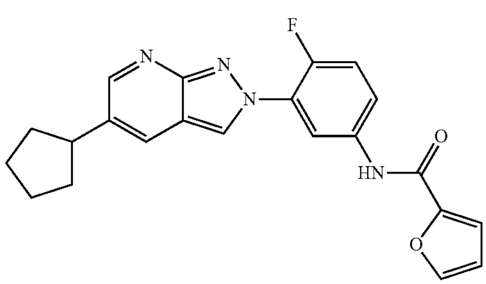 [SMILES: O=C(Nc1ccc(F)c(-n2cc3cc(C4CCCC4)cnc3n2)c1)c1ccco1] | ¹H NMR (400 MHz, Methanol-d₄) δ 8.71 (m, 1H), 8.69-8.65 (m, 1H), 8.43 (m, 1H), 8.15 (m, 1H), 7.92 (m, 1H), 7.80-7.76 (m, 1H), 7.46 (m, 1H), 7.33-7.29 (m, 1H), 6.67 (m, 1H), 3.25-3.18 (m, 1H), 2.27-2.14 (m, 3H), 1.85-1.66 (m, 5H). Method 2: RT = 1.27 min.; M + H = 391.3 |

TABLE 2-continued

| Cpd No. | Structure | ¹HNMR and HPLC retention time and/or MS |
|---|---|---|
| 57 | 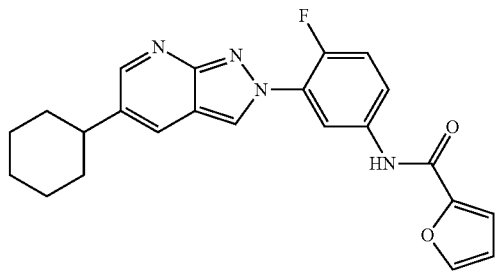 [SMILES: O=C(Nc1ccc(F)c(-n2cc3cc(C4CCCCC4)cnc3n2)c1)c1ccco1] | ¹H NMR (400 MHz, Methanol-d₄) δ 8.67 (m, 1H), 8.53 (m, 1H), 8.07 (m, 1H), 8.00 (m, 1H), 7.77 (m, 1H), 7.47 (m, 1H), 7.34-7.29 (m, 1H), 7.19 (m, 1H), 6.67 (m, 1H), 2.88 (m, 2H), 1.98 (m, 3H), 1.88-1.72 (m, 3H), 1.40-1.28 (m, 3H). M + H = 405.3 |
| 58 | 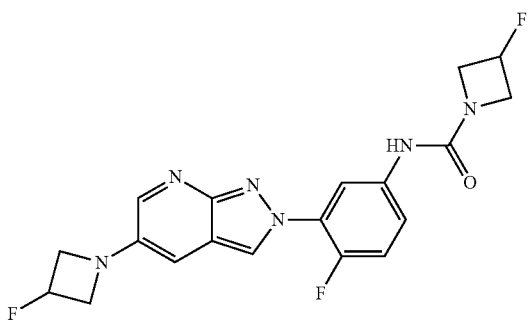 [SMILES: O=C(Nc1ccc(F)c(-n2cc3cc(N4CC(F)C4)cnc3n2)c1)N1CC(F)C1] | ¹H NMR (400 MHz, DMSO) δ 8.95 (s, 1 H), 8.56 (d, J = 2.63 Hz, 1 H), 8.30 (d, J = 2.89 Hz, 1 H), 8.19 (dd, J = 7.09, 2.70 Hz, 1 H), 7.60-7.69 (m, 1 H), 7.42 (dd, J = 11.36, 9.10 Hz, 1 H), 7.00 (d, J = 2.76 Hz, 1 H), 5.28-5.63 (m, 2 H), 4.20-4.37 (m, 4 H), 3.93-4.09 (m, 4 H). Method 1: RT = 2.61 min. M + H = 403.2 |
| 59 | 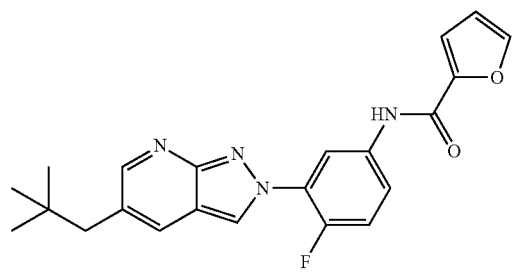 [SMILES: CC(C)(C)Cc1cnc2nn(-c3cc(NC(=O)c4ccco4)ccc3F)cc2c1] | ¹H NMR (400 MHz, Methanol-d₄) δ 8.73 (m, 1H), 8.55 (m, 1H), 8.43 (m, 1H), 8.09 (m, 1H), 7.93 (m, 1H), 7.78 (m, 1H), 7.45 (m, 1H), 7.31 (m, 1H), 6.70-6.64 (m, 1H), 2.70 (s, 2H), 0.99 (s, 9H). Method 2: RT = 1.29 min.; M + H = 393.3 |
| 60 | 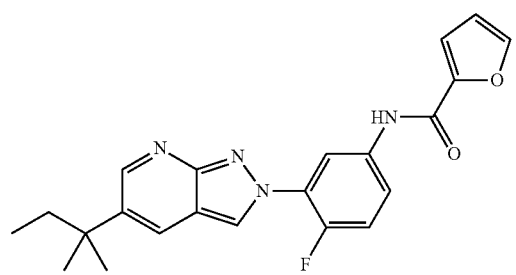 [SMILES: CCC(C)(C)c1cnc2nn(-c3cc(NC(=O)c4ccco4)ccc3F)cc2c1] | ¹H NMR (400 MHz, Methanol-d₄) δ 8.66 (m, 1H), 8.64-8.54 (m, 1H), 8.12 (m, 1H), 7.94 (m, 1H), 7.77 (m, 1H), 7.40 (m, 1H), 7.30 (m, 1H), 7.18 (m, 1H), 6.67 (m, 1H), 2.03-1.79 (m, 2H), 1.51 (s, 3H), 1.39 (s, 3H), 0.75 (m, 3H). Method 2: RT = 1.11 min.; M + H = 393.3 |
| 61 | 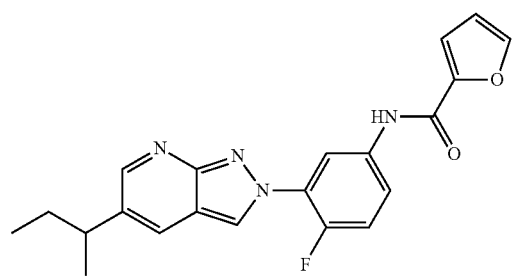 [SMILES: CCC(C)c1cnc2nn(-c3cc(NC(=O)c4ccco4)ccc3F)cc2c1] | ¹H NMR (400 MHz, Methanol-d₄) δ 8.61 (m, 1H), 8.48-8.38 (m, 1H), 8.15-8.04 (m, 1H), 7.93 (m, 1H), 7.81-7.74 (m, 1H), 7.53-7.43 (m, 1H), 7.31 (m, 1H), 7.10 (m, 1H), 6.67 (m, 1H), 2.86-2.75 (m, 1H), 1.89-1.66 (m, 2H), 1.54-1.27 (m, 3H), 1.06-0.82 (m, 3H). Method 1: RT = 3.09 min.; M + H = 379.3 |

TABLE 2-continued

| Cpd No. | Structure | ¹HNMR and HPLC retention time and/or MS |
|---|---|---|
| 62 | 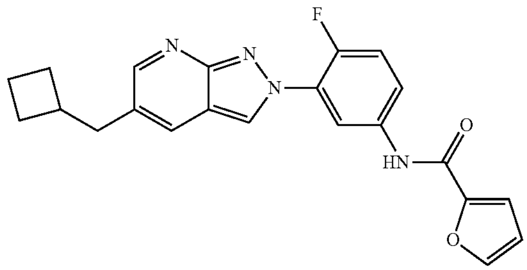 [SMILES: O=C(Nc1ccc(F)c(-n2cc3cc(CC4CCC4)cnc3n2)c1)c1ccco1] | ¹H NMR (400 MHz, Methanol-d₄) δ 8.74-8.66 (m, 1H), 8.58 (m, 1H), 8.42 (m, 1H), 8.12-8.04 (m, 1H), 7.92 (m, 1H), 7.78 (m, 1H), 7.45 (m, 1H), 7.31 (m, 1H), 6.67 (m, 1H), 2.84 (m, 2H), 2.69 (m, 1H), 2.15-2.05 (m, 1H), 1.98-1.67 (m, 3H), 1.51-1.35 (m, 1H), 1.00 (m, 1H). Method 1: RT = 3.26 min.; M + H = 391.3 |
| 63 | 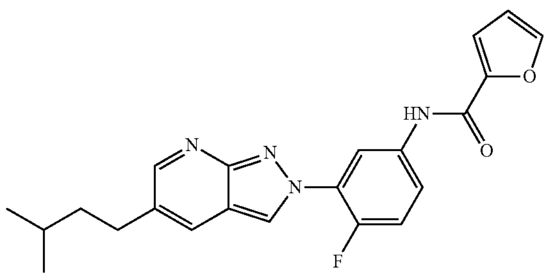 [SMILES: CC(C)CCc1cnc2nn(-c3cc(NC(=O)c4ccco4)ccc3F)cc2c1] | ¹H NMR (400 MHz, Methanol-d₄) δ 8.71 (m, 1H), 8.59 (m, 1H), 8.42 (m, 1H), 8.12-8.05 (m, 1H), 7.95-7.88 (m, 1H), 7.78 (m, 1H), 7.45 (m, 1H), 7.31 (m, 1H), 6.70-6.64 (m, 1H), 2.87-2.75 (m, 2H), 1.82-1.56 (m, 3H), 1.05-0.82 (m, 6H). Method 2: RT = 1.32 min.; M + H = 393.3 |
| 64 | 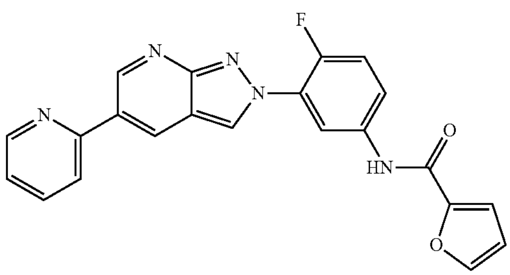 [SMILES: O=C(Nc1ccc(F)c(-n2cc3cc(-c4ccccn4)cnc3n2)c1)c1ccco1] | ¹H NMR (400 MHz, Methanol-d₄) δ 9.42-9.35 (m, 1H), 8.94-8.90 (m, 1H), 8.89-8.85 (m, 1H), 8.73-8.66 (m, 1H), 8.51-8.45 (m, 1H), 8.06-7.89 (m, 3H), 7.81-7.76 (m, 1H), 7.51-7.40 (m, 2H), 7.35-7.29 (m, 1H), 6.70-6.64 (m, 1H). Method 2: RT = 1.01 min.; M + H = 400.3 |
| 65 | 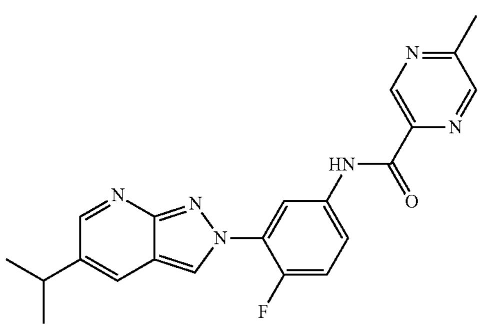 [SMILES: Cc1cnc(C(=O)Nc2ccc(F)c(-n3cc4cc(C(C)C)cnc4n3)c2)cn1] | ¹H NMR (400 MHz, Methanol-d₄) δ 9.21 (m, 1H), 8.73 (m, 1H), 8.67 (m, 2H), 8.56 (m, 1H), 8.14 (m, 1H), 8.00 (m, 1H), 7.47 (m, 1H), 3.14 (m, 1H), 2.68 (s, 3H), 1.39 (2s, 6H). Method 1: RT = 3.11 min.; M + H = 391.3 |
| 66 | 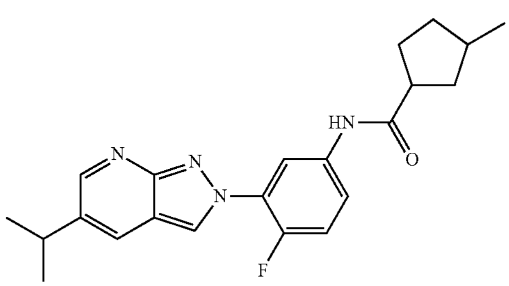 [SMILES: CC1CCC(C(=O)Nc2ccc(F)c(-n3cc4cc(C(C)C)cnc4n3)c2)C1] | ¹H NMR (400 MHz, Methanol-d₄) δ 8.69 (m, 1H), 8.66 (m, 1H), 8.31-8.26 (m, 1H), 8.13 (m, 1H), 7.76 (m, 1H), 7.39 (m, 1H), 3.13 (m, 1H), 3.03-2.84 (m, 1H), 2.35-1.70 (m, 6H), 1.38 (m, 7H), 1.06 (m, 3H). Method 1: RT = 3.36 min.; M + H = 381.4 |

TABLE 2-continued

| Cpd No. | Structure | ¹HNMR and HPLC retention time and/or MS |
|---|---|---|
| 67 | 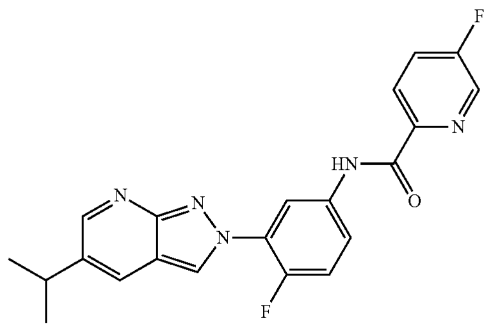 [SMILES: CC(C)c1cnc2nn(-c3cc(NC(=O)c4ccc(F)cn4)ccc3F)cc2c1] | ¹H NMR (400 MHz, Methanol-d₄) δ 8.74-8.69 (m, 1H), 8.69-8.64 (m, 1H), 8.64-8.59 (m, 1H), 8.59-8.53 (m, 1H), 8.33-8.26 (m, 1H), 8.16-8.10 (m, 1H), 8.01-7.94 (m, 1H), 7.86-7.77 (m, 1H), 7.51-7.41 (m, 1H), 3.14 (m, 1H), 1.39 (2s, 6H). Method 1: RT = 3.22 min.; M + H = 394.3 |
| 68 | 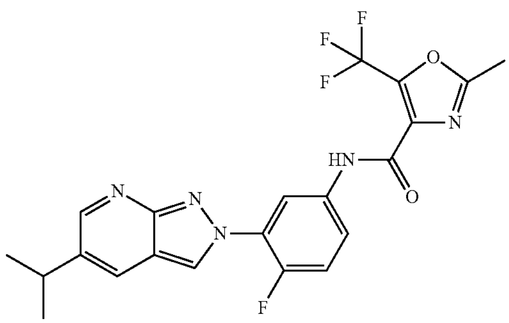 [SMILES: Cc1nc(C(=O)Nc2ccc(F)c(-n3cc4cc(C(C)C)cnc4n3)c2)c(C(F)(F)F)o1] | ¹H NMR (400 MHz, Methanol-d₄) δ 8.73 (m, 1H), 8.67 (m, 1H), 8.48 (m, 1H), 8.14 (m, 1H), 7.91 (m, 1H), 7.47 (m, 1H), 3.19-3.09 (m, 1H), 2.62 (s, 3H), 1.39 (2s, 6H). Method 1: RT = 3.29 min.; M + H = 448.3 |
| 69 | 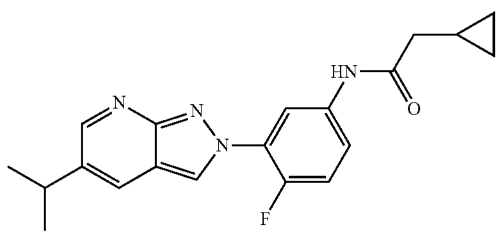 [SMILES: CC(C)c1cnc2nn(-c3cc(NC(=O)CC4CC4)ccc3F)cc2c1] | ¹H NMR (400 MHz, Methanol-d₄) δ 8.45 (m, 1H), 8.41 (m, 1H), 8.05 (m, 1H), 7.88 (m, 1H), 7.52 (m, 1H), 7.15 (m, 1H), 2.89 (m, 1H), 2.09-2.01 (m, 2H), 1.13 (2s, 6H), 0.96-0.83 (m, 1H), 0.42-0.29 (m, 2H), 0.08-0.05 (m, 2H). Method 1: RT = 3.06 min.; M + H = 353.3 |
| 70 | 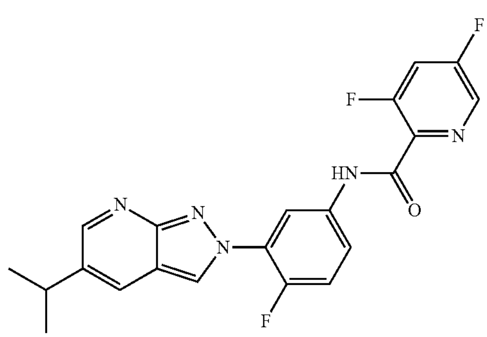 [SMILES: CC(C)c1cnc2nn(-c3cc(NC(=O)c4ncc(F)cc4F)ccc3F)cc2c1] | ¹H NMR (400 MHz, Methanol-d₄) δ 8.72 (m, 1H), 8.67(m, 1H), 8.56-8.48 (m, 2H), 8.14 (m, 1H), 7.96 (m, 1H), 7.80 (m, 1H), 7.47 (m, 1H), 3.14 (m, 1H), 1.39 (2s, 6H). Method 1: RT = 3.12 min.; M + H = 412.3 |
| 71 | 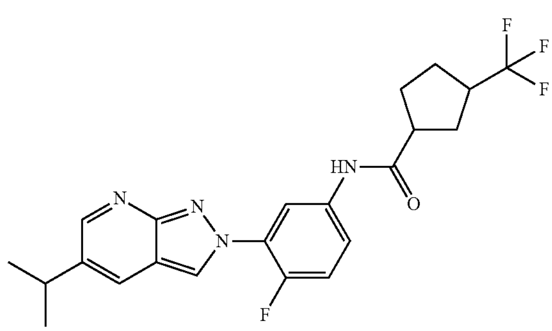 [SMILES: CC(C)c1cnc2nn(-c3cc(NC(=O)C4CCC(C(F)(F)F)C4)ccc3F)cc2c1] | ¹H NMR (400 MHz, Methanol-d₄) δ 8.69 (m, 1H), 8.66 (m, 1H), 8.30 (m, 1H), 8.15-8.09 (m, 1H), 7.76 (m, 1H), 7.40 (m, 1H), 3.18-3.07 (m, 1H), 3.07-2.74 (m, 2H), 2.27-1.73 (m, 6H), 1.56-1.17 (2s, 6H). Method 1: RT = 3.35 min.; M + H = 435.3 |

TABLE 2-continued

| Cpd No. | Structure | ¹HNMR and HPLC retention time and/or MS |
|---|---|---|
| 72 | 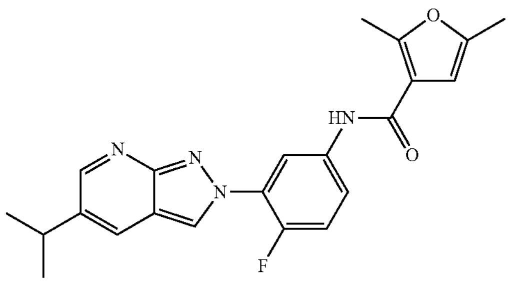 [SMILES: Cc1cc(C(=O)Nc2ccc(F)c(-n3cc4cc(C(C)C)cnc4n3)c2)c(C)o1] | ¹H NMR (400 MHz, Methanol-d₄) δ 8.71 (m, 1H), 8.66 (m, 1H), 8.36 (m, 1H), 8.14 (m, 1H), 7.84 (m, 1H), 7.46-7.38 (m, 1H), 6.53-6.45 (m, 1H), 3.14 (m, 1H), 2.54 (s, 3H), 2.29 (s, 3H), 1.39 (2s, 6H). Method 1: RT = 3.31 min.; M + H = 393.3 |
| 73 | 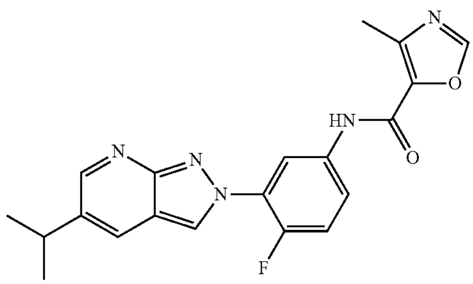 [SMILES: Cc1ncoc1C(=O)Nc1ccc(F)c(-n2cc3cc(C(C)C)cnc3n2)c1] | ¹H NMR (400 MHz, Methanol-d₄) δ 8.72 (m, 1H), 8.67 (m, 1H), 8.44 (m, 1H), 8.28 (m, 1H), 8.14 (m, 1H), 7.90 (m, 1H), 7.45 (m, 1H), 3.14 (m, 1H), 2.53 (s, 3H), 1.39 (2s, 6H). Method 1: RT = 3.00 min.; M + H = 380.3 |
| 74 | 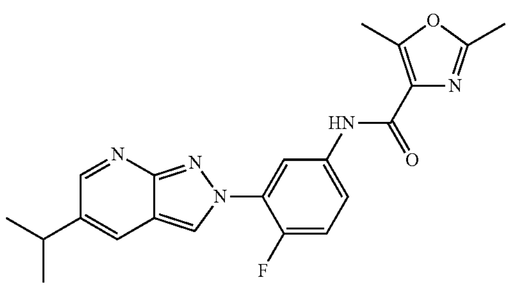 [SMILES: Cc1nc(C(=O)Nc2ccc(F)c(-n3cc4cc(C(C)C)cnc4n3)c2)c(C)o1] | ¹H NMR (400 MHz, Methanol-d₄) δ 8.70 (m, 1H), 8.66 (m, 1H), 8.46 (m, 1H), 8.13 (m, 1H), 7.85 (m, 1H), 7.47-7.36 (m, 1H), 3.14 (m, 1H), 2.62 (s, 3H), 2.46 (s, 3H), 1.49-1.19 (2s, 6H). Method 1: RT = 3.23 min.; M + H = 394.3 |
| 75 | 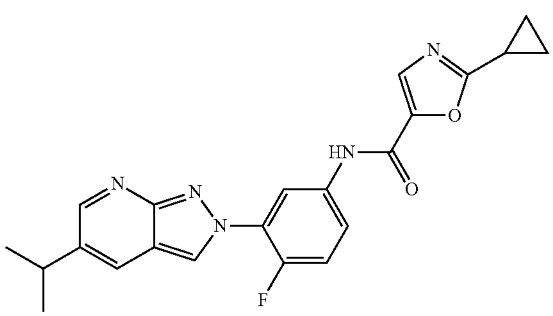 [SMILES: CC(C)c1cnc2nn(-c3cc(NC(=O)c4cnc(C5CC5)o4)ccc3F)cc2c1] | ¹H NMR (400 MHz, Methanol-d₄) δ 8.75-8.69 (m, 1H), 8.69-8.63 (m, 1H), 8.45-8.39 (m, 1H), 8.16-8.09 (m, 1H), 7.95-7.87 (m, 1H), 7.51-7.41 (m, 1H), 3.20-3.06 (m, 1H), 2.29-2.19 (m, 1H), 1.39 (2s, 6H), 1.27-1.14 (m, 4H). Method 1: RT = 3.15 min.; M + H = 406.3 |
| 76 | 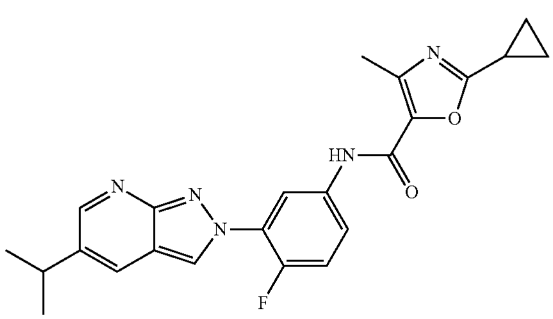 [SMILES: Cc1nc(C2CC2)oc1C(=O)Nc1ccc(F)c(-n2cc3cc(C(C)C)cnc3n2)c1] | ¹H NMR (400 MHz, Methanol-d₄) δ 8.74-8.68 (m, 1H), 8.69-8.62 (m, 1H), 8.46-8.39 (m, 1H), 8.16-8.09 (m, 1H), 7.92-7.83 (m, 1H), 7.48-7.38 (m, 1H), 3.20-3.08 (m, 1H), 2.49-2.39 (m, 3H), 2.23-2.12 (m, 1H), 1.38 (2s, 6H), 1.29-1.12 (m, 4H). Method 1: RT = 3.24 min.; M + H = 420.3 |

TABLE 2-continued

| Cpd No. | Structure | ¹HNMR and HPLC retention time and/or MS |
|---|---|---|
| 77 | 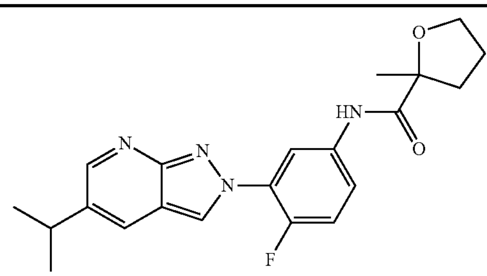 | ¹H NMR (400 MHz, Methanol-d₄) δ 8.72-8.67 (m, 1H), 8.67-8.63 (m, 1H), 8.39-8.33 (m, 1H), 8.15-8.09 (m, 1H), 7.85-7.77 (m, 1H), 7.45-7.37 (m, 1H), 4.13-3.97 (m, 2H), 3.22-3.09 (m, 1H), 2.47-2.31 (m, 1H), 2.09-1.77 (m, 4H), 1.50 (s, 3H), 1.38 (2s, 6H). Method 1: RT = 3.10 min.; M + H = 383.3 |
| 78 | 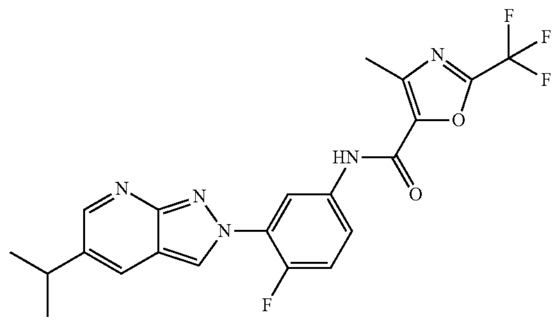 [SMILES: Cc1nc(C(F)(F)F)oc1C(=O)Nc1ccc(F)c(-n2cc3cc(C(C)C)cnc3n2)c1] | ¹H NMR (400 MHz, Methanol-d₄) δ 8.72 (m, 1H), 8.66 (m, 1H), 8.47 (m, 1H), 8.13 (m, 1H), 7.89 (m, 1H), 7.49-7.41 (m, 1H), 3.14 (m, 1H), 2.63-2.47 (s, 3H), 1.38 (2s, 6H). Method 1: RT = 3.39 min.; M + H = 448.3 |
| 79 | 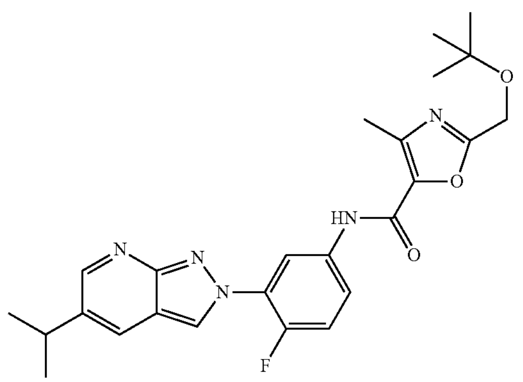 [SMILES: Cc1nc(COC(C)(C)C)oc1C(=O)Nc1ccc(F)c(-n2cc3cc(C(C)C)cnc3n2)c1] | ¹H NMR (400 MHz, Methanol-d₄) δ 8.72 (m, 1H), 8.66 (m, 1H), 8.43 (m, 1H), 8.13 (m, 1H), 7.89 (m, 1H), 7.45 (m, 1H), 4.61 (s, 2H), 3.14 (m, 1H), 2.50 (s, 3H), 1.49-1.34 (2s, 6H), 1.34-1.20 (s, 9H). Method 1: RT = 3.36 min.; M + H = 466.4 |
| 80 | 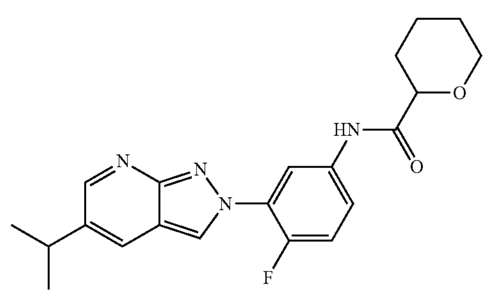 [SMILES: CC(C)c1cnc2nn(-c3cc(NC(=O)C4CCCCO4)ccc3F)cc2c1] | ¹H NMR (400 MHz, Methanol-d₄) δ 8.69 (m, 1H), 8.66 (m, 1H), 8.36 (m, 1H), 8.13 (m, 1H), 7.80 (m, 1H), 7.41 (m, 1H), 4.16 (m, 1H), 3.97 (m, 1H), 3.60 (m, 1H), 3.13 (m, 1H), 2.12-2.04 (m, 1H), 2.01-1.92 (m, 1H), 1.75-1.49 (m, 4H), 1.38 (2s, 6H). Method 1: RT = 3.17 min.; M + H = 383.3 |
| 81 | 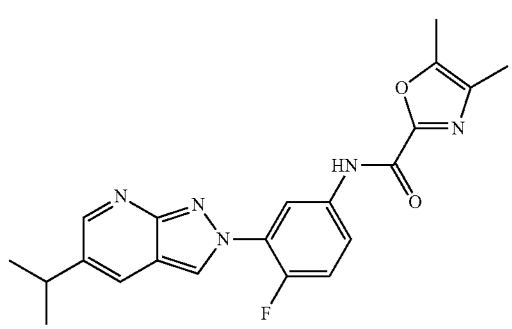 | ¹H NMR (400 MHz, Methanol-d₄) δ 8.74-8.68 (m, 1H), 8.68-8.63 (m, 1H), 8.49-8.44 (m, 1H), 8.16-8.09 (m, 1H), 7.95-7.87 (m, 1H), 7.50-7.39 (m, 1H), 3.21-3.06 (m, 1H), 2.39 (s, 3H), 2.19 (s, 3H), 1.38 (2s, 6H). Method 1: RT = 3.18 min.; M + H = 394.3 |

TABLE 2-continued

| Cpd No. | Structure | ¹HNMR and HPLC retention time and/or MS |
|---|---|---|
| 82 | 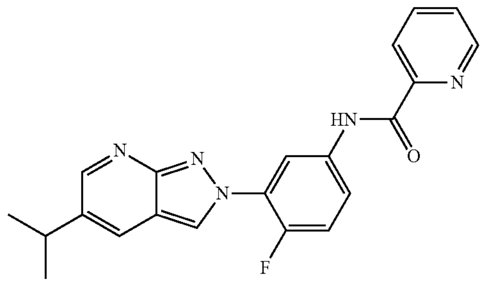 [SMILES: CC(C)c1cnc2nn(-c3cc(NC(=O)c4ccccn4)ccc3F)cc2c1] | ¹H NMR (400 MHz, Methanol-d₄) δ 8.76-8.69 (m, 2H), 8.67 (m, 1H), 8.59 (m, 1H), 8.24 (m, 1H), 8.14 (m, 1H), 8.07-7.96 (m, 2H), 7.62 (m, 1H), 7.47 (m, 1H), 3.14 (m, 1H), 1.57-1.21 (2s, 6H). Method 1: RT = 3.18 min.; M + H = 376.3 |
| 83 | 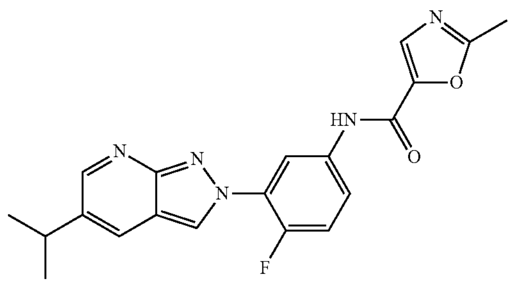 [SMILES: Cc1ncc(C(=O)Nc2ccc(F)c(-n3cc4cc(C(C)C)cnc4n3)c2)o1] | ¹H NMR (400 MHz, Methanol-d₄) δ 8.74-8.69 (m, 1H), 8.68-8.63 (m, 1H), 8.46-8.40 (m, 1H), 8.16-8.11 (m, 1H), 7.94-7.87 (m, 1H), 7.79-7.75 (m, 1H), 7.50-7.41 (m, 1H), 3.21-3.07 (m, 1H), 2.59 (s, 3H), 1.39 (2s, 6H). Method 1: RT = 3.01 min.; M + H = 380.3 |
| 84 | 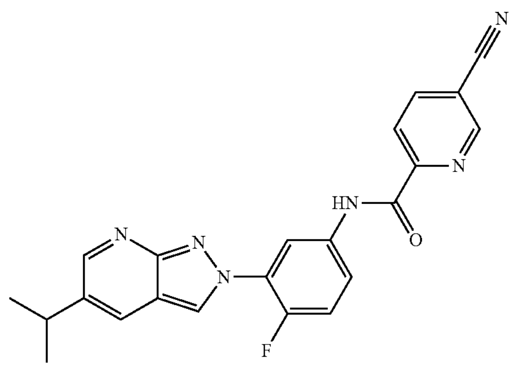 [SMILES: CC(C)c1cnc2nn(-c3cc(NC(=O)c4ccc(C#N)cn4)ccc3F)cc2c1] | ¹H NMR (400 MHz, Methanol-d₄) δ 9.06 (m, 1H), 8.73 (m, 1H), 8.67 (m, 1H), 8.60 (m, 1H), 8.45-8.34 (m, 2H), 8.17-8.12 (m, 1H), 8.01 (m, 1H), 7.48 (m, 1H), 3.14 (m, 1H), 1.39 (2s, 6H). Method 1: RT = 3.15 min.; M + H = 401.3 |
| 85 | 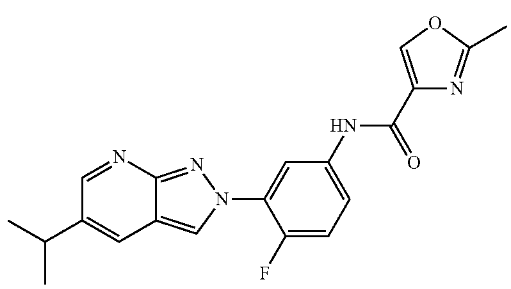 [SMILES: Cc1nc(C(=O)Nc2ccc(F)c(-n3cc4cc(C(C)C)cnc4n3)c2)co1] | ¹H NMR (400 MHz, Methanol-d₄) δ 8.71 (m, 1H), 8.66 (m, 1H), 8.47 (m, 1H), 8.41 (m, 1H), 8.14 (m, 1H), 7.90 (m, 1H), 7.45 (m, 1H), 3.14 m, 1H), 1.39 (2s, 6H). Method 1: RT = 3.08 min.; M + H = 380.3 |
| 86 | 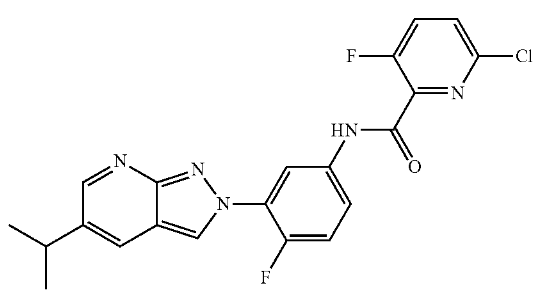 [SMILES: CC(C)c1cnc2nn(-c3cc(NC(=O)c4nc(Cl)ccc4F)ccc3F)cc2c1] | ¹H NMR (400 MHz, Methanol-d₄) δ 8.73 (m, 1H), 8.67 (m, 1H), 8.51 (m, 1H), 8.14 (m, 1H), 7.95 (m, 1H), 7.86 (m, 1H), 7.73 (m, 1H), 7.48 (m, 1H), 3.20-3.08 (m, 1H), 1.45-1.20 (2s, 6H). Method 1: RT = 3.22 min.; M + H = 428.3 |

TABLE 2-continued

| Cpd No. | Structure | ¹HNMR and HPLC retention time and/or MS |
|---|---|---|
| 87 | 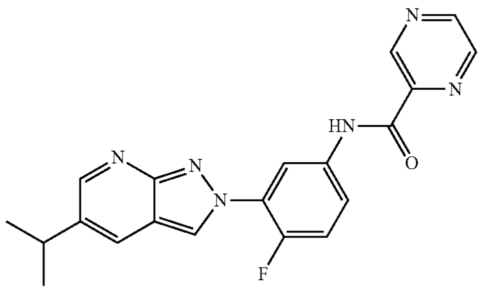 [SMILES: CC(C)c1cnc2nn(-c3cc(NC(=O)c4cnccn4)ccc3F)cc2c1] | ¹H NMR (400 MHz, Methanol-d₄) δ 9.36 (m, 1H), 8.84 (m, 1H), 8.76 (m, 1H), 8.72 (m, 1H), 8.66 (m, 1H), 8.57 (m, 1H), 8.13 (m, 1H), 7.99 (m, 1H), 7.46 (m, 1H), 3.13 (m, 1H), 1.38 (2s, 6H). Method 1: RT = 3.05 min.; M + H = 377.3 |
| 88 | 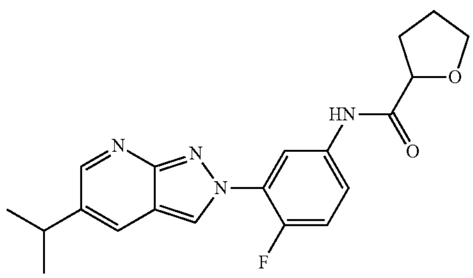 [SMILES: CC(C)c1cnc2nn(-c3cc(NC(=O)C4CCCO4)ccc3F)cc2c1] | ¹H NMR (400 MHz, Methanol-d₄) δ 8.69 (m, 1H), 8.66 (m, 1H), 8.36 (m, 1H), 8.12 (m, 1H), 7.81 (m, 1H), 7.41 (m, 1H), 4.46 (m, 1H), 4.12 (m, 1H), 3.94 (m, 1H), 3.13 (m, 1H), 2.36 (m, 1H), 2.10 (m, 1H), 1.97 (m, 2H), 1.38 (2s, 6H). Method 1: RT = 2.93 min.; M + H = 369.3 |
| 89 | 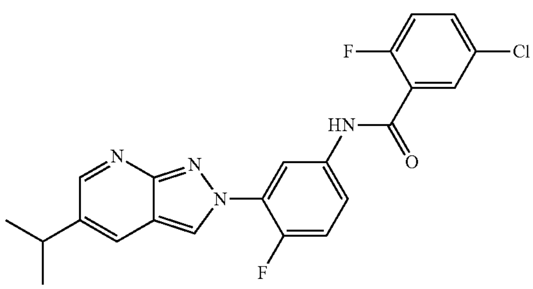 [SMILES: CC(C)c1cnc2nn(-c3cc(NC(=O)c4cc(Cl)ccc4F)ccc3F)cc2c1] | ¹H NMR (400 MHz, Methanol-d4) δ 8.73 (m, 1H), 8.66 (m, 1H), 8.43 (m, 1H), 8.14 (m, 1H), 7.92-7.85 (m, 1H), 7.76 (m, 1H), 7.59 (m, 1H), 7.46 (m, 1H), 7.30 (m, 1H), 3.14 (m, 1H), 1.38 (d, J = 6.9 Hz, 6H). Method 1: RT = 3.35 min.; M + H = 427.3 |
| 90 | 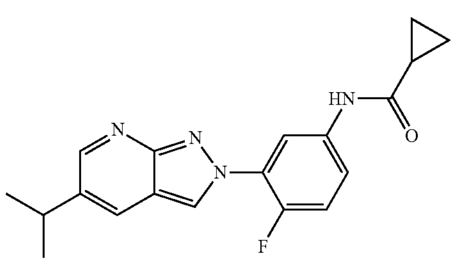 [SMILES: CC(C)c1cnc2nn(-c3cc(NC(=O)C4CC4)ccc3F)cc2c1] | ¹H NMR (400 MHz, Methanol-d₄) δ 8.69 (m, 1H), 8.65 (m, 1H), 8.28 (m, 1H), 8.13 (m, 1H), 7.74 (m, 1H), 7.39 (m, 1H), 3.13 (m, 1H), 1.79 (m, 1H), 1.38 (2s, 6H), 1.01-0.84 (m, 4H). Method 1: RT = 3.07 min.; M + H = 339.3 |
| 91 | 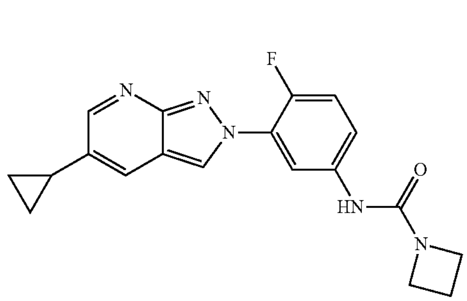 [SMILES: O=C(Nc1ccc(F)c(-n2cc3cc(C4CC4)cnc3n2)c1)N1CCC1] | ¹H NMR (400 MHz, Methanol-d₄) δ 8.64-8.57 (m, 2H), 8.14-8.09 (m, 1H), 7.94-7.89 (m, 1H), 7.66-7.59 (m, 1H), 7.36-7.29 (m, 1H), 4.17-4.05 (m, 4H), 2.39-2.26 (m, 2H), 2.17-2.06 (m, 1H), 1.13-1.04 (m, 2H), 0.87-0.77 (m, 2H). Method 1: RT = 2.82 min.; M + H = 352.3 |

TABLE 2-continued

| Cpd No. | Structure | ¹HNMR and HPLC retention time and/or MS |
|---|---|---|
| 92 | 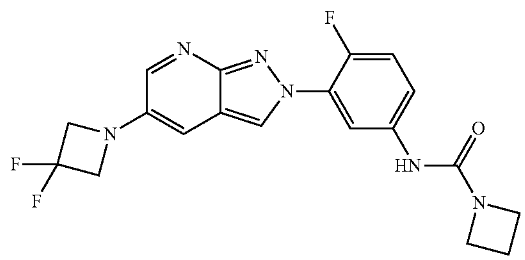 [SMILES: O=C(Nc1ccc(F)c(-n2cc3cc(N4CC(F)(F)C4)cnc3n2)c1)N1CCC1] | ¹H NMR (400 MHz, DMSO) δ 8.69 (s, 1 H), 8.62 (d, J = 2.64 Hz, 1 H), 8.36 (d, J = 2.76 Hz, 1 H), 8.22 (dd, J = 7.09, 2.70 Hz, 1 H), 7.65-7.72 (m, 1 H), 7.42 (dd, J = 11.29, 9.16 Hz, 1 H), 7.15 (d, J = 2.89 Hz, 1 H), 4.41 (t, J = 12.23 Hz, 4 H), 3.98 (t, J = 7.53 Hz, 4 H), 2.20 (quin, J = 7.56 Hz, 2 H). Method 1: RT = 2.81 min. M + H = 403.2, |
| 93 | 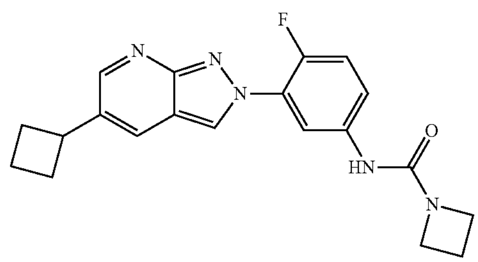 [SMILES: O=C(Nc1ccc(F)c(-n2cc3cc(C4CCC4)cnc3n2)c1)N1CCC1] | ¹H NMR (400 MHz, Methanol-d₄) δ 8.76-8.65 (m, 1H), 8.64-8.58 (m, 1H), 8.14-8.06 (m, 1H), 7.67-7.60 (m, 1H), 7.38-7.30 (m, 1H), 7.18-7.01 (m, 1H), 4.17-3.96 (m, 4H), 3.84-3.69 (m, 1H), 2.62-2.09 (m, 7H), 2.04-1.93 (m, 1H). Method 1: RT = 2.94 min.; M + H = 366.3 |
| 94 | 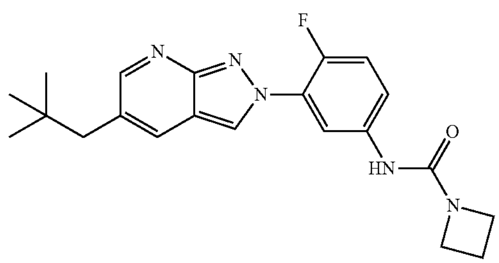 [SMILES: CC(C)(C)Cc1cnc2nn(-c3cc(NC(=O)N4CCC4)ccc3F)cc2c1] | ¹H NMR (400 MHz, Methanol-d₄) δ 8.71-8.66 (m, 1H), 8.56-8.50 (m, 1H), 8.15-8.09 (m, 1H), 8.09-8.04 (m, 1H), 7.68-7.60 (m, 1H), 7.38-7.30 (m, 1H), 4.18-4.04 (m, 4H), 2.69 (s, 2H), 2.40-2.27 (m, 2H), 0.99 (s, 9H). Method 1: RT = 3.19 min.; M + H = 382.4 |
| 95 | 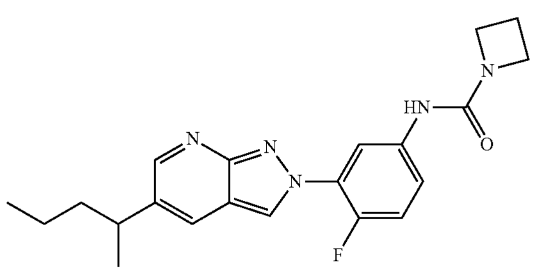 [SMILES: CCCC(C)c1cnc2nn(-c3cc(NC(=O)N4CCC4)ccc3F)cc2c1] | ¹H NMR (400 MHz, Methanol-d₄) δ 8.69-8.64 (m, 1H), 8.62-8.56 (m, 1H), 8.15-8.05 (m, 2H), 7.67-7.61 (m, 1H), 7.37-7.30 (m, 1H), 4.17-4.05 (m, 4H), 2.84-2.75 (m, 2H), 2.39-2.26 (m, 2H), 1.80-1.66 (m, 2H), 1.48-1.34 (m, 4H), 1.01-0.87 (m, 3H). Method 1: RT = 3.22 min.; M + H = 382.4 |
| 96 | 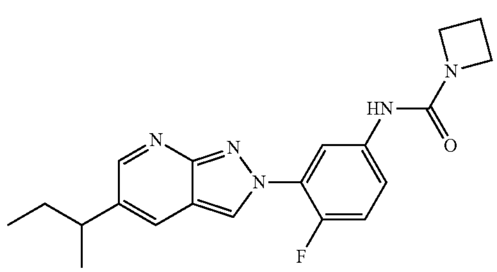 [SMILES: CCC(C)c1cnc2nn(-c3cc(NC(=O)N4CCC4)ccc3F)cc2c1] | ¹H NMR (400 MHz, Methanol-d₄) δ 8.65 (m, 1H), 8.59 (m, 1H), 8.15-8.06 (m, 2H), 7.64 (m, 1H), 7.34 (m, 1H), 4.17-4.05 (m, 4H), 2.85-2.76 (m, 2H), 2.32 (m, 2H), 1.78-1.64 (m, 2H), 1.43 (m, 3H), 1.00 (m, 3H). Method 1: RT = 3.13 min.; M + H = 368.3 |
| 97 | 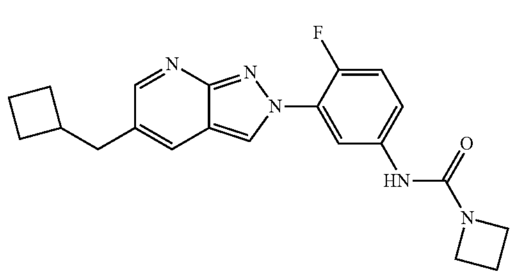 [SMILES: O=C(Nc1ccc(F)c(-n2cc3cc(CC4CCC4)cnc3n2)c1)N1CCC1] | ¹H NMR (400 MHz, Methanol-d₄) δ 8.71-8.62 (m, 1H), 8.63-8.52 (m, 1H), 8.14-8.07 (m, 1H), 8.07-8.01 (m, 1H), 7.64 (m, 1H), 7.33 (m, 1H), 4.19-4.04 (m, 4H), 2.87 (m, 2H), 2.68 (m, 1H), 2.39-2.27 (m, 2H), 2.16-2.03 (m, 2H), 1.99-1.76 (m, 4H). Method 1: RT = 3.11 min.; M + H = 380.3 |

TABLE 2-continued

| Cpd No. | Structure | ¹HNMR and HPLC retention time and/or MS |
|---|---|---|
| 98 | 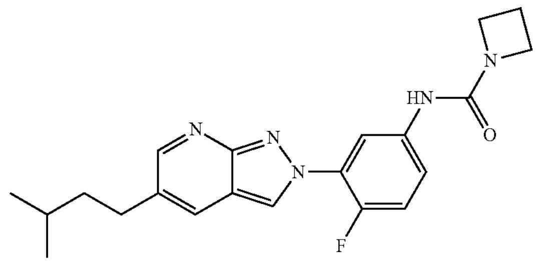 [SMILES: CC(C)CCc1cnc2nn(-c3cc(NC(=O)N4CCC4)ccc3F)cc2c1] | ¹H NMR (400 MHz, Methanol-d₄) δ 8.65 (m, 1H), 8.57 (m, 1H), 8.15-8.02 (m, 2H), 7.64 (m, 1H), 7.33 (m, 1H), 4.18-4.01 (m, 4H), 2.92-2.69 (m, 2H), 2.32 (m, 2H), 1.84-1.53 (m, 3H), 1.06-0.89 (m, 6H). Method 1: RT = 3.18 min.; M + H = 382.4 |
| 99 | 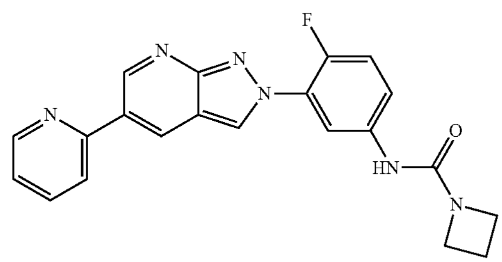 [SMILES: O=C(Nc1ccc(F)c(-n2cc3cc(-c4ccccn4)cnc3n2)c1)N1CCC1] | ¹H NMR (400 MHz, Methanol-d₄) δ 9.37 (m, 1H), 8.87 (m, 2H), 8.70 (m, 1H), 8.17 (m, 1H), 8.05-7.92 (m, 2H), 7.66 (m, 1H), 7.43 (m, 1H), 7.36 (m, 1H), 4.17-4.07 (m, 4H), 2.33 (m, 2H). Method 1: RT = 2.66 min.; M + H = 389.3 |
| 100 | 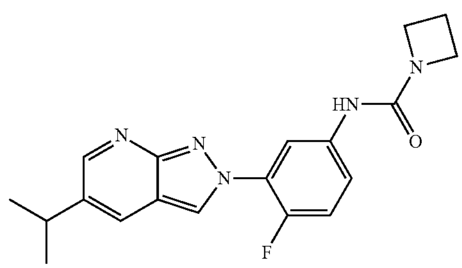 | ¹H NMR (400 MHz, DMSO-d6) δ 8.78 (d, J = 2.63 Hz, 1 H), 8.73 (s, 1 H), 8.68 (d, J = 2.38 Hz, 1 H), 8.24 (dd, J = 7.03, 2.76 Hz, 1 H), 8.05 (d, J = 1.88 Hz, 1 H), 7.66-7.73 (m, 1 H), 7.44 (dd, J = 11.29, 9.16 Hz, 1 H), 3.98 (t, J = 7.59 Hz, 4 H), 3.02-3.14 (m, 1 H), 2.10-2.27 (m, 2 H), 1.30 (d, J = 6.90 Hz, 6 H). Method 2: RT = 0.94 min.; M + H = 354.1 |
| 101 | 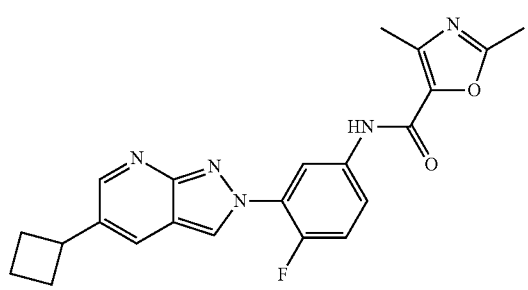 [SMILES: Cc1nc(C)c(C(=O)Nc2ccc(F)c(-n3cc4cc(C5CCC5)cnc4n3)c2)o1] | ¹H NMR (400 MHz, Methanol-d₄) δ 9.07 (m, 1H), 8.79 (m, 1H), 8.49 (m, 1H), 7.87 (m, 1H), 7.52-7.43 (m, 1H), 7.36-7.29 (m, 1H), 2.69-2.56 (m, 2H), 2.55 (m, 3H), 2.46 (m, 3H), 2.34-2.12 (m, 3H), 2.07-1.93 (m, 2H). Method 1: RT = 3.08 min.; M + H = 406.3 |
| 102 | 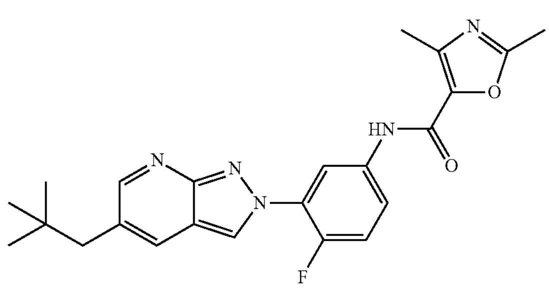 [SMILES: Cc1nc(C)c(C(=O)Nc2ccc(F)c(-n3cc4cc(CC(C)(C)C)cnc4n3)c2)o1] | ¹H NMR (400 MHz, Methanol-d₄) δ 8.83 (m, 1H), 8.62 (m, 1H), 8.48 (m, 1H), 8.25-8.20 (m, 1H), 7.92-7.86 (m, 1H), 7.50-7.43 (m, 1H), 2.73 (s, 2H), 2.55 (m, 3H), 2.46 (m, 3H), 1.00 (m, 9H). Method 1: RT = 3.28 min.; M + H = 422.3 |

TABLE 2-continued

| Cpd No. | Structure | ¹HNMR and HPLC retention time and/or MS |
|---|---|---|
| 103 | 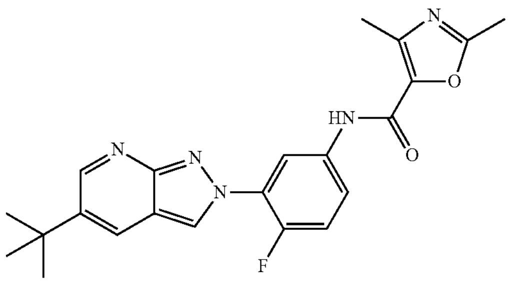 [SMILES: Cc1nc(C)c(C(=O)Nc2ccc(F)c(-n3cc4cc(C(C)(C)C)cnc4n3)c2)o1] | ¹H NMR (400 MHz, Methanol-d₄) δ 8.79-8.68 (m, 2H), 8.13 (m, 1H), 7.98-7.91 (m, 1H), 7.47-7.38 (m, 1H), 7.31-7.24 (m, 1H), 2.55 (m, 3H), 2.46 (m, 3H), 1.55 (m, 9H). Method 1: RT = 2.90 min.; M + H = 408.3 |
| 104 | 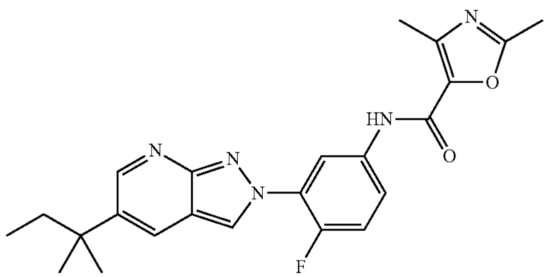 [SMILES: CCC(C)(C)c1cnc2nn(-c3cc(NC(=O)c4oc(C)nc4C)ccc3F)cc2c1] | ¹H NMR (400 MHz, Methanol-d₄) δ 8.86 (m, 1H), 8.78 (m, 1H), 8.14 (m, 1H), 7.94 (m, 1H), 7.42 (m, 1H), 7.38-7.32 (m, 1H), 2.54 (m, 3H), 2.46 (m, 3H), 1.98-1.81 (m, 2H), 1.53 (s, 3H), 1.42 (s, 3H), 0.84-0.74 (m, 3H). Method 1: RT = 2.96 min.; M + H = 422.4 |
| 105 | 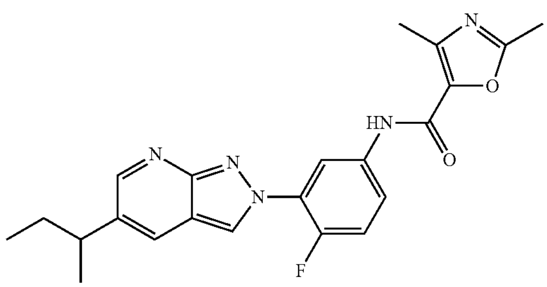 [SMILES: CCC(C)c1cnc2nn(-c3cc(NC(=O)c4oc(C)nc4C)ccc3F)cc2c1] | ¹H NMR (400 MHz, Methanol-d4) δ 8.78-8.70 (m, 1H), 8.67-8.58 (m, 1H), 8.52-8.42 (m, 1H), 7.92-7.84 (m, 1H), 7.52-7.44 (m, 1H), 7.27 (m, 1H), 2.55 (m, 3H), 2.46 (m, 3H), 1.89 (m, 2H), 1.53-1.40 (m, 3H), 1.04-0.89 (m, 3H), 0.80 (m, 1H). Method 1: RT = 3.13 min.; M + H = 408.3 |
| 106 | 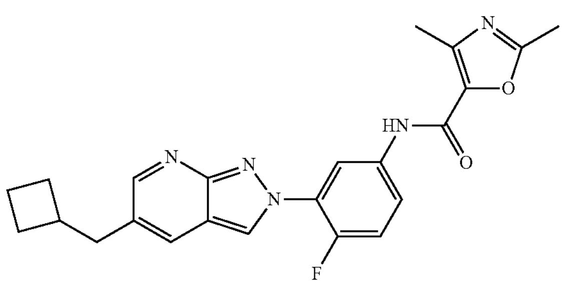 [SMILES: Cc1nc(C)c(C(=O)Nc2ccc(F)c(-n3cc4cc(CC5CCC5)cnc4n3)c2)o1] | ¹H NMR (400 MHz, Methanol-d4) δ 8.77 (m, 1H), 8.62 (m, 1H), 8.45 (m, 1H), 8.17 (m, 1H), 7.88 (m, 1H), 7.45 (m, 1H), 2.90 (m, 2H), 2.74-2.65 (m, 1H), 2.55 (s, 3H), 2.46 (s, 3H), 2.10 (m, 2H), 1.96-1.80 (m, 4H). Method 1: RT = 3.24 min.; M + H = 420.3 |
| 107 | 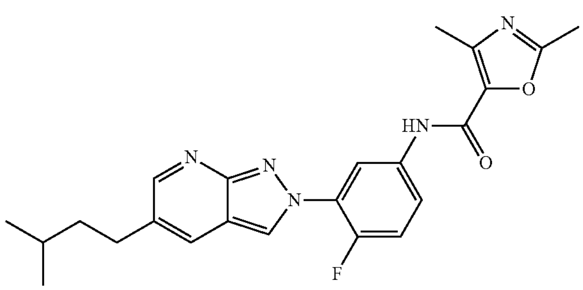 [SMILES: Cc1nc(C)c(C(=O)Nc2ccc(F)c(-n3cc4cc(CCC(C)C)cnc4n3)c2)o1] | ¹H NMR (400 MHz, Methanol-d4) δ 8.85 (m, 1H), 8.73-8.66 (m, 1H), 8.49 (m, 1H), 8.31 (m, 1H), 7.87 (m, 1H), 7.46 (m, 1H), 2.88-2.80 (m, 2H), 2.55 (s, 3H), 2.46 (s, 3H), 1.72-1.59 (m, 3H), 1.03-0.92 (m, 6H). Method 1: RT = 3.30 min.; M + H = 422.4 |

TABLE 2-continued

| Cpd No. | Structure | ¹HNMR and HPLC retention time and/or MS |
|---|---|---|
| 108 | 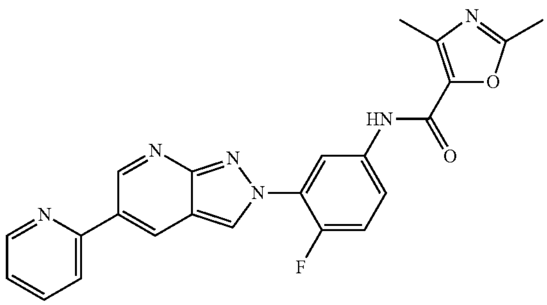 [SMILES: Cc1nc(C)c(C(=O)Nc2ccc(F)c(-n3cc4cc(-c5ccccn5)cnc4n3)c2)o1] | ¹H NMR (400 MHz, Methanol-d₄) δ 9.38 (m, 1H), 8.96 (m, 1H), 8.92 (m, 1H), 8.79-8.71 (m, 1H), 8.50 (m, 1H), 8.12-8.04 (m, 2H), 7.90 (m, 1H), 7.56-7.42 (m, 2H), 2.55 (m, 3H), 2.47 (m, 3H). Method 1: RT = 2.78 min.; M + H = 429.3 |
| 109 | 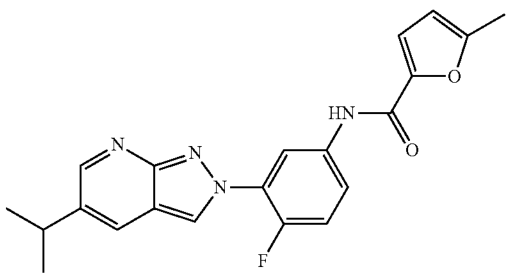 [SMILES: Cc1ccc(C(=O)Nc2ccc(F)c(-n3cc4cc(C(C)C)cnc4n3)c2)o1] | ¹H NMR (400 MHz, Methanol-d₄) δ 8.71 (m, 1H), 8.66 (m, 1H), 8.42 (m, 1H), 8.14 (dd, J = 2.2, 0.7 Hz, 1H), 7.91 (ddd, J = 9.1, 4.2, 2.7 Hz, 1H), 7.44 (dd, J = 11.0, 9.1 Hz, 1H), 7.21 (d, J = 3.4 Hz, 1H), 6.31-6.24 (m, 1H), 3.14 (p, J = 6.9 Hz, 1H), 2.44 (s, 3H), 1.49-1.29 (m, 6H). Method 2: RT = 1.07 min.; M + H = 379.3 |
| 110 | 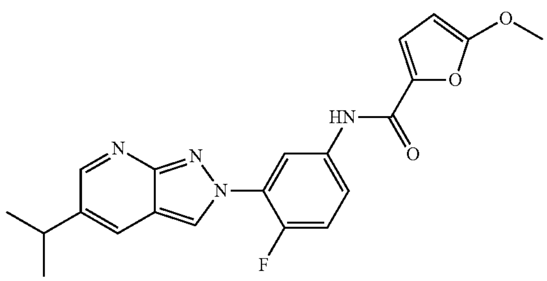 [SMILES: COc1ccc(C(=O)Nc2ccc(F)c(-n3cc4cc(C(C)C)cnc4n3)c2)o1] | ¹H NMR (400 MHz, Methanol-d₄) δ 8.71 (m, 1H), 8.66 (m, 1H), 8.38 (m, 1H), 8.14 (m, 1H), 7.87 (m, 1H), 7.43 (m, 1H), 7.29 (m, 1H), 5.57(m, 1H), 4.02-3.89 (m, 3H), 3.18-3.10 (m, 1H), 1.39 (2s, 6H). Method 2: RT = 1.05 min.; M + H = 395.3 |
| 111 | 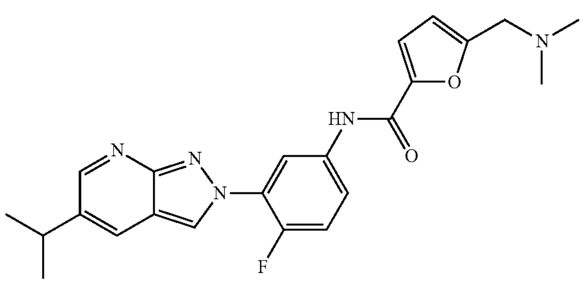 [SMILES: CC(C)c1cnc2nn(-c3cc(NC(=O)c4ccc(CN(C)C)o4)ccc3F)cc2c1] | ¹H NMR (400 MHz, Methanol-d4) δ 8.73 (m, 1H), 8.66 (m, 1H), 8.45 (m, 1H), 8.14 (m, 1H), 7.92 (m, 1H), 7.46 (m, 1H), 7.23 (m, 1H), 6.55 (m, 1H), 3.65 (s, 2H), 3.14 (m, 1H), 2.37 (2s, 6H), 1.47-1.31 (2s, 6H). Method 2: RT = 0.74 min.; M + H = 422.3 |
| 112 | 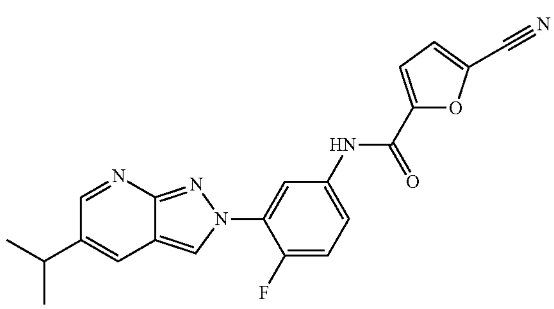 [SMILES: CC(C)c1cnc2nn(-c3cc(NC(=O)c4ccc(C#N)o4)ccc3F)cc2c1] | ¹H NMR (400 MHz, Methanol-d₄) δ 8.73 (m, 1H), 8.67 (m, 1H), 8.47 (m, 1H), 8.14 (m, 1H), 7.93 (m, 1H), 7.54-7.40 (m, 3H), 3.16-3.09 (m, 1H), 1.39 (2s, 6H). Method 2: RT = 1.08 min.; M + H = 390.3 |

TABLE 2-continued

| Cpd No. | Structure | ¹HNMR and HPLC retention time and/or MS |
|---|---|---|
| 113 | 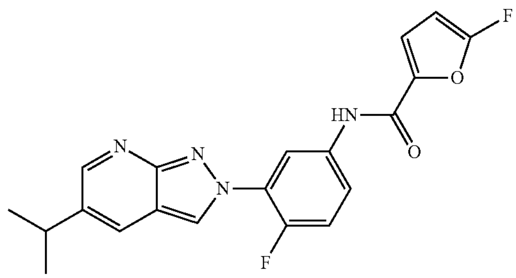 [SMILES: CC(C)c1cnc2nn(-c3cc(NC(=O)c4ccc(F)o4)ccc3F)cc2c1] | ¹H NMR (400 MHz, Methanol-$d_4$) δ 8.72 (m, 1H), 8.67 (m, 1H), 8.40 (m, 1H), 8.14 (m, 1H), 7.89 (m, 1H), 7.45 (m, 1H), 7.31 (m, 1H), 5.90 (m, 1H), 3.19-3.10 (m, 1H), 1.39 (2s, 6H). Method 2: RT = 1.07 min.; M + H = 383.3 |
| 114 | 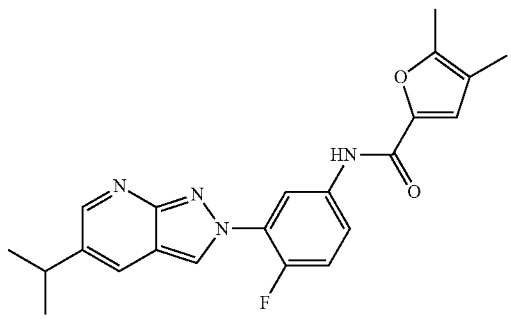 [SMILES: Cc1cc(C(=O)Nc2ccc(F)c(-n3cc4cc(C(C)C)cnc4n3)c2)oc1C] | ¹H NMR (400 MHz, Methanol-$d_4$) δ 8.70 (m, 1H), 8.66 (m, 1H), 8.40 (m, 1H), 8.13 (m, 1H), 7.89 (m, 1H), 7.48-7.38 (m, 1H), 7.09 (m, 1H), 3.14 (m, 1H), 2.40-2.21 (m, 3H), 2.03 (m, 3H), 1.62-1.15 (2s, 6H). Method 2: RT = 1.13 min.; M + H = 393.3 |
| 115 | 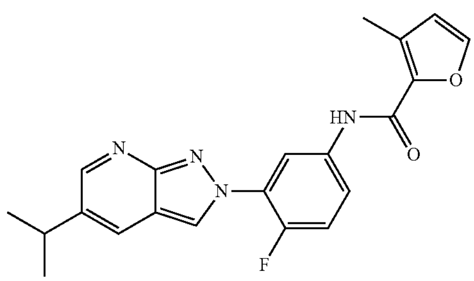 [SMILES: Cc1ccoc1C(=O)Nc1ccc(F)c(-n2cc3cc(C(C)C)cnc3n2)c1] | ¹H NMR (400 MHz, Methanol-$d_4$) δ 8.71 (m, 1H), 8.66 (m, 1H), 8.42 (m, 1H), 8.13 (m, 1H), 7.87 (m, 1H), 7.60 (m, 1H), 7.42 (m, 1H), 6.51 (m, 1H), 3.14 (m, 1H), 2.41 (s, 3H), 1.44-1.26 (2s, 6H). Method 2: RT = 1.11 min.; M + H = 379.3 |
| 116 | 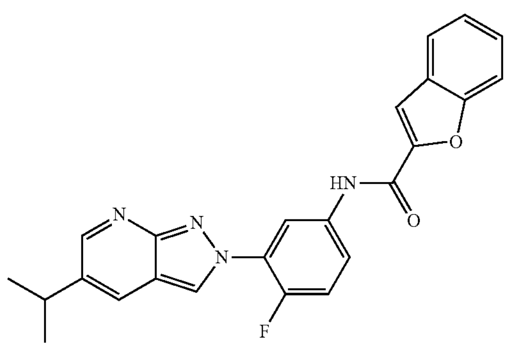 [SMILES: CC(C)c1cnc2nn(-c3cc(NC(=O)c4cc5ccccc5o4)ccc3F)cc2c1] | ¹H NMR (400 MHz, Methanol-$d_4$) δ 8.72 (m, 1H), 8.66 (m, 1H), 8.50 (m, 1H), 8.13 (m, 1H), 7.97 (m, 1H), 7.79-7.74 (m, 1H), 7.69-7.62 (m, 2H), 7.53-7.42 (m, 2H), 7.39-7.31 (m, 1H), 3.13 (m, 1H), 1.38 (2s, 6H). Method 2: RT = 1.17 min.; M + H = 415.3 |
| 117 | 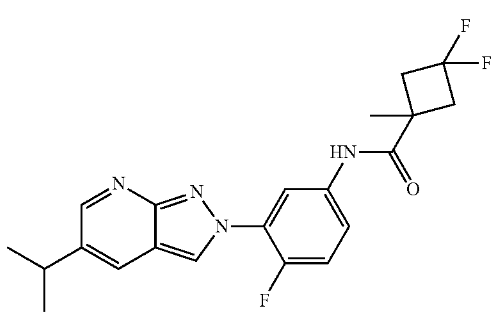 [SMILES: CC(C)c1cnc2nn(-c3cc(NC(=O)C4(C)CC(F)(F)C4)ccc3F)cc2c1] | ¹H NMR (400 MHz, Methanol-$d_4$) δ 8.70 (m, 1H), 8.66 (m, 1H), 8.32 (m, 1H), 8.13 (m, 1H), 7.79 (m, 1H), 7.41 (m, 1H), 3.19-3.04 (m, 3H), 2.60-2.47 (m, 2H), 1.61 (s, 3H), 1.38 (2s, 6H). Method 2: RT = 1.12 min.; M + H = 403.3 |

TABLE 2-continued

| Cpd No. | Structure | ¹HNMR and HPLC retention time and/or MS |
|---|---|---|
| 118 | 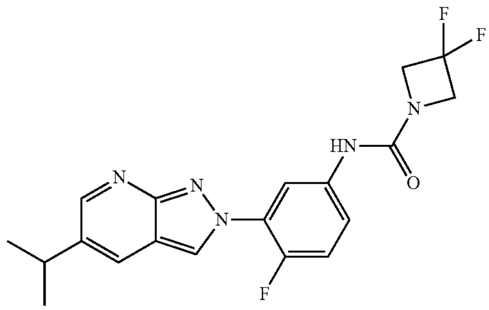 | ¹H NMR (400 MHz, Methanol-d₄) δ 8.70 (m, 1H), 8.66 (m, 1H), 8.32 (m, 1H), 8.13 (m, 1H), 7.77 (m, 1H), 7.41 (m, 1H), 3.21-3.05 (m, 2H), 2.98-2.72 (m, 4H), 1.57-1.19 (2s, 6H). Method 2: RT = 1.08 min.; M + H = 389.3 |
| 119 | 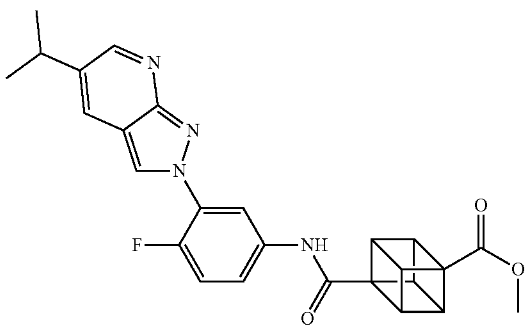 [SMILES: COC(=O)C12C3C4C1C1C2C3C41C(=O)Nc1ccc(F)c(-n2cc3cc(C(C)C)cnc3n2)c1] | ¹H NMR (400 MHz, Methanol-d₄) δ 8.69 (m, 1H), 8.66 (m, 1H), 8.35 (m, 1H), 8.13 (m, 1H), 7.82 (m, 1H), 7.40 (m, 1H), 4.33 (m, 3H), 4.25 (m, 3H), 3.73 (s, 3H), 3.13 (m, 1H), 1.43-1.28 (2s, 6H). Method 2: RT = 1.07 min.; M + H = 459.3 |
| 120 | 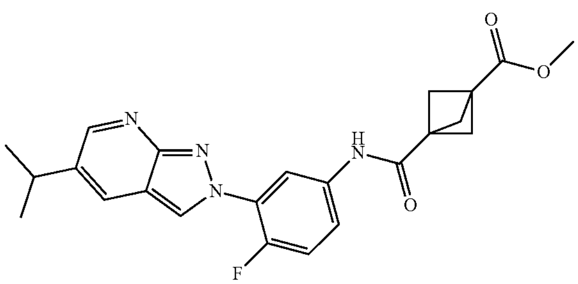 [SMILES: COC(=O)C12CC(C(=O)Nc3ccc(F)c(-n4cc5cc(C(C)C)cnc5n4)c3)(C1)C2] | ¹H NMR (400 MHz, Methanol-d₄) δ 8.69 (m, 1H), 8.66 (m, 1H), 8.33 (m, 1H), 8.13 (m, 1H), 7.81 (m, 1H), 7.41 (m, 1H), 3.76-3.64 (m, 3H), 3.13 (m, 1H), 2.48-2.26 (m, 6H), 1.48-1.17 (2s, 6H). Method 2: RT-1.04 min.; M + H = 423.3 |
| 121 | 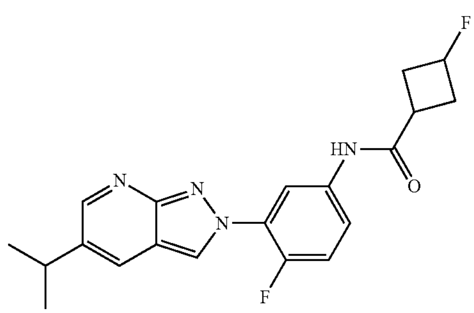 [SMILES: CC(C)c1cnc2nn(-c3cc(NC(=O)C4CC(F)C4)ccc3F)cc2c1] | ¹H NMR (400 MHz, Methanol-d₄) δ 8.70 (m, 1H), 8.66 (m, 1H), 8.31 (m, 1H), 8.13 (m, 1H), 7.75 (m, 1H), 7.40 (m, 1H), 5.37-5.12 (m, 1H), 3.29-3.22 (m, 1H), 3.14 (m, 1H), 2.73-2.41 (m, 4H), 1.60-1.16 (2s, 6H). Method 1: RT = 3.06 min.; M + H = 371.3 |
| 122 | 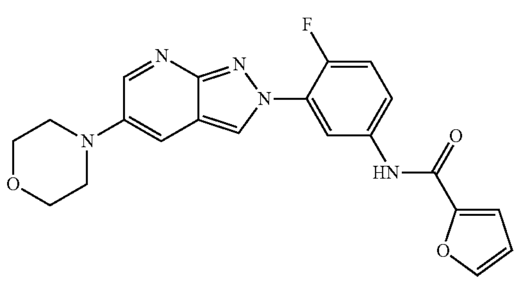 [SMILES: O=C(Nc1ccc(F)c(-n2cc3cc(N4CCOCC4)cnc3n2)c1)c1ccco1] | ¹H NMR (400 MHz, Methanol-d₄), δ 8.86 (s, 1 H), 8.81 (s, 1 H), 7.63-7.67 (m, 1 H), 8.51 (dd, J = 6.72, 2.45 Hz, 1 H), 7.92 (brs, 1 H), 7.85-7.89 (m, 1 H), 7.77 (s, 1 H), 7.46 (dd, J = 11.07, 9.11 Hz, 1 H), 7.31 (d, J = 3.55 Hz, 1 H), 6.67 (dd, J = 3.48, 1.77 Hz, 1 H), 3.90-3.93 (m, 4 H), 3.25-3.28 (m, 4 H).Method 1: RT = 2.65 min.; M + H = 408.1 |

TABLE 2-continued

| Cpd No. | Structure | ¹HNMR and HPLC retention time and/or MS |
|---|---|---|
| 123 | 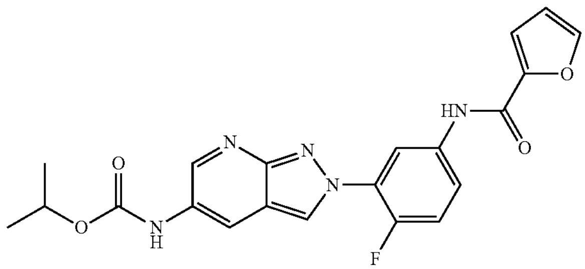 [SMILES: CC(C)OC(=O)Nc1cnc2nn(-c3cc(NC(=O)c4ccco4)ccc3F)cc2c1] | ¹H NMR (400 MHz, Methanol-d₄), δ 8.91-8.94 (m, 2 H), 8.73 (brs, 1 H), 8.54 (dd, J = 6.78, 2.64 Hz, 1 H), 7.87-7.91 (m, 1 H), 7.78 (s, 1 H),.7.47 (dd, J = 10.85, 9.10 Hz, 1 H), 7.32 (d, J = 3.14 Hz, 1 H), 6.67 (dd, J = 3.51, 1.76 Hz, 1 H), 5.01-5.09 (m, 1 H), 1.35 (d, J = 6.15 Hz, 6 H). Method 1: RT = 3.03 min.; M + H = 424.1 |
| 124 | 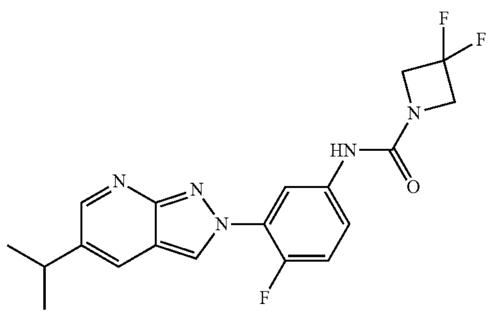 | ¹H NMR (400 MHz, DMSO-d6) δ 9.24 (br s, 1 H), 8.80 (d, J = 2.51 Hz, 1 H), 8.69 (d, J = 2.13 Hz, 1 H), 8.22 (dd, J = 7.03, 2.64 Hz, 1 H), 8.05 (d, J = 2.01 Hz, 1 H), 7.63-7.74 (m, 1 H), 7.49 (dd, J = 11.17, 9.29 Hz, 1 H), 4.41 (t, J = 12.74 Hz, 4 H), 3.08 (quin, J = 6.81 Hz, 1 H), 1.30 (d, J = 6.90 Hz, 6 H). Method 1: RT = 3.07 min.; M + H = 390.1 |
| 125 | 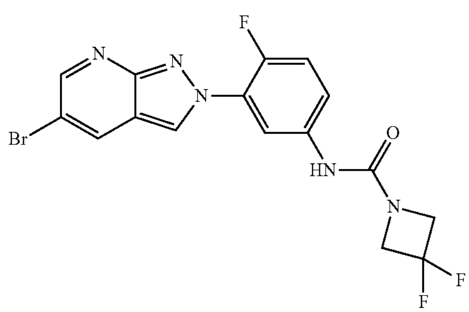 [SMILES: O=C(Nc1ccc(F)c(-n2cc3cc(Br)cnc3n2)c1)N1CC(F)(F)C1] | ¹H NMR (400 MHz, DMSO-d₆), δ 9.25 (s, 1 H), 8.91 (br s, 1 H), 8.76 (br s, 1 H), 8.63 (br s, 1 H), 8.25 (br s, 1 H), 7.69 (br s, 1 H), 7.51 (br t, J = 10.16 Hz, 1 H), 4.41 (br t, J = 12.67 Hz, 4 H). Method 1: RT = 2.98 min. |
| 126 | 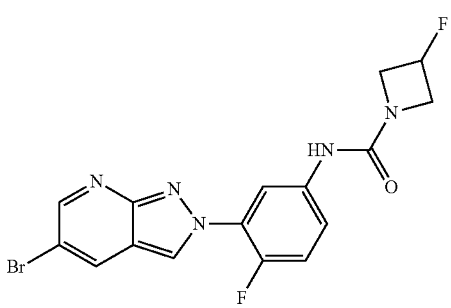 [SMILES: O=C(Nc1ccc(F)c(-n2cc3cc(Br)cnc3n2)c1)N1CC(F)C1] | ¹H NMR (400 MHz, DMSO-d₆), δ 8.98 (s, 1 H), 8.90 (d, J = 2.51 Hz, 1 H), 8.76 (d, J = 2.51 Hz, 1 H), 8.63 (d, J = 2.51 Hz, 1 H), 8.24 (dd, J = 7.03, 2.76 Hz, 1 H), 7.67-7.74 (m, 1 H), 7.49 (dd, J = 11.17, 9.16 Hz, 1 H), 5.29-5.51 (m, 1 H), 4.25-4.39 (m, 2 H), 3.96-4.10 (m, 2H).<br>Method 1: RT = 2.82 min. |
| 127 | 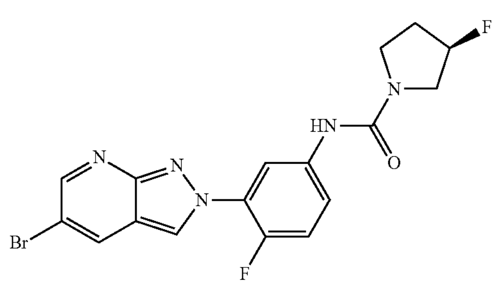 [SMILES: O=C(Nc1ccc(F)c(-n2cc3cc(Br)cnc3n2)c1)N1CC[C@@H](F)C1] | ¹H NMR (400 MHz, DMSO-d₆), δ 8.90 (d, J = 2.26 Hz, 1 H), 8.76 (d, J = 2.51 Hz, 1 H), 8.66 (s, 1 H), 8.63 (d, J = 2.26 Hz, 1 H), 8.27 (dd, J = 7.03, 2.76 Hz, 1 H), 7.71-7.77 (m, 1 H), 7.48 (dd, J = 11.17, 9.16 Hz, 1 H), 5.28-5.48 (m, 1 H), 3.40-3.78 (m, 4 H), 2.01-2.27 (m, 2 H). Method 1: RT = 2.89 min. |

TABLE 2-continued

| Cpd No. | Structure | ¹HNMR and HPLC retention time and/or MS |
|---|---|---|
| 128 | 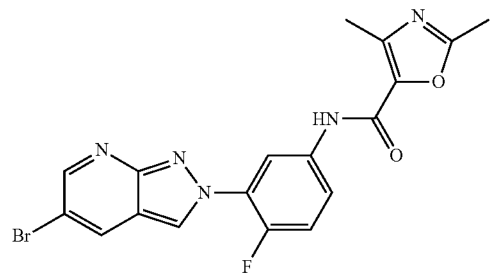 [SMILES: Cc1nc(C)c(C(=O)Nc2ccc(F)c(-n3cc4cc(Br)cnc4n3)c2)o1] | ¹H NMR (400 MHz, DMSO-d$_6$), δ 10.53 (s, 1 H), 8.94 (d, J = 2.51 Hz, 1 H), 8.77 (d, J = 2.26 Hz, 1 H), 8.64 (d, J = 2.26 Hz, 1 H), 8.58 (dd, J = 7.15, 2.64 Hz, 1 H), 7.89-7.97 (m, 1 H), 7.59 (dd, J = 11.17, 9.16 Hz, 1 H), 2.52-2.53 (s, 3 H), 2.40 (s, 3 H). Method 1: RT = 3.03 min |
| 129 | 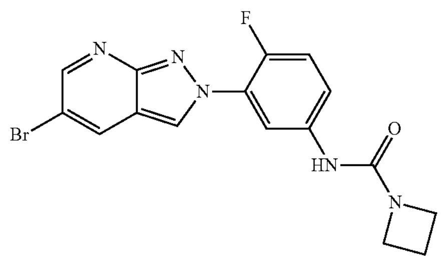 [SMILES: O=C(Nc1ccc(F)c(-n2cc3cc(Br)cnc3n2)c1)N1CCC1] | ¹H NMR (400 MHz, DMSO-d6), δ 8.89 (d, J = 2.01 Hz, 1 H), 8.70-8.80 (m, 2 H), 8.62 (d, J = 2.26 Hz, 1 H), 8.25 (dd, J = 6.90, 2.38 Hz, 1 H), 7.72 (br d, J = 9.03 Hz, 1 H), 7.46 (br t, J = 10.16 Hz, 1 H), 3.98 (br t, J = 7.53 Hz, 4 H), 2.20 (quin, J = 7.59 Hz, 2 H). Method 1: RT = 2.82 min. |
| 130 | 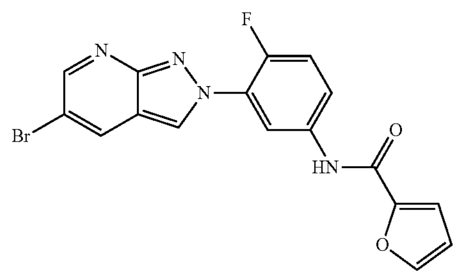 [SMILES: O=C(Nc1ccc(F)c(-n2cc3cc(Br)cnc3n2)c1)c1ccco1] | ¹H NMR (400 MHz, DMSO-d$_6$), δ 10.58 (br s, 1 H), 8.94 (d, J = 2.26 Hz, 1 H), 8.77 (d, J = 2.26 Hz, 1 H), 8.64 (d, J = 2.26 Hz, 1 H), 8.53 (dd, J = 7.03, 2.51 Hz, 1 H), 7.92-8.02 (m, 2 H), 7.60 (dd, J = 11.04, 9.29 Hz, 1 H), 7.40 (d, J = 3.26 Hz, 1 H), 6.74 (dd, J = 3.26, 1.51 Hz, 1 H). Method 1: RT = 2.98 min. |
| 131 | 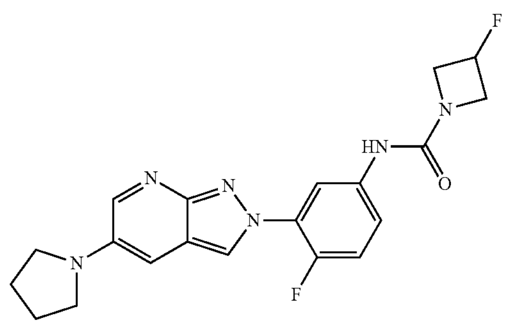 [SMILES: O=C(Nc1ccc(F)c(-n2cc3cc(N4CCCC4)cnc3n2)c1)N1CC(F)C1] | ¹H NMR (400 MHz, Methanol-d$_4$), δ 8.47 (d, J = 2.89 Hz, 1 H), 8.38 (d, J = 2.63 Hz, 1 H), 8.07 (dd, J = 6.84, 2.70 Hz, 1 H), 7.58-7.62 (m, 1 H), 7.31 (dd, J = 11.11, 9.10 Hz, 1 H), 7.00 (d, J = 2.76 Hz, 1 H), 5.27-5.46 (m, 1 H), 4.33-4.43 (m, 2H), 4.08-4.18 (m, 2H), 3.40 (t, J = 6.53 Hz, 4 H), 2.05-2.12 (m, 4 H). Method 1: RT = 3.01 min.; M + H = 399.1 |
| 132 | 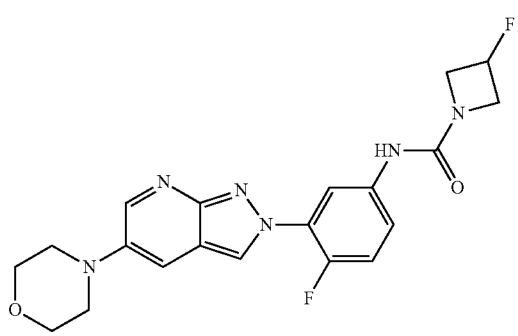 [SMILES: O=C(Nc1ccc(F)c(-n2cc3cc(N4CCOCC4)cnc3n2)c1)N1CC(F)C1] | ¹H NMR (400 MHz, Methanol-d$_4$), δ 8.47 (d, J = 2.89 Hz, 1 H), 8.38 (d, J = 2.63 Hz, 1 H), 8.07 (dd, J = 6.84, 2.70 Hz, 1 H), 7.58-7.62 (m, 1 H), 7.31 (dd, J = 11.11, 9.10 Hz, 1 H), 7.00 (d, J = 2.76 Hz, 1 H), 5.27-5.46 (m, 1 H), 4.33-4.43 (m, 2H), 4.08-4.18 (m, 2H), 3.40 (t, J = 6.53 Hz, 4 H), 2.05-2.12 (m, 4 H). Method 1: RT = 2.65 min.; M + H = 415.2 |

TABLE 2-continued

| Cpd No. | Structure | ¹HNMR and HPLC retention time and/or MS |
|---|---|---|
| 133 | 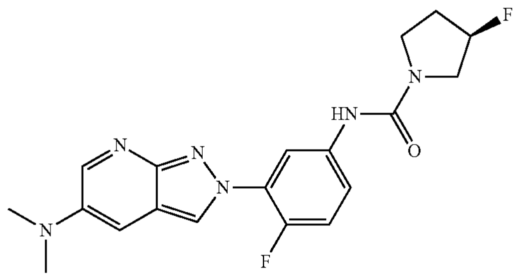 [SMILES: CN(C)c1cnc2nn(-c3cc(NC(=O)N4CC[C@@H](F)C4)ccc3F)cc2c1] | ¹H NMR (400 MHz, METHANOL-d4) δ 8.96 (br s, 1 H), 8.87 (s, 1 H), 8.32 (dd, J = 6.27, 2.01 Hz, 1 H), 8.21 (br d, J = 4.27 Hz, 1 H), 7.54-7.71 (m, 1 H), 7.41 (dd, J = 10.92, 9.16 Hz, 1 H), 5.22-5.49 (m, 1 H), 3.52-3.89 (m, 4 H), 3.21 (d, J = 1.25 Hz, 6 H), 2.03-2.46 (m, 2 H). Method 1: RT = 2.75 min.; M + H = 387.1 |
| 134 | 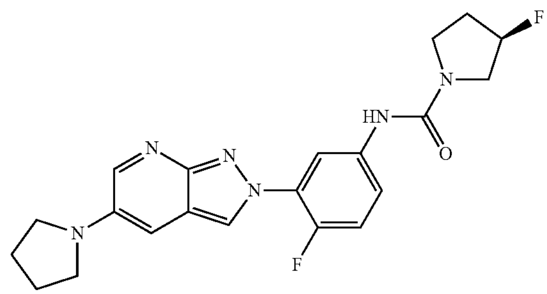 [SMILES: O=C(Nc1ccc(F)c(-n2cc3cc(N4CCCC4)cnc3n2)c1)N1CC[C@@H](F)C1] | ¹H NMR (400 MHz, Methanol-d₄), δ 8.69 (d, J = 2.26 Hz, 1 H), 8.58 (d, J = 2.51 Hz, 1 H), 8.21 (dd, J = 6.84, 2.70 Hz, 1 H), 7.57-7.61 (m, 1 H), 7.51 (d, J = 2.64 Hz, 1 H), 7.36 (dd, J = 10.98, 9.10 Hz, 1 H), 5.27-5.40 (m, 1 H), 3.43-3.84 (m, 8H), 1.99-2.37 (m, 6 H). Method 1: RT = 2.98 min.; M + H = 413.1 |
| 135 | 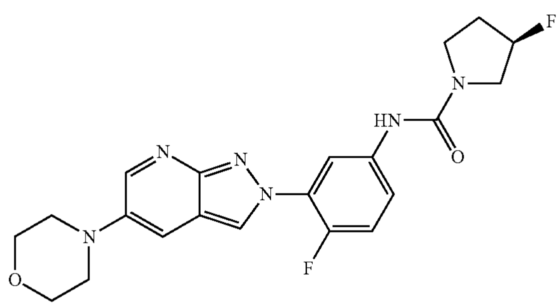 | ¹H NMR (400 MHz, Methanol-d₄), δ 8.97-9.03 (m, 2 H), 8.26-8.31 (m, 2 H), 7.58-7.62 (m, 1 H), 7.37 (dd, J = 10.92, 9.16 Hz, 1 H), 5.27-5.40 (m, 1 H), 3.90-3.93 (m, 4H), 3.55-3.84 (m, 4H), 3.31-3.33 (m, 4H), 1.97-2.36 (m, 2 H). Method 1: RT = 2.58 min.; M + H = 429.1 |
| 136 | 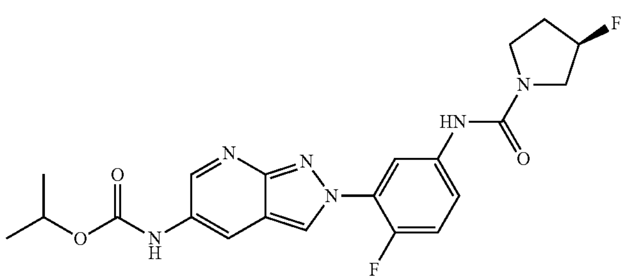 [SMILES: CC(C)OC(=O)Nc1cnc2nn(-c3cc(NC(=O)N4CC[C@@H](F)C4)ccc3F)cc2c1] | ¹H NMR (400 MHz, Methanol-d₄), δ 8.62 (dd, J = 9.10, 2.32 Hz, 2 H), 8.44 (brs, 1 H), 8.10 (dd, J = 6.78, 2.64 Hz, 1 H), 7.60-7.64 (m, 1 H), 7.34 (dd, J = 10.92, 9.16 Hz, 1 H), 5.26-5.39 (m, 1 H), 4.98-5.04 (m, 1H), 3.53-3.82 (m, 4H), 2.07-2.35 (m, 2 H), 1.33 (d, J = 2.67 Hz, 6 H). Method 1: RT = 2.92 min.; M + H = 445.1 |
| 137 | 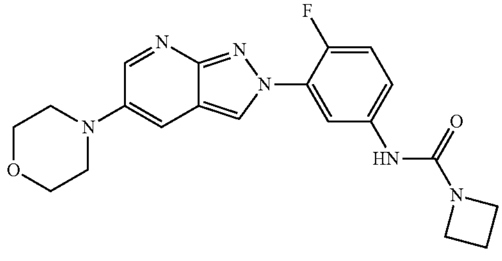 | ¹H NMR (400 MHz, Methanol-d₄), δ 8.68 (d, J = 2.76 Hz, 1 H), 8.54 (d, J = 2.38 Hz, 1 H), 8.09 (dd, J = 6.84, 2.70 Hz, 1 H), 7.60-7.64 (m, 1 H), 7.53 (d, J = 2.64 Hz, 1 H), 7.32 (dd, J = 10.98, 9.10 Hz, 1 H), 4.11 (t, J = 7.65 Hz, 4 H), 3.90-3.92 (m, 4 H), 3.19-3.21 (m, 4 H), 2.29-2.36 (m, 2 H). Method 1: RT = 2.58 min.; M + H = 397.2 |

TABLE 2-continued

| Cpd No. | Structure | ¹HNMR and HPLC retention time and/or MS |
|---|---|---|
| 138 | 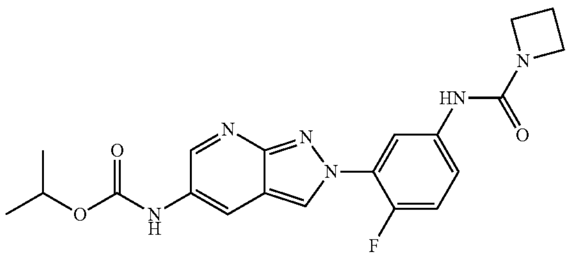 [SMILES: CC(C)OC(=O)Nc1cnc2nn(-c3cc(NC(=O)N4CCC4)ccc3F)cc2c1] | ¹H NMR (400 MHz, Methanol-d₄), δ 8.61-8.63 (m, 2 H), 8.45 (brs, 1 H), 8.09 (dd, J = 6.78, 2.64 Hz, 1 H), 7.62-7.64 (m, 1 H), 7.30-7.35 (m, 1 H), 7.30-7.35 (m, 1 H), 4.98-5.04 (m, 1H), 4.11 (t, J = 7.65 Hz, 4 H), 2.32 (t, J = 7.62 Hz, 2 H), 1.33 (d, J = 6.15 Hz, 6 H). Method 1: RT = 2.87 min.; M + H = 413.1 |
| 139 | 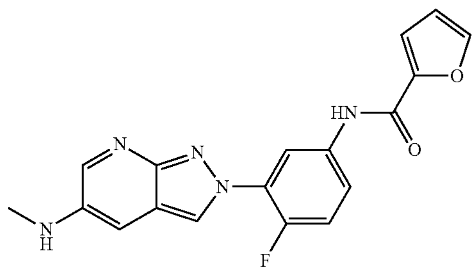 [SMILES: CNc1cnc2nn(-c3cc(NC(=O)c4ccco4)ccc3F)cc2c1] | ¹H NMR (400 MHz, DMSO-d6) δ 10.49 (s, 1 H), 8.43-8.63 (m, 2 H), 8.35 (d, J = 2.76 Hz, 1 H), 7.98 (d, J = 1.00 Hz, 1 H), 7.82-7.94 (m, 1 H), 7.53 (dd, J = 11.29, 9.03 Hz, 1 H), 7.39 (d, J = 3.01 Hz, 1 H), 6.67-6.84 (m, 2 H), 6.09 (q, J = 4.77 Hz, 1 H), 2.73 (d, J = 5.02 Hz, 3 H). Method 1: RT = 2.67 min.; M + H = 352.0 |
| 140 | 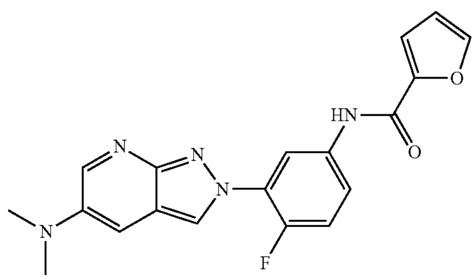 [SMILES: CN(C)c1cnc2nn(-c3cc(NC(=O)c4ccco4)ccc3F)cc2c1] | ¹H NMR (400 MHz, DMSO-d₆) δ 10.51 (s, 1 H), 8.71 (d, J = 3.01 Hz, 1 H), 8.58 (d, J = 2.76 Hz, 1 H), 8.49 (dd, J = 7.15, 2.64 Hz, 1 H), 7.98 (d, J = 1.00 Hz, 1 H), 7.86-7.94 (m, 1 H), 7.54 (dd, J = 11.42, 9.16 Hz, 1 H), 7.39 (d, J = 3.51 Hz, 1 H), 7.16 (d, J = 2.76 Hz, 1 H), 6.73 (dd, J = 3.39, 1.63 Hz, 1 H), 2.96 (s, 6 H).Method 1: RT = 2.82 min.; M + H = 366.1 |
| 141 | 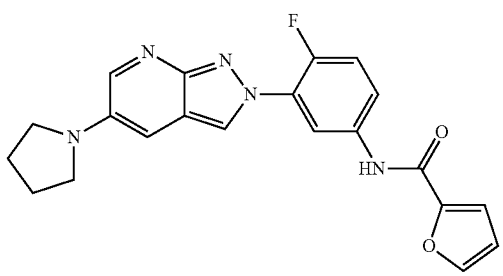 [SMILES: O=C(Nc1ccc(F)c(-n2cc3cc(N4CCCC4)cnc3n2)c1)c1ccco1] | ¹H NMR (400 MHz, Methanol-d₄), δ 8.48 (d, J = 2.89 Hz, 1 H), 8.42 (d, J = 2.51 Hz, 1 H), 8.35 (dd, J = 6.90, 2.64 Hz, 1 H), 7.76-7.89 (m, 1 H), 7.76 (d, J = 0.88 Hz, 1 H), 7.40 (dd, J = 11.04, 9.03 Hz, 1 H), 7.30 (d, J = 3.26 Hz, 1 H), 7.01 (d, J = 2.76 Hz, 1 H), 6.66 (dd, J = 3.45, 1.69 Hz, 1 H), 3.39-3.42 (m, 4 H), 2.07-2.10 (m, 4 H). Method 1: RT = 3.18 min.; M + H = 392.2 |
| 142 | 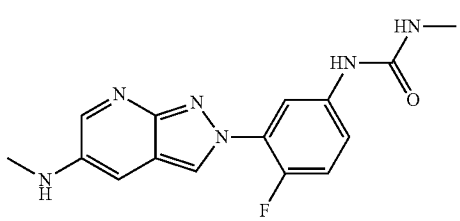 | ¹H NMR (400 MHz, METHANOL-d4) δ 8.68 (d, J = 2.45 Hz, 1 H), 8.52 (br s, 1 H), 8.17 (dd, J = 6.85, 2.69 Hz, 1 H), 7.54 (d, J = 2.45 Hz, 1 H), 7.42-7.50 (m, 1 H), 7.35 (dd, J = 11.00, 9.05 Hz, 1 H), 2.95 (s, 3 H), 2.80 (s, 3 H). Method 1: RT = 2.56 min.; M + H = 315.1 |
| 143 | 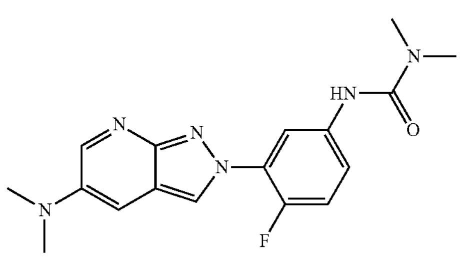 | ¹H NMR (400 MHz, METHANOL-d4) δ 9.00 (d, J = 2.01 Hz, 1 H), 8.91 (d, J = 2.76 Hz, 1 H), 8.31 (d, J = 2.76 Hz, 1 H), 8.25 (dd, J = 6.78, 2.51 Hz, 1 H), 7.54-7.62 (m, 1 H), 7.40 (dd, J = 10.92, 9.16 Hz, 1 H), 3.24 (s, 6 H), 3.07 (s, 6 H). Method 1: RT = 2.60 min.; M + H = 343.1 |

TABLE 2-continued

| Cpd No. | Structure | ¹HNMR and HPLC retention time and/or MS |
|---|---|---|
| 144 | 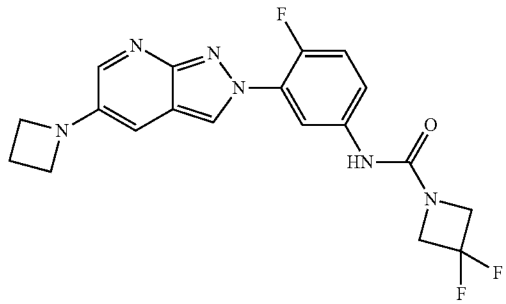 [SMILES: O=C(Nc1ccc(F)c(-n2cc3cc(N4CCC4)cnc3n2)c1)N1CC(F)(F)C1] | ¹H NMR (400 MHz, DMSO), δ 9.19 (s, 1 H), 8.53 (d, J = 2.69 Hz, 1 H), 8.26 (d, J = 2.69 Hz, 1 H), 8.19 (dd, J = 6.97, 2.69 Hz, 1 H), 7.61-7.65 (m, 1 H), 7.45 (dd, J = 11.37, 9.17 Hz, 1 H), 6.88 (d, J = 2.81 Hz, 1 H), 4.40 (t, J = 12.65 Hz, 4 H), 3.91 (d, J = 7.15 Hz, 4 H), 2.32-2.39 (m, 2 H). Method 1: RT = 2.82 min.; M + H = 403.1 |
| 145 | 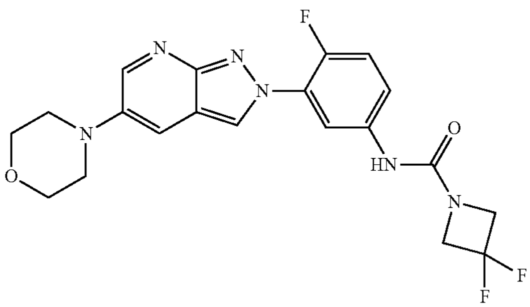 [SMILES: O=C(Nc1ccc(F)c(-n2cc3cc(N4CCOCC4)cnc3n2)c1)N1CC(F)(F)C1] | ¹H NMR (400 MHz, DMSO), δ 9.20 (s, 1 H), 8.74 (d, J = 2.81 Hz, 1 H), 8.65 (d, J = 2.69 Hz, 1 H), 8.21 (dd, J = 7.09, 2.69 Hz, 1 H), 7.64-7.68 (m, 1 H), 7.47 (dd, J = 11.31, 9.11 Hz, 1 H), 7.40 (d, J = 2.81 Hz, 1 H), 4.41 (t, J = 12.65 Hz, 4 H), 3.79-3.82 (m, 4 H), 3.14-3.16 (m, 4 H). Method 1: RT = 2.65 min.; M + H = 433.1 |
| 146 | 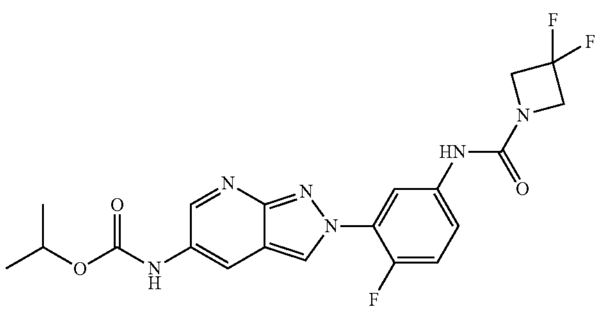 [SMILES: CC(C)OC(=O)Nc1cnc2nn(-c3cc(NC(=O)N4CC(F)(F)C4)ccc3F)cc2c1] | ¹H NMR (400 MHz, DMSO), δ 9.89(s, 1 H), 9.20 (s, 1 H), 8.79 (d, J = 2.57 Hz, 1 H), 8.65 (d, J = 2.45 Hz, 1 H), 8.36 (s, 1 H), 8.20 (dd, J = 7.03, 2.75 Hz, 1 H), 7.63-7.67 (m, 1 H), 7.47 (dd, J = 11.25, 9.05 Hz, 1 H), 4.92-4.96 (m, 1H), 4.40 (t, J = 12.72 Hz, 4 H), 1.28 (d, J = 6.36 Hz, 6 H). Method 1: RT = 2.89 min.; M + H = 449.1 |
| 147 | 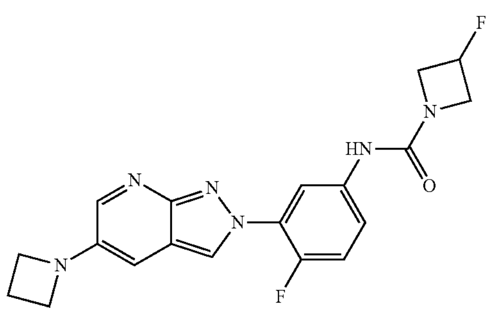 [SMILES: O=C(Nc1ccc(F)c(-n2cc3cc(N4CCC4)cnc3n2)c1)N1CC(F)C1] | ¹H NMR (400 MHz, DMSO), δ 8.92 (s, 1 H), 8.52 (d, J = 2.76 Hz, 1 H), 8.25 (d, J = 2.76 Hz, 1 H), 8.19 (dd, J = 7.09, 2.70 Hz, 1 H) 7.61-7.69 (m, 1 H), 7.42 (dd, J = 11.36, 9.10 Hz, 1 H), 6.88 (d, J = 2.76 Hz, 1 H), 5.28-5.49 (m, 1 H), 4.24-4.38 (m, 2 H), 3.95-4.08 (m, 2 H), 3.91 (t, J = 7.15 Hz, 4 H), 2.33-2.41 (m, 2 H). Method 1: RT = 2.75 min.; M + H = 385.2 |
| 148 | 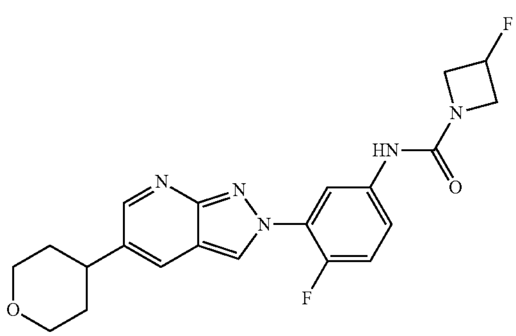 [SMILES: O=C(Nc1ccc(F)c(-n2cc3cc(C4CCOCC4)cnc3n2)c1)N1CC(F)C1] | ¹H NMR (400 MHz, DMSO-d6), δ 8.98 (s, 1 H), 8.81 (d, J = 2.76 Hz, 1 H), 8.70 (d, J = 2.26 Hz, 1 H), 8.23 (dd, J = 7.03, 2.76 Hz, 1 H), 8.07 (d, J = 1.76 Hz, 1 H), 7.65-7.72 (m, 1 H), 7.47 (dd, J = 11.29, 9.29 Hz, 1 H), 5.29-5.51 (m, 1 H), 4.25-4.39 (m, 2 H), 3.96-4.09 (m, 4 H), 3.44-3.54 (m, 2 H), 2.91-3.02 (m, 1 H), 1.68-1.86 (m, 4 H). Method 1: RT = 2.65 min.; M + H = 414.2 |

TABLE 2-continued

| Cpd No. | Structure | ¹HNMR and HPLC retention time and/or MS |
|---|---|---|
| 149 | 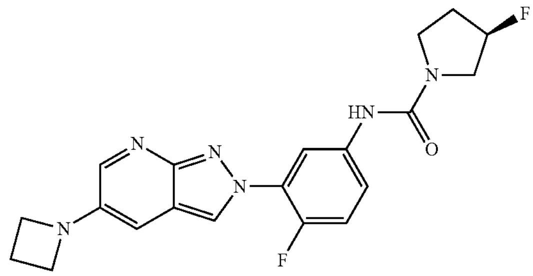 | ¹H NMR (400 MHz, DMSO), δ 8.60 (s, 1 H), 8.53 (d, J = 2.76 Hz, 1 H), 8.25 (d, J = 2.76 Hz, 1 H), 8.21 (dd, J = 7.03, 2.76 Hz, 1 H), 7.64-7.71 (m, 1 H), 7.41 (dd, J = 11.29, 9.16 Hz, 1 H), 6.88 (d, J = 2.76 Hz, 1 H), 5.28-5.46 (m, 1 H), 3.91 (t, J = 7.22 Hz, 4 H), 3.62-3.73 (m, 2 H), 3.39-3.55 (m, 2 H), 2.32-2.40 (m, 2 H), 1.99-2.22 (m, 2 H). Method 1: RT = 2.76 min.; M + H = 399.2 |
| 150 | 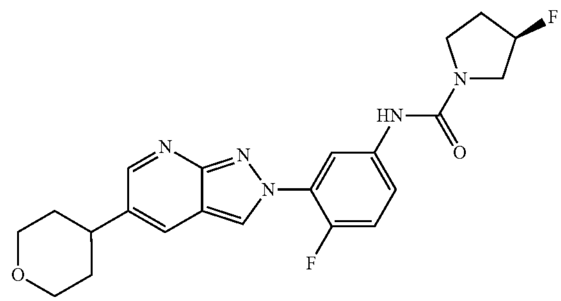 [SMILES: O=C(Nc1ccc(F)c(-n2cc3cc(C4CCOCC4)cnc3n2)c1)N1CC[C@@H](F)C1] | ¹H NMR (400 MHz, Methanol-d₄), δ 9.15 ( (d, J = 2.01 Hz, 1 H)), 8.98 (s, 1 H), 8.85 (d, J = 1.88 Hz, 1 H), 8.33 (dd, J = 6.78, 9.16 Hz, 1 H), 7.61-7.65 (m, 1 H), 7.42 (dd, J = 11.04, 9.16 Hz, 1 H), 5.28-5.41 (m, 1 H), 4.11-4.14 (m, 2 H), 3.57-3.85 (m, 6 H), 3.14-3.20 (m, 1 H), 2.11-2.32 (m, 2 H), 1.91-1.97 (m, 4 H). Method 1: RT = 2.60 min.; M + H = 428.2 |
| 151 | 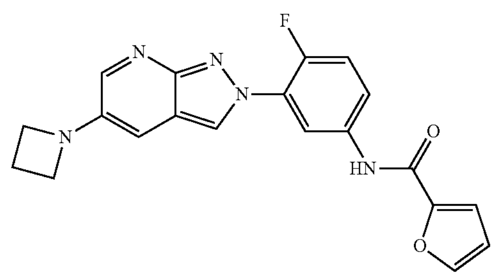 [SMILES: O=C(Nc1ccc(F)c(-n2cc3cc(N4CCC4)cnc3n2)c1)c1ccco1] | ¹H NMR (400 MHz, DMSO), δ 10.52 (s, 1 H), 8.56 (d, J = 2.76 Hz, 1 H), 8.48 (dd, J = 7.03, 2.63 Hz, 1 H), 8.27 (d, J = 2.76 Hz, 1 H), 7.97 (dd, J = 1.69, 0.82 Hz, 1 H), 7.86-7.91 (m, 1 H), 7.54 (dd, J = 11.36, 9.10 Hz, 1 H), 7.38 (dd, J = 3.51, 0.75 Hz, 1 H), 6.89 (d, J = 2.76 Hz, 1 H), 6.73 (dd, J = 3.51, 1.76 Hz, 1 H), 3.91 (t, J = 7.22 Hz, 4 H), 2.33-2.39 (m, 2 H) Method 1: RT = 2.90 min.; M + H = 378.2 |
| 152 | 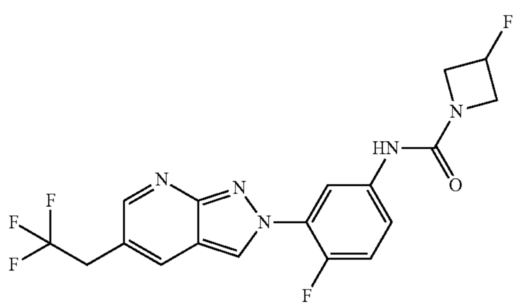 [SMILES: O=C(Nc1ccc(F)c(-n2cc3cc(CC(F)(F)F)cnc3n2)c1)N1CC(F)C1] | ¹H NMR (400 MHz, DMSO-d6), δ 8.98 (s, 1 H), 8.95 (d, J = 2.51 Hz, 1 H), 8.69 (d, J = 2.01 Hz, 1 H), 8.33 (d, J = 1.76 Hz, 1 H), 8.24 (dd, J = 6.90, 2.63 Hz, 1 H), 7.67-7.74 (m, 1 H), 7.48 (dd, J = 11.29, 9.29 Hz, 1 H), 5.30-5.52 (m, 1 H), 4.26-4.39 (m, 2 H), 3.97-4.09 (m, 2 H), 3.87 (q, J = 11.71 Hz, 2 H). Method 1: RT = 2.76 min.; M + H = 412.2 |
| 153 | 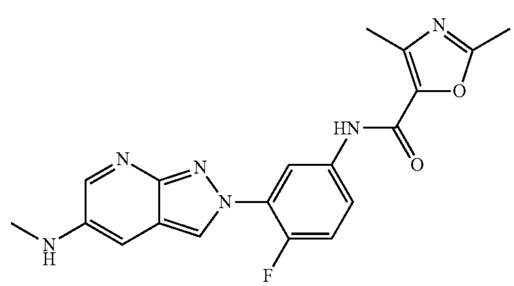 | ¹H NMR (400 MHz, METHANOL-d4), δ 8.99 (d, J = 2.20 Hz, 1 H), 8.71 (d, J = 2.69 Hz, 1 H), 8.62 (dd, J = 6.85, 2.69 Hz, 1 H), 8.07 (d, J = 2.44 Hz, 1 H), 7.82-7.88 (m, 1 H), 7.51 (dd, J = 10.88, 9.17 Hz, 1 H), 3.04 (s, 3 H), 2.58 (s, 3 H), 2.49 (s, 3 H). Method 1: RT = 2.76 min.; M + H = 381.1 |

TABLE 2-continued

| Cpd No. | Structure | ¹HNMR and HPLC retention time and/or MS |
|---|---|---|
| 154 | 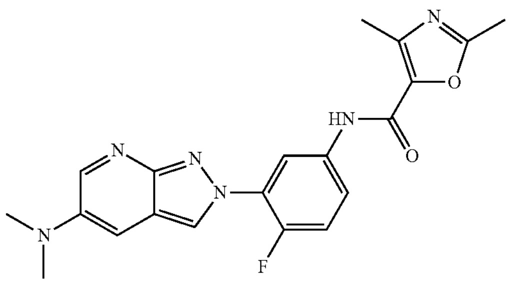 | ¹H NMR (400 MHz, METHANOL-d4), δ 8.92 (d, J = 2.20 Hz, 1 H), 8.80 (d, J = 2.69 Hz, 1 H), 8.53 (dd, J = 6.85, 2.69 Hz, 1 H), 8.17 (d, J = 2.93 Hz, 1 H), 7.69-7.77 (m, 1 H), 7.40 (dd, J = 11.00, 9.29 Hz, 1 H), 3.12 (s, 6 H), 2.46 (s, 3 H), 2.37 (s, 3 H). Method 1: RT = 2.84 min.; M + H = 395.1 |
| 155 | 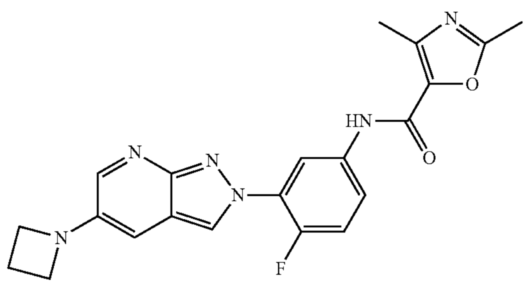 [SMILES: Cc1nc(C)c(C(=O)Nc2ccc(F)c(-n3cc4cc(N5CCC5)cnc4n3)c2)o1] | ¹NMR (400 MHz, DMSO-d6) δ 10.48 (s, 1 H), 8.57 (d, J = 2.64 Hz, 1 H), 8.54 (dd, J = 7.15, 2.64 Hz, 1 H), 8.28 (d, J = 2.76 Hz, 1 H), 7.84-7.90 (m, 1 H), 7.54 (dd, J = 11.29, 9.03 Hz, 1 H), 6.90 (d, J = 2.76 Hz, 1 H), 3.93 (t, J = 7.15 Hz, 4 H), 2.50-2.50 (m, 3 H), 2.40 (s, 3 H), 2.33-2.39 (m, 2 H). Method 1: RT = 2.89 min.; M + H = 407.1 |
| 156 | 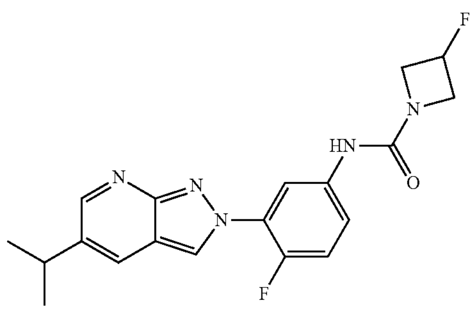 | ¹H NMR (400 MHz, DMSO-d6) δ 8.96 (br s, 1 H), 8.79 (d, J = 2.57 Hz, 1 H), 8.69 (d, J = 2.32 Hz, 1 H), 8.23 (dd, J = 6.97, 2.69 Hz, 1 H), 8.05 (d, J = 1.96 Hz, 1 H), 7.64-7.73 (m, 1 H), 7.46 (dd, J = 11.25, 9.17 Hz, 1 H), 5.28-5.52 (m, 1 H), 4.26-4.39 (m, 2 H), 3.96-4.10 (m, 2 H), 3.03-3.14 (m, 1 H), 1.30 (d, J = 6.97 Hz, 6 H). Method 2: RT = 0.95 min.; M + H = 372.2 |
| 157 | 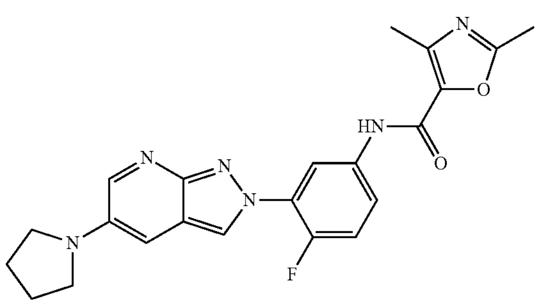 [SMILES: Cc1nc(C)c(C(=O)Nc2ccc(F)c(-n3cc4cc(N5CCCC5)cnc4n3)c2)o1] | ¹H NMR (400 MHz, DMSO-d6) δ 10.51 (s, 1 H), 8.65 (d, J = 2.64 Hz, 1 H), 8.59 (d, J = 2.89 Hz, 1 H), 8.55-8.58 (m, 1 H), 7.83-7.90 (m, 1 H), 7.55 (dd, J = 11.29, 9.16 Hz, 1 H), 7.12 (br s, 1 H), 3.38 (br t, J = 6.40 Hz, 4 H), 2.50 (br s, 3 H), 2.40 (s, 3 H), 1.97-2.06 (m, 4H). Method 1: RT = 3.12 min.; M + H = 421.1 |
| 158 | 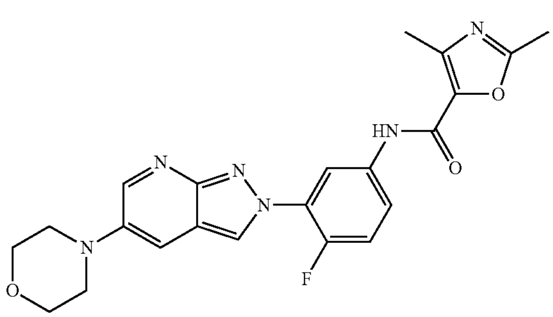 [SMILES: Cc1nc(C)c(C(=O)Nc2ccc(F)c(-n3cc4cc(N5CCOCC5)cnc4n3)c2)o1] | ¹H NMR (400 MHz, DMSO-d6) δ 10.52 (s, 1 H), 8.81 (d, J = 2.76 Hz, 1 H), 8.73 (d, J = 2.64 Hz, 1 H), 8.55 (dd, J = 7.03, 2.64 Hz, 1 H), 7.86-7.92 (m, 1 H), 7.54-7.59 (m, 1 H), 7.50-7.54 (m, 1 H), 3.79-3.84 (m, 4 H), 3.15-3.21 (m, 4 H), 2.49-2.50 (m, 3 H), 2.40 (s, 3 H). Method 1: RT = 2.79 min.; M + H = 437.1 |

TABLE 2-continued

| Cpd No. | Structure | ¹HNMR and HPLC retention time and/or MS |
|---|---|---|
| 159 | 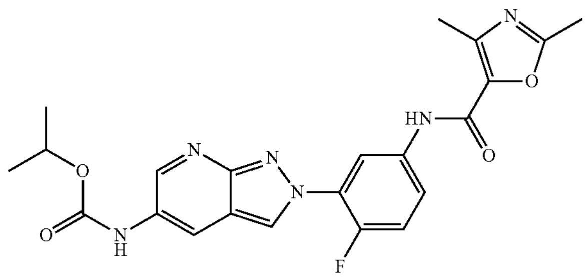 [SMILES: Cc1nc(C)c(C(=O)Nc2ccc(F)c(-n3cc4cc(NC(=O)OC(C)C)cnc4n3)c2)o1] | ¹H NMR (400 MHz, DMSO-d6) δ 10.52 (s, 1 H), 9.95 (br s, 1 H), 8.85 (d, J = 2.38 Hz, 1 H), 8.69 (d, J = 2.51 Hz, 1 H), 8.56 (dd, J = 7.03, 2.63 Hz, 1 H), 8.40 (br s, 1 H), 7.86-7.93 (m, 1 H), 7.57 (dd, J = 11.04, 9.16 Hz, 1 H), 4.95 (dt, J = 12.55, 6.27 Hz, 1 H), 2.50-2.50 (m, 3 H), 2.40 (s, 3 H), 1.30 (d, J = 6.27 Hz, 6 H). Method 1: RT = 2.97 min.; M + H = 453.2 |
| 160 | 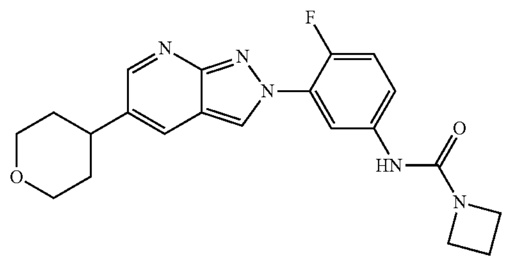 [SMILES: O=C(Nc1ccc(F)c(-n2cc3cc(C4CCOCC4)cnc3n2)c1)N1CCC1] | ¹H NMR (400 MHz, METHANOL-d4), δ 8.71 (d, J = 2.26 Hz, 1 H), 8.68 (d, J = 2.26 Hz, 1 H), 8.17 (d, J = 2.01 Hz, 1 H), 8.14 (dd, J = 7.03, 2.51 Hz, 1 H), 7.65 (dt, J = 9.29, 3.39 Hz, 1 H), 7.32-7.39 (m, 1 H), 4.09-4.16 (m, 6 H), 3.61-3.69 (m, 2 H), 3.05 (br s, 1 H), 2.34 (quin, J = 7.65 Hz, 2 H), 1.86-1.95 (m, 4 H). Method 1: RT = 2.68 min.; M + H = 396.2 |
| 161 | 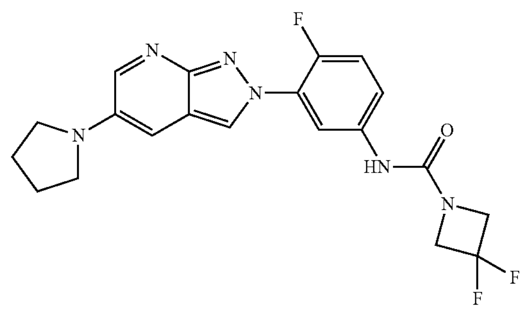 [SMILES: O=C(Nc1ccc(F)c(-n2cc3cc(N4CCCC4)cnc3n2)c1)N1CC(F)(F)C1] | ¹H NMR (400 MHz, DMSO), δ 9.19 (s, 1 H), 8.50 (dd, J = 6.59, 2.82 Hz, 2 H), 8.20 (dd, J = 7.03, 2.76 Hz, 1 H), 7.58-7.66 (m, 1 H), 7.44 (dd, J = 11.42, 9.16 Hz, 1 H), 6.88 (d, J = 2.76 Hz, 1 H), 4.40 (t, J = 12.67 Hz, 4 H), 3.35 (br s, 4 H), 1.93-2.03 (m, 4 H), Method 1: RT = 3.16 min.; M + H = 417.2 |
| 162 | 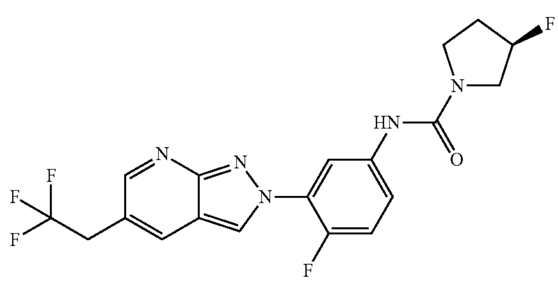 [SMILES: O=C(Nc1ccc(F)c(-n2cc3cc(CC(F)(F)F)cnc3n2)c1)N1CC[C@@H](F)C1] | ¹H NMR (400 MHz, Methanol-d₄), δ 9.09 (d, J = 2.01 Hz, 1 H,) 8.91 (s, 1 H), 8.78 (s, 1 H), 8.27 (dd, J = 6.78, 2.76 Hz, 1 H), 7.65 (ddd, J = 9.07, 4.11, 2.76 Hz, 1 H), 7.41 (dd, J = 10.92, 9.03 Hz, 1 H), 5.24-5.43 (m, 1 H), 3.54-3.91 (m, 6 H), 2.07-2.37 (m, 2 H) Method 1: RT = 2.82 min.; M + H = 426.2 |
| 163 | 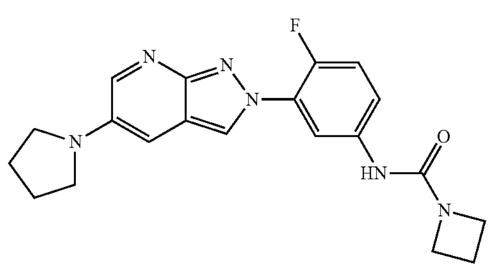 [SMILES: O=C(Nc1ccc(F)c(-n2cc3cc(N4CCCC4)cnc3n2)c1)N1CCC1] | ¹H NMR (400 MHz, Methanol-d₄), δ 8.68 (s, 1 H), 8.50 (dd, J = 12.61, 2.82 Hz, 2 H), 8.21 (dd, J = 7.09, 2.70 Hz, 1 H), 7.61-7.67 (m, 1 H), 7.40 (dd, J = 11.36, 9.10 Hz, 1 H), 6.89 (d, J = 2.76 Hz, 1 H), 3.97 (t, J = 7.53 Hz, 4 H), 3.36 (br s, 4 H), 2.19 (quin, J = 7.56 Hz, 2 H), 1.95-2.04 (m, 4 H) Method 1: RT = 2.95 min.; M + H = 381.2 |

TABLE 2-continued

| Cpd No. | Structure | ¹HNMR and HPLC retention time and/or MS |
|---|---|---|
| 164 | 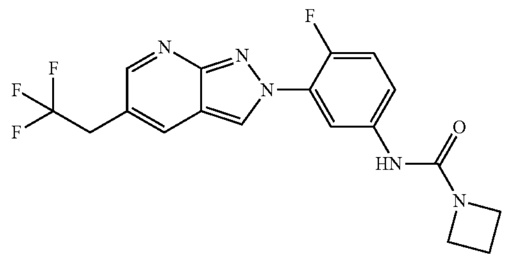 [SMILES: O=C(Nc1ccc(F)c(-n2cc3cc(CC(F)(F)F)cnc3n2)c1)N1CCC1] | ¹H NMR (400 MHz, DMSO-d6) δ 8.79 (d, J = 2.26 Hz, 1 H) 8.68 (d, J = 2.01 Hz, 1 H) 8.36 (d, J = 1.51 Hz, 1 H) 8.15 (dd, J = 6.65, 2.64 Hz, 1 H) 7.67 (ddd, J = 9.10, 4.20, 2.76 Hz, 1 H) 7.35-7.36 (m, 1 H) 7.26-7.47 (m, 1 H) 4.13 (t, J = 7.65 Hz, 4 H) 3.74 (q, J = 10.88 Hz, 2 H) 2.34 (quin, J = 7.65 Hz, 2 H) Method 1: RT = 2.75 min.; M + H = 394.2 |
| 165 | 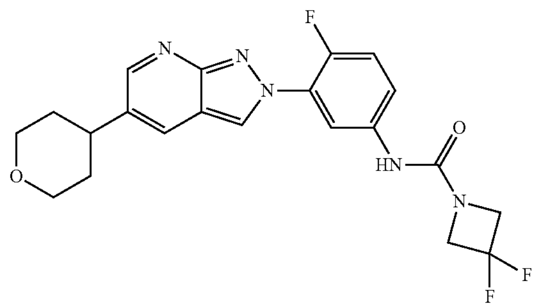 [SMILES: O=C(Nc1ccc(F)c(-n2cc3cc(C4CCOCC4)cnc3n2)c1)N1CC(F)(F)C1] | ¹H NMR (400 MHz, DMSO-d6), δ 9.24 (s, 1 H), 8.82 (d, J = 2.51 Hz, 1 H), 8.70 (d, J = 2.26 Hz, 1 H), 8.23 (dd, J = 6.90, 2.89 Hz, 1 H), 8.07 (d, J = 2.01 Hz, 1 H), 7.65-7.71 (m, 1 H), 7.49 (dd, J = 11.29, 9.03 Hz, 1 H), 4.41 (t, J = 12.67 Hz, 4 H), 4.00 (dd, J = 10.54, 3.76 Hz, 2 H), 3.45-3.54 (m, 2 H), 2.92-3.01 (m, 1 H), 1.69-1.86 (m, 4 H). Method 1: RT = 2.81 min.; M + H = 432.2 |
| 166 | 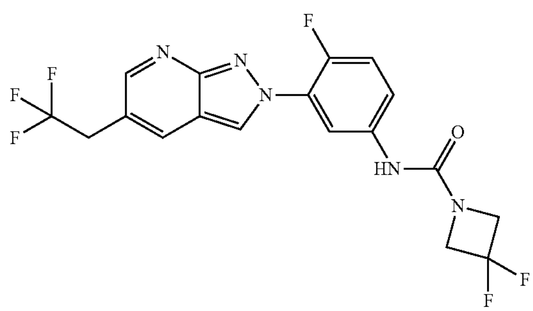 [SMILES: O=C(Nc1ccc(F)c(-n2cc3cc(CC(F)(F)F)cnc3n2)c1)N1CC(F)(F)C1] | ¹H NMR (400 MHz, DMSO-d6), δ 9.24 (s, 1 H), 8.96 (d, J = 2.51 Hz, 1 H), 8.69 (d, J = 2.01 Hz, 1 H), 8.34 (s, 1 H), 8.24 (dd, J = 7.03, 2.51 Hz, 1 H), 7.66-7.73 (m, 1 H), 7.51 (dd, J = 11.29, 9.29 Hz, 1 H), 4.42 (t, J = 12.80 Hz, 4 H), 3.87 (q, J = 11.46 Hz, 2 H). Method 1: RT = 2.85 min.; M + H = 430.1 |
| 167 | 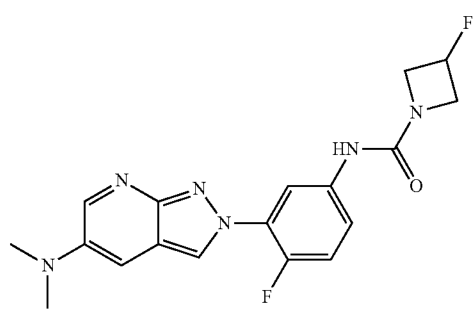 | ¹H NMR (400 MHz, DMSO-d6) δ 8.92 (s, 1 H), 8.70 (d, J = 2.93 Hz, 1 H), 8.55 (d, J = 2.93 Hz, 1 H), 8.21 (dd, J = 6.97, 2.57 Hz, 1 H), 7.56-7.74 (m, 1 H), 7.43 (dd, J = 11.49, 9.05 Hz, 1 H), 7.16 (d, J = 2.93 Hz, 1 H), 5.25-5.57 (m, 1 H), 4.22-4.40 (m, 2 H), 3.87-4.12 (m, 2 H), 2.96 (s, 6 H) Method 1: RT = 2.69 min.; M + H = 373.1 |
| 168 | 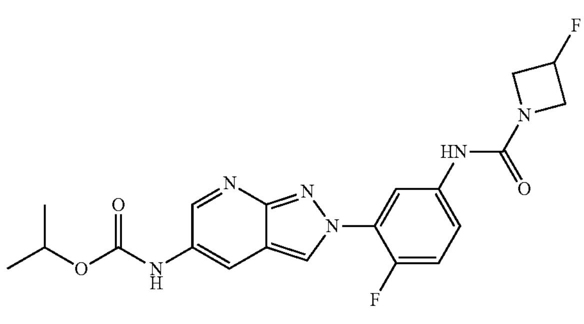 [SMILES: CC(C)OC(=O)Nc1cnc2nn(-c3cc(NC(=O)N4CC(F)C4)ccc3F)cc2c1] | ¹H NMR (400 MHz, Methanol-d₄), δ 8.64 (br d, J = 2.26 Hz, 1 H), 8.61 (br d, J = 2.64 Hz, 1 H), 8.44 (br s, 1 H), 8.10 (dd, J = 6.71, 2.70 Hz, 1 H), 7.60-7.67 (m, 1 H), 7.33 (dd, J = 10.92, 9.16 Hz, 1 H), 5.25-5.47 (m, 1 H), 5.01 (dt, J = 12.52, 6.23 Hz, 1 H), 4.32-4.43 (m, 2 H), 4.07-4.19 (m, 2 H), 1.33 (d, J = 6.27 Hz, 6 H). Method 1: RT = 2.88 min.; M + H = 431.1 |

TABLE 2-continued

| Cpd No. | Structure | ¹HNMR and HPLC retention time and/or MS |
|---|---|---|
| 169 | 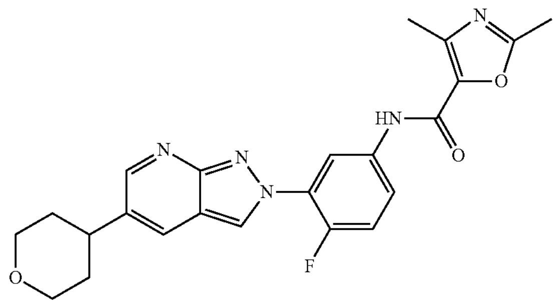 | ¹H NMR (400 MHz, DMSO-d6), δ 10.57 (s, 1 H), 9.05 (d, J = 2.51 Hz, 1 H), 8.88 (d, J = 2.01 Hz, 1 H), 8.59 (dd, J = 7.03, 2.51 Hz, 1 H), 8.43 (d, J = 1.76 Hz, 1 H), 7.89-7.99 (m, 1 H), 7.59 (dd, J = 11.04, 9.03 Hz, 1 H), 4.00 (br dd, J = 10.79, 3.26 Hz, 2 H), 3.48 (td, J = 11.36, 2.38 Hz, 2 H), 2.98-3.10 (m, 1 H), 2.50 (br s, 3 H), 2.39 (s, 3 H), 1.70-1.89 (m, 4 H). Method 1: RT = 2.77 min.; M + H = 436.2 |
| 170 | 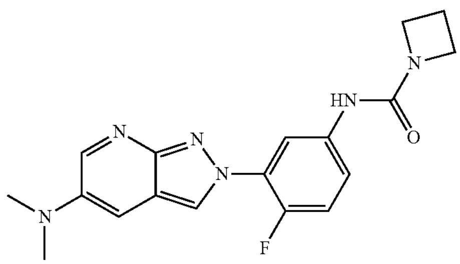 [SMILES: CN(C)c1cnc2nn(-c3cc(NC(=O)N4CCC4)ccc3F)cc2c1] | ¹H NMR (400 MHz, DMSO-d6) δ 8.69 (d, J = 3.01 Hz, 1 H), 8.66-8.68 (m, 1 H), 8.53 (d, J = 2.76 Hz, 1 H), 8.21 (dd, J = 7.03, 2.76 Hz, 1 H), 7.57-7.77 (m, 1 H), 7.40 (dd, J = 11.29, 9.03 Hz, 1 H), 7.15 (d, J = 2.76 Hz, 1 H), 3.98 (t, J = 7.53 Hz, 4 H), 2.95 (s, 6H), 2.20 (quin, J = 7.59 Hz, 2 H). Method 1: RT = 2.62 min.; M + H = 355.2 |
| 171 | 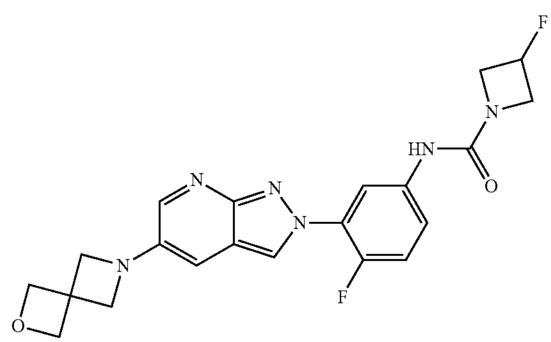 [SMILES: O=C(Nc1ccc(F)c(-n2cc3cc(N4CC5(COC5)C4)cnc3n2)c1)N1CC(F)C1] | ¹H NMR (400 MHz, DMSO-d6) δ 8.93 (s, 1H), 8.55 (d, J = 2.7 Hz, 1H), 8.27 (d, J = 2.8 Hz, 1H), 8.20 (dd, J = 7.1, 2.7 Hz, 1H), 7.64 (ddd, J = 9.1, 4.1, 2.7 Hz, 1H), 7.43 (dd, J = 11.4, 9.1 Hz, 1H), 6.94 (d, J = 2.8 Hz, 1H), 5.40 (dtt, J = 57.5, 6.1, 3.1 Hz, 1H), 4.75 (s, 4H), 4.31 (dddd, J = 21.8, 10.4, 6.0, 1.4 Hz, 2H), 4.10 (s, 4H), 4.08-3.96 (m, 2H). Method 1: RT = 2.55 min.; M + H = 427.2 |
| 172 | 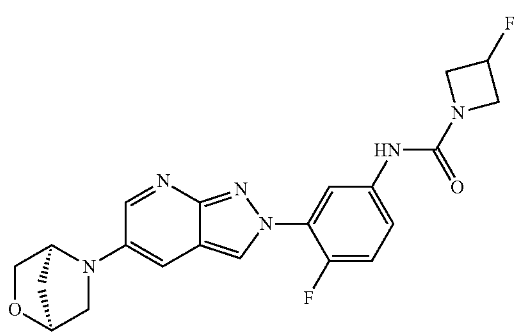 [SMILES: O=C(Nc1ccc(F)c(-n2cc3cc(N4C[C@@H]5C[C@H]4CO5)cnc3n2)c1)N1CC(F)C1] | ¹H NMR (400 MHz, DMSO-d6) δ 8.93 (s, 1H), 8.54 (d, J = 2.9 Hz, 1H), 8.51 (d, J = 2.8 Hz, 1H), 8.20 (dd, J = 7.1, 2.7 Hz, 1H), 7.64 (ddd, J = 9.0, 4.1, 2.7 Hz, 1H), 7.43 (dd, J = 11.4, 9.1 Hz, 1H), 7.07 (d, J = 2.9 Hz, 1H), 5.40 (ddq, J = 57.5, 6.1, 3.0 Hz, 1H), 4.69 (d, J = 23.8 Hz, 2H), 4.40-4.23 (m, 2H), 4.09-4.05 (m, 1H), 4.04-3.95 (m, 1H), 3.82-3.70 (m, 2H), 3.70-3.58 (m, 1H), 3.08 (ddd, J = 9.6, 1.4, 0.7 Hz, 1H), 1.99-1.84 (m, 2H). Method 2: RT = 0.90 min.; M + H = 427.2 |
| 173 | 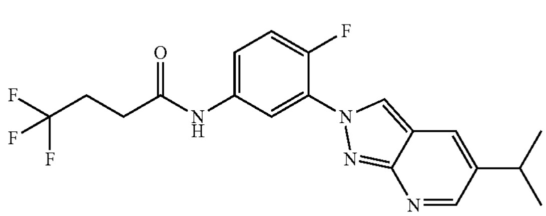 [SMILES: CC(C)c1cnc2nn(-c3cc(NC(=O)CCC(F)(F)F)ccc3F)cc2c1] | ¹H NMR (400 MHz, DMSO-d6) δ 10.45 (s, 1H), 8.81 (d, J = 2.7 Hz, 1H), 8.69 (d, J = 2.3 Hz, 1H), 8.36 (dd, J = 7.0, 2.7 Hz, 1H), 8.05 (dd, J = 2.3, 0.8 Hz, 1H), 7.68 (ddd, J = 9.1, 4.2, 2.7 Hz, 1H), 7.54 (dd, J = 11.2, 9.0 Hz, 1H), 3.08 (pd, J = 6.9, 0.8 Hz, 1H), 2.72-2.55 (m, 4H), 1.30 (d, J = 6.9 Hz, 6H). Method 1: RT = 3.19 min.; M + H = 395.2 |

TABLE 2-continued

| Cpd No. | Structure | ¹HNMR and HPLC retention time and/or MS |
|---|---|---|
| 174 | 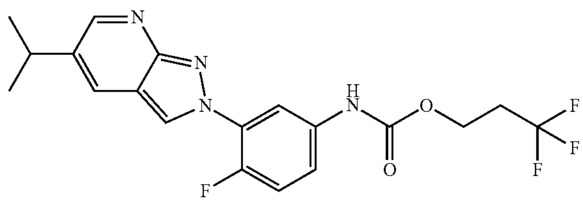 [SMILES: CC(C)c1cnc2nn(-c3cc(NC(=O)OCCC(F)(F)F)ccc3F)cc2c1] | ¹H NMR (400 MHz, DMSO-d6) δ 10.13 (s, 1H), 8.80 (d, J = 2.7 Hz, 1H), 8.69 (d, J = 2.3 Hz, 1H), 8.26-8.15 (m, 1H), 8.05 (dd, J = 2.3, 0.8 Hz, 1H), 7.65-7.45 (m, 2H), 4.35 (t, J = 6.0 Hz, 2H), 3.18-3.00 (m, 1H), 2.74 (qt, J = 11.5, 5.9 Hz, 2H), 1.30 (d, J = 6.9 Hz, 6H). Method 1: RT = 3.25 min.; M + H = 411.2 |
| 175 | 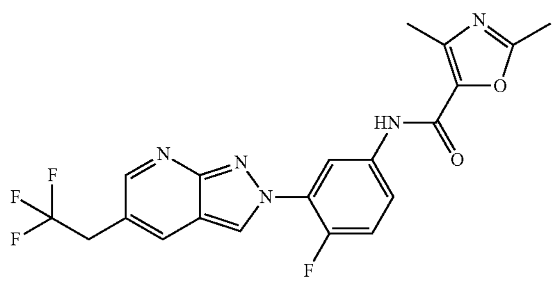 [SMILES: Cc1nc(C)c(C(=O)Nc2ccc(F)c(-n3cc4cc(CC(F)(F)F)cnc4n3)c2)o1] | ¹H NMR (400 MHz, DMSO-d6) δ 10.54 (s, 1 H), 9.00 (d, J = 2.51 Hz, 1 H), 8.71 (d, J = 2.01 Hz, 1 H), 8.58 (dd, J = 7.03, 2.51 Hz, 1 H), 8.36 (s, 1 H), 7.86-7.97 (m, 1 H), 7.52-7.67 (m, 1 H), 3.88 (q, J = 11.13 Hz, 2 H), 2.40 (s, 6 H). Method 1: RT = 2.88 min.; M + H = 434.1 |
| 176 | 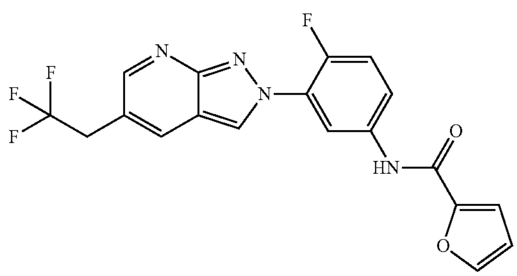 [SMILES: O=C(Nc1ccc(F)c(-n2cc3cc(CC(F)(F)F)cnc3n2)c1)c1ccco1] | ¹H NMR (400 MHz, Methanol-d₄), δ 8.91 (d, J = 1.88 Hz, 1 H), 8.74 (s, 1 H), 8.44-8.51 (m, 2 H), 7.93 (dt, J = 7.18, 4.44 Hz, 1 H), 7.78 (d, J = 1.13 Hz, 1 H), 7.48 (dd, J = 11.11, 9.22 Hz, 1 H), 7.32 (d, J = 3.51 Hz, 1 H), 6.68 (dd, J = 3.58, 1.69 Hz, 1 H), 3.77 (q, J = 10.75 Hz, 2 H) Method 1: RT = 2.86 min.; M + H = 405.1 |
| 177 | 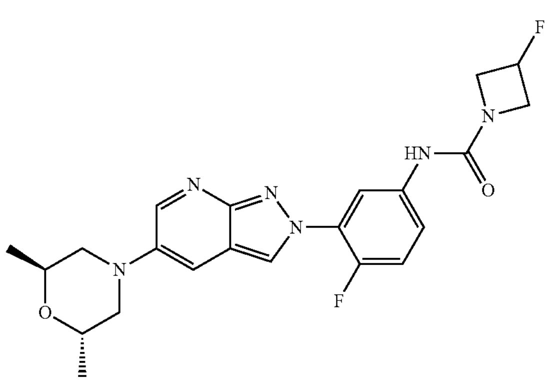 [SMILES: C[C@H]1CN(c2cnc3nn(-c4cc(NC(=O)N5CC(F)C5)ccc4F)cc3c2)C[C@H](C)O1] | ¹H NMR (400 MHz, DMSO-d6), δ 8.94 (s, 1 H), 8.71 (d, J = 2.76 Hz, 1 H), 8.61 (d, J = 2.51 Hz, 1 H), 8.21 (dd, J = 7.03, 2.51 Hz, 1 H), 7.65 (dt, J = 8.60, 3.61 Hz, 1 H), 7.44 (dd, J = 11.17, 9.16 Hz, 1 H), 7.37 (d, J = 2.51 Hz, 1 H) ,5.28-5.54 (m, 1 H), 4.24-4.40 (m, 2 H), 3.93-4.19 (m, 4 H), 3.18 (dd, J = 11.67, 2.89 Hz, 2 H), 2.87 (dd, J = 11.67, 5.90 Hz, 2 H), 1.26 (d, J = 6.27 Hz, 6 H). Method 2: RT = 0.92 min.; M + H = 443.2 |
| 178 | 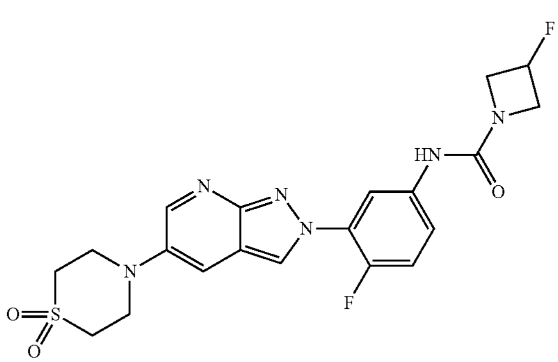 [SMILES: O=C(Nc1ccc(F)c(-n2cc3cc(N4CCS(=O)(=O)CC4)cnc3n2)c1)N1CC(F)C1] | ¹H NMR (400 MHz, DMSO-d6), δ 8.95 (s, 1 H), 8.76 (d, J = 2.76 Hz, 1 H), 8.64 (d, J = 2.76 Hz, 1 H), 8.20 (dd, J = 7.03, 2.51 Hz, 1 H), 7.62-7.69 (m, 1 H), 7.60 (d, J = 3.01 Hz, 1 H), 7.45 (dd, J = 11.29, 9.03 Hz, 1 H), 5.28-5.55 (m, 1 H), 4.24-4.41 (m, 2 H), 3.94-4.10 (m, 2 H), 3.67-3.82 (m, 4 H), 3.25-3.31 (m, 4 H). Method 2: RT = 0.72 min.; M + H = 463.1 |

| Cpd No. | Structure | ¹HNMR and HPLC retention time and/or MS |
|---|---|---|
| 179 | 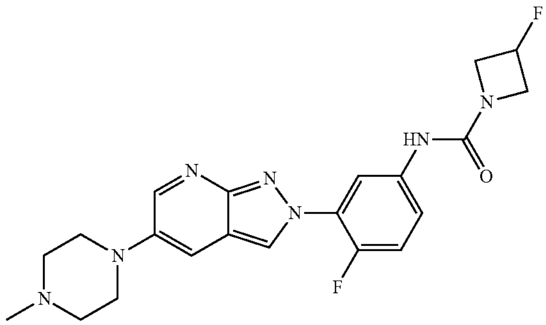 [SMILES: CN1CCN(c2cnc3nn(-c4cc(NC(=O)N5CC(F)C5)ccc4F)cc3c2)CC1] | ¹H NMR (400 MHz, METHANOL-d4), δ 8.68 (d, J = 2.76 Hz, 1 H), 8.55 (d, J = 2.26 Hz, 1 H), 8.11 (dd, J = 6.78, 2.76 Hz, 1 H), 7.60-7.67 (m, 1 H), 7.55 (d, J = 2.76 Hz, 1 H), 7.35 (dd, J = 10.92, 9.16 Hz, 1 H), 5.27-5.49 (m, 1 H), 4.34-4.47 (m, 2 H), 4.08-4.21 (m, 2 H), 3.22-3.31 (m, 4 H), 2.68-2.76 (m, 4 H), 2.41 (s, 3 H). Method 2: RT = 0.51 min.; M + H = 428.2 |
| 180 | 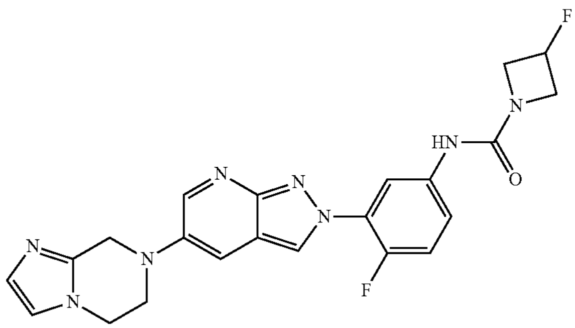 [SMILES: O=C(Nc1ccc(F)c(-n2cc3cc(N4CCn5ccnc5C4)cnc3n2)c1)N1CC(F)C1] | ¹H NMR (400 MHz, DMSO-d6), δ 8.95 (s, 1 H), 8.87 (d, J = 3.01 Hz, 1 H), 8.66 (d, J = 2.76 Hz, 1 H), 8.21 (dd, J = 7.15, 2.64 Hz, 1 H), 7.66 (dt, J = 8.85, 3.48 Hz, 1 H), 7.54 (d, J = 3.01 Hz, 1 H), 7.45 (dd, J = 11.29, 9.29 Hz, 1 H), 7.14 (d, J = 1.00 Hz, 1 H), 6.92 (d, J = 1.00 Hz, 1 H), 5.30-5.51 (m, 1 H), 4.40 (s, 2 H), 4.26-4.38 (m, 2 H), 4.15 (t, J = 5.40 Hz, 2 H), 3.97-4.09 (m, 2 H), 3.76 (t, J = 5.40 Hz, 2 H). Method 2: RT = 0.53 min.; M + H = 451.2 |
| 181 | 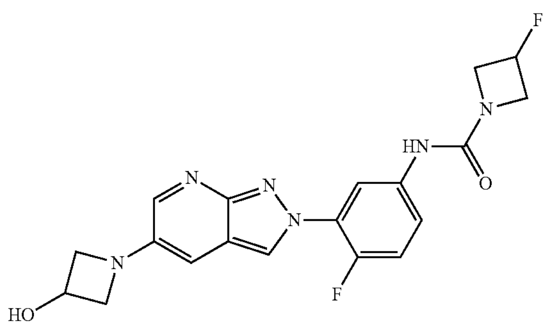 [SMILES: O=C(Nc1ccc(F)c(-n2cc3cc(N4CC(O)C4)cnc3n2)c1)N1CC(F)C1] | ¹H NMR (400 MHz, DMSO-d6), δ 8.93 (s, 1 H), 8.54 (d, J = 2.76 Hz, 1 H), 8.28 (d, J = 2.76 Hz, 1 H), 8.20 (dd, J = 7.15, 2.64 Hz, 1 H), 7.61-7.70 (m, 1 H), 7.43 (dd, J = 11.42, 9.16 Hz, 1 H), 6.92 (d, J = 2.76 Hz, 1 H), 5.68 (d, J = 6.78 Hz, 1 H), 5.28-5.51 (m, 1 H), 4.57-4.67 (m, 1 H), 4.25-4.40 (m, 2 H), 4.20 (t, J = 7.15 Hz, 2 H), 3.94-4.11 (m, 2 H), 3.56-3.65 (m, 2 H). Method 2: RT = 0.70 min.; M + H = 401.1 |
| 182 | 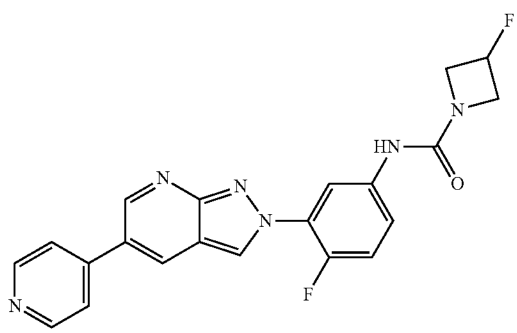 [SMILES: O=C(Nc1ccc(F)c(-n2cc3cc(-c4ccncc4)cnc3n2)c1)N1CC(F)C1] | ¹H NMR (400 MHz, DMSO-d6), δ 9.17 (d, J = 2.26 Hz, 1 H), 9.03 (d, J = 2.51 Hz, 1 H), 9.00 (s, 1 H), 8.75 (d, J = 2.51 Hz, 1 H), 8.67-8.73 (m, 2 H), 8.28 (dd, J = 6.90, 2.64 Hz, 1 H), 7.84-7.90 (m, 2 H), 7.68-7.75 (m, 1 H), 7.50 (dd, J = 11.29, 9.03 Hz, 1 H), 5.30-5.52 (m, 1 H), 4.27-4.40 (m, 2 H), 3.97-4.10 (m, 2 H). Method 2: RT = 0.58 min.; M + H = 407.1 |

TABLE 2-continued

| Cpd No. | Structure | ¹HNMR and HPLC retention time and/or MS |
|---|---|---|
| 183 | 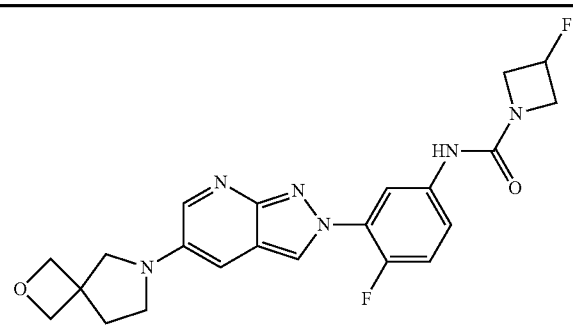 | ¹H NMR (400 MHz, METHANOL-d4), δ 8.50 (d, J = 2.76 Hz, 1 H), 8.44 (d, J = 2.51 Hz, 1 H), 8.10 (dd, J = 6.78, 2.76 Hz, 1 H), 7.59-7.65 (m, 1 H), 7.34 (dd, J = 10.79, 9.03 Hz, 1 H), 7.09 (d, J = 2.76 Hz, 1 H), 5.28-5.49 (m, 1 H), 4.77-4.82 (m, 2 H), 4.70-4.74 (m, 2 H), 4.34-4.46 (m, 2 H), 4.09-4.21 (m, 2 H), 3.71 (s, 2 H), 3.48 (t, J = 6.78 Hz, 2 H), 2.42 (t, J = 6.78 Hz, 2 H). Method 2: RT = 0.82 min.; M + H = 441.2 |
| 184 | 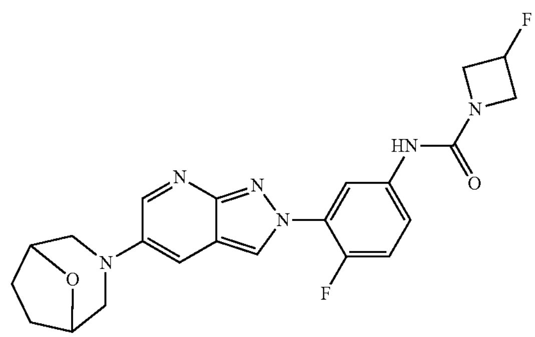 [SMILES: O=C(Nc1ccc(F)c(-n2cc3cc(N4CC5CCC(C4)O5)cnc3n2)c1)N1CC(F)C1] | ¹H NMR (400 MHz, DMSO), δ 8.93 (s, 1 H), 8.73 (d, J = 2.81 Hz, 1 H), 8.57 (d, J = 2.69 Hz, 1 H), 8.19 (dd, J = 7.03, 2.63 Hz, 1 H), 7.60-7.68 (m, 1 H), 7.42 (dd, J = 11.31, 9.11 Hz, 1 H), 7.23 (d, J = 2.81 Hz, 1 H), 5.27-5.50 (m, 1 H), 4.44 (br s, 2 H), 4.24-4.37 (m, 2 H), 3.94-4.07 (m, 2 H), 3.42 (br d, J = 10.88 Hz, 2 H), 2.81-2.92 (m, 2 H), 1.80-1.99 (m, 4 H) Method 1: RT = 2.70 min.; M + H = 441.3 |
| 185 | 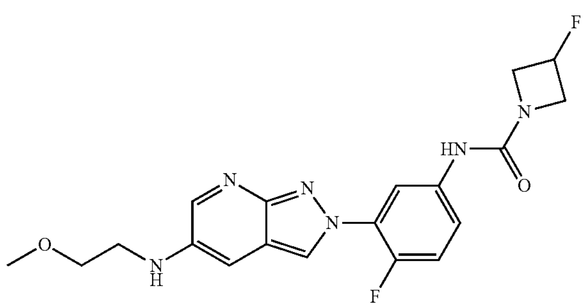 [SMILES: COCCNc1cnc2nn(-c3cc(NC(=O)N4CC(F)C4)ccc3F)cc2c1] | ¹H NMR (400 MHz, DMSO) δ 8.90 (s, 1 H), 8.33-8.47 (m, 2 H), 8.17 (dd, J = 6.96, 2.57 Hz, 1 H), 7.62 (dt, J = 8.78, 3.51 Hz, 1 H), 7.41 (dd, J = 11.29, 9.16 Hz, 1 H), 6.83 (d, J = 2.51 Hz, 1 H), 6.02 (br t, J = 5.14 Hz, 1 H), 5.24-5.51 (m, 1 H), 4.21-4.40 (m, 2 H), 3.92-4.09 (m, 2 H), 3.57 (br t, J = 5.52 Hz, 2 H), 3.31 (s, 3 H), 3.20-3.25 (m, 2 H) Method 1: RT = 2.60 min.; M + H = 403.2 |
| 186 | 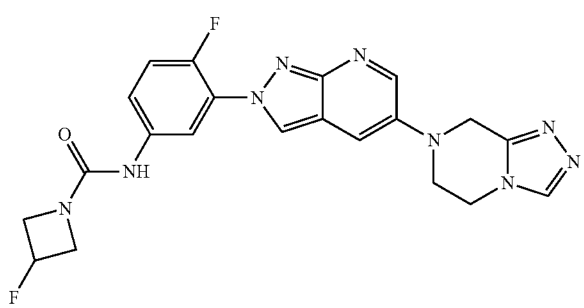 [SMILES: O=C(Nc1ccc(F)c(-n2cc3cc(N4CCn5cnnc5C4)cnc3n2)c1)N1CC(F)C1] | ¹H NMR (400 MHz, DMSO) δ 8.95 (s, 1 H), 8.86 (d, J = 2.76 Hz, 1 H), 8.66 (d, J = 2.51 Hz, 1 H), 8.51 (s, 1 H), 8.21 (dd, J = 6.90, 2.64 Hz, 1 H), 7.62-7.69 (m, 1 H), 7.57 (d, J = 2.76 Hz, 1 H), 7.44 (dd, J = 10.98, 9.22 Hz, 1 H), 5.29-5.50 (m, 1 H), 4.57 (s, 2 H), 4.26-4.37 (m, 2 H), 4.21 (br t, J = 5.40 Hz, 2 H), 3.95-4.09 (m, 2 H), 3.76 (br t, J = 5.33 Hz, 2 H) Method 1: RT = 2.27 min.; M + H = 452.2 |
| 187 | 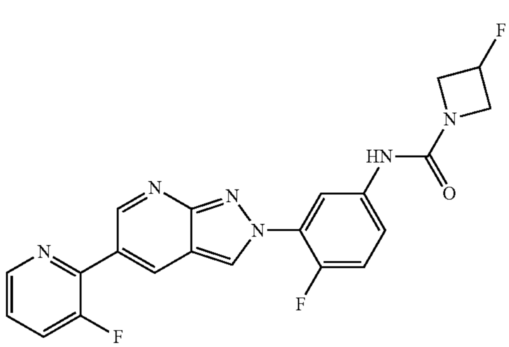 [SMILES: O=C(Nc1ccc(F)c(-n2cc3cc(-c4ncccc4F)cnc3n2)c1)N1CC(F)C1] | ¹H NMR (400 MHz, DMSO-d6) δ 9.27 (s, 1 H), 9.00-9.09 (m, 2 H), 8.82 (s, 1 H), 8.63 (br d, J = 4.39 Hz, 1 H), 8.29 (dd, J = 6.90, 2.51 Hz, 1 H), 7.93 (dd, J = 10.73, 8.47 Hz, 1 H), 7.72 (dt, J = 8.60, 3.48 Hz, 1 H), 7.52-7.58 (m, 1 H), 7.46-7.51 (m, 1 H), 5.28-5.55 (m, 1 H), 4.25-4.44 (m, 2 H), 3.93-4.14 (m, 2 H). Method 1: RT = 2.74 min.; M + H = 425.1 |

TABLE 2-continued

| Cpd No. | Structure | ¹HNMR and HPLC retention time and/or MS |
|---|---|---|
| 188 | 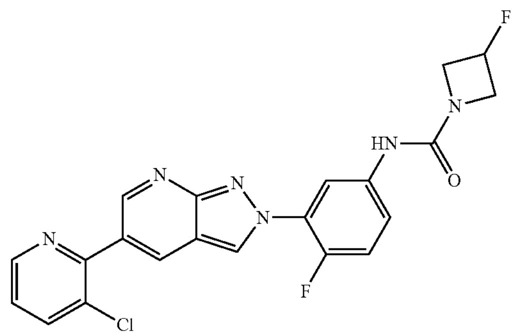 [SMILES: O=C(Nc1ccc(F)c(-n2cc3cc(-c4ncccc4Cl)cnc3n2)c1)N1CC(F)C1] | ¹H NMR (400 MHz, DMSO-d6) δ 9.02-9.05 (m, 2 H), 9.00 (d, J = 2.38 Hz, 1 H), 8.72 (dd, J = 4.64, 1.38 Hz, 1 H), 8.69 (d, J = 2.26 Hz, 1 H), 8.29 (dd, J = 6.96, 2.70 Hz, 1 H), 8.14 (dd, J = 8.16, 1.38 Hz, 1 H), 7.69-7.76 (m, 1 H), 7.52-7.55 (m, 1 H), 7.47-7.51 (m, 1 H), 5.28-5.53 (m, 1 H), 4.28-4.39 (m, 2 H), 3.97-4.10 (m, 2 H). Method 1: RT = 2.76 min.; M + H = 441.0 |
| 189 | 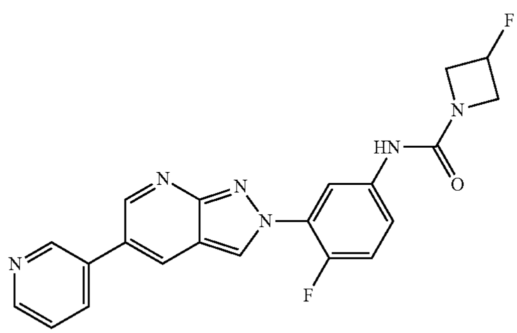 [SMILES: O=C(Nc1ccc(F)c(-n2cc3cc(-c4cccnc4)cnc3n2)c1)N1CC(F)C1] | ¹H NMR (400 MHz, DMSO-d6) δ 9.11 (d, J = 2.38 Hz, 1 H), 9.03 (d, J = 1.88 Hz, 1 H), 9.01 (s, 1 H), 8.99 (d, J = 2.51 Hz, 1 H), 8.62-8.66 (m, 2 H), 8.28 (dd, J = 6.90, 2.64 Hz, 1 H), 8.24 (dt, J = 8.22, 1.79 Hz, 1 H), 7.69-7.75 (m, 1 H), 7.56 (dd, J = 7.40, 4.77 Hz, 1 H), 7.50 (dd, J = 11.17, 9.16 Hz, 1 H), 5.23-5.56 (m, 1 H), 4.27-4.41 (m, 2 H), 3.97-4.11 (m, 2 H). Method 1: RT = 2.40 min.; M + H = 407.1 |
| 190 | 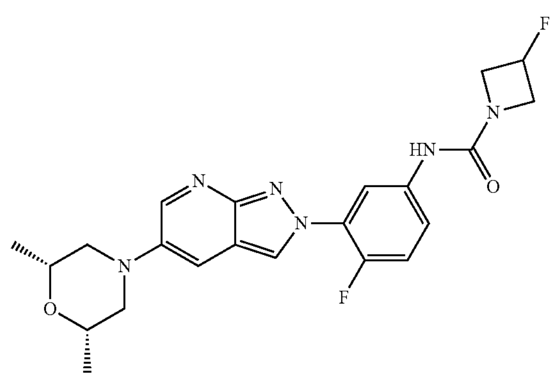 [SMILES: C[C@@H]1CN(c2cnc3nn(-c4cc(NC(=O)N5CC(F)C5)ccc4F)cc3c2)C[C@H](C)O1] | ¹H NMR (400 MHz, DMSO) δ 8.91 (s, 1 H), 8.73 (d, J = 2.76 Hz, 1 H), 8.58 (d, J = 2.64 Hz, 1 H), 8.18 (dd, J = 7.03, 2.64 Hz, 1 H), 7.57-7.68 (m, 1 H), 7.41 (dd, J = 11.29, 9.03 Hz, 1 H), 7.35 (d, J = 2.76 Hz, 1 H), 5.25-5.49 (m, 1 H), 4.23-4.36 (m, 2 H), 3.93-4.07 (m, 2 H), 3.69-3.84 (m, 2 H), 3.56 (br d, J = 10.92 Hz, 2 H), 2.24-2.32 (m, 2 H), 1.15 (d, J = 6.15 Hz, 6 H). Method 1: RT = 2.77 min. M + H = 443.3 |
| 191 | 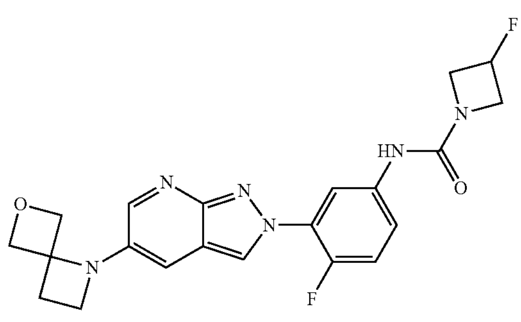 [SMILES: O=C(Nc1ccc(F)c(-n2cc3cc(N4CCC45COC5)cnc3n2)c1)N1CC(F)C1] | ¹H NMR (400 MHz, DMSO) δ 8.94 (s, 1 H) 8.60,(d, J = 2.76 Hz, 1 H), 8.56 (d, J = 2.76 Hz, 1 H), 8.22 (dd, J = 7.09, 2.70 Hz, 1 H), 7.62-7.69 (m, 1 H), 7.44 (dd, J = 11.29, 9.16 Hz, 1 H), 7.18 (d, J = 2.76 Hz, 1 H), 5.30-5.51 (m, 1 H), 5.10 (d, J = 8.28 Hz, 2 H), 4.75 (d, J = 8.28 Hz, 2 H), 4.26-4.38 (m, 2 H), 3.96-4.09 (m, 2 H), 3.74 (t, J = 6.96 Hz, 2 H), 2.58 (br s, 2 H). Method 1: RT = 2.65 min. M + H = 427.2 |

TABLE 2-continued

| Cpd No. | Structure | ¹HNMR and HPLC retention time and/or MS |
|---|---|---|
| 192 | 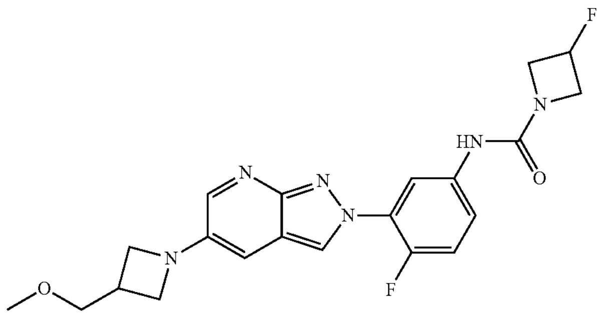 [SMILES: COCC1CN(c2cnc3nn(-c4cc(NC(=O)N5CC(F)C5)ccc4F)cc3c2)C1] | ¹H NMR (400 MHz, DMSO) δ 8.94 (s, 1 H), 8.52 (d, J = 2.69 Hz, 1 H), 8.26 (d, J = 2.81 Hz, 1 H), 8.19 (dd, J = 7.03, 2.63 Hz, 1 H), 7.60-7.68 (m, 1 H), 7.42 (dd, J = 11.37, 9.17 Hz, 1 H), 6.88 (d, J = 2.69 Hz, 1 H), 5.28-5.50 (m, 1 H), 4.24-4.37 (m, 2 H), 4.02-4.08 (m, 1 H), 3.98 (t, J = 7.64 Hz, 3 H), 3.65 (dd, J = 7.15, 5.69 Hz, 2 H), 3.56 (d, J = 6.60 Hz, 2 H), 3.29 (s, 3 H), 2.96 (m, 1 H). Method 1: RT = 2.76 min. M + H = 429.3 |
| 193 | 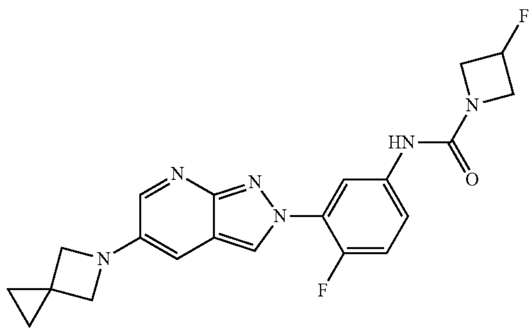 [SMILES: O=C(Nc1ccc(F)c(-n2cc3cc(N4CC5(CC5)C4)cnc3n2)c1)N1CC(F)C1] | ¹H NMR (400 MHz, DMSO) δ 8.92 (s, 1 H), 8.52 (d, J = 2.76 Hz, 1 H), 8.28 (d, J = 2.76 Hz, 1 H), 8.19 (dd, J = 7.03, 2.64 Hz, 1 H), 7.59-7.67 (m, 1 H), 7.42 (dd, J = 11.36, 9.10 Hz, 1 H), 6.91 (d, J = 2.89 Hz, 1 H), 5.27-5.50 (m, 1 H), 4.23-4.38 (m, 2 H), 3.94-4.10 (m, 6 H), 0.68 (s, 4 H). Method 1: RT = 2.92 min. M + H = 411.3 + |
| 194 | 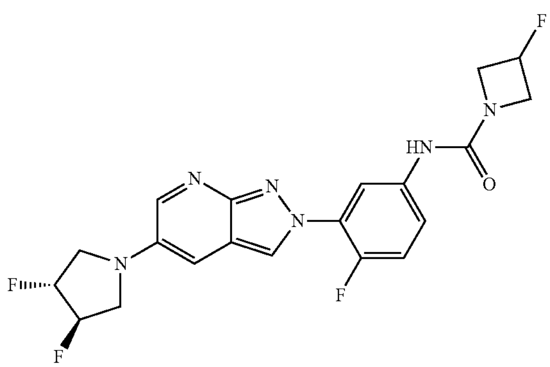 [SMILES: O=C(Nc1ccc(F)c(-n2cc3cc(N4C[C@@H](F)[C@H](F)C4)cnc3n2)c1)N1CC(F)C1] | ¹H NMR (400 MHz, DMSO) δ 8.88 (s, 1 H), 8.48-8.59 (m, 2 H), 8.17 (dd, J = 7.03, 2.64 Hz, 1 H), 7.54-7.67 (m, 1 H), 7.39 (dd, J = 11.36, 9.10 Hz, 1 H), 7.03 (d, J = 2.89 Hz, 1 H), 5.19-5.63 (m, 3 H), 4.19-4.40 (m, 2 H), 3.93-4.06 (m, 2 H), 3.57-3.87 (m, 4 H). Method 1: RT = 2.77 min. M + H = 435.1 |
| 195 | 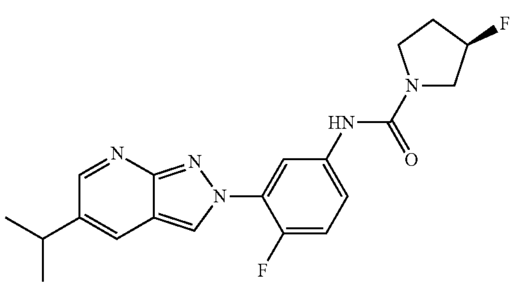 [SMILES: CC(C)c1cnc2nn(-c3cc(NC(=O)N4CC[C@@H](F)C4)ccc3F)cc2c1] | ¹H NMR (400 MHz, DMSO-d6) δ 8.79 (d, J = 2.51 Hz, 1 H), 8.69 (d, J = 2.13 Hz, 1 H), 8.64 (s, 1 H), 8.26 (dd, J = 6.96, 2.57 Hz, 1 H), 8.05 (d, J = 2.01 Hz, 1 H), 7.68-7.76 (m, 1 H), 7.46 (dd, J = 11.17, 9.16 Hz, 1 H), 5.27-5.49 (m, 1 H), 3.62-3.77 (m, 2 H), 3.40-3.59 (m, 2 H), 3.08 (dt, J = 13.61, 6.74 Hz, 1 H), 2.02-2.25 (m, 2 H), 1.31 (d, J = 6.90 Hz, 6 H). Method 1: RT = 2.95 min.; M + H = 386.1, |
| 196 | 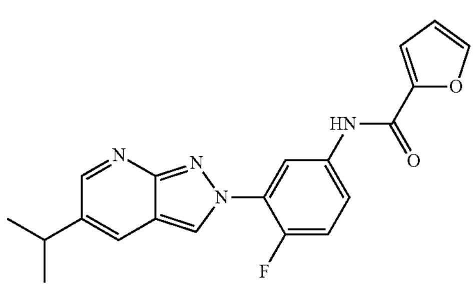 [SMILES: CC(C)c1cnc2nn(-c3cc(NC(=O)c4ccco4)ccc3F)cc2c1] | ¹H NMR (400 MHz, DMSO-d6) δ 10.54 (br s, 1 H), 8.83 (d, J = 2.51 Hz, 1 H), 8.70 (d, J = 2.26 Hz, 1 H), 8.51 (dd, J = 7.03, 2.64 Hz, 1 H), 8.07 (d, J = 2.01 Hz, 1 H), 7.98 (d, J = 0.88 Hz, 1 H), 7.91-7.96 (m, 1 H), 7.57 (dd, J = 11.17, 9.16 Hz, 1 H), 7.40 (d, J = 3.14 Hz, 1 H), 6.74 (dd, J = 3.45, 1.69 Hz, 1 H), 3.04-3.14 (m, 1 H), 1.31 (d, J = 6.90 Hz, 6 H). Method 1: RT = 3.04 min.; M + H = 365.0 |

TABLE 2-continued

| Cpd No. | Structure | ¹HNMR and HPLC retention time and/or MS |
|---|---|---|
| 197 | 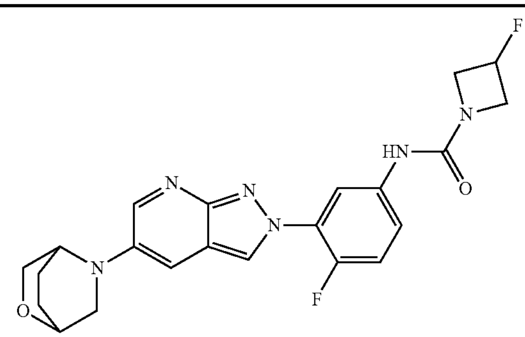 | ¹H NMR (400 MHz, DMSO) δ 8.87-8.98 (m, H), 8.60 (d, J = 2.89 Hz, 1 H), 8.48 (d, J = 2.76 Hz, 1 H), 8.18 (dd, J = 7.03, 2.64 Hz, 1 H), 7.58-7.65 (m, 1 H), 7.41 (dd, J = 11.42, 9.16 Hz, 1 H), 7.04 (d, J = 3.01 Hz, 1 H), 5.26-5.49 (m, 1 H), 4.23-4.36 (m, 2 H), 3.91-4.10 (m, 5 H), 3.73 (br d, J = 10.42 Hz, 1 H), 3.40 (br d, J = 9.66 Hz, 2 H), 1.65-2.09 (m, 4 H). Method 1: RT = 2.69 min.; M + H = 441.3 |
| 198 | 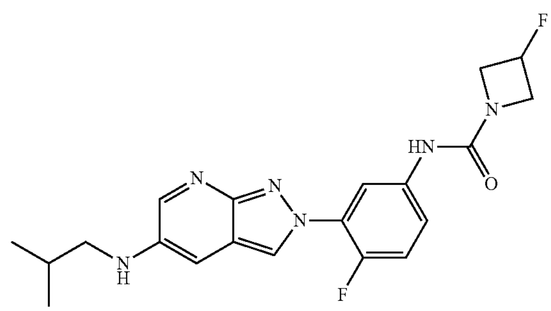 [SMILES: CC(C)CNc1cnc2nn(-c3cc(NC(=O)N4CC(F)C4)ccc3F)cc2c1] | ¹H NMR (400 MHz, DMSO-d₆) δ 8.92 (s, 1 H), 8.40 (dd, J = 2.64, 1.88 Hz, 2 H), 8.17 (dd, J = 7.03, 2.76 Hz, 1 H), 7.57-7.72 (m, 1 H), 7.37-7.46 (m, 1 H), 6.76 (d, J = 2.76 Hz, 1 H), 6.05 (t, J = 5.52 Hz, 1 H), 5.29-5.57 (m, 1 H), 4.24-4.40 (m, 2 H), 3.94-4.11 (m, 2 H), 2.85 (t, J = 6.02 Hz, 2 H), 1.93 (dquin, J = 13.35, 6.58, 6.58, 6.58, 6.58 Hz, 1 H), 0.99 (d, J = 6.53 Hz, 6 H) Method 1: RT = 3.00 min.; M + H = 401.4 |
| 199 | 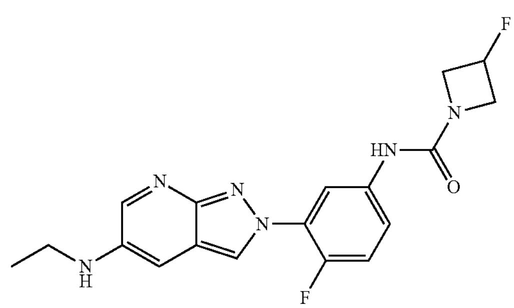 [SMILES: CCNc1cnc2nn(-c3cc(NC(=O)N4CC(F)C4)ccc3F)cc2c1] | ¹H NMR (400 MHz, DMSO-d₆) δ 8.93 (s, 1 H), 8.34-8.43 (m, 2 H), 8.17 (dd, J = 7.03, 2.51 Hz, 1 H), 7.59-7.68 (m, 1 H), 7.41 (dd, J = 11.42, 9.16 Hz, 1 H), 6.77 (d, J = 2.76 Hz, 1 H), 5.97 (t, J = 5.02 Hz, 1 H), 5.27-5.53 (m, 1 H), 4.24-4.40 (m, 2 H), 3.93-4.10 (m, 2 H), 3.01-3.10 (m, 2 H), 1.24 (t, J = 7.15 Hz, 3 H). Method 2: RT = 0.80 min.; M + H = 373.4 |
| 200 | 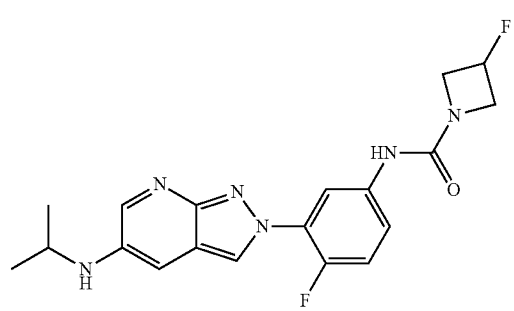 [SMILES: CC(C)Nc1cnc2nn(-c3cc(NC(=O)N4CC(F)C4)ccc3F)cc2c1] | ¹H NMR (400 MHz, DMSO) δ 8.93 (s, 1 H), 8.40 (d, J = 2.81 Hz, 1 H), 8.33 (d, J = 2.81 Hz, 1 H), 8.15-8.21 (m, 1 H), 7.60-7.71 (m, 1 H), 7.37-7.48 (m, 1 H), 6.79 (d, J = 2.69 Hz, 1 H), 5.84 (br d, J = 7.58 Hz, 1 H), 5.27-5.52 (m, 1 H), 4.26-4.38 (m, 2 H), 3.96-4.09 (m, 2 H), 3.44-3.57 (m, 1 H), 1.19 (d, J = 6.24 Hz, 6 H). Method 1: RT = 2.78 min.; M + H = 387.2 |
| 201 | 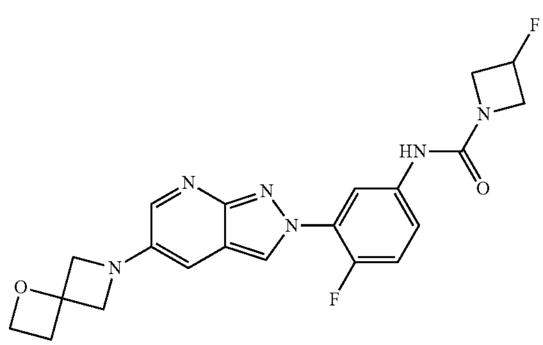 | ¹H NMR (400 MHz, DMSO) δ 8.94 (s, 1 H), 8.55 (d, J = 2.64 Hz, 1 H), 8.28 (d, J = 2.76 Hz, 1 H), 8.19 (dd, J = 7.03, 2.76 Hz, 1 H), 7.62-7.70 (m, 1 H), 7.43 (dd, J = 11.29, 9.16 Hz, 1 H), 6.95 (d, J = 2.76 Hz, 1 H), 5.26-5.51 (m, 1 H), 4.47 (t, J = 7.53 Hz, 2 H), 4.18-4.37 (m, 4 H), 3.92-4.08 (m, 4 H), 2.91 (t, J = 7.53 Hz, 2 H). Method 2: RT = 0.78 min.; M + H = 427.3 |

TABLE 2-continued

| Cpd No. | Structure | ¹HNMR and HPLC retention time and/or MS |
|---|---|---|
| 202 | 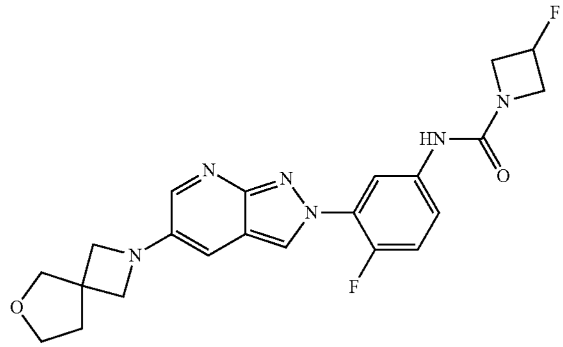 [SMILES: O=C(Nc1ccc(F)c(-n2cc3cc(N4CC5(CCOC5)C4)cnc3n2)c1)N1CC(F)C1] | ¹H NMR (400 MHz, DMSO) δ 8.92 (s, 1 H), 8.54 (d, J = 2.64 Hz, 1 H), 8.28 (d, J = 2.76 Hz, 1 H), 8.19 (dd, J = 7.03, 2.64 Hz, 1 H), 7.61-7.69 (m, 1 H), 7.42 (dd, J = 11.36, 9.10 Hz, 1 H), 6.93 (d, J = 2.76 Hz, 1 H), 5.24-5.50 (m, 1 H), 4.23-4.38 (m, 2 H), 3.86-4.06 (m, 6 H), 3.83 (s, 2 H), 3.74 (t, J = 6.96 Hz, 2 H), 2.16 (t, J = 6.96 Hz, 2 H). Method 2: RT = 0.80 min.; M + H = 441.3 |
| 203 | 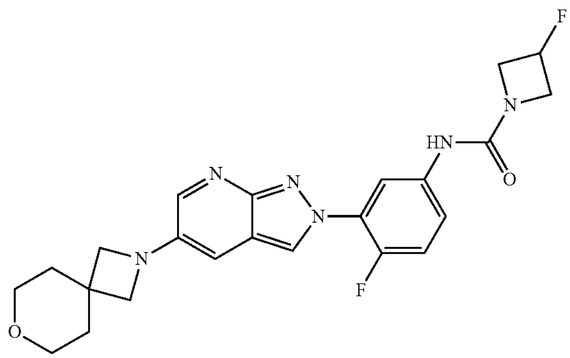 [SMILES: O=C(Nc1ccc(F)c(-n2cc3cc(N4CC5(CCOCC5)C4)cnc3n2)c1)N1CC(F)C1] | ¹H NMR (400 MHz, DMSO) δ 8.93 (s, 1 H), 8.53 (d, J = 2.64 Hz, 1 H), 8.28 (d, J = 2.76 Hz, 1 H), 8.15-8.24 (m, 1 H), 7.60-7.67 (m, 1 H), 7.42 (dd, J = 11.36, 9.10 Hz, 1 H), 6.89 (d, J = 2.76 Hz, 1 H), 5.28-5.50 (m, 1 H), 4.24-4.37 (m, 2 H), 3.89-4.08 (m, 2 H), 3.72 (s, 4 H), 3.43-3.62 (m, 4 H), 1.73-1.84 (m, 4 H). Method 2: RT = 0.85 min.; M + H = 455.3 |
| 204 | 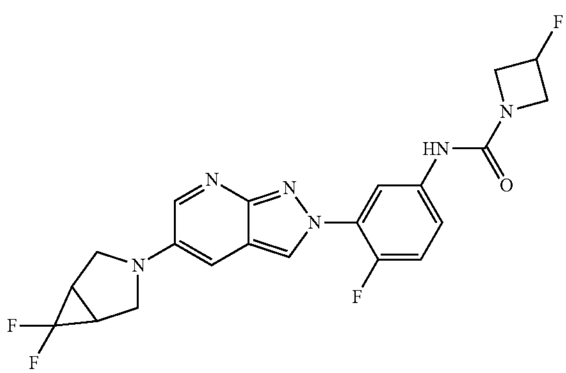 [SMILES: O=C(Nc1ccc(F)c(-n2cc3cc(N4CC5C(C4)C5(F)F)cnc3n2)c1)N1CC(F)C1] | ¹H NMR (400 MHz, DMSO-d6) δ 8.92 (s, 1 H), 8.53 (br d, J = 2.76 Hz, 1 H), 8.50 (br d, J = 2.76 Hz, 1 H), 8.19-8.28 (m, 1 H), 7.62-7.71 (m, 1 H), 7.43 (dd, J = 11.29, 9.16 Hz, 1 H), 6.96 (d, J = 2.76 Hz, 1 H), 5.29-5.50 (m, 1 H), 4.21-4.45 (m, 2 H), 3.89-4.13 (m, 2 H), 3.77 (d, J = 10.04 Hz, 2 H), 3.65 (br d, J = 8.91 Hz, 2 H), 2.68-2.80 (m, 2 H). Method 1: RT = 2.84 min.; M + H = 447.3 |
| 205 | 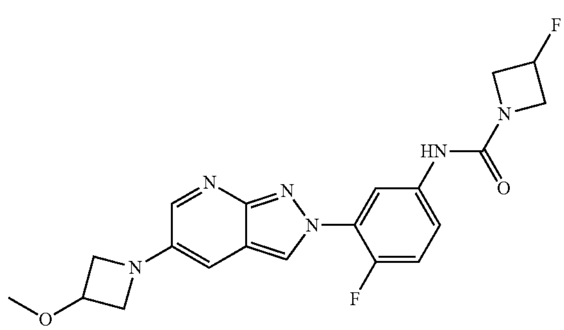 [SMILES: COC1CN(c2cnc3nn(-c4cc(NC(=O)N5CC(F)C5)ccc4F)cc3c2)C1] | ¹H NMR (400 MHz, DMSO) δ 8.92 (s, 1 H), 8.51 (d, J = 2.76 Hz, 1 H), 8.26 (d, J = 2.76 Hz, 1 H), 8.17 (dd, J = 7.09, 2.70 Hz, 1 H), 7.58-7.65 (m, 1 H), 7.40 (dd, J = 11.36, 9.10 Hz, 1 H), 6.91 (d, J = 2.76 Hz, 1 H), 5.23-5.50 (m, 1 H), 4.23-4.37 (m, 3 H), 4.10-4.19 (m, 2 H), 3.93-4.07 (m, 2 H), 3.68 (dd, J = 8.22, 4.33 Hz, 2 H), 3.20-3.27 (m, 3 H). Method 1: RT = 2.59 min.; M + H = 415.2 |

TABLE 2-continued

| Cpd No. | Structure | ¹HNMR and HPLC retention time and/or MS |
|---|---|---|
| 206 | 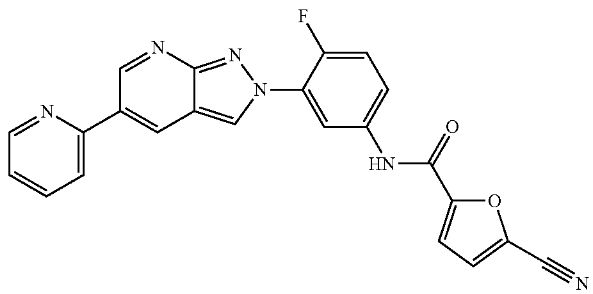 [SMILES: N#Cc1ccc(C(=O)Nc2ccc(F)c(-n3cc4cc(-c5ccccn5)cnc4n3)c2)o1] | ¹H NMR (400 MHz, DMSO-d6) δ 10.94 (s, 1H), 9.49 (d, J = 2.3 Hz, 1H), 9.08 (d, J = 2.5 Hz, 1H), 8.97 (d, J = 2.3 Hz, 1H), 8.75 (ddd, J = 0.9, 1.9, 4.8 Hz, 1H), 8.56 (dd, J = 2.7, 7.0 Hz, 1H), 8.15 (dt, J = 1.1, 8.1 Hz, 1H), 8.07-7.92 (m, 2H), 7.82 (d, J = 3.8 Hz, 1H), 7.65 (dd, J = 9.1, 11.2 Hz, 1H), 7.59 (d, J = 3.8 Hz, 1H), 7.45 (ddd, J = 1.1, 4.8, 7.5 Hz, 1H). Method 1: RT = 2.83 min.; M + H = 425.4 |
| 207 | 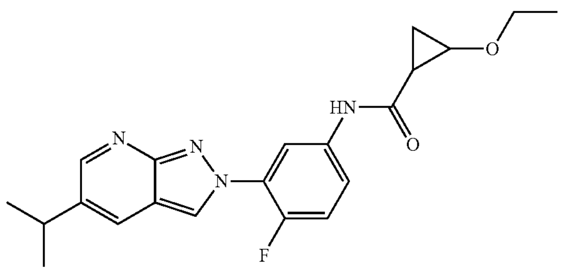 [SMILES: CCOC1CC1C(=O)Nc1ccc(F)c(-n2cc3cc(C(C)C)cnc3n2)c1] | ¹H NMR (400 MHz, Methylene Chloride-d₂) δ 8.67 (m, 1H), 8.48 (m, 1H), 8.19 (m, 1H), 7.93-7.83 (m, 2H), 7.26 (m, 1H), 3.68-3.49 (m, 3H), 3.08 (m, 1H), 1.90-1.76 (m, 2H), 1.37-1.32 (m, 6H), 1.28-1.07 (m, 4H). Method 1: RT = 3.08 min.; M + H = 383.3 |
| 208 | 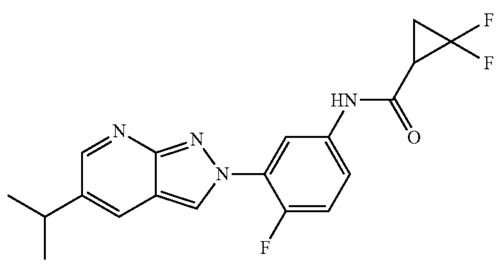 [SMILES: CC(C)c1cnc2nn(-c3cc(NC(=O)C4CC4(F)F)ccc3F)cc2c1] | ¹H NMR (400 MHz, Methylene Chloride-d₂) δ 9.91 (s, 1H), 8.68 (m, 1H), 8.47 (m, 1H), 8.19 (m, 1H), 8.11-8.02 (m, 1H), 7.97 (m, 1H), 7.27 (m, 1H), 3.09 (m, 1H), 2.63 (m, 1H), 2.16 (m, 1H), 1.70 (m, 1H), 1.33 (m, 6H). Method 1: RT = 3.04 min.; M + H = 375.3 |
| 209 | 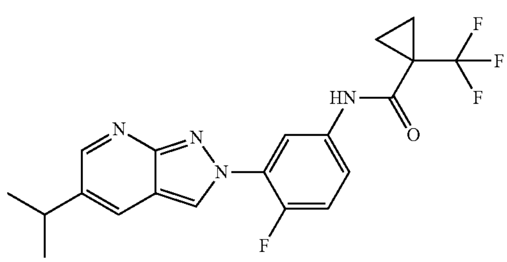 [SMILES: CC(C)c1cnc2nn(-c3cc(NC(=O)C4(C(F)(F)F)CC4)ccc3F)cc2c1] | ¹H NMR (400 MHz, Methylene Chloride-d₂) δ 8.78 (m, 2H), 8.35 (m, 1H), 8.30 (m, 1H), 7.99 (m, 1H), 7.81 (m, 1H), 7.36 (m, 1H), 3.19 (m, 1H), 2.30-2.18 (m, 2H), 2.03-1.95 (m, 2H), 1.42-1.34 (m, 6H). Method 1: RT = 3.14 min.; M + H = 407.2 |
| 210 | 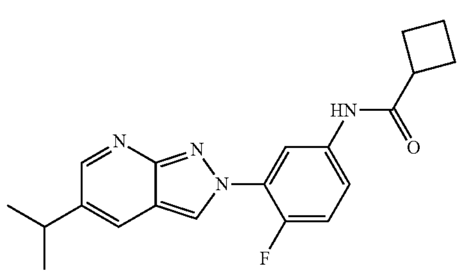 [SMILES: CC(C)c1cnc2nn(-c3cc(NC(=O)C4CCC4)ccc3F)cc2c1] | ¹H NMR (400 MHz, Methylene Chloride-d2) δ 8.66 (m, 1H), 8.48 (m, 1H), 8.18 (m, 1H), 7.92-7.88 (m, 2H), 7.27 (m, 1H), 3.24-3.13 (m, 1H), 3.08 (m, 1H), 2.41-2.29 (m, 2H), 2.25-2.12 (m, 2H), 2.05-1.89 (m, 2H), 1.37-1.31 (m, 6H). Method 1: RT = 3.14 min.; M + H = 353.3 |

TABLE 2-continued

| Cpd No. | Structure | ¹HNMR and HPLC retention time and/or MS |
|---|---|---|
| 211 | 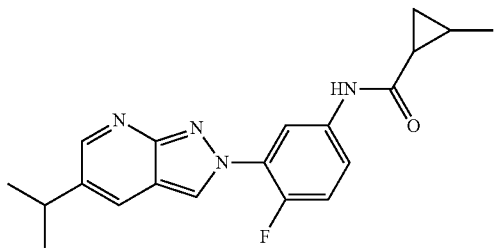 [SMILES: CC(C)c1cnc2nn(-c3cc(NC(=O)C4CC4C)ccc3F)cc2c1] | ¹H NMR (400 MHz, Methylene Chloride-d2) δ 8.66 (m, 1H), 8.49-8.40 (m, 2H), 8.17 (m, 1H), 7.92-7.84 (m, 2H), 7.24 (m, 1H), 3.07 (m, 1H), 1.46-1.36 (m, 1H), 1.36-1.30 (m, 6H), 1.30-1.24 (m, 1H), 1.24-1.15 (m, 1H), 1.10 (m, 3H), 0.65 (m, 1H). Method 1: RT = 3.16 min.; M + H = 353.3 |
| 212 | 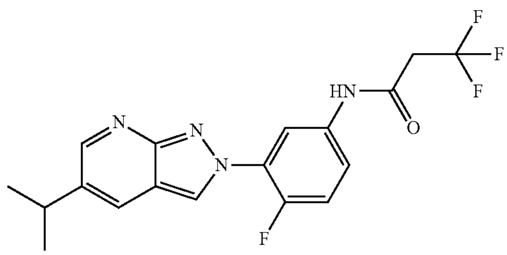 [SMILES: CC(C)c1cnc2nn(-c3cc(NC(=O)CC(F)(F)F)ccc3F)cc2c1] | ¹H NMR (400 MHz, Methylene Chloride-d2) δ 9.74 (m, 1H), 8.64 (m, 1H), 8.44 (m, 1H), 8.15 (m, 1H), 8.05 (m, 1H), 7.93 (m, 1H), 7.31 (m, 1H), 3.30 (m, 2H), 3.08 (m, 1H), 1.46-1.17 (m, 6H). Method 1: RT = 3.08 min.; M + H = 381.2 |
| 213 | 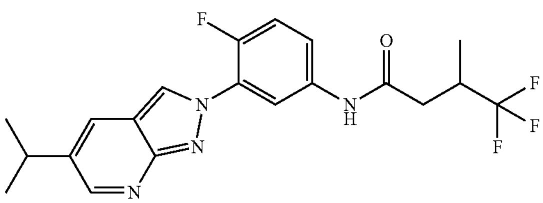 [SMILES: CC(C)c1cnc2nn(-c3cc(NC(=O)CC(C)C(F)(F)F)ccc3F)cc2c1] | ¹H NMR (400 MHz, Methylene Chloride-d2) δ 9.14 (m, 1H), 8.64 (m, 1H), 8.45 (m, 1H), 8.22 (m, 1H), 8.00 (m 1H) 7.91 (m 1H) 7.28 (m, 1H), 3.07 (m, 1H), 2.96-2.84 (m, 1H), 2.71 (m, 1H), 2.27 (m, 1H), 1.33 (m, 6H), 1.15 (m, 3H). Method 1: RT = 3.27 min.; M + H = 409.3 |
| 214 | 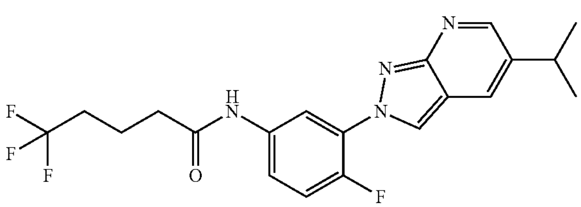 [SMILES: CC(C)c1cnc2nn(-c3cc(NC(=O)CCCC(F)(F)F)ccc3F)cc2c1] | ¹H NMR (400 MHz, Methylene Chloride-d2) δ 8.88 (m, 1H), 8.64 (m, 1H), 8.45 (m, 1H), 8.19 (m, 1H), 7.99-7.92 (m, 1H), 7.90 (m, 1H), 7.27 (m, 1H), 3.07 (m, 1H), 2.43 (m, 2H), 2.24-2.07 (m, 2H), 1.97-1.86 (m, 2H), 1.33 (m, 6H). Method 1: RT = 3.23 min.; M + H = 409.3 |
| 215 | 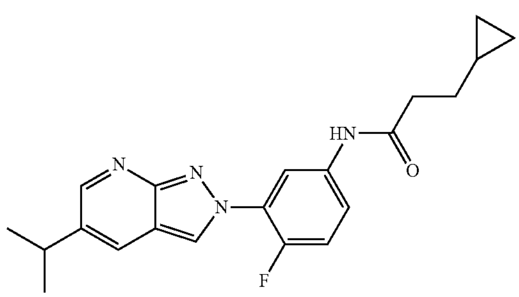 [SMILES: CC(C)c1cnc2nn(-c3cc(NC(=O)CCC4CC4)ccc3F)cc2c1] | ¹H NMR (400 MHz, Methylene Chloride-d2) δ 8.66 (m, 1H), 8.47 (m, 1H), 8.19 (m, 2H), 7.92-7.86 (m, 2H), 7.27 (m, 1H), 3.08 (m, 1H), 2.47-2.39 (m, 2H), 1.58 (m, 2H), 1.38-1.29 (m, 6H), 0.78-0.66 (m, 1H), 0.45-0.38 (m, 2H), 0.07-0.01 (m, 2H). Method 1: RT = 3.23 min.; M + H = 367.3 |
| 216 | 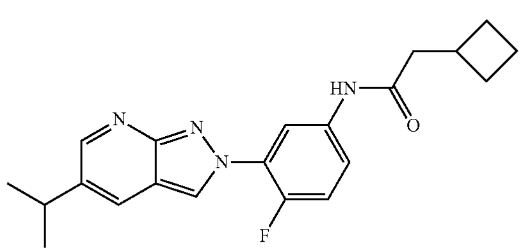 [SMILES: CC(C)c1cnc2nn(-c3cc(NC(=O)CC4CCC4)ccc3F)cc2c1] | ¹H NMR (400 MHz, Methylene Chloride-d2) δ 8.66 (m, 1H), 8.47 (m, 1H), 8.18 (m, 1H), 8.05 (m, 1H), 7.91-7.83 (m, 2H), 7.26 (m, 1H), 3.08 (m, 1H), 2.74 (m, 1H), 2.44 (m, 2H), 2.17-2.10 (m, 2H), 1.94-1.78 (m, 2H), 1.78-1.66 (m, 2H), 1.37-1.30 (m, 6H). Method 1: RT = 3.19 min.; M + H = 367.3 |

TABLE 2-continued

| Cpd No. | Structure | ¹HNMR and HPLC retention time and/or MS |
|---|---|---|
| 217 | 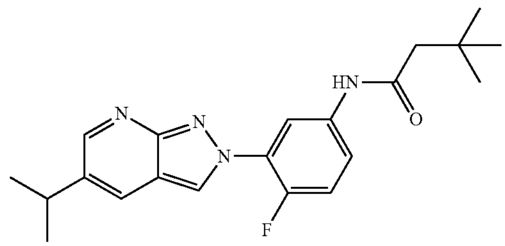 [SMILES: CC(C)c1cnc2nn(-c3cc(NC(=O)CC(C)(C)C)ccc3F)cc2c1] | ¹H NMR (400 MHz, Methylene Chloride-d2) δ 8.66 (m, 1H), 8.48 (m, 1H), 8.21 (m, 1H), 7.89 (m, 1H), 7.84 (m, 1H), 7.79 (m, 1H), 7.27 (m, 1H), 3.08 (m, 1H), 2.20 (m, 2H), 1.38-1.21 (m, 6H), 1.11-0.89 (m, 9H). Method 1: RT = 3.29 min.; M + H = 369.3 |
| 218 | 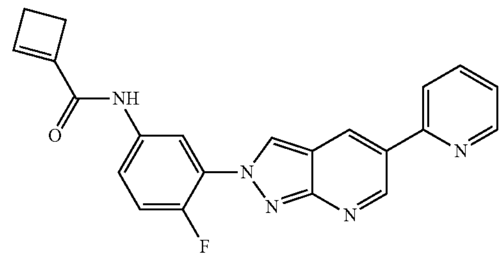 [SMILES: O=C(Nc1ccc(F)c(-n2cc3cc(-c4ccccn4)cnc3n2)c1)C1=CCC1] | ¹H NMR (400 MHz, DMSO-d₆) δ 10.13 (s, 1H), 9.48 (d, J = 2.3 Hz, 1H), 9.04 (d, J = 2.5 Hz, 1H), 8.95 (d, J = 2.3 Hz, 1H), 8.77-8.70 (m, 1H), 8.64-8.58 (m, 1H), 8.40 (d, J = 8.4 Hz, 1H), 7.58 (dd, J = 11.2, 9.1 Hz, 1H), 7.46-7.37 (m, 3H), 6.86 (d, J = 1.3 Hz, 1H), 2.77-2.72 (m, 2H), 2.48-2.42 (m, 2H). Method 1: RT = 2.80 min.; M + H = 386.1 |
| 219 | 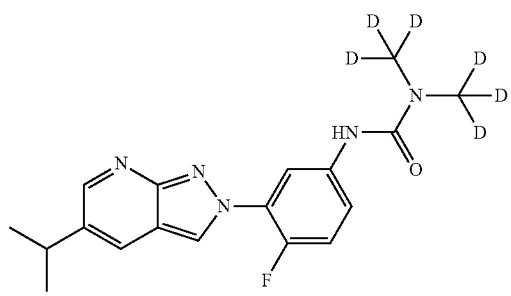 [SMILES: [2H]C([2H])([2H])N(C(=O)Nc1ccc(F)c(-n2cc3cc(C(C)C)cnc3n2)c1)C([2H])([2H])[2H]] | ¹H NMR (400 MHz, Chloroform-d) δ 8.70 (m, 1H), 8.51 (m, 1H), 7.96 (m, 1H), 7.90-7.81 (m, 2H), 7.27-7.19 (m, 1H), 6.73 (m, 1H), 3.08 (m, 1H), 1.43-1.28 (m, 6H). Method 2: RT = 0.90 min.; M + H = 348.3 |
| 220 | 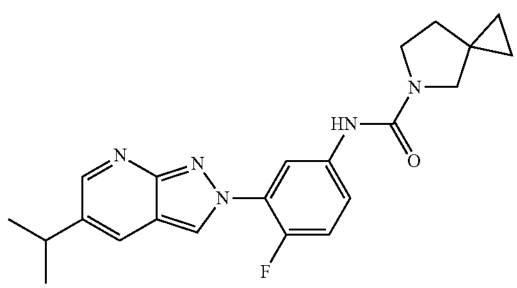 [SMILES: CC(C)c1cnc2nn(-c3cc(NC(=O)N4CCC5(CC5)C4)ccc3F)cc2c1] | ¹H NMR (400 MHz, Chloroform-d) δ 8.71 (m, 1H), 8.52 (m, 1H), 8.14-7.90 (m, 2H), 7.87 (m, 1H), 7.28-7.20 (m, 1H), 6.44 (m, 1H), 3.76-3.57 (m, 2H), 3.46-3.31 (m, 2H), 3.08 (m, 1H), 1.98-1.78 (m, 2H), 1.54-1.18 (m, 6H), 0.74-0.54 (m, 4H). Method 2: RT = 1.05 min.; M + H = 394.3 |
| 221 | 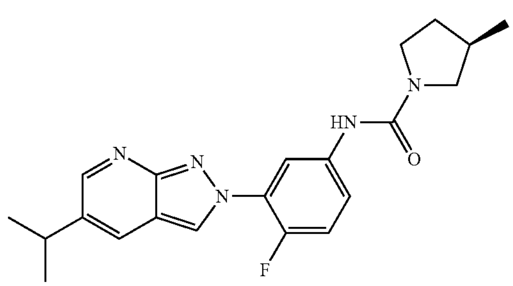 [SMILES: CC(C)c1cnc2nn(-c3cc(NC(=O)N4CC[C@@H](C)C4)ccc3F)cc2c1] | ¹H NMR (400 MHz, Chloroform-d) δ 8.71 (m, 1H), 8.49 (m, 1H), 8.15-7.89 (m, 2H), 7.89-7.84 (m, 1H), 7.24 (m, 1H), 6.50 (m, 1H), 3.63 (m, 2H), 3.50-3.38 (m, 1H), 3.16-2.93 (m, 2H), 2.46-2.04 (m, 2H), 1.68-1.56 (m, 1H), 1.51-1.20 (m, 6H), 1.12 (m, 3H). Method 2: RT = 1.02 min.; M + H = 382.3 |

TABLE 2-continued

| Cpd No. | Structure | ¹HNMR and HPLC retention time and/or MS |
|---|---|---|
| 222 | 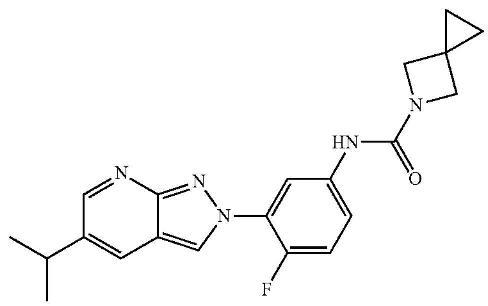 [SMILES: CC(C)c1cnc2nn(-c3cc(NC(=O)N4CC5(CC5)C4)ccc3F)cc2c1] | ¹H NMR (400 MHz, Chloroform-d) δ 8.70 (m, 1H), 8.51 (m, 1H), 7.99-7.91 (m, 2H), 7.87 (m, 1H), 7.28-7.21 (m, 1H), 6.52 (m, 1H), 4.15 (m, 4H), 3.08 (m, 1H), 1.53-1.18 (m, 6H), 0.70 (m, 4H). Method 2: RT = 1.01 min.; M + H = 380.3 |
| 223 | 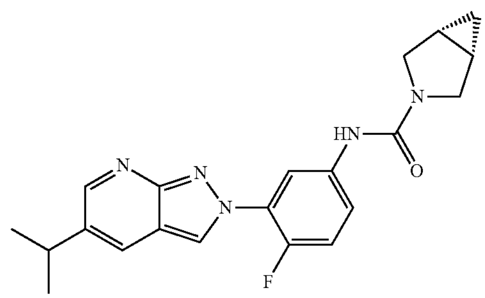 [SMILES: CC(C)c1cnc2nn(-c3cc(NC(=O)N4C[C@H]5C[C@H]5C4)ccc3F)cc2c1] | ¹H NMR (400 MHz, Chloroform-d) δ 8.71 (m, 1H), 8.51 (m, 1H), 8.13-7.80 (m, 3H), 7.27-7.19 (m, 1H), 6.38 (m, 1H), 3.71-3.51 (m, 4H), 3.08 (m, 1H), 1.61-1.31 (m, 6H), 1.24 (m, 2H), 0.81 (m, 1H), 0.31 (m, 1H). Method 2: RT = 0.99 min.; M + H = 380.3 |
| 224 | 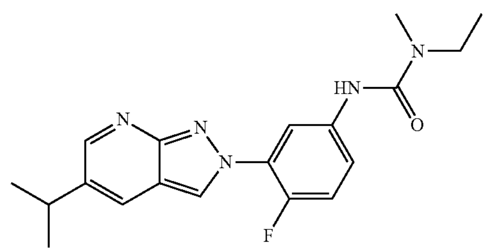 [SMILES: CCN(C)C(=O)Nc1ccc(F)c(-n2cc3cc(C(C)C)cnc3n2)c1] | ¹H NMR (400 MHz, Chloroform-d) δ 8.71 (m, 1H), 8.53 (m, 1H), 7.96 (m, 1H), 7.92-7.83 (m, 2H), 7.27-7.21 (m, 1H), 6.55 (m, 1H), 3.45 (m, 2H), 3.10 (m, 1H), 3.06-2.98 (m, 3H), 1.37 (m, 6H), 1.26-1.22 (m, 3H). Method 2: RT = 0.96 min.; M + H = 356.3 |
| 225 | 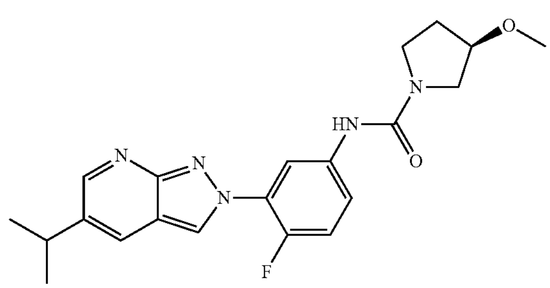 [SMILES: CO[C@@H]1CCN(C(=O)Nc2ccc(F)c(-n3cc4cc(C(C)C)cnc4n3)c2)C1] | ¹H NMR (400 MHz, Chloroform-d) δ 8.71 (m, 1H), 8.53-8.45 (m, 1H), 8.17-7.84 (m, 3H), 7.27-7.19 (m, 1H), 6.60 (m, 1H), 4.12-3.95 (m, 1H), 3.69-3.50 (m, 4H), 3.44-3.29 (m, 3H), 3.09 (m, 1H), 2.24-2.01 (m, 2H), 1.54-1.18 (m, 6H). Method 2: RT = 0.92 min.; M + H = 398.3 |
| 226 | 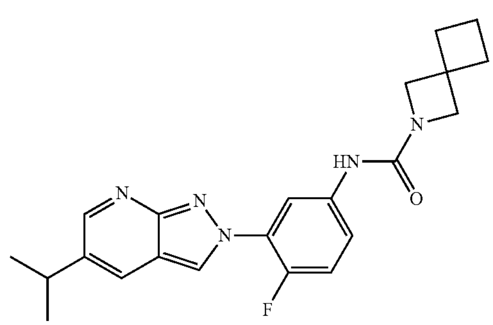 [SMILES: CC(C)c1cnc2nn(-c3cc(NC(=O)N4CC5(CCC5)C4)ccc3F)cc2c1] | ¹H NMR (400 MHz, Chloroform-d) δ 8.71 (m, 1H), 8.51 (m, 1H), 7.97-7.89 (m, 2H), 7.87 (m, 1H), 7.28-7.19 (m, 1H), 6.28 (m, 1H), 4.04 (m, 4H), 3.09 (m, 1H), 2.22 (m, 4H), 1.94-1.83 (m, 2H), 1.49-1.14 (m, 6H). Method 2: RT = 1.06 min.; M + H = 394.3 |

TABLE 2-continued

| Cpd No. | Structure | ¹HNMR and HPLC retention time and/or MS |
|---|---|---|
| 227 | 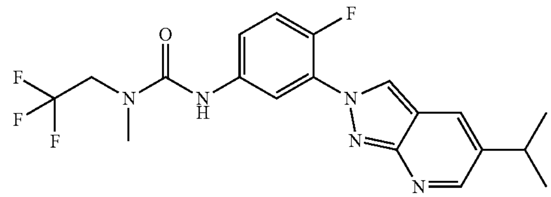 [SMILES: CC(C)c1cnc2nn(-c3cc(NC(=O)N(C)CC(F)(F)F)ccc3F)cc2c1] | ¹H NMR (400 MHz, Chloroform-d) δ 8.71 (m, 1H), 8.49 (m, 1H), 8.09 (m, 1H), 7.87 (m, 1H), 7.81 (m, 1H), 7.28-7.20 (m, 1H), 7.09 (m, 1H), 4.08 (m, 2H), 3.19 (m, 3H), 3.09 (m, 1H), 1.37 (m, 6H). Method 2: RT = 1.04 min.; M + H = 410.3 |
| 228 | 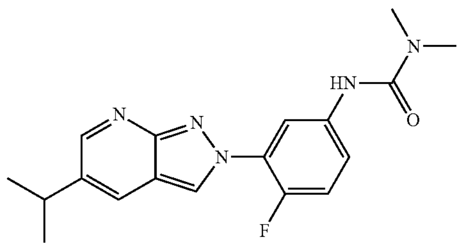 [SMILES: CC(C)c1cnc2nn(-c3cc(NC(=O)N(C)C)ccc3F)cc2c1] | ¹H NMR (400 MHz, Chloroform-d) δ 8.71 (m, 1H), 8.51 (m, 1H), 7.96 (m, 1H), 7.89-7.81 (m, 2H), 7.24 (m, 1H), 6.71 (m, 1H), 3.51 (m, 1H), 3.09-3.03 (m, 6H), 1.42-1.28 (m, 6H). Method 2: RT = 0.90 min.; M + H = 342.3 |
| 229 | 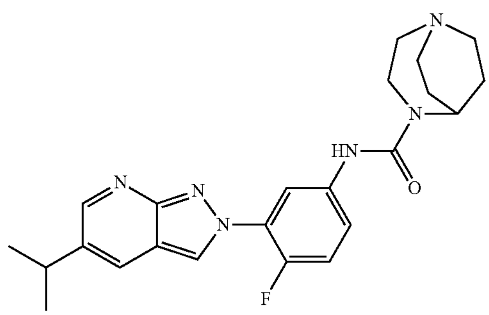 [SMILES: CC(C)c1cnc2nn(-c3cc(NC(=O)N4CCN5CCC4CC5)ccc3F)cc2c1] | ¹H NMR (400 MHz, Chloroform-d) δ 8.62 (m, 1H), 8.44 (m, 1H), 7.89 (m, 1H), 7.81-7.77 (m, 1H), 7.75 (m, 1H), 7.18-7.12 (m, 1H), 6.61 (m, 1H), 4.13 (m, 1H), 3.73-3.62 (m, 2H), 3.13-2.90 (m, 6H), 2.06-1.97 (m, 3H), 1.77-1.74 (m, 2H), 1.28 (m, 6H). Method 1: RT = 2.42 min.; M + H = 423.3 |
| 230 | 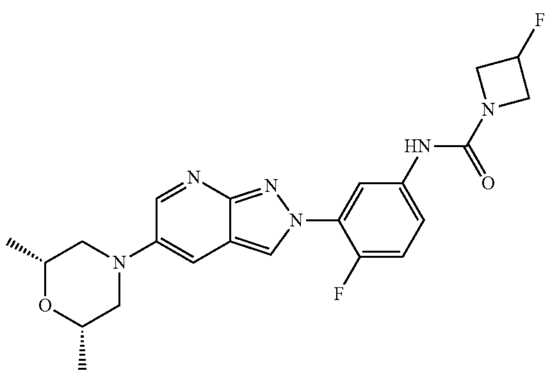 | ¹H NMR (400 MHz, DMSO) δ ppm 8.91 (s, 1 H), 8.73 (d, J = 2.76 Hz, 1 H), 8.58 (d, J = 2.64 Hz, 1 H), 8.18 (dd, J = 7.03, 2.64 Hz, 1 H), 7.57-7.68 (m, 1 H), 7.41 (dd, J = 11.29, 9.03 Hz, 1 H), 7.35 (d, J = 2.76 Hz, 1 H), 5.25-5.49 (m, 1 H), 4.23-4.36 (m, 2 H), 3.93-4.07 (m, 2 H), 3.69-3.84 (m, 2 H), 3.56 (br d, J = 10.92 Hz, 2 H), 2.24-2.32 (m, 2 H), 1.15 (d, J = 6.15 Hz, 6 H). Method 1: RT = 2.79 min.; M + H = 433.3 |
| 231 | 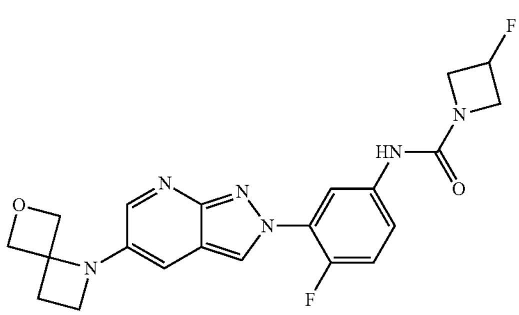 [SMILES: O=C(Nc1ccc(F)c(-n2cc3cc(N4CCC45COC5)cnc3n2)c1)N1CC(F)C1] | ¹H NMR (400 MHz, DMSO) δ ppm 8.94 (s, 1 H) 8.60,(d, J = 2.76 Hz, 1 H), 8.56 (d, J = 2.76 Hz, 1 H), 8.22 (dd, J = 7.09, 2.70 Hz, 1 H), 7.62-7.69 (m, 1 H), 7.44 (dd, J = 11.29, 9.16 Hz, 1 H), 7.18 (d, J = 2.76 Hz, 1 H), 5.30-5.51 (m, 1 H), 5.10 (d, J = 8.28 Hz, 2 H), 4.75 (d, J = 8.28 Hz, 2 H), 4.26-4.38 (m, 2 H), 3.96-4.09 (m, 2 H), 3.74 (t, J = 6.96 Hz, 2 H), 2.58 (br s, 2 H). Method 1: RT = 2.65 min.; M + H = 427.2 |

TABLE 2-continued

| Cpd No. | Structure | ¹HNMR and HPLC retention time and/or MS |
|---|---|---|
| 232 | 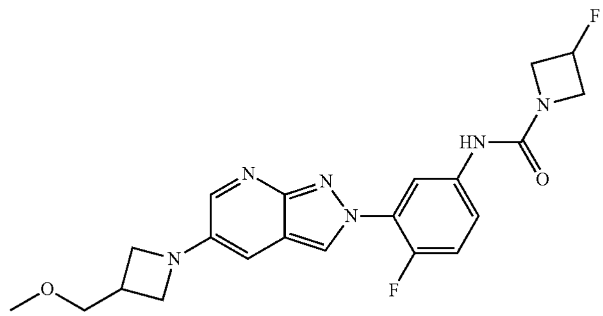 [SMILES: COCC1CN(c2cnc3nn(-c4cc(NC(=O)N5CC(F)C5)ccc4F)cc3c2)C1] | ¹H NMR (400 MHz, DMSO) δ ppm 8.94 (s, 1 H), 8.52 (d, J = 2.69 Hz, 1 H), 8.26 (d, J = 2.81 Hz, 1 H), 8.19 (dd, J = 7.03, 2.63 Hz, 1 H), 7.60-7.68 (m, 1 H), 7.42 (dd, J = 11.37, 9.17 Hz, 1 H), 6.88 (d, J = 2.69 Hz, 1 H), 5.28-5.50 (m, 1 H), 4.24-4.37 (m, 2 H), 4.02-4.08 (m, 1 H), 3.98 (t, J = 7.64 Hz, 3 H), 3.65 (dd, J = 7.15, 5.69 Hz, 2 H), 3.56 (d, J = 6.60 Hz, 2 H), 3.29 (s, 3 H), 2.96 (m, 1 H). Method 1: RT = 2.70 min.; M + H = 429.3 |
| 233 | 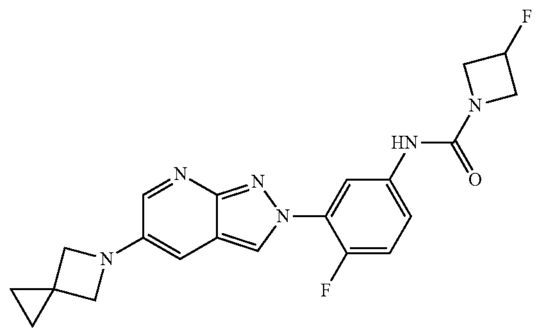 [SMILES: O=C(Nc1ccc(F)c(-n2cc3cc(N4CC5(CC5)C4)cnc3n2)c1)N1CC(F)C1] | ¹H NMR (400 MHz, DMSO) δ ppm 8.92 (s, 1 H), 8.52 (d, J = 2.76 Hz, 1 H), 8.28 (d, J = 2.76 Hz, 1 H), 8.19 (dd, J = 7.03, 2.64 Hz, 1 H), 7.59-7.67 (m, 1 H), 7.42 (dd, J = 11.36, 9.10 Hz, 1 H), 6.91 (d, J = 2.89 Hz, 1 H), 5.27-5.50 (m, 1 H), 4.23-4.38 (m, 2 H), 3.94-4.10 (m, 6 H), 0.68 (s, 4 H). Method 1: RT = 2.92 min.; M + H = 411.3 |
| 234 | 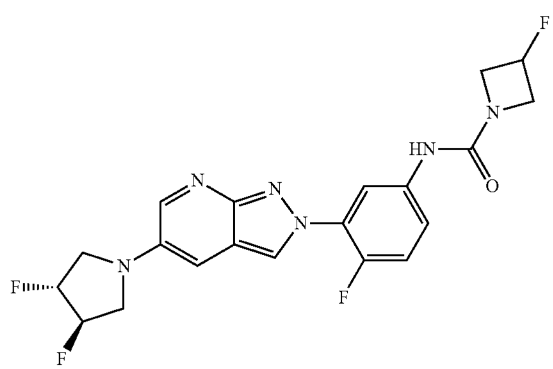 [SMILES: O=C(Nc1ccc(F)c(-n2cc3cc(N4C[C@@H](F)[C@H](F)C4)cnc3n2)c1)N1CC(F)C1] | ¹H NMR (400 MHz, DMSO) δ 8.88 (s, 1 H), 8.48-8.59 (m, 2 H), 8.17 (dd, J = 7.03, 2.64 Hz, 1 H), 7.54-7.67 (m, 1 H), 7.39 (dd, J = 11.36, 9.10 Hz, 1 H), 7.03 (d, J = 2.89 Hz, 1 H), 5.19-5.63 (m, 3 H), 4.19-4.40 (m, 2 H), 3.93-4.06 (m, 2 H), 3.57-3.87 (m, 4 H). Method 1: RT = 2.77 min.; M + H = 435.1 |
| 235 | 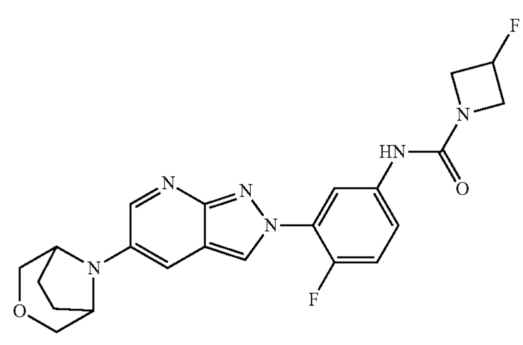 [SMILES: O=C(Nc1ccc(F)c(-n2cc3cc(N4C5CCC4COC5)cnc3n2)c1)N1CC(F)C1] | ¹H NMR (400 MHz, DMSO) δ 8.93-9.02 (m, H), 8.68 (d, J = 2.76 Hz, 1 H), 8.53 (d, J = 2.76 Hz, 1 H), 8.20 (dd, J = 7.03, 2.64 Hz, 1 H), 7.62-7.69 (m, 1 H), 7.43 (dd, J = 11.36, 9.10 Hz, 1 H), 7.35 (d, J = 2.76 Hz, 1 H), 5.28-5.51 (m, 1 H), 4.20-4.38 (m, 4 H), 3.94-4.14 (m, 2 H), 3.79 (d, J = 10.79 Hz, 2 H), 3.50 (br d, J = 10.67 Hz, 2 H), 1.88-2.01 (m, 4 H). Method 1: RT = 2.63 min.; M + H = 441.3 |

TABLE 2-continued

| Cpd No. | Structure | ¹HNMR and HPLC retention time and/or MS |
|---|---|---|
| 236 | 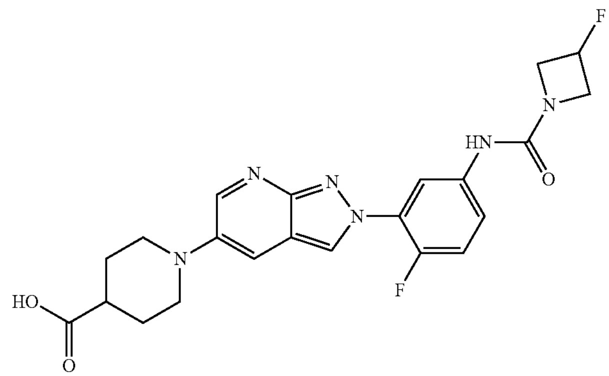 [SMILES: O=C(O)C1CCN(c2cnc3nn(-c4cc(NC(=O)N5CC(F)C5)ccc4F)cc3c2)CC1] | ¹H NMR (400 MHz, DMSO) δ 8.96 (s, 1 H), 8.69 (d, J = 2.69 Hz, 1 H), 8.59 (d, J = 2.57 Hz, 1 H), 8.19 (dd, J = 7.03, 2.63 Hz, 1 H), 7.61-7.70 (m, 1 H), 7.31-7.47 (m, 2 H), 5.27-5.50 (m, 1 H), 4.23-4.39 (m, 2 H), 3.93-4.08 (m, 2 H), 3.56 (br d, J = 11.98 Hz, 2 H), 2.74 (br t, J = 10.45 Hz, 2 H), 2.23-2.33 (m, 1 H), 1.94 (br d, J = 10.76 Hz, 2 H), 1.65-1.80 (m, 2 H). Method 1: RT = 2.55 min.; M + H = 457.3 |
| 237 | 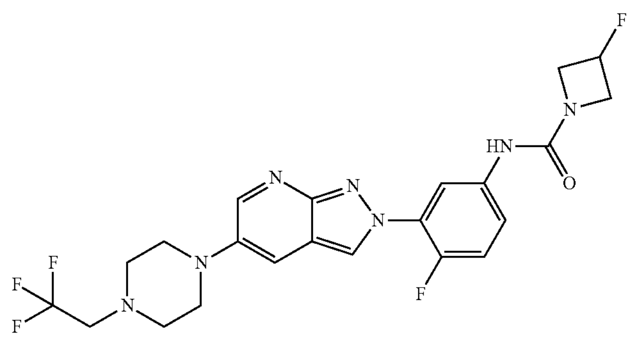 [SMILES: O=C(Nc1ccc(F)c(-n2cc3cc(N4CCN(CC(F)(F)F)CC4)cnc3n2)c1)N1CC(F)C1] | ¹H NMR (400 MHz, DMSO) δ 8.96 (s, 1 H), 8.72 (d, J = 2.76 Hz, 1 H), 8.62 (d, J = 2.76 Hz, 1 H), 8.20 (dd, J = 7.03, 2.76 Hz, 1 H), 7.59-7.72 (m, 1 H), 7.44 (t, J = 10.41 Hz, 1 H), 7.38 (s, 1 H), 5.26-5.52 (m, 1 H), 4.25-4.39 (m, 2 H), 3.96-4.10 (m, 2 H), 3.23-3.31 (m, 2 H), 3.12-3.21 (m, 4 H), 2.76-2.90 (m, 4 H). Method 1: RT = 2.88 min.; M + H = 496.4 |
| 238 | 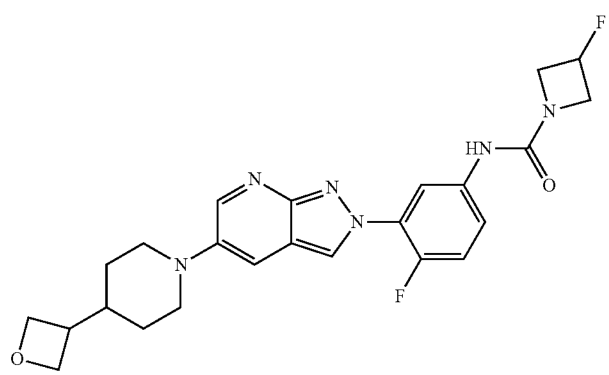 [SMILES: O=C(Nc1ccc(F)c(-n2cc3cc(N4CCC(C5COC5)CC4)cnc3n2)c1)N1CC(F)C1] | ¹H NMR (400 MHz, DMSO) δ 8.89-8.98 (m, 1 H), 8.71 (d, J = 2.89 Hz, 1 H), 8.62 (d, J = 2.64 Hz, 1 H), 8.19 (dd, J = 7.03, 2.64 Hz, 1 H), 7.58-7.70 (m, 1 H), 7.36-7.51 (m, 2 H), 5.22-5.54 (m, 1 H), 4.63 (dd, J = 7.84, 5.96 Hz, 2 H), 4.22-4.46 (m, 4 H), 3.92-4.11 (m, 2 H), 3.58-3.76 (m, 2 H), 2.60-2.84 (m, 3 H), 1.65-1.85 (m, 3 H), 1.17-1.32 (m, 2 H). Method 1: RT = 2.74 min.; M + H = 469.3 |
| 239 | 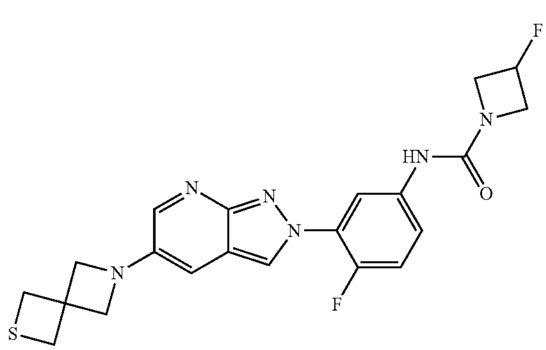 [SMILES: O=C(Nc1ccc(F)c(-n2cc3cc(N4CC5(CSC5)C4)cnc3n2)c1)N1CC(F)C1] | ¹H NMR (400 MHz, DMSO) δ 8.93 (s, 1 H) 8.54 (d, J = 2.76 Hz, 1 H), 8.26 (d, J = 2.76 Hz, 1 H), 8.19 (dd, J = 7.09, 2.70 Hz, 1 H), 7.60-7.67 (m, 1 H), 7.42 (dd, J = 11.36, 9.10 Hz, 1 H), 6.93 (d, J = 2.76 Hz, 1 H), 5.29-5.51 (m, 1 H), 4.23-4.38 (m, 2 H), 3.92-4.09 (m, 6 H), 3.41 (s, 4 H). Method 1: RT = 2.84 min.; M + H = 443.3 |

TABLE 2-continued

| Cpd No. | Structure | ¹HNMR and HPLC retention time and/or MS |
|---|---|---|
| 240 | 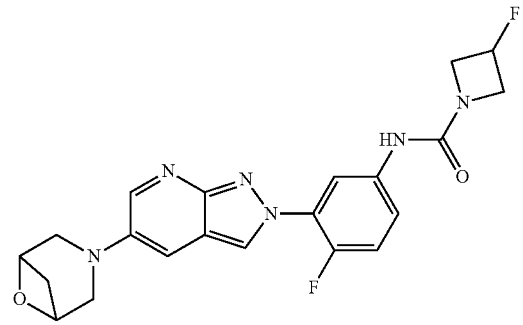 [SMILES: O=C(Nc1ccc(F)c(-n2cc3cc(N4CC5CC(C4)O5)cnc3n2)c1)N1CC(F)C1] | ¹H NMR (400 MHz, DMSO) δ 8.93 (s, 1 H), 8.68 (d, J = 2.89 Hz, 1 H), 8.53 (d, J = 2.76 Hz, 1 H), 8.20 (dd, J = 7.09, 2.70 Hz, 1 H), 7.59-7.65 (m, 1 H), 7.41 (dd, J = 11.36, 9.10 Hz, 1 H), 7.11 (d, J = 3.01 Hz, 1 H), 5.27-5.48 (m, 1 H), 4.73 (d, J = 6.27 Hz, 2 H) 4.23-4.36 (m, 2 H), 3.93-4.06 (m, 2 H), 3.70 (d, J = 11.29 Hz, 2 H) 3.48 (br d, J = 10.92 Hz, 2 H), 3.08-3.16 (m, 1 H), 1.99 (d, J = 8.53 Hz, 1 H). Method 1: RT = 2.52 min.; M + H = 427.3 |
| 241 | 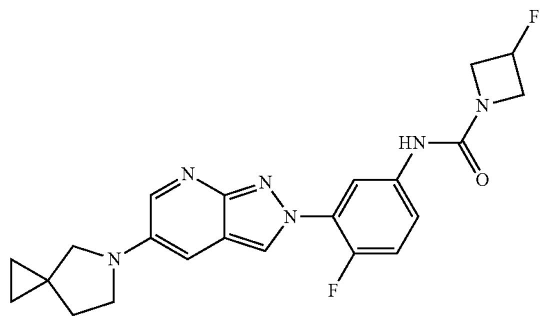 [SMILES: O=C(Nc1ccc(F)c(-n2cc3cc(N4CCC5(CC5)C4)cnc3n2)c1)N1CC(F)C1] | ¹H NMR (400 MHz, DMSO-d6) δ 8.91 (s, 1 H), 8.49 (dd, J = 7.09, 2.82 Hz, 2 H), 8.20 (dd, J = 7.03, 2.64 Hz, 1 H), 7.60-7.67 (m, 1 H), 7.42 (dd, J = 11.48, 9.10 Hz, 1 H), 6.88 (d, J = 2.89 Hz, 1 H), 5.28-5.50 (m, 1 H), 4.24-4.39 (m, 2 H), 3.97-4.08 (m, 2 H), 3.51 (t, J = 6.78 Hz, 2 H), 3.30 (s, 2 H), 1.96 (t, J = 6.78 Hz, 2 H), 0.60-0.71 (m, 4 H). Method 1: RT = 3.16 min.; M + H = 425.3 |
| 242 | 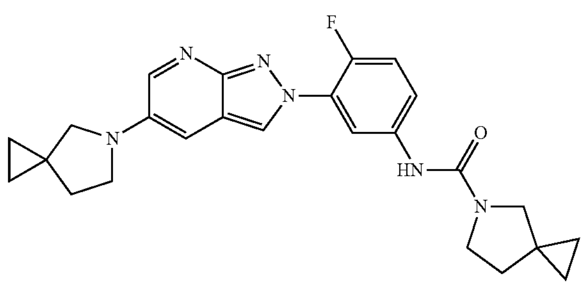 [SMILES: O=C(Nc1ccc(F)c(-n2cc3cc(N4CCC5(CC5)C4)cnc3n2)c1)N1CCC2(CC2)C1] | ¹H NMR (400 MHz, DMSO) δ 8.41-8.52 (m, 3 H), 8.23 (dd, J = 7.09, 2.70 Hz, 1 H), 7.60-7.69 (m, 1 H), 7.38 (dd, J = 11.42, 9.16 Hz, 1 H), 6.86 (d, J = 2.89 Hz, 1 H), 3.52 (dt, J = 15.34, 6.89 Hz, 3 H), 3.28 (s, 5 H), 1.95 (t, J = 6.78 Hz, 2 H), 1.81 (t, J = 6.78 Hz, 2 H), 0.52-0.71 (m, 8 H). Method 1: RT = 3.26 min.; M + H = 447.3 |
| 243 | 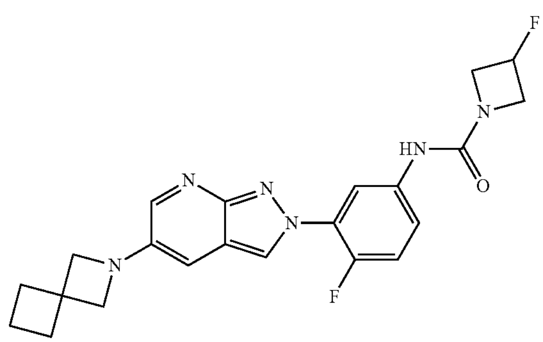 [SMILES: O=C(Nc1ccc(F)c(-n2cc3cc(N4CC5(CCC5)C4)cnc3n2)c1)N1CC(F)C1] | ¹H NMR (400 MHz, DMSO) δ 8.89 (s, 1 H), 8.50 (d, J = 2.76 Hz, 1 H), 8.22 (s, 1 H), 8.16 (d, J = 6.68 Hz, 1 H), 7.59-7.64 (m, 1 H), 7.40 (dd, J = 11.36, 9.10 Hz, 1 H), 6.85 (d, J = 2.76 Hz, 1 H), 5.25-5.49 (m, 1 H), 4.14-4.36 (m, 2 H), 3.93-4.05 (m, 2 H), 3.86 (s, 4 H), 2.18 (t, J = 7.59 Hz, 4 H), 1.82 (quin, J = 7.53 Hz, 2 H). Method 1: RT = 3.06 min.; M + H = 425.3 |
| 244 | 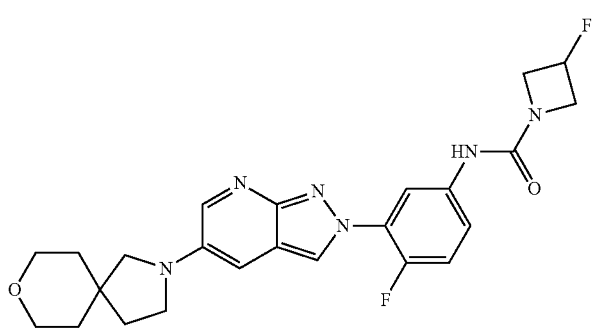 [SMILES: O=C(Nc1ccc(F)c(-n2cc3cc(N4CCC5(CCOCC5)C4)cnc3n2)c1)N1CC(F)C1] | ¹H NMR (400 MHz, DMSO) δ 8.92 (s, 1 H), 8.49 (dd, J = 9.47, 2.82 Hz, 2 H), 8.20 (dd, J = 7.03, 2.64 Hz, 1 H), 7.60-7.67 (m, 1 H), 7.41 (dd, J = 11.36, 9.10 Hz, 1 H), 6.88 (d, J = 2.89 Hz, 1 H), 5.27-5.50 (m, 1 H), 4.24-4.37 (m, 2 H), 3.94-4.08 (m, 2 H), 3.55-3.69 (m, 4 H), 3.41-3.46 (m, 2 H), 3.28 (s, 2 H), 1.92 (t, J = 6.96 Hz, 2 H), 1.46-1.63 (m, 4 H). Method 1: RT = 2.86 min.; M + H = 469.3 |

TABLE 2-continued

| Cpd No. | Structure | ¹HNMR and HPLC retention time and/or MS |
|---|---|---|
| 245 | 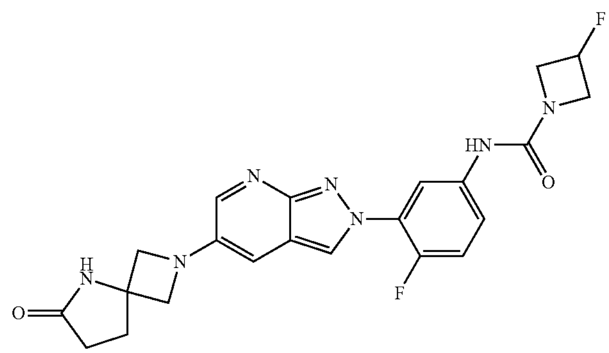 [SMILES: O=C1CCC2(CN(c3cnc4nn(-c5cc(NC(=O)N6CC(F)C6)ccc5F)cc4c3)C2)N1] | ¹H NMR (400 MHz, DMSO) δ 8.91 (s, 1 H), 8.55 (d, J = 2.64 Hz, 1 H), 8.29 (d, J = 2.89 Hz, 2 H), 8.19 (dd, J = 7.03, 2.76 Hz, 1 H), 7.60-7.66 (m, 1 H), 7.42 (dd, J = 11.29, 9.16 Hz, 1 H), 6.98 (d, J = 2.76 Hz, 1 H), 5.27-5.49 (m, 1 H), 4.23-4.36 (m, 2 H), 3.94-4.09 (m, 4 H), 3.86 (d, J = 7.78 Hz, 2 H), 2.38 (br d, J = 7.78 Hz, 2 H), 2.21-2.28 (m, 2 H). Method 1: RT = 2.41 min.; M + H = 454.3 |
| 246 | 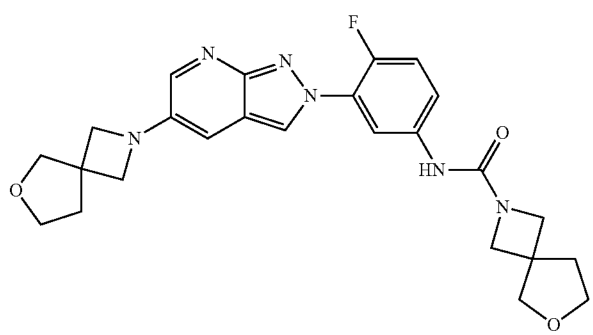 [SMILES: O=C(Nc1ccc(F)c(-n2cc3cc(N4CC5(CCOC5)C4)cnc3n2)c1)N1CC2(CCOC2)C1] | ¹H NMR (400 MHz, DMSO-d6) δ 8.78 (s, 1 H), 8.53 (d, J = 2.76 Hz, 1 H), 8.28 (d, J = 2.76 Hz, 1 H), 8.21 (dd, J = 7.15, 2.64 Hz, 1 H), 7.60-7.71 (m, 1 H), 7.41 (dd, J = 11.36, 9.10 Hz, 1 H), 6.94 (d, J = 2.76 Hz, 1 H), 3.93 (d, J = 12.05 Hz, 8 H), 3.84 (s, 2 H), 3.67-3.80 (m, 6 H) 2.09-2.21 (m, 4 H). Method 1: RT = 2.64 min.; M + H = 479.4 |
| 247 | 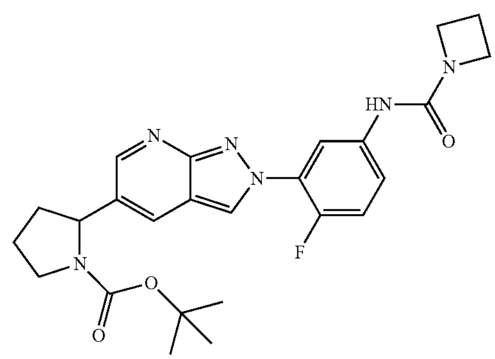 [SMILES: CC(C)(C)OC(=O)N1CCCC1c1cnc2nn(-c3cc(NC(=O)N4CCC4)ccc3F)cc2c1] | ¹H NMR (400 MHz, Methanol-d4) δ 8.83-8.71 (m, 1H), 8.64 (d, J = 4.8 Hz, 1H), 8.12 (dd, J = 6.8, 2.7 Hz, 1H), 7.65 (dt, J = 9.3, 3.6 Hz, 1H), 7.35 (dd, J = 10.9, 9.1 Hz, 1H), 7.09-6.97 (m, 1H), 5.32-5.14 (m, 1H), 4.17-4.01 (m, 4H), 3.83-3.56 (m, 2H), 2.63-2.44 (m, 1H), 2.39-2.25 (m, 2H), 2.09-1.93 (m, 3H), 1.47 (s, 3H), 1.07 (s, 6H). Method 2: RT = 0.93 min.; M + H = 481.3 |
| 248 | 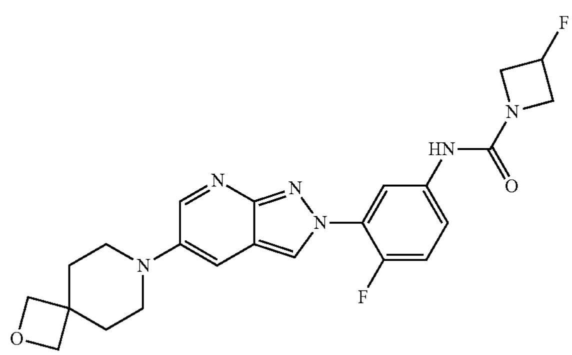 [SMILES: O=C(Nc1ccc(F)c(-n2cc3cc(N4CCC5(CC4)COC5)cnc3n2)c1)N1CC(F)C1] | ¹H NMR (400 MHz, DMSO) δ 8.95 (s, 1 H) 8.70 (d, J = 2.76 Hz, 1 H), 8.60 (d, J = 2.76 Hz, 1 H), 8.19 (dd, J = 7.09, 2.70 Hz, 1 H), 7.61-7.69 (m, 1 H), 7.44 (dd, J = 11.23, 9.10 Hz, 1 H), 7.37 (d, J = 2.76 Hz, 1 H), 5.27-5.51 (m, 1 H), 4.25-4.40 (m, 6 H), 3.96-4.09 (m, 2 H), 3.02-3.10 (m, 4 H), 1.91-2.00 (m, 4 H). Method 1: RT = 2.65 min.; M + H = 455.3 |

TABLE 2-continued

| Cpd No. | Structure | ¹HNMR and HPLC retention time and/or MS |
|---|---|---|
| 249 | 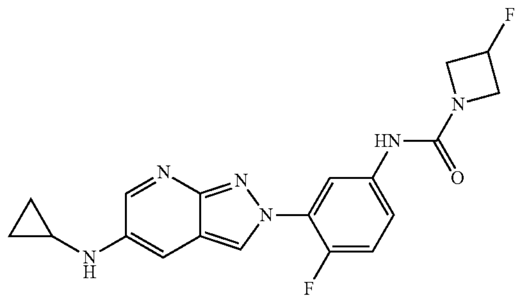 [SMILES: O=C(Nc1ccc(F)c(-n2cc3cc(NC4CC4)cnc3n2)c1)N1CC(F)C1] | ¹H NMR (400 MHz, DMSO-d6) δ 8.93 (s, 1 H), 8.48 (d, J = 2.89 Hz, 1 H), 8.29 (d, J = 2.76 Hz, 1 H), 8.17 (dd, J = 7.15, 2.64 Hz, 1 H), 7.59-7.66 (m, 1 H), 7.41 (dd, J = 11.42, 9.16 Hz, 1 H), 7.09 (d, J = 2.64 Hz, 1 H), 6.47 (s, 1 H), 5.28-5.50 (m, 1 H), 4.24-4.38 (m, 2 H), 3.94-4.08 (m, 2 H), 2.37 (br s, 1 H), 0.70-0.77 (m, 2 H), 0.39-0.47 (m, 2 H). Method 1: RT = 2.78 min.; M + H = 385.1 |
| 250 | 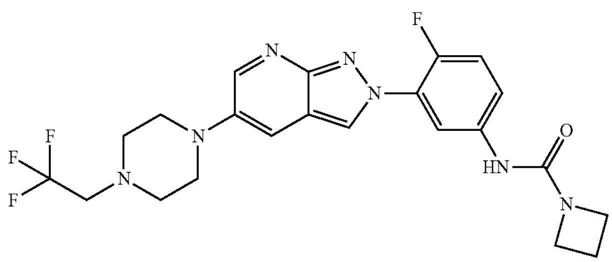 [SMILES: O=C(Nc1ccc(F)c(-n2cc3cc(N4CCN(CC(F)(F)F)CC4)cnc3n2)c1)N1CCC1] | ¹H NMR (400 MHz, DMSO) δ 8.66-8.73 (m, 2 H), 8.60 (d, J = 2.76 Hz, 1 H), 8.20 (dd, J = 7.03, 2.64 Hz, 1 H), 7.62-7.69 (m, 1 H), 7.35-7.45 (m, 2 H), 3.96 (t, J = 7.53 Hz, 4 H), 3.22-3.30 (m, 2 H), 3.11-3.19 (m, 4 H), 2.78-2.86 (m, 4 H), 2.19 (quin, J = 7.56 Hz, 2 H). Method 1: RT = 2.95 min.; M + H = 478.1 |
| 251 | 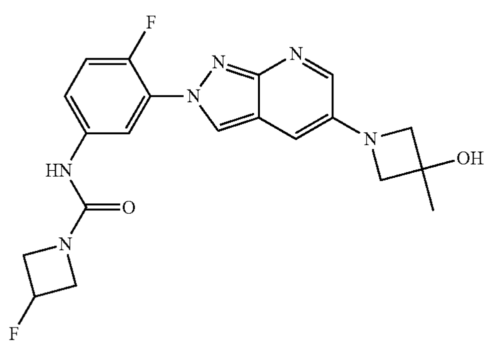 [SMILES: CC1(O)CN(c2cnc3nn(-c4cc(NC(=O)N5CC(F)C5)ccc4F)cc3c2)C1] | ¹H NMR (400 MHz, DMSO) δ 8.87-8.99 (m, 1 H), 8.52 (d, J = 2.51 Hz, 1 H), 8.28 (d, J = 2.64 Hz, 1 H), 8.20 (dd, J = 6.96, 2.45 Hz, 1 H), 7.64 (dt, J = 8.72, 3.36 Hz, 1 H), 7.42 (dd, J = 11.17, 9.29 Hz, 1 H), 6.92 (d, J = 2.64 Hz, 1 H), 5.28-5.69 (m, 2 H), 4.22-4.42 (m, 2 H), 3.94-4.10 (m, 2 H), 3.87 (d, J = 7.40 Hz, 2 H), 3.69 (d, J = 7.28 Hz, 2 H), 1.49 (s, 3 H). Method 1: RT = 2.53 min.; M + H = 415.3 |
| 252 | 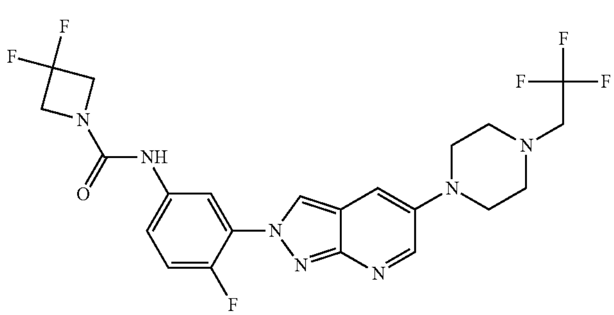 [SMILES: O=C(Nc1ccc(F)c(-n2cc3cc(N4CCN(CC(F)(F)F)CC4)cnc3n2)c1)N1CC(F)(F)C1] | ¹H NMR (400 MHz, DMSO) δ 9.20 (s, 1 H), 8.72 (d, J = 2.76 Hz, 1 H), 8.62 (d, J = 2.64 Hz, 1 H), 8.30 (d, J = 2.38 Hz, 1 H), 7.59-7.68 (m, 1 H), 7.46 (dd, J = 11.23, 9.22 Hz, 1 H), 7.38 (d, J = 2.13 Hz, 1 H), 4.40 (t, J = 12.74 Hz, 4 H), 3.21-3.27 (m, 2 H), 3.12-3.18 (m, 4 H), 2.78-2.86 (m, 4 H). Method 1: RT = 2.99 min.; M + H = 514.3 |

TABLE 2-continued

| Cpd No. | Structure | ¹HNMR and HPLC retention time and/or MS |
|---|---|---|
| 253 | 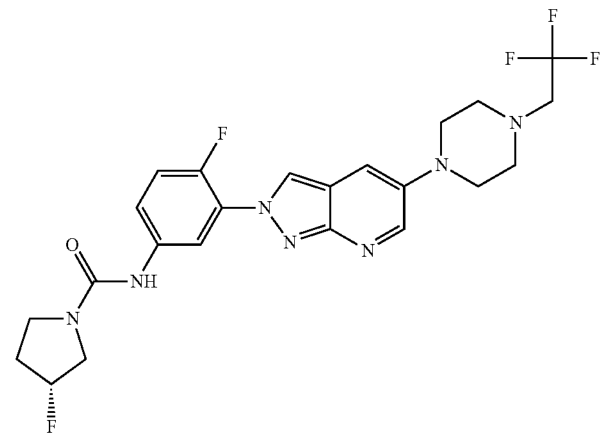 [SMILES: O=C(Nc1ccc(F)c(-n2cc3cc(N4CCN(CC(F)(F)F)CC4)cnc3n2)c1)N1CC[C@@H](F)C1] | ¹H NMR (400 MHz, DMSO) δ 8.72 (d, J = 2.76 Hz, 1 H), 8.54-8.64 (m, 2 H), 8.22 (dd, J = 7.03, 2.64 Hz, 1 H), 7.68 (dt, J = 8.97, 3.48 Hz, 1 H), 7.33-7.49 (m, 2 H), 5.25-5.49 (m, 1 H), 3.38-3.79 (m, 6 H), 3.16 (br d, J = 4.89 Hz, 4 H), 2.83 (br d, J = 4.27 Hz, 4 H), 2.00-2.26 (m, 2 H). Method 1: RT = 2.95 min.; M + H = 510.3 |
| 254 | 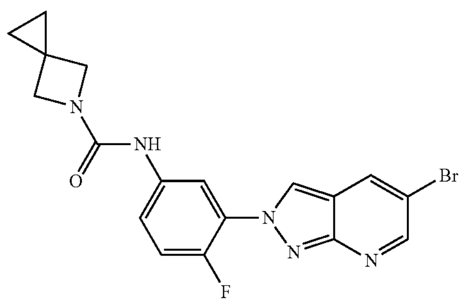 [SMILES: O=C(Nc1ccc(F)c(-n2cc3cc(Br)cnc3n2)c1)N1CC2(CC2)C1] | ¹H NMR (400 MHz, DMSO-d6), δ 8.90 (d, J = 2.45 Hz, 1 H), 8.85 (s, 1 H), 8.74-8.78 (m, 1 H), 8.61-8.65 (m, 1 H), 8.26 (dd, J = 7.09, 2.69 Hz, 1 H), 7.69-7.76 (m, 1 H), 7.47 (dd, J = 11.25, 9.29 Hz, 1 H), 4.05 (s, 4 H), 0.66 (s, 4 H). Method 1: RT = 2.95 min.; M + H = 416.0, 418.0 |
| 255 | 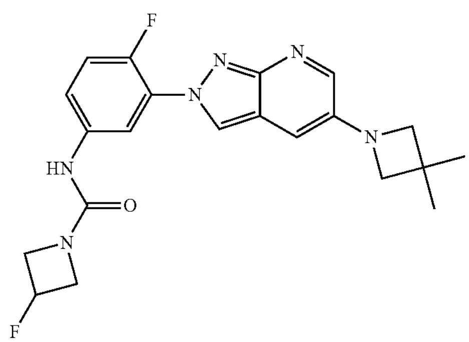 [SMILES: CC1(C)CN(c2cnc3nn(-c4cc(NC(=O)N5CC(F)C5)ccc4F)cc3c2)C1] | ¹H NMR (500 MHz, DMSO-d6) δ 8.91 (s, 1H), 8.52 (d, J = 2.7 Hz, 1H), 8.26 (d, J = 2.8 Hz, 1H), 8.20 (dd, J = 7.0, 2.7 Hz, 1H), 7.65 (ddd, J = 9.1, 4.1, 2.7 Hz, 1H), 7.43 (dd, J = 11.4, 9.1 Hz, 1H), 6.87 (d, J = 2.8 Hz, 1H), 5.51-5.26 (m, 1H), 4.39-4.23 (m, 2H), 4.09-3.94 (m, 2H), 3.65 (s, 4H), 1.32 (s, 6H). Method 1: RT = 3.08 min.; M + H = 413.2 |
| 256 | trans - racemic | ¹H NMR (500 MHz, DMSO-d6) δ 10.74 (s, 1H), 9.48 (d, J = 2.3 Hz, 1H), 9.03 (d, J = 2.4 Hz, 1H), 8.94 (d, J = 2.3 Hz, 1H), 8.74 (ddd, J = 4.8, 1.9, 0.9 Hz, 1H), 8.39 (dd, J = 7.0, 2.7 Hz, 1H), 8.21-8.10 (m, 1H), 7.96 (td, J = 7.7, 1.8 Hz, 1H), 7.75-7.62 (m, 1H), 7.57 (dd, J = 11.1, 9.0 Hz, 1H), 7.42 (ddd, J = 7.5, 4.8, 1.1 Hz, 1H), 4.92 (dddd, J = 64.6, 6.3, 3.3, 1.6 Hz, 1H), 2.41-2.24 (m, 1H), 1.57 (dddd, J = 22.4, 10.3, 6.6, 3.3 Hz, 1H), 1.28 (dq, J = 13.0, 6.5 Hz, 1H). Method 1: RT = 2.79 min.; M + H = 392.1 |

TABLE 2-continued

| Cpd No. | Structure | ¹HNMR and HPLC retention time and/or MS |
|---|---|---|
| 257 | 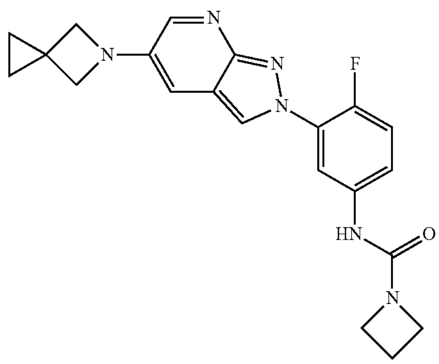 [SMILES: O=C(Nc1ccc(F)c(-n2cc3cc(N4CC5(CC5)C4)cnc3n2)c1)N1CCC1] | ¹H NMR (400 MHz, DMSO) δ 8.69 (s, 1 H), 8.52 (d, J = 2.63 Hz, 1 H), 8.28 (d, J = 2.76 Hz, 1 H), 8.20 (dd, J = 7.03, 2.63 Hz, 1 H), 7.62-7.69 (m, 1 H), 7.40 (dd, J = 11.29, 9.16 Hz, 1 H), 6.91 (d, J = 2.76 Hz, 1 H), 4.01 (s, 4 H), 3.97 (t, J = 7.53 Hz, 4 H), 2.19 (quin, J = 7.56 Hz, 2 H), 0.68 (s, 4 H). Method 1: RT = 2.90 min.; M + H = 393.2 |
| 258 | 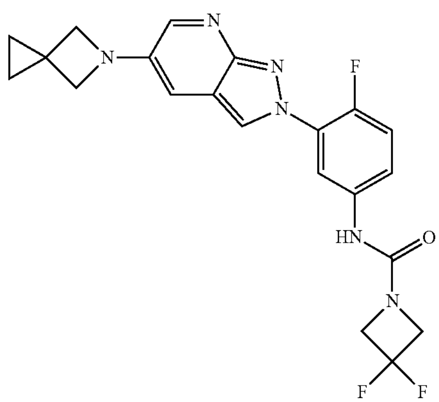 [SMILES: O=C(Nc1ccc(F)c(-n2cc3cc(N4CC5(CC5)C4)cnc3n2)c1)N1CC(F)(F)C1] | ¹H NMR (400 MHz, DMSO) δ 9.21 (br s, 1 H), 8.54 (s, 1 H), 8.28 (d, J = 1.63 Hz, 1 H), 8.20 (br d, J = 6.65 Hz, 1 H), 7.63 (br d, J = 8.41 Hz, 1 H), 7.45 (t, J = 9.91 Hz, 1 H), 6.92 (d, J = 2.01 Hz, 1 H), 4.40 (t, J = 12.86 Hz, 4 H), 4.02 (s, 4 H), 0.68 (s, 4 H). Method 1: RT = 3.03 min.; M + H = 429.2 |
| 259 | 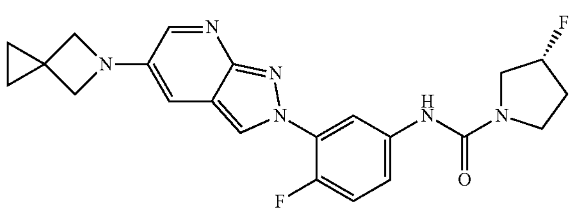 [SMILES: O=C(Nc1ccc(F)c(-n2cc3cc(N4CC5(CC5)C4)cnc3n2)c1)N1CC[C@@H](F)C1] | ¹H NMR (400 MHz, DMSO) δ 8.60 (s, 1 H), 8.54 (br s, 1 H), 8.28 (d, J = 2.76 Hz, 1 H), 8.22 (dd, J = 7.03, 2.76 Hz, 1 H), 7.64-7.72 (m, 1 H), 7.41 (dd, J = 11.17, 9.16 Hz, 1 H), 6.92 (d, J = 2.76 Hz, 1 H), 5.27-5.48 (m, 1 H), 4.02 (s, 4 H), 3.57-3.77 (m, 4 H), 2.03-2.24 (m, 2 H), 0.68 (s, 4 H). Method 1: RT = 2.93 min.; M + H = 425.2 |
| 260 | 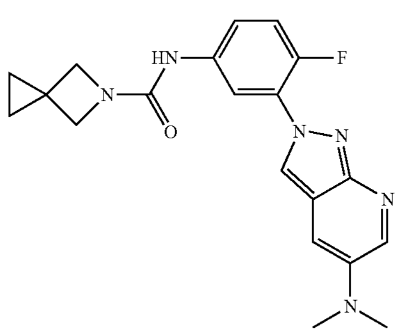 [SMILES: CN(C)c1cnc2nn(-c3cc(NC(=O)N4CC5(CC5)C4)ccc3F)cc2c1] | ¹H NMR (400 MHz, DMSO-d6) δ 8.81 (s, 1 H), 8.70 (d, J = 2.93 Hz, 1 H), 8.55 (d, J = 2.69 Hz, 1 H), 8.22 (dd, J = 7.09, 2.69 Hz, 1 H), 7.63-7.72 (m, 1 H), 7.42 (dd, J = 11.37, 9.17 Hz, 1 H), 7.15 (d, J = 2.93 Hz, 1 H), 3.97-4.14 (m, 4 H), 2.95 (s, 6 H), 0.65 (s, 4 H). Method 1: RT = 2.87 min.; M + H = 381.0 |

TABLE 2-continued

| Cpd No. | Structure | ¹HNMR and HPLC retention time and/or MS |
|---|---|---|
| 261 | 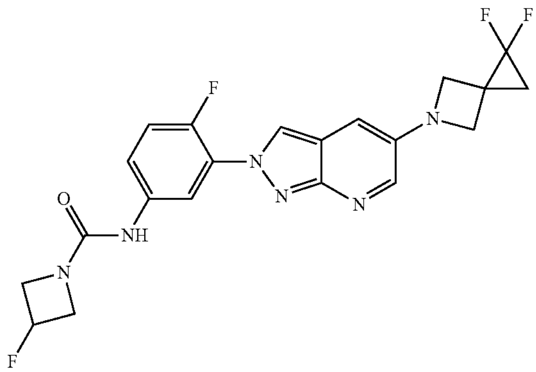 [SMILES: O=C(Nc1ccc(F)c(-n2cc3cc(N4CC5(C4)CC5(F)F)cnc3n2)c1)N1CC(F)C1] | ¹H NMR (400 MHz, DMSO) δ 8.94 (s, 1 H), 8.56 (dd, J = 8.28, 2.38 Hz, 2 H), 8.21 (dd, J = 6.96, 2.57 Hz, 1 H), 7.64 (dt, J = 8.91, 3.26 Hz, 1 H), 7.43 (dd, J = 10.79, 9.54 Hz, 1 H), 7.08 (d, J = 2.51 Hz, 1 H), 5.27-5.50 (m, 1 H), 4.24-4.39 (m, 2 H), 3.92-4.11 (m, 2 H), 3.83 (br t, J = 13.30 Hz, 2 H), 3.59 (br t, J = 7.15 Hz, 2 H), 2.60 (br d, J = 7.53 Hz, 2 H), Method 1: RT = 2.67 min.; M + H = 447.2 |
| 262 | 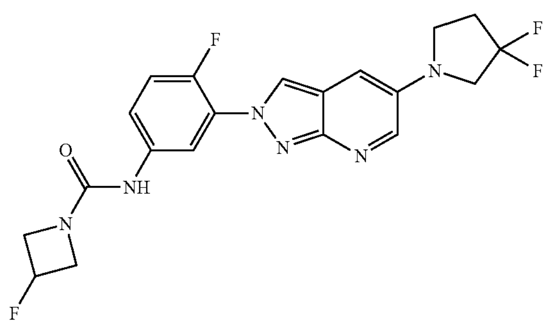 [SMILES: O=C(Nc1ccc(F)c(-n2cc3cc(N4CCC(F)(F)C4)cnc3n2)c1)N1CC(F)C1] | ¹H NMR (400 MHz, DMSO) δ 8.95 (s, 1 H), 8.58 (d, J = 2.76 Hz, 1 H), 8.35 (d, J = 2.76 Hz, 1 H), 8.20 (dd, J = 7.03, 2.64 Hz, 1 H), 7.60-7.68 (m, 1 H), 7.44 (dd, J = 11.36, 9.10 Hz, 1 H), 7.05 (d, J = 2.76 Hz, 1 H), 5.28-5.51 (m, 1 H), 4.24-4.38 (m, 2 H), 4.10-4.17 (m, 2 H), 3.95-4.10 (m, 4 H), 1.79 (t, J = 8.91 Hz, 2 H). Method 1: RT = 2.84 min.; M + H = 434.9 |
| 263 | 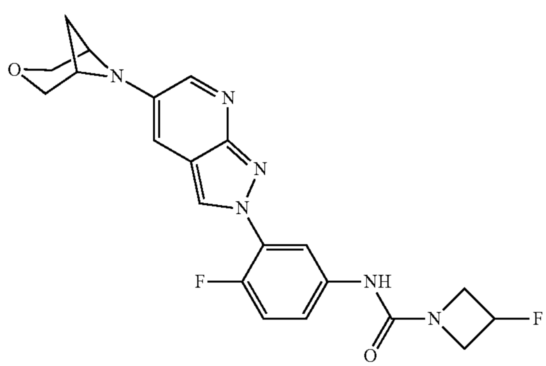 [SMILES: O=C(Nc1ccc(F)c(-n2cc3cc(N4C5COCC4C5)cnc3n2)c1)N1CC(F)C1] | ¹H NMR (400 MHz, DMSO) δ 8.96 (s, 1 H), 8.53 (d, J = 1.88 Hz, 1 H), 8.37 (d, J = 1.88 Hz, 1 H), 8.19 (dd, J = 6.96, 2.45 Hz, 1 H), 7.62-7.69 (m, 1 H), 7.39-7.50 (m, 1 H), 7.14 (d, J = 2.01 Hz, 1 H), 5.28-5.52 (m, 1 H), 4.41 (br d, J = 6.02 Hz, 2 H), 4.26-4.38 (m, 2 H), 4.21 (br d, J = 10.92 Hz, 2 H), 3.96-4.10 (m, 2 H), 3.70 (br d, J = 10.92 Hz, 2 H), 2.72-2.76 (m, 1 H), 1.88 (d, J = 8.03 Hz, 1 H). Method 1: RT = 2.49 min.; M + H = 427.3 |
| 264 | 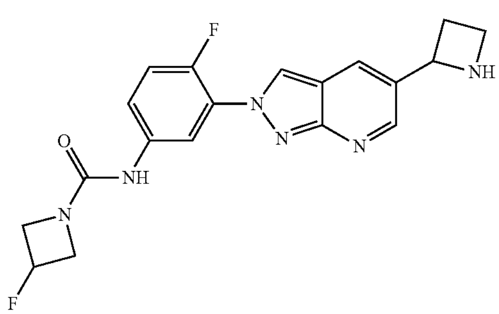 [SMILES: O=C(Nc1ccc(F)c(-n2cc3cc(C4CCN4)cnc3n2)c1)N1CC(F)C1] | ¹H NMR (400 MHz, DMSO-d6) δ 9.38 (s, 1H), 9.07-8.96 (m, 2H), 8.84 (d, J = 4.3 Hz, 1H), 8.30 (dd, J = 7.0, 2.7 Hz, 1H), 7.72-7.62 (m, 1H), 7.52 (dd, J = 11.2, 9.1 Hz, 1H), 7.33 (dd, J = 4.4, 1.2 Hz, 1H), 6.04 (s, 1H), 5.41 (dtt, J = 57.4, 6.1, 3.1 Hz, 1H), 4.40-4.25 (m, 2H), 4.27-4.16 (m, 1H), 4.10-3.94 (m, 2H), 3.90-3.77 (m, 1H), 3.06-2.94 (m, 1H), 2.86 (dtd, J = 11.7, 8.7, 4.4 Hz, 1H). Method 1: RT = 1.69 min.; M + H = 385.2 |

TABLE 2-continued

| Cpd No. | Structure | ¹HNMR and HPLC retention time and/or MS |
|---|---|---|
| 265 | 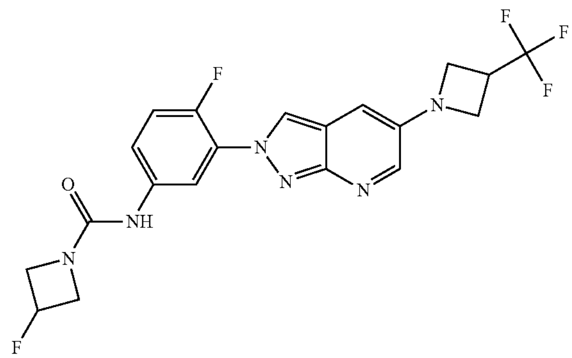 [SMILES: O=C(Nc1ccc(F)c(-n2cc3cc(N4CC(C(F)(F)F)C4)cnc3n2)c1)N1CC(F)C1] | ¹H NMR (400 MHz, DMSO) δ 8.93 (s, 1 H), 8.58 (d, J = 2.76 Hz 1 H) 8.32 (d, J = 2.76 Hz, 1 H), 8.20 (dd, J = 7.03, 2.64 Hz, 1 H), 7.65 (dd, J = 7.34, 4.58 Hz, 1 H), 7.44 (dd, J = 11.17, 9.16 Hz, 1 H), 7.03 (d, J = 2.89 Hz, 1 H), 5.29-5.51 (m, 1 H), 4.24-4.38 (m, 2 H), 4.18 (t, J = 8.34 Hz, 2 H), 3.95-4.10 (m, 4 H), 3.65-3.85 (m, 1 H). Method 1: RT = 2.86 min.; M + H = 453.1 |
| 266 | 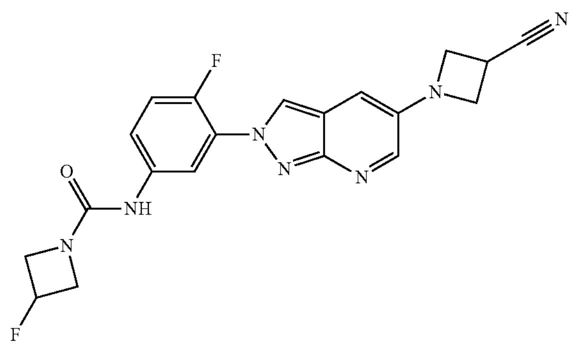 [SMILES: N#CC1CN(c2cnc3nn(-c4cc(NC(=O)N5CC(F)C5)ccc4F)cc3c2)C1] | ¹H NMR (400 MHz, DMSO) δ 8.93 (s, 1 H), 8.60 (d, J = 2.76 Hz, 1 H), 8.31 (d, J = 2.76 Hz, 1 H), 8.20 (dd, J = 6.96, 2.57 Hz, 1 H), 7.60-7.69 (m, 1 H), 7.44 (dd, J = 11.04, 9.16 Hz, 1 H), 7.04 (d, J = 2.76 Hz, 1 H), 5.27-5.54 (m, 1 H), 4.26-4.38 (m, 2 H), 4.17-4.24 (m, 2 H), 3.95-4.13 (m, 4 H), 3.85-3.94 (m, 1 H). Method 1: RT = 2.44 min.; M + H = 410.3 |
| 267 | 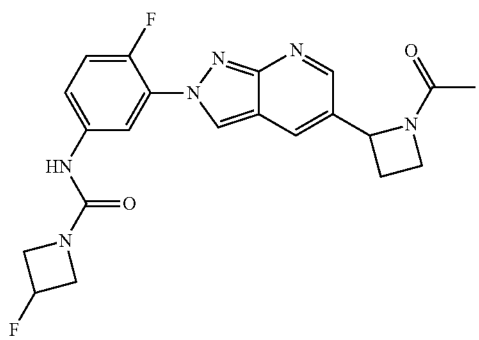 [SMILES: CC(=O)N1CCC1c1cnc2nn(-c3cc(NC(=O)N4CC(F)C4)ccc3F)cc2c1] | ¹H NMR (400 MHz, Methanol-d4) δ 8.86 (dd, J = 3.4, 2.2 Hz, 1H), 8.74 (d, J = 4.4 Hz, 0.5H), 8.67 (d, J = 4.5 Hz, 0.5H), 8.17 (dd, J = 6.8, 2.7 Hz, 0.5H), 8.13 (dd, J = 6.8, 2.7 Hz, 0.5H), 7.66 (dddd, J = 8.8, 4.3, 2.7, 1.7 Hz, 1H), 7.37 (ddd, J = 10.9, 9.1, 3.7 Hz, 1H), 7.28 (dd, J = 4.4, 0.8 Hz, 0.5H), 7.18 (dd, J = 4.5, 0.9 Hz, 0.5H), 5.93 (dd, J = 9.2, 5.6 Hz, 0.5H), 5.73 (dd, J = 9.3, 6.1 Hz, 0.5H), 5.37 (dtt, J = 57.1, 6.1, 3.2 Hz, 1H), 4.48-4.32 (m, 3H), 4.24-4.15 (m, 2H), 4.11 (ddd, J = 10.3, 3.2, 1.4 Hz, 1H), 3.05-2.91 (m, 1H), 2.34-2.21 (m, 1H), 2.03 (s, 1.5H), 1.71 (s, 1.5H). Method 2: RT = 0.66 min.; M + H = 427.2 |
| 268 | | ¹H NMR (400 MHz, DMSO-d6) δ 10.69 (s, 1 H), 8.64 (d, J = 2.69 Hz, 1 H), 8.37 (d, J = 2.81 Hz, 1 H), 8.32 (dd, J = 7.03, 2.51 Hz, 1 H), 7.61-7.67 (m, 1 H), 7.52 (dd, J = 11.19, 9.11 Hz, 1 H), 7.15 (d, J = 2.81 Hz, 1 H), 4.80-5.03 (m, 1 H), 4.41 (t, J = 12.29 Hz, 4 H), 2.24-2.33 (m, 1 H), 1.46-1.67 (m, 1 H), 1.27 (dd, J = 13.27, 6.54 Hz, 1 H). Method 1: RT = 2.89 min.; M + H = 406.0 | or

TABLE 2-continued
| Cpd No. | Structure | ¹HNMR and HPLC retention time and/or MS |
|---|---|---|
| | 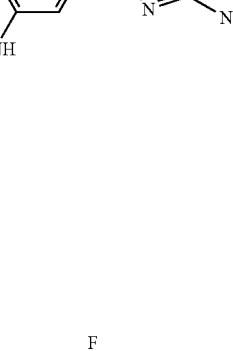 | |
| 269 | 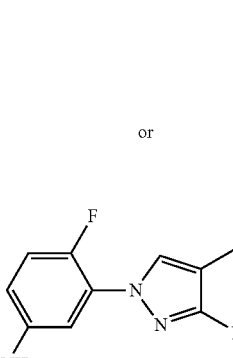
or
 | ¹H NMR (400 MHz, DMSO-d6) δ 10.75 (s, 1 H), 9.48 (d, J = 2.26 Hz, 1 H), 9.03 (d, J = 2.38 Hz, 1 H), 8.95 (d, J = 2.26 Hz, 1 H), 8.74 (d, J = 4.14 Hz, 1 H), 8.39 (dd, J = 6.96, 2.57 Hz, 1 H), 8.13 (d, J = 8.03 Hz, 1 H), 7.96 (td, J = 7.75, 1.69 Hz, 1 H), 7.65-7.74 (m, 1 H), 7.57 (dd, J = 11.11, 9.10 Hz, 1 H), 7.42 (dd, J = 7.22, 5.21 Hz, 1 H), 4.78-5.06 (m, 1 H), 2.26-2.35 (m, 1 H), 1.49-1.66 (m, 1 H), 1.24-1.33 (m, 1 H). Method 1: RT = 2.80 min.; M + H = 392.2 |
| 270 | 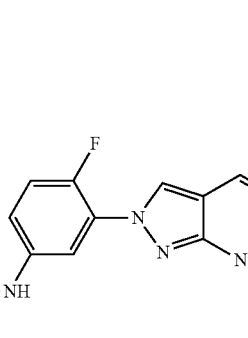 | ¹H NMR (400 MHz, DMSO) δ 8.94 (s, 1 H), 8.72 (d, J = 2.81 Hz, 1 H), 8.63 (d, J = 2.57 Hz, 1 H), 8.16-8.27 (m, 1 H), 7.61-7.67 (m, 1 H), 7.40-7.47 (m, 2 H), 5.26-5.54 (m, 1 H), 4.24-4.40 (m, 2 H), 3.96-4.08 (m, 2 H), 3.29-3.33 (m, 1 H), 3.21 (br d, J = 5.01 Hz, 4 H), 3.11 (br d, J = 4.40 Hz, 4 H). Method 1: RT = 1.86 min.; M + H = 414.3 |

TABLE 2-continued

| Cpd No. | Structure | ¹HNMR and HPLC retention time and/or MS |
|---|---|---|
| 271 | 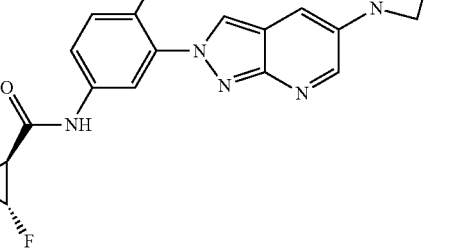<br>or<br>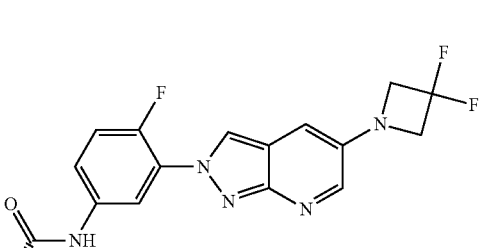 | ¹H NMR (400 MHz, DMSO-d6) δ 10.75 (s, 1 H), 8.70 (d, J = 2.69 Hz, 1 H), 8.43 (d, J = 2.81 Hz, 1 H), 8.38 (dd, J = 6.97, 2.57 Hz, 1 H), 7.66-7.77 (m, 1 H), 7.52-7.63 (m, 1 H), 7.20 (d, J = 2.81 Hz, 1 H), 4.85-5.08 (m, 1 H), 4.47 (t, J = 12.23 Hz, 4 H), 2.27-2.39 (m, 1 H), 1.52-1.72 (m, 1 H), 1.33 (dq, J = 13.11, 6.43 Hz, 1 H). Method 1: RT = 2.89 min.; M + H = 406.0 |
| 272 | <br>trans - racemic | ¹H NMR (400 MHz, DMSO-d6) δ 10.74 (s, 1 H), 8.56 (d, J = 2.57 Hz, 1 H), 8.25-8.37 (m, 2 H), 7.58-7.68 (m, 1 H), 7.45-7.56 (m, 1 H), 6.92 (d, J = 2.69 Hz, 1 H), 4.78-5.05 (m, 1 H), 4.03 (s, 4 H), 2.23-2.33 (m, 1 H), 1.48-1.63 (m, 1 H), 1.23-1.33 (m, 1 H), 0.69 (s, 4 H). Method 1: RT = 3.13 min.; M + H = 396.3 |
| 273 | 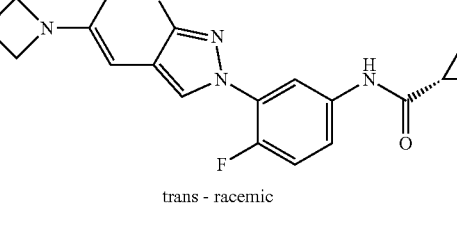<br>or<br>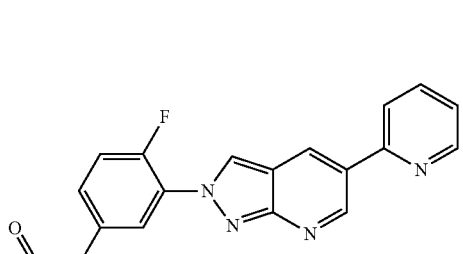 | ¹H NMR (400 MHz, DMSO-d6) δ 10.75 (s, 1 H), 9.48 (d, J = 2.08 Hz, 1 H), 9.03 (d, J = 2.32 Hz, 1 H), 8.95 (d, J = 2.20 Hz, 1 H), 8.74 (d, J = 4.52 Hz, 1 H), 8.40 (dd, J = 7.03, 2.51 Hz, 1 H), 8.13 (d, J = 8.07 Hz, 1 H), 7.96 (td, J = 7.79, 1.77 Hz, 1 H), 7.69 (dt, J = 8.47, 3.53 Hz, 1 H), 7.57 (dd, J = 11.00, 9.17 Hz, 1 H), 7.42 (dd, J = 7.09, 5.14 Hz, 1 H), 4.80-5.05 (m, 1 H), 2.25-2.34 (m, 1 H), 1.48-1.67 (m, 1 H), 1.28 (dq, J = 13.13, 6.67 Hz, 1 H). Method 1: RT = 2.82 min.; M + H = 392.2 |

TABLE 2-continued

| Cpd No. | Structure | ¹HNMR and HPLC retention time and/or MS |
|---|---|---|
| 274 | 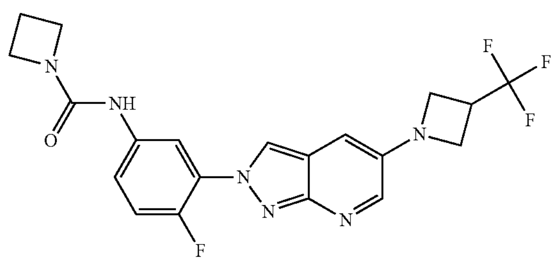 [SMILES: O=C(Nc1ccc(F)c(-n2cc3cc(N4CC(C(F)(F)F)C4)cnc3n2)c1)N1CCC1] | |
| 275 | 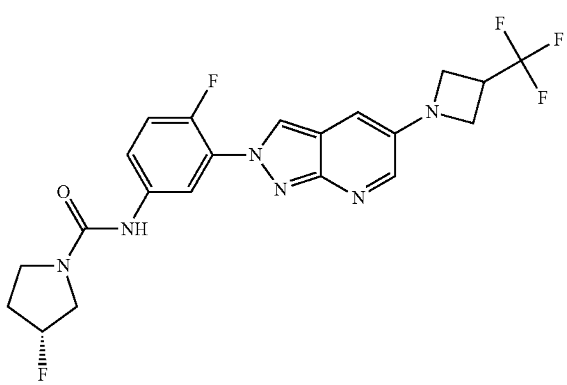 [SMILES: O=C(Nc1ccc(F)c(-n2cc3cc(N4CC(C(F)(F)F)C4)cnc3n2)c1)N1CC[C@@H](F)C1] | ¹H NMR (400 MHz, DMSO) δ 8.68 (s, 1 H), 8.57 (d, J = 2.57 Hz, 1 H), 8.32 (d, J = 2.69 Hz, 1 H), 8.20 (dd, J = 7.09, 2.69 Hz, 1 H), 7.62-7.69 (m, 1 H), 7.41 (dd, J = 11.25, 9.17 Hz, 1 H), 7.03 (d, J = 2.81 Hz, 1 H), 4.13-4.22 (m, 2 H), 3.98 (q, J = 7.78 Hz, 6 H), 3.76 (br dd, J = 9.54, 4.77 Hz, 1 H), 2.19 (quin, J = 7.55 Hz, 2 H). Method 1: RT = 2.87 min.; M + H = 435.3 |
| 276 | 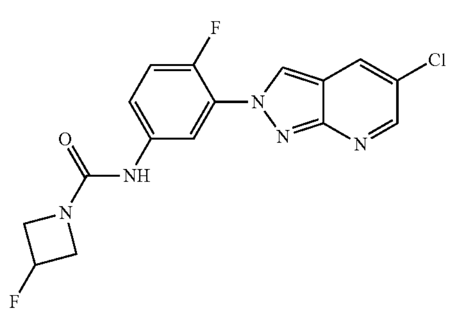 [SMILES: O=C(Nc1ccc(F)c(-n2cc3cc(Cl)cnc3n2)c1)N1CC(F)C1] | ¹H NMR (400 MHz, DMSO) δ 8.52-8.66 (m, 2 H), 8.32 (d, J = 2.81 Hz, 1 H), 8.23 (dd, J = 6.97, 2.57 Hz, 1 H), 7.68 (dt, J = 9.08, 3.35 Hz, 1 H), 7.42 (dd, J = 11.19, 9.23 Hz, 1 H), 7.03 (d, J = 2.69 Hz, 1 H), 5.24-5.50 (m, 1 H), 4.09-4.26 (m, 2 H), 3.99 (dd, J = 8.01, 5.44 Hz, 2 H), 3.50-3.84 (m, 4 H), 3.38-3.47 (m, 1 H), 1.97-2.29 (m, 2 H). Method 1: RT = 2.86 min.; M + H = 467.3 |
| | | ¹H NMR (400 MHz, DMSO-d6) δ 8.99 (s, 1 H), 8.90 (d, J = 2.51 Hz, 1 H), 8.70 (d, J = 2.51 Hz, 1 H), 8.47 (d, J = 2.51 Hz, 1 H), 8.24 (dd, J = 7.03, 2.76 Hz, 1 H), 7.64-7.76 (m, 1 H), 7.48 (dd, J = 11.17, 9.16 Hz, 1 H), 5.26-5.53 (m, 1 H), 4.23-4.40 (m, 2 H), 3.94-4.12 (m, 2 H). Method 1: RT = 2.76 min.; M + H = 364.0 |

TABLE 2-continued

| Cpd No. | Structure | ¹HNMR and HPLC retention time and/or MS |
|---|---|---|
| 277 | 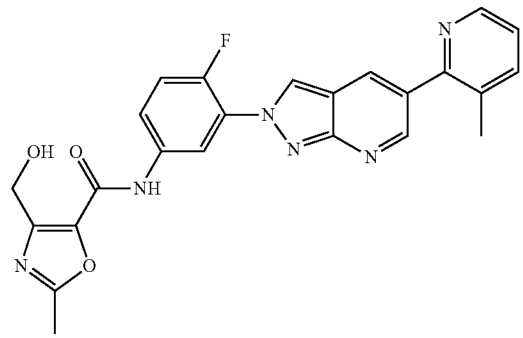 [SMILES: Cc1nc(CO)c(C(=O)Nc2ccc(F)c(-n3cc4cc(-c5ncccc5C)cnc4n3)c2)o1] | ¹H NMR (400 MHz, DMSO-d6) δ ppm 9.00 (d, J = 2.20 Hz, 1 H), 8.94 (d, J = 1.96 Hz, 1 H), 8.53-8.63 (m, 2 H), 8.51 (d, J = 2.20 Hz, 1 H), 7.85-7.95 (m, 1 H), 7.81 (br d, J = 7.34 Hz, 1 H), 7.55-7.67 (m, 1 H), 7.37 (dd, J = 7.46, 4.77 Hz, 1 H), 4.69 (s, 2 H), 2.55 (s, 3 H), 2.45 (s, 3 H). Method 1: RT = 2.50 min.; M + H = 459.0 |
| 278 | 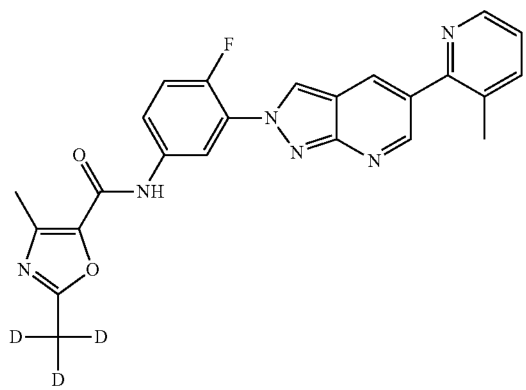 [SMILES: [2H]C([2H])([2H])c1nc(C)c(C(=O)Nc2ccc(F)c(-n3cc4cc(-c5ncccc5C)cnc4n3)c2)o1] | ¹H NMR (400 MHz, DMSO-d6) δ 10.5 4 (s, 1 H), 9.00 (d, J = 2.32 Hz, 1 H), 8.93 (d, J = 2.20 Hz, 1 H), 8.60 (td, J = 6.91, 3.30 Hz, 2 H), 8.51 (d, J = 2.20 Hz, 1 H), 7.89-7.97 (m, 1 H), 7.84 (d, J = 7.46 Hz, 1 H), 7.60 (dd, J = 11.07, 9.23 Hz, 1 H), 7.40 (dd, J = 7.58, 4.77 Hz, 1 H), 2.45 (s, 3 H), 2.41 (s, 3 H). Method 1: RT = 2.61 min.; M + H = 446.1 |
| 279 | 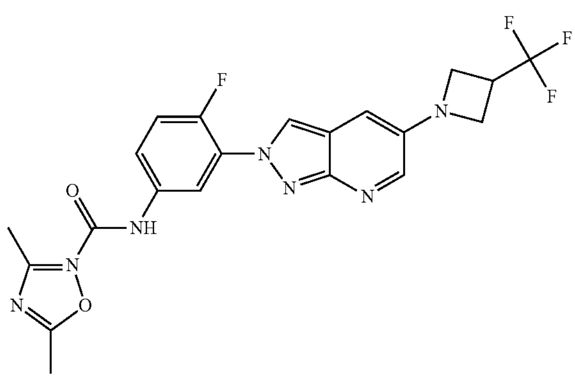 | ¹H NMR (400 MHz, Methanol-d4) δ 8.51 (d, J = 2.6 Hz, 1H), 8.38 (dd, J = 6.9, 2.7 Hz, 1H), 8.28 (d, J = 2.8 Hz, 1H), 7.85 (ddd, J = 9.1, 4.2, 2.7 Hz, 1H), 7.41 (dd, J = 11.1, 9.1 Hz, 1H), 7.10 (d, J = 2.8 Hz, 1H), 4.23 (t, J = 8.2 Hz, 2H), 4.08 (dd, J = 8.0, 5.4 Hz, 2H), 3.64 (qt, J = 8.8, 5.4 Hz, 1H), 2.55 (s, 3H), 2.46 (s, 3H). |
| 280 | 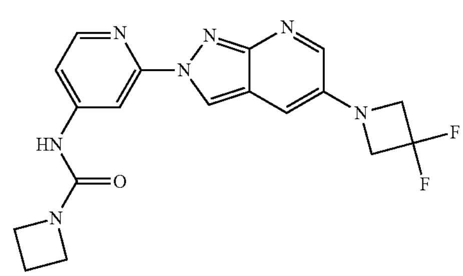 [SMILES: O=C(Nc1ccnc(-n2cc3cc(N4CC(F)(F)C4)cnc3n2)c1)N1CCC1] | ¹H NMR (400 MHz, DMSO-d6) δ 9.18 (s, 1 H), 8.99 (s, 1 H), 8.44 (d, J = 1.76 Hz, 1 H), 8.36 (d, J = 2.76 Hz, 1 H), 8.31 (d, J = 5.77 Hz, 1 H), 7.67 (dd, J = 5.52, 2.01 Hz, 1 H), 7.14 (d, J = 2.76 Hz, 1 H), 4.42 (t, J = 12.17 Hz, 4 H), 4.04 (t, J = 7.53 Hz, 4 H), 2.16-2.29 (m, 2 H). Method 1: RT = 2.76 min.; M + H = 386.0 |

TABLE 2-continued

| Cpd No. | Structure | ¹HNMR and HPLC retention time and/or MS |
|---|---|---|
| 281 | 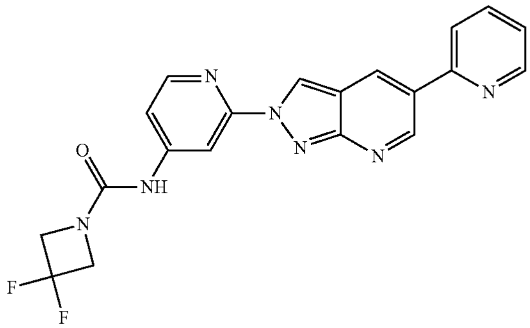 [SMILES: O=C(Nc1ccnc(-n2cc3cc(-c4ccccn4)cnc3n2)c1)N1CC(F)(F)C1] | ¹H NMR (400 MHz, DMSO-d6) δ 9.70 (s, 1 H), 9.47 (d, J = 2.20 Hz, 1 H), 9.38 (s, 1 H), 8.95 (d, J = 2.20 Hz, 1 H), 8.71-8.77 (m, 1 H), 8.49 (d, J = 1.71 Hz, 1 H), 8.42 (d, J = 5.62 Hz, 1 H), 8.12 (d, J = 8.07 Hz, 1 H), 7.96 (td, J = 7.76, 1.83 Hz, 1 H), 7.72 (dd, J = 5.62, 1.96 Hz, 1 H), 7.39-7.47 (m, 1 H), 4.49 (t, J = 12.72 Hz, 4 H). Method 1: RT = 2.81 min.; M + H = 408.0 |
| 282 | 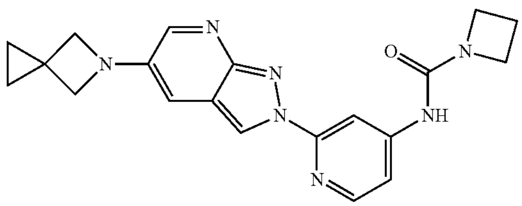 [SMILES: O=C(Nc1ccnc(-n2cc3cc(N4CC5(CC5)C4)cnc3n2)c1)N1CCC1] | ¹H NMR (400 MHz, DMSO-d6) δ 9.16 (s, 1 H), 8.91 (s, 1 H), 8.42 (d, J = 1.76 Hz, 1 H), 8.26-8.32 (m, 2 H), 7.66 (dd, J = 5.77, 2.01 Hz, 1 H), 6.91 (d, J = 2.76 Hz, 1 H), 4.00-4.08 (m, 8 H), 2.17-2.28 (m, 2 H), 0.68 (s, 4 H). Method 1: RT = 2.93 min.; M + H = 376.0 |
| 283 | 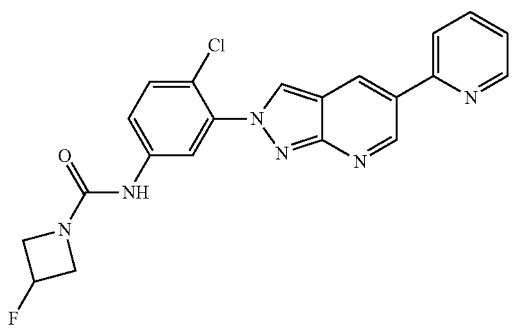 [SMILES: O=C(Nc1ccc(Cl)c(-n2cc3cc(-c4ccccn4)cnc3n2)c1)N1CC(F)C1] | ¹H NMR (400 MHz, DMSO-d6) δ 9.47 (d, J = 2.26 Hz, 1 H), 9.08 (br s, 1 H), 8.90-9.00 (m, 2 H), 8.70-8.79 (m, 1 H), 8.13 (d, J = 8.03 Hz, 1 H), 8.03 (d, J = 2.51 Hz, 1 H), 7.96 (td, J = 7.72, 1.88 Hz, 1 H), 7.72-7.78 (m, 1 H), 7.66 (d, J = 9.03 Hz, 1 H), 7.42 (ddd, J = 7.53, 4.77, 1.00 Hz, 1 H), 5.28-5.53 (m, 1 H), 4.25-4.42 (m, 2 H), 3.95-4.11 (m, 2 H). Method 1: RT = 2.69 min.; M + H = 423.0 |
| 284 | 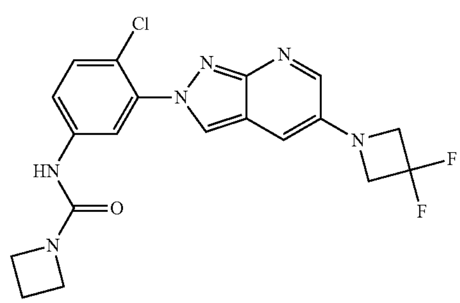 [SMILES: O=C(Nc1ccc(Cl)c(-n2cc3cc(N4CC(F)(F)C4)cnc3n2)c1)N1CCC1] | ¹H NMR (400 MHz, DMSO) δ 8.80 (s, 1 H), 8.55 (s, 1 H), 8.35 (d, J = 2.81 Hz, 1 H), 7.96 (d, J = 2.45 Hz, 1 H), 7.71 (dd, J = 8.99, 2.51 Hz, 1 H), 7.58 (d, J = 9.05 Hz, 1 H), 7.16 (d, J = 2.81 Hz, 1 H), 4.40 (br t, J = 12.23 Hz, 4 H), 3.96 (br t, J = 7.52 Hz, 4 H), 2.08-2.32 (m, 2 H). Method 1: RT = 2.81 min.; M + H = 419.2 |
| 285 | 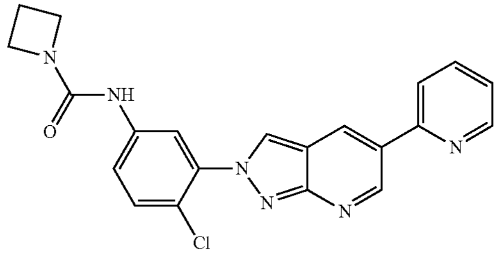 [SMILES: O=C(Nc1ccc(Cl)c(-n2cc3cc(-c4ccccn4)cnc3n2)c1)N1CCC1] | ¹H NMR (400 MHz, DMSO) δ 9.46 (d, J = 1.96 Hz, 1 H), 8.93 (s, 2 H), 8.82 (s, 1 H), 8.73 (br d, J = 4.04 Hz, 1 H), 8.12 (br d, J = 8.07 Hz, 1 H) 8.04 (d, J = 2.20 Hz, 1 H) 7.94 (br t, J = 7.15 Hz, 1 H) 7.75 (dd, J = 8.86, 2.26 Hz, 1 H), 7.62 (d, J = 8.93 Hz, 1 H), 7.41 (dd, J = 6.97, 5.01 Hz, 1 H), 3.97 (br t, J = 7.46 Hz, 4 H), 2.19 (quin, J = 7.55 Hz, 2 H). Method 1: RT = 2.69 min.; M + H = 405.2 |

TABLE 2-continued

| Cpd No. | Structure | ¹HNMR and HPLC retention time and/or MS |
|---|---|---|
| 286 | 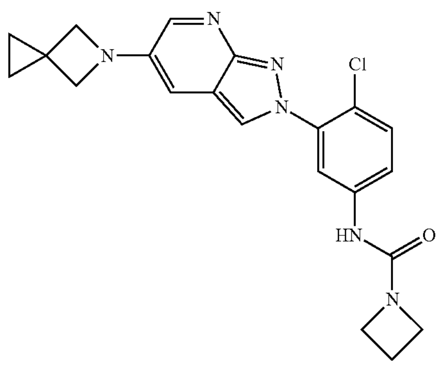 | ¹H NMR (400 MHz, DMSO) δ 8.79 (s, 1 H), 8.45 (s, 1 H), 8.27 (d, J = 2.57 Hz, 1 H), 7.96 (d, J = 2.32 Hz, 1 H), 7.71 (dd, J = 8.86, 2.38 Hz, 1 H), 7.57 (d, J = 8.80 Hz, 1 H), 6.93 (d, J = 2.69 Hz, 1 H), 4.01 (s, 4 H), 3.96 (br t, J = 7.58 Hz, 4 H), 2.19 (quin, J = 7.61 Hz, 2 H), 0.68 (s, 4 H). Method 1: RT = 2.98 min.; M + H = 409.3 |
| 287 | 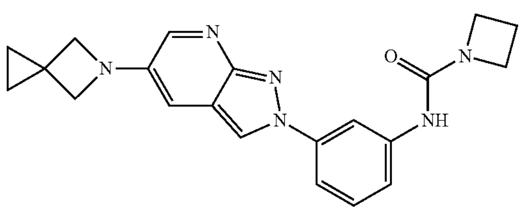 [SMILES: O=C(Nc1cccc(-n2cc3cc(N4CC5(CC5)C4)cnc3n2)c1)N1CCC1] | ¹H NMR (400 MHz, DMSO-d6) δ 8.70 (s, 1 H), 8.68 (s, 1 H), 8.29 (s, 1 H), 8.25 (d, J = 2.81 Hz, 1 H), 7.52-7.66 (m, 2 H), 7.37-7.45 (m, 1 H), 6.90 (d, J = 2.69 Hz, 1 H), 3.97-4.05 (m, 8 H), 2.18-2.23 (m, 2 H), 0.69 (s, 4 H). Method 1: RT = 2.82 min.; M + H = 375.1 |
| 288 | 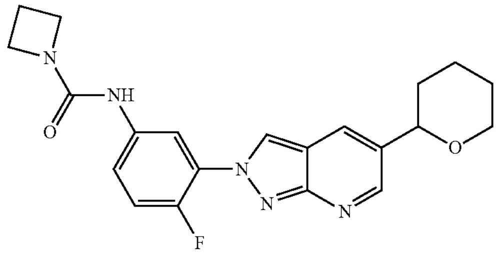 [SMILES: O=C(Nc1ccc(F)c(-n2cc3cc(C4CCCCO4)cnc3n2)c1)N1CCC1] | ¹H NMR (400 MHz, Methanol-d4) δ 9.03 (d, J = 2.2 Hz, 1H), 8.73 (d, J = 4.9 Hz, 1H), 8.19 (dd, J = 6.8, 2.7 Hz, 1H), 7.63 (ddd, J = 9.1, 4.2, 2.7 Hz, 1H), 7.37 (dd, J = 10.9, 9.1 Hz, 1H), 7.32 (dd, J = 5.0, 0.9 Hz, 1H), 4.92 (ddt, J = 2.7, 1.4, 0.7 Hz, 1H), 4.23 (d, J = 10.3 Hz, 1H), 4.17-4.07 (m, 2H), 3.74 (td, J = 11.6, 2.5 Hz, 1H), 3.37-3.32 (m, 2H), 2.33 (p, J = 7.6 Hz, 2H), 2.15-1.98 (m, 2H), 1.92-1.57 (m, 4H). Method 2: RT = 0.89 min.; M + H = 396.0 |
| 289 | 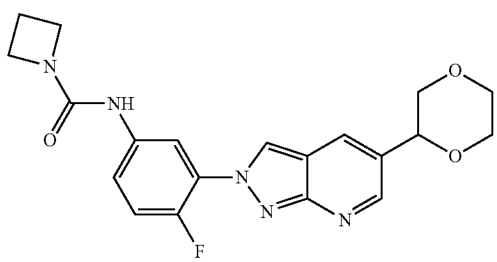 [SMILES: O=C(Nc1ccc(F)c(-n2cc3cc(C4COCCO4)cnc3n2)c1)N1CCC1] | ¹H NMR (400 MHz, Methanol-d4) δ 9.05 (d, J = 2.2 Hz, 1H), 8.73 (d, J = 4.8 Hz, 1H), 8.18 (dd, J = 6.8, 2.7 Hz, 1H), 7.63 (ddd, J = 9.1, 4.1, 2.7 Hz, 1H), 7.37 (dd, J = 10.9, 9.1 Hz, 1H), 7.32 (dd, J = 4.8, 0.9 Hz, 1H), 5.20-5.12 (m, 1H), 4.17-4.04 (m, 4H), 3.99 (ddd, J = 11.8, 10.6, 3.0 Hz, 1H), 3.89-3.75 (m, 2H), 3.59 (dd, J = 11.5, 9.9 Hz, 1H), 3.40-3.32 (m, 2H), 2.33 (p, J = 7.7 Hz, 2H). Method 2: RT = 0.74 min.; M + H = 398.0 |
| 290 | 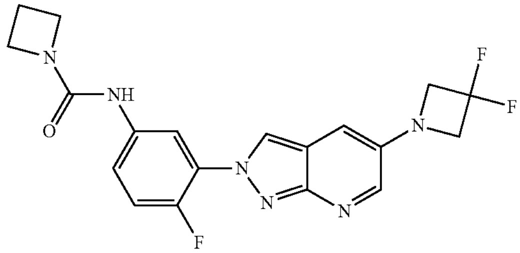 [SMILES: O=C(Nc1ccc(F)c(-n2cc3cc(N4CC(F)(F)C4)cnc3n2)c1)N1CCC1] | ¹H NMR (400 MHz, DMSO) δ 8.69 (s, 1 H), 8.62 (d, J = 2.64 Hz, 1 H), 8.36 (d, J = 2.76 Hz, 1 H), 8.22 (dd, J = 7.09, 2.70 Hz, 1 H), 7.65-7.72 (m, 1 H), 7.42 (dd, J = 11.29, 9.16 Hz, 1 H), 7.15 (d, J = 2.89 Hz, 1 H), 4.41 (t, J = 12.23 Hz, 4 H), 3.98 (t, J = 7.53 Hz, 4 H), 2.20 (quin, J = 7.56 Hz, 2 H). Method 1: RT = 2.73 min.; LCMS: M + H = 403.2 |

TABLE 2-continued

| Cpd No. | Structure | ¹HNMR and HPLC retention time and/or MS |
|---|---|---|
| 291 | 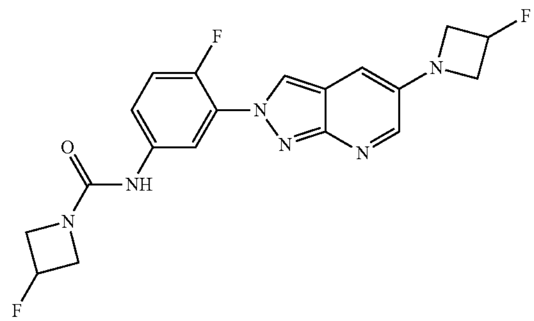 [SMILES: O=C(Nc1ccc(F)c(-n2cc3cc(N4CC(F)C4)cnc3n2)c1)N1CC(F)C1] | ¹H NMR (400 MHz, DMSO) δ 8.95 (s, 1 H), 8.56 (d, J = 2.63 Hz, 1 H), 8.30 (d, J = 2.89 Hz, 1 H), 8.19 (dd, J = 7.09, 2.70 Hz, 1 H), 7.60-7.69 (m, 1 H), 7.42 (dd, J = 11.36, 9.10 Hz, 1 H), 7.00 (d, J = 2.76 Hz, 1 H), 5.28-5.63 (m, 2 H), 4.20-4.37 (m, 4 H), 3.93-4.09 (m, 4 H). Method 1: RT = 2.63 min.; M + H = 403.2 |
| 292 | 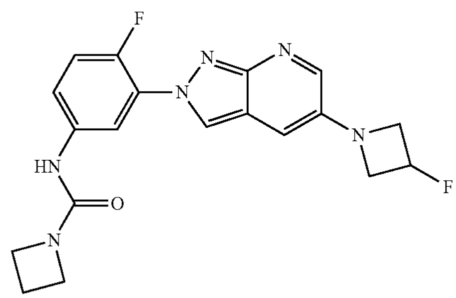 [SMILES: O=C(Nc1ccc(F)c(-n2cc3cc(N4CC(F)C4)cnc3n2)c1)N1CCC1] | ¹H NMR (400 MHz, DMSO) δ 8.70 (s, 1 H), 8.56 (d, J = 2.76 Hz, 1 H), 8.31 (d, J = 2.76 Hz, 1 H), 8.21 (dd, J = 7.03, 2.64 Hz, 1 H), 7.59-7.72 (m, 1 H), 7.41 (dd, J = 11.36, 9.10 Hz, 1 H), 7.01 (d, J = 2.76 Hz, 1 H), 5.39-5.66 (m, 1 H), 4.20-4.36 (m, 2 H), 3.89-4.09 (m, 6 H), 2.12-2.28 (m, 2 H). Method 1: RT = 2.63 min.; M + H = 385.3 |
| 293 | 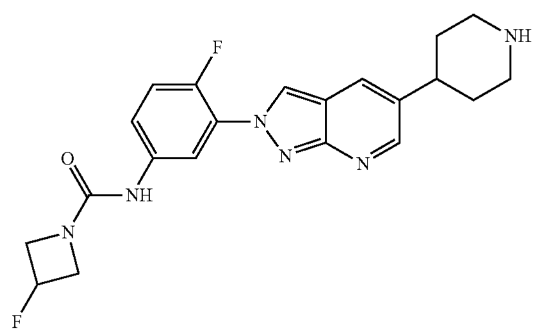 [SMILES: O=C(Nc1ccc(F)c(-n2cc3cc(C4CCNCC4)cnc3n2)c1)N1CC(F)C1] | ¹H NMR (400 MHz, DMSO-d6) δ 9.05 (s, 1 H), 8.83 (d, J = 2.26 Hz, 1 H), 8.66 (s, 1 H), 8.44 (br s, 1 H), 8.24 (dd, J = 7.03, 2.51 Hz, 1 H), 8.05 (s, 1 H), 7.64-7.73 (m, 1 H), 7.47 (dd, J = 11.17, 9.16 Hz, 1 H), 5.28-5.52 (m, 1 H), 4.25-4.41 (m, 2 H), 3.96-4.11 (m, 2 H), 3.29 (br d, J = 9.03 Hz, 2 H), 2.91 (br d, J = 8.28 Hz, 3 H), 1.96 (br d, J = 12.55 Hz, 2 H), 1.82 (br d, J = 11.04 Hz, 2 H). Method 2: RT = 0.51 min.; M + H = 413.2 |
| 294 | 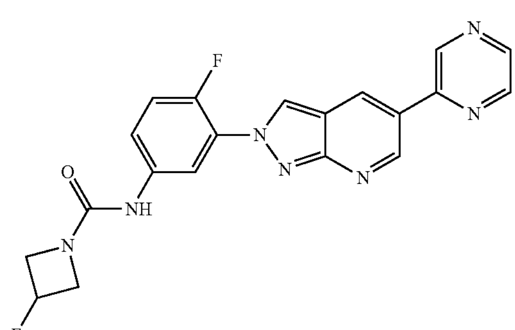 | ¹H NMR (400 MHz, DMSO-d6) δ 9.48 (d, J = 2.26 Hz, 1 H), 9.42 (d, J = 1.25 Hz, 1 H), 9.01-9.13 (m, 3 H), 8.76-8.83 (m, 1 H), 8.68 (d, J = 2.51 Hz, 1 H), 8.29 (dd, J = 7.03, 2.51 Hz, 1 H), 7.67-7.78 (m, 1 H), 7.50 (dd, J = 11.17, 9.16 Hz, 1 H), 5.26-5.57 (m, 1 H), 4.21-4.46 (m, 2 H), 3.92-4.15 (m, 2 H). Method 1: RT = 2.53 min.; M + H = 408.1 |

TABLE 2-continued

| Cpd No. | Structure | ¹HNMR and HPLC retention time and/or MS |
|---|---|---|
| 295 | 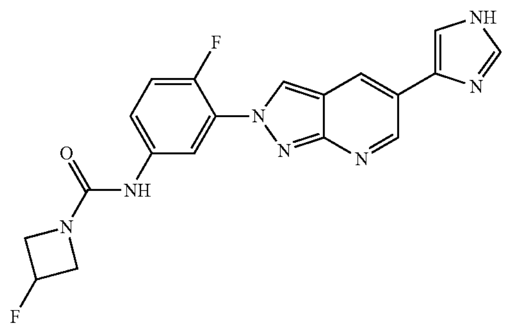 [SMILES: O=C(Nc1ccc(F)c(-n2cc3cc(-c4c[nH]cn4)cnc3n2)c1)N1CC(F)C1] | ¹H NMR (400 MHz, METHANOL-d4) δ 9.14 (d, J = 2.26 Hz, 1 H), 8.77 (d, J = 2.26 Hz, 1 H), 8.57 (d, J = 2.26 Hz, 1 H), 8.17 (dd, J = 6.78, 2.76 Hz, 1 H), 7.85 (d, J = 1.00 Hz, 1 H), 7.64-7.71 (m, 2 H), 7.38 (dd, J = 11.04, 9.03 Hz, 1 H), 5.27-5.51 (m, 1 H), 4.35-4.47 (m, 2 H), 4.09-4.23 (m, 2 H). Method 1: RT = 1.95 min.; M + H = 396.1 |
| 296 | 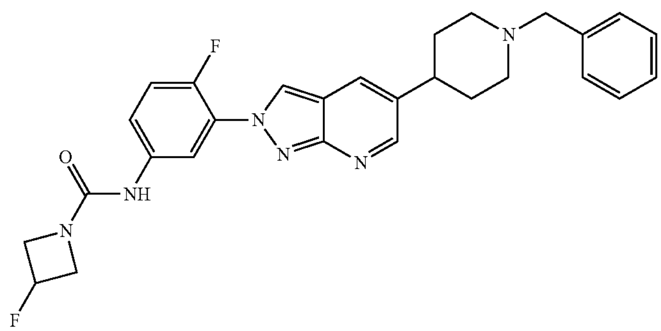 [SMILES: O=C(Nc1ccc(F)c(-n2cc3cc(C4CCN(Cc5ccccc5)CC4)cnc3n2)c1)N1CC(F)C1] | ¹H NMR (400 MHz, METHANOL-d4) δ 8.69 (d, J = 2.45 Hz, 1 H), 8.65 (d, J = 2.20 Hz, 1 H), 8.11-8.18 (m, 2 H), 7.61-7.69 (m, 1 H), 7.27-7.43 (m, 6 H), 5.26-5.49 (m, 1 H), 4.33-4.46 (m, 2 H), 4.08-4.21 (m, 2 H), 3.63 (s, 2 H), 3.11 (br d, J = 11.74 Hz, 2 H), 2.72-2.85 (m, 1 H), 2.20-2.31 (m, 2 H), 1.82-2.01 (m, 4 H). Method 1: RT = 2.16 min.; M + H = 503.2 |
| 297 | 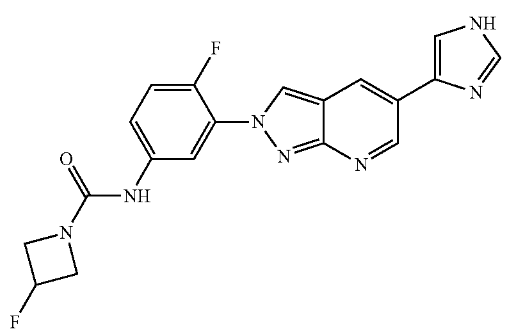 [SMILES: O=C(Nc1ccc(F)c(-n2cc3cc(-c4c[nH]cn4)cnc3n2)c1)N1CC(F)C1] | ¹H NMR (400 MHz, DMSO-d6) δ 13.13 (br s, 1 H), 9.08 (d, J = 2.26 Hz, 1 H), 9.02 (s, 1 H), 8.84 (d, J = 2.51 Hz, 1 H), 8.47 (s, 1 H), 8.40 (d, J = 2.26 Hz, 1 H), 8.26 (dd, J = 7.03, 2.76 Hz, 2 H), 7.69 (ddd, J = 9.16, 4.14, 2.76 Hz, 1 H), 7.48 (dd, J = 11.17, 9.16 Hz, 1 H), 5.30-5.51 (m, 1 H), 4.26-4.40 (m, 2 H), 3.97-4.10 (m, 2 H). Method 2: RT = 0.69 min.; M + H = 396.1 |
| 298 | 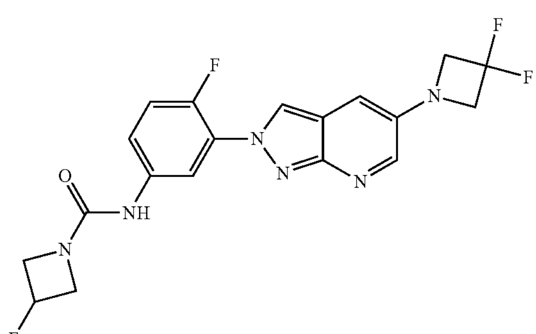 | ¹H NMR (400 MHz, DMSO), δ 8.94 (s, 1 H), 8.62 (d, J = 2.57 Hz, 1 H), 8.36 (d, J = 2.81 Hz, 1 H), 8.20 (dd, J = 7.03, 2.63 Hz, 1 H), 7.57-7.71 (m, 1 H), 7.44 (dd, J = 11.19, 9.11 Hz, 1 H), 7.14 (d, J = 2.81 Hz, 1 H), 5.26-5.53 (m, 1 H), 4.22-4.51 (m, 6 H), 3.91-4.11 (m, 2 H). Method 1: RT = 2.74 min.; M + H = 421.2 |

TABLE 2-continued

| Cpd No. | Structure | ¹HNMR and HPLC retention time and/or MS |
|---|---|---|
| 299 | 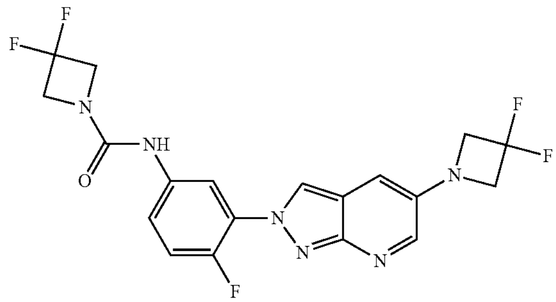 [SMILES: O=C(Nc1ccc(F)c(-n2cc3cc(N4CC(F)(F)C4)cnc3n2)c1)N1CC(F)(F)C1] | ¹H NMR (400 MHz, DMSO) δ 9.19 (s, 1 H) 8.62 (d, J = 2.76 Hz, 1 H), 8.35 (d, J = 2.89 Hz, 1 H), 8.19 (dd, J = 7.03, 2.64 Hz, 1 H), 7.61-7.67 (m, 1 H), 7.45 (dd, J = 11.36, 9.10 Hz, 1 H), 7.13 (d, J = 2.76 Hz, 1 H), 4.35-4.45 (m, 8 H) Method 1: RT = 2.90 min.; M + H = 439.2 |
| 300 | 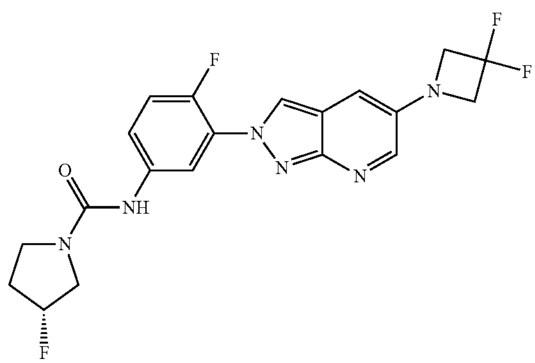 [SMILES: O=C(Nc1ccc(F)c(-n2cc3cc(N4CC(F)(F)C4)cnc3n2)c1)N1CC[C@@H](F)C1] | ¹H NMR (400 MHz, DMSO) δ 8.57-8.65 (m, 2 H) 8.35 (d, J = 2.76 Hz, 1 H) 8.22 (dd, J = 7.09, 2.70 Hz, 1 H) 7.64-7.72 (m, 1 H) 7.42 (dd, J = 11.29, 9.16 Hz, 1 H) 7.14 (d, J = 2.76 Hz, 1 H) 5.27-5.47 (m, 1 H) 4.40 (t, J = 12.23 Hz, 4 H) 3.39-3.76 (m, 4 H) 1.98-2.25 (m, 2 H). Method 1: RT = 2.73 min.; M + H = 435.3 |
| 301 | 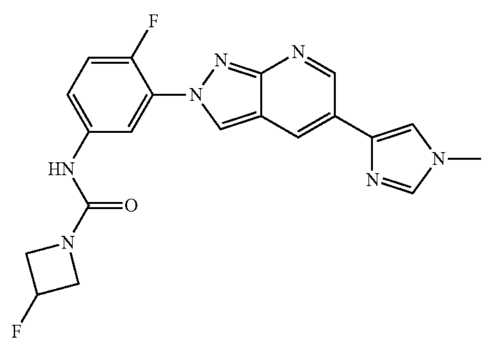 [SMILES: Cn1cnc(-c2cnc3nn(-c4cc(NC(=O)N5CC(F)C5)ccc4F)cc3c2)c1] | ¹H NMR (400 MHz, METHANOL-d4) δ 9.11 (d, J = 1.96 Hz, 1 H), 8.76 (d, J = 2.20 Hz, 1 H), 8.54 (d, J = 1.96 Hz, 1 H), 8.16 (dd, J = 6.72, 2.57 Hz, 1 H), 7.76 (s, 1 H), 7.63-7.70 (m, 2 H), 7.37 (dd, J = 11.00, 9.29 Hz, 1 H), 5.27-5.50 (m, 1 H), 4.33-4.48 (m, 2 H), 4.09-4.22 (m, 2 H), 3.84 (s, 3 H). Method 1: RT = 1.97 min.; M + H = 410.2 |
| 302 | 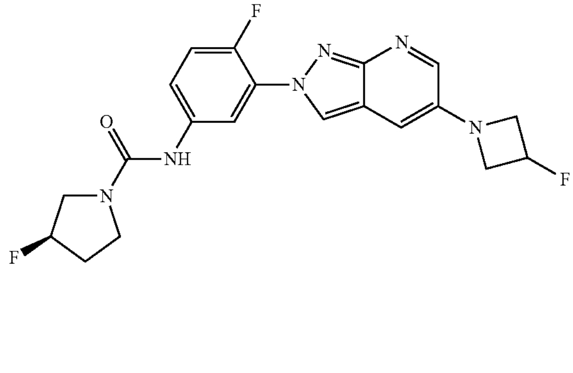 [SMILES: O=C(Nc1ccc(F)c(-n2cc3cc(N4CC(F)C4)cnc3n2)c1)N1CC[C@@H](F)C1] | ¹H NMR (400 MHz, DMSO), δ 8.55-8.62 (m, 2 H), 8.31 (d, J = 2.76 Hz, 1 H), 8.22 (dd, J = 7.03, 2.76 Hz, 1 H), 7.68 (dt, J = 8.97, 3.42 Hz, 1 H), 7.42 (dd, J = 11.29, 9.16 Hz, 1 H), 7.01 (d, J = 2.76 Hz, 1 H), 5.28-5.64 (m, 2 H), 4.20-4.33 (m, 2 H), 3.93-4.07 (m, 2 H), 3.60-3.76 (m, 4 H), 2.10-2.22 (m, 2 H). Method 2: RT = 0.83 min.; M + H = 417.1 |

TABLE 2-continued

| Cpd No. | Structure | ¹HNMR and HPLC retention time and/or MS |
|---|---|---|
| 303 | 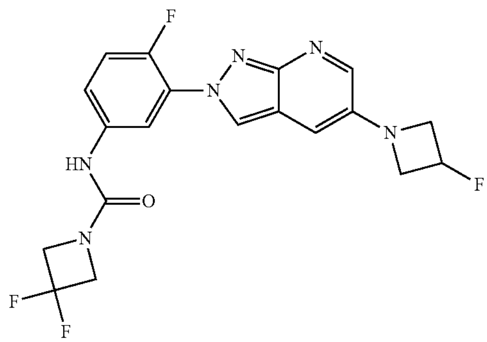 [SMILES: O=C(Nc1ccc(F)c(-n2cc3cc(N4CC(F)C4)cnc3n2)c1)N1CC(F)(F)C1] | ¹H NMR (400 MHz, DMSO) δ 9.22 (s, 1 H), 8.58 (d, J = 2.64 Hz, 1 H), 8.31 (d, J = 2.76 Hz, 1 H), 8.20 (dd, J = 6.96, 2.70 Hz, 1 H), 7.61-7.68 (m, 1 H), 7.46 (dd, J = 11.29, 9.16 Hz, 1 H), 7.01 (d, J = 2.89 Hz, 1 H), 5.42-5.64 (m, 1 H), 4.41 (t, J = 12.67 Hz, 4 H), 4.21-4.33 (m, 2 H), 3.93-4.06 (m, 2 H). Method 1: RT = 2.74 min.; M + H = 421.3 |
| 304 | 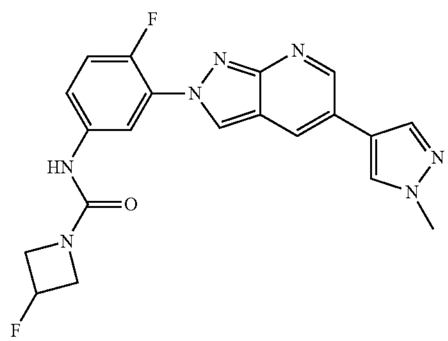 [SMILES: Cn1cc(-c2cnc3nn(-c4cc(NC(=O)N5CC(F)C5)ccc4F)cc3c2)cn1] | ¹H NMR (400 MHz, DMSO-d6) δ 9.02 (d, J = 2.26 Hz, 1 H), 8.98 (s, 1 H), 8.84 (d, J = 2.76 Hz, 1 H), 8.36 (d, J = 2.26 Hz, 1 H), 8.31 (s, 1 H), 8.25 (dd, J = 7.03, 2.76 Hz, 1 H), 8.02 (s, 1 H), 7.65-7.73 (m, 1 H), 7.48 (dd, J = 11.17, 9.16 Hz, 1 H), 5.29-5.52 (m, 1 H), 4.26-4.39 (m, 2 H), 3.97-4.10 (m, 2 H), 3.91 (s, 3 H). Method 2: RT = 0.75 min.; M + H = 410.2 |
| 305 | 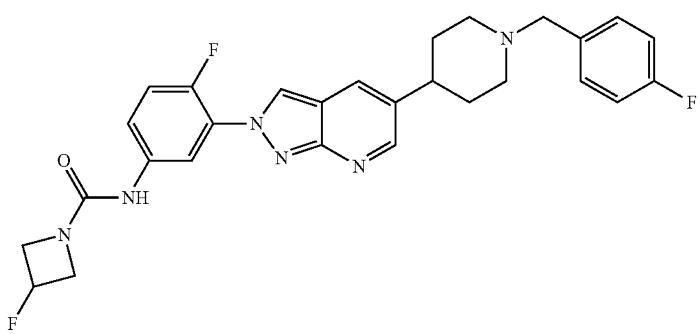 [SMILES: O=C(Nc1ccc(F)c(-n2cc3cc(C4CCN(Cc5ccc(F)cc5)CC4)cnc3n2)c1)N1CC(F)C1] | ¹H NMR (400 MHz, METHANOL-d4) δ 8.69 (d, J = 2.51 Hz, 1 H), 8.65 (d, J = 2.26 Hz, 1 H), 8.12-8.17 (m, 2 H), 7.62-7.68 (m, 1 H), 7.32-7.45 (m, 3 H), 7.06-7.13 (m, 2 H), 5.27-5.48 (m, 1 H), 4.33-4.46 (m, 2 H), 4.07-4.23 (m, 2 H), 3.61 (s, 2 H), 3.08 (br d, J = 11.80 Hz, 2 H), 2.70-2.86 (m, 1 H), 2.24 (td, J = 11.86, 2.38 Hz, 2 H), 1.93-2.01 (m, 2 H), 1.81-1.93 (m, 2 H). Method 2: RT = 0.64 min.; M + H = 521.2 |
| 306 | 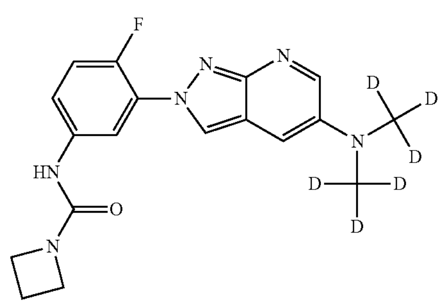 [SMILES: [2H]C([2H])([2H])N(c1cnc2nn(-c3cc(NC(=O)N4CCC4)ccc3F)cc2c1)C([2H])([2H])[2H]] | ¹H NMR (400 MHz, DMSO-d6) δ 8.67-8.74 (m, 2 H), 8.54 (d, J = 2.69 Hz, 1 H), 8.22 (dd, J = 7.21, 2.81 Hz, 1 H), 7.59-7.77 (m, 1 H), 7.41 (dd, J = 11.37, 9.17 Hz, 1 H), 7.14 (d, J = 2.93 Hz, 1 H), 3.98 (t, J = 7.58 Hz, 4 H), 2.20 (t, J = 7.58 Hz, 2 H). Method 1: RT = 2.62 min.; M + H = 361.2 |

TABLE 2-continued

| Cpd No. | Structure | ¹HNMR and HPLC retention time and/or MS |
|---|---|---|
| 307 | 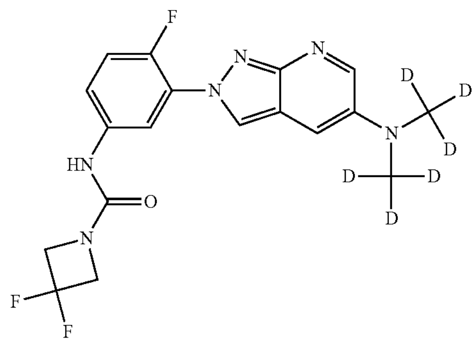 [SMILES: [2H]C([2H])([2H])N(c1cnc2nn(-c3cc(NC(=O)N4CC(F)(F)C4)ccc3F)cc2c1)C([2H])([2H])[2H]] | ¹H NMR1H NMR (400 MHz, DMSO-d6) δ 9.23 (s, 1 H), 8.69 (d, J = 2.93 Hz, 1 H), 8.56 (d, J = 2.93 Hz, 1 H), 8.21 (dd, J = 6.85, 2.69 Hz, 1 H), 7.60-7.72 (m, 1 H), 7.46 (dd, J = 11.37, 9.17 Hz, 1 H), 7.14 (d, J = 2.93 Hz, 1 H), 4.41 (t, J = 12.72 Hz, 4 H). Method 1: RT = 2.73 min.; M + H = 397.2 |
| 308 | 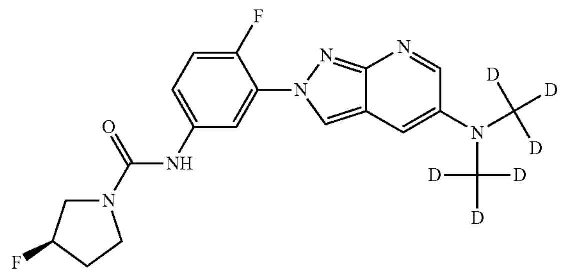 [SMILES: [2H]C([2H])([2H])N(c1cnc2nn(-c3cc(NC(=O)N4CC[C@@H](F)C4)ccc3F)cc2c1)C([2H])([2H])[2H]] | ¹H NMR (400 MHz, DMSO-d6) δ 8.69 (d, J = 2.93 Hz, 1 H), 8.62 (s, 1 H) 8.55 (d, J = 2.69 Hz, 1 H), 8.24 (dd, J = 7.21, 2.81 Hz, 1 H), 7.64-7.74 (m, 1 H), 7.43 (dd, J = 11.25, 9.05 Hz, 1 H), 7.14 (d, J = 2.93 Hz, 1 H), 5.27-5.50 (m, 1 H), 3.51-3.77 (m, 4 H), 2.04-2.25 (m, 2 H). Method 2: RT = 0.79 min.; M + H = 393.2 |
| 309 | 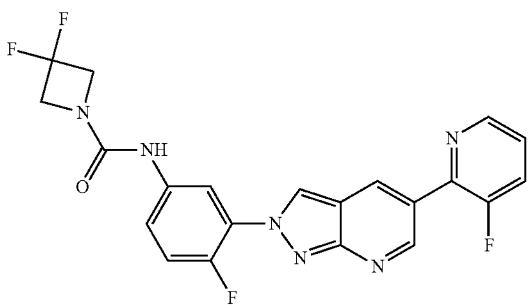 [SMILES: O=C(Nc1ccc(F)c(-n2cc3cc(-c4ncccc4F)cnc3n2)c1)N1CC(F)(F)C1] | ¹H NMR (400 MHz, DMSO-d6) δ 9.27 (s, 2 H), 9.06 (d, J = 2.01 Hz, 1 H), 8.82 (s, 1 H), 8.63 (br d, J = 4.27 Hz, 1 H), 8.28 (dd, J = 6.78, 2.51 Hz, 1 H), 7.93 (dd, J = 11.42, 8.41 Hz, 1 H), 7.67-7.76 (m, 1 H), 7.47-7.59 (m, 2 H), 4.42 (t, J = 12.67 Hz, 4 H). Method 1: RT = 2.85 min.; M + H = 443.1 |
| 310 | 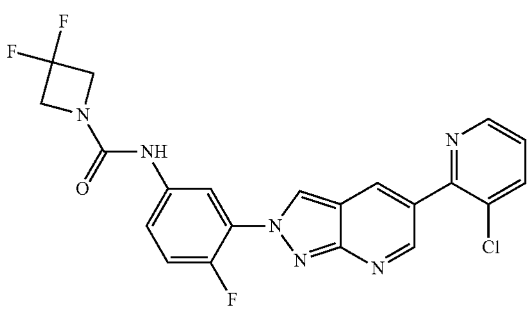 [SMILES: O=C(Nc1ccc(F)c(-n2cc3cc(-c4ncccc4Cl)cnc3n2)c1)N1CC(F)(F)C1] | ¹H NMR (400 MHz, DMSO-d6) δ 9.28 (s, 1 H), 9.02 (dd, J = 16.81, 2.01 Hz, 2 H), 8.64-8.75 (m, 2 H), 8.28 (dd, J = 6.78, 2.51 Hz, 1 H), 8.14 (d, J = 8.28 Hz, 1 H), 7.67-7.77 (m, 1 H), 7.45-7.57 (m, 2 H), 4.43 (t, J = 12.67 Hz, 4 H). Method 1: RT = 2.86 min.; M + H = 459.1 |
| 311 | 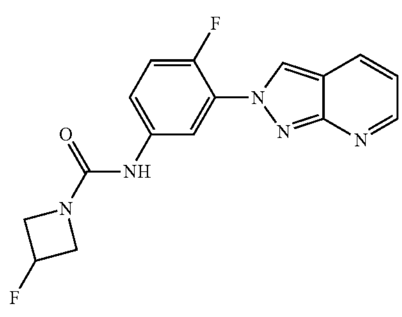 [SMILES: O=C(Nc1ccc(F)c(-n2cc3cccnc3n2)c1)N1CC(F)C1] | ¹H NMR (400 MHz, DMSO-d6) δ 8.98 (s, 1 H), 8.90 (d, J = 2.26 Hz, 1 H), 8.72 (d, J = 3.01 Hz, 1 H), 8.31 (d, J = 8.28 Hz, 1 H), 8.25 (dd, J = 7.03, 2.51 Hz, 1 H), 7.66-7.73 (m, 1 H), 7.43-7.51 (m, 1 H), 7.20 (dd, J = 8.41, 4.14 Hz, 1 H), 5.29-5.51 (m, 1 H), 4.24-4.39 (m, 2 H), 3.96-4.10 (m, 2 H). Method 1: RT = 2.41 min.; M + H = 330.1 |

TABLE 2-continued

| Cpd No. | Structure | ¹HNMR and HPLC retention time and/or MS |
|---|---|---|
| 312 | 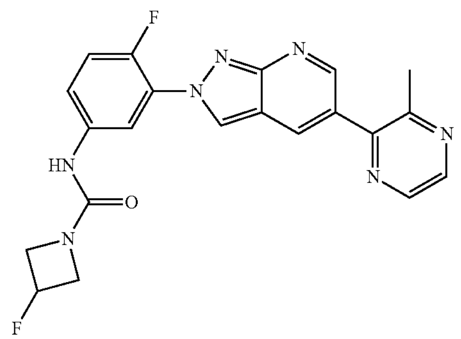 [SMILES: Cc1nccnc1-c1cnc2nn(-c3cc(NC(=O)N4CC(F)C4)ccc3F)cc2c1] | ¹H NMR (400 MHz, DMSO-d6) δ 8.93-9.06 (m, 3 H), 8.54-8.68 (m, 3 H), 8.29 (dd, J = 6.90, 2.38 Hz, 1 H), 7.67-7.76 (m, 1 H), 7.49 (t, J = 10.16 Hz, 1 H), 5.27-5.55 (m, 1 H), 4.25-4.42 (m, 2 H), 3.94-4.14 (m, 2 H), 2.68 (s, 3 H). Method 1: RT = 2.48 min.; M + H = 422.1 |
| 313 | 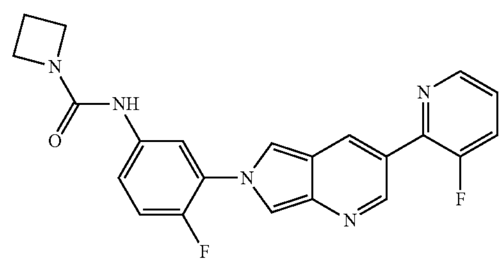 [SMILES: O=C(Nc1ccc(F)c(-n2cc3cc(-c4ncccc4F)cnc3c2)c1)N1CCC1] | ¹H NMR (400 MHz, DMSO-d6) δ 9.27 (s, 1 H), 9.04 (d, J = 2.26 Hz, 1 H), 8.82 (d, J = 1.51 Hz, 1 H), 8.75 (s, 1 H), 8.63 (br d, J = 4.52 Hz, 1 H), 8.30 (dd, J = 6.90, 2.64 Hz, 1 H), 7.93 (dd, J = 10.92, 8.91 Hz, 1 H), 7.73 (dt, J = 9.03, 3.39 Hz, 1 H), 7.55 (dt, J = 8.34, 4.24 Hz, 1 H), 7.48 (dd, J = 11.29, 9.03 Hz, 1 H), 3.91-4.07 (m, 4 H), 2.21 (quin, J = 7.53 Hz, 2H). Method 2: RT = 0.85 min.; M + H = 407.1 |
| 314 | 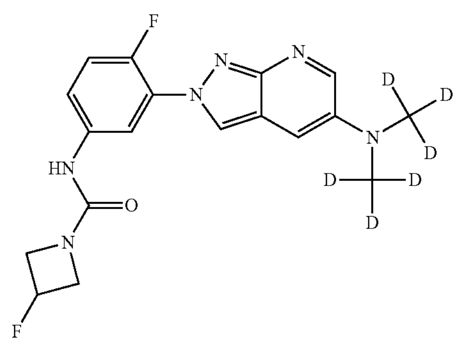 [SMILES: [2H]C([2H])([2H])N(c1cnc2nn(-c3cc(NC(=O)N4CC(F)C4)ccc3F)cc2c1)C([2H])([2H])[2H]] | ¹H NMR (400 MHz, DMSO-d6) δ 8.94 (s, 1 H), 8.69 (d, J = 3.01 Hz, 1 H), 8.54 (d, J = 2.76 Hz, 1 H), 8.21 (dd, J = 7.03, 2.76 Hz, 1 H), 7.61-7.71 (m, 1 H), 7.43 (dd, J = 11.42, 9.16 Hz, 1 H), 7.14 (d, J = 3.01 Hz, 1 H), 5.28-5.53 (m, 1 H), 4.22-4.43 (m, 2 H), 3.92-4.11 (m, 2 H). Method 1: RT = 2.63 min.; M + H = 379.3 |
| 315 | 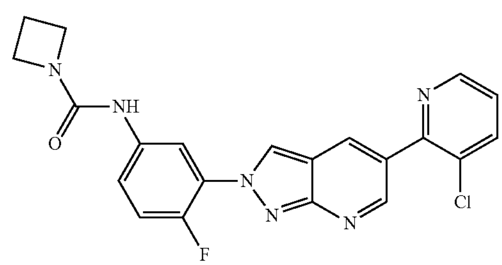 [SMILES: O=C(Nc1ccc(F)c(-n2cc3cc(-c4ncccc4Cl)cnc3n2)c1)N1CCC1] | ¹H NMR (400 MHz, DMSO-d6) δ 9.02 (d, J = 2.51 Hz, 1 H), 9.00 (d, J = 2.26 Hz, 1 H), 8.76 (s, 1 H), 8.72 (dd, J = 4.64, 1.38 Hz, 1 H), 8.68 (d, J = 2.26 Hz, 1 H), 8.29 (dd, J = 6.90, 2.64 Hz, 1 H), 8.14 (dd, J = 8.16, 1.38 Hz, 1 H), 7.68-7.82 (m, 1 H), 7.40-7.55 (m, 2 H), 3.99 (t, J = 7.53 Hz, 4 H), 2.21 (quin, J = 7.59 Hz, 2 H). Method 1: RT = 2.73 min.; M + H = 423.1 |
| 316 | 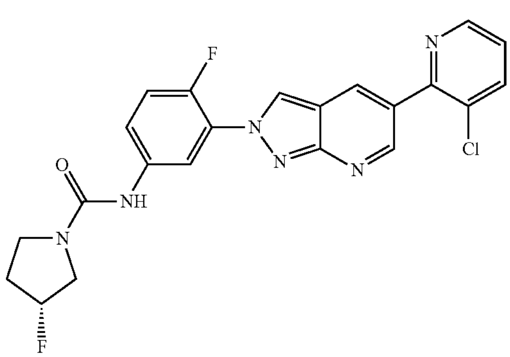 [SMILES: O=C(Nc1ccc(F)c(-n2cc3cc(-c4ncccc4Cl)cnc3n2)c1)N1CC[C@@H](F)C1] | ¹H NMR (400 MHz, DMSO-d6) δ 9.04 (d, J = 2.45 Hz, 1 H), 9.00 (d, J = 2.20 Hz, 1 H), 8.72 (dd, J = 4.65, 1.47 Hz, 1 H), 8.65-8.70 (m, 2 H), 8.32 (dd, J = 6.85, 2.69 Hz, 1 H), 8.14 (dd, J = 8.19, 1.35 Hz, 1 H), 7.71-7.80 (m, 1 H), 7.45-7.56 (m, 2 H), 5.26-5.52 (m, 1 H), 3.40-3.81 (m, 4 H), 2.01-2.28 (m, 2 H). Method 2: RT = 0.89 min.; M + H = 455.2 |

TABLE 2-continued

| Cpd No. | Structure | ¹HNMR and HPLC retention time and/or MS |
|---|---|---|
| 317 | 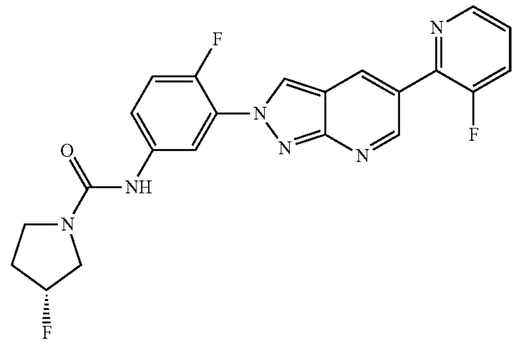 [SMILES: O=C(Nc1ccc(F)c(-n2cc3cc(-c4ncccc4F)cnc3n2)c1)N1CC[C@@H](F)C1] | ¹H NMR (400 MHz, DMSO-d6) δ 9.27 (dd, J = 2.20, 1.22 Hz, 1 H), 9.05 (d, J = 2.45 Hz, 1 H), 8.80-8.86 (m, 1 H), 8.67 (s, 1 H), 8.63 (dt, J = 4.65, 1.71 Hz, 1 H), 8.31 (dd, J = 7.09, 2.69 Hz, 1 H), 7.93 (ddd, J = 11.68, 8.38, 1.22 Hz, 1 H), 7.71-7.79 (m, 1 H), 7.55 (dt, J = 8.38, 4.25 Hz, 1 H), 7.49 (dd, J = 11.25, 9.05 Hz, 1 H), 5.26-5.54 (m, 1 H), 3.42-3.80 (m, 4 H), 2.01-2.27 (m, 2 H).<br>Method 2: RT = 0.87 min.; M + H = 439.1 |
| 318 | 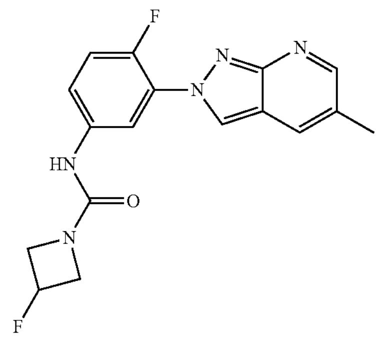 [SMILES: Cc1cnc2nn(-c3cc(NC(=O)N4CC(F)C4)ccc3F)cc2c1] | ¹H NMR (400 MHz, METHANOL-d4) δ 8.65 (d, J = 2.45 Hz, 1 H), 8.60 (d, J = 2.20 Hz, 1 H), 8.14 (dd, J = 6.72, 2.81 Hz, 1 H), 8.09 (dd, J = 2.08, 1.10 Hz, 1 H), 7.62-7.70 (m, 1 H), 7.36 (dd, J = 11.00, 9.05 Hz, 1 H), 5.26-5.51 (m, 1 H), 4.33-4.48 (m, 2 H), 4.06-4.23 (m, 2 H), 2.50 (d, J = 0.98 Hz, 3 H).<br>Method 1: RT = 2.62 min.; M + H = 344.1 |
| 319 | 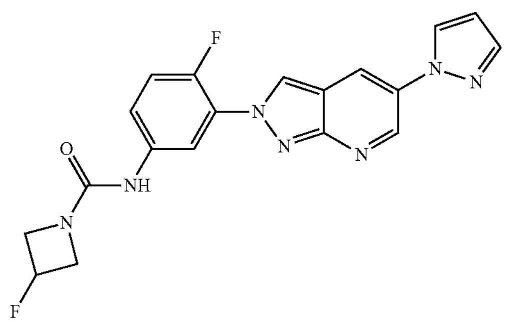 [SMILES: O=C(Nc1ccc(F)c(-n2cc3cc(-n4cccn4)cnc3n2)c1)N1CC(F)C1] | ¹H NMR (400 MHz, DMSO-d6) δ 9.29-9.35 (m, 1 H), 8.94-9.07 (m, 2 H), 8.64 (d, J = 2.51 Hz, 1 H), 8.62 (d, J = 2.76 Hz, 1 H), 8.27 (dd, J = 7.03, 2.76 Hz, 1 H), 7.85 (d, J = 1.76 Hz, 1 H), 7.67-7.75 (m, 1 H), 7.67-7.75 (m, 1 H), 7.50 (dd, J = 11.17, 9.16 Hz, 1 H), 6.61-6.68 (m, 1 H), 5.27-5.61 (m, 1 H), 4.23-4.43 (m, 2 H), 3.95-4.14 (m, 2 H).<br>Method 1: RT = 2.59 min.; M + H = 396.1 |
| 320 | 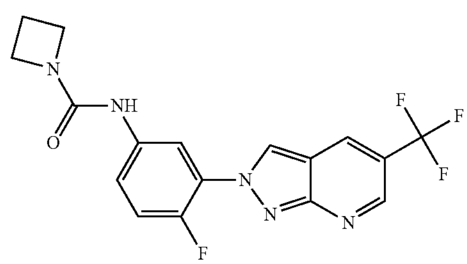 [SMILES: O=C(Nc1ccc(F)c(-n2cc3cc(C(F)(F)F)cnc3n2)c1)N1CCC1] | ¹H NMR (400 MHz, DMSO-d6) δ 9.14 (d, J = 2.26 Hz, 1 H), 9.01 (d, J = 2.51 Hz, 1 H), 8.86-8.91 (m, 1 H), 8.78 (s, 1 H), 8.30 (dd, J = 6.90, 2.64 Hz, 1 H), 7.70-7.78 (m, 1 H), 7.49 (dd, J = 11.17, 9.16 Hz, 1 H), 3.98 (t, J = 7.53 Hz, 4 H), 2.15-2.27 (m, 2 H).<br>Method 1: RT = 2.82 min.; M + H = 380.1 |
| 321 | 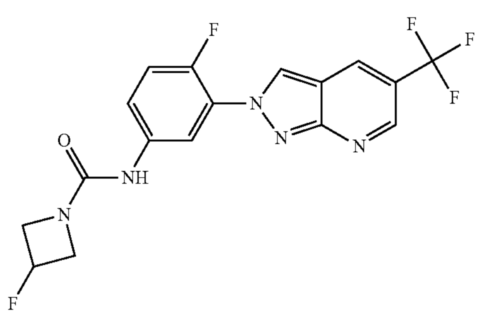 [SMILES: O=C(Nc1ccc(F)c(-n2cc3cc(C(F)(F)F)cnc3n2)c1)N1CC(F)C1] | ¹H NMR (400 MHz, DMSO-d6) δ 9.14 (d, J = 2.45 Hz, 1 H), 8.94-9.07 (m, 2 H), 8.88 (d, J = 1.22 Hz, 1 H), 8.28 (dd, J = 6.85, 2.69 Hz, 1 H), 7.67-7.80 (m, 1 H), 7.51 (dd, J = 11.13, 9.17 Hz, 1 H), 5.27-5.56 (m, 1 H), 4.23-4.44 (m, 2 H), 3.93-4.13 (m, 2 H).<br>Method 1: RT = 2.83 min.; M + H = 398.0 |

TABLE 2-continued

| Cpd No. | Structure | ¹HNMR and HPLC retention time and/or MS |
|---|---|---|
| 322 | 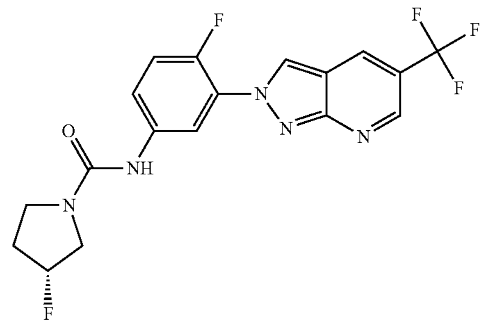 [SMILES: O=C(Nc1ccc(F)c(-n2cc3cc(C(F)(F)F)cnc3n2)c1)N1CC[C@@H](F)C1] | ¹H NMR (400 MHz, DMSO-d6) δ 9.14 (d, J = 2.20 Hz, 1 H), 9.01 (d, J = 2.20 Hz, 1 H), 8.88 (d, J = 1.22 Hz, 1 H), 8.67 (s, 1 H), 8.32 (dd, J = 7.09, 2.69 Hz, 1 H), 7.73-7.81 (m, 1 H), 7.50 (dd, J = 11.13, 9.17 Hz, 1 H), 5.28-5.51 (m, 1 H), 3.41-3.78 (m, 4 H), 1.98-2.30 (m, 2 H). Method 1: RT = 2.83 min.; M + H = 412.1 |
| 323 | 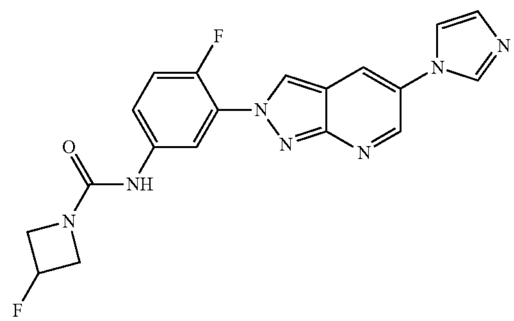 [SMILES: O=C(Nc1ccc(F)c(-n2cc3cc(-n4ccnc4)cnc3n2)c1)N1CC(F)C1] | ¹H NMR (400 MHz, DMSO-d6) δ 9.06 (d, J = 2.51 Hz, 1 H), 9.00 (d, J = 2.26 Hz, 2 H), 8.51 (d, J = 2.51 Hz, 1 H), 8.27 (dd, J = 7.03, 2.76 Hz, 1 H), 7.86 (br s, 1 H), 7.64-7.77 (m, 1 H), 7.50 (dd, J = 11.04, 9.29 Hz, 1 H), 7.19 (br s, 1 H) 5.26-5.57 (m, 1 H), 4.26-4.44 (m, 2 H), 3.94-4.14 (m, 2 H). Method 1: RT = 1.83 min.; M + H = 396.1 |
| 324 | 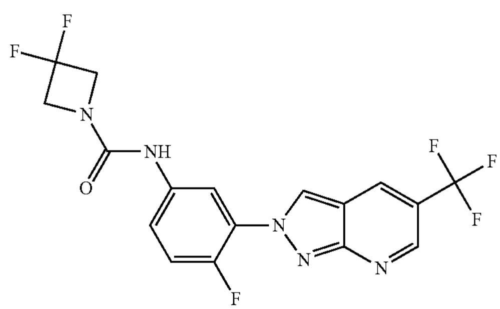 [SMILES: O=C(Nc1ccc(F)c(-n2cc3cc(C(F)(F)F)cnc3n2)c1)N1CC(F)(F)C1] | ¹H NMR (400 MHz, DMSO-d6) δ 9.27 (br s, 1 H), 9.15 (d, J = 2.26 Hz, 1 H), 9.01 (d, J = 2.26 Hz, 1 H), 8.89 (dd, J = 2.26, 1.00 Hz, 1 H), 8.28 (dd, J = 6.90, 2.63 Hz, 1 H), 7.69-7.76 (m, 1 H), 7.54 (dd, J = 11.17, 9.16 Hz, 1 H), 4.42 (t, J = 12.67 Hz, 4 H). Method 2: RT = 0.98 min.; M + H = 416.0 |
| 325 | 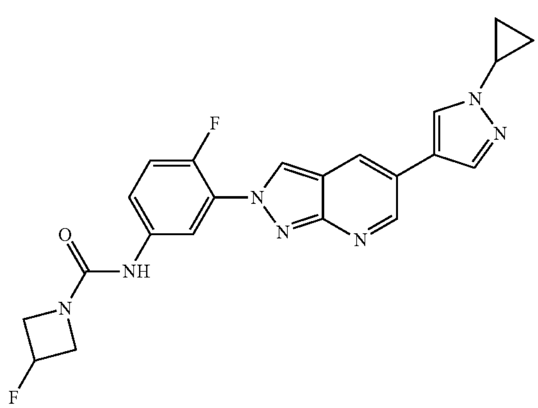 [SMILES: O=C(Nc1ccc(F)c(-n2cc3cc(-c4cnn(C5CC5)c4)cnc3n2)c1)N1CC(F)C1] | ¹H NMR (400 MHz, DMSO-d6) δ 9.04 (d, J = 2.45 Hz, 1 H), 8.97 (s, 1 H), 8.84 (d, J = 2.44 Hz, 1 H), 8.42 (s, 1 H), 8.37 (d, J = 2.20 Hz, 1 H), 8.24 (dd, J = 7.09, 2.69 Hz, 1 H), 8.02 (s, 1 H), 7.63-7.73 (m, 1 H), 7.47 (dd, J = 11.13, 9.17 Hz, 1 H), 5.28-5.53 (m, 1 H), 4.24-4.41 (m, 2 H), 3.95-4.11 (m, 2 H), 3.78 (tt, J = 7.34, 3.79 Hz, 1 H), 0.96-1.17 (m, 4 H). Method 1: RT = 2.73 min.; M + H = 436.1 |

TABLE 2-continued

| Cpd No. | Structure | ¹HNMR and HPLC retention time and/or MS |
|---|---|---|
| 326 | 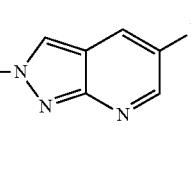 | ¹H NMR (400 MHz, DMSO) δ 10.54 (s, 1 H), 8.63 (d, J = 2.38 Hz, 1 H), 8.29-8.41 (m, 2 H), 7.66 (br d, J = 9.29 Hz, 1 H), 7.40-7.55 (m, 1 H), 7.14 (d, J = 2.64 Hz, 1 H), 4.40 (t, J = 12.17 Hz, 4 H), 1.72-1.85 (m, 1 H), 0.83 (br d, J = 6.02 Hz, 4 H). Method 2: RT = 0.93 min.; M + H = 388.2 |
| 327 | 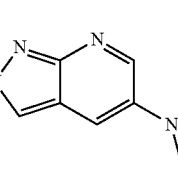 | ¹H NMR (400 MHz, DMSO) δ 10.53 (s, 1 H), 8.58 (d, J = 2.51 Hz, 1 H), 8.26-8.39 (m, 2 H), 7.60-7.71 (m, 1 H), 7.40-7.55 (m, 1 H), 7.00 (d, J = 2.76 Hz, 1 H), 5.39-5.67 (m, 1 H), 4.19-4.35 (m, 2 H), 3.92-4.09 (m, 2 H), 1.74-1.82 (m, 1 H), 0.83 (br d, J = 5.90 Hz, 4 H). Method 1: RT = 2.79 min.; M + H = 370.2 |
| 328 | 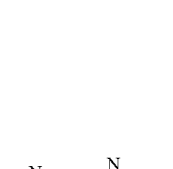 | ¹H NMR (400 MHz, DMSO-d6) δ 9.02 (d, J = 2.69 Hz, 1 H), 8.97 (d, J = 2.44 Hz, 1 H), 8.44 (d, J = 2.69 Hz, 1 H), 8.26 (dd, J = 7.09, 2.69 Hz, 1 H), 8.20 (d, J = 1.47 Hz, 1 H), 7.67-7.74 (m, 1 H), 7.44-7.56 (m, 2 H), 5.29-5.52 (m, 1 H), 4.26-4.39 (m, 2 H), 3.96-4.11 (m, 2 H), 2.21 (s, 3 H). Method 1: RT = 1.87 min.; M + H = 410.1 |
| 329 | 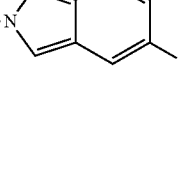 | ¹H NMR (400 MHz, DMSO-d6) δ 9.43 (d, J = 2.20 Hz, 1 H), 8.97-9.05 (m, 2 H), 8.91 (d, J = 2.45 Hz, 1 H), 8.74 (d, J = 3.18 Hz, 1 H) ,8.28 (dd, J = 7.09, 2.69 Hz, 1 H), 8.21 (dd, J = 8.93, 4.28 Hz, 1 H), 7.92 (td, J = 8.80, 2.93 Hz, 1 H), 7.68-7.75 (m, 1 H), 7.50 (dd, J = 11.25, 9.05 Hz, 1 H), 5.29-5.53 (m, 1 H), 4.25-4.41 (m, 2 H), 3.95-4.12 (m, 2 H). Method 2: RT = 0.88 min.; M + H = 425.0 |
| 330 | 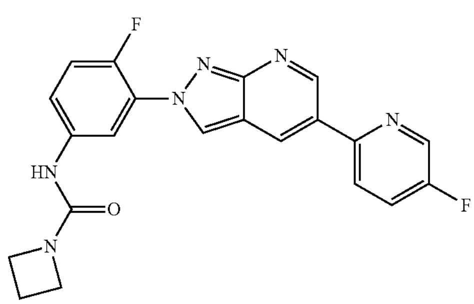 [SMILES: O=C(Nc1ccc(F)c(-n2cc3cc(-c4ccc(F)cn4)cnc3n2)c1)N1CCC1] | ¹H NMR (400 MHz, DMSO-d6) δ 9.43 (d, J = 2.20 Hz, 1 H), 9.00 (d, J = 2.45 Hz, 1 H), 8.90 (d, J = 2.20 Hz, 1 H), 8.70-8.81 (m, 2 H), 8.29 (dd, J = 7.09, 2.69 Hz, 1 H), 8.21 (dd, J = 8.80, 4.16 Hz, 1 H), 7.91 (td, J = 8.68, 2.93 Hz, 1 H), 7.68-7.77 (m, 1 H), 7.47 (dd, J = 11.13, 9.17 Hz, 1 H), 3.99 (t, J = 7.58 Hz, 4 H), 2.21 (quin, J = 7.52 Hz, 2 H). Method 1: RT = 2.82 min.; M + H = 407.0 |

TABLE 2-continued

| Cpd No. | Structure | ¹HNMR and HPLC retention time and/or MS |
|---|---|---|
| 331 | 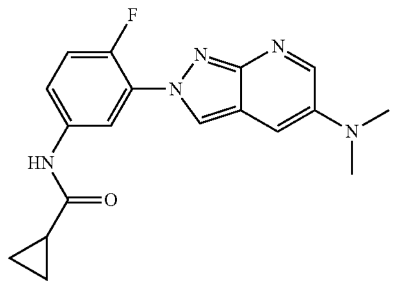 [SMILES: CN(C)c1cnc2nn(-c3cc(NC(=O)C4CC4)ccc3F)cc2c1] | ¹H NMR (400 MHz, DMSO) δ 10.53 (s, 1 H), 8.70 (d, J = 2.93 Hz, 1 H), 8.56 (d, J = 2.69 Hz, 1 H), 8.35 (dd, J = 7.15, 2.63 Hz, 1 H), 7.63-7.71 (m, 1 H), 7.48 (dd, J = 11.31, 9.11 Hz, 1 H), 7.15 (d, J = 2.93 Hz, 1 H), 2.95 (s, 6 H), 1.79 (quin, J = 6.24 Hz, 1 H) 0.79-0.87 (m, 4 H). Method 2: RT = 0.85 min.; M + H = 340.2 |
| 332 | 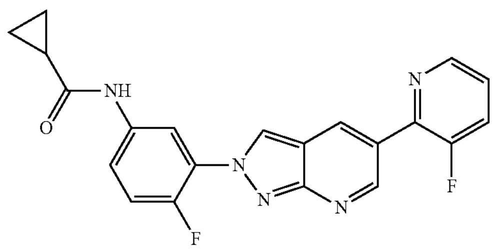 [SMILES: O=C(Nc1ccc(F)c(-n2cc3cc(-c4ncccc4F)cnc3n2)c1)C1CC1] | ¹H NMR (400 MHz, DMSO) δ 10.50 (s, 1 H), 9.18 (d, J = 0.88 Hz, 1 H), 8.97 (d, J = 2.51 Hz, 1 H) 8.69-8.81 (m, 1 H) 8.54 (dd, J = 4.52, 1.88 Hz, 1 H), 8.33 (dd, J = 7.09, 2.57 Hz, 1 H), 7.84 (dd, J = 10.98, 8.85 Hz, 1 H), 7.57-7.69 (m, 1 H), 7.38-7.53 (m, 2 H), 1.61-1.75 (m, 1 H), 0.67-0.85 (m, 4 H). Method 1: RT = 2.85 min.; M + H = 392.2 |
| 333 | 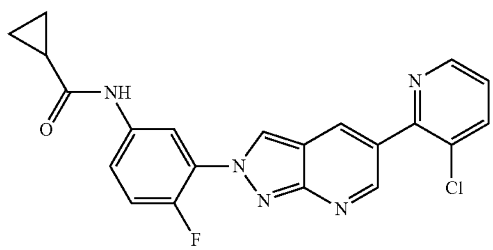 [SMILES: O=C(Nc1ccc(F)c(-n2cc3cc(-c4ncccc4Cl)cnc3n2)c1)C1CC1] | ¹H NMR (400 MHz, DMSO) δ 10.57 (s, 1 H), 9.03 (d, J = 2.26 Hz, 1 H), 8.99 (d, J = 2.38 Hz, 1 H), 8.65-8.73 (m, 2 H), 8.41 (br d, J = 7.28 Hz, 1 H), 8.13 (d, J = 8.16 Hz, 1 H), 7.71 (br s, 1 H), 7.48-7.58 (m, 2 H), 1.73-1.83 (m, 1 H), 0.80-0.88 (m, 4 H). Method 1: RT = 2.87 min.; M + H = 408.2 |
| 334 | 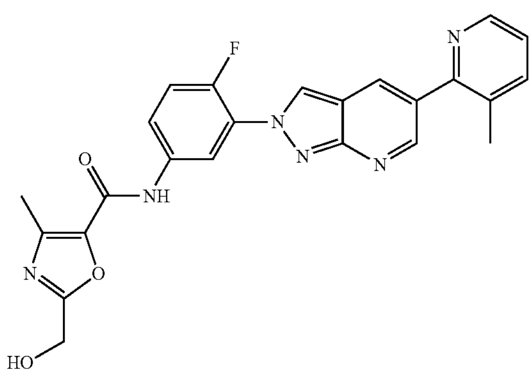 [SMILES: Cc1cccnc1-c1cnc2nn(-c3cc(NC(=O)c4oc(CO)nc4C)ccc3F)cc2c1] | ¹H NMR (400 MHz, DMSO-d6) δ 10.63 (s, 1 H), 9.00 (d, J = 2.20 Hz, 1 H), 8.94 (d, J = 2.20 Hz, 1 H), 8.62 (dd, J = 7.09, 2.45 Hz, 1 H), 8.57 (d, J = 3.67 Hz, 1 H), 8.51 (d, J = 2.20 Hz, 1 H), 7.91-8.01 (m, 1 H), 7.81 (d, J = 7.34 Hz, 1 H), 7.60 (dd, J = 11.00, 9.05 Hz, 1 H), 7.37 (dd, J = 7.70, 4.77 Hz, 1 H), 5.83 (t, J = 5.99 Hz, 1 H), 4.60 (d, J = 6.11 Hz, 2 H), 2.45 (s, 6 H). Method 1: RT = 2.57 min.; M + H = 459.0 |
| 335 | 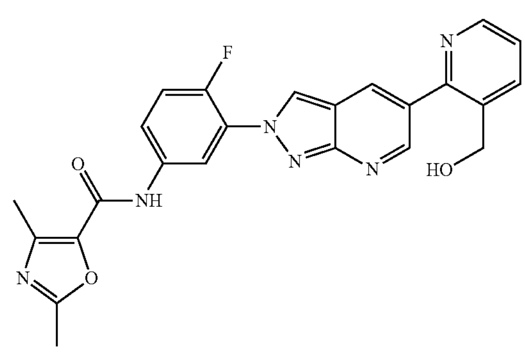 [SMILES: Cc1nc(C)c(C(=O)Nc2ccc(F)c(-n3cc4cc(-c5ncccc5CO)cnc4n3)c2)o1] | ¹H NMR (400 MHz, DMSO-d6) δ 10.55 (s, 1 H), 9.03 (d, J = 2.20 Hz, 1 H), 8.98 (d, J = 2.20 Hz, 1 H), 8.65 (dd, J = 4.65, 1.71 Hz, 1 H), 8.61 (dd, J = 7.09, 2.45 Hz, 1 H), 8.57 (d, J = 2.20 Hz, 1 H), 8.00-8.07 (m, 1 H), 7.94 (dt, J = 9.05, 3.42 Hz, 1 H), 7.60 (dd, J = 11.00, 9.29 Hz, 1 H), 7.48 (dd, J = 7.70, 4.77 Hz, 1 H), 5.55 (br s, 1 H), 4.60 (s, 2 H), 2.52 (br s, 3 H), 2.41 (s, 3 H). Method 1: RT = 2.49 min.; M + H = 458.9 |

TABLE 2-continued

| Cpd No. | Structure | ¹HNMR and HPLC retention time and/or MS |
|---|---|---|
| 336 | 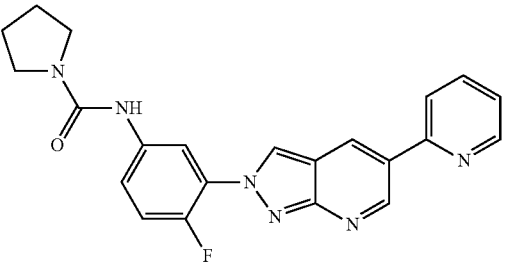 [SMILES: O=C(Nc1ccc(F)c(-n2cc3cc(-c4ccccn4)cnc3n2)c1)N1CCCC1] | ¹H NMR (400 MHz, DMSO) δ 9.46 (d, J = 2.32 Hz, 1 H), 8.99 (d, J = 2.32 Hz, 1 H), 8.93 (d, J = 2.32 Hz, 1 H), 8.73 (d, J = 4.04 Hz, 1 H), 8.51 (s, 1 H), 8.30 (dd, J = 6.97, 2.57 Hz, 1 H), 8.11 (d, J = 7.95 Hz, 1 H), 7.95 (td, J = 7.76, 1.71 Hz, 1 H), 7.74 (dt, J = 8.99, 3.45 Hz, 1 H), 7.37-7.50 (m, 2 H), 3.42-3.48 (m, 4 H), 1.86 (br s, 4 H) Method 1: RT = 2.67 min.; M + H = 403.3 |
| 337 | 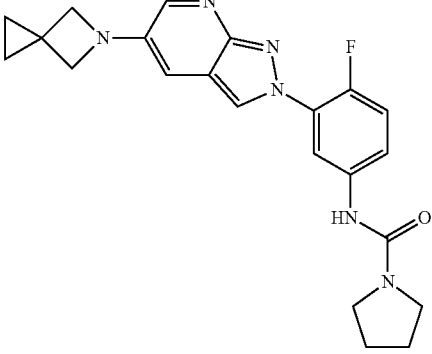 | ¹H NMR (400 MHz, DMSO) δ 8.52 (d, J = 2.64 Hz, 1 H), 8.46 (s, 1 H), 8.28 (d, J = 2.76 Hz, 1 H), 8.23 (dd, J = 7.09, 2.57 Hz, 1 H), 7.67 (dt, J = 8.60, 3.54 Hz, 1 H), 7.40 (dd, J = 11.29, 9.16 Hz, 1 H), 6.92 (d, J = 2.76 Hz, 1 H), 4.02 (s, 4 H), 3.46-3.49 (m, 4 H), 1.86 (br t, J = 6.34 Hz, 4 H), 0.68 (s, 4 H), M + H = 407.3 |
| 338 | 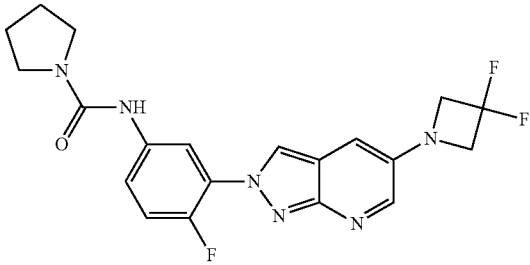 [SMILES: O=C(Nc1ccc(F)c(-n2cc3cc(N4CC(F)(F)C4)cnc3n2)c1)N1CCCC1] | ¹H NMR (400 MHz, DMSO) δ 8.62 (d, J = 2.69 Hz, 1 H), 8.47 (s, 1 H), 8.36 (d, J = 2.81 Hz, 1 H), 8.23 (dd, J = 7.09, 2.69 Hz, 1 H), 7.65-7.73 (m, 1 H), 7.41 (dd, J = 11.25, 9.17 Hz, 1 H), 7.14 (d, J = 2.81 Hz, 1 H), 4.40 (t, J = 12.23 Hz, 4 H), 3.38-3.41 (m, 4 H), 1.86 (br t, J = 6.48 Hz, 4 H) Method 1: RT = 2.86 min.; M + H = 417.0 |
| 339 | 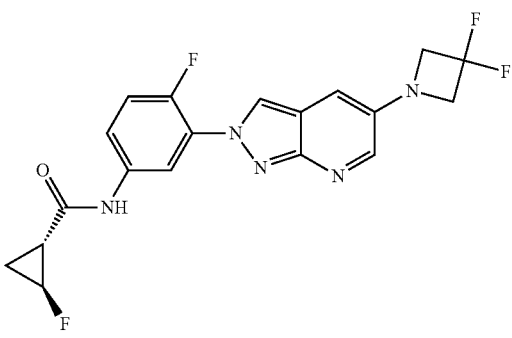<br>trans - racemic | ¹H NMR (400 MHz, DMSO-d6) δ 10.69 (s, 1 H), 8.64 (d, J = 2.64 Hz, 1 H), 8.37 (d, J = 2.89 Hz, 1 H), 8.32 (dd, J = 7.03, 2.63 Hz, 1 H), 7.59-7.69 (m, 1 H), 7.51 (dd, J = 11.11, 9.10 Hz, 1 H), 7.14 (d, J = 2.76 Hz, 1 H), 4.79-5.06 (m, 1 H), 4.41 (t, J = 12.23 Hz, 4 H), 2.23-2.33 (m, 1 H), 1.49-1.64 (m, 1 H), 1.27 (dq, J = 13.11, 6.46 Hz, 1 H). Method 2: RT = 0.97 min.; M + H = 406.2 |
| 340 | 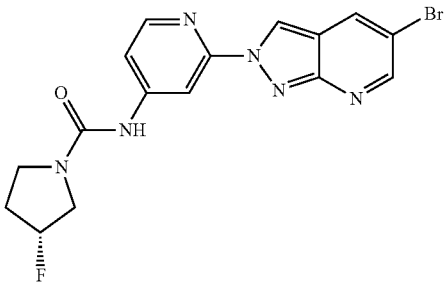 [SMILES: O=C(Nc1ccnc(-n2cc3cc(Br)cnc3n2)c1)N1CC[C@@H](F)C1] | ¹H NMR (400 MHz, METHANOL-d4) δ 9.12 (s, 1 H), 8.59 (d, J = 2.20 Hz, 1 H), 8.41-8.47 (m, 1 H), 8.33 (d, J = 1.96 Hz, 1 H), 8.24 (d, J = 5.62 Hz, 1 H), 7.64 (dd, J = 5.75, 2.08 Hz, 1 H), 5.13-5.36 (m, 1 H), 3.48-3.79 (m, 4 H), 1.99-2.28 (m, 2 H). Method 2: RT = 0.90 min.; M + H = 405.1, 407.1 |

TABLE 2-continued

| Cpd No. | Structure | ¹HNMR and HPLC retention time and/or MS |
|---|---|---|
| 341 | 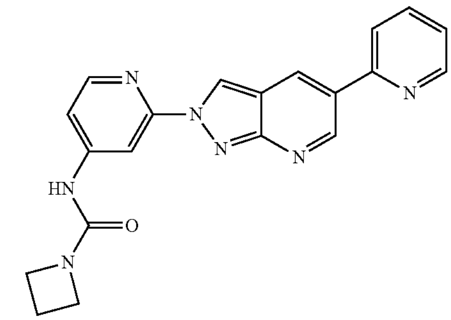 [SMILES: O=C(Nc1ccnc(-n2cc3cc(-c4ccccn4)cnc3n2)c1)N1CCC1] | ¹H NMR (400 MHz, DMSO-d6), δ 9.46 (d, J = 2.20 Hz, 1 H), 9.37 (s, 1 H), 9.26 (s, 1 H), 8.95 (d, J = 2.45 Hz, 1 H), 8.74 (d, J = 3.91 Hz, 1 H), 8.52 (d, J = 1.71 Hz, 1 H), 8.37 (d, J = 5.62 Hz, 1 H), 8.12 (d, J = 8.07 Hz, 1 H), 7.96 (td, J = 7.70, 1.71 Hz, 1 H), 7.74 (dd, J = 5.62, 1.96 Hz, 1 H), 7.42 (dd, J = 7.09, 5.14 Hz, 1 H), 4.05 (t, J = 7.58 Hz, 4 H), 2.23 (quin, J = 7.58 Hz, 2 H). Method 1: RT = 2.67 min.; M + H = 372.0 |
| 342 | 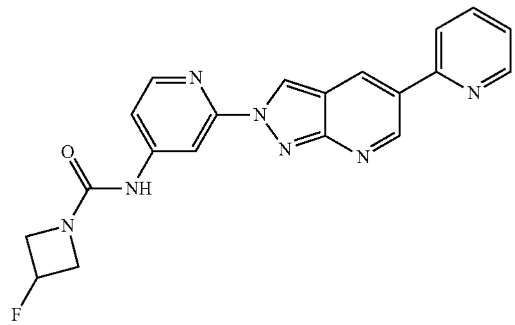 [SMILES: O=C(Nc1ccnc(-n2cc3cc(-c4ccccn4)cnc3n2)c1)N1CC(F)C1] | ¹H NMR (400 MHz, DMSO-d6), δ 9.43-9.50 (m, 2 H), 9.38 (s, 1 H), 8.95 (d, J = 2.26 Hz, 1 H), 8.74 (d, J = 4.02 Hz, 1 H), 8.50 (d, J = 1.76 Hz, 1 H), 8.39 (d, J = 5.77 Hz, 1 H), 8.13 (d, J = 8.03 Hz, 1 H), 7.97 (td, J = 7.78, 1.76 Hz, 1 H), 7.73 (dd, J = 5.65, 1.88 Hz, 1 H), 7.43 (dd, J = 6.78, 4.77 Hz, 1 H), 5.31-5.54 (m, 1 H), 4.32-4.48 (m, 2 H), 4.01-4.17 (m, 2 H). Method 1: RT = 2.67 min.; M + H = 390.0 |
| 343 | 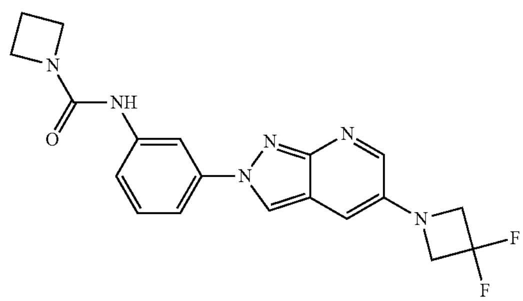 [SMILES: O=C(Nc1cccc(-n2cc3cc(N4CC(F)(F)C4)cnc3n2)c1)N1CCC1] | ¹H NMR (400 MHz, DMSO-d6) δ 8.80 (s, 1 H), 8.68 (s, 1 H), 8.30-8.35 (m, 2 H), 7.63 (br d, J = 8.41 Hz, 1 H), 7.59 (br d, J = 8.03 Hz, 1 H), 7.39-7.47 (m, 1 H), 7.13 (d, J = 2.76 Hz, 1 H), 4.41 (t, J = 12.23 Hz, 4 H), 3.99 (t, J = 7.53 Hz, 4 H), 2.21 (quin, J = 7.56 Hz, 2 H). Method 2: RT = 0.84 min.; M + H = 385.2 |
| 344 | 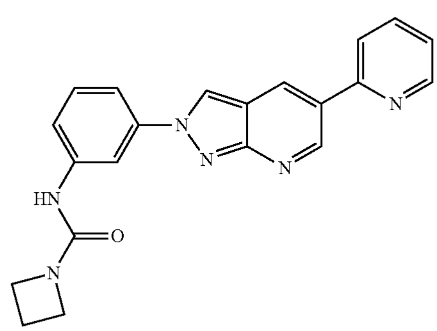 [SMILES: O=C(Nc1cccc(-n2cc3cc(-c4ccccn4)cnc3n2)c1)N1CCC1] | ¹H NMR (400 MHz, DMSO-d6) δ 9.44 (d, J = 2.20 Hz, 1 H), 9.18 (s, 1 H), 8.91 (d, J = 2.32 Hz, 1 H), 8.70-8.78 (m, 2 H), 8.36-8.42 (m, 1 H), 8.14 (d, J = 8.07 Hz, 1 H), 7.95 (td, J = 7.73, 1.77 Hz, 1 H), 7.65-7.71 (m, 2 H), 7.44-7.51 (m, 1 H), 7.42 (dd, J = 7.15, 5.20 Hz, 1 H), 4.01 (t, J = 7.58 Hz, 4 H), 2.22 (quin, J = 7.58 Hz, 2 H), 1.47-1.61 (m, 1 H), 1.19-1.34 (m, 1 H), 1.00-1.08 (m, 1 H), 0.85 (t, J = 7.40 Hz, 1 H). Method 2: RT = 0.74 min.; M + H = 371.0 |
| 345 | 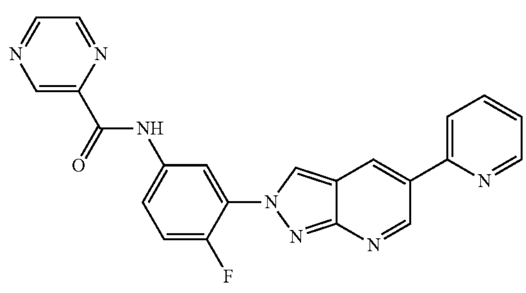 [SMILES: O=C(Nc1ccc(F)c(-n2cc3cc(-c4ccccn4)cnc3n2)c1)c1cnccn1] | ¹H NMR (400 MHz, DMSO-d₆) δ 11.31 (s, 1H), 9.60 (d, J = 2.3 Hz, 1H), 9.45 (d, J = 1.5 Hz, 1H), 9.18 (d, J = 2.5 Hz, 1H), 9.08 (t, J = 2.1 Hz, 2H), 8.97 (dd, J = 2.5, 1.5 Hz, 1H), 8.92-8.79 (m, 2H), 8.31-8.15 (m, 2H), 8.08 (td, J = 7.7, 1.9 Hz, 1H), 7.76 (dd, J = 11.1, 9.1 Hz, 1H), 7.54 (ddd, J = 7.5, 4.8, 1.0 Hz, 1H). Method 1: RT = 2.71 min.; M + H = 412.10 |

TABLE 2-continued

| Cpd No. | Structure | ¹HNMR and HPLC retention time and/or MS |
|---|---|---|
| 346 | 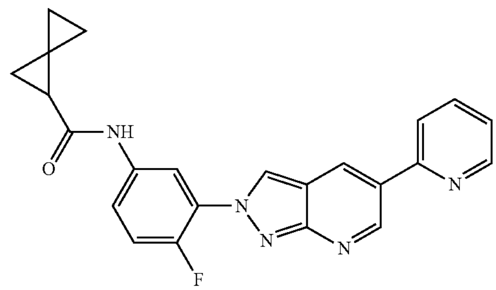 [SMILES: O=C(Nc1ccc(F)c(-n2cc3cc(-c4ccccn4)cnc3n2)c1)C1CC12CC2] | ¹H NMR (400 MHz, DMSO-d₆) δ 10.52 (s, 1H), 9.59 (d, J = 2.3 Hz, 1H), 9.13 (d, J = 2.5 Hz, 1H), 9.05 (d, J = 2.3 Hz, 1H), 8.85 (ddd, J = 4.8, 1.9, 0.9 Hz, 1H), 8.55 (dd, J = 7.0, 2.7 Hz, 1H), 8.24 (dt, J = 8.1, 1.1 Hz, 1H), 8.07 (td, J = 7.7, 1.8 Hz, 1H), 7.81 (ddd, J = 9.1, 4.2, 2.7 Hz, 1H), 7.65 (dd, J = 11.1, 9.1 Hz, 1H), 7.53 (ddd, J = 7.5, 4.8, 1.0 Hz, 1H), 2.26 (dd, J = 7.4, 4.3 Hz, 1H), 1.59-1.44 (m, 2H), 1.12-0.84 (m, 4H). Method 1: RT = 2.85 min.; M + H = 400.1 |
| 347 | 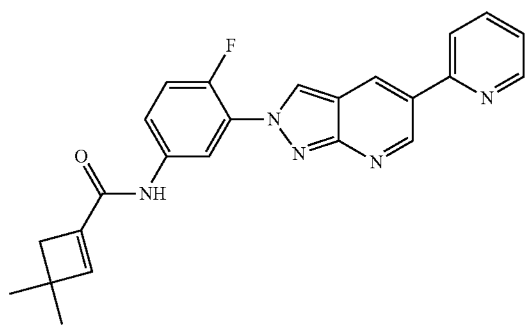 [SMILES: CC1(C)C=C(C(=O)Nc2ccc(F)c(-n3cc4cc(-c5ccccn5)cnc4n3)c2)C1] | ¹H NMR (400 MHz, DMSO-d₆) δ 10.12 (s, 1H), 9.48 (d, J = 2.3 Hz, 1H), 9.04 (d, J = 2.5 Hz, 1H), 8.95 (d, J = 2.3 Hz, 1H), 8.74 (ddd, J = 4.8, 1.8, 0.9 Hz, 1H), 8.48 (dd, J = 7.1, 2.7 Hz, 1H), 8.13 (dt, J = 8.0, 1.1 Hz, 1H), 8.02-7.87 (m, 2H), 7.57 (dd, J = 11.2, 9.1 Hz, 1H), 7.43 (ddd, J = 7.5, 4.8, 1.0 Hz, 1H), 6.93 (s, 1H), 2.47 (s, 2H), 1.24 (s, 6H). Method 1: RT = 3.08 min.; M + H = 414.1 |
| 348 | 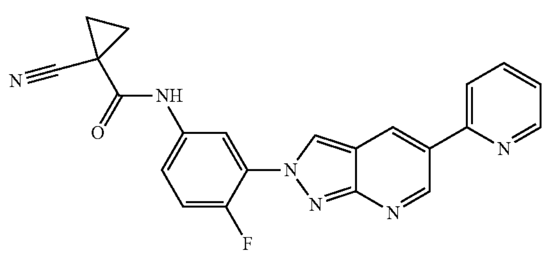 [SMILES: N#CC1(C(=O)Nc2ccc(F)c(-n3cc4cc(-c5ccccn5)cnc4n3)c2)CC1] | ¹H NMR (400 MHz, DMSO-d₆) δ 10.38 (s, 1H), 9.48 (d, J = 2.3 Hz, 1H), 9.04 (d, J = 2.5 Hz, 1H), 8.95 (d, J = 2.3 Hz, 1H), 8.74 (ddd, J = 4.8, 1.9, 1.0 Hz, 1H), 8.41 (dd, J = 7.0, 2.7 Hz, 1H), 8.13 (dt, J = 8.0, 1.1 Hz, 1H), 7.96 (td, J = 7.7, 1.9 Hz, 1H), 7.80 (ddd, J = 9.1, 4.2, 2.7 Hz, 1H), 7.59 (dd, J = 11.2, 9.1 Hz, 1H), 7.43 (ddd, J = 7.5, 4.8, 1.0 Hz, 1H), 1.73 (d, J = 1.0 Hz, 4H). Method 2: RT = 0.83 min.; M + H = 399.1 |
| 349 | cis - racemic | ¹H NMR (400 MHz, DMSO-d₆) δ 10.65 (s, 1H), 9.48 (d, J = 2.3 Hz, 1H), 9.04 (d, J = 2.5 Hz, 1H), 8.95 (d, J = 2.3 Hz, 1H), 8.74 (ddd, J = 4.8, 1.8, 1.0 Hz, 1H), 8.43 (dd, J = 7.0, 2.7 Hz, 1H), 8.13 (dt, J = 8.0, 1.1 Hz, 1H), 7.96 (td, J = 7.7, 1.8 Hz, 1H), 7.74 (ddd, J = 9.1, 4.2, 2.7 Hz, 1H), 7.57 (dd, J = 11.2, 9.1 Hz, 1H), 7.42 (ddd, J = 7.5, 4.8, 1.1 Hz, 1H), 4.98 (dtd, J = 66.2, 6.2, 3.7 Hz, 1H), 2.04 (ddt, J = 9.2, 7.0, 3.6 Hz, 1H), 1.67 (dtd, J = 23.2, 6.7, 3.6 Hz, 1H), 1.19 (ddt, J = 12.5, 9.2, 6.4 Hz, 1H). Method 2: RT = 0.80 min.; M + H = 392.1 |
| 350 | 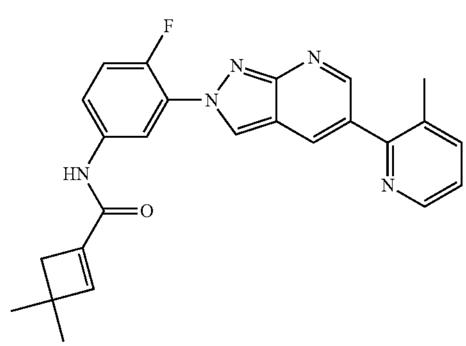 [SMILES: Cc1cccnc1-c1cnc2nn(-c3cc(NC(=O)C4=CC(C)(C)C4)ccc3F)cc2c1] | ¹H NMR (400 MHz, Methanol-d₄) δ 8.78 (d, J = 2.4 Hz, 1H), 8.76 (d, J = 2.3 Hz, 1H), 8.44-8.39 (m, 1H), 8.38 (d, J = 2.2 Hz, 1H), 8.32 (dd, J = 6.8, 2.7 Hz, 1H), 7.88 (s, 1H), 7.81-7.72 (m, 2H), 7.39-7.26 (m, 2H), 6.83 (s, 1H), 2.43 (s, 2H), 2.35 (s, 3H), 1.19 (s, 6H). Method 2: RT = 0.90 min.; M + H = 428.1 |

TABLE 2-continued

| Cpd No. | Structure | $^1$HNMR and HPLC retention time and/or MS |
|---|---|---|
| 351 | 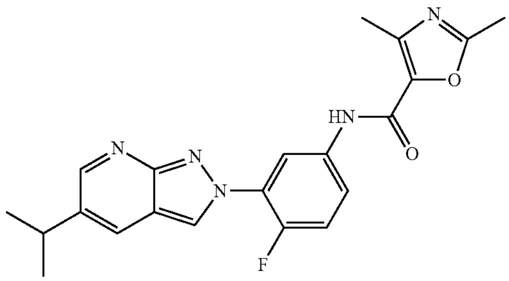 | $^1$H NMR (400 MHz, DMSO-d$_6$) δ ppm 10.52 (br s, 1 H), 8.83 (d, J = 2.64 Hz, 1 H), 8.70 (d, J = 2.26 Hz, 1 H), 8.56 (dd, J = 7.03, 2.64 Hz, 1 H), 8.07 (d, J = 1.76 Hz, 1 H), 7.86-7.94 (m, 1 H), 7.56 (dd, J = 11.11, 9.10 Hz, 1 H), 3.04-3.15 (m, 1 H), 2.50-2.51 (m, 3 H), 2.40 (s, 3 H), 1.31 (d, J = 6.90 Hz, 6 H); M + H 394.1 |
| 352 | 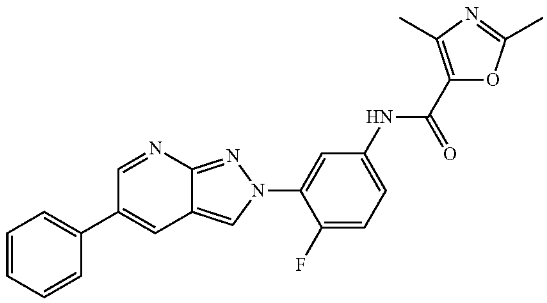 [SMILES: Cc1nc(C)c(C(=O)Nc2ccc(F)c(-n3cc4cc(-c5ccccc5)cnc4n3)c2)o1] | $^1$H NMR (400 MHz, CD$_3$OD) 9.00-8.99 (d, J = 2.4, 1H), 8.84-8.83 (d, J = 2.4, 1H), 8.50-8.49 (d, J = 2.0, 1H), 8.47-8.45 (dd, J = 2.4, 6.8, 1H), 7.90-7.86 (m, 1H), 7.74-7.71 (m, 2H), 7.53-7.50 (m, 2H), 7.47-7.42 (m, 2H), 2.54 (s, 3H), 2.45 (s, 3H).; M + H = 428.1 |
| 353 | 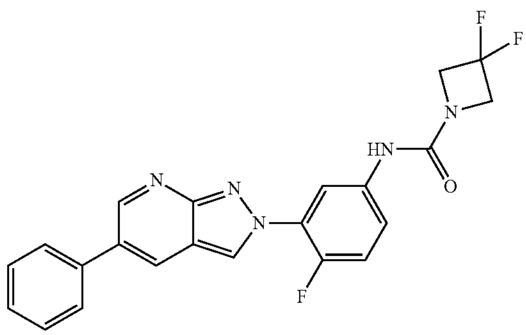 [SMILES: O=C(Nc1ccc(F)c(-n2cc3cc(-c4ccccc4)cnc3n2)c1)N1CC(F)(F)C1] | $^1$H NMR (400 MHz, DMSO-d$_6$) 9.25 (s, 1H), 9.06-9.05 (d, J = 2.8, 1H), 8.96-8.95 (d, J = 2.0, 1H), 8.52-8.51 (d, J = 2.4, 1H), 8.27-8.25 (m, 1H), 7.80-7.78 (d, J = 7.2, 2H), 7.72-7.67 (m, 1H), 7.56-7.48 (m, 3H), 7.44-7.41 (m, 1H), 4.44-4.38 (t, J = 16.4, 4H). |

Biological Assays

The assays described herein illustrate and do not limit the scope of the invention.

Abbreviations

Abbreviations as used herein below have the corresponding meaning:
CPRG Chlorophenol Red-P-D-galactopyranoside
ATP adenosine triphosphate
BSA bovine serum albumin
DMSO dimethyl sulfoxide
FBS fetal bovine serum
PBS phosphate buffered saline
RPMI 1640 Rosweli Park Memorial Institute (RPMI) 1640 medium In Vitro Assay for Growth Inhibition of Leishmania donovani Axenic Amastiqote Leishmania donovani axenic amastigote parasites are grown at 37° C., 5% CO$_2$ in media made of RPMI 1640, 4 mM L-glutamine, 20% heat inactivated FBS, 100 units/ml of penicillin and 100 μg/ml of streptomycin, 23 μM folic acid, 100 μM adenosine, 22 mM D-glucose, 25 mM MES. The pH of media is adjusted to 5.5 at 37° C. using HCl. 20 μL of media is first dispensed into 384 well plates and 100 nL of the compounds of invention in DMSO are added to the plate wells. At the same time control compounds and DMSO are added to plates to serve as the positive and negative controls, respectively. 40 μL of parasite culture (9600 parasites) are then added to the plate wells. The plates are then placed into incubators. After two days incubation, 20 μL of Cell Titer-Glo® (Promega) is added to the plate wells. The luminescence signal of each well is measured using the Envision reader (Perkin Elmer).

Assay for Inhibition of Parasitemia of Leishmania donovani in Mouse Macrophages

The assay measures the increase in the parasite number in the assayed plate well using a DNA intercalating dye, SYBR Green I® dye (INVITROGEN) to stain Leishmania cell nuclei. L. donovani HU3 strain is propagated by infecting BALB/c mice through tail vein injection with 10$^7$ Leishmania parasites. Infected mice are allowed to develop infection during 9-11 weeks post-infection. During this time, the parasites accumulate in the infected mouse spleens to large numbers, and the infected mice serve as the source of parasites for the in vitro measurement of compound efficacies. To assay a compound for anti-leishmanial activity, peritoneal macrophages isolated from non-infected BALB/c mice are seeded into 384-well plates at density $2\times10^4$ macrophages per well in 25 mL of medium (RPMI1640, 10% fetal serum albumin, 10 mM HEPES, 1 mM sodium pyruvate, 1% Pen/Strep). Subsequently, the seeded plates are placed into an incubator set to maintain 37° C. temperature and atmosphere with 5% $CO_2$.

The next day, Leishmania parasites are isolated from the spleens of mice infected for 9-11 weeks and $4\times10^5$ isolated parasites in 10 mL of the above media are added to each plate well. Plates are then returned into incubators and infection is allowed to proceed for 24 hours. After the infection of macrophages is completed, 5 mL of compounds of the invention in the above medium, which also contains 5% DMSO, are added to plate wells containing infected macrophages. At the same time control compounds (miltefosine and amphotericin B) and DMSO are added to plates to serve as the positive and negative controls, respectively. After the compound addition, the plates are returned into incubator and cells infected with parasites are cultured for 5 days. At the end of cultivation, 40 mL of 8% paraformaldehyde is added to plate wells and incubated for 15 min at room temperature. Following the incubation, the paraformaldehyde from plate wells is aspirated, and 40 mL of PBS containing 0.2% Triton X-100 is added to wells. After 15 min incubation, the solution is aspirated from wells again, and replaced with Sybr® Green Dye solution in PBS (1:125,000 dilution). Infected cells are imaged with Evotec Opera high-content microscope, and the number of parasites in well is determined by counting parasite nuclei visualized by staining with Sybr® Green dye.

Assay for Growth Inhibition of Kinetoplastid Parasite Trypanosoma cruzi

Compounds of the invention can be assayed for inhibitor activity against Trypanosoma cruzi amastigotes cultured in 3T3 fibroblast cells. The assay is done using the mammalian stage (amastigotes) of T. cruzi that replicates in the intracellular space of host cells. The host cells are initially infected with the culture-derived trypomastigotes that rapidly invade and then divide as amastigotes. The protocol uses the Tulahuen strain of T. cruzi that has been engineered to express the E. coli beta-galactosidase gene (Lac-Z) (Antimicr. Agents Chemoth. 40:2592, 1996). This allows for a colorimetric readout by using the substrate CPRG and an absorbance plate reader.

3T3 fibroblast cells are re-suspended in RPMI-1640 medium without phenol red medium supplemented with 10% FBS (heat inactivated), 100 µg/ml penicillin, and 100 µg/ml streptomycin. Forty µL of suspension (1,000 cells) is dispensed into 384-well plates and incubated overnight at 37° C. temperature and in atmosphere containing 5% $CO_2$. The following day, 100 nL of compounds of the invention in DMSO are added to plate wells containing 3T3 cells. At the same time control compounds (benznidazole and nifurtimox) and DMSO are added to plates to serve as the positive and negative controls, respectively. After that, 10 µL of media containing 10,000 T. cruzi trypomastigotes are added to each plate well and plates are placed back into incubators. After 6 day incubation, 10 µL of reagent solution (0.6 mM CPRG, 0.6% NP-40 in PBS) is added to plates and incubated at room temperature for 2 hours. Absorbance is then measured on SpectraMax GEMINI fluorimeter to determine relative number of T. cruzi cells present in each plate well.

Assay for Growth Inhibition Against Trypanosoma brucei brucei

The proliferation is quantified by the addition of Cell TiterGlo® (Promega®) a luminescent cell viability assay that measures the number of viable cells in culture based on the quantification of cellular ATP amount, which is an indicator of metabolically active cells.

Trypanosoma brucei brucei (Lister 427) strain was grown in Hirumi 9 (HMI-9) media supplemented with 10% v/v fetal bovine serum (FBS) and 10% v/v serum plus. For measurement of cell proliferation inhibition, test compounds were three fold serially diluted in duplicates to 384-well white plates, resulting in 10 dilutions for each compound. A volume of 40 µL of T. b. brucei culture (10,000 parasites/mL) was added to each well, and the assay plates were incubated at 37° C. for 2 days in a $CO_2$ incubator. Growth inhibition was monitored by measuring ATP levels, which, is used as a surrogate marker for growth. Relative luminescence units were measured using TECAN® M1000 after 30 min of adding 40 µl of Cell TiterGlo®. $IC_{50}$ values were determined by analyzing the data using HELIOS software. $IC_{50}$ is defined as the lowest concentration of the compound that inhibited 50% growth of the T. b. brucei wild type strain compared to untreated controls.

Table 3 shows the inhibitory efficacy of the compounds ($EC_{50}$) against L. donovani axenic amastigotes in vitro (column 2); L. donovani in mouse peritoneal macrophages (column 3); T. cruzi (column 4); and T. brucei brucei (column 5). Compounds of the invention have an $EC_{50}$ ranging from >10 µM to <0.01 µM. In particular embodiments, compounds of the invention have an $EC_{50}$<1 µM, <500 nM, <100 nM or <50 nM.

TABLE 3

| Cpd. No. | L. donovani amastigotes $EC_{50}$ (µM) | L. donovani in Mouse Macrophages $EC_{50}$ (µM) | Buckner infectious T. cruzi $EC_{50}$ (µM) | T. Brucei (HAT) $EC_{50}$ (µM) |
|---|---|---|---|---|
| 1 | 0.0071 | n.d. | 0.0052 | <0.023 |
| 2 | 0.003 | 0.0044 | 0.0010 | <0.023 |
| 3 | 0.0018 | 0.0020 | 0.0016 | <0.023 |
| 4 | 0.0013 | n.d. | 0.0010 | <0.023 |
| 5 | 0.0036 | n.d. | 0.0053 | <0.023 |
| 6 | 0.012 | n.d. | 0.0099 | <0.023 |
| 7 | 0.0077 | 0.004 | 0.0016 | <0.023 |
| 8 | 0.0077 | 0.0033 | 0.0045 | <0.023 |
| 9 | 0.0087 | 0.011 | 0.0098 | 0.035 |
| 10 | 0.016 | 0.0078 | 0.0048 | <0.023 |
| 11 | 0.0028 | n.d. | 0.0010 | >50 |
| 12 | 0.041 | n.d. | n.d. | <0.023 |
| 13 | 0.071 | n.d. | n.d. | <0.023 |
| 14 | 0.012 | 0.0097 | 0.0020 | <0.023 |
| 15 | 0.013 | 0.017 | 0.005 | <0.023 |
| 16 | 0.089 | n.d. | 0.012 | n.d. |
| 17 | 0.064 | n.d. | 0.016 | n.d. |
| 18 | 0.29 | n.d. | 0.16 | n.d. |
| 19 | 0.011 | 0.081 | 0.011 | <0.023 |
| 20 | 0.010 | 0.037 | 0.0042 | <0.023 |
| 21 | 0.0077 | 0.0065 | 0.0017 | <0.023 |
| 22 | 0.028 | 21 | 0.0072 | <0.023 |
| 23 | 0.14 | 0.11 | 0.078 | <0.023 |
| 24 | 0.88 | 1.0 | 0.44 | 0.61 |
| 25 | 0.021 | 0.047 | 0.017 | <0.023 |
| 26 | 0.0096 | n.d. | 0.012 | <0.023 |
| 27 | 0.033 | 0.015 | 0.038 | <0.023 |
| 28 | 0.0013 | 0.0020 | 0.0010 | <0.023 |
| 29 | 0.0082 | 0.0097 | 0.011 | <0.023 |
| 30 | 0.59 | n.d. | n.d. | n.d. |
| 31 | 0.0062 | n.d. | 0.0083 | <0.023 |
| 32 | 0.012 | 0.013 | 0.005 | <0.023 |
| 33 | 0.29 | 0.56 | 0.72 | 0.28 |
| 34 | 0.20 | 0.27 | 0.16 | 0.15 |
| 35 | 0.58 | 0.52 | 0.38 | 0.85 |
| 36 | 0.21 | 0.25 | n.d. | n.d. |
| 37 | 0.023 | n.d. | 0.026 | <0.023 |
| 38 | 0.031 | 0.033 | 0.062 | 0.024 |
| 39 | 0.0024 | 0.0038 | 0.0020 | <0.023 |

TABLE 3-continued

| Cpd. No. | L. donovani amastigotes EC$_{50}$ (μM) | L. donovani in Mouse Macrophages EC$_{50}$ (μM) | Buckner infectious T. cruzi EC$_{50}$ (μM) | T. Brucei (HAT) EC$_{50}$ (μM) |
|---|---|---|---|---|
| 40 | n.d. | n.d. | n.d. | <0.023 |
| 41 | 0.02 | n.d. | n.d. | n.d. |
| 42 | 0.0030 | 0.006 | 0.0018 | <0.023 |
| 43 | 0.0047 | n.d. | 0.0052 | n.d. |
| 44 | 0.029 | 0.032 | 0.022 | n.d. |
| 45 | 0.04 | n.d. | 0.028 | <0.023 |
| 46 | 0.0084 | 0.0035 | 0.0017 | <0.023 |
| 47 | 0.023 | 0.027 | 0.0028 | n.d. |
| 48 | 0.35 | 0.33 | 0.29 | 0.050 |
| 49 | 25 | 12 | 12 | 3.4 |
| 50 | 0.078 | 0.10 | 0.079 | <0.023 |
| 51 | 0.015 | n.d. | 0.019 | <0.023 |
| 52 | 0.019 | 0.011 | 0.013 | <0.023 |
| 53 | 0.0013 | 0.0020 | 0.0010 | <0.023 |
| 54 | 0.028 | n.d. | 0.0041 | n.d. |
| 55 | 0.057 | 0.035 | 0.0063 | n.d. |
| 56 | 0.24 | 0.55 | n.d. | n.d. |
| 57 | 0.71 | n.d. | 0.36 | n.d. |
| 58 | n.d. | n.d. | n.d. | <0.023 |
| 59 | 0.068 | 0.021 | 0.0047 | <0.023 |
| 60 | 2.0 | 2.4 | 0.44 | 1.3 |
| 61 | 0.24 | n.d. | 0.052 | n.d. |
| 62 | 0.039 | n.d. | 0.0051 | <0.023 |
| 63 | 0.089 | 0.09 | 0.014 | n.d. |
| 64 | 0.0022 | 0.0039 | 0.0010 | <0.023 |
| 65 | 1.0 | 1.2 | 0.96 | 1.4 |
| 66 | 0.74 | 0.87 | 0.15 | 0.12 |
| 67 | 0.21 | 0.31 | 0.042 | >50 |
| 68 | 2.2 | 2.8 | 0.16 | 0.51 |
| 69 | 0.17 | 0.15 | 0.068 | 0.04 |
| 70 | 0.14 | 0.10 | 0.022 | 0.038 |
| 71 | 4.8 | 2.8 | 1.4 | 3.0 |
| 72 | 2.1 | 1.4 | 0.18 | 0.42 |
| 73 | 0.10 | 0.22 | 0.057 | 0.037 |
| 74 | 0.76 | 0.82 | 0.057 | 0.11 |
| 75 | 0.20 | 0.17 | 0.12 | 0.17 |
| 76 | 1.1 | 0.93 | 0.41 | 0.48 |
| 77 | 17 | n.d. | 6.5 | 8.5 |
| 78 | 0.80 | 0.87 | 0.45 | 0.53 |
| 79 | 3.0 | 2.4 | 0.14 | 0.35 |
| 80 | 0.41 | 0.41 | 0.092 | 0.17 |
| 81 | 3.16 | 3.6 | 0.42 | 0.36 |
| 82 | 0.47 | 0.31 | 0.059 | 0.054 |
| 83 | 0.014 | 0.0070 | 0.0073 | <0.023 |
| 84 | 2.4 | 6.9 | 3.7 | 2.03 |
| 85 | 1.2 | 0.75 | 0.15 | 0.18 |
| 86 | 0.13 | 0.12 | 0.014 | <0.023 |
| 87 | 0.062 | 0.071 | 0.016 | <0.023 |
| 88 | 5.3 | 3.2 | 1.8 | 1.5 |
| 89 | 0.47 | 0.27 | 0.032 | 0.033 |
| 90 | 0.28 | 0.31 | 0.14 | 0.077 |
| 91 | 0.0087 | 0.0086 | 0.0041 | <0.023 |
| 92 | n.d. | n.d. | n.d. | <0.023 |
| 93 | 0.034 | 0.032 | 0.0070 | <0.023 |
| 94 | 0.012 | 0.0081 | 0.0018 | <0.023 |
| 95 | 0.42 | 0.35 | 0.17 | 0.085 |
| 96 | 0.023 | 0.021 | 0.018 | <0.023 |
| 97 | 0.012 | 0.44 | 0.0088 | <0.023 |
| 98 | 0.025 | 0.023 | 0.015 | <0.023 |
| 99 | 0.0013 | 0.0020 | 0.0010 | >50 |
| 100 | 0.0092 | n.d. | 0.0042 | <0.023 |
| 101 | 0.30 | 0.31 | 0.13 | 0.15 |
| 102 | 0.11 | n.d. | 0.046 | n.d. |
| 103 | 0.68 | 0.40 | 0.15 | 0.31 |
| 104 | 3.1 | 2.1 | 1.2 | 4.2 |
| 105 | 0.72 | 0.89 | 0.43 | 0.38 |
| 106 | 0.13 | 0.085 | 0.061 | >50 |
| 107 | 0.22 | 0.13 | 0.077 | 0.088 |
| 108 | 0.0033 | 0.004 | 0.0038 | <0.023 |
| 109 | 0.074 | n.d. | 0.015 | n.d. |
| 110 | 0.64 | n.d. | 0.15 | n.d. |
| 111 | 8.7 | n.d. | 2.9 | 10 |
| 112 | 0.016 | n.d. | 0.0028 | <0.023 |
| 113 | 0.037 | n.d. | 0.00522 | n.d. |
| 114 | 0.31 | n.d. | 0.045 | 0.054 |
| 115 | 0.15 | n.d. | 0.014 | <0.023 |
| 116 | 3.1 | n.d. | 0.88 | 1.5 |
| 117 | 9.3 | n.d. | 5.5 | 13 |
| 118 | 0.69 | n.d. | 1.1 | 1.4 |
| 119 | 1.6 | n.d. | 4.5 | 13 |
| 120 | 5.2 | n.d. | 4.3 | 1.8 |
| 121 | 0.21 | n.d. | n.d. | 0.12 |
| 122 | 0.015 | n.d. | 0.0042 | n.d. |
| 123 | 0.0094 | 0.0089 | 0.0044 | <0.023 |
| 124 | 0.018 | n.d. | 0.016 | n.d. |
| 125 | 0.044 | 0.031 | 0.034 | <0.023 |
| 126 | 0.024 | 0.014 | 0.014 | <0.023 |
| 127 | 0.025 | 0.017 | 0.0068 | <0.023 |
| 128 | 0.38 | 0.19 | 0.14 | 0.18 |
| 129 | 0.029 | 0.031 | 0.015 | <0.023 |
| 130 | 0.19 | 0.16 | 0.036 | 0.040 |
| 131 | 0.007 | 0.0051 | 0.0052 | <0.023 |
| 132 | 0.011 | 0.007 | 0.013 | <0.023 |
| 133 | 0.012 | 0.0080 | 0.0059 | <0.023 |
| 134 | 0.023 | 0.0054 | 0.02 | <0.023 |
| 135 | 0.0046 | 0.0086 | 0.0066 | <0.023 |
| 136 | 0.030 | 0.019 | 0.17 | <0.023 |
| 137 | 0.0088 | 0.0060 | 0.0051 | <0.023 |
| 138 | 0.011 | 0.0057 | 0.047 | <0.023 |
| 139 | 0.74 | 0.32 | 3.0 | <0.023 |
| 140 | 0.10 | 0.041 | 0.023 | <0.023 |
| 141 | 0.08 | 0.012 | 0.022 | <0.023 |
| 142 | 7.8 | 9.2 | 11 | 4.3 |
| 143 | 0.15 | 0.11 | n.d. | <0.023 |
| 144 | 0.023 | 0.023 | 0.017 | <0.023 |
| 145 | 0.0054 | 0.0047 | 0.018 | <0.023 |
| 146 | 0.026 | 0.012 | 0.085 | <0.023 |
| 147 | 0.0061 | 0.026 | 0.0048 | <0.023 |
| 148 | 0.0081 | 0.012 | 0.014 | <0.023 |
| 149 | 0.011 | 0.0079 | 0.0054 | <0.023 |
| 150 | 0.014 | 0.025 | 0.021 | <0.023 |
| 151 | 0.06 | 0.013 | 0.012 | <0.023 |
| 152 | 0.0037 | 0.0053 | 0.0017 | <0.023 |
| 153 | 0.21 | 27 | 0.15 | 0.50 |
| 154 | 0.053 | 0.078 | 0.023 | 0.037 |
| 155 | 0.053 | 0.022 | 0.018 | <0.023 |
| 156 | 0.0093 | n.d. | 0.0051 | <0.023 |
| 157 | 0.025 | 0.018 | 0.013 | <0.023 |
| 158 | 0.016 | 0.016 | 0.015 | <0.023 |
| 159 | 0.013 | 0.017 | 0.037 | <0.023 |
| 160 | 0.0043 | 0.0098 | 0.0051 | <0.023 |
| 161 | 0.0077 | 0.0073 | 0.0098 | <0.023 |
| 162 | 0.007 | 0.0045 | 0.0018 | <0.023 |
| 163 | 0.0058 | 0.0041 | 0.0027 | <0.023 |
| 164 | 0.006 | 0.01 | 0.0017 | <0.023 |
| 165 | 0.010 | 0.010 | 0.04 | <0.023 |
| 166 | 0.0025 | 0.0037 | 0.0017 | <0.023 |
| 167 | 0.0029 | 0.0082 | 0.0022 | <0.023 |
| 168 | 0.0032 | 0.0082 | 0.027 | <0.023 |
| 169 | 0.010 | 0.030 | 0.014 | <0.023 |
| 170 | 0.008 | 0.011 | 0.0046 | <0.023 |
| 171 | 0.0095 | 0.016 | 0.047 | <0.023 |
| 172 | 0.0067 | 0.011 | 0.033 | <0.023 |
| 173 | 0.41 | 0.50 | 0.14 | 0.12 |
| 174 | 2 | 2.7 | 0.72 | 1.0 |
| 175 | 0.024 | 0.0081 | 0.0049 | <0.023 |
| 176 | 0.071 | 0.069 | 0.0095 | n.d. |
| 177 | 0.027 | n.d. | 0.055 | <0.023 |
| 178 | 0.16 | n.d. | 1.6 | 0.036 |
| 179 | 0.41 | n.d. | 0.043 | <0.023 |
| 180 | 0.55 | n.d. | 3.9 | 0.038 |
| 181 | 0.025 | n.d. | 0.82 | <0.023 |
| 182 | 0.0076 | n.d. | 0.0067 | <0.023 |
| 183 | 0.012 | n.d. | 0.055 | <0.023 |
| 184 | 0.0073 | n.d. | n.d. | <0.023 |
| 185 | 0.2 | n.d. | n.d. | <0.023 |
| 186 | 0.46 | n.d. | n.d. | 0.24 |
| 187 | 0.0013 | n.d. | n.d. | <0.023 |
| 188 | 0.0024 | n.d. | n.d. | <0.023 |
| 189 | 0.003 | n.d. | n.d. | <0.023 |

TABLE 3-continued

| Cpd. No. | L. donovani amastigotes EC$_{50}$ (μM) | L. donovani in Mouse Macrophages EC$_{50}$ (μM) | Buckner infectious T. cruzi EC$_{50}$ (μM) | T. Brucei (HAT) EC$_{50}$ (μM) |
|---|---|---|---|---|
| 190 | n.d. | n.d. | n.d. | >50 |
| 191 | n.d. | n.d. | n.d. | <0.023 |
| 192 | n.d. | n.d. | n.d. | <0.023 |
| 193 | n.d. | n.d. | n.d. | <0.023 |
| 194 | n.d. | n.d. | n.d. | <0.023 |
| 195 | 0.010 | 0.0064 | 0.004 | <0.023 |
| 196 | 0.076 | 27 | 0.012 | <0.023 |
| 197 | 0.199 | 0.013 | 0.037 | 0.005 |
| 198 | 0.546 | 0.049 | 0.023 | 0.005 |
| 199 | 0.502 | 0.021 | 0.024 | 0.005 |
| 200 | 0.974 | 0.007 | 0.015 | 0.005 |
| 201 | 0.192 | 0.004 | 0.02 | 0.005 |
| 202 | 0.463 | 0.01 | 0.025 | 0.005 |
| 203 | 0.49 | 0.009 | 0.02 | 0.005 |
| 204 | 0.074 | 0.004 | 0.002 | 0.005 |
| 205 | 0.197 | 0.011 | 0.015 | 0.005 |
| 206 | 0.002 | 0.013 | 0.001 | 0.005 |
| 207 | 1.827 | 2.062 | 1.271 | 1.821 |
| 208 | 0.921 | 1.918 | 0.358 | 0.375 |
| 209 | 25.0 | 0.381 | 5.09 | 6.538 |
| 210 | 0.494 | n.d. | 0.079 | n.d. |
| 211 | 0.496 | 0.302 | 0.072 | 0.035 |
| 212 | 11.31 | 8.86 | 1.753 | 2.027 |
| 213 | 1.561 | n.d. | 0.363 | n.d. |
| 214 | 4.6 | 0.658 | 1.415 | 1.056 |
| 215 | 4.7 | 2.975 | 0.738 | 0.947 |
| 216 | 3.7 | 4.67 | 0.435 | 0.620 |
| 217 | 14.46 | n.d. | 4.35 | n.d. |
| 218 | 0.004 | 0.212 | 0.038 | 0.003 |
| 219 | 0.034 | n.d. | 0.015 | 0.017 |
| 220 | 0.015 | n.d. | 0.006 | 0.042 |
| 221 | 0.003 | n.d. | 0.001 | 0.009 |
| 222 | 0.08 | n.d. | 0.045 | 0.073 |
| 223 | 0.082 | n.d. | 0.037 | 0.064 |
| 224 | 0.111 | n.d. | 0.046 | 0.067 |
| 225 | 0.037 | n.d. | 0.05 | 0.238 |
| 226 | 0.134 | n.d. | 0.129 | 0.343 |
| 227 | 0.03 | n.d. | 0.011 | 0.059 |
| 228 | 0.031 | n.d. | 0.01 | 0.030 |
| 229 | 25.0 | n.d. | 15.55 | 12.500 |
| 230 | 0.037 | 0.022 | 0.047 | 0.005 |
| 231 | 0.034 | 0.113 | 0.126 | 0.006 |
| 232 | 0.012 | 0.01 | 0.012 | 0.005 |
| 233 | 0.013 | 0.01 | 0.005 | 0.004 |
| 234 | 0.027 | 0.003 | 0.009 | 0.005 |
| 235 | 0.011 | 0.01 | 0.011 | 0.005 |
| 236 | 0.264 | 29.67 | 20.0 | 1.463 |
| 237 | 0.016 | 0.009 | 0.021 | 0.005 |
| 238 | 0.025 | 0.032 | 0.033 | 0.005 |
| 239 | 1.761 | 0.009 | 0.01 | 0.005 |
| 240 | 0.579 | 0.027 | 0.021 | 0.005 |
| 241 | 1.191 | 0.006 | 0.003 | 0.005 |
| 242 | 1.972 | 0.106 | 0.007 | 0.013 |
| 243 | 2.105 | 0.065 | 0.082 | 0.005 |
| 244 | 0.55 | 0.021 | 0.014 | 0.005 |
| 245 | 0.311 | 1.491 | 0.951 | 0.062 |
| 246 | 0.535 | 0.379 | 2.845 | 0.396 |
| 247 | 0.04 | 0.023 | 0.014 | 0.005 |
| 248 | 0.117 | 0.008 | 0.011 | 0.005 |
| 249 | 0.864 | 0.125 | 0.11 | 0.005 |
| 250 | 0.043 | 0.01 | 0.001 | 0.005 |
| 251 | 0.024 | n.d. | 0.367 | 0.005 |
| 252 | 0.183 | n.d. | 0.022 | 0.005 |
| 253 | 0.003 | n.d. | 0.004 | 0.005 |
| 254 | 0.091 | 0.673 | 0.05 | 0.259 |
| 255 | 0.042 | 0.028 | 0.015 | 0.005 |
| 256 | 0.011 | 0.038 | 0.005 | 0.027 |
| 257 | 0.014 | 0.007 | 0.002 | 0.004 |
| 258 | 0.023 | 0.039 | 0.012 | 0.028 |
| 259 | 0.012 | 0.016 | 0.003 | 0.004 |
| 260 | 0.221 | 0.224 | 0.049 | 0.043 |
| 261 | 0.004 | n.d. | 0.002 | n.d. |
| 262 | 0.033 | n.d. | 0.004 | n.d. |
| 263 | 0.012 | 0.068 | 0.045 | 0.010 |
| 264 | 0.357 | 13.68 | 0.48 | 0.384 |
| 265 | 0.003 | 0.004 | 0.002 | 0.001 |
| 266 | 0.008 | 0.029 | 0.065 | 0.005 |
| 267 | 1.713 | 13.83 | 9.4 | 0.081 |
| 268 | 0.084 | 0.273 | 0.082 | 0.116 |
| 269 | 0.019 | 0.032 | 0.009 | 0.020 |
| 270 | 0.233 | 2.174 | 1.703 | 0.079 |
| 271 | 0.12 | 0.003 | 0.144 | 0.388 |
| 272 | 0.131 | 0.085 | 0.114 | 0.351 |
| 273 | 0.027 | 0.006 | 0.017 | 0.045 |
| 274 | 0.002 | 0.003 | 0.001 | 0.001 |
| 275 | 0.003 | 0.003 | 0.001 | 0.001 |
| 276 | 0.029 | 0.1 | 0.021 | 0.033 |
| 277 | 0.04 | 0.138 | 0.144 | 0.082 |
| 278 | 0.007 | n.d. | n.d. | 0.013 |
| 279 | 0.01 | n.d. | 0.003 | n.d. |
| 280 | 0.033 | 0.028 | 0.048 | 0.040 |
| 281 | 0.009 | 0.026 | 0.015 | 0.014 |
| 282 | 0.034 | 0.07 | 0.04 | 0.027 |
| 283 | 0.007 | 0.019 | 0.005 | 0.008 |
| 284 | 0.027 | 0.056 | 0.015 | 0.015 |
| 285 | 0.004 | 0.009 | 0.003 | 0.004 |
| 286 | 0.025 | 0.047 | 0.014 | 0.030 |
| 287 | 0.021 | 0.03 | 0.021 | 0.010 |
| 288 | 0.176 | n.d. | n.d. | 0.260 |
| 289 | 0.199 | n.d. | n.d. | 0.208 |
| 290 | 0.007 | 0.004 | 0.004 | 0.004 |
| 291 | 0.01 | 0.005 | 0.005 | 0.005 |
| 292 | 0.005 | 0.008 | 0.003 | 0.005 |
| 293 | 6.82 | 17.61 | 1.207 | 0.167 |
| 294 | 0.004 | 0.004 | 0.005 | 0.005 |
| 295 | 0.292 | 1.973 | 4.29 | 0.038 |
| 296 | 0.216 | 0.002 | 0.005 | 0.005 |
| 297 | 0.105 | 0.472 | 0.73 | 0.005 |
| 298 | 0.014 | 0.004 | 0.004 | 0.004 |
| 299 | 0.029 | 0.007 | 0.014 | 0.005 |
| 300 | 0.022 | 0.006 | 0.004 | 0.003 |
| 301 | 0.073 | 0.097 | 0.472 | 0.008 |
| 302 | 0.118 | 0.015 | 0.002 | 0.005 |
| 303 | 0.49 | 0.015 | 0.01 | 0.005 |
| 304 | 0.004 | 0.003 | 0.03 | 0.005 |
| 305 | 0.11 | 0.003 | 0.001 | 0.005 |
| 306 | 0.09 | 0.004 | 0.002 | 0.005 |
| 307 | 0.281 | 0.012 | 0.016 | 0.005 |
| 308 | 0.568 | 0.002 | 0.004 | 0.005 |
| 309 | 0.001 | 0.002 | 0.001 | 0.005 |
| 310 | 0.002 | 0.002 | 0.001 | 0.005 |
| 311 | 0.058 | 0.033 | 0.031 | 0.027 |
| 312 | 0.003 | 0.002 | 0.004 | 0.033 |
| 313 | 0.001 | 0.002 | 0.001 | 0.005 |
| 314 | 0.242 | 0.006 | 0.005 | n.d. |
| 315 | 0.002 | 0.002 | 0.001 | 0.005 |
| 316 | 0.002 | 0.002 | 0.001 | 0.005 |
| 317 | 0.002 | 0.002 | 0.001 | 0.005 |
| 318 | 0.027 | 0.032 | 0.013 | 0.015 |
| 319 | 0.001 | n.d. | 0.001 | 0.005 |
| 320 | 0.008 | n.d. | 0.002 | 0.005 |
| 321 | 0.018 | n.d. | 0.011 | 0.005 |
| 322 | 0.012 | n.d. | 0.003 | 0.005 |
| 323 | 0.012 | 0.113 | 0.062 | 0.015 |
| 324 | 0.015 | 0.045 | 0.016 | 0.037 |
| 325 | 0.008 | 0.05 | 0.036 | 0.011 |
| 326 | 0.189 | 0.761 | 0.119 | 0.236 |
| 327 | 0.351 | 1.205 | 0.149 | 0.232 |
| 328 | 0.023 | 0.16 | 0.083 | 0.017 |
| 329 | 0.001 | 0.002 | 0.001 | 0.002 |
| 330 | 0.001 | 0.002 | 0.001 | 0.001 |
| 331 | 0.217 | 0.91 | 0.138 | 0.206 |
| 332 | 0.028 | 0.075 | 0.015 | 0.038 |
| 333 | 0.043 | n.d. | 0.016 | n.d. |
| 334 | 0.236 | 1.866 | 1.459 | 0.269 |
| 335 | 0.013 | 0.111 | 0.47 | 0.036 |
| 336 | 0.002 | 0.004 | 0.001 | 0.001 |
| 337 | n.d. | 0.013 | 0.004 | 0.007 |
| 338 | 0.005 | 0.002 | 0.003 | 0.003 |
| 339 | 1.586 | 0.31 | 0.112 | 0.163 |

TABLE 3-continued

| Cpd. No. | L. donovani amastigotes EC$_{50}$ (μM) | L. donovani in Mouse Macrophages EC$_{50}$ (μM) | Buckner infectious T. cruzi EC$_{50}$ (μM) | T. Brucei (HAT) EC$_{50}$ (μM) |
|---|---|---|---|---|
| 340 | 0.225 | 0.087 | 0.061 | 0.035 |
| 341 | 0.006 | 0.033 | 0.01 | 0.009 |
| 342 | 0.007 | 0.024 | 0.017 | 0.010 |
| 343 | 0.01 | 0.032 | 0.014 | 0.009 |
| 344 | 0.002 | 0.005 | 0.003 | 0.001 |
| 345 | 0.011 | 0.033 | 0.004 | 0.005 |
| 346 | 0.239 | 0.155 | 0.034 | 0.041 |
| 347 | 0.007 | 0.015 | 0.002 | 0.007 |
| 348 | 0.347 | 0.963 | 0.142 | 0.112 |
| 349 | 0.096 | 0.102 | 0.085 | 0.043 |

TABLE 3-continued

| Cpd. No. | L. donovani amastigotes EC$_{50}$ (μM) | L. donovani in Mouse Macrophages EC$_{50}$ (μM) | Buckner infectious T. cruzi EC$_{50}$ (μM) | T. Brucei (HAT) EC$_{50}$ (μM) |
|---|---|---|---|---|
| 350 | 0.016 | 0.058 | 0.016 | 0.028 |
| 351 | 0.049 | 0.024 | 0.015 | 0.031 |
| 352 | 0.017 | 0.031 | n.d. | 0.039 |
| 353 | 0.005 | 0.004 | n.d. | 0.013 |

Table 4 compares the activity of a compound of Formula (I) with compounds having a different core. EC$_{50}$ values are obtained from assays described above unless otherwise indicated.

TABLE 4

| Structure | L. donovani amastigotes EC$_{50}$ (nM) | Buckner infectious T. cruzi EC$_{50}$ (nM) |
|---|---|---|
| [4-fluoro-3-(5-isopropyl-2H-pyrazolo[3,4-b]pyridin-2-yl)phenyl]-2,4-dimethyloxazole-5-carboxamide | 18 nM | 15 nM |
| [4-fluoro-3-(6-isopropylimidazo[1,2-a]pyrimidin-2-yl)phenyl]-2,4-dimethyloxazole-5-carboxamide | 180 nM | 48 nM |
| [4-fluoro-3-(6-isopropyl-[1,2,4]triazolo[1,5-a]pyrimidin-2-yl)phenyl]-2,4-dimethyloxazole-5-carboxamide | 210 nM | 45 nM |
| [4-fluoro-3-(6-tert-butyl-[1,2,4]triazolo[1,5-a]pyrimidin-2-yl)phenyl]-2,4-dimethyloxazole-5-carboxamide | 80 nM | 22 nM |

TABLE 4-continued

| | L. donovani amastigotes EC$_{50}$ (nM) | Buckner infectious T. cruzi EC$_{50}$ (nM) |
|---|---|---|
| 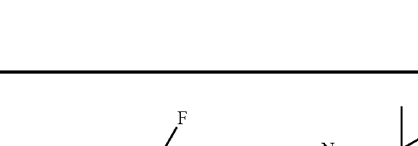 | 367 nM | 57 nM |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I):

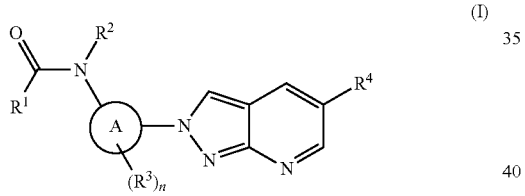

or a pharmaceutically acceptable salt, or stereoisomer thereof; wherein

Ring A is phenyl or pyridinyl;

$R^1$ is selected from:
(a) $C_{1-6}$alkyl that is unsubstituted or substituted by 1 to 3 substituents independently selected from halogen and $C_{3-6}$cycloalkyl; and said $C_{3-6}$cycloalkyl is unsubstituted or substituted by 1 to 2 substituents independently selected from halogen and $C_{1-4}$alkyl;
(b) $C_{1-4}$alkoxy that is unsubstituted or substituted by $C_{1-4}$haloalkyl;
(c) —$NR^{5a}R^{5b}$ wherein $R^{5a}$ and $R^{5b}$ are independently hydrogen, $C_{1-4}$alkyl or $C_{1-4}$ haloalkyl; or $R^{5a}$ and $R^{5b}$ together with the nitrogen atom to which both are attached form a 4- to 7-membered heterocycloalkyl comprising 1 to 3 heteroatoms independently selected from N, O and S as ring atoms;
wherein the 4 to 7-membered heterocycloalkyl is unsubstituted or substituted by 1 to 2 substituents independently selected from halogen, $C_{1-4}$alkyl, and $C_{1-4}$alkoxy; or two substituents on the same or different ring atoms of the 4- to 7-membered heterocycloalkyl, together with the atoms to which they are attached, form a spiro, bridged or fused Ring B attached to the 4- to 7-membered heterocycloalkyl;

wherein Ring B is $C_{3-6}$cycloalkyl or a 3- to 7-membered heterocycloalkyl comprising 1 to 3 heteroatoms independently selected from N, O or S as ring atoms;
(d) monocyclic $C_{3-6}$cycloalkyl, $O_{3-6}$ cycloalkenyl or spiropentyl; each of which is unsubstituted or substituted by 1 to 3 substituents independently selected from halogen, cyano, $C_{1-4}$alkyl, and $C_{1-4}$haloalkyl, and $C_{1-4}$alkoxy;
(e) phenyl or a 5-6 membered heteroaryl comprising 1 to 2 heteroatoms independently selected from N, O and S as ring atoms; each of which is unsubstituted or substituted by 1 to 2 substituents independently selected from halogen, cyano, $C_{1-4}$alkyl, $C_{1-4}$haloalkyl, $C_{1-4}$alkoxy$C_{1-4}$alkyl, $C_{1-4}$ hydroxyalkyl, $C_{1-4}$alkoxy, and $C_{3-6}$ cycloalkyl;

$R^2$ and $R^7$ are independently hydrogen or $C_{1-4}$alkyl;

$R^3$ is hydrogen or halogen, and n is 0 or 1; and $R^4$ is selected from
(a) hydrogen;
(b) halogen;
(c) $C_{1-6}$haloalkyl or $C_{1-6}$alkyl that is unsubstituted or substituted by $C_{3-6}$cycloalkyl; and said $C_{3-6}$cycloalkyl is unsubstituted or substituted by 1 to 2 substituents independently selected from halogen and $C_{1-4}$alkyl;
(d) —$NR^{6a}R^{6b}$ wherein $R^{6a}$ is hydrogen or $C_{1-4}$alkyl; $R^{6b}$ is hydrogen, $C_{1-4}$alkoxycarbonyl, $C_{1-4}$ haloalkyl, $C_{3-6}$ cycloalkyl, or $C_{1-4}$alkyl that is unsubstituted or substituted by $C_{1-4}$alkoxy; or $R^{6a}$ and $R^{6b}$ together with the nitrogen atom to which both are attached form a 4- to 7-membered heterocycloalkyl comprising 1 to 2 heteroatoms independently selected from N, O and S as ring atoms;
wherein the 4- to 7-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, oxo, 1,1-dioxo, —$C(O)$—$OR^7$ or a 4-6 membered heterocycloalkyl comprising 1-2 heteroatoms independently selected from N, O and S; or two substituents on the same or different ring atoms of the 4- to 7-membered heterocycloalkyl, together with the atoms to which they are attached, form a spiro, bridged or fused Ring C attached to the 4- to 7-membered heterocycloalkyl;
wherein Ring C is selected from $C_{3-6}$cycloalkyl, and 3- to 7-membered heterocycloalkyl comprising 1 to 3 heteroatoms independently selected from N, O or S as ring atoms; and is independently unsubstituted or substituted by 1 to 2 substituents independently selected from halogen, and oxo;

(e) $C_{3-6}$cycloalkyl;

(f) 4- to 6-membered heterocycloalkyl comprising 1 to 2 heteroatoms independently selected from N, O and S as ring atoms; and is unsubstituted or substituted by —C(O)OR$^8$, —C(O)R$^8$ wherein R$^8$ is $C_{1-4}$ alkyl, and aryl$C_{1-4}$ alkyl that is unsubstituted or substituted by 1 to 2 halo substituents; and (g) 5- to 6-membered heteroaryl comprising 1 to 2 heteroatoms independently selected from N, O and S as ring atoms; which is unsubstituted or substituted by 1 to 2 substituents independently selected from halogen, $C_{1-4}$alkyl, $C_{1-4}$ hydroxyalkyl, and $C_{3-6}$cycloalkyl.

2. The compound according to claim 1 or a pharmaceutically acceptable salt thereof, wherein Ring A is phenyl.

3. The compound according to claim 1 or a pharmaceutically acceptable salt thereof, wherein Ring A is pyridinyl.

4. The compound according to claim 1 or a pharmaceutically acceptable salt thereof, wherein R$^1$ is selected from —(CH$_2$)$_{1-3}$CF$_3$, —(CH$_2$)—CH(CH$_3$)—CF$_3$, —(CH—$_2$)—C(CH$_3$)$_3$, —O(CH$_2$)$_2$CF$_3$, —(CH$_2$)$_{0-2}$-cyclopropyl, —(CH$_2$)$_{0-2}$-cyclobutyl, —NHCH$_3$, —N(CH$_3$)$_2$, —N(CD$_3$)$_2$, —N(CH$_3$)(CH$_2$CH$_3$), —N(CH$_3$)(CH$_2$CF$_3$),

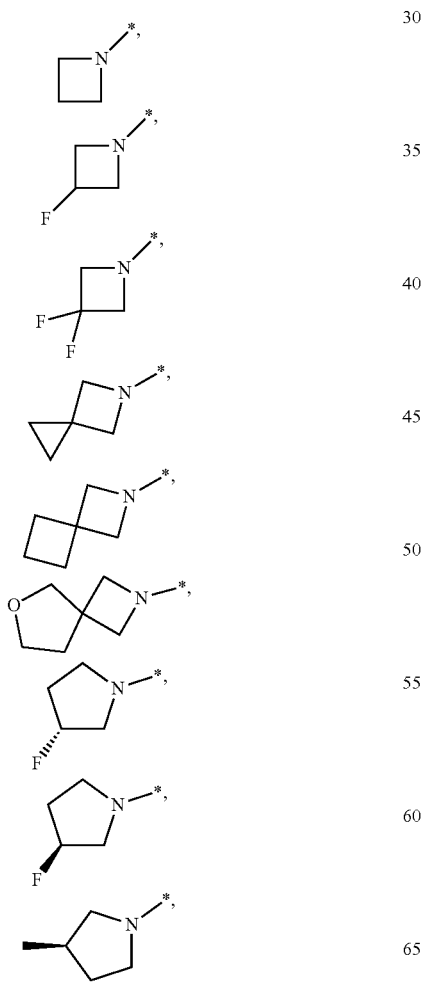

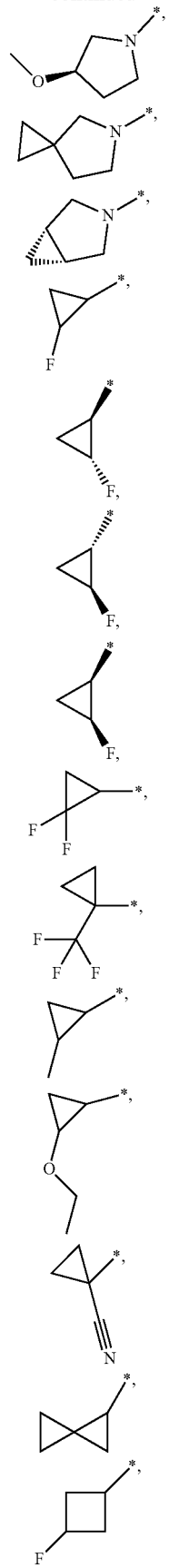

265
-continued
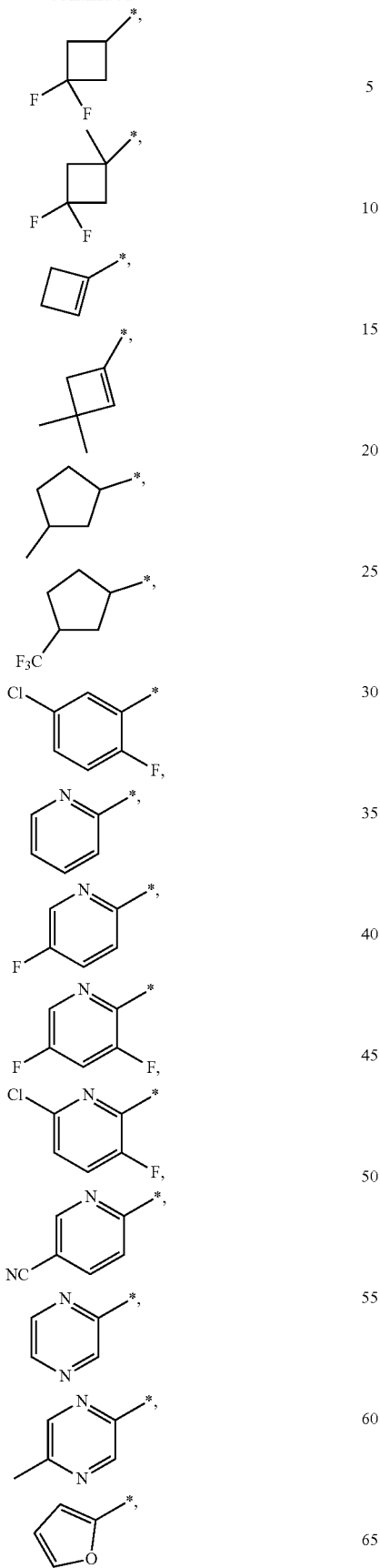
266
-continued
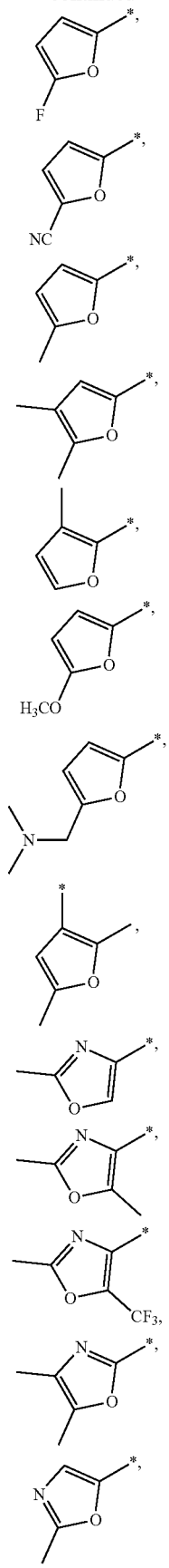

-continued

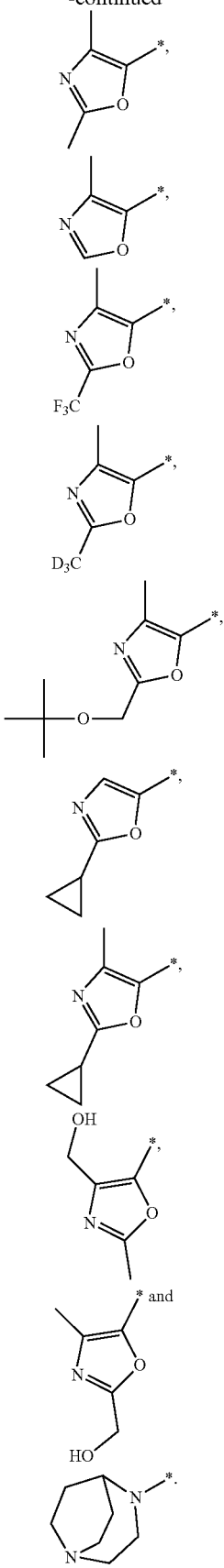

5. The compound according to claim 1 or a pharmaceutically acceptable salt thereof, wherein $R^1$ is azetidinyl, which is unsubstituted or substituted by 1 to 2 substituents independently selected from halogen and $C_{1-4}$alkyl; or two substituents on the same ring atom of the azetidinyl, together with the ring atom to which both are attached, form a spiro cyclopropyl or spiro tetrahydrofuranyl attached to the azetidinyl ring.

6. The compound according to claim 1 or a pharmaceutically acceptable salt thereof, wherein $R^1$ is selected from

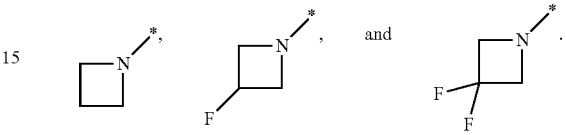

7. The compound according to claim 1 or a pharmaceutically acceptable salt thereof, wherein $R^3$ is halo and n is 1.

8. The compound according to claim 7 or a pharmaceutically acceptable salt thereof, wherein $R^3$ is fluoro.

9. The compound according to claim 1 or a pharmaceutically acceptable salt thereof, wherein $R^4$ is selected from hydrogen, chloro, bromo, methyl, iso-propyl, —$(CH_2)_{1-2}CH(CH_3)_2$, —$(CH_2)_{0-1}C(CH_3)_3$, —$C(CH_3)_2CH_2CH_3$, —$CH(CH_3)(CH_2)_{1-2}CH_3$, —$CH_2$-cyclobutyl, —$(CH_2)_{0-1}$ $CF_3$, —NH—$(CH_2)_{0-1}CH_3$, —N—$(CD_3)_2$, —N$(CH_3)_2$, —NH—CH—$(CH_3)_2$, —NH—$(CH_2)$—CH—$(CH_3)_2$, —NHC(O)OCH$(CH_3)_2$, —NH$(CH_2)_{20}CH_3$,

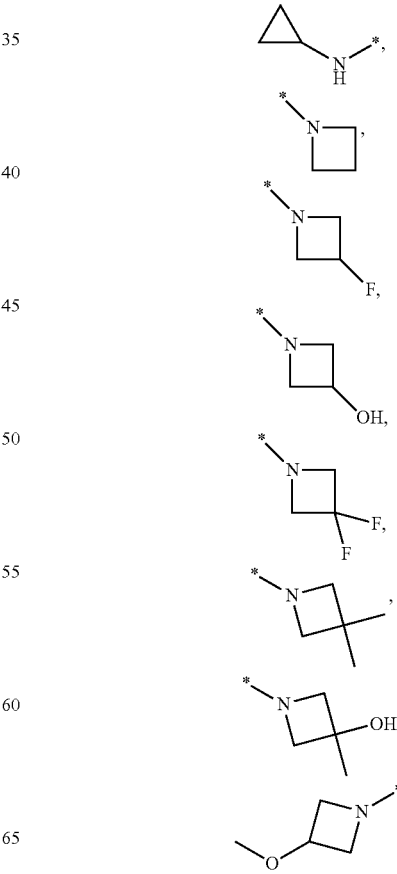

269
-continued
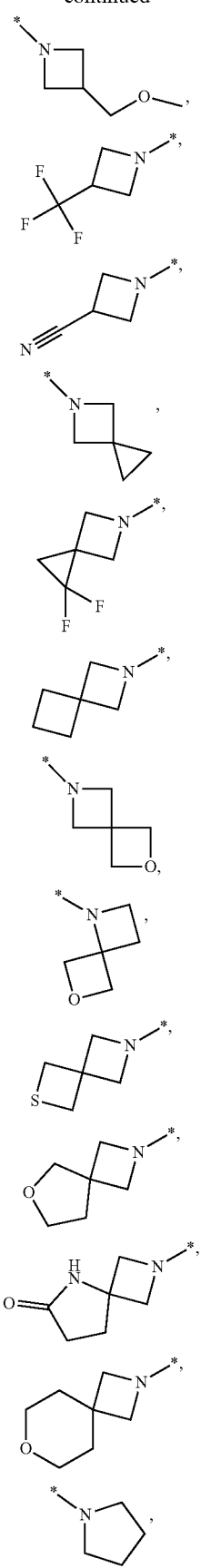
270
-continued
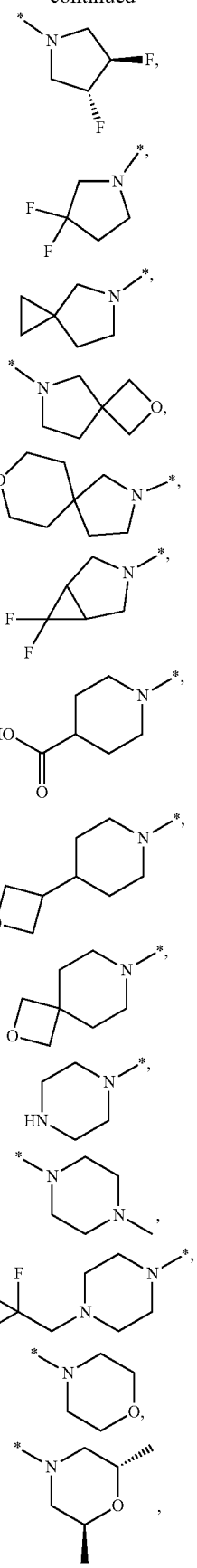

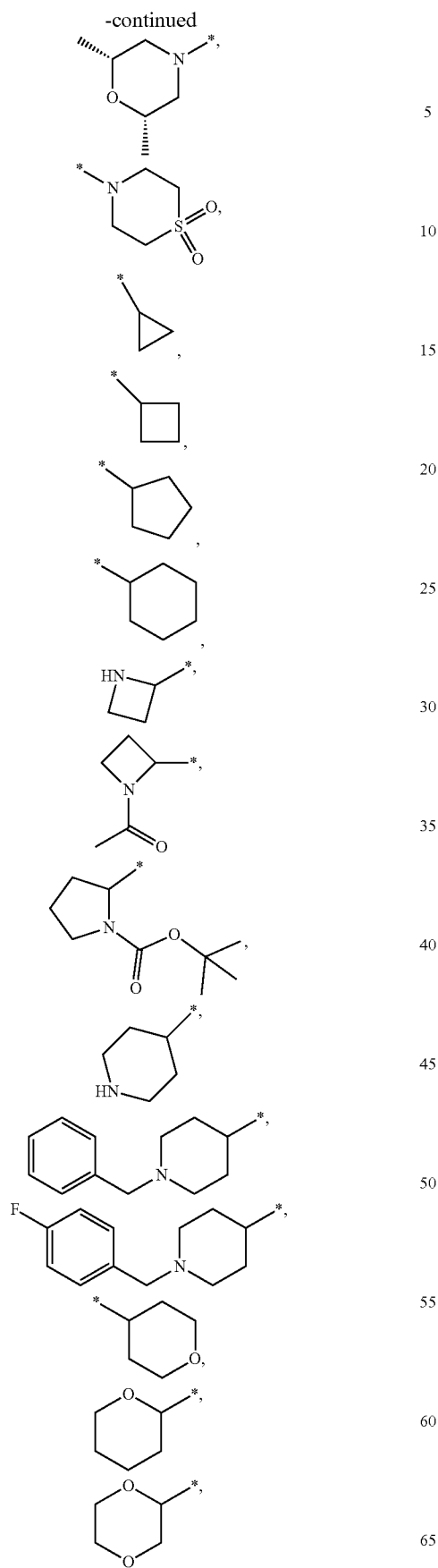
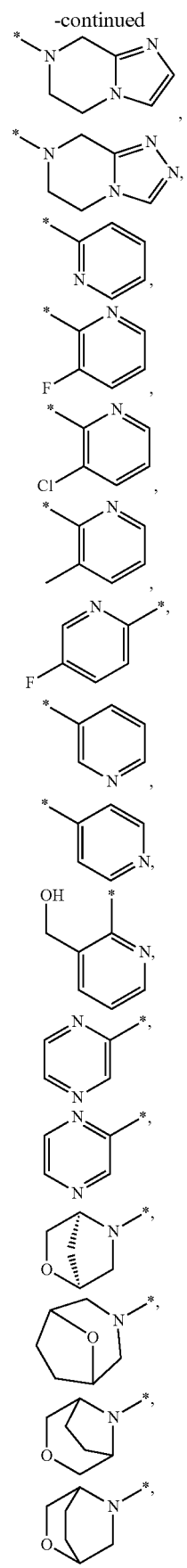

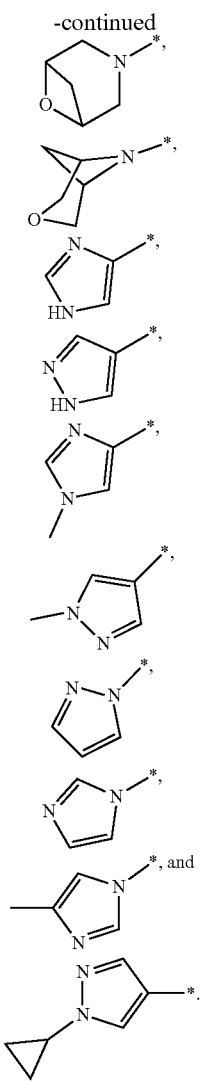

10. The compound according to claim 1 or a pharmaceutically acceptable salt thereof, wherein $R^4$ is —$NR^{6a}R^{6b}$;
$R^{6a}$ is hydrogen or $C_{1-4}$alkyl;
$R^{6b}$ is hydrogen, $C_{1-4}$alkoxycarbonyl or $C_{1-4}$alkyl that is unsubstituted or substituted by $C_{1-4}$alkoxy; or $R^{6a}$ and $R^{6b}$ together with the nitrogen atom to which both are attached form a 4- to 6-membered heterocycloalkyl optionally comprising 1 to 2 additional heteroatoms independently selected from N, O and S as ring atoms;
wherein the 4- to 6-membered heterocycloalkyl is unsubstituted or substituted by 1 to 2 substituents independently selected from halogen, cyano, hydroxyl, $C_{1-4}$alkyl, $C_{1-4}$haloalkyl, $C_{1-4}$alkoxy$C_{1-4}$alkyl, $C_{1-4}$alkoxy, and oxo; or two substituents on the same or different ring atoms of the 4- to 6-membered heterocycloalkyl, together with the atoms to which they are attached, form a spiro, bridged or fused, Ring C attached to the 4- to 6-membered heterocycloalkyl;
wherein Ring C is selected from $C_{3-6}$cycloalkyl; and 3- to 5-membered heterocycloalkyl comprising 1 to 3 heteroatoms independently selected from N, O or S as ring atoms; and Ring C is independently unsubstituted or substituted by 1 to 2 substituents independently selected from halogen, and oxo.

11. The compound according to claim 1 or a pharmaceutically acceptable salt thereof, wherein $R^4$ is selected from

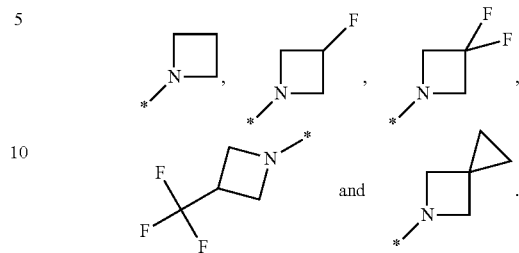

12. The compound according to claim 1 or a pharmaceutically acceptable salt thereof, wherein $R^4$ is selected from

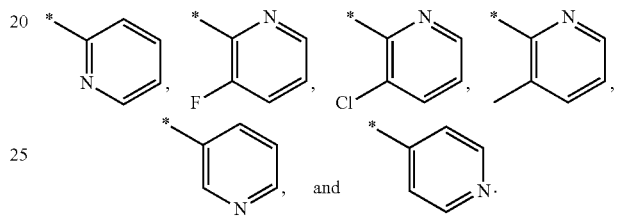

13. A compound or a pharmaceutically acceptable salt thereof, selected from
N-{4-fluoro-3-[5-(3-methylpyridin-2-yl)-2H-pyrazolo[3,4-b]pyridin-2-yl]phenyl}-2,4-dimethyl-1,3-oxazole-5-carboxamide;
N-{4-fluoro-3-[5-(3-methylpyridin-2-yl)-2H-pyrazolo[3,4-b]pyridin-2-yl]phenyl}furan-2-carboxamide;
N-{4-fluoro-3-[5-(3-methylpyridin-2-yl)-2H-pyrazolo[3,4-b]pyridin-2-yl]phenyl}azetidine-1-carboxamide;
(3R)-3-fluoro-N-{4-fluoro-3-[5-(3-methylpyridin-2-yl)-2H-pyrazolo[3,4-b]pyridin-2-yl]phenyl}pyrrolidine-1-carboxamide;
3,3-difluoro-N-{4-fluoro-3-[5-(3-methylpyridin-2-yl)-2H-pyrazolo[3,4-b]pyridin-2-yl]phenyl}azetidine-1-carboxamide;
3-fluoro-N-{4-fluoro-3-[5-(3-methylpyridin-2-yl)-2H-pyrazolo[3,4-b]pyridin-2-yl]phenyl}azetidine-1-carboxamide;
N-{4-fluoro-3-[5-(2-methylpropyl)-2H-pyrazolo[3,4-b]pyridin-2-yl]phenyl}azetidine-1-carboxamide;
3,3-difluoro-N-{4-fluoro-3-[5-(2-methylpropyl)-2H-pyrazolo[3,4-b]pyridin-2-yl]phenyl}azetidine-1-carboxamide;
N-{3-[5-(dimethylamino)-2H-pyrazolo[3,4-b]pyridin-2-yl]-4-fluorophenyl}-3,3-difluoroazetidine-1-carboxamide;
N-{3-[5-(azetidin-1-yl)-2H-pyrazolo[3,4-b]pyridin-2-yl]-4-fluorophenyl}azetidine-1-carboxamide;
5-fluoro-N-{4-fluoro-3-[5-(pyridin-2-yl)-2H-pyrazolo[3,4-b]pyridin-2-yl]phenyl}furan-2-carboxamide;
N-{4-fluoro-3-[5-(pyridin-2-yl)-2H-pyrazolo[3,4-b]pyridin-2-yl]phenyl}cyclopropanecarboxamide;
2-cyclopropyl-N-{4-fluoro-3-[5-(pyridin-2-yl)-2H-pyrazolo[3,4-b]pyridin-2-yl]phenyl}acetamide;
3-fluoro-N-{4-fluoro-3-[5-(2-methylpropyl)-2H-pyrazolo[3,4-b]pyridin-2-yl]phenyl}azetidine-1-carboxamide;

N-(3-{5-cyclopropyl-2H-pyrazolo[3,4-b]pyridin-2-yl}-4-fluorophenyl)-3-fluoroazetidine-1-carboxamide;
N-{4-fluoro-3-[5-(2-methylpropyl)-2H-pyrazolo[3,4-b]pyridin-2-yl]phenyl}-2,4-dimethyl-1,3-oxazole-5-carboxamide;
N-(3-{5-cyclopropyl-2H-pyrazolo[3,4-b]pyridin-2-yl}-4-fluorophenyl)-2,4-dimethyl-1,3-oxazole-5-carboxamide;
N-(3-{5-cyclopentyl-2H-pyrazolo[3,4-b]pyridin-2-yl}-4-fluorophenyl)-3-fluoroazetidine-1-carboxamide;
N-(3-{5-cyclohexyl-2H-pyrazolo[3,4-b]pyridin-2-yl}-4-fluorophenyl)-3-fluoroazetidine-1-carboxamide;
N-(3-{5-cyclobutyl-2H-pyrazolo[3,4-b]pyridin-2-yl}-4-fluorophenyl)-3-fluoroazetidine-1-carboxamide;
N-{3-[5-(2,2-dimethylpropyl)-2H-pyrazolo[3,4-b]pyridin-2-yl]-4-fluorophenyl}-3-fluoroazetidine-1-carboxamide;
N-(3-{5-tert-butyl-2H-pyrazolo[3,4-b]pyridin-2-yl}-4-fluorophenyl)-3-fluoroazetidine-1-carboxamide;
3-fluoro-N-{4-fluoro-3-[5-(pentan-2-yl)-2H-pyrazolo[3,4-b]pyridin-2-yl]phenyl}azetidine-1-carboxamide;
3-fluoro-N-{4-fluoro-3-[5-(2-methylbutan-2-yl)-2H-pyrazolo[3,4-b]pyridin-2-yl]phenyl}azetidine-1-carboxamide;
N-{3-[5-(butan-2-yl)-2H-pyrazolo[3,4-b]pyridin-2-yl]-4-fluorophenyl}-3-fluoroazetidine-1-carboxamide;
N-{3-[5-(cyclobutylmethyl)-2H-pyrazolo[3,4-b]pyridin-2-yl]-4-fluorophenyl}-3-fluoroazetidine-1-carboxamide;
3-fluoro-N-{4-fluoro-3-[5-(3-methylbutyl)-2H-pyrazolo[3,4-b]pyridin-2-yl]phenyl}azetidine-1-carboxamide;
3-fluoro-N-{4-fluoro-3-[5-(pyridin-2-yl)-2H-pyrazolo[3,4-b]pyridin-2-yl]phenyl}azetidine-1-carboxamide;
N-(3-{5-cyclopropyl-2H-pyrazolo[3,4-b]pyridin-2-yl}-4-fluorophenyl)-3,3-difluoroazetidine-1-carboxamide;
N-(3-{5-cyclopentyl-2H-pyrazolo[3,4-b]pyridin-2-yl}-4-fluorophenyl)-3,3-difluoroazetidine-1-carboxamide;
N-(3-{5-cyclobutyl-2H-pyrazolo[3,4-b]pyridin-2-yl}-4-fluorophenyl)-3,3-difluoroazetidine-1-carboxamide;
N-{3-[5-(2,2-dimethylpropyl)-2H-pyrazolo[3,4-b]pyridin-2-yl]-4-fluorophenyl}-3,3-difluoroazetidine-1-carboxamide;
N-(3-{5-tert-butyl-2H-pyrazolo[3,4-b]pyridin-2-yl}-4-fluorophenyl)-3,3-difluoroazetidine-1-carboxamide;
3,3-difluoro-N-{4-fluoro-3-[5-(pentan-2-yl)-2H-pyrazolo[3,4-b]pyridin-2-yl]phenyl}azetidine-1-carboxamide;
3,3-difluoro-N-{4-fluoro-3-[5-(2-methylbutan-2-yl)-2H-pyrazolo[3,4-b]pyridin-2-yl]phenyl}azetidine-1-carboxamide;
N-{3-[5-(butan-2-yl)-2H-pyrazolo[3,4-b]pyridin-2-yl]-4-fluorophenyl}-3,3-difluoroazetidine-1-carboxamide;
N-{3-[5-(cyclobutylmethyl)-2H-pyrazolo[3,4-b]pyridin-2-yl]-4-fluorophenyl}-3,3-difluoroazetidine-1-carboxamide;
3,3-difluoro-N-{4-fluoro-3-[5-(3-methylbutyl)-2H-pyrazolo[3,4-b]pyridin-2-yl]phenyl}azetidine-1-carboxamide;
3,3-difluoro-N-{4-fluoro-3-[5-(pyridin-2-yl)-2H-pyrazolo[3,4-b]pyridin-2-yl]phenyl}azetidine-1-carboxamide;
N-{4-fluoro-3-[5-(3-fluoroazetidin-1-yl)-2H-pyrazolo[3,4-b]pyridin-2-yl]phenyl}azetidine-1-carboxamide;
(3R)-3-fluoro-N-{4-fluoro-3-[5-(2-methylpropyl)-2H-pyrazolo[3,4-b]pyridin-2-yl]phenyl}pyrrolidine-1-carboxamide;
(3R)-N-(3-{5-cyclopropyl-2H-pyrazolo[3,4-b]pyridin-2-yl}-4-fluorophenyl)-3-fluoropyrrolidine-1-carboxamide;
(3R)-N-(3-{5-cyclopentyl-2H-pyrazolo[3,4-b]pyridin-2-yl}-4-fluorophenyl)-3-fluoropyrrolidine-1-carboxamide;
(3R)-N-(3-{5-cyclohexyl-2H-pyrazolo[3,4-b]pyridin-2-yl}-4-fluorophenyl)-3-fluoropyrrolidine-1-carboxamide;
(3R)-N-(3-{5-cyclobutyl-2H-pyrazolo[3,4-b]pyridin-2-yl}-4-fluorophenyl)-3-fluoropyrrolidine-1-carboxamide;
(3R)-N-{3-[5-(2,2-dimethylpropyl)-2H-pyrazolo[3,4-b]pyridin-2-yl]-4-fluorophenyl}-3-fluoropyrrolidine-1-carboxamide;
(3R)-N-(3-{5-tert-butyl-2H-pyrazolo[3,4-b]pyridin-2-yl}-4-fluorophenyl)-3-fluoropyrrolidine-1-carboxamide;
(3R)-3-fluoro-N-{4-fluoro-3-[5-(pentan-2-yl)-2H-pyrazolo[3,4-b]pyridin-2-yl]phenyl}pyrrolidine-1-carboxamide;
(3R)-3-fluoro-N-{4-fluoro-3-[5-(2-methylbutan-2-yl)-2H-pyrazolo[3,4-b]pyridin-2-yl]phenyl}pyrrolidine-1-carboxamide;
(3R)-N-{3-[5-(butan-2-yl)-2H-pyrazolo[3,4-b]pyridin-2-yl]-4-fluorophenyl}-3-fluoropyrrolidine-1-carboxamide;
(3R)-N-{3-[5-(cyclobutylmethyl)-2H-pyrazolo[3,4-b]pyridin-2-yl]-4-fluorophenyl}-3-fluoropyrrolidine-1-carboxamide;
(3R)-3-fluoro-N-{4-fluoro-3-[5-(3-methylbutyl)-2H-pyrazolo[3,4-b]pyridin-2-yl]phenyl}pyrrolidine-1-carboxamide;
(3R)-3-fluoro-N-{4-fluoro-3-[5-(pyridin-2-yl)-2H-pyrazolo[3,4-b]pyridin-2-yl]phenyl}pyrrolidine-1-carboxamide;
N-{4-fluoro-3-[5-(2-methylpropyl)-2H-pyrazolo[3,4-b]pyridin-2-yl]phenyl}furan-2-carboxamide;
N-(3-{5-cyclopropyl-2H-pyrazolo[3,4-b]pyridin-2-yl}-4-fluorophenyl)furan-2-carboxamide;
N-(3-{5-cyclopentyl-2H-pyrazolo[3,4-b]pyridin-2-yl}-4-fluorophenyl)furan-2-carboxamide;
N-(3-{5-cyclohexyl-2H-pyrazolo[3,4-b]pyridin-2-yl}-4-fluorophenyl)furan-2-carboxamide;
3-fluoro-N-{4-fluoro-3-[5-(3-fluoroazetidin-1-yl)-2H-pyrazolo[3,4-b]pyridin-2-yl]phenyl}azetidine-1-carboxamide;
N-{3-[5-(2,2-dimethylpropyl)-2H-pyrazolo[3,4-b]pyridin-2-yl]-4-fluorophenyl}furan-2-carboxamide;
N-{4-fluoro-3-[5-(2-methylbutan-2-yl)-2H-pyrazolo[3,4-b]pyridin-2-yl]phenyl}furan-2-carboxamide;
N-{3-[5-(butan-2-yl)-2H-pyrazolo[3,4-b]pyridin-2-yl]-4-fluorophenyl}furan-2-carboxamide;
N-{3-[5-(cyclobutylmethyl)-2H-pyrazolo[3,4-b]pyridin-2-yl]-4-fluorophenyl}furan-2-carboxamide;
N-{4-fluoro-3-[5-(3-methylbutyl)-2H-pyrazolo[3,4-b]pyridin-2-yl]phenyl}furan-2-carboxamide;
N-{4-fluoro-3-[5-(pyridin-2-yl)-2H-pyrazolo[3,4-b]pyridin-2-yl]phenyl}furan-2-carboxamide;
N-{4-fluoro-3-[5-(propan-2-yl)-2H-pyrazolo[3,4-b]pyridin-2-yl]phenyl}-5-methylpyrazine-2-carboxamide;
N-{4-fluoro-3-[5-(propan-2-yl)-2H-pyrazolo[3,4-b]pyridin-2-yl]phenyl}-3-methylcyclopentane-1-carboxamide;
5-fluoro-N-{4-fluoro-3-[5-(propan-2-yl)-2H-pyrazolo[3,4-b]pyridin-2-yl]phenyl}pyridine-2-carboxamide;

N-{4-fluoro-3-[5-(propan-2-yl)-2H-pyrazolo[3,4-b]pyridin-2-yl]phenyl}-2-methyl-5-(trifluoromethyl)-1,3-oxazole-4-carboxamide;
2-cyclopropyl-N-{4-fluoro-3-[5-(propan-2-yl)-2H-pyrazolo[3,4-b]pyridin-2-yl]phenyl}acetamide;
3,5-difluoro-N-{4-fluoro-3-[5-(propan-2-yl)-2H-pyrazolo[3,4-b]pyridin-2-yl]phenyl}pyridine-2-carboxamide;
N-{4-fluoro-3-[5-(propan-2-yl)-2H-pyrazolo[3,4-b]pyridin-2-yl]phenyl}-3-(trifluoromethyl)cyclopentane-1-carboxamide;
N-{4-fluoro-3-[5-(propan-2-yl)-2H-pyrazolo[3,4-b]pyridin-2-yl]phenyl}-2,5-dimethylfuran-3-carboxamide;
N-{4-fluoro-3-[5-(propan-2-yl)-2H-pyrazolo[3,4-b]pyridin-2-yl]phenyl}-4-methyl-1,3-oxazole-5-carboxamide;
N-{4-fluoro-3-[5-(propan-2-yl)-2H-pyrazolo[3,4-b]pyridin-2-yl]phenyl}-2,5-dimethyl-1,3-oxazole-4-carboxamide;
2-cyclopropyl-N-{4-fluoro-3-[5-(propan-2-yl)-2H-pyrazolo[3,4-b]pyridin-2-yl]phenyl}-1,3-oxazole-5-carboxamide;
2-cyclopropyl-N-{4-fluoro-3-[5-(propan-2-yl)-2H-pyrazolo[3,4-b]pyridin-2-yl]phenyl}-4-methyl-1,3-oxazole-5-carboxamide;
N-{4-fluoro-3-[5-(propan-2-yl)-2H-pyrazolo[3,4-b]pyridin-2-yl]phenyl}-2-methyloxolane-2-carboxamide;
N-{4-fluoro-3-[5-(propan-2-yl)-2H-pyrazolo[3,4-b]pyridin-2-yl]phenyl}-4-methyl-2-(trifluoromethyl)-1,3-oxazole-5-carboxamide;
2-[(tert-butoxy)methyl]-N-{4-fluoro-3-[5-(propan-2-yl)-2H-pyrazolo[3,4-b]pyridin-2-yl]phenyl}-4-methyl-1,3-oxazole-5-carboxamide;
N-{4-fluoro-3-[5-(propan-2-yl)-2H-pyrazolo[3,4-b]pyridin-2-yl]phenyl}oxane-2-carboxamide;
N-{4-fluoro-3-[5-(propan-2-yl)-2H-pyrazolo[3,4-b]pyridin-2-yl]phenyl}-4,5-dimethyl-1,3-oxazole-2-carboxamide;
N-{4-fluoro-3-[5-(propan-2-yl)-2H-pyrazolo[3,4-b]pyridin-2-yl]phenyl}pyridine-2-carboxamide;
N-{4-fluoro-3-[5-(propan-2-yl)-2H-pyrazolo[3,4-b]pyridin-2-yl]phenyl}-2-methyl-1,3-oxazole-5-carboxamide;
5-cyano-N-{4-fluoro-3-[5-(propan-2-yl)-2H-pyrazolo[3,4-b]pyridin-2-yl]phenyl}pyridine-2-carboxamide;
N-{4-fluoro-3-[5-(propan-2-yl)-2H-pyrazolo[3,4-b]pyridin-2-yl]phenyl}-2-methyl-1,3-oxazole-4-carboxamide;
6-chloro-3-fluoro-N-{4-fluoro-3-[5-(propan-2-yl)-2H-pyrazolo[3,4-b]pyridin-2-yl]phenyl}pyridine-2-carboxamide;
N-{4-fluoro-3-[5-(propan-2-yl)-2H-pyrazolo[3,4-b]pyridin-2-yl]phenyl}pyrazine-2-carboxamide;
N-{4-fluoro-3-[5-(propan-2-yl)-2H-pyrazolo[3,4-b]pyridin-2-yl]phenyl}oxolane-2-carboxamide;
5-chloro-2-fluoro-N-{4-fluoro-3-[5-(propan-2-yl)-2H-pyrazolo[3,4-b]pyridin-2-yl]phenyl}benzamide;
N-{4-fluoro-3-[5-(propan-2-yl)-2H-pyrazolo[3,4-b]pyridin-2-yl]phenyl}cyclopropanecarboxamide;
N-(3-{5-cyclopropyl-2H-pyrazolo[3,4-b]pyridin-2-yl}-4-fluorophenyl)azetidine-1-carboxamide;
N-{3-[5-(3,3-difluoroazetidin-1-yl)-2H-pyrazolo[3,4-b]pyridin-2-yl]-4-fluorophenyl}azetidine-1-carboxamide;
N-(3-{5-cyclobutyl-2H-pyrazolo[3,4-b]pyridin-2-yl}-4-fluorophenyl)azetidine-1-carboxamide;
N-{3-[5-(2,2-dimethylpropyl)-2H-pyrazolo[3,4-b]pyridin-2-yl]-4-fluorophenyl}azetidine-1-carboxamide;
N-{4-fluoro-3-[5-(pentan-2-yl)-2H-pyrazolo[3,4-b]pyridin-2-yl]phenyl}azetidine-1-carboxamide;
N-{3-[5-(butan-2-yl)-2H-pyrazolo[3,4-b]pyridin-2-yl]-4-fluorophenyl}azetidine-1-carboxamide;
N-{3-[5-(cyclobutylmethyl)-2H-pyrazolo[3,4-b]pyridin-2-yl]-4-fluorophenyl}azetidine-1-carboxamide;
N-{4-fluoro-3-[5-(3-methylbutyl)-2H-pyrazolo[3,4-b]pyridin-2-yl]phenyl}azetidine-1-carboxamide;
N-{4-fluoro-3-[5-(pyridin-2-yl)-2H-pyrazolo[3,4-b]pyridin-2-yl]phenyl}azetidine-1-carboxamide;
N-{4-fluoro-3-[5-(propan-2-yl)-2H-pyrazolo[3,4-b]pyridin-2-yl]phenyl}azetidine-1-carboxamide;
N-(3-{5-cyclobutyl-2H-pyrazolo[3,4-b]pyridin-2-yl}-4-fluorophenyl)-2,4-dimethyl-1,3-oxazole-5-carboxamide;
N-{3-[5-(2,2-dimethylpropyl)-2H-pyrazolo[3,4-b]pyridin-2-yl]-4-fluorophenyl}-2,4-dimethyl-1,3-oxazole-5-carboxamide;
N-(3-{5-tert-butyl-2H-pyrazolo[3,4-b]pyridin-2-yl}-4-fluorophenyl)-2,4-dimethyl-1,3-oxazole-5-carboxamide;
N-{4-fluoro-3-[5-(2-methylbutan-2-yl)-2H-pyrazolo[3,4-b]pyridin-2-yl]phenyl}-2,4-dimethyl-1,3-oxazole-5-carboxamide;
N-{3-[5-(butan-2-yl)-2H-pyrazolo[3,4-b]pyridin-2-yl]-4-fluorophenyl}-2,4-dimethyl-1,3-oxazole-5-carboxamide;
N-{3-[5-(cyclobutylmethyl)-2H-pyrazolo[3,4-b]pyridin-2-yl]-4-fluorophenyl}-2,4-dimethyl-1,3-oxazole-5-carboxamide;
N-{4-fluoro-3-[5-(3-methylbutyl)-2H-pyrazolo[3,4-b]pyridin-2-yl]phenyl}-2,4-dimethyl-1,3-oxazole-5-carboxamide;
N-{4-fluoro-3-[5-(pyridin-2-yl)-2H-pyrazolo[3,4-b]pyridin-2-yl]phenyl}-2,4-dimethyl-1,3-oxazole-5-carboxamide;
N-{4-fluoro-3-[5-(propan-2-yl)-2H-pyrazolo[3,4-b]pyridin-2-yl]phenyl}-5-methylfuran-2-carboxamide;
N-{4-fluoro-3-[5-(propan-2-yl)-2H-pyrazolo[3,4-b]pyridin-2-yl]phenyl}-5-methoxyfuran-2-carboxamide;
5-[(dimethylamino)methyl]-N-{4-fluoro-3-[5-(propan-2-yl)-2H-pyrazolo[3,4-b]pyridin-2-yl]phenyl}furan-2-carboxamide;
5-cyano-N-{4-fluoro-3-[5-(propan-2-yl)-2H-pyrazolo[3,4-b]pyridin-2-yl]phenyl}furan-2-carboxamide;
5-fluoro-N-{4-fluoro-3-[5-(propan-2-yl)-2H-pyrazolo[3,4-b]pyridin-2-yl]phenyl}furan-2-carboxamide;
N-{4-fluoro-3-[5-(propan-2-yl)-2H-pyrazolo[3,4-b]pyridin-2-yl]phenyl}-4,5-dimethylfuran-2-carboxamide;
N-{4-fluoro-3-[5-(propan-2-yl)-2H-pyrazolo[3,4-b]pyridin-2-yl]phenyl}-3-methylfuran-2-carboxamide;
N-{4-fluoro-3-[5-(propan-2-yl)-2H-pyrazolo[3,4-b]pyridin-2-yl]phenyl}-1-benzofuran-2-carboxamide;
3,3-difluoro-N-{4-fluoro-3-[5-(propan-2-yl)-2H-pyrazolo[3,4-b]pyridin-2-yl]phenyl}-1-methylcyclobutane-1-carboxamide;
3,3-difluoro-N-{4-fluoro-3-[5-(propan-2-yl)-2H-pyrazolo[3,4-b]pyridin-2-yl]phenyl}cyclobutane-1-carboxamide;
methyl 8-({4-fluoro-3-[5-(propan-2-yl)-2H-pyrazolo[3,4-b]pyridin-2-yl]phenyl}carbamoyl)cubane-1-carboxylate;
methyl 3-({4-fluoro-3-[5-(propan-2-yl)-2H-pyrazolo[3,4-b]pyridin-2-yl]phenyl}carbamoyl)bicyclo[1.1.1]pentane-1-carboxylate;

3-fluoro-N-{4-fluoro-3-[5-(propan-2-yl)-2H-pyrazolo[3,4-b]pyridin-2-yl]phenyl}cyclobutane-1-carboxamide;

N-{4-fluoro-3-[5-(morpholin-4-yl)-2H-pyrazolo[3,4-b]pyridin-2-yl]phenyl}furan-2-carboxamide;

propan-2-yl N-{2-[2-fluoro-5-(furan-2-amido)phenyl]-2H-pyrazolo[3,4-b]pyridin-5-yl}carbamate;

3,3-difluoro-N-{4-fluoro-3-[5-(propan-2-yl)-2H-pyrazolo[3,4-b]pyridin-2-yl]phenyl}azetidine-1-carboxamide;

N-(3-{5-bromo-2H-pyrazolo[3,4-b]pyridin-2-yl}-4-fluorophenyl)-3,3-difluoroazetidine-1-carboxamide;

N-(3-{5-bromo-2H-pyrazolo[3,4-b]pyridin-2-yl}-4-fluorophenyl)-3-fluoroazetidine-1-carboxamide;

(3R)—N-(3-{5-bromo-2H-pyrazolo[3,4-b]pyridin-2-yl}-4-fluorophenyl)-3-fluoropyrrolidine-1-carboxamide;

N-(3-{5-bromo-2H-pyrazolo[3,4-b]pyridin-2-yl}-4-fluorophenyl)-2,4-dimethyl-1,3-oxazole-5-carboxamide;

N-(3-{5-bromo-2H-pyrazolo[3,4-b]pyridin-2-yl}-4-fluorophenyl)azetidine-1-carboxamide;

N-(3-{5-bromo-2H-pyrazolo[3,4-b]pyridin-2-yl}-4-fluorophenyl)furan-2-carboxamide;

3-fluoro-N-{4-fluoro-3-[5-(pyrrolidin-1-yl)-2H-pyrazolo[3,4-b]pyridin-2-yl]phenyl}azetidine-1-carboxamide;

3-fluoro-N-{4-fluoro-3-[5-(morpholin-4-yl)-2H-pyrazolo[3,4-b]pyridin-2-yl]phenyl}azetidine-1-carboxamide;

(3R)—N-{3-[5-(dimethylamino)-2H-pyrazolo[3,4-b]pyridin-2-yl]-4-fluorophenyl}-3-fluoropyrrolidine-1-carboxamide;

(3R)-3-fluoro-N-{4-fluoro-3-[5-(pyrrolidin-1-yl)-2H-pyrazolo[3,4-b]pyridin-2-yl]phenyl}pyrrolidine-1-carboxamide;

(3R)-3-fluoro-N-{4-fluoro-3-[5-(morpholin-4-yl)-2H-pyrazolo[3,4-b]pyridin-2-yl]phenyl}pyrrolidine-1-carboxamide;

propan-2-yl N-[2-(2-fluoro-5-{[(3R)-3-fluoropyrrolidine-1-carbonyl]amino}phenyl)-2H-pyrazolo[3,4-b]pyridin-5-yl]carbamate;

N-{4-fluoro-3-[5-(morpholin-4-yl)-2H-pyrazolo[3,4-b]pyridin-2-yl]phenyl}azetidine-1-carboxamide;

propan-2-yl N-(2-{5-[(azetidine-1-carbonyl)amino]-2-fluorophenyl}-2H-pyrazolo[3,4-b]pyridin-5-yl)carbamate;

N-{4-fluoro-3-[5-(methylamino)-2H-pyrazolo[3,4-b]pyridin-2-yl]phenyl}furan-2-carboxamide;

N-{3-[5-(dimethylamino)-2H-pyrazolo[3,4-b]pyridin-2-yl]-4-fluorophenyl}furan-2-carboxamide;

N-{4-fluoro-3-[5-(pyrrolidin-1-yl)-2H-pyrazolo[3,4-b]pyridin-2-yl]phenyl}furan-2-carboxamide;

1-{4-fluoro-3-[5-(methylamino)-2H-pyrazolo[3,4-b]pyridin-2-yl]phenyl}-3-methylurea;

1-{3-[5-(dimethylamino)-2H-pyrazolo[3,4-b]pyridin-2-yl]-4-fluorophenyl}-3,3-dimethylurea;

N-{3-[5-(azetidin-1-yl)-2H-pyrazolo[3,4-b]pyridin-2-yl]-4-fluorophenyl}-3,3-difluoroazetidine-1-carboxamide;

3,3-difluoro-N-{4-fluoro-3-[5-(morpholin-4-yl)-2H-pyrazolo[3,4-b]pyridin-2-yl]phenyl}azetidine-1-carboxamide;

propan-2-yl N-(2-{5-[(3,3-difluoroazetidine-1-carbonyl)amino]-2-fluorophenyl}-2H-pyrazolo[3,4-b]pyridin-5-yl)carbamate;

N-{3-[5-(azetidin-1-yl)-2H-pyrazolo[3,4-b]pyridin-2-yl]-4-fluorophenyl}-3-fluoroazetidine-1-carboxamide;

3-fluoro-N-{4-fluoro-3-[5-(oxan-4-yl)-2H-pyrazolo[3,4-b]pyridin-2-yl]phenyl}azetidine-1-carboxamide;

(3R)—N-{3-[5-(azetidin-1-yl)-2H-pyrazolo[3,4-b]pyridin-2-yl]-4-fluorophenyl}-3-fluoropyrrolidine-1-carboxamide;

(3R)-3-fluoro-N-{4-fluoro-3-[5-(oxan-4-yl)-2H-pyrazolo[3,4-b]pyridin-2-yl]phenyl}pyrrolidine-1-carboxamide;

N-{3-[5-(azetidin-1-yl)-2H-pyrazolo[3,4-b]pyridin-2-yl]-4-fluorophenyl}furan-2-carboxamide;

3-fluoro-N-{4-fluoro-3-[5-(2,2,2-trifluoroethyl)-2H-pyrazolo[3,4-b]pyridin-2-yl]phenyl}azetidine-1-carboxamide;

N-{4-fluoro-3-[5-(methylamino)-2H-pyrazolo[3,4-b]pyridin-2-yl]phenyl}-2,4-dimethyl-1,3-oxazole-5-carboxamide;

N-{3-[5-(dimethylamino)-2H-pyrazolo[3,4-b]pyridin-2-yl]-4-fluorophenyl}-2,4-dimethyl-1,3-oxazole-5-carboxamide;

N-{3-[5-(azetidin-1-yl)-2H-pyrazolo[3,4-b]pyridin-2-yl]-4-fluorophenyl}-2,4-dimethyl-1,3-oxazole-5-carboxamide;

3-fluoro-N-{4-fluoro-3-[5-(propan-2-yl)-2H-pyrazolo[3,4-b]pyridin-2-yl]phenyl}azetidine-1-carboxamide;

N-{4-fluoro-3-[5-(pyrrolidin-1-yl)-2H-pyrazolo[3,4-b]pyridin-2-yl]phenyl}-2,4-dimethyl-1,3-oxazole-5-carboxamide;

N-{4-fluoro-3-[5-(morpholin-4-yl)-2H-pyrazolo[3,4-b]pyridin-2-yl]phenyl}-2,4-dimethyl-1,3-oxazole-5-carboxamide;

propan-2-yl N-{2-[5-(dimethyl-1,3-oxazole-5-amido)-2-fluorophenyl]-2H-pyrazolo[3,4-b]pyridin-5-yl}carbamate;

N-{4-fluoro-3-[5-(oxan-4-yl)-2H-pyrazolo[3,4-b]pyridin-2-yl]phenyl}azetidine-1-carboxamide;

3,3-difluoro-N-{4-fluoro-3-[5-(pyrrolidin-1-yl)-2H-pyrazolo[3,4-b]pyridin-2-yl]phenyl}azetidine-1-carboxamide;

(3R)-3-fluoro-N-{4-fluoro-3-[5-(2,2,2-trifluoroethyl)-2H-pyrazolo[3,4-b]pyridin-2-yl]phenyl}pyrrolidine-1-carboxamide;

N-{4-fluoro-3-[5-(pyrrolidin-1-yl)-2H-pyrazolo[3,4-b]pyridin-2-yl]phenyl}azetidine-1-carboxamide;

N-{4-fluoro-3-[5-(2,2,2-trifluoroethyl)-2H-pyrazolo[3,4-b]pyridin-2-yl]phenyl}azetidine-1-carboxamide;

3,3-difluoro-N-{4-fluoro-3-[5-(oxan-4-yl)-2H-pyrazolo[3,4-b]pyridin-2-yl]phenyl}azetidine-1-carboxamide;

3,3-difluoro-N-{4-fluoro-3-[5-(2,2,2-trifluoroethyl)-2H-pyrazolo[3,4-b]pyridin-2-yl]phenyl}azetidine-1-carboxamide;

N-{3-[5-(dimethylamino)-2H-pyrazolo[3,4-b]pyridin-2-yl]-4-fluorophenyl}-3-fluoroazetidine-1-carboxamide;

propan-2-yl N-(2-{2-fluoro-5-[(3-fluoroazetidine-1-carbonyl)amino]phenyl}-2H-pyrazolo[3,4-b]pyridin-5-yl)carbamate;

N-{4-fluoro-3-[5-(oxan-4-yl)-2H-pyrazolo[3,4-b]pyridin-2-yl]phenyl}-2,4-dimethyl-1,3-oxazole-5-carboxamide;

N-{3-[5-(dimethylamino)-2H-pyrazolo[3,4-b]pyridin-2-yl]-4-fluorophenyl}azetidine-1-carboxamide;

3-fluoro-N-[4-fluoro-3-(5-{2-oxa-6-azaspiro[3.3]heptan-6-yl}-2H-pyrazolo[3,4-b]pyridin-2-yl)phenyl]azetidine-1-carboxamide;

3-fluoro-N-(4-fluoro-3-{5-[(1S,4S)-2-oxa-5-azabicyclo[2.2.1]heptan-5-yl]-2H-pyrazolo[3,4-b]pyridin-2-yl}phenyl)azetidine-1-carboxamide;

4,4,4-trifluoro-N-{4-fluoro-3-[5-(propan-2-yl)-2H-pyrazolo[3,4-b]pyridin-2-yl]phenyl}butanamide;

3,3,3-trifluoropropyl N-{4-fluoro-3-[5-(propan-2-yl)-2H-pyrazolo[3,4-b]pyridin-2-yl]phenyl}carbamate;

N-{4-fluoro-3-[5-(2,2,2-trifluoroethyl)-2H-pyrazolo[3,4-b]pyridin-2-yl]phenyl}-2,4-dimethyl-1,3-oxazole-5-carboxamide;
N-{4-fluoro-3-[5-(2,2,2-trifluoroethyl)-2H-pyrazolo[3,4-b]pyridin-2-yl]phenyl}furan-2-carboxamide;
N-(3-{5-[(2S,6S)-2,6-dimethylmorpholin-4-yl]-2H-pyrazolo[3,4-b]pyridin-2-yl}-4-fluorophenyl)-3-fluoroazetidine-1-carboxamide;
3-fluoro-N-{4-fluoro-3-[5-(4-methylpiperazin-1-yl)-2H-pyrazolo[3,4-b]pyridin-2-yl]phenyl}azetidine-1-carboxamide;
3-fluoro-N-[4-fluoro-3-(5-{5H,6H,7H,8H-imidazo[1,2-a]pyrazin-7-yl}-2H-pyrazolo[3,4-b]pyridin-2-yl)phenyl]azetidine-1-carboxamide;
3-fluoro-N-{4-fluoro-3-[5-(3-hydroxyazetidin-1-yl)-2H-pyrazolo [3,4-b]pyridin-2-yl]phenyl}azetidine-1-carboxamide;
3-fluoro-N-{4-fluoro-3-[5-(pyridin-4-yl)-2H-pyrazolo[3,4-b]pyridin-2-yl]phenyl}azetidine-1-carboxamide;
3-fluoro-N-[4-fluoro-3-(5-{2-oxa-6-azaspiro[3.4]octan-6-yl}-2H-pyrazolo[3,4-b]pyridin-2-yl)phenyl]azetidine-1-carboxamide;
3-fluoro-N-[4-fluoro-3-(5-{8-oxa-3-azabicyclo[3.2.1]octan-3-yl}-2H-pyrazolo[3,4-b]pyridin-2-yl)phenyl]azetidine-1-carboxamide;
3-fluoro-N-(4-fluoro-3-{5-[(2-methoxyethyl)amino]-2H-pyrazolo[3,4-b]pyridin-2-yl}phenyl)azetidine-1-carboxamide;
3-fluoro-N-[4-fluoro-3-(5-{5H,6H,7H,8H-[1,2,4]triazolo[4,3-a]pyrazin-7-yl}-2H-pyrazolo[3,4-b]pyridin-2-yl)phenyl]azetidine-1-carboxamide;
3-fluoro-N-{4-fluoro-3-[5-(3-fluoropyridin-2-yl)-2H-pyrazolo[3,4-b]pyridin-2-yl]phenyl}azetidine-1-carboxamide;
N-{3-[5-(3-chloropyridin-2-yl)-2H-pyrazolo[3,4-b]pyridin-2-yl]-4-fluorophenyl}-3-fluoroazetidine-1-carboxamide;
3-fluoro-N-{4-fluoro-3-[5-(pyridin-3-yl)-2H-pyrazolo[3,4-b]pyridin-2-yl]phenyl}azetidine-1-carboxamide;
N-(3-{5-[(2R,6S)-2,6-dimethylmorpholin-4-yl]-2H-pyrazolo[3,4-b]pyridin-2-yl}-4-fluorophenyl)-3-fluoroazetidine-1-carboxamide;
3-fluoro-N-[4-fluoro-3-(5-{6-oxa-1-azaspiro[3.3]heptan-1-yl}-2H-pyrazolo[3,4-b]pyridin-2-yl)phenyl]azetidine-1-carboxamide;
3-fluoro-N-(4-fluoro-3-{5-[3-(methoxymethyl)azetidin-1-yl]-2H-pyrazolo[3,4-b]pyridin-2-yl}phenyl)azetidine-1-carboxamide;
N-[3-(5-{5-azaspiro[2.3]hexan-5-yl}-2H-pyrazolo[3,4-b]pyridin-2-yl)-4-fluorophenyl]-3-fluoroazetidine-1-carboxamide;
N-(3-{5-[(3R,4R)-3,4-difluoropyrrolidin-1-yl]-2H-pyrazolo[3,4-b]pyridin-2-yl}-4-fluorophenyl)-3-fluoroazetidine-1-carboxamide;
(3R)-3-fluoro-N-{4-fluoro-3-[5-(propan-2-yl)-2H-pyrazolo[3,4-b]pyridin-2-yl]phenyl}pyrrolidine-1-carboxamide;
N-{4-fluoro-3-[5-(propan-2-yl)-2H-pyrazolo[3,4-b]pyridin-2-yl]phenyl}furan-2-carboxamide;
3-fluoro-N-[4-fluoro-3-(5-{2-oxa-5-azabicyclo[2.2.2]octan-5-yl}-2H-pyrazolo[3,4-b]pyridin-2-yl)phenyl]azetidine-1-carboxamide;
3-fluoro-N-(4-fluoro-3-{5-[(2-methylpropyl)amino]-2H-pyrazolo[3,4-b]pyridin-2-yl}phenyl)azetidine-1-carboxamide;
N-{3-[5-(ethylamino)-2H-pyrazolo[3,4-b]pyridin-2-yl]-4-fluorophenyl}-3-fluoroazetidine-1-carboxamide;
3-fluoro-N-(4-fluoro-3-{5-[(propan-2-yl)amino]-2H-pyrazolo[3,4-b]pyridin-2-yl}phenyl)azetidine-1-carboxamide;
3-fluoro-N-[4-fluoro-3-(5-{1-oxa-6-azaspiro[3.3]heptan-6-yl}-2H-pyrazolo[3,4-b]pyridin-2-yl)phenyl]azetidine-1-carboxamide;
3-fluoro-N-[4-fluoro-3-(5-{6-oxa-2-azaspiro[3.4]octan-2-yl}-2H-pyrazolo[3,4-b]pyridin-2-yl)phenyl]azetidine-1-carboxamide;
3-fluoro-N-[4-fluoro-3-(5-{7-oxa-2-azaspiro[3.5]nonan-2-yl}-2H-pyrazolo[3,4-b]yl)phenyl]azetidine-1-carboxamide;
N-[3-(5-{6,6-difluoro-3-azabicyclo[3.1 0.0]hexan-3-yl}-2H-pyrazolo[3,4-b]pyridin-2-yl)-4-fluorophenyl]-3-fluoroazetidine-1-carboxamide;
3-fluoro-N-{4-fluoro-3-[5-(3-methoxyazetidin-1-yl)-2H-pyrazolo[3,4-b]pyridin-2-yl]phenyl}azetidine-1-carboxamide;
5-cyano-N-{4-fluoro-3-[5-(pyridin-2-yl)-2H-pyrazolo[3,4-b]pyridin-2-yl]phenyl}furan-2-carboxamide;
2-ethoxy-N-{4-fluoro-3-[5-(propan-2-yl)-2H-pyrazolo[3,4-b]pyridin-2-yl]phenyl}cyclopropane-1-carboxamide;
2,2-difluoro-N-{4-fluoro-3-[5-(propan-2-yl)-2H-pyrazolo[3,4-b]pyridin-2-yl]phenyl}cyclopropane-1-carboxamide;
N-{4-fluoro-3-[5-(propan-2-yl)-2H-pyrazolo[3,4-b]pyridin-2-yl]phenyl}-1-(trifluoromethyl)cyclopropane-1-carboxamide;
N-{4-fluoro-3-[5-(propan-2-yl)-2H-pyrazolo[3,4-b]pyridin-2-yl]phenyl}cyclobutanecarboxamide;
N-{4-fluoro-3-[5-(propan-2-yl)-2H-pyrazolo[3,4-b]pyridin-2-yl]phenyl}-2-methylcyclopropane-1-carboxamide;
3,3,3-trifluoro-N-{4-fluoro-3-[5-(propan-2-yl)-2H-pyrazolo[3,4-b]pyridin-2-yl]phenyl}propanamide;
4,4,4-trifluoro-N-{4-fluoro-3-[5-(propan-2-yl)-2H-pyrazolo[3,4-b]pyridin-2-yl]phenyl}-3-methylbutanamide;
5,5,5-trifluoro-N-{4-fluoro-3-[5-(propan-2-yl)-2H-pyrazolo[3,4-b]pyridin-2-yl]phenyl}pentanamide;
3-cyclopropyl-N-{4-fluoro-3-[5-(propan-2-yl)-2H-pyrazolo[3,4-b]pyridin-2-yl]phenyl}propanamide;
2-cyclobutyl-N-{4-fluoro-3-[5-(propan-2-yl)-2H-pyrazolo[3,4-b]pyridin-2-yl]phenyl}acetamide;
N-{4-fluoro-3-[5-(propan-2-yl)-2H-pyrazolo[3,4-b]pyridin-2-yl]phenyl}-3,3-dimethylbutanamide;
N-{4-fluoro-3-[5-(pyridin-2-yl)-2H-pyrazolo[3,4-b]pyridin-2-yl]phenyl}cyclobut-1-ene-1-carboxamide;
1-{4-fluoro-3-[5-(propan-2-yl)-2H-pyrazolo[3,4-b]pyridin-2-yl]phenyl}-3,3-bis($^2$H$_3$)methylurea;
N-{4-fluoro-3-[5-(propan-2-yl)-2H-pyrazolo[3,4-b]pyridin-2-yl]phenyl}-5-azaspiro[2.4]heptane-5-carboxamide;
(3R)—N-{4-fluoro-3-[5-(propan-2-yl)-2H-pyrazolo[3,4-b]pyridin-2-yl]phenyl}-3-methylpyrrolidine-1-carboxamide;
N-{4-fluoro-3-[5-(propan-2-yl)-2H-pyrazolo[3,4-b]pyridin-2-yl]phenyl}-5-azaspiro[2.3]hexane-5-carboxamide;
(1R,5S)—N-{4-fluoro-3-[5-(propan-2-yl)-2H-pyrazolo[3,4-b]pyridin-2-yl]phenyl}-3-azabicyclo[3.1 0.0]hexane-3-carboxamide;
3-ethyl-1-{4-fluoro-3-[5-(propan-2-yl)-2H-pyrazolo[3,4-b]pyridin-2-yl]phenyl}-3-methylurea;
(3R)—N-{4-fluoro-3-[5-(propan-2-yl)-2H-pyrazolo[3,4-b]pyridin-2-yl]phenyl}-3-methoxypyrrolidine-1-carboxamide;

N-{4-fluoro-3-[5-(propan-2-yl)-2H-pyrazolo[3,4-b]pyridin-2-yl]phenyl}-2-azaspiro[3.3]heptane-2-carboxamide;
1-{4-fluoro-3-[5-(propan-2-yl)-2H-pyrazolo[3,4-b]pyridin-2-yl]phenyl}-3-methyl-3-(2,2,2-trifluoroethyl)urea;
1-{4-fluoro-3-[5-(propan-2-yl)-2H-pyrazolo[3,4-b]pyridin-2-yl]phenyl}-3,3-dimethylurea;
N-{4-fluoro-3-[5-(propan-2-yl)-2H-pyrazolo[3,4-b]pyridin-2-yl]phenyl}-1,4-diazabicyclo[3.2 0.2]nonane-4-carboxamide;
N-(3-{5-[(2R,6S)-2,6-dimethylmorpholin-4-yl]-2H-pyrazolo[3,4-b]pyridin-2-yl}-4-fluorophenyl)-3-fluoroazetidine-1-carboxamide;
3-fluoro-N-[4-fluoro-3-(5-{6-oxa-1-azaspiro[3.3]heptan-1-yl}-2H-pyrazolo[3,4-b]pyridin-2-yl)phenyl]azetidine-1-carboxamide;
3-fluoro-N-(4-fluoro-3-{5-[3-(methoxymethyl)azetidin-1-yl]-2H-pyrazolo[3,4-b]pyridin-2-yl}phenyl)azetidine-1-carboxamide;
N-[3-(5-{5-azaspiro[2.3]hexan-5-yl}-2H-pyrazolo[3,4-b]pyridin-2-yl)-4-fluorophenyl]-3-fluoroazetidine-1-carboxamide;
N-(3-{5-[(3R,4R)-3,4-difluoropyrrolidin-1-yl]-2H-pyrazolo[3,4-b]pyridin-2-yl}-4-fluorophenyl)-3-fluoroazetidine-1-carboxamide;
3-fluoro-N-[4-fluoro-3-(5-{3-oxa-8-azabicyclo[3.2.1]octan-8-yl}-2H-pyrazolo[3,4-b]pyridin-2-yl)phenyl]azetidine-1-carboxamide;
1-(2-{2-fluoro-5-[(3-fluoroazetidine-1-carbonyl)amino]phenyl}-2H-pyrazolo[3,4-b]pyridin-5-yl)piperidine-4-carboxylic acid;
3-fluoro-N-(4-fluoro-3-{5-[4-(2,2,2-trifluoroethyl)piperazin-1-yl]-2H-pyrazolo[3,4-b]pyridin-2-yl}phenyl)azetidine-1-carboxamide;
3-fluoro-N-(4-fluoro-3-{5-[4-(oxetan-3-yl)piperidin-1-yl]-2H-pyrazolo[3,4-b]pyridin-2-yl}phenyl)azetidine-1-carboxamide;
3-fluoro-N-[4-fluoro-3-(5-{2-thia-6-azaspiro[3.3]heptan-6-yl}-2H-pyrazolo[3,4-b]pyridin-2-yl)phenyl]azetidine-1-carboxamide;
3-fluoro-N-(4-fluoro-3-(5-{6-oxa-3-azabicyclo[3.1.1]heptan-3-yl}-2H-pyrazolo[3,4-b]pyridin-2-yl)phenyl]azetidine-1-carboxamide;
N-[3-(5-{5-azaspiro[2.4]heptan-5-yl}-2H-pyrazolo[3,4-b]pyridin-2-yl)-4-fluorophenyl]-3-fluoroazetidine-1-carboxamide;
N-[3-(5-{5-azaspiro[2.4]heptan-5-yl}-2H-pyrazolo[3,4-b]pyridin-2-yl)-4-fluorophenyl]-5-azaspiro[2.4]heptane-5-carboxamide;
N-[3-(5-{2-azaspiro[3.3]heptan-2-yl}-2H-pyrazolo[3,4-b]pyridin-2-yl)-4-fluorophenyl]-3-fluoroazetidine-1-carboxamide;
3-fluoro-N-[4-fluoro-3-(5-{8-oxa-2-azaspiro[4.5]decan-2-yl}-2H-pyrazolo[3,4-b]pyridin-2-yl)phenyl]azetidine-1-carboxamide;
3-fluoro-N-[4-fluoro-3-(5-{6-oxo-2,5-diazaspiro[3.4]octan-2-yl}-2H-pyrazolo[3,4-b]pyridin-2-yl)phenyl]azetidine-1-carboxamide;
N-[4-fluoro-3-(5-{6-oxa-2-azaspiro[3.4]octan-2-yl}-2H-pyrazolo[3,4-b]pyridin-2-yl)phenyl]-6-oxa-2-azaspiro[3.4]octane-2-carboxamide;
1 tert-butyl 2-(2-{5-[(azetidine-1-carbonyl)amino]-2-fluorophenyl}-2H-pyrazolo[3,4-b]pyridin-5-yl)pyrrolidine-1-carboxylate;
3-fluoro-N-[4-fluoro-3-(5-{2-oxa-7-azaspiro[3.5]nonan-7-yl}-2H-pyrazolo[3,4-b]pyridin-2-yl)phenyl]azetidine-1-carboxamide;
N-{3-[5-(cyclopropylamino)-2H-pyrazolo[3,4-b]pyridin-2-yl]-4-fluorophenyl}-3-fluoroazetidine-1-carboxamide;
N-(4-fluoro-3-{5-[4-(2,2,2-trifluoroethyl)piperazin-1-yl]-2H-pyrazolo[3,4-b]pyridin-2-yl}phenyl)azetidine-1-carboxamide;
3-fluoro-N-{4-fluoro-3-[5-(3-hydroxy-3-methylazetidin-1-yl)-2H-pyrazolo[3,4-b]pyridin-2-yl]phenyl}azetidine-1-carboxamide;
3,3-difluoro-N-(4-fluoro-3-{5-[4-(2,2,2-trifluoroethyl)piperazin-1-yl]-2H-pyrazolo[3,4-b]pyridin-2-yl}phenyl)azetidine-1-carboxamide;
(3R)-3-fluoro-N-(4-fluoro-3-{5-[4-(2,2,2-trifluoroethyl)piperazin-1-yl]-2H-pyrazolo[3,4-b]pyridin-2-yl}phenyl)pyrrolidine-1-carboxamide;
N-(3-{5-bromo-2H-pyrazolo[3,4-b]pyridin-2-yl}-4-fluorophenyl)-5-azaspiro[2.3]hexane-5-carboxamide;
N-{3-[5-(3,3-dimethylazetidin-1-yl)-2H-pyrazolo[3,4-b]pyridin-2-yl]-4-fluorophenyl}-3-fluoroazetidine-1-carboxamide;
(1S,2R)-2-fluoro-N-{4-fluoro-3-[5-(pyridin-2-yl)-2H-pyrazolo[3,4-b]pyridin-2-yl]phenyl}cyclopropane-1-carboxamide;
N-[3-(5-{5-azaspiro[2.3]hexan-5-yl}-2H-pyrazolo[3,4-b]pyridin-2-yl)-4-fluorophenyl]azetidine-1-carboxamide;
N-[3-(5-{5-azaspiro[2.3]hexan-5-yl}-2H-pyrazolo[3,4-b]pyridin-2-yl)-4-fluorophenyl]-3,3-difluoroazetidine-1-carboxamide;
(3R)—N-[3-(5-{5-azaspiro[2.3]hexan-5-yl}-2H-pyrazolo[3,4-b]pyridin-2-yl)-4-fluorophenyl]-3-fluoropyrrolidine-1-carboxamide;
N-{3-[5-(dimethylamino)-2H-pyrazolo[3,4-b]pyridin-2-yl]-4-fluorophenyl}-5-azaspiro[2.3]hexane-5-carboxamide;
N-[3-(5-{1,1-difluoro-5-azaspiro[2.3]hexan-5-yl}-2H-pyrazolo[3,4-b]pyridin-2-yl)-4-fluorophenyl]-3-fluoroazetidine-1-carboxamide;
N-{3-[5-(3,3-difluoropyrrolidin-1-yl)-2H-pyrazolo[3,4-b]pyridin-2-yl]-4-fluorophenyl}-3-fluoroazetidine-1-carboxamide;
3-fluoro-N-[4-fluoro-3-(5-{3-oxa-6-azabicyclo[3.1 0.1]heptan-6-yl}-2H-pyrazolo[3,4-b]pyridin-2-yl)phenyl]azetidine-1-carboxamide;
N-{3-[5-(azetidin-2-yl)-2H-pyrazolo[3,4-b]pyridin-2-yl]-4-fluorophenyl}-3-fluoroazetidine-1-carboxamide;
3-fluoro-N-(4-fluoro-3-{5-[3-(trifluoromethyl)azetidin-1-yl]-2H-pyrazolo[3,4-b]pyridin-2-yl}phenyl)azetidine-1-carboxamide;
N-{3-[5-(3-cyanoazetidin-1-yl)-2H-pyrazolo[3,4-b]pyridin-2-yl]-4-fluorophenyl}-3-fluoroazetidine-1-carboxamide;
N-{3-[5-(1-acetylazetidin-2-yl)-2H-pyrazolo[3,4-b]pyridin-2-yl]-4-fluorophenyl}-3-fluoroazetidine-1-carboxamide;
(1S,2R)—N-{3-[5-(3,3-difluoroazetidin-1-yl)-2H-pyrazolo[3,4-b]pyridin-2-yl]-4-fluorophenyl}-2-fluorocyclopropane-1-carboxamide;
(1R,2S)-2-fluoro-N-{4-fluoro-3-[5-(pyridin-2-yl)-2H-pyrazolo[3,4-b]pyridin-2-yl]phenyl}cyclopropane-1-carboxamide;
3-fluoro-N-{4-fluoro-3-[5-(piperazin-1-yl)-2H-pyrazolo[3,4-b]pyridin-2-yl]phenyl}azetidine-1-carboxamide;

(1R,2S)—N-{3-[5-(3,3-difluoroazetidin-1-yl)-2H-pyrazolo[3,4-b]pyridin-2-yl]-4-fluorophenyl}-2-fluorocyclopropane-1-carboxamide;

(1R,2S)—N-[3-(5-{5-azaspiro[2.3]hexan-5-yl}-2H-pyrazolo[3,4-b]pyridin-2-yl)-4-fluorophenyl]-2-fluorocyclopropane-1-carboxamide;

(1S,2R)-2-fluoro-N-{4-fluoro-3-[5-(pyridin-2-yl)-2H-pyrazolo[3,4-b]pyridin-2-yl]phenyl}cyclopropane-1-carboxamide;

N-(4-fluoro-3-{5-[3-(trifluoromethyl)azetidin-1-yl]-2H-pyrazolo[3,4-b]pyridin-2-yl}phenyl)azetidine-1-carboxamide;

(3R)-3-fluoro-N-(4-fluoro-3-{5-[3-(trifluoromethyl)azetidin-1-yl]-2H-pyrazolo[3,4-b]pyridin-2-yl}phenyl)pyrrolidine-1-carboxamide;

N-(3-{5-chloro-2H-pyrazolo[3,4-b]pyridin-2-yl}-4-fluorophenyl)-3-fluoroazetidine-1-carboxamide;

N-{4-fluoro-3-[5-(3-methylpyridin-2-yl)-2H-pyrazolo[3,4-b]pyridin-2-yl]phenyl}-4-(hydroxymethyl)-2-methyl-1,3-oxazole-5-carboxamide;

N-{4-fluoro-3-[5-(3-methylpyridin-2-yl)-2H-pyrazolo[3,4-b]pyridin-2-yl]phenyl}-2-($^2$H$_3$)methyl-4-methyl-1,3-oxazole-5-carboxamide;

N-(4-fluoro-3-{5-[3-(trifluoromethyl)azetidin-1-yl]-2H-pyrazolo[3,4-b]pyridin-2-yl}phenyl)-2,4-dimethyl-1,3-oxazole-5-carboxamide;

N-{2-[5-(3,3-difluoroazetidin-1-yl)-2H-pyrazolo[3,4-b]pyridin-2-yl]pyridin-4-yl}azetidine-1-carboxamide;

3,3-difluoro-N-{2-[5-(pyridin-2-yl)-2H-pyrazolo[3,4-b]pyridin-2-yl]pyridin-4-yl}azetidine-1-carboxamide;

N-[2-(5-{5-azaspiro[2.3]hexan-5-yl}-2H-pyrazolo[3,4-b]pyridin-2-yl)pyridin-4-yl]azetidine-1-carboxamide;

N-{4-chloro-3-[5-(pyridin-2-yl)-2H-pyrazolo[3,4-b]pyridin-2-yl]phenyl}-3-fluoroazetidine-1-carboxamide;

N-{4-chloro-3-[5-(3,3-difluoroazetidin-1-yl)-2H-pyrazolo[3,4-b]pyridin-2-yl]phenyl}azetidine-1-carboxamide;

N-{4-chloro-3-[5-(pyridin-2-yl)-2H-pyrazolo[3,4-b]pyridin-2-yl]phenyl}azetidine-1-carboxamide;

N-[3-(5-{5-azaspiro[2.3]hexan-5-yl}-2H-pyrazolo[3,4-b]pyridin-2-yl)-4-chlorophenyl]azetidine-1-carboxamide;

N-[3-(5-{5-azaspiro[2.3]hexan-5-yl}-2H-pyrazolo[3,4-b]pyridin-2-yl)phenyl]azetidine-1-carboxamide;

N-{4-fluoro-3-[5-(oxan-2-yl)-2H-pyrazolo[3,4-b]pyridin-2-yl]phenyl}azetidine-1-carboxamide;

N-{3-[5-(1,4-dioxan-2-yl)-2H-pyrazolo[3,4-b]pyridin-2-yl]-4-fluorophenyl}azetidine-1-carboxamide;

N-{3-[5-(3,3-difluoroazetidin-1-yl)-2H-pyrazolo[3,4-b]pyridin-2-yl]-4-fluorophenyl}azetidine-1-carboxamide;

3-fluoro-N-{4-fluoro-3-[5-(3-fluoroazetidin-1-yl)-2H-pyrazolo[3,4-b]pyridin-2-yl]phenyl}azetidine-1-carboxamide;

N-{4-fluoro-3-[5-(3-fluoroazetidin-1-yl)-2H-pyrazolo[3,4-b]pyridin-2-yl]phenyl}azetidine-1-carboxamide;

3-fluoro-N-{4-fluoro-3-[5-(piperidin-4-yl)-2H-pyrazolo[3,4-b]pyridin-2-yl]phenyl}azetidine-1-carboxamide;

3-fluoro-N-{4-fluoro-3-[5-(pyrazin-2-yl)-2H-pyrazolo[3,4-b]pyridin-2-yl]phenyl}azetidine-1-carboxamide;

3-fluoro-N-{4-fluoro-3-[5-(1H-imidazol-4-yl)-2H-pyrazolo[3,4-b]pyridin-2-yl]phenyl}azetidine-1-carboxamide;

N-{3-[5-(1-benzylpiperidin-4-yl)-2H-pyrazolo[3,4-b]pyridin-2-yl]-4-fluorophenyl}-3-fluoroazetidine-1-carboxamide;

3-fluoro-N-{4-fluoro-3-[5-(1H-pyrazol-4-yl)-2H-pyrazolo[3,4-b]pyridin-2-yl]phenyl}azetidine-1-carboxamide;

N-{3-[5-(3,3-difluoroazetidin-1-yl)-2H-pyrazolo[3,4-b]pyridin-2-yl]-4-fluorophenyl}-3-fluoroazetidine-1-carboxamide;

N-{3-[5-(3,3-difluoroazetidin-1-yl)-2H-pyrazolo[3,4-b]pyridin-2-yl]-4-fluorophenyl}-3,3-difluoroazetidine-1-carboxamide;

(3R)—N-{3-[5-(3,3-difluoroazetidin-1-yl)-2H-pyrazolo[3,4-b]pyridin-2-yl]-4-fluorophenyl}-3-fluoropyrrolidine-1-carboxamide;

3-fluoro-N-{4-fluoro-3-[5-(1-methyl-1H-imidazol-4-yl)-2H-pyrazolo[3,4-b]pyridin-2-yl]phenyl}azetidine-1-carboxamide;

(3R)-3-fluoro-N-{4-fluoro-3-[5-(3-fluoroazetidin-1-yl)-2H-pyrazolo[3,4-b]pyridin-2-yl]phenyl}pyrrolidine-1-carboxamide;

3,3-difluoro-N-{4-fluoro-3-[5-(3-fluoroazetidin-1-yl)-2H-pyrazolo[3,4-b]pyridin-2-yl]phenyl}azetidine-1-carboxamide;

3-fluoro-N-{4-fluoro-3-[5-(1-methyl-1H-pyrazol-4-yl)-2H-pyrazolo[3,4-b]pyridin-2-yl]phenyl}azetidine-1-carboxamide;

3-fluoro-N-[4-fluoro-3-(5-{1-[(4-fluorophenyl)methyl]piperidin-4-yl}-2H-pyrazolo[3,4-b]pyridin-2-yl)phenyl]azetidine-1-carboxamide;

N-(3-{5-[bis($^2$H$_3$)methylamino]-2H-pyrazolo[3,4-b]pyridin-2-yl}-4-fluorophenyl)azetidine-1-carboxamide;

N-(3-{5-[bis($^2$H$_3$)methylamino]-2H-pyrazolo[3,4-b]pyridin-2-yl}-4-fluorophenyl)-3,3-difluoroazetidine-1-carboxamide;

(3R)—N-(3-{5-[bis($^2$H3)methylamino]-2H-pyrazolo[3,4-b]pyridin-2-yl}-4-fluorophenyl)-3-fluoropyrrolidine-1-carboxamide;

3,3-difluoro-N-{4-fluoro-3-[5-(3-fluoropyridin-2-yl)-2H-pyrazolo[3,4-b]pyridin-2-yl]phenyl}azetidine-1-carboxamide;

N-{3-[5-(3-chloropyridin-2-yl)-2H-pyrazolo[3,4-b]pyridin-2-yl]-4-fluorophenyl}-3,3-difluoroazetidine-1-carboxamide;

3-fluoro-N-(4-fluoro-3-{2H-pyrazolo[3,4-b]pyridin-2-yl}phenyl)azetidine-1-carboxamide;

3-fluoro-N-{4-fluoro-3-[5-(3-methylpyrazin-2-yl)-2H-pyrazolo[3,4-b]pyridin-2-yl]phenyl}azetidine-1-carboxamide;

N-{4-fluoro-3-[5-(3-fluoropyridin-2-yl)-2H-pyrazolo[3,4-b]pyridin-2-yl]phenyl}azetidine-1-carboxamide;

N-(3-{5-[bis($^2$H3)methylamino]-2H-pyrazolo[3,4-b]pyridin-2-yl}-4-fluorophenyl)-3-fluoroazetidine-1-carboxamide;

N-{3-[5-(3-chloropyridin-2-yl)-2H-pyrazolo[3,4-b]pyridin-2-yl]-4-fluorophenyl}azetidine-1-carboxamide;

(3R)—N-{3-[5-(3-chloropyridin-2-yl)-2H-pyrazolo[3,4-b]pyridin-2-yl]-4-fluorophenyl}-3-fluoropyrrolidine-1-carboxamide;

(3R)-3-fluoro-N-{4-fluoro-3-[5-(3-fluoropyridin-2-yl)-2H-pyrazolo[3,4-b]pyridin-2-yl]phenyl}pyrrolidine-1-carboxamide;

3-fluoro-N-(4-fluoro-3-{5-methyl-2H-pyrazolo[3,4-b]pyridin-2-yl}phenyl)azetidine-1-carboxamide;

3-fluoro-N-{4-fluoro-3-[5-(1H-pyrazol-1-yl)-2H-pyrazolo[3,4-b]pyridin-2-yl]phenyl}azetidine-1-carboxamide;

N-{4-fluoro-3-[5-(trifluoromethyl)-2H-pyrazolo[3,4-b]pyridin-2-yl]phenyl}azetidine-1-carboxamide;

3-fluoro-N-{4-fluoro-3-[5-(trifluoromethyl)-2H-pyrazolo[3,4-b]pyridin-2-yl]phenyl}azetidine-1-carboxamide;
(3R)-3-fluoro-N-{4-fluoro-3-[5-(trifluoromethyl)-2H-pyrazolo[3,4-b]pyridin-2-yl]phenyl}pyrrolidine-1-carboxamide;
3-fluoro-N-{4-fluoro-3-[5-(1H-imidazol-1-yl)-2H-pyrazolo[3,4-b]pyridin-2-yl]phenyl}azetidine-1-carboxamide;
3,3-difluoro-N-{4-fluoro-3-[5-(trifluoromethyl)-2H-pyrazolo[3,4-b]pyridin-2-yl]phenyl}azetidine-1-carboxamide;
N-{3-[5-(1-cyclopropyl-1H-pyrazol-4-yl)-2H-pyrazolo[3,4-b]pyridin-2-yl]-4-fluorophenyl}-3-fluoroazetidine-1-carboxamide;
N-{3-[5-(3,3-difluoroazetidin-1-yl)-2H-pyrazolo[3,4-b]pyridin-2-yl]-4-fluorophenyl}cyclopropanecarboxamide;
N-{4-fluoro-3-[5-(3-fluoroazetidin-1-yl)-2H-pyrazolo[3,4-b]pyridin-2-yl]phenyl}cyclopropanecarboxamide;
3-fluoro-N-{4-fluoro-3-[5-(4-methyl-1H-imidazol-1-yl)-2H-pyrazolo[3,4-b]pyridin-2-yl]phenyl}azetidine-1-carboxamide;
3-fluoro-N-{4-fluoro-3-[5-(5-fluoropyridin-2-yl)-2H-pyrazolo[3,4-b]pyridin-2-yl]phenyl}azetidine-1-carboxamide;
N-{4-fluoro-3-[5-(5-fluoropyridin-2-yl)-2H-pyrazolo[3,4-b]pyridin-2-yl]phenyl}azetidine-1-carboxamide;
N-{3-[5-(dimethylamino)-2H-pyrazolo[3,4-b]pyridin-2-yl]-4-fluorophenyl}cyclopropanecarboxamide;
N-{4-fluoro-3-[5-(3-fluoropyridin-2-yl)-2H-pyrazolo[3,4-b]pyridin-2-yl]phenyl}cyclopropanecarboxamide;
N-{3-[5-(3-chloropyridin-2-yl)-2H-pyrazolo[3,4-b]pyridin-2-yl]-4-fluorophenyl}cyclopropanecarboxamide;
N-{4-fluoro-3-[5-(3-methylpyridin-2-yl)-2H-pyrazolo[3,4-b]pyridin-2-yl]phenyl}-2-(hydroxymethyl)-4-methyl-1,3-oxazole-5-carboxamide;
N-(4-fluoro-3-{5-[3-(hydroxymethyl)pyridin-2-yl]-2H-pyrazolo[3,4-b]pyridin-2-yl}phenyl)-2,4-dimethyl-1,3-oxazole-5-carboxamide;
N-{4-fluoro-3-[5-(pyridin-2-yl)-2H-pyrazolo[3,4-b]pyridin-2-yl]phenyl}pyrrolidine-1-carboxamide;
N-[3-(5-{5-azaspiro[2.3]hexan-5-yl}-2H-pyrazolo[3,4-b]pyridin-2-yl)-4-fluorophenyl]pyrrolidine-1-carboxamide;
N-{3-[5-(3,3-difluoroazetidin-1-yl)-2H-pyrazolo[3,4-b]pyridin-2-yl]-4-fluorophenyl}pyrrolidine-1-carboxamide;
(1R,2S)—N-{3-[5-(3,3-difluoroazetidin-1-yl)-2H-pyrazolo[3,4-b]pyridin-2-yl]-4-fluorophenyl}-2-fluorocyclopropane-1-carboxamide;
(3R)—N-(2-{5-bromo-2H-pyrazolo[3,4-b]pyridin-2-yl}pyridin-4-yl)-3-fluoropyrrolidine-1-carboxamide;
N-{2-[5-(pyridin-2-yl)-2H-pyrazolo[3,4-b]pyridin-2-yl]pyridin-4-yl}azetidine-1-carboxamide;
3-fluoro-N-{2-[5-(pyridin-2-yl)-2H-pyrazolo[3,4-b]pyridin-2-yl]pyridin-4-yl}azetidine-1-carboxamide;
N-{3-[5-(3,3-difluoroazetidin-1-yl)-2H-pyrazolo[3,4-b]pyridin-2-yl]phenyl}azetidine-1-carboxamide;
N-{3-[5-(pyridin-2-yl)-2H-pyrazolo[3,4-b]pyridin-2-yl]phenyl}azetidine-1-carboxamide;
N-{4-fluoro-3-[5-(pyridin-2-yl)-2H-pyrazolo[3,4-b]pyridin-2-yl]phenyl}pyrazine-2-carboxamide;
N-{4-fluoro-3-[5-(pyridin-2-yl)-2H-pyrazolo[3,4-b]pyridin-2-yl]phenyl}spiro[2.2]pentane-1-carboxamide;
N-{4-fluoro-3-[5-(pyridin-2-yl)-2H-pyrazolo[3,4-b]pyridin-2-yl]phenyl}-3,3-dimethylcyclobut-1-ene-1-carboxamide;
1-cyano-N-{4-fluoro-3-[5-(pyridin-2-yl)-2H-pyrazolo[3,4-b]pyridin-2-yl]phenyl}cyclopropane-1-carboxamide;
(1S,2S)-2-fluoro-N-{4-fluoro-3-[5-(pyridin-2-yl)-2H-pyrazolo[3,4-b]pyridin-2-yl]phenyl}cyclopropane-1-carboxamide;
N-{4-fluoro-3-[5-(3-methylpyridin-2-yl)-2H-pyrazolo[3,4-b]pyridin-2-yl]phenyl}-3,3-dimethylcyclobut-1-ene-1-carboxamide;
N-(4-fluoro-3-(5-isopropyl-2H-pyrazolo[3,4-b]pyridin-2-yl)phenyl)-2,4-dimethyloxazole-5-carboxamide;
N-(4-fluoro-3-(5-phenyl-2H-pyrazolo[3,4-b]pyridin-2-yl)phenyl)-2,4-dimethyloxazole-5-carboxamide; and
3,3-difluoro-N-(4-fluoro-3-(5-phenyl-2H-pyrazolo[3,4-b]pyridin-2-yl)phenyl)azetidine-1-carboxamide.

14. A pharmaceutical composition comprising a compound according to claim 1 or a pharmaceutically acceptable salt thereof, and at least one excipient.

15. A combination comprising a compound according to claim 1 or a pharmaceutically acceptable salt thereof, and one or more therapeutically active agent.

16. A method for treating a disorder or disease selected from leishmaniasis, Chagas diseases and human African trypanosomiasis, comprising administering to a subject in need thereof a therapeutically effective amount of a compound of according to claim 1, and optionally in combination with a second agent.

17. The method of claim 16, wherein said disease is leishmaniasis selected from visceral leishmaniasis and cutaneous leishmaniasis.

18. The method of claim 17, wherein said second agent selected from stibogluconate, meglumine antimoniate, amphotericin, miltefosine, and paromomycin.

19. The method of claim 16, wherein said disease is Chagas disease; and said second agent is selected from benznidazole, nifurtimox and amphotericin.

20. The method of claim 16, wherein said disease is human African trypanosomiasis; and said second agent is pentamidine, suramin, melarsoprol, eflornithine, or nifurtimox.

* * * * *